United States Patent
Borzilleri et al.

(10) Patent No.: US 9,346,795 B2
(45) Date of Patent: May 24, 2016

(54) SUBSTITUTED SULFONAMIDES USEFUL AS ANTIAPOPTOTIC BCL INHIBITORS

(75) Inventors: Robert M. Borzilleri, New Hope, PA (US); Zhen-Wei Cai, Belle Mead, NJ (US); Andrew J. Tebben, New Hope, PA (US); Heidi L. Perez, Ewing, NJ (US); Liping Zhang, East Windsor, NJ (US); Gretchen M. Schroeder, Ewing, NJ (US); Donna D. Wei, Belle Mead, NJ (US)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

(21) Appl. No.: 14/122,173
(22) PCT Filed: May 23, 2012
(86) PCT No.: PCT/US2012/039094
§ 371 (c)(1),
(2), (4) Date: Nov. 25, 2013
(87) PCT Pub. No.: WO2012/162365
PCT Pub. Date: Nov. 29, 2012

(65) Prior Publication Data
US 2014/0135318 A1 May 15, 2014

Related U.S. Application Data

(60) Provisional application No. 61/489,865, filed on May 25, 2011.

(51) Int. Cl.

| A61K 31/47 | (2006.01) |
|---|---|
| A61K 31/55 | (2006.01) |
| A61K 31/54 | (2006.01) |
| A61K 31/497 | (2006.01) |
| A61K 31/535 | (2006.01) |
| C07D 417/10 | (2006.01) |
| C07D 413/10 | (2006.01) |
| C07D 403/10 | (2006.01) |
| C07D 401/10 | (2006.01) |
| C07D 403/12 | (2006.01) |
| C07D 403/14 | (2006.01) |
| C07D 413/12 | (2006.01) |

(52) U.S. Cl.
CPC ............ *C07D 417/10* (2013.01); *C07D 401/10* (2013.01); *C07D 403/10* (2013.01); *C07D 403/12* (2013.01); *C07D 403/14* (2013.01); *C07D 413/10* (2013.01); *C07D 413/12* (2013.01)

(58) Field of Classification Search
CPC .. C07D 417/10; C07D 413/10; C07D 403/10; C07D 401/10; A61K 31/47; A61K 31/55; A61K 31/54; A61K 31/497; A61K 31/535
USPC ............ 514/221, 314, 235.2, 253.06, 230.5, 514/224.2; 540/567; 544/128, 47, 90, 363; 546/165
See application file for complete search history.

(56) References Cited

U.S. PATENT DOCUMENTS 6,831,193 B2  12/2004  Lee et al.
7,601,844 B2  10/2009  Carter et al.

FOREIGN PATENT DOCUMENTS

| JP | 2006/316054 | 11/2006 |
|---|---|---|
| WO | WO 97/45016 | 12/1997 |
| WO | WO 2006/048330 | 5/2006 |
| WO | WO 2008/024337 | 2/2008 |
| WO | WO 2009/103439 | 8/2009 |
| WO | WO 2009/103440 | 8/2009 |
| WO | WO 2009/105751 | 8/2009 |
| WO | WO 2009/124962 | 10/2009 |
| WO | WO 2010/065824 | 6/2010 |

OTHER PUBLICATIONS

Porter, J., et al., "Tetrahydroisoquinoline amide substituted phenyl pyrazoles as selective Bcl-2 inhibitors," Bioorganic & Medicinal Chemistry Letters 19 (2009) pp. 230-233.
Degterev, A., et al., "Identification of small-molecule inhibitors of interaction between the BH3 domain and Bcl-$x_L$," Nature Cell Biology, vol. 3 (2001) pp. 173-182.
Perez, H.L., et al., "Identification of a phenylacylsulfonamide series of dual Bcl-2/Bcl-xL antagonists," Bioorganic & Medicinal Chemistry Letters 22 (2012) pp. 3946-3950.
Schroeder, G.M., et al., "Pyrazole and pyrimidine phenylacylsulfonamides as dual Bcl-2/Bcl-xL antagonists," Bioorganic & Medicinal Chemistry Letters 22 (2012) pp. 3951-3956.
International Search Report for PCT/US2012/039094, mailed Jul. 18, 2012.
English translation of Japanese Office Action dated Dec. 15, 2015.

*Primary Examiner* — James O Wilson
*Assistant Examiner* — Ebenezer O Sackey
(74) *Attorney, Agent, or Firm* — Gary D. Greenblatt

(57) ABSTRACT

Disclosed are compounds of Formula (I), or a pharmaceutically acceptable salt thereof, wherein: W and Q and G are defined herein. Also disclosed are methods of using such compounds as inhibitors of Bcl-2 family antiapoptotic proteins for the treatment of cancer; and pharmaceutical compositions comprising such compounds.

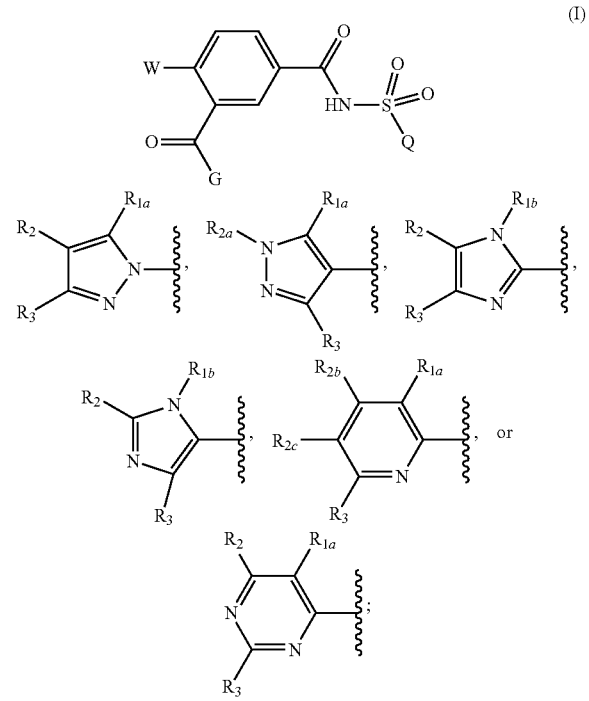

12 Claims, No Drawings

SUBSTITUTED SULFONAMIDES USEFUL AS ANTIAPOPTOTIC BCL INHIBITORS

FIELD OF THE INVENTION

The invention relates to substituted sulfonamide compounds that are useful as anti-cancer agents. This invention also relates to a method of using the compounds in the treatment of proliferative and other diseases and to pharmaceutical compositions containing the compounds.

BACKGROUND OF THE INVENTION

Apoptosis, or programmed cell death, plays an important role ensuring a proper balance between cell proliferation and cell loss in multicellular organisms. Disruption of this pathway is implicated in many human diseases, including cancer (Reed, J. C., *Cell Death and Differentiation*, 13:1379-1386 (2006)). Targeting critical apoptosis regulators is an attractive approach for the development of anticancer therapeutics and therapies for other human diseases caused by biologically impaired apoptosis.

Proteins belonging to the Bcl-2 (B-cell lymphocyte/leukemia-2) family play a central role in regulating apoptosis (Chan, S.-L. et al., *Clin. and Exper. Pharmacol. and Physiol.*, 31:119-128 (2004)). This family contains proteins promoting cell survival (Bcl-2, Bcl-b, Bcl-Xl, Bcl-w, Mcl-1, A1) and proteins promoting cell death (i.e., Bak, Bax, Bim, Bid, etc). Family members share up to four Bcl-2 homology (BH) domains and formation of homo- or heterodimers via these BH domains modulates each other's function(s) as cell death agonists or antagonists. Cellular ratios between proapoptotic and prosurvival family members dictate cellular fate. For example, prosurvival Bcl-2 family protein levels are elevated in many cancers enabling tumor cells more resistant to apoptosis. Consequently, antagonizing prosurvival Bcl-2 family protein function in tumor cells is a promising strategy for the development of anticancer therapeutics. Conceptually this therapeutic strategy is also applicable towards other diseases brought about by the disrupted cellular balance of proapoptotic and prosurvival Bcl-2 family proteins.

There remains a need for compounds that are useful as Bcl-2 family prosurvival protein antagonists.

Applicants have found potent compounds that have activity as small molecule Bcl-2 family prosurvival protein antagonists for cancer treatment and other diseases caused by impaired apoptosis. These compounds are provided to be useful as pharmaceuticals with desired stability, bioavailability, therapeutic index, and toxicity values that are important to their drugability.

SUMMARY OF THE INVENTION

The invention is directed to compounds of Formula (I) that are useful as inhibitors of Bcl-2 family antiapoptotic proteins, and are useful for the treatment of cancer, or stereoisomers, tautomers, pharmaceutically acceptable salts, solvates or prodrugs thereof.

The present invention also provides processes and intermediates for making the compounds of the present invention or stereoisomers, tautomers, pharmaceutically acceptable salts, solvates, or prodrugs thereof.

The present invention also provides pharmaceutical compositions comprising a pharmaceutically acceptable carrier and at least one of the compounds of the present invention or stereoisomers, tautomers, pharmaceutically acceptable salts, solvates, or prodrugs thereof.

The present invention also provides a method for inhibition of Bcl-2 family antiapoptotic proteins comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method for treating cancers comprising administering to a host in need of such treatment a therapeutically effective amount of at least one of the compounds of the present invention or stereoisomers, tautomers, pharmaceutically acceptable salts, solvates, or prodrugs thereof.

The present invention also provides the compounds of the present invention or stereoisomers, tautomers, pharmaceutically acceptable salts, solvates, or prodrugs thereof, for use in therapy.

The present invention also provides the use of the compounds of the present invention or stereoisomers, tautomers, pharmaceutically acceptable salts, solvates, or prodrugs thereof, for the manufacture of a medicament for the treatment of cancers.

These and other features of the invention will be set forth in the expanded form as the disclosure continues.

DETAILED DESCRIPTION OF THE INVENTION

The first aspect of the invention provides substituted sulfonamide compounds of Formula (I):

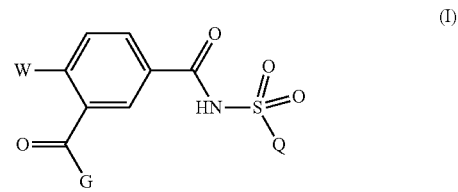

or pharmaceutically acceptable salts or prodrugs thereof, wherein:

W is:

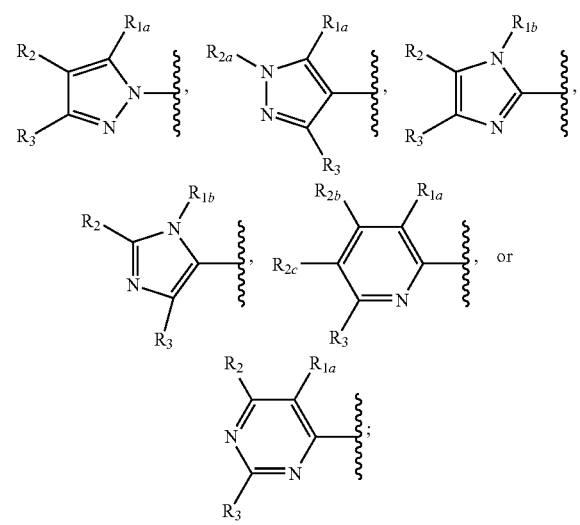

Q is:
(a) naphthalenyl or isoquinolinyl, each substituted with zero to 3 substituents independently selected from —OH, —CN, halo, —NO$_2$, —C(O)OH, —C(O)O(C$_{1-4}$ alkyl), —S(O)$_2$(C$_{1-4}$ alkyl), —S(CH$_2$)$_{1-3}$C(O)OH, —S(CH$_2$)$_{1-3}$NH$_2$, C$_{1-4}$ alkoxy, —OCH(CH$_3$)CH$_2$N(C$_{1-4}$ alkyl)$_2$, —O(CH$_2$)$_{1-3}$R$_x$, —O(CH$_2$)$_3$N(CH$_3$)$_2$, —O(CH$_2$)$_{1-4}$OH, —O(CH$_2$)$_{1-4}$O(C$_{1-4}$ alkyl), —O(CH$_2$)$_{1-4}$O(phenyl), —N(C$_{1-4}$ alkyl)$_2$, —C(O)N(C$_{1-4}$ alkyl)$_2$, —C(O)R$_x$, and/or —NHC(O)R$_x$;

(b)

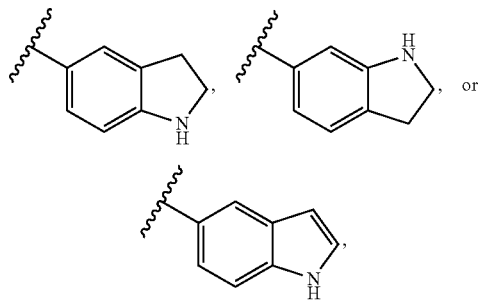

each substituted with zero to 3 substituents independently selected from halo, C$_{1-4}$ alkyl, C(O)(C$_{1-4}$ alkyl), —C(O)R$_x$, —C(O)(CH$_2$)$_{1-3}$R$_x$, —C(O)O(C$_{1-4}$ alkyl), —(CH$_2$)$_{1-3}$R$_x$, —C(O)(CH$_2$)$_{1-3}$S(phenyl), —(CH$_2$)$_{1-3}$S(phenyl), C$_{2-4}$ alkenyl, and/or morpholinyl; or (c) C$_{1-6}$ alkyl or —(CH$_2$)$_{1-3}$(trimethylsilyl) provided that W is

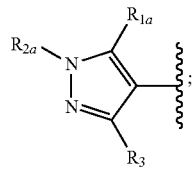

each R$_x$ is independently C$_{3-6}$ cycloalkyl, phenyl, chlorophenyl, difluorophenyl, dichlorophenyl, benzoic acid, methyl benzoate, methylsulfonylphenyl, pyridinyl, chloropyridinyl, furanyl, pyrrolidinyl, piperidinyl, morpholinyl, (morpholinoethoxy)pyridinyl, N-methylpyrrolidinyl, N-methylpiperazinyl, N-methyl-1H-imidazolyl, 1-methyl-1H-indolyl, and/or N-(2-hydroxyethyl)piperazinyl;

G is:

(a) —N(C$_{1-4}$ alkyl)$_2$; or (b) a bicyclic heterocyclyl selected from:

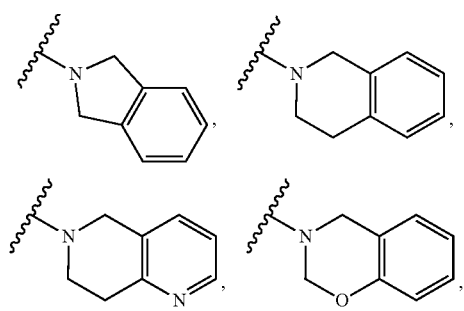

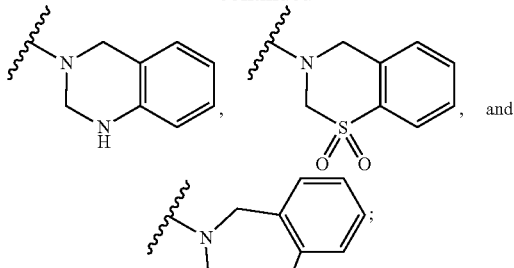

wherein said bicyclic heterocyclyl is substituted with zero to 3 substituents independently selected from: halo, C$_{1-4}$ alkyl, C$_{1-4}$ fluoroalkyl, C$_{1-4}$ hydroxyalkyl, C$_{1-4}$ alkoxy, —(CH$_2$)$_{0-3}$C(O)OH, —(CH$_2$)$_{1-3}$NH$_2$, —(CH$_2$)$_{1-3}$N$_3$, —(CH$_2$)$_{1-3}$N(CH$_3$)(C$_{1-4}$ hydroxyalkyl), —(CH$_2$)$_{1-3}$N(CH$_3$)((CH$_2$)$_{1-3}$OCH$_3$), —(CH$_2$)$_{1-3}$O(CH$_2$)$_{1-3}$N(C$_{1-4}$ alkyl)$_2$, —(CH$_2$)$_{1-3}$O(CH$_2$)$_{1-3}$OH, —(CH$_2$)$_{1-3}$O(CH$_2$)$_{1-3}$(C$_{1-4}$ alkyl), —(CH$_2$)$_{1-3}$O(CH$_2$)$_{1-3}$O(phenyl), —(CH$_2$)$_{1-3}$O(CH$_2$)$_{1-3}$CH$_3$, —(CH$_2$)$_{1-3}$ R$_x$, —(CH$_2$)$_{0-3}$N(CH$_3$)$_2$, —N(CH$_3$)((CH$_2$)$_{1-3}$O (C$_{1-4}$ alkyl),

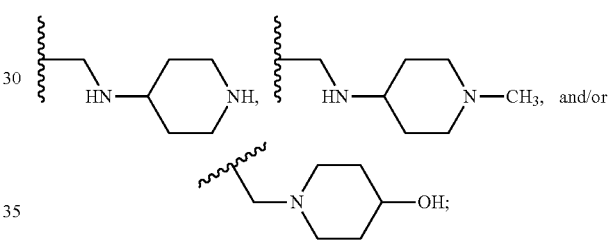

R$_{1a}$ is H, halo, C$_{1-6}$ alkyl, —CF$_3$, C$_{1-4}$ hydroxyalkyl, —(CH$_2$)$_{1-3}$O(C$_{1-4}$ alkyl), —(CH$_2$)$_{1-3}$O(C$_{1-4}$ hydroxyalkyl), —(CH$_2$)$_{0-3}$C(O)OH, —(CH$_2$)$_{0-3}$N(C$_{1-4}$ alkyl)$_2$, —(CH$_2$)$_{0-3}$C(O)NH(C$_{1-4}$ alkyl), —(CH$_2$)$_{1-3}$R$_x$, —(CH$_2$)$_{0-3}$ OC(O)NH$_2$, —(CH$_2$)$_{0-3}$C(O)NHS(O)$_2$(C$_{3-6}$ cycloalkyl), —(CH$_2$)$_{1-3}$OC(O)R$_x$, or —(CH$_2$)$_{0-3}$OC(O)NH(CH$_2$)$_{1-3}$ R$_x$;

R$_{1b}$ is H, C$_{1-6}$ alkyl, —CF$_3$, C$_{1-4}$ hydroxyalkyl, —(CH$_2$)$_{1-3}$O (C$_{1-4}$ alkyl), —(CH$_2$)$_{1-3}$O(C$_{1-4}$ hydroxyalkyl), —(CH$_2$)$_{0-3}$ C(O)OH, —(CH$_2$)$_{0-3}$N(C$_{1-4}$ alkyl)$_2$, —(CH$_2$)$_{0-3}$C(O)NH (C$_{1-4}$ alkyl), —(CH$_2$)$_{1-3}$R$_x$, —(CH$_2$)$_{0-3}$OC(O)NH$_2$, —(CH$_2$)$_{0-3}$C(O)NHS(O)$_2$(C$_{3-6}$ cycloalkyl), —(CH$_2$)$_{1-3}$ OC(O)R$_x$, or —(CH$_2$)$_{0-3}$OC(O)NH(CH$_2$)$_{1-3}$R$_x$;

R$_2$ is:

(a) H, Cl, Br, C$_{1-3}$ hydroxyalkyl, —(CH$_2$)$_{0-3}$C(O)OH, or —(CH$_2$)$_{0-3}$N(CH$_3$)$_2$; or (b) phenyl substituted with zero to 2 substituents independently selected from C$_{1-4}$ alkyl, —(CH$_2$)$_{0-3}$OH, —O(CH$_3$)$_{0-3}$ CH$_3$, —O(CH$_2$)$_{1-3}$OH, —O(CH$_2$)$_{1-2}$CH(OH)(CH$_2$)$_{1-2}$ OH, —O(C$_{2-4}$ alkenyl), —OR$_x$, —C(O)O (C$_{1-4}$ alkyl), and/or phenyl;

R$_{2a}$ is:

(a) H, C$_{1-3}$ hydroxyalkyl, —(CH$_2$)$_{0-3}$C(O)OH, or —(CH$_2$)$_{0-3}$ N(CH$_3$)$_2$; or (b) phenyl substituted with zero to 2 substituents independently selected from C$_{1-4}$ alkyl, —(CH$_2$)$_{0-3}$OH, —O(CH$_3$)$_{0-3}$ CH$_3$, —O(CH$_2$)$_{1-3}$OH, —O(CH$_2$)$_{1-2}$CH (OH)(CH$_2$)$_{1-2}$OH, —O(C$_{2-4}$ alkenyl), —OR$_x$, —C(O)O(C$_{1-4}$ alkyl), and/or phenyl;
one of R$_{2b}$ and R$_{2c}$ is H and the other of R$_{2b}$ and R$_{2c}$ is R$_2$;
R$_3$ is —(CH$_2$)$_{1-3}$OH, —C(O)OH, —C(O)O(C$_{1-4}$ alkyl), —C(O)NR$_a$R$_b$, or —NR$_a$R$_b$;
R$_a$ is H, C$_{1-6}$ alkyl, or C$_{1-4}$ fluoroalkyl; and
R$_b$ is
(a) C$_{1-6}$ alkyl, C$_{1-4}$ fluoroalkyl, —(CH$_2$)$_{1-3}$C(O)OH, —(CH$_2$)$_{1-3}$C(O)O(C$_{1-4}$ alkyl), —(CH$_2$)$_{1-3}$(C$_{3-6}$ cycloalkyl), —CH$_2$(naphthalenyl), —(CH$_2$)$_{1-3}$C(O)NHCH(C$_{1-4}$ hydroxyalkyl)$_2$, —(CH$_2$)$_{1-3}$C(O)NHCH(C$_{1-4}$ hydroxyalkyl)$_3$, or —(CH$_2$)$_{1-3}$C(O)NH(CH$_2$)$_{1-3}$R$_x$;
(b) —(CH$_2$)$_{0-2}$(phenyl) wherein said phenyl is substituted with zero to 2 substituents independently selected from Cl, I, C$_{1-4}$ alkyl, C$_{1-4}$ alkoxy, —(CH$_2$)$_{0-3}$C(O)OH, —C(O)O(C$_{1-4}$alkyl), —(CH$_2$)$_{1-3}$C(O)O(C$_{1-4}$alkyl), phenyl, halophenyl, halophenoxy, phenyl acetic acid, and/or —(CH$_2$)$_{1-3}$C(O)R$_x$; or
(c)

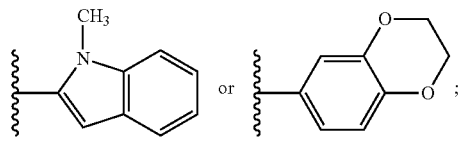 [SMILES: *c1cc2ccccc2n1C ; *c1ccc2c(c1)OCCO2]

or R$_a$ and R$_b$ together with the nitrogen atom to which they are attached, form a pyrrolidinyl ring substituted with zero to 1 substituent selected from C$_{1-4}$alkyl and —(CH$_2$)$_{1-3}$(phenyl).

One embodiment provides compounds of Formula (I) or pharmaceutically acceptable salts or prodrugs thereof, wherein:
W is:

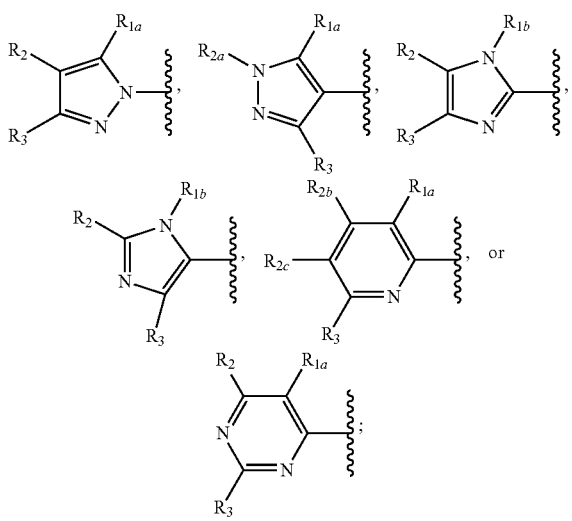

Q is:
(a) naphthalenyl substituted with zero to 3 substituents independently selected from —OH, —CN, Cl, Br, I, —NO$_2$, —N(CH$_3$)$_2$, —C(O)OH, —C(O)OCH$_2$CH$_3$, —S(O)$_2$CH$_2$CH$_3$, C$_{1-3}$ alkoxy, —OCH(CH$_3$)CH$_2$N(CH$_3$)$_2$, —O(CH$_2$)$_3$N(CH$_3$)$_2$, —OCH$_2$(phenyl), —OCH$_2$(dichlorophenyl), —OCH$_2$(benzoic acid), —OCH$_2$(methyl benzoate), —OCH$_2$(methylsulfonylphenyl), —OCH$_2$(furanyl), —OCH$_2$(N-methyl-1H-imidazolyl), —O(CH$_2$)$_2$(N-methylpyrrolidinyl), —O(CH$_2$)$_{2-3}$(morpholinyl), —O(CH$_2$)$_3$(pyrrolidinyl), —O(CH$_2$)$_3$(piperidinyl), O(CH$_2$)$_3$(N-methylpiperazinyl), —O(CH$_2$)$_3$(pyridinyl), —OCH$_2$CH$_2$OH, —OCH$_2$CH$_2$O(C$_{1-2}$ alkyl), —OCH$_2$CH$_2$O(phenyl), —C(O)N(CH$_3$)$_2$, —C(O)(N-methylpiperazinyl), —C(O)(morpholinyl), and/or —NHC(O)(dichlorophenyl);
(b) isoquinolinyl substituted with —OCH$_2$CH$_2$(morpholinyl), —SCH$_2$CH$_2$NH$_2$, or —SCH$_2$C(O)OH;
(c)

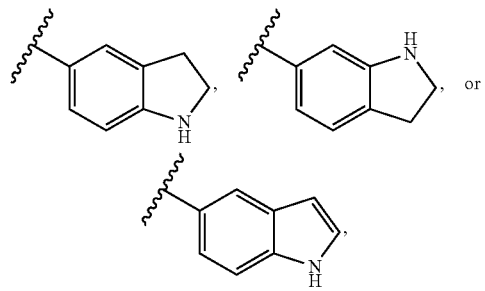

each substituted with zero to 3 substituents independently selected from Cl, Br, I, —CH$_2$CH$_3$, —CH$_2$(cyclohexyl), —CH$_2$(phenyl), —CH$_2$(difluorophenyl), —(CH$_2$)$_{1-2}$(dichlorophenyl), —CH$_2$(chloropyridinyl), —CH$_2$(1-methyl-1H-indolyl), —(CH$_2$)$_{1-3}$(morpholinyl), —C(O)(cyclohexyl), —C(O)(dichlorophenyl), —C(O)(morpholinyl), —C(O)((morpholinoethoxy)pyridinyl), —C(O)OCH$_3$, —C(O)CH$_2$(dichlorophenyl), —C(O)(CH$_2$)$_{1-3}$(morpholinyl), —C(O)CH$_2$S(phenyl), —CH$_2$CH$_2$S(phenyl), —CH=CHCH$_3$, —CH=CHCH$_2$CH$_3$, and/or morpholinyl; or
(d) ethyl, pentyl, or —CH$_2$CH$_2$(trimethylsilyl)), provided that W is

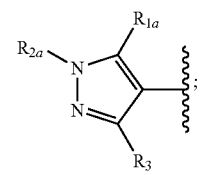

G is:
(a) —N(CH$_3$)$_2$; or
(b) a bicyclic heterocyclyl selected from:

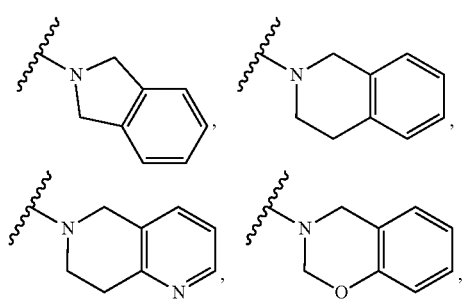

-continued

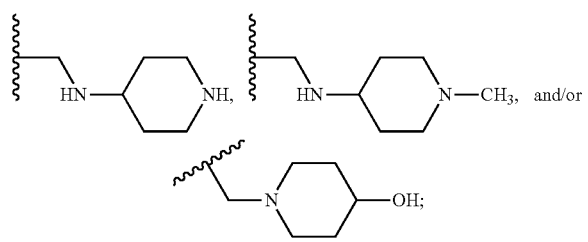

wherein said bicyclic heterocyclyl is substituted with zero to 2 substituents independently selected from: Br, —CH$_3$, —CF$_3$, —CH$_2$OH, —CH$_2$NH$_2$, —CH$_2$N$_3$, —CH$_2$N(CH$_3$)(CH$_2$CH$_2$OH), —CH$_2$N(CH$_3$)(CH$_2$CH$_2$OCH$_3$), —CH$_2$OCH$_2$CH$_2$N(CH$_3$)$_2$, —CH$_2$OCH$_2$CH$_2$OH, —CH$_2$OCH$_2$CH$_2$O(phenyl), —CH$_2$OCH$_2$CH$_2$CH$_2$OCH$_3$, —CH$_2$(pyrrolidinyl), —CH$_2$(N-methyl piperazinyl), —CH$_2$(N-(2-hydroxyethyl)piperazinyl), —CH$_2$(morpholinyl), —OCH$_3$, —C(O)OH, —(CH$_2$)$_{0-1}$N(CH$_3$)$_2$, —N(CH$_3$)(CH$_2$CH$_2$OCH$_3$),

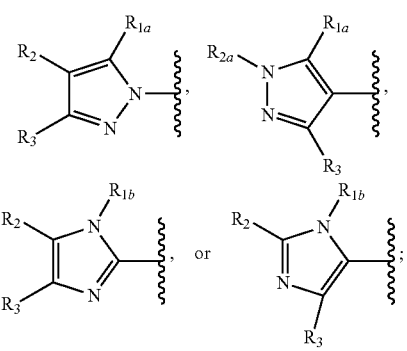

$R_{1a}$ is H, Cl, Br, —CH$_3$, butyl, —CF$_3$, —(CH$_2$)$_{2-3}$OH, —CH$_2$CH$_2$OCH$_3$, —CH$_2$CH$_2$OCH$_2$CH$_2$OH, —CH$_2$C(O)OH, —(CH$_2$)$_3$N(CH$_3$)$_2$, —CH$_2$C(O)NHCH$_3$, —(CH$_2$)$_{1-3}$(phenyl), —(CH$_2$)$_{2-3}$(morpholinyl), —(CH$_2$)$_{2-3}$(N-methyl piperazinyl), —(CH$_2$)$_2$OC(O)NH$_2$, —CH$_2$C(O)NHS(O)$_2$(cyclopropyl), —(CH$_2$)$_2$OC(O)(N-methyl piperazinyl), or —(CH$_2$)$_2$OC(O)NH(CH$_2$)$_2$(N-methyl piperazinyl);

$R_{1b}$ is H, Cl, Br, —CH$_3$, butyl, —CF$_3$, —(CH$_2$)$_{2-3}$OH, —CH$_2$CH$_2$OCH$_3$, —CH$_2$CH$_2$OCH$_2$CH$_2$OH, —CH$_2$C(O)OH, —(CH$_2$)$_3$N(CH$_3$)$_2$, —CH$_2$C(O)NHCH$_3$, —(CH$_2$)$_{1-3}$(phenyl), —(CH$_2$)$_{2-3}$(morpholinyl), —(CH$_2$)$_{2-3}$(N-methyl piperazinyl), —(CH$_2$)$_2$OC(O)NH$_2$, —CH$_2$C(O)NHS(O)$_2$(cyclopropyl), —(CH$_2$)$_2$OC(O)(N-methyl piperazinyl), or —(CH$_2$)$_2$OC(O)NH(CH$_2$)$_2$(N-methyl piperazinyl);

$R_2$ is:
(a) H, Cl, Br, C$_{1-3}$ hydroxyalkyl, —(CH$_2$)$_2$C(O)OH, or —(CH$_2$)$_3$N(CH$_3$)$_2$; or
(b) phenyl substituted with zero to 1 substituent selected from propyl, —(CH$_2$)$_{0-2}$OH, —O(CH$_3$)$_{0-3}$CH$_3$, —O(CH$_2$)$_3$OH, —OCH$_2$CH(OH)CH$_2$OH, —C(O)OH, —OCH$_2$CH=CH$_2$, —O(phenyl), —O(chlorophenyl), —C(O)OCH$_3$, and phenyl;

$R_{2a}$ is:
(a) H, C$_{1-3}$ hydroxyalkyl, —(CH$_2$)$_2$C(O)OH, or —(CH$_2$)$_3$N(CH$_3$)$_2$; or
(b) phenyl substituted with zero to 1 substituent selected from propyl, —(CH$_2$)$_{0-2}$OH, —O(CH$_3$)$_{0-3}$CH$_3$, —O(CH$_2$)$_3$OH, —OCH$_2$CH(OH)CH$_2$OH, —C(O)OH, —OCH$_2$CH=CH$_2$, —O(phenyl), —O(chlorophenyl), —C(O)OCH$_3$, and phenyl;

one of $R_{2b}$ and $R_{2c}$ is H and the other of $R_{2b}$ and $R_{2c}$ is $R_2$;

$R_3$ is —CH$_2$OH, —C(O)OH, —C(O)OCH$_2$CH$_3$, —C(O)NR$_a$R$_b$, or —NR$_a$R$_b$;

$R_a$ is H, C$_{1-5}$ alkyl, or C$_{1-4}$ fluoroalkyl; and $R_b$ is
(a) C$_{1-5}$ alkyl, C$_{3-4}$ fluoroalkyl, —(CH$_2$)$_2$C(O)OH, —(CH$_2$)$_2$C(O)O(butyl), —CH$_2$(cyclopropyl), —CH$_2$(naphthalenyl), —(CH$_2$)$_2$C(O)NHCH(C$_{1-2}$ hydroxyalkyl)$_2$, —(CH$_2$)$_2$ C(O)NHC(CH$_2$OH)$_3$, or —(CH$_2$)$_2$C(O)NHCH$_2$CH$_2$(N-methyl piperazinyl);

(b) —(CH$_2$)$_{0-2}$(phenyl) wherein said phenyl is substituted with zero to 2 substituents independently selected from Cl, I, C$_{1-4}$ alkyl, C$_{1-4}$ alkoxy, —(CH$_2$)$_{0-2}$C(O)OH, —C(O)OCH$_3$, —CH$_2$C(O)OCH$_2$CH$_3$, phenyl, chlorophenyl, fluorophenoxy, chlorophenoxy, phenyl acetic acid, and/or —(CH$_2$)$_2$C(O)(piperidinyl carboxylic acid); or (c)

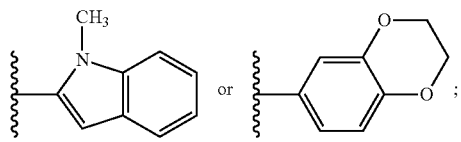 [SMILES: *c1cc2ccccc2n1C ; *c1ccc2c(c1)OCCO2]

or $R_a$ and $R_b$ together with the nitrogen atom to which they are attached, form a pyrrolidinyl ring substituted with zero to 1 substituent selected from propyl and —CH$_2$CH$_2$(phenyl).

One embodiment provides compounds of Formula (I), pharmaceutically acceptable salts or prodrugs thereof, wherein W is:

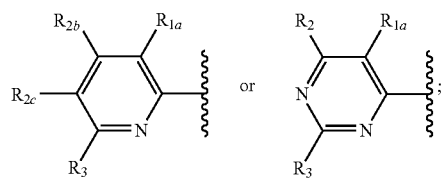

wherein G, Q, $R_{1a}$, $R_{1b}$, $R_2$, and $R_3$ are defined in the first aspect.

One embodiment provides compounds of Formula (I), pharmaceutically acceptable salts or prodrugs thereof, wherein W is:

wherein G, Q, $R_{1a}$, $R_2$, $R_{2b}$, $R_{2c}$, and $R_3$ are defined in the first aspect.

One embodiment provides compounds of Formula (I) or pharmaceutically acceptable salts or prodrugs thereof, wherein:
W is

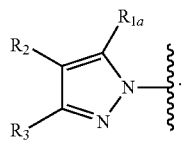

Compounds of this embodiment are represented by Formula (II):

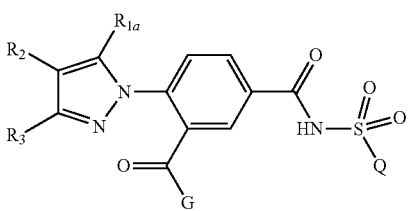

or pharmaceutically acceptable salts or prodrugs thereof, wherein $R_1$, $R_{1a}$, $R_2$, $R_3$, G and Q are defined in the first aspect.

One embodiment provides compounds of Formula (II) or pharmaceutically acceptable salts or prodrugs thereof, wherein:

Q is
(a) naphthalenyl substituted with zero to 3 substituents independently selected from —OH, —CN, Cl, Br, I, —NO$_2$, —N(CH$_3$)$_2$, —C(O)OH, —C(O)OCH$_2$CH$_3$, —S(O)$_2$CH$_2$CH$_3$, $C_{1-3}$ alkoxy, —OCH(CH$_3$)CH$_2$N(CH$_3$)$_2$, —O(CH$_2$)$_3$N(CH$_3$)$_2$, —OCH$_2$(phenyl), —OCH$_2$(dichlorophenyl), —OCH$_2$(benzoic acid), —OCH$_2$(methyl benzoate), —OCH$_2$(methylsulfonylphenyl), —OCH$_2$(furanyl), —OCH$_2$(N-methyl-1H-imidazolyl), —O(CH$_2$)$_2$(N-methylpyrrolidinyl), —O(CH$_2$)$_{2-3}$(morpholinyl), —O(CH$_2$)$_3$(pyrrolidinyl), —O(CH$_2$)$_3$(piperidinyl), O(CH$_2$)$_3$(N-methyl piperazinyl), —O(CH$_2$)$_3$(pyridinyl), —O(CH$_2$)$_2$OH, —O(CH$_2$)$_2$O(C$_{1-2}$ alkyl), —O(CH$_2$)$_2$O(phenyl), —C(O)N(CH$_3$)$_2$, —C(O)(N-methylpiperazinyl), —C(O)(morpholinyl), and/or —NHC(O)(dichlorophenyl);
(b) isoquinolinyl substituted with —OCH$_2$CH$_2$(morpholinyl), —SCH$_2$CH$_2$NH$_2$, or —SCH$_2$C(O)OH; or
(c)

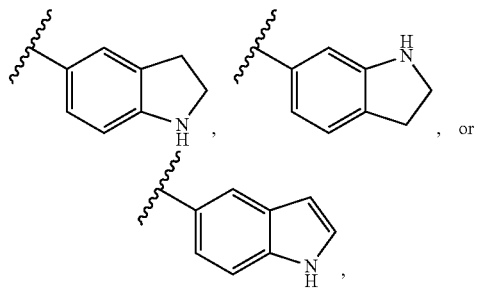

each substituted with zero to 3 substituents independently selected from Cl, Br, I, —CH$_2$CH$_3$, —CH$_2$(cyclohexyl), —CH$_2$(phenyl), —CH$_2$(difluorophenyl), —(CH$_2$)$_{1-2}$(dichlorophenyl), —CH$_2$(chloropyridinyl), —CH$_2$(1-methyl-1H-indolyl), —(CH$_2$)$_{1-3}$(morpholinyl), —C(O)(cyclohexyl), —C(O)(dichlorophenyl), —C(O)(morpholinyl), —C(O)((morpholinoethoxy)pyridinyl), —C(O)OCH$_3$, —C(O)CH$_2$(dichlorophenyl), —C(O)(CH$_2$)$_{1-3}$(morpholinyl), —C(O)CH$_2$S(phenyl), —CH$_2$CH$_2$S(phenyl), —CH=CHCH$_3$, —CH=CHCH$_2$CH$_3$, and/or morpholinyl;

G is a bicyclic heterocyclyl selected from:

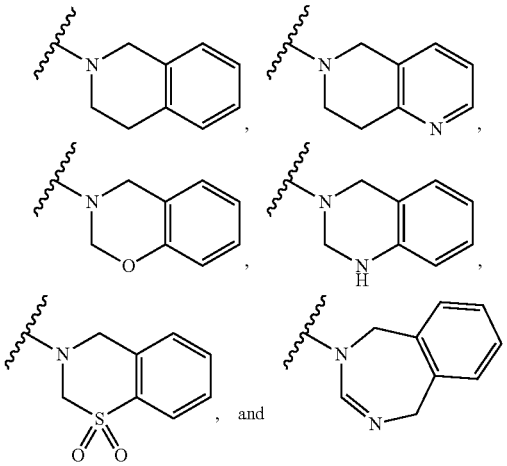

, and

;

wherein said bicyclic heterocyclyl is substituted with zero to 2 substituents independently selected from: Br, —CH$_3$, —CF$_3$, —CH$_2$OH, —CH$_2$NH$_2$, —CH$_2$N(CH$_3$)(CH$_2$CH$_2$OH), —CH$_2$N(CH$_3$)(CH$_2$CH$_2$OCH$_3$), —CH$_2$OCH$_2$CH$_2$N(CH$_3$)$_2$, —CH$_2$O(CH$_2$)$_2$OH, —CH$_2$O(CH$_2$)$_2$O(phenyl), —CH$_2$O(CH$_2$)$_3$OCH$_3$, —CH$_2$(pyrrolidinyl), —CH$_2$(N-methyl piperazinyl), —CH$_2$(N-(2-hydroxyethyl)piperazinyl), —CH$_2$(morpholinyl), —OCH$_3$, —C(O)OH, —(CH$_2$)$_{0-1}$N(CH$_3$)$_2$, —N(CH$_3$)(CH$_2$CH$_2$OCH$_3$),

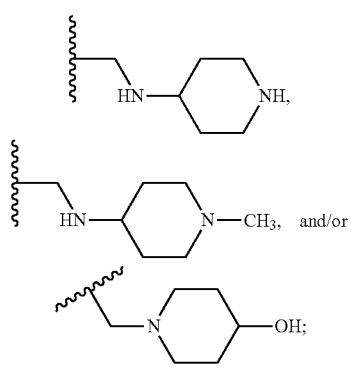

$R_{1a}$ is H, —CH$_3$, —CF$_3$, —(CH$_2$)$_2$OH, —CH$_2$C(O)OH, —(CH$_2$)$_2$OC(O)NH$_2$, —CH$_2$C(O)NHS(O)$_2$(cyclopropyl), —(CH$_2$)$_2$OC(O)(N-methyl piperazinyl), or —(CH$_2$)$_2$OC(O)NHCH$_2$CH$_2$(N-methyl piperazinyl);
$R_2$ is H, Cl, Br, $C_{1-3}$ hydroxyalkyl, —(CH$_2$)$_2$C(O)OH, —(CH$_2$)$_3$N(CH$_3$)$_2$, or benzoic acid;
$R_3$ is —N(C$_{3-4}$alkyl)$_2$ or —C(O)NR$_a$R$_b$;
$R_a$ is H, $C_{1-4}$ alkyl, or $C_{3-4}$ fluoroalkyl; and
$R_b$ is:
(a) $C_{1-4}$ alkyl, $C_{3-4}$ fluoroalkyl, —(CH$_2$)$_2$C(O)OH, —(CH$_2$)$_2$C(O)O(butyl), —CH$_2$(naphthalenyl), —(CH$_2$)$_2$C(O)

NHCH(CH$_2$OH)$_2$, —(CH$_2$)$_2$C(O)NHC(CH$_2$OH)$_3$, or —(CH$_2$)$_2$C(O)NHCH$_2$CH$_2$(N-methyl piperazinyl);

(b) —(CH$_2$)$_{0-2}$(phenyl) wherein said phenyl is substituted with zero to 2 substituents independently selected from Cl, I, C$_{1-4}$ alkyl, C$_{1-4}$ alkoxy, —C(O)OH, —(CH$_2$)$_{0-2}$C(O)OH, —C(O)OCH$_3$, —CH$_2$C(O)OCH$_2$CH$_3$, phenyl, chlorophenyl, fluorophenoxy, chlorophenoxy, phenyl acetic acid, and/or —(CH$_2$)$_2$C(O)(piperidinyl carboxylic acid); or (c)

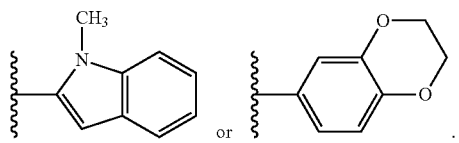 [SMILES: *c1cc2ccccc2n1C ; *c1ccc2c(c1)OCCO2]

One embodiment provides compounds of Formula (I) or pharmaceutically acceptable salts or prodrugs thereof, wherein:

W is

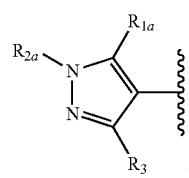

Compounds of this embodiment are represented by Formula (III):

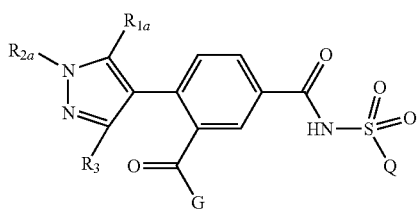

(III)

or pharmaceutically acceptable salts or prodrugs thereof, wherein R$_{1a}$, R$_{2a}$, R$_3$, G and Q are defined in the first aspect.

One embodiment provides compounds of Formula (III) or pharmaceutically acceptable salts or prodrugs thereof, wherein:

Q is ethyl, pentyl, —(CH$_2$)$_2$(trimethylsilyl), or naphthalenyl substituted zero to 2 substituents independently selected from Cl and/or Br;

G is

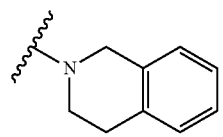 [SMILES: *N1CCc2ccccc2C1]

substituted with zero to 1 substituent selected from —CH$_2$OH, —CH$_2$N$_3$, and —CH$_2$NH$_2$;

R$_{1a}$ is —CH$_3$ or butyl;

R$_{2a}$ is phenyl substituted with zero to 1 substituent selected from propyl, —OH, —(CH$_2$)$_2$OH, —OCH$_3$, —O(CH$_2$)$_3$CH$_3$, —O(CH$_2$)$_3$OH, —OCH$_2$CH(OH)CH$_2$OH, —OCH$_2$CH═CH$_2$, —O(phenyl), —O(chlorophenyl), C(O)OCH$_3$, and phenyl; and R$_3$ is —CH$_2$OH, —C(O)OH, or —C(O)OCH$_2$CH$_3$.

One embodiment provides compounds of Formula (I) or pharmaceutically acceptable salts or prodrugs thereof, wherein:

W is

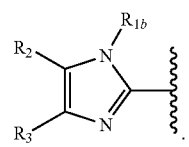

Compounds of this embodiment are represented by Formula (IV):

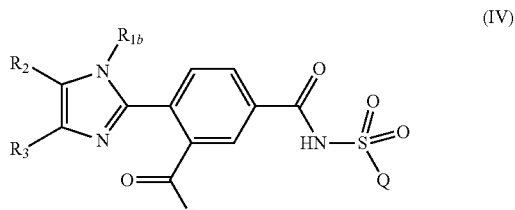

(IV)

or pharmaceutically acceptable salts or prodrugs thereof, wherein R$_{1b}$, R$_2$, R$_3$, G and Q are defined in the first aspect.

One embodiment provides compounds of Formula (IV) or pharmaceutically acceptable salts or prodrugs thereof, wherein:

Q is naphthalenyl substituted with zero to 1 substituent selected from Cl and I;

G is

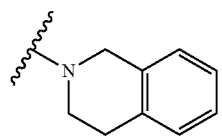 [SMILES: *N1CCc2ccccc2C1]

substituted with zero to 1 substituent selected from —CH$_2$OH and —CH$_2$NH$_2$;

R$_{1b}$ is H, —CH$_3$, —(CH$_2$)$_{2-3}$OH, —(CH$_2$)$_{1-3}$(phenyl), —(CH$_2$)$_{2-3}$(morpholinyl), —(CH$_2$)$_{2-3}$(N-methyl piperazinyl), —(CH$_2$)$_2$OCH$_3$, —(CH$_2$)$_2$O(CH$_2$)$_2$OH, —(CH$_2$)$_3$N(CH$_3$)$_2$, —CH$_2$C(O)OH, or —CH$_2$C(O)NHCH$_3$;

R$_2$ is H; and

R$_3$ is —C(O)N(n-butyl)$_2$.

One embodiment provides compounds of Formula (I) or pharmaceutically acceptable salts or prodrugs thereof, wherein:

W is

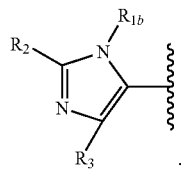

Compounds of this embodiment are represented by Formula (V):

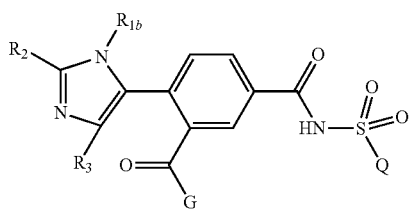

or pharmaceutically acceptable salts or prodrugs thereof, wherein $R_{1b}$, $R_2$, $R_3$, G and Q are defined in the first aspect.

One embodiment provides compounds of Formula (V) or pharmaceutically acceptable salts or prodrugs thereof, wherein:

Q is naphthalenyl substituted Cl or I;
G is

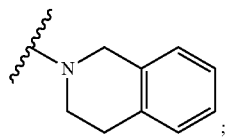 [SMILES: *N1CCc2ccccc2C1]

$R_{1b}$ is —CH$_3$;
$R_2$ is H; and
$R_3$ is —C(O)N(n-butyl)$_2$.

One embodiment provides compounds of Formula (I) or pharmaceutically acceptable salts or prodrugs thereof, wherein:

W is

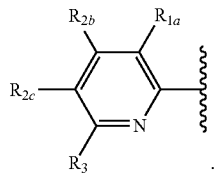

Compounds of this embodiment are represented by Formula (VI):

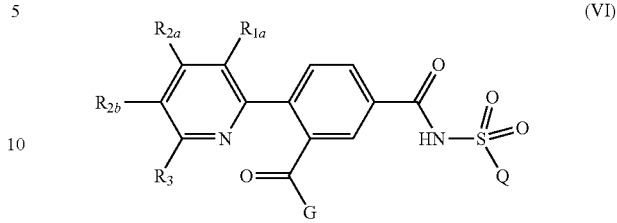

or pharmaceutically acceptable salts or prodrugs thereof, wherein $R_{1a}$, $R_{2b}$, $R_{2c}$, $R_3$, G and Q are defined in the first aspect.

One embodiment provides compounds of Formula (VI) or pharmaceutically acceptable salts or prodrugs thereof, wherein:

Q is:
(a) naphthalenyl substituted with zero to 1 substituent selected from Cl; or
(b)

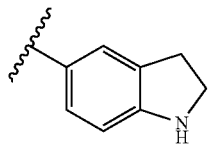 [SMILES: *c1ccc2c(c1)CCN2]

substituted with zero to 1 substituent selected from —CH$_2$(dichlorophenyl);
G is

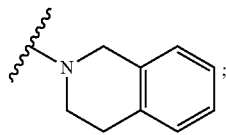 [SMILES: *N1CCc2ccccc2C1]

$R_{1a}$ is H or Br;
$R_{2b}$ is H;
$R_{2c}$ is H; and
$R_3$ is —N(n-butyl)$_2$ or —C(O)N(n-butyl)$_2$.

One embodiment provides compounds of Formula (I) or pharmaceutically acceptable salts or prodrugs thereof, wherein:

W is

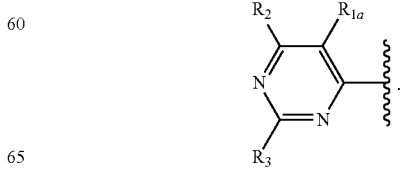

Compounds of this embodiment are represented by Formula (VII):

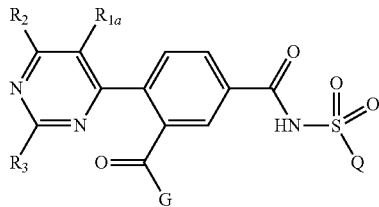

(VII)

or pharmaceutically acceptable salts or prodrugs thereof, wherein $R_{1a}$, $R_2$, $R_3$, G and Q are defined in the first aspect.

One embodiment provides compounds of Formula (VII) or pharmaceutically acceptable salts or prodrugs thereof, wherein:

Q is:
(a) naphthalenyl substituted with zero to 1 substituent selected from Cl and I; or
(b)

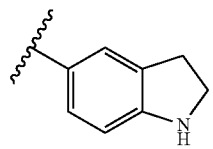 [SMILES: *c1ccc2c(c1)CCN2]

substituted with zero to 1 substituent selected from —CH$_2$CH$_3$ and —CH$_2$(dichlorophenyl);

G is:
(a) —N(CH$_3$)$_2$;
(b)

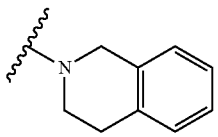 [SMILES: *N1CCc2ccccc2C1]

substituted with zero to 1 substituent selected from —CF$_3$, —CH$_2$OH, and —CH$_2$NH$_2$; or
(c)

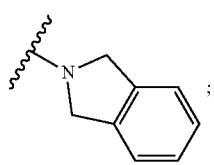 [SMILES: *N1Cc2ccccc2C1]

;

$R_{1a}$ is H, Cl, Br, —CH$_3$, or —C(O)OCH$_2$CH$_3$;
$R_2$ is H;
$R_3$ is —NR$_a$R$_b$;
$R_a$ is C$_{2-5}$ alkyl; and
$R_b$ is C$_{2-5}$ alkyl, —CH$_2$(cyclopropyl), or —CH$_2$(dichlorophenyl);
or $R_a$ and $R_b$ together with the nitrogen atom to which they are attached, form a pyrrolidinyl ring substituted with zero to 1 substituent selected from propyl and —CH$_2$CH$_2$(phenyl).

One embodiment provides compounds of Formula (I) or pharmaceutically acceptable salts or prodrugs thereof, wherein:

W is:

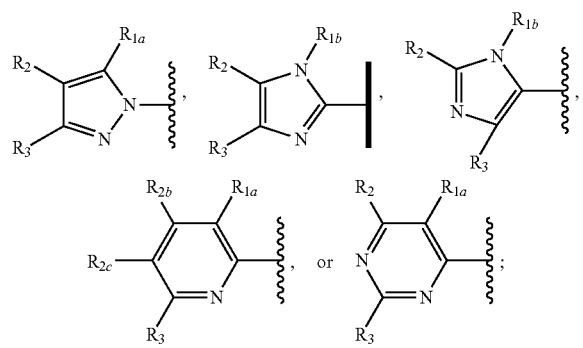

Q is:
(a) naphthalenyl substituted with zero to 3 substituents independently selected from —OH, —CN, Cl, Br, I, —NO$_2$, —N(CH$_3$)$_2$, —C(O)OH, —C(O)OCH$_2$CH$_3$, —S(O)$_2$CH$_2$CH$_3$, C$_{1-3}$ alkoxy, —OCH(CH$_3$)CH$_2$N(CH$_3$)$_2$, —O(CH$_2$)$_3$N(CH$_3$)$_2$, —OCH$_2$(phenyl), —OCH$_2$(dichlorophenyl), —OCH$_2$(benzoic acid), —OCH$_2$(methyl benzoate), —OCH$_2$(methylsulfonylphenyl), —OCH$_2$(furanyl), —OCH$_2$(N-methyl-1H-imidazolyl), —O(CH$_2$)$_2$(N-methylpyrrolidinyl), —O(CH$_2$)$_{2-3}$(morpholinyl), —O(CH$_2$)$_3$(pyrrolidinyl), —O(CH$_2$)$_3$(piperidinyl), O(CH$_2$)$_3$(N-methylpiperazinyl), —O(CH$_2$)$_3$(pyridinyl), —OCH$_2$CH$_2$OH, —OCH$_2$CH$_2$O(C$_{1-2}$ alkyl), —OCH$_2$CH$_2$O(phenyl), —C(O)N(CH$_3$)$_2$, —C(O)(N-methylpiperazinyl), —C(O)(morpholinyl), and/or —NHC(O)(dichlorophenyl);
(b) isoquinolinyl substituted with —OCH$_2$CH$_2$(morpholinyl), —SCH$_2$CH$_2$NH$_2$, or —SCH$_2$C(O)OH; or
(c)

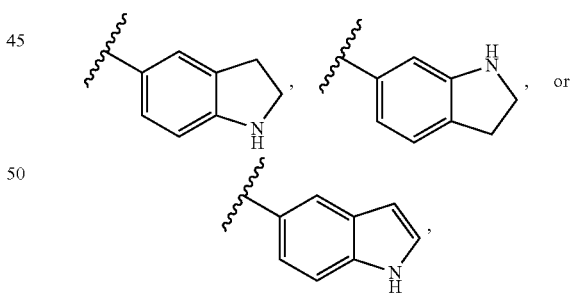

each substituted with zero to 3 substituents independently selected from Cl, Br, I, —CH$_2$CH$_3$, —CH$_2$(cyclohexyl), —CH$_2$(phenyl), —CH$_2$(difluorophenyl), —(CH$_2$)$_{1-2}$(dichlorophenyl), —CH$_2$(chloropyridinyl), —CH$_2$(1-methyl-1H-indolyl), —(CH$_2$)$_{1-3}$(morpholinyl), —C(O)(cyclohexyl), —C(O)(dichlorophenyl), —C(O)(morpholinyl), —C(O)((morpholinoethoxy)pyridinyl), —C(O)OCH$_3$, —C(O)CH$_2$(dichlorophenyl), —C(O)(CH$_2$)$_{1-3}$(morpholinyl), —C(O)CH$_2$S(phenyl), —CH$_2$CH$_2$S(phenyl), —CH=CHCH$_3$, —CH=CHCH$_2$CH$_3$, and/or morpholinyl;

G is:
(a) —N(CH$_3$)$_2$; or
(b) a bicyclic heterocyclyl selected from:

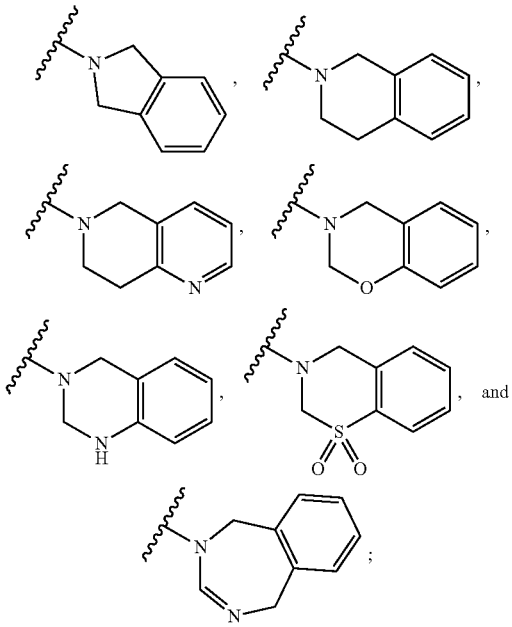

wherein said bicyclic heterocyclyl is substituted with zero to 2 substituents independently selected from: Br, —CH$_3$, —CF$_3$, —CH$_2$OH, —CH$_2$NH$_2$, —CH$_2$N$_3$, —CH$_2$N(CH$_3$)(CH$_2$CH$_2$OH), —CH$_2$N(CH$_3$)(CH$_2$CH$_2$OCH$_3$), —CH$_2$OCH$_2$CH$_2$N(CH$_3$)$_2$, —CH$_2$OCH$_2$CH$_2$OH, —CH$_2$OCH$_2$CH$_2$O(phenyl), —CH$_2$OCH$_2$CH$_2$CH$_2$OCH$_3$, —CH$_2$(pyrrolidinyl), —CH$_2$(N-methyl piperazinyl), —CH$_2$(N-(2-hydroxyethyl)piperazinyl), —CH$_2$(morpholinyl), —OCH$_3$, —C(O)OH, —(CH$_2$)$_{0-1}$N(CH$_3$)$_2$, —N(CH$_3$)(CH$_2$CH$_2$OCH$_3$),

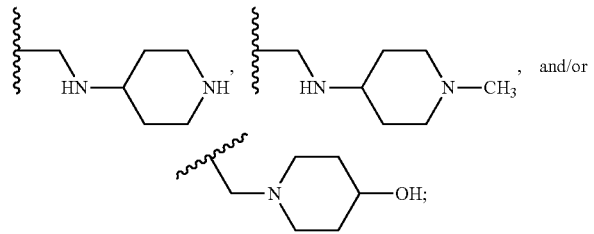

$R_{1a}$ is H, Cl, Br, —CH$_3$, butyl, —CF$_3$, —(CH$_2$)$_{2-3}$OH, —CH$_2$CH$_2$OCH$_3$, —CH$_2$CH$_2$OCH$_2$CH$_2$OH, —CH$_2$C(O)OH, —(CH$_2$)$_3$N(CH$_3$)$_2$, —CH$_2$C(O)NHCH$_3$, —(CH$_2$)$_{1-3}$(phenyl), —(CH$_2$)$_{2-3}$(morpholinyl), —(CH$_2$)$_{2-3}$(N-methyl piperazinyl), —(CH$_2$)$_2$OC(O)NH$_2$, —CH$_2$C(O)NHS(O)$_2$(cyclopropyl), —(CH$_2$)$_2$OC(O)(N-methyl piperazinyl), or —(CH$_2$)$_2$OC(O)NH(CH$_2$)$_2$(N-methyl piperazinyl);

$R_{1b}$ is H, —CH$_3$, butyl, —CF$_3$, —(CH$_2$)$_{2-3}$OH, —CH$_2$CH$_2$OCH$_3$, —CH$_2$CH$_2$OCH$_2$CH$_2$OH, —CH$_2$C(O)OH, —(CH$_2$)$_3$N(CH$_3$)$_2$, —CH$_2$C(O)NHCH$_3$, —(CH$_2$)$_{1-3}$(phenyl), —(CH$_2$)$_{2-3}$(morpholinyl), —(CH$_2$)$_{2-3}$(N-methyl piperazinyl), —(CH$_2$)$_2$OC(O)NH$_2$, —CH$_2$C(O)NHS(O)$_2$(cyclopropyl), —(CH$_2$)$_2$OC(O)(N-methyl piperazinyl), or —(CH$_2$)$_2$OC(O)NH(CH$_2$)$_2$(N-methyl piperazinyl);

$R_2$ is:
(a) H, Cl, Br, C$_{1-3}$ hydroxyalkyl, —(CH$_2$)$_2$C(O)OH, or —(CH$_2$)$_3$N(CH$_3$)$_2$; or
(b) phenyl substituted with zero to 1 substituent selected from propyl, —(CH$_2$)$_{0-2}$OH, —O(CH$_3$)$_{0-3}$CH$_3$, —O(CH$_2$)$_3$OH, —OCH$_2$CH(OH)CH$_2$OH, —C(O)OH, —OCH$_2$CH=CH$_2$, —O(phenyl), —O(chlorophenyl), —C(O)OCH$_3$, and phenyl;

one of $R_{2b}$ and $R_{2c}$ is H and the other of $R_{2b}$ and $R_{2c}$ is $R_2$;
$R_3$ is —C(O)NR$_a$R$_b$ or —NR$_a$R$_b$;
$R_a$ is H, C$_{1-5}$ alkyl, or C$_{1-4}$ fluoroalkyl; and
$R_b$ is
(a) C$_{1-5}$ alkyl, C$_{3-4}$ fluoroalkyl, —(CH$_2$)$_2$C(O)OH, —(CH$_2$)$_2$C(O)O(butyl), —CH$_2$(cyclopropyl), —CH$_2$(naphthalenyl), —(CH$_2$)$_2$C(O)NHCH(C$_{1-2}$ hydroxyalkyl)$_2$, —(CH$_2$)$_2$C(O)NHC(CH$_2$OH)$_3$, or —(CH$_2$)$_2$C(O)NHCH$_2$CH$_2$(N-methyl piperazinyl);
(b) —(CH$_2$)$_{0-2}$(phenyl) wherein said phenyl is substituted with zero to 2 substituents independently selected from Cl, I, C$_{1-4}$ alkyl, C$_{1-4}$ alkoxy, —(CH$_2$)$_{0-2}$C(O)OH, —C(O)OCH$_3$, —CH$_2$C(O)OCH$_2$CH$_3$, phenyl, chlorophenyl, fluorophenoxy, chlorophenoxy, phenyl acetic acid, and/or —(CH$_2$)$_2$C(O)(piperidinyl carboxylic acid); or
(c)

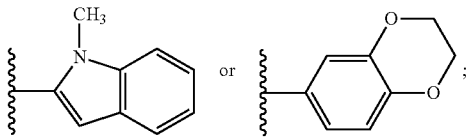 [SMILES: *c1cc2ccccc2n1C ; *c1ccc2c(c1)OCCO2]

or $R_a$ and $R_b$ together with the nitrogen atom to which they are attached, form a pyrrolidinyl ring substituted with zero to 1 substituent selected from propyl and —CH$_2$CH$_2$(phenyl).

One embodiment provides compounds of Formula (I) or pharmaceutically acceptable salts or prodrugs thereof, wherein Q is naphthalenyl substituted with zero to 3 substituents independently selected from —OH, —CN, halo, —NO$_2$, —C(O)OH, —C(O)O(C$_{1-4}$ alkyl), —S(O)$_2$(C$_{1-4}$ alkyl), C$_{1-4}$ alkoxy, —OCH(CH$_3$)CH$_2$N(C$_{1-4}$ alkyl)$_2$, —O(CH$_2$)$_{1-3}$R$_x$, —O(CH$_2$)$_3$N(CH$_3$)$_2$, —O(CH$_2$)$_{1-4}$OH, —O(CH$_2$)$_{1-4}$O(C$_{1-4}$ alkyl), —O(CH$_2$)$_{1-4}$O(phenyl), —N(C$_{1-4}$ alkyl)$_2$, —C(O)N(C$_{1-4}$alkyl)$_2$, —C(O)R$_x$, and/or —NHC(O)R$_x$; wherein each R$_x$ is independently C$_{3-6}$ cycloalkyl, phenyl, chlorophenyl, difluorophenyl, dichlorophenyl, benzoic acid, methyl benzoate, methylsulfonylphenyl, pyridinyl, chloropyridinyl, furanyl, pyrrolidinyl, piperidinyl, morpholinyl, (morpholinoethoxy)pyridinyl, N-methylpyrrolidinyl, N-methylpiperazinyl, N-methyl-1H-imidazolyl, 1-methyl-1H-indolyl, and/or N-(2-hydroxyethyl)piperazinyl. For example, included in the present embodiment are compounds in which Q is naphthalenyl substituted with zero to 3 substituents independently selected from —OH, —CN, Cl, Br, I, —NO$_2$, —N(CH$_3$)$_2$, —C(O)OH, —C(O)OCH$_2$CH$_3$, —S(O)$_2$CH$_2$CH$_3$, C$_{1-3}$ alkoxy, —OCH(CH$_3$)CH$_2$N(CH$_3$)$_2$, —O(CH$_2$)$_3$N(CH$_3$)$_2$, —OCH$_2$(phenyl), —OCH$_2$(dichlorophenyl), —OCH$_2$(benzoic acid), —OCH$_2$(methyl benzoate), —OCH$_2$(methylsulfonylphenyl), —OCH$_2$(furanyl), —OCH$_2$(N-methyl-1H-imidazolyl), —O(CH$_2$)$_2$(N-methylpyrrolidinyl), —O(CH$_2$)$_{2-3}$(morpholinyl), —O(CH$_2$)$_3$(pyrrolidinyl), —O(CH$_2$)$_3$(piperidinyl), O(CH$_2$)$_3$(N-methylpiperazinyl), —O(CH$_2$)$_3$(pyridinyl), —OCH$_2$CH$_2$OH, —OCH$_2$CH$_2$O(C$_{1-2}$ alkyl), —OCH$_2$CH$_2$O(phenyl), —C(O)N(CH$_3$)$_2$, —C(O)(N-methylpiperazinyl), —C(O)(morpholinyl), and/or —NHC(O)(dichlorophenyl).

One embodiment provides compounds of Formula (I) or pharmaceutically acceptable salts or prodrugs thereof, wherein Q is isoquinolinyl substituted with —OCH$_2$CH$_2$(morpholinyl), —SCH$_2$CH$_2$NH$_2$, or —SCH$_2$C(O)OH.

One embodiment provides compounds of Formula (I) or pharmaceutically acceptable salts or prodrugs thereof, wherein Q is:

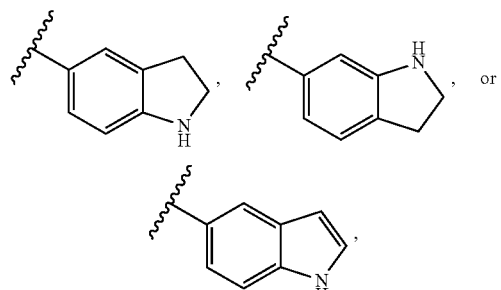

each substituted with zero to 3 substituents independently selected from halo, C$_{1-4}$ alkyl, C(O)(C$_{1-4}$ alkyl), —C(O)R$_x$, —C(O)(CH$_2$)$_{1-3}$R$_x$, —C(O)O(C$_{1-4}$ alkyl), —(CH$_2$)$_{1-3}$R$_x$, —C(O)(CH$_2$)$_{1-3}$S(phenyl), —(CH$_2$)$_{1-3}$S(phenyl), C$_{2-4}$ alkenyl, and/or morpholinyl. For example, included in the present embodiment are compounds in which Q is:

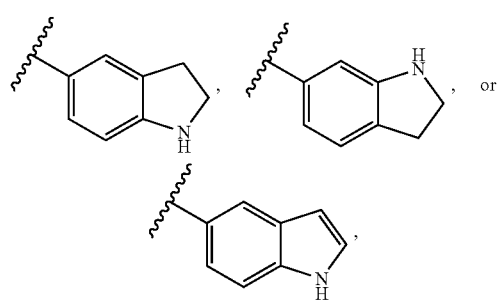

each substituted with zero to 3 substituents independently selected from Cl, Br, I, —CH$_2$CH$_3$, —CH$_2$(cyclohexyl), —CH$_2$(phenyl), —CH$_2$(difluorophenyl), —(CH$_2$)$_{1-2}$(dichlorophenyl), —CH$_2$(chloropyridinyl), —CH$_2$(1-methyl-1H-indolyl), —(CH$_2$)$_{1-3}$(morpholinyl), —C(O)(cyclohexyl), —C(O)(dichlorophenyl), —C(O)(morpholinyl), —C(O)((morpholinoethoxy)pyridinyl), —C(O)OCH$_3$, —C(O)CH$_2$(dichlorophenyl), —C(O)(CH$_2$)$_{1-3}$(morpholinyl), —C(O)CH$_2$S(phenyl), —CH$_2$CH$_2$S(phenyl), —CH=CHCH$_3$, —CH=CHCH$_2$CH$_3$, and/or morpholinyl.

One embodiment provides compounds of Formula (III) or pharmaceutically acceptable salts or prodrugs thereof, wherein Q is C$_{1-6}$ alkyl or —(CH$_2$)$_{1-3}$(trimethylsilyl), with the proviso that W is

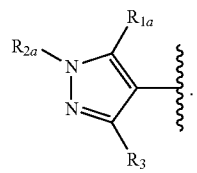

Included in this embodiment are compounds in which Q is ethyl, pentyl, or —CH$_2$CH$_2$(trimethylsilyl)).

One embodiment provides compounds of Formula (I) or pharmaceutically acceptable salts or prodrugs thereof, wherein G is —N(C$_{1-4}$alkyl)$_2$. Included in this embodiment are compounds in which G is —N(CH$_3$)$_2$. Also include in this embodiment are compounds in which Q is naphthalenyl substituted with zero to 1 substituent selected from Cl or I;

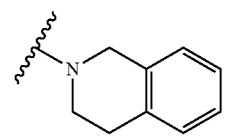 [SMILES: *N1CCc2ccccc2C1]

substituted with zero to 1 substituent selected from —CF$_3$, —CH$_2$OH, or —CH$_2$NH$_2$; or

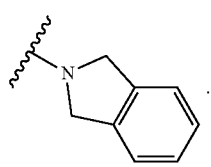 [SMILES: *N1Cc2ccccc2C1]

One embodiment provides compounds of Formula (I) or pharmaceutically acceptable salts or prodrugs thereof, wherein G is a bicyclic heterocyclyl selected from:

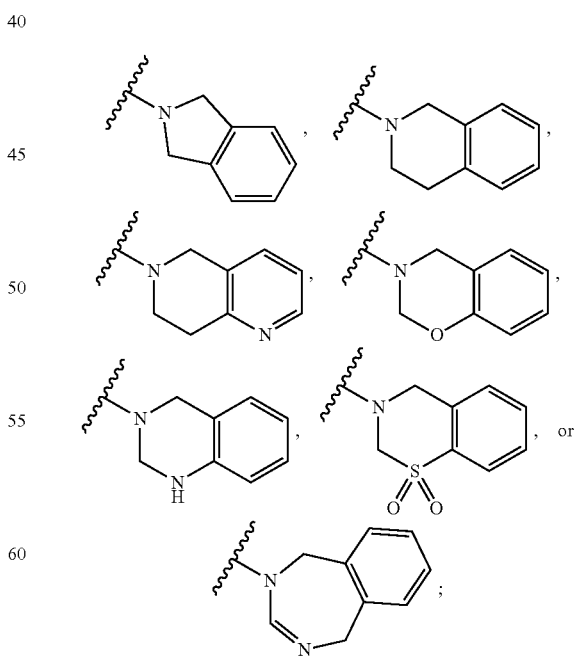

wherein said bicyclic heterocyclyl is substituted with zero to 3 substituents independently selected from: halo, C$_{1-4}$ alkyl, $C_{1-4}$ fluoroalkyl, $C_{1-4}$ hydroxyalkyl, $C_{1-4}$ alkoxy, —$(CH_2)_{0-3}$C(O)OH, —$(CH_2)_{1-3}NH_2$, —$(CH_2)_{1-3}N_3$, —$(CH_2)_{1-3}N(CH_3)(C_{1-4}$ hydroxyalkyl), —$(CH_2)_{1-3}N(CH_3)((CH_2)_{1-3}OCH_3)$, —$(CH_2)_{1-3}O(CH_2)_{1-3}N(C_{1-4}$ alkyl$)_2$, —$(CH_2)_{1-3}O$$(CH_2)_{1-3}OH$, —$(CH_2)_{1-3}O(CH_2)_{1-3}(C_{1-4}$ alkyl), —$(CH_2)_{1-3}$$O(CH_2)_{1-3}O$(phenyl), —$(CH_2)_{1-3}O(CH_2)_{1-3}CH_3$, —$(CH_2)_{1-3}$ $R_x$, —$(CH_2)_{0-3}N(CH_3)_2$, —$N(CH_3)((CH_2)_{1-3}O$ ($C_{1-4}$ alkyl),

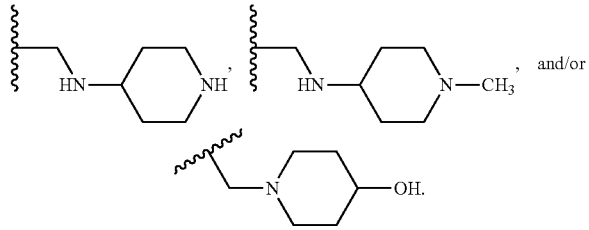

One embodiment provides compounds of Formula (I) or pharmaceutically acceptable salts or prodrugs thereof, wherein G is a bicyclic heterocyclyl selected from:

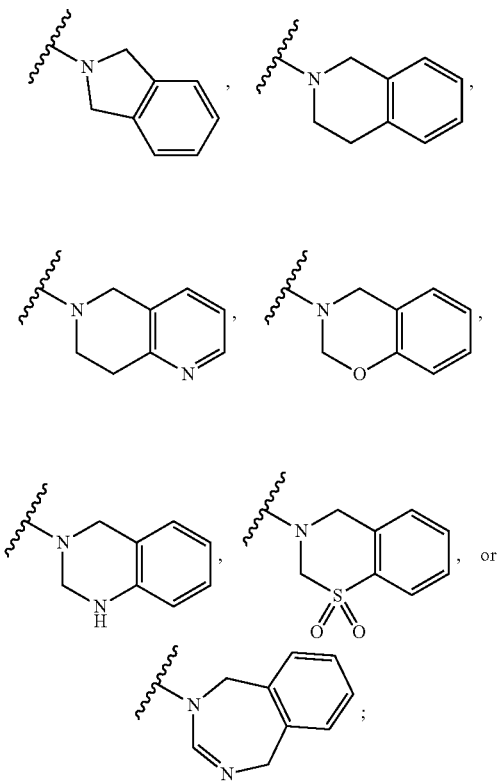

wherein said bicyclic heterocyclyl is substituted with zero to 2 substituents independently selected from: Br, —$CH_3$, —$CF_3$, —$CH_2OH$, —$CH_2NH_2$, —$CH_2N_3$, —$CH_2N(CH_3)$(CH_2CH_2OH), —$CH_2N(CH_3)(CH_2CH_2OCH_3)$, —$CH_2OCH_2CH_2N(CH_3)_2$, —$CH_2OCH_2CH_2OH$, —$CH_2OCH_2CH_2O$(phenyl), —$CH_2OCH_2CH_2CH_2OCH_3$, —$CH_2$(pyrrolidinyl), —$CH_2$(N-methyl piperazinyl), —$CH_2$(N-(2-hydroxyethyl)piperazinyl), —$CH_2$(morpholinyl), —$OCH_3$, —C(O)OH, —$(CH_2)_{0-1}N(CH_3)_2$, —$N(CH_3)$(CH_2CH_2OCH_3)$,

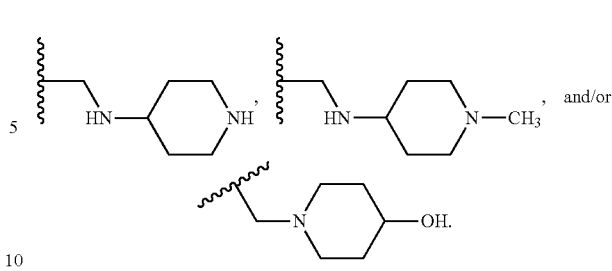

One embodiment provides compounds of Formula (I) or pharmaceutically acceptable salts or prodrugs thereof, wherein $R_{1a}$ is H, Cl, Br, —$CH_3$, butyl, —$CF_3$, —$(CH_2)_{2-3}$OH, —$CH_2CH_2OCH_3$, —$CH_2CH_2OCH_2CH_2OH$, —$CH_2C(O)OH$, —$(CH_2)_3N(CH_3)_2$, —$CH_2C(O)NHCH_3$, —$(CH_2)_{1-3}$(phenyl), —$(CH_2)_{2-3}$(morpholinyl), —$(CH_2)_{2-3}$(N-methyl piperazinyl), —$(CH_2)_2OC(O)NH_2$, —$CH_2C(O)NHS(O)_2$(cyclopropyl), —$(CH_2)_2OC(O)$(N-methyl piperazinyl), or —$(CH_2)_2OC(O)NH(CH_2)_2$(N-methyl piperazinyl). Included in this embodiment are compounds in which $R_{1a}$ is H, —$CH_3$, butyl, —$CF_3$, —$(CH_2)_2OH$, —$CH_2C(O)OH$, —$(CH_2)_2OC(O)NH_2$, —$CH_2C(O)NHS(O)_2$(cyclopropyl), —$(CH_2)_2OC(O)$(N-methyl piperazinyl), or —$(CH_2)_2OC(O)NHCH_2CH_2$(N-methyl piperazinyl). Also included in this embodiment are compounds in which $R_1$ is H, —$CH_3$, —$(CH_2)_{2-3}OH$, —$(CH_2)_{1-3}$(phenyl), —$(CH_2)_{2-3}$(morpholinyl), —$(CH_2)_{2-3}$(N-methyl piperazinyl), —$(CH_2)_2OCH_3$, —$(CH_2)_2O(CH_2)_2$OH, —$(CH_2)_3N(CH_3)_2$, —$CH_2C(O)OH$, or —$CH_2C(O)$$NHCH_3$.

One embodiment provides compounds of Formula (I) or pharmaceutically acceptable salts or prodrugs thereof, wherein $R_{1b}$ is H, —$CH_3$, butyl, —$CF_3$, —$(CH_2)_{2-3}OH$, —$CH_2CH_2OCH_3$, —$CH_2CH_2OCH_2CH_2OH$, —$CH_2C(O)$OH, —$(CH_2)_3N(CH_3)_2$, —$CH_2C(O)NHCH_3$, —$(CH_2)_{1-3}$(phenyl), —$(CH_2)_{2-3}$(morpholinyl), —$(CH_2)_{2-3}$(N-methyl piperazinyl), —$(CH_2)_2OC(O)NH_2$, —$CH_2C(O)NHS(O)_2$(cyclopropyl), —$(CH_2)_2OC(O)$(N-methyl piperazinyl), or —$(CH_2)_2OC(O)NH(CH_2)_2$(N-methyl piperazinyl). Included in this embodiment are compounds in which $R_{1a}$ is H, —$CH_3$, butyl, —$CF_3$, —$(CH_2)_2OH$, —$CH_2C(O)OH$, —$(CH_2)_2OC(O)NH_2$, —$CH_2C(O)NHS(O)_2$(cyclopropyl), —$(CH_2)_2OC(O)$(N-methyl piperazinyl), or —$(CH_2)_2OC(O)NHCH_2CH_2$(N-methyl piperazinyl). Also included in this embodiment are compounds in which $R_1$ is H, —$CH_3$, —$(CH_2)_{2-3}OH$, —$(CH_2)_{1-3}$(phenyl), —$(CH_2)_{2-3}$(morpholinyl), —$(CH_2)_{2-3}$(N-methyl piperazinyl), —$(CH_2)_2OCH_3$, —$(CH_2)_2O(CH_2)_2$OH, —$(CH_2)_3N(CH_3)_2$, —$CH_2C(O)OH$, or —$CH_2C(O)$$NHCH_3$.

One embodiment provides compounds of Formula (I) or pharmaceutically acceptable salts or prodrugs thereof, wherein $R_2$ is H, Cl, Br, $C_{1-3}$ hydroxyalkyl, —$(CH_2)_2C(O)$OH, or —$(CH_2)_3N(CH_3)_2$. Included in this embodiment are compounds in which $R_2$ is H.

One embodiment provides compounds of Formula (I) or pharmaceutically acceptable salts or prodrugs thereof, wherein $R_2$ is phenyl substituted with zero to 1 substituent selected from propyl, —$(CH_2)_{0-2}$OH, —$O(CH_3)_{0-3}CH_3$, —$O(CH_2)_3OH$, —$OCH_2CH(OH)CH_2OH$, —C(O)OH, —$OCH_2CH$=$CH_2$, —$O$(phenyl), —$O$(chlorophenyl), —$C(O)OCH_3$, or phenyl. Included in this embodiment are compounds in which $R_2$ is phenyl substituted with zero to 1 substituent selected from propyl, —OH, —$(CH_2)_2OH$, —$OCH_3$, —$O(CH_2)_2CH_3$, —$O(CH_2)_3OH$, —$OCH_2CH$(OH)$CH_2OH$, —$OCH_2CH$=$CH_2$, —$O$(phenyl), —$O$(chlorophenyl), $C(O)OCH_3$, and phenyl.

One embodiment provides compounds of Formula (I) or pharmaceutically acceptable salts or prodrugs thereof, wherein $R_3$ is —$CH_2OH$, —$C(O)OH$, —$C(O)OCH_2CH_3$, —$C(O)NR_aR_b$, or —$NR_aR_b$. Included in this embodiment are compounds in which $R_3$ is —$N(C_{3-4}\text{alkyl})_2$ or —$C(O)NR_aR_b$, such as, for example, $R_3$ is —$C(O)N(\text{n-butyl})_2$ or —$C(O)N(\text{n-butyl})_2$. Also included in this embodiment are compounds in which $R_3$ is —$CH_2OH$, —$C(O)OH$, or —$C(O)OCH_2CH_3$.

One embodiment provides compounds of Formula (I) or pharmaceutically acceptable salts or prodrugs thereof, wherein $R_a$ is H, $C_{1-5}$ alkyl, or $C_{1-4}$ fluoroalkyl. Included in this embodiment are compounds in which $R_a$ is H, $C_{1-4}$ alkyl, or $C_{3-4}$ fluoroalkyl.

One embodiment provides compounds of Formula (I) or pharmaceutically acceptable salts or prodrugs thereof, wherein $R_b$ is $C_{1-5}$ alkyl, $C_{3-4}$ fluoroalkyl, —$(CH_2)_2C(O)OH$, —$(CH_2)_2C(O)O(\text{butyl})$, —$CH_2(\text{cyclopropyl})$, —$CH_2(\text{naphthalenyl})$, —$(CH_2)_2C(O)NHCH(C_{1-2}\text{ hydroxyalkyl})_2$, —$(CH_2)_2C(O)NHC(CH_2OH)_3$, or —$(CH_2)_2C(O)NHCH_2CH_2(\text{N-methyl piperazinyl})$. Included in this embodiment are compounds in which $R_b$ is $C_{1-4}$ alkyl, $C_{3-4}$ fluoroalkyl, —$(CH_2)_2C(O)OH$, —$(CH_2)_2C(O)O(\text{butyl})$, —$CH_2(\text{naphthalenyl})$, —$(CH_2)_2C(O)NHCH(CH_2OH)_2$, —$(CH_2)_2C(O)NHC(CH_2OH)_3$, or —$(CH_2)_2C(O)NHCH_2CH_2(\text{N-methyl piperazinyl})$. Also included in this embodiment are compounds in which $R_b$ is $C_{2-5}$ alkyl, —$CH_2(\text{cyclopropyl})$, or —$CH_2(\text{dichlorophenyl})$.

One embodiment provides compounds of Formula (I) or pharmaceutically acceptable salts or prodrugs thereof, wherein $R_b$ is —$(CH_2)_{0-2}(\text{phenyl})$ wherein said phenyl is substituted with zero to 2 substituents independently selected from Cl, I, $C_{1-4}$ alkyl, $C_{1-4}$ alkoxy, —$(CH_2)_{0-2}C(O)OH$, —$C(O)OCH_3$, —$CH_2C(O)OCH_2CH_3$, phenyl, chlorophenyl, fluorophenoxy, chlorophenoxy, phenyl acetic acid, and/or —$(CH_2)_2C(O)(\text{piperidinyl carboxylic acid})$. Included in this embodiment are compounds in which $R_b$ is —$(CH_2)_{0-2}(\text{phenyl})$ wherein said phenyl is substituted with zero to 2 substituents independently selected from Cl, I, $C_{1-4}$ alkyl, $C_{1-4}$ alkoxy, —$C(O)OH$, —$(CH_2)_{0-2}C(O)OH$, —$C(O)OCH_3$, —$CH_2C(O)OCH_2CH_3$, phenyl, chlorophenyl, fluorophenoxy, chlorophenoxy, phenyl acetic acid, and/or —$(CH_2)_2C(O)(\text{piperidinyl carboxylic acid})$.

One embodiment provides compounds of Formula (I) or pharmaceutically acceptable salts or prodrugs thereof, wherein $R_b$ is:

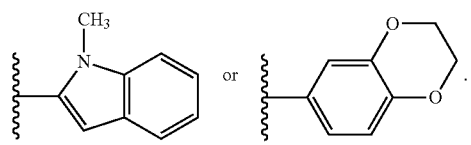 [SMILES: *c1cc2ccccc2n1C ; *c1ccc2c(c1)OCCO2]

One embodiment provides compounds of Formula (I) or pharmaceutically acceptable salts or prodrugs thereof, wherein $R_a$ and $R_b$ together with the nitrogen atom to which they are attached, form a pyrrolidinyl ring substituted with zero to 1 substituent selected from propyl or —$CH_2CH_2(\text{phenyl})$.

One embodiment provides compounds of Formula (I), pharmaceutically acceptable salts or prodrugs thereof, wherein said compound is selected from N,N-Dibutyl-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (1); N,N-dibutyl-4-chloro-1-(4-(5-chloronaphthalen-2-ylsulfonylcarbamoyl)-2-(1,2,3,4-tetrahydroisoquinoline-2-carbonyl)phenyl)-5-methyl-1H-pyrazole-3-carboxamide (2); N,N-dibutyl-4-chloro-1-(4-(6-(dimethylamino)naphthalen-2-ylsulfonylcarbamoyl)-2-(1,2,3,4-tetrahydroisoquinoline-2-carbonyl)phenyl)-5-methyl-1H-pyrazole-3-carboxamide (3); N,N-dibutyl-4-chloro-1-(4-(5-(dimethylamino)naphthalen-1-ylsulfonylcarbamoyl)-2-(1,2,3,4-tetrahydroisoquinoline-2-carbonyl)phenyl)-5-methyl-1H-pyrazole-3-carboxamide (4); N,N-dibutyl-4-chloro-1-(4-(8-chloronaphthalen-2-ylsulfonylcarbamoyl)-2-(1,2,3,4-tetrahydroisoquinoline-2-carbonyl)phenyl)-5-methyl-1H-pyrazole-3-carboxamide (5); N,N-dibutyl-4-chloro-1-(4-(6-chloronaphthalen-2-ylsulfonylcarbamoyl)-2-(1,2,3,4-tetrahydroisoquinoline-2-carbonyl)phenyl)-5-methyl-1H-pyrazole-3-carboxamide (6); N,N-dibutyl-4-chloro-1-(4-(8-iodonaphthalen-2-ylsulfonylcarbamoyl)-2-(1,2,3,4-tetrahydroisoquinoline-2-carbonyl)phenyl)-5-methyl-1H-pyrazole-3-carboxamide (7); N,N-dibutyl-4-chloro-1-(4-(8-cyanonaphthalen-2-ylsulfonylcarbamoyl)-2-(1,2,3,4-tetrahydroisoquinoline-2-carbonyl)phenyl)-5-methyl-1H-pyrazole-3-carboxamide (8); ethyl 7-(N-(4-(4-chloro-3-(dibutylcarbamoyl)-5-methyl-1H-pyrazol-1-yl)-3-(1,2,3,4-tetrahydroisoquinoline-2-carbonyl)benzoyl)sulfamoyl)-1-naphthoate (9); N,N-dibutyl-4-chloro-1-(4-(7-chloronaphthalen-2-ylsulfonylcarbamoyl)-2-(1,2,3,4-tetrahydroisoquinoline-2-carbonyl)phenyl)-5-methyl-1H-pyrazole-3-carboxamide (10); N,N-dibutyl-4-chloro-1-(4-(7-iodonaphthalen-2-ylsulfonylcarbamoyl)-2-(1,2,3,4-tetrahydroisoquinoline-2-carbonyl)phenyl)-5-methyl-1H-pyrazole-3-carboxamide (11); N,N-dibutyl-4-chloro-5-methyl-1-(4-(5-nitronaphthalen-1-ylsulfonylcarbamoyl)-2-(1,2,3,4-tetrahydroisoquinoline-2-carbonyl)phenyl)-1H-pyrazole-3-carboxamide (12); N,N-dibutyl-4-chloro-5-methyl-1-(4-(5-nitronaphthalen-2-ylsulfonylcarbamoyl)-2-(1,2,3,4-tetrahydroisoquinoline-2-carbonyl)phenyl)-1H-pyrazole-3-carboxamide (13); N,N-dibutyl-4-chloro-1-(4-(6-chloronaphthalen-2-ylsulfonylcarbamoyl)-2-(1,2,3,4-tetrahydroisoquinoline-2-carbonyl)phenyl)-5-methyl-1H-pyrazole-3-carboxamide (14); N,N-dibutyl-4-chloro-1-(4-(7-cyanonaphthalen-2-ylsulfonylcarbamoyl)-2-(1,2,3,4-tetrahydroisoquinoline-2-carbonyl)phenyl)-5-methyl-1H-pyrazole-3-carboxamide (15); ethyl 7-(N-(4-(4-chloro-3-(dibutylcarbamoyl)-5-methyl-1H-pyrazol-1-yl)-3-(1,2,3,4-tetrahydroisoquinoline-2-carbonyl)benzoyl)sulfamoyl)-2-naphthoate (16); ethyl 7-(N-(4-(4-chloro-3-(dibutylcarbamoyl)-5-methyl-1H-pyrazol-1-yl)-3-(1,2,3,4-tetrahydroisoquinoline-2-carbonyl)benzoyl)sulfamoyl)-2-naphthoate (17); 1-(4-(7-(benzyloxy)naphthalen-2-ylsulfonylcarbamoyl)-2-(1,2,3,4-tetrahydroisoquinoline-2-carbonyl)phenyl)-N,N-dibutyl-4-chloro-5-methyl-1H-pyrazole-3-carboxamide (18); N,N-dibutyl-4-chloro-1-(4-(8-(3,4-dichlorobenzamido)naphthalen-2-ylsulfonylcarbamoyl)-2-(1,2,3,4-tetrahydroisoquinoline-2-carbonyl)phenyl)-5-methyl-1H-pyrazole-3-carboxamide (19); N,N-dibutyl-4-chloro-5-methyl-1-(4-(7-(4-(methylsulfonyl)benzyloxy)-naphthalen-2-ylsulfonylcarbamoyl)-2-(1,2,3,4-tetrahydroisoquinoline-2-carbonyl)phenyl)-1H-pyrazole-3-carboxamide (20); N,N-dibutyl-4-chloro-1-(4-(8-(3,4-dichlorobenzyloxy)naphthalen-2-ylsulfonylcarbamoyl)-2-(1,2,3,4-tetrahydroisoquinoline-2-carbonyl)phenyl)-5-methyl-1H-pyrazole-3-carboxamide (21); N,N-dibutyl-4-chloro-1-(4-(7-(3,4-dichlorobenzyloxy)naphthalen-2-ylsulfonylcarbamoyl)-2-(1,2,3,4-tetrahydroisoquinoline-2-carbonyl)phenyl)-5-methyl-1H-pyrazole-3-carboxamide (22); N,N-dibutyl-4-chloro-5-methyl-1-(4-(7-((tetrahydrofuran-2-yl)methoxy)naphthalen-2-ylsulfonylcarbamoyl)-2-(1,2,3,4-tetrahydroisoquinoline-2-carbonyl)phenyl)-1H- pyrazole-3-carboxamide (23); N,N-dibutyl-4-chloro-1-(4-(7-isopropoxynaphthalen-2-ylsulfonylcarbamoyl)-2-(1,2,3,4-tetrahydroisoquinoline-2-carbonyl)phenyl)-5-methyl-1H-pyrazole-3-carboxamide (24); N,N-dibutyl-4-chloro-5-methyl-1-(4-(7-(2-phenoxyethoxy)naphthalen-2-ylsulfonylcarbamoyl)-2-(1,2,3,4-tetrahydroisoquinoline-2-carbonyl)phenyl)-1H-pyrazole-3-carboxamide (25); methyl 4-((7-(N-(4-(4-chloro-3-(dibutylcarbamoyl)-5-methyl-1H-pyrazol-1-yl)-3-(1,2,3,4-tetrahydroisoquinoline-2-carbonyl)benzoyl)sulfamoyl)naphthalen-1-yloxy)methyl)benzoate (26); N,N-dibutyl-4-chloro-5-methyl-1-(4-(8-(2-morpholinoethoxy)naphthalen-2-ylsulfonylcarbamoyl)-2-(1,2,3,4-tetrahydroisoquinoline-2-carbonyl)phenyl)-1H-pyrazole-3-carboxamide (27); N,N-dibutyl-4-chloro-1-(4-(7-(2-methoxyethoxy)naphthalen-2-ylsulfonylcarbamoyl)-2-(1,2,3,4-tetrahydroisoquinoline-2-carbonyl)phenyl)-5-methyl-1H-pyrazole-3-carboxamide (28); N,N-dibutyl-4-chloro-1-(4-(7-methoxynaphthalen-2-ylsulfonylcarbamoyl)-2-(1,2,3,4-tetrahydroisoquinoline-2-carbonyl)phenyl)-5-methyl-1H-pyrazole-3-carboxamide (29); N,N-dibutyl-4-chloro-1-(4-(7-(2-ethoxyethoxy)naphthalen-2-ylsulfonylcarbamoyl)-2-(1,2,3,4-tetrahydroisoquinoline-2-carbonyl)phenyl)-5-methyl-1H-pyrazole-3-carboxamide (30); 1-(4-(8-bromo-5-(dimethylamino)naphthalen-2-ylsulfonylcarbamoyl)-2-(1,2,3,4-tetrahydroisoquinoline-2-carbonyl)phenyl)-N,N-dibutyl-4-chloro-5-methyl-1H-pyrazole-3-carboxamide (31); N,N-dibutyl-4-chloro-5-methyl-1-(4-(8-(3-morpholinopropoxy)naphthalen-2-ylsulfonylcarbamoyl)-2-(1,2,3,4-tetrahydroisoquinoline-2-carbonyl)phenyl)-1H-pyrazole-3-carboxamide (32); N,N-dibutyl-4-chloro-5-methyl-1-(4-(7-(2-morpholinoethoxy)naphthalen-2-ylsulfonylcarbamoyl)-2-(1,2,3,4-tetrahydroisoquinoline-2-carbonyl)phenyl)-1H-pyrazole-3-carboxamide (33); N,N-dibutyl-4-chloro-5-methyl-1-(4-(7-(3-morpholinopropoxy)naphthalen-2-ylsulfonylcarbamoyl)-2-(1,2,3,4-tetrahydroisoquinoline-2-carbonyl)phenyl)-1H-pyrazole-3-carboxamide (34); N,N-dibutyl-4-chloro-5-methyl-1-(4-(7-(3-(4-methylpiperazin-1-yl)propoxy)naphthalen-2-ylsulfonylcarbamoyl)-2-(1,2,3,4-tetrahydroisoquinoline-2-carbonyl)phenyl)-1H-pyrazole-3-carboxamide (35); N,N-dibutyl-4-chloro-5-methyl-1-(4-(7-((1-methyl-1H-imidazol-2-yl)methoxy)naphthalen-2-ylsulfonylcarbamoyl)-2-(1,2,3,4-tetrahydroisoquinoline-2-carbonyl)phenyl)-1H-pyrazole-3-carboxamide (36); N,N-dibutyl-4-chloro-1-(4-(7-(1-(dimethylamino)propan-2-yloxy)naphthalen-2-ylsulfonylcarbamoyl)-2-(1,2,3,4-tetrahydroisoquinoline-2-carbonyl)phenyl)-5-methyl-1H-pyrazole-3-carboxamide (37); N,N-dibutyl-4-chloro-5-methyl-1-(4-((7-(2-(1-methylpyrrolidin-2-yl)ethoxy)naphthalene-2-sulfonamido)methyl)-2-(1,2,3,4-tetrahydroisoquinoline-2-carbonyl)phenyl)-1H-pyrazole-3-carboxamide (38); N,N-dibutyl-4-chloro-1-(4-(7-(3-(dimethylamino)propoxy)-naphthalen-2-ylsulfonylcarbamoyl)-2-(1,2,3,4-tetrahydroisoquinoline-2-carbonyl)phenyl)-5-methyl-1H-pyrazole-3-carboxamide (39); N,N-dibutyl-4-chloro-5-methyl-1-(4-(7-(3-(pyrrolidin-1-yl)propoxy)naphthalen-2-ylsulfonylcarbamoyl)-2-(1,2,3,4-tetrahydroisoquinoline-2-carbonyl)phenyl)-1H-pyrazole-3-carboxamide (40); N,N-dibutyl-4-chloro-5-methyl-1-(4-(7-(3-(piperidin-1-yl)propoxy)naphthalen-2-ylsulfonylcarbamoyl)-2-(1,2,3,4-tetrahydroisoquinoline-2-carbonyl)phenyl)-1H-pyrazole-3-carboxamide (41); N,N-Dibutyl-4-chloro-5-methyl-1-(4-(7-(3-(pyridin-4-yl)propoxy)naphthalen-2-ylsulfonylcarbamoyl)-2-(1,2,3,4-tetrahydroisoquinoline-2-carbonyl)phenyl)-1H-pyrazole-3-carboxamide (42); 1-(4-(8-bromo-5-chloronaphthalen-2-ylsulfonylcarbamoyl)-2-(1,2,3,4-tetrahydroisoquinoline-2-carbonyl)phenyl)-N,N-dibutyl-4-chloro-5-methyl-1H-pyrazole-3-carboxamide (43); N,N-dibutyl-4-chloro-1-(4-(5,8-dichloronaphthalen-2-ylsulfonylcarbamoyl)-2-(1,2,3,4-tetrahydroisoquinoline-2-carbonyl)phenyl)-5-methyl-1H-pyrazole-3-carboxamide (44); 7-(N-(4-(4-Chloro-3-(dibutylcarbamoyl)-5-methyl-1H-pyrazol-1-yl)-3-(1,2,3,4-tetrahydroisoquinoline-2-carbonyl)benzoyl)sulfamoyl)-1-naphthoic acid (45); N,N-Dibutyl-4-chloro-5-methyl-1-(4-(7-(4-methylpiperazine-1-carbonyl)naphthalen-2-ylsulfonylcarbamoyl)-2-(1,2,3,4-tetrahydroisoquinoline-2-carbonyl)phenyl)-1H-pyrazole-3-carboxamide (46); N,N-Dibutyl-4-chloro-5-methyl-1-(4-(7-(morpholine-4-carbonyl)naphthalen-2-ylsulfonylcarbamoyl)-2-(1,2,3,4-tetrahydroisoquinoline-2-carbonyl)phenyl)-1H-pyrazole-3-carboxamide (47); N,N-Dibutyl-4-chloro-1-(4-(7-(dimethylcarbamoyl)naphthalen-2-ylsulfonylcarbamoyl)-2-(1,2,3,4-tetrahydroisoquinoline-2-carbonyl)phenyl)-5-methyl-1H-pyrazole-3-carboxamide (48); 4-((7-(N-(4-(4-Chloro-3-(dibutylcarbamoyl)-5-methyl-1H-pyrazol-1-yl)-3-(1,2,3,4-tetrahydroisoquinoline-2-carbonyl)benzoyl)sulfamoyl)naphthalen-1-yloxy)methyl)benzoic acid (49); N,N-Dibutyl-4-chloro-1-(4-(7-(2-hydroxyethoxy)naphthalen-2-ylsulfonylcarbamoyl)-2-(1,2,3,4-tetrahydroisoquinoline-2-carbonyl)phenyl)-5-methyl-1H-pyrazole-3-carboxamide (50); N,N-Dibutyl-4-chloro-1-(4-(7-hydroxynaphthalen-2-ylsulfonylcarbamoyl)-2-(1,2,3,4-tetrahydroisoquinoline-2-carbonyl)phenyl)-5-methyl-1H-pyrazole-3-carboxamide (51); N,N-Dibutyl-4-chloro-1-(4-(indolin-5-ylsulfonylcarbamoyl)-2-(1,2,3,4-tetrahydroisoquinoline-2-carbonyl)phenyl)-5-methyl-1H-pyrazole-3-carboxamide (52); N,N-dibutyl-4-chloro-1-(4-(1-ethylindolin-5-ylsulfonylcarbamoyl)-2-(1,2,3,4-tetrahydroisoquinoline-2-carbonyl)phenyl)-5-methyl-1H-pyrazole-3-carboxamide (53); 1-(4-(1H-indol-5-ylsulfonylcarbamoyl)-2-(1,2,3,4-tetrahydroisoquinoline-2-carbonyl)phenyl)-N,N-dibutyl-4-chloro-5-methyl-1H-pyrazole-3-carboxamide (54); N,N-dibutyl-4-chloro-1-(4-(1-(cyclohexanecarbonyl)indolin-5-ylsulfonylcarbamoyl)-2-(1,2,3,4-tetrahydroisoquinoline-2-carbonyl)phenyl)-5-methyl-1H-pyrazole-3-carboxamide (55); N,N-dibutyl-4-chloro-1-(4-(1-ethyl-1H-indol-5-ylsulfonylcarbamoyl)-2-(1,2,3,4-tetrahydroisoquinoline-2-carbonyl)phenyl)-5-methyl-1H-pyrazole-3-carboxamide (56); N,N-dibutyl-4-chloro-1-(4-(1-(cyclohexylmethyl)indolin-5-ylsulfonylcarbamoyl)-2-(1,2,3,4-tetrahydroisoquinoline-2-carbonyl)phenyl)-5-methyl-1H-pyrazole-3-carboxamide (57); N,N-dibutyl-4-chloro-1-(4-(1-(3,4-dichlorobenzoyl)indolin-5-ylsulfonylcarbamoyl)-2-(1,2,3,4-tetrahydroisoquinoline-2-carbonyl)phenyl)-5-methyl-1H-pyrazole-3-carboxamide (58); N,N-dibutyl-4-chloro-1-(4-(1-(3,4-dichlorobenzyl)indolin-5-ylsulfonylcarbamoyl)-2-(1,2,3,4-tetrahydroisoquinoline-2-carbonyl)phenyl)-(5-methyl-1H-pyrazole-3-carboxamide (59); 1-(4-(1-acetylindolin-6-ylsulfonylcarbamoyl)-2-(1,2,3,4-tetrahydroisoquinoline-2-carbonyl)phenyl)-N,N-dibutyl-4-chloro-5-methyl-1H-pyrazole-3-carboxamide (60); 1-(4-(1-benzylindolin-5-ylsulfonylcarbamoyl)-2-(1,2,3,4-tetrahydroisoquinoline-2-carbonyl)phenyl)-N,N-dibutyl-4-chloro-5-methyl-1H-pyrazole-3-carboxamide (61); N,N-dibutyl-4-chloro-1-(4-(1-(3,4-difluorobenzyl)indolin-5-ylsulfonylcarbamoyl)-2-(1,2,3,4-tetrahydroisoquinoline-2-carbonyl)phenyl)-5-methyl-1H-pyrazole-3-carboxamide (62); N,N-dibutyl-4-chloro-1-(4-(1-ethylindolin-6-ylsulfonylcarbamoyl)-2-(1,2,3,4-tetrahydroisoquinoline-2-carbonyl)phenyl)-5-methyl-1H-pyrazole-3-carboxamide (63); N,N-dibutyl-4-chloro-1-(4-(2-(3,4-dichlorophenyl)acetyl)indolin-5-ylsulfonylcarbamoyl)-2-(1,2,3,4-tetrahydroisoquinoline-2-carbonyl)phenyl)-5-methyl-1H-pyrazole-3-carboxamide (64); N,N-dibutyl-4-chloro-1-(4-(1-(3,4-dichlorophenethyl) indolin-5-ylsulfonylcarbamoyl)-2-(1,2,3,4-tetrahydroisoquinoline-2-carbonyl)phenyl)-5-methyl-1H-pyrazole-3-carboxamide (65); N,N-dibutyl-4-chloro-5-methyl-1-(4-(1-(2-(phenylthio)acetyl)indolin-5-ylsulfonylcarbamoyl)-2-(1,2,3,4-tetrahydroisoquinoline-2-carbonyl)phenyl)-1H-pyrazole-3-carboxamide (66); N,N-dibutyl-4-chloro-5-methyl-1-(4-(1-(2-(phenylthio)ethyl)indolin-5-ylsulfonylcarbamoyl)-2-(1,2,3,4-tetrahydroisoquinoline-2-carbonyl)phenyl)-1H-pyrazole-3-carboxamide (67); N,N-dibutyl-4-chloro-1-(4-(1-(3,4-dichlorobenzyl)-1H-indol-5-ylsulfonylcarbamoyl)-2-(1,2,3,4-tetrahydroisoquinoline-2-carbonyl)phenyl)-5-methyl-1H-pyrazole-3-carboxamide (68); N,N-dibutyl-4-chloro-1-(4-(1-(((6-chloropyridin-2-yl)methyl)indolin-5-ylsulfonylcarbamoyl)-2-(1,2,3,4-tetrahydroisoquinoline-2-carbonyl)phenyl)-5-methyl-1H-pyrazole-3-carboxamide (69); N,N-dibutyl-4-chloro-5-methyl-1-(4-(1-((1-methyl-1H-indol-6-yl)methyl)indolin-5-ylsulfonylcarbamoyl)-2-(1,2,3,4-tetrahydroisoquinoline-2-carbonyl)phenyl)-1H-pyrazole-3-carboxamide (70); 1-(4-(5-bromo-1-ethylindolin-6-ylsulfonylcarbamoyl)-2-(1,2,3,4-tetrahydroisoquinoline-2-carbonyl)phenyl)-N,N-dibutyl-4-chloro-5-methyl-1H-pyrazole-3-carboxamide (71); 1-(4-(5-bromo-1-(3,4-dichlorobenzyl)indolin-6-ylsulfonylcarbamoyl)-2-(1,2,3,4-tetrahydroisoquinoline-2-carbonyl)phenyl)-N,N-dibutyl-4-chloro-5-methyl-1H-pyrazole-3-carboxamide (72); methyl 5-(N-(4-(4-chloro-3-(dibutylcarbamoyl)-5-methyl-1H-pyrazol-1-yl)-3-(1,2,3,4-tetrahydroisoquinoline-2-carbonyl)benzoyl)sulfamoyl)-1-(3,4-dichlorobenzyl)indoline-2-carboxylate (73); N,N-dibutyl-4-chloro-5-methyl-1-(4-(1-(morpholine-4-carbonyl)indolin-5-ylsulfonylcarbamoyl)-2-(1,2,3,4-tetrahydroisoquinoline-2-carbonyl)phenyl)-1H-pyrazole-3-carboxamide (74); N,N-dibutyl-4-chloro-5-methyl-1-(4-(1-(2-morpholinoacetyl)indolin-5-ylsulfonylcarbamoyl)-2-(1,2,3,4-tetrahydroisoquinoline-2-carbonyl)phenyl)-1H-pyrazole-3-carboxamide (75); 1-(4-(7-bromo-1-ethylindolin-5-ylsulfonylcarbamoyl)-2-(1,2,3,4-tetrahydroisoquinoline-2-carbonyl)phenyl)-N,N-dibutyl-4-chloro-5-methyl-1H-pyrazole-3-carboxamide (76); N,N-dibutyl-4-chloro-5-methyl-1-(4-(1-(2-morpholinoethyl)indolin-5-ylsulfonylcarbamoyl)-2-(1,2,3,4-tetrahydroisoquinoline-2-carbonyl)phenyl)-1H-pyrazole-3-carboxamide (77); N,N-dibutyl-4-chloro-5-methyl-1-(4-(1-((2-(2-morpholinoethoxy)pyridin-3-yl)methyl)indolin-5-ylsulfonylcarbamoyl)-2-(1,2,3,4-tetrahydroisoquinoline-2-carbonyl)phenyl)-1H-pyrazole-3-carboxamide (78); 1-(4-(3-bromo-1H-indol-5-ylsulfonylcarbamoyl)-2-(1,2,3,4-tetrahydroisoquinoline-2-carbonyl)phenyl)-N,N-dibutyl-4-chloro-5-methyl-1H-pyrazole-3-carboxamide (79); 1-(4-(3-bromo-1-ethyl-1H-indol-5-ylsulfonylcarbamoyl)-2-(1,2,3,4-tetrahydroisoquinoline-2-carbonyl)phenyl)-N,N-dibutyl-4-chloro-5-methyl-1H-pyrazole-3-carboxamide (80); N,N-dibutyl-4-chloro-5-methyl-1-(4-(1-(3-morpholinopropanoyl)indolin-5-ylsulfonylcarbamoyl)-2-(1,2,3,4-tetrahydroisoquinoline-2-carbonyl)phenyl)-1H-pyrazole-3-carboxamide (81); N,N-dibutyl-4-chloro-5-methyl-1-(4-(1-(3-morpholinopropyl)-1H-indol-5-ylsulfonylcarbamoyl)-2-(1,2,3,4-tetrahydroisoquinoline-2-carbonyl)phenyl)-1H-pyrazole-3-carboxamide (82); N,N-dibutyl-4-chloro-1-(4-(3-chloro-1-ethyl-1H-indol-5-ylsulfonylcarbamoyl)-2-(1,2,3,4-tetrahydroisoquinoline-2-carbonyl)phenyl)-5-methyl-1H-pyrazole-3-carboxamide (83); N,N-dibutyl-4-chloro-1-(4-(1-ethyl-3-iodo-1H-indol-5-ylsulfonylcarbamoyl)-2-(1,2,3,4-tetrahydroisoquinoline-2-carbonyl)phenyl)-5-methyl-1H-pyrazole-3-carboxamide (84); N,N-dibutyl-4-chloro-1-(4-(3,7-dibromo-1-ethyl-1H-indol-5-ylsulfonylcarbamoyl)-2-(1,2,3,4-tetrahydroisoquinoline-2-carbonyl)phenyl)-5-methyl-1H-pyrazole-3-carboxamide (85); N,N-Dibutyl-4-chloro-1-(4-(indolin-6-ylsulfonylcarbamoyl)-2-(1,2,3,4-tetrahydroisoquinoline-2-carbonyl)phenyl)-5-methyl-1H-pyrazole-3-carboxamide (86); (E)-1-(4-(5-(But-1-enyl)-1-ethylindolin-6-ylsulfonylcarbamoyl)-2-(1,2,3,4-tetrahydroisoquinoline-2-carbonyl)phenyl)-N,N-dibutyl-4-chloro-5-methyl-1H-pyrazole-3-carboxamide (87); N,N-Dibutyl-4-chloro-1-(4-(1-ethyl-5-morpholinoindolin-6-ylsulfonylcarbamoyl)-2-(1,2,3,4-tetrahydroisoquinoline-2-carbonyl)phenyl)-5-methyl-1H-pyrazole-3-carboxamide (88); (E)-N,N-Dibutyl-4-chloro-1-(4-(1-ethyl-5-(prop-1-enyl)indolin-6-ylsulfonylcarbamoyl)-2-(1,2,3,4-tetrahydroisoquinoline-2-carbonyl)phenyl)-5-methyl-1H-pyrazole-3-carboxamide (89); N,N-Dibutyl-4-chloro-1-(4-(1-(3,4-dichlorobenzyl)indolin-6-ylsulfonylcarbamoyl)-2-(1,2,3,4-tetrahydroisoquinoline-2-carbonyl)phenyl)-5-methyl-1H-pyrazole-3-carboxamide (90); N,N-Dibutyl-4-chloro-1-(2-((S)-3-(hydroxymethyl)-1,2,3,4-tetrahydroisoquinoline-2-carbonyl)-4-(naphthalen-2-ylsulfonylcarbamoyl)phenyl)-5-methyl-1H-pyrazole-3-carboxamide (91); 1-(2-((S)-3-(Aminomethyl)-1,2,3,4-tetrahydroisoquinoline-2-carbonyl)-4-(naphthalen-2-ylsulfonylcarbamoyl)phenyl)-N,N-dibutyl-4-chloro-5-methyl-1H-pyrazole-3-carboxamide (92); (3R)-2-(2-(4-Chloro-3-(dibutylcarbamoyl)-5-methyl-1H-pyrazol-1-yl)-5-(naphthalen-2-ylsulfonylcarbamoyl)benzoyl)-1,2,3,4-tetrahydroisoquinoline-3-carboxylic acid (93); (3S)-2-(2-(4-Chloro-3-(dibutylcarbamoyl)-5-methyl-1H-pyrazol-1-yl)-5-(naphthalen-2-ylsulfonylcarbamoyl)benzoyl)-1,2,3,4-tetrahydroisoquinoline-3-carboxylic acid (94); N,N-Dibutyl-4-chloro-1-(2-((R)-3-(hydroxymethyl)-1,2,3,4-tetrahydroisoquinoline-2-carbonyl)-4-(naphthalen-2-ylsulfonylcarbamoyl)phenyl)-5-methyl-1H-pyrazole-3-carboxamide (95); N,N-Dibutyl-4-chloro-1-(2-(3,4-dihydro-2H-benzo[e][1,3]oxazine-3-carbonyl)-4-(naphthalen-2-ylsulfonylcarbamoyl)phenyl)-5-methyl-1H-pyrazole-3-carboxamide (96); N,N-Dibutyl-4-chloro-5-methyl-1-(2-(1-methyl-1,2,3,4-tetrahydroisoquinoline-2-carbonyl)-4-(naphthalen-2-ylsulfonylcarbamoyl)phenyl)-1H-pyrazole-3-carboxamide (97); N,N-Dibutyl-4-chloro-1-(2-(4,4-dimethyl-1,2,3,4-tetrahydroisoquinoline-2-carbonyl)-4-(naphthalen-2-ylsulfonylcarbamoyl)phenyl)-5-methyl-1H-pyrazole-3-carboxamide (98); 1-(2-(7-Bromo-1,2,3,4-tetrahydroisoquinoline-2-carbonyl)-4-(naphthalen-2-ylsulfonylcarbamoyl)phenyl)-N,N-dibutyl-4-chloro-5-methyl-1H-pyrazole-3-carboxamide (99); 2-(2-(4-Chloro-3-(dibutylcarbamoyl)-5-methyl-1H-pyrazol-1-yl)-5-(naphthalen-2-ylsulfonylcarbamoyl)benzoyl)-1,2,3,4-tetrahydroisoquinoline-7-carboxylic acid (100); N,N-Dibutyl-4-chloro-5-methyl-1-(4-(naphthalen-2-ylsulfonylcarbamoyl)-2-(7-(trifluoromethyl)-1,2,3,4-tetrahydroisoquinoline-2-carbonyl)phenyl)-1H-pyrazole-3-carboxamide (101); 1-(2-(3-Bromo-5,6,7,8-tetrahydro-1,6-naphthyridine-6-carbonyl)-4-(naphthalen-2-ylsulfonylcarbamoyl)phenyl)-N,N-dibutyl-4-chloro-5-methyl-1H-pyrazole-3-carboxamide (102); N,N-Dibutyl-4-chloro-5-methyl-1-(4-(naphthalen-2-ylsulfonylcarbamoyl)-2-(1,2,3,4-tetrahydroquinazoline-3-carbonyl)phenyl)-1H-pyrazole-3-carboxamide (103); N,N-Dibutyl-4-chloro-1-(2-(1,1-dioxido-3,4-dihydro-2H-benzo[e][1,3]thiazine-3-carbonyl)-4-(naphthalen-2-ylsulfonylcarbamoyl)phenyl)-5-methyl-1H-pyrazole-3-carboxamide (104); N,N-Dibutyl-4-chloro-1-(2-((S)-3-((3-methoxypropoxy)methyl)-1,2,3,4-tetrahydroisoquinoline-2-carbonyl)-4-(naphthalen-2-ylsulfonylcarbamoyl)phenyl)-5-methyl-1H-pyrazole-3-carboxamide (105); N,N-Dibutyl-4-chloro-5-methyl-1-(2-((S)-3-(((1-methylpiperidin-4-ylamino)methyl)-1,2,3,4- tetrahydroisoquinoline-2-carbonyl)-4-(naphthalen-2-ylsulfonylcarbamoyl)phenyl)-1H-pyrazole-3-carboxamide (106); N,N-Dibutyl-4-chloro-5-methyl-1-(4-(naphthalen-2-ylsulfonylcarbamoyl)-2-((S)-3-((piperidin-4-ylamino)methyl)-1,2,3,4-tetrahydroisoquinoline-2-carbonyl)phenyl)-1H-pyrazole-3-carboxamide (107); N,N-dibutyl-4-chloro-1-(2-((S)-3-((dimethylamino)methyl)-1,2,3,4-tetrahydroisoquinoline-2-carbonyl)-4-(naphthalen-2-ylsulfonylcarbamoyl)phenyl)-5-methyl-1H-pyrazole-3-carboxamide (108); N,N-dibutyl-4-chloro-5-methyl-1-(2-((S)-3-(morpholinomethyl)-1,2,3,4-tetrahydroisoquinoline-2-carbonyl)-4-(naphthalen-2-ylsulfonylcarbamoyl)phenyl)-1H-pyrazole-3-carboxamide (109); N,N-dibutyl-4-chloro-1-(2-((S)-3-((4-hydroxypiperidin-1-yl)methyl)-1,2,3,4-tetrahydroisoquinoline-2-carbonyl)-4-(naphthalen-2-ylsulfonylcarbamoyl)phenyl)-5-methyl-1H-pyrazole-3-carboxamide (110); N,N-dibutyl-4-chloro-5-methyl-1-(4-(naphthalen-2-ylsulfonylcarbamoyl)-2-((S)-3-(pyrrolidin-1-ylmethyl)-1,2,3,4-tetrahydroisoquinoline-2-carbonyl)phenyl)-1H-pyrazole-3-carboxamide (111); N,N-dibutyl-4-chloro-5-methyl-1-(2-((S)-3-((4-methylpiperazin-1-yl)methyl)-1,2,3,4-tetrahydroisoquinoline-2-carbonyl)-4-(naphthalen-2-ylsulfonylcarbamoyl)phenyl)-1H-pyrazole-3-carboxamide (112); N,N-dibutyl-4-chloro-1-(2-((S)-3-(((2-methoxyethyl)(methyl)amino)-methyl)-1,2,3,4-tetrahydroisoquinoline-2-carbonyl)-4-(naphthalen-2-ylsulfonylcarbamoyl)phenyl)-5-methyl-1H-pyrazole-3-carboxamide (113); N,N-dibutyl-4-chloro-1-(2-((S)-3-(((2-hydroxyethyl)(methyl)amino)-methyl)-1,2,3,4-tetrahydroisoquinoline-2-carbonyl)-4-(naphthalen-2-ylsulfonylcarbamoyl)phenyl)-5-methyl-1H-pyrazole-3-carboxamide (114); N,N-dibutyl-4-chloro-1-(2-((S)-3-((4-(2-hydroxyethyl)piperazin-1-yl)methyl)-1,2,3,4-tetrahydroisoquinoline-2-carbonyl)-4-(naphthalen-2-ylsulfonylcarbamoyl)phenyl)-5-methyl-1H-pyrazole-3-carboxamide (115); N,N-dibutyl-4-chloro-1-(2-((S)-3-((2-(dimethylamino)ethoxy)methyl)-1,2,3,4-tetrahydroisoquinoline-2-carbonyl)-4-(naphthalen-2-ylsulfonylcarbamoyl)phenyl)-5-methyl-1H-pyrazole-3-carboxamide (116); 1-(2-((S)-3-((2-(benzyloxy)ethoxy)methyl)-1,2,3,4-tetrahydroisoquinoline-2-carbonyl)-4-(naphthalen-2-ylsulfonylcarbamoyl)phenyl)-N,N-dibutyl-4-chloro-5-methyl-1H-pyrazole-3-carboxamide (117); N,N-dibutyl-4-chloro-5-methyl-1-(2-(3-((4-methylpiperazin-1-yl)methyl)-1,2,3,4-tetrahydroisoquinoline-2-carbonyl)-4-(naphthalen-2-ylsulfonylcarbamoyl)phenyl)-1H-pyrazole-3-carboxamide (118); N,N-Dibutyl-4-chloro-1-(2-((S)-3-((2-hydroxyethoxy)methyl)-1,2,3,4-tetrahydroisoquinoline-2-carbonyl)-4-(naphthalen-2-ylsulfonylcarbamoyl)phenyl)-S-methyl-1H-pyrazole-3-carboxamide (119); N,N-Dibutyl-4-chloro-1-(2-(3-(dimethylamino)-2,5-dihydro-1H-benzo[e][1,3]diazepine-2-carbonyl)-4-(naphthalen-2-ylsulfonylcarbamoyl)phenyl)-5-methyl-1H-pyrazole-3-carboxamide (120); (Z)—N,N-Dibutyl-4-chloro-1-(2-(3-((2-methoxyethyl)(methyl)amino)-2,5-dihydro-1H-benzo[e][1,3]diazepine-2-carbonyl)-4-(naphthalen-2-ylsulfonylcarbamoyl)phenyl)-5-methyl-1H-pyrazole-3-carboxamide (121); 3-(4-(N-Butyl-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamido)phenyl)propanoic acid (122); N-Butyl-4-chloro-N-(4-iodophenyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (123); 1-(3-(4-(N-Butyl-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamido)phenyl)propanoyl)piperidine-4-carboxylic acid (124); 4-Chloro-N-(3,4-dichlorobenzyl)-N,5-dimethyl-1-(4-(naphthalen-2-ylsulfonylcarbamoyl)-2-(1,2,3,4-tetrahydroisoquinoline-2-carbonyl)phenyl)-1H-pyrazole-3-carboxamide (125); N-butyl-4-chloro-N-(3,4-dichlorobenzyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (126); N-butyl-4-chloro-N-(3,4-dichlorophenethyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (127); N-butyl-4-chloro-5-methyl-1-(4-(naphthalen-2-ylsulfonylcarbamoyl)-2-(1,2,3,4-tetrahydroisoquinoline-2-carbonyl)phenyl)-N-(4,4,4-trifluorobutyl)-1H-pyrazole-3-carboxamide (128); 4-chloro-5-methyl-1-(4-(naphthalen-2-ylsulfonylcarbamoyl)-2-(1,2,3,4-tetrahydroisoquinoline-2-carbonyl)phenyl)-N,N-bis(4,4,4-trifluorobutyl)-1H-pyrazole-3-carboxamide (129); 4-chloro-5-methyl-1-(4-(naphthalen-2-ylsulfonylcarbamoyl)-2-(1,2,3,4-tetrahydroisoquinoline-2-carbonyl)phenyl)-N,N-bis(3,3,3-trifluoropropyl)-1H-pyrazole-3-carboxamide (130); N-butyl-4-chloro-N-(3-isopropoxybenzyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (131); N-butyl-4-chloro-N-(3-(4-chlorophenoxy)benzyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (132); N-(4-butoxybenzyl)-N-butyl-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (133); N-butyl-4-chloro-N-(3,4-dichlorophenyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (134); N-butyl-4-chloro-N-(3-chlorobenzyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (135); N-butyl-4-chloro-N-(4-chlorobenzyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (136); N-butyl-4-chloro-N-(4-(4-fluorophenoxy)phenyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (137); N-butyl-4-chloro-N-(4-(4-chlorophenoxy)phenyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (138); N-butyl-4-chloro-5-methyl-N-(1-methyl-1H-indol-2-yl)-1-(4-(naphthalen-2-ylsulfonylcarbamoyl)-2-(1,2,3,4-tetrahydroisoquinoline-2-carbonyl)phenyl)-1H-pyrazole-3-carboxamide (139); N-butyl-4-chloro-N-(3,4-dimethoxyphenyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (140); N-butyl-4-chloro-N-(4-isopropoxyphenyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (141); N-butyl-4-chloro-N-(3-chloro-4-methylphenyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (142); N-(biphenyl-4-yl)-N-butyl-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (143); N-butyl-4-chloro-N-(4-methoxyphenyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (144); N-butyl-4-chloro-N-(3-methoxyphenyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (145); N-butyl-N-(3-tert-butylphenyl)-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (146); N-(biphenyl-3-yl)-N-butyl-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (147); N-butyl-N-(4-tert-butylphenyl)-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (148); N-butyl-4-chloro-N-(2,3-dihydrobenzo[b][1,4]dioxin-6-yl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (149); N-butyl-4-chloro-N-(3-isopropoxyphenyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (150); N-butyl-4-chloro-5-methyl-N-(naphthalen-2-ylmethyl)-1-(4-(naphthalen-2-ylsulfonylcarbamoyl)-2-(1,2,3,4-tetrahydroisoquinoline-2-carbonyl)phenyl)-1H-pyrazole-3-carboxamide (151); N-butyl-4-chloro-N-(3'-chlorobiphenyl-3-yl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (152); N-butyl-4-chloro-N-(4'-chlorobiphenyl-3-yl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (153); methyl 4-(N-butyl-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamido)benzoate (154); 4-(N-butyl-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamido)benzyl propionate (155); N-Butyl-4-chloro-5-methyl-1-(4-(naphthalen-2-ylsulfonylcarbamoyl)-2-(1,2,3,4-tetrahydroisoquinoline-2-carbonyl)phenyl)-N-phenyl-1H-pyrazole-3-carboxamide (156); N-Benzyl-N-butyl-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (157); N-Butyl-4-chloro-5-methyl-N-(3-(2-(4-methylpiperazin-1-yl)ethylamino)-3-oxopropyl)-1-(4-(naphthalen-2-ylsulfonylcarbamoyl)-2-(1,2,3,4-tetrahydroisoquinoline-2-carbonyl)phenyl)-1H-pyrazole-3-carboxamide (158); N-Butyl-4-chloro-N-(3-(1,3-dihydroxypropan-2-ylamino)-3-oxopropyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (159); N-Butyl-4-chloro-N-(3-(1,3-dihydroxy-2-(hydroxymethyl)propan-2-ylamino)-3-oxopropyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (160); 4-(N-Butyl-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamido)benzoic acid (161); 2-(4-(N-Butyl-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamido)phenyl)acetic acid (162); 4-Bromo-N,N-dibutyl-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (163); N,N-Dibutyl-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (164); N,N-Dibutyl-4-(hydroxymethyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (165); 3-(3-(Dibutylcarbamoyl)-5-methyl-1-(4-(naphthalen-2-ylsulfonylcarbamoyl)-2-(1,2,3,4-tetrahydroisoquinoline-2-carbonyl)phenyl)-1H-pyrazol-4-yl)propanoic acid (166); N,N-Dibutyl-4-(3-(dimethylamino)propyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (167); N,N-Dibutyl-1-(4-(naphthalen-2-ylsulfonylcarbamoyl)-2-(1,2,3,4-tetrahydroisoquinoline-2-carbonyl)phenyl)-1H-pyrazole-3-carboxamide (168); N,N-Dibutyl-4-chloro-1-(4-(naphthalen-2-ylsulfonylcarbamoyl)-2-(1,2,3,4-tetrahydroisoquinoline-2-carbonyl)phenyl)-1H-pyrazole-3-carboxamide (169); N,N-Dibutyl-4-chloro-5-(2-hydroxyethyl)-1-(4-(naphthalen-2-ylsulfonylcarbamoyl)-2-(1,2,3,4-tetrahydroisoquinoline-2-carbonyl)phenyl)-1H-pyrazole-3-carboxamide (170); 2-(4-Chloro-3-(dibutylcarbamoyl)-1-(4-(naphthalen-2-ylsulfonylcarbamoyl)-2-(1,2,3,4-tetrahydroisoquinoline-2-carbonyl)phenyl)-1H-pyrazol-5-yl)acetic acid (171); N,N-Dibutyl-4-chloro-5-(2-(cyclopropanesulfonamido)-2-oxoethyl)-1-(4-(naphthalen-2-ylsulfonylcarbamoyl)-2-(1,2,3,4-tetrahydroisoquinoline-2-carbonyl)phenyl)-1H-pyrazole-3-carboxamide (172); 2-(4-Chloro-3-(dibutylcarbamoyl)-1-(4-(naphthalen-2-ylsulfonylcarbamoyl)-2-(1,2,3,4-tetrahydroisoquinoline-2-carbonyl)phenyl)-1H-pyrazol-5-yl)ethyl carbamate (173); 2-(4-Chloro-3-(dibutylcarbamoyl)-1-(4-(naphthalen-2-ylsulfonylcarbamoyl)-2-(1,2,3,4-tetrahydroisoquinoline-2-carbonyl)phenyl)-1H-pyrazol-5-yl)ethyl 4-methylpiperazine-1-carboxylate (174); 2-(4-Chloro-3-(dibutylcarbamoyl)-1-(4-(naphthalen-2-ylsulfonylcarbamoyl)-2-(1,2,3,4-tetrahydroisoquinoline-2-carbonyl)phenyl)-1H-pyrazol-5-yl)ethyl 2-(4-methylpiperazin-1-yl)ethylcarbamate (175); tert-Butyl 3-(N-butyl-4-chloro-1-(4-(7-iodonaphthalen-2-ylsulfonylcarbamoyl)-2-(1,2,3,4-tetrahydroisoquinoline-2-carbonyl)phenyl)-5-methyl-1H-pyrazole-3-carboxamido)propanoate (176); N,N-Dibutyl-4-chloro-1-(4-(8-chloronaphthalen-2-ylsulfonylcarbamoyl)-2-((S)-3-(hydroxymethyl)-1,2,3,4-tetrahydroisoquinoline-2-carbonyl)phenyl)-5-methyl-1H-pyrazole-3-carboxamide (177); N-Butyl-4-chloro-N-(3,4-dichlorobenzyl)-1-(4-(8-(ethylsulfonyl)naphthalen-2-ylsulfonylcarbamoyl)-2-(1,2,3,4-tetrahydroisoquinoline-2-carbonyl)phenyl)-5-methyl-1H-pyrazole-3-carboxamide (178); N-Butyl-4-chloro-N-(3,4-dichlorobenzyl)-1-(4-(7-iodonaphthalen-2-ylsulfonylcarbamoyl)-2-(1,2,3,4-tetrahydroisoquinoline-2-carbonyl)phenyl)-5-methyl-1H-pyrazole-3-carboxamide (179); N-Butyl-4-chloro-N-(3,4-dichlorobenzyl)-5-methyl-1-(4-(7-(4-methylpiperazine-1-carbonyl)naphthalen-2-ylsulfonylcarbamoyl)-2-(1,2,3,4-tetrahydroisoquinoline-2-carbonyl)phenyl)-1H-pyrazole-3-carboxamide (180); N-Butyl-4-chloro-1-(4-(8-chloronaphthalen-2-ylsulfonylcarbamoyl)-2-((S)-3-(hydroxymethyl)-1,2,3,4-tetrahydroisoquinoline-2-carbonyl)phenyl)-N-(3,4-dichlorobenzyl)-5-methyl-1H-pyrazole-3-carboxamide (181); N-Butyl-4-chloro-1-(4-(8-chloronaphthalen-2-ylsulfonylcarbamoyl)-2-((S)-3-(2-hydroxyethyl)(methyl)amino)methyl)-1,2,3,4-tetrahydroisoquinoline-2-carbonyl)phenyl)-N-(3,4-dichlorobenzyl)-5-methyl-1H-pyrazole-3-carboxamide (182); N,N-Dibutyl-4-chloro-1-(2-((S)-3-(hydroxymethyl)-1,2,3,4-tetrahydroisoquinoline-2-carbonyl)-4-(8-(2-morpholinoethoxy)naphthalen-2-ylsulfonylcarbamoyl)phenyl)-5-methyl-1H-pyrazole-3-carboxamide (183); N,N-Dibutyl-4-chloro-1-(2-((S)-3-((dimethylamino)methyl)-1,2,3,4- tetrahydroisoquinoline-2-carbonyl)-4-(8-(2-morpholinoethoxy)naphthalen-2-ylsulfonylcarbamoyl) phenyl)-5-methyl-1H-pyrazole-3-carboxamide (184); N,N-Dibutyl-4-chloro-5-methyl-1-(4-(8-(2-morpholinoethoxy) naphthalen-2-ylsulfonylcarbamoyl)-2-((S)-3-(morpholinomethyl)-1,2,3,4-tetrahydroisoquinoline-2-carbonyl)phenyl)-1H-pyrazole-3-carboxamide (185); N-Butyl-4-chloro-N-(3,4-dichlorobenzyl)-5-methyl-1-(4-(8-(2-morpholinoethoxy)naphthalen-2-ylsulfonylcarbamoyl)-2-((S)-3-(morpholinomethyl)-1,2,3,4-tetrahydroisoquinoline-2-carbonyl)phenyl)-1H-pyrazole-3-carboxamide (186); N-Butyl-4-chloro-N-(3,4-dichlorobenzyl)-1-(2-((S)-3-(hydroxymethyl)-1,2,3,4-tetrahydroisoquinoline-2-carbonyl)-4-(8-(2-morpholinoethoxy)naphthalen-2-ylsulfonylcarbamoyl)phenyl)-5-methyl-1H-pyrazole-3-carboxamide (187); 1-(2-((S)-3-(Aminomethyl)-1,2,3,4-tetrahydroisoquinoline-2-carbonyl)-4-(8-(2-morpholinoethoxy)naphthalen-2-ylsulfonylcarbamoyl)phenyl)-N-butyl-4-chloro-N-(3,4-dichlorobenzyl)-5-methyl-1H-pyrazole-3-carboxamide (188); N,N-Dibutyl-4-chloro-1-(4-(1-(3,4-dichlorobenzyl) indolin-5-ylsulfonylcarbamoyl)-2-((S)-3-(hydroxymethyl)-1,2,3,4-tetrahydroisoquinoline-2-carbonyl)phenyl)-5-methyl-1H-pyrazole-3-carboxamide (189); N,N-Dibutyl-4-chloro-1-(4-(1-ethylindolin-5-ylsulfonylcarbamoyl)-2-((S)-3-(hydroxymethyl)-1,2,3,4-tetrahydroisoquinoline-2-carbonyl)phenyl)-5-methyl-1H-pyrazole-3-carboxamide (190); 4-(4-Chloro-3-(dibutylamino)-5-methyl-1H-pyrazol-1-yl)-N-(naphthalen-2-ylsulfonyl)-3-(1,2,3,4-tetrahydroisoquinoline-2-carbonyl)benzamide (191); 4-(4-Chloro-3-(dipropylamino)-5-methyl-1H-pyrazol-1-yl)-3-((S)-3-(hydroxymethyl)-1,2,3,4-tetrahydroisoquinoline-2-carbonyl)-N-(naphthalen-2-ylsulfonyl)benzamide (192); 4-(4-Chloro-3-(dipropylamino)-5-methyl-1H-pyrazol-1-yl)-N-(8-chloronaphthalen-2-ylsulfonyl)-3-((S)-3-(hydroxymethyl)-1,2,3,4-tetrahydroisoquinoline-2-carbonyl)benzamide (193); 3-((S)-3-(Aminomethyl)-1,2,3,4-tetrahydroisoquinoline-2-carbonyl)-4-(4-chloro-3-(dipropylamino)-5-methyl-1H-pyrazol-1-yl)-N-(8-chloronaphthalen-2-ylsulfonyl)benzamide (194); 4-(4-Chloro-3-(dipropylamino)-5-(trifluoromethyl)-1H-pyrazol-1-yl)-N-(8-chloronaphthalen-2-ylsulfonyl)-3-((S)-3-(hydroxymethyl)-1,2,3,4-tetrahydroisoquinoline-2-carbonyl)benzamide (195); 4-(4-Chloro-3-(dipropylamino)-5-(trifluoromethyl)-1H-pyrazol-1-yl)-N-(8-chloronaphthalen-2-ylsulfonyl)-3-(1,2,3,4-tetrahydroisoquinoline-2-carbonyl)benzamide (196); 3-(N-butyl-4-chloro-1-(4-(1-(3,4-dichlorobenzyl)indolin-5-ylsulfonylcarbamoyl)-2-(1,2,3,4-tetrahydroisoquinoline-2-carbonyl)phenyl)-5-methyl-1H-pyrazole-3-carboxamido) propanoic acid (197); N,N-dibutyl-4-chloro-1-(4-(1-(3,4-dichlorobenzyl)-1H-indol-5-ylsulfonylcarbamoyl)-2-((S)-3-(hydroxymethyl)-1,2,3,4-tetrahydroisoquinoline-2-carbonyl)phenyl)-5-methyl-1H-pyrazole-3-carboxamide (198); 1-(4-(3-bromo-1-(3,4-dichlorobenzyl)-1H-indol-5-ylsulfonylcarbamoyl)-2-((S)-3-(hydroxymethyl)-1,2,3,4-tetrahydroisoquinoline-2-carbonyl)phenyl)-N,N-dibutyl-4-chloro-5-methyl-1H-pyrazole-3-carboxamide (199); N-butyl-4-chloro-1-(4-(1-(3,4-dichlorobenzyl)indolin-5-ylsulfonylcarbamoyl)-2-(1,2,3,4-tetrahydroisoquinoline-2-carbonyl)phenyl)-5-methyl-N-(3-(2-(4-methylpiperazin-1-yl)ethylamino)-3-oxopropyl)-1H-pyrazole-3-carboxamide (200); 1-(2-((S)-3-(aminomethyl)-1,2,3,4-tetrahydroisoquinoline-2-carbonyl)-4-(3-bromo-1-(3,4-dichlorobenzyl)-1H-indol-5-ylsulfonylcarbamoyl)phenyl)-N,N-dibutyl-4-chloro-5-methyl-1H-pyrazole-3-carboxamide (201); N,N-dibutyl-4-chloro-1-(4-(8-chloronaphthalen-2-ylsulfonylcarbamoyl)-2-((S)-3-((3-methoxypropoxy) methyl)-1,2,3,4-tetrahydroisoquinoline-2-carbonyl)phenyl)-5-methyl-1H-pyrazole-3-carboxamide (202); 1-(2-((S)-3-(aminomethyl)-1,2,3,4-tetrahydroisoquinoline-2-carbonyl)-4-(8-chloronaphthalen-2-ylsulfonylcarbamoyl)phenyl)-N,N-dibutyl-4-chloro-5-methyl-1H-pyrazole-3-carboxamide (203); (Z)—N-(8-bromo-5-chloronaphthalen-2-ylsulfonyl)-4-(4-chloro-3-(dipropylamino)-5-methyl-1H-pyrazol-1-yl)-3-(3-(dimethylamino)-2,5-dihydro-1H-benzo[e][1,3]diazepine-2-carbonyl)benzamide (204); 1-(4-(7-bromo-1-ethylindolin-5-ylsulfonylcarbamoyl)-2-((S)-3-(hydroxymethyl)-1,2,3,4-tetrahydroisoquinoline-2-carbonyl)phenyl)-N,N-dibutyl-4-chloro-5-methyl-1H-pyrazole-3-carboxamide (205); 4-chloro-1-(4-(1-ethylindolin-5-ylsulfonylcarbamoyl)-2-((S)-3-(hydroxymethyl)-1,2,3,4-tetrahydroisoquinoline-2-carbonyl)phenyl)-5-methyl-N,N-dipropyl-1H-pyrazole-3-carboxamide (206); N-(8-bromo-5-chloronaphthalen-2-ylsulfonyl)-4-(4-chloro-3-(dipropylamino)-5-methyl-1H-pyrazol-1-yl)-3-((S)-3-(hydroxymethyl)-1,2,3,4-tetrahydroisoquinoline-2-carbonyl)benzamide (207); 1-(4-(7-bromo-1-ethyl-1H-indol-5-ylsulfonylcarbamoyl)-2-((S)-3-(hydroxymethyl)-1,2,3,4-tetrahydroisoquinoline-2-carbonyl)phenyl)-N,N-dibutyl-4-chloro-5-methyl-1H-pyrazole-3-carboxamide (208); 1-(4-(7-bromo-1-ethylindolin-5-ylsulfonylcarbamoyl)-2-((S)-3-(hydroxymethyl)-1,2,3,4-tetrahydroisoquinoline-2-carbonyl)phenyl)-4-chloro-5-methyl-N,N-dipropyl-1H-pyrazole-3-carboxamide (209); N,N-dibutyl-4-chloro-1-(4-(3,7-dibromo-1-ethyl-1H-indol-5-ylsulfonylcarbamoyl)-2-((S)-3-(hydroxymethyl)-1,2,3,4-tetrahydroisoquinoline-2-carbonyl)phenyl)-5-methyl-1H-pyrazole-3-carboxamide (210); 1-(2-(6-bromo-1,2,3,4-tetrahydroisoquinoline-2-carbonyl)-4-(1-(3,4-dichlorobenzyl)indolin-5-ylsulfonylcarbamoyl)phenyl)-N,N-dibutyl-4-chloro-5-methyl-1H-pyrazole-3-carboxamide (211); N,N-dibutyl-4-chloro-1-(4-(1-(3,4-dichlorobenzyl)indolin-5-ylsulfonylcarbamoyl)-2-(6,7-dimethoxy-1,2,3,4-tetrahydroisoquinoline-2-carbonyl) phenyl)-5-methyl-1H-pyrazole-3-carboxamide (212); 2-(4'-((N-butyl-4-chloro-1-(4-(1-(3,4-dichlorobenzyl)indolin-5-ylsulfonylcarbamoyl)-2-(1,2,3,4-tetrahydroisoquinoline-2-carbonyl)phenyl)-5-methyl-1H-pyrazole-3-carboxamido) methyl)biphenyl-4-yl)acetic acid (213); 2-(4'-((4-chloro-1-(4-(1-(3,4-dichlorobenzyl)indolin-5-ylsulfonylcarbamoyl)-2-(1,2,3,4-tetrahydroisoquinoline-2-carbonyl)phenyl)-5-methyl-1H-pyrazole-3-carboxamido)methyl)biphenyl-4-yl) acetic acid (214); 4-(3-(dibutylcarbamoyl)-1-(4-(1-(3,4-dichlorobenzyl)indolin-5-ylsulfonylcarbamoyl)-2-(1,2,3,4-tetrahydroisoquinoline-2-carbonyl)phenyl)-5-methyl-1H-pyrazol-4-yl)benzoic acid (215); 4-chloro-1-(4-(1-(3,4-dichlorobenzyl)indolin-5-ylsulfonylcarbamoyl)-2-(1,2,3,4-tetrahydroisoquinoline-2-carbonyl)phenyl)-5-methyl-N,N-dipropyl-1H-pyrazole-3-carboxamide (216); 1-(4-(8-bromo-5-chloronaphthalen-2-ylsulfonylcarbamoyl)-2-(1,2,3,4-tetrahydroisoquinoline-2-carbonyl)phenyl)-N-butyl-4-chloro-N-(4'-chlorobiphenyl-3-yl)-5-methyl-1H-pyrazole-3-carboxamide (217); 1-(4-(8-bromo-5-chloronaphthalen-2-ylsulfonylcarbamoyl)-2-(1,2,3,4-tetrahydroisoquinoline-2-carbonyl)phenyl)-N-butyl-4-chloro-N-(3'-chlorobiphenyl-3-yl)-5-methyl-1H-pyrazole-3-carboxamide (218); N-butyl-4-chloro-N-((4'-chlorobiphenyl-4-yl)methyl)-1-(4-(1-(3,4-dichlorobenzyl)indolin-5-ylsulfonylcarbamoyl)-2-(1,2,3,4-tetrahydroisoquinoline-2-carbonyl)phenyl)-5-methyl-1H-pyrazole-3-carboxamide (219); N-butyl-4-chloro-N-(4-(4-chlorophenoxy)phenyl)-1-(4-(1-(3,4-dichlorobenzyl) indolin-5-ylsulfonylcarbamoyl)-2-(1,2,3,4-tetrahydroisoquinoline-2-carbonyl)phenyl)-5-methyl-1H-pyrazole-3-carboxamide (220); N-butyl-4-chloro-N-(4'- chlorobiphenyl-3-yl)-1-(4-(5,8-dichloronaphthalen-2-ylsulfonylcarbamoyl)-2-(1,2,3,4-tetrahydroisoquinoline-2-carbonyl)phenyl)-5-methyl-1H-pyrazole-3-carboxamide (221); N-butyl-4-chloro-N-(3'-chlorobiphenyl-3-yl)-1-(4-(5,8-dichloronaphthalen-2-ylsulfonylcarbamoyl)-2-(1,2,3,4-tetrahydroisoquinoline-2-carbonyl)phenyl)-5-methyl-1H-pyrazole-3-carboxamide (222); 1-(4-(((1-((2-Aminoethyl)thio)isoquinolin-6-yl)sulfonyl)carbamoyl)-2-(1,2,3,4-tetrahydroisoquinoline-2-carbonyl)phenyl)-N,N-dibutyl-4-chloro-5-methyl-1H-pyrazole-3-carboxamide (330); and 2-((6-(N-(4-(4-Chloro-3-(dibutylcarbamoyl)-5-methyl-1H-pyrazol-1-yl)-3-(1,2,3,4-tetrahydroisoquinoline-2-carbonyl)benzoyl)sulfamoyl)isoquinolin-1-yl)thio)acetic acid (331).

One embodiment provides compounds of Formula (I), pharmaceutically acceptable salts or prodrugs thereof, wherein said compound is selected from Ethyl 5-butyl-4-(4-(naphthalen-2-ylsulfonylcarbamoyl)-2-(1,2,3,4-tetrahydroisoquinoline-2-carbonyl)phenyl)-1-phenyl-1H-pyrazole-3-carboxylate (223); Ethyl 5-methyl-4-(4-(naphthalen-2-ylsulfonylcarbamoyl)-2-(1,2,3,4-tetrahydroisoquinoline-2-carbonyl)phenyl)-1-phenyl-1H-pyrazole-3-carboxylate (224); Ethyl 5-butyl-1-(4-methoxyphenyl)-4-(4-(naphthalen-2-ylsulfonylcarbamoyl)-2-(1,2,3,4-tetrahydroisoquinoline-2-carbonyl)phenyl)-1H-pyrazole-3-carboxylate (225); Ethyl 5-butyl-1-(4-isopropylphenyl)-4-(4-(naphthalen-2-ylsulfonylcarbamoyl)-2-(1,2,3,4-tetrahydroisoquinoline-2-carbonyl)phenyl)-1H-pyrazole-3-carboxylate (226); Ethyl 5-butyl-4-(4-(naphthalen-2-ylsulfonylcarbamoyl)-2-(1,2,3,4-tetrahydroisoquinoline-2-carbonyl)phenyl)-1-(3-phenoxyphenyl)-1H-pyrazole-3-carboxylate (227); Ethyl 5-butyl-4-(4-(naphthalen-2-ylsulfonylcarbamoyl)-2-(1,2,3,4-tetrahydroisoquinoline-2-carbonyl)phenyl)-1-(4-phenoxyphenyl)-1H-pyrazole-3-carboxylate (228); Ethyl 5-butyl-1-(4-(4-chlorophenoxy)phenyl)-4-(4-(naphthalen-2-ylsulfonylcarbamoyl)-2-(1,2,3,4-tetrahydroisoquinoline-2-carbonyl)phenyl)-1H-pyrazole-3-carboxylate (229); Ethyl 5-butyl-1-(4-(3-chlorophenoxy)phenyl)-4-(4-(naphthalen-2-ylsulfonylcarbamoyl)-2-(1,2,3,4-tetrahydroisoquinoline-2-carbonyl)phenyl)-1H-pyrazole-3-carboxylate (230); Ethyl 1-(4-butoxyphenyl)-5-butyl-4-(4-(naphthalen-2-ylsulfonylcarbamoyl)-2-(1,2,3,4-tetrahydroisoquinoline-2-carbonyl)phenyl)-1H-pyrazole-3-carboxylate (231); Ethyl 5-butyl-1-(4-(2-hydroxyethyl)phenyl)-4-(4-(naphthalen-2-ylsulfonylcarbamoyl)-2-(1,2,3,4-tetrahydroisoquinoline-2-carbonyl)phenyl)-1H-pyrazole-3-carboxylate (232); Ethyl 1-(4-(allyloxy)phenyl)-5-butyl-4-(4-(naphthalen-2-ylsulfonylcarbamoyl)-2-(1,2,3,4-tetrahydroisoquinoline-2-carbonyl)phenyl)-1H-pyrazole-3-carboxylate (233); Ethyl 1-(biphenyl-4-yl)-5-butyl-4-(4-(naphthalen-2-ylsulfonylcarbamoyl)-2-(1,2,3,4-tetrahydroisoquinoline-2-carbonyl)phenyl)-1H-pyrazole-3-carboxylate (234); Ethyl 5-butyl-1-(3-(methoxycarbonyl)phenyl)-4-(4-(naphthalen-2-ylsulfonylcarbamoyl)-2-(1,2,3,4-tetrahydroisoquinoline-2-carbonyl)phenyl)-1H-pyrazole-3-carboxylate (235); 4-(5-Butyl-3-(hydroxymethyl)-1-phenyl-1H-pyrazol-4-yl)-N-(naphthalen-2-ylsulfonyl)-3-(1,2,3,4-tetrahydroisoquinoline-2-carbonyl)benzamide (236); 5-Butyl-4-(4-(naphthalen-2-ylsulfonylcarbamoyl)-2-(1,2,3,4-tetrahydroisoquinoline-2-carbonyl)phenyl)-1-phenyl-1H-pyrazole-3-carboxylic acid (237); 4-(5-Butyl-3-(hydroxymethyl)-1-(3-(hydroxymethyl)phenyl)-1H-pyrazol-4-yl)-N-(naphthalen-2-ylsulfonyl)-3-(1,2,3,4-tetrahydroisoquinoline-2-carbonyl)benzamide (238); Ethyl 5-butyl-1-(4-(2-(1,2,3,4-tetrahydroisoquinoline-2-carbonyl)-4-(2-(trimethylsilyl)ethylsulfonylcarbamoyl)phenyl)-1H-pyrazole-3-carboxylate (239); 4-(5-Butyl-3-(hydroxymethyl)-1-phenyl-1H-pyrazol-4-yl)-3-(1,2,3,4-tetrahydroisoquinoline-2-carbonyl)-N-(2-(trimethylsilyl)ethylsulfonyl)benzamide (240); 4-(5-butyl-3-(hydroxymethyl)-1-(4-phenoxyphenyl)-1H-pyrazol-4-yl)-N-(naphthalen-2-ylsulfonyl)-3-(1,2,3,4-tetrahydroisoquinoline-2-carbonyl)benzamide (241); 4-(5-butyl-1-(4-(4-chlorophenoxy)phenyl)-3-(hydroxymethyl)-1H-pyrazol-4-yl)-N-(naphthalen-2-ylsulfonyl)-3-(1,2,3,4-tetrahydroisoquinoline-2-carbonyl)benzamide (242); 4-(S-butyl-1-(4-(3-chlorophenoxy)phenyl)-3-(hydroxymethyl)-1H-pyrazol-4-yl)-N-(naphthalen-2-ylsulfonyl)-3-(1,2,3,4-tetrahydroisoquinoline-2-carbonyl)benzamide (243); 4-(S-butyl-1-(4-butoxyphenyl)-3-(hydroxymethyl)-1H-pyrazol-4-yl)-N-(naphthalen-2-ylsulfonyl)-3-(1,2,3,4-tetrahydroisoquinoline-2-carbonyl)benzamide (244); 4-(5-butyl-1-(4-(2-hydroxyethyl)phenyl)-3-(hydroxymethyl)-1H-pyrazol-4-yl)-N-(naphthalen-2-ylsulfonyl)-3-(1,2,3,4-tetrahydroisoquinoline-2-carbonyl)benzamide (245); 4-(1-(4-(allyloxy)phenyl)-5-butyl-3-(hydroxymethyl)-1H-pyrazol-4-yl)-N-(naphthalen-2-ylsulfonyl)-3-(1,2,3,4-tetrahydroisoquinoline-2-carbonyl)benzamide (246); 4-(1-(biphenyl-4-yl)-5-butyl-3-(hydroxymethyl)-1H-pyrazol-4-yl)-N-(naphthalen-2-ylsulfonyl)-3-(1,2,3,4-tetrahydroisoquinoline-2-carbonyl)benzamide (247); ethyl 5-butyl-4-(4-(8-chloronaphthalen-2-ylsulfonylcarbamoyl)-2-(1,2,3,4-tetrahydroisoquinoline-2-carbonyl)phenyl)-1-(4-(3-chlorophenoxy)phenyl)-1H-pyrazole-3-carboxylate (248); ethyl 5-butyl-1-(4-(3-chlorophenoxy)phenyl)-4-(4-(ethylsulfonylcarbamoyl)-2-(1,2,3,4-tetrahydroisoquinoline-2-carbonyl)phenyl)-1H-pyrazole-3-carboxylate (249); ethyl 5-butyl-1-(4-(3-chlorophenoxy)phenyl)-4-(4-(pentylsulfonylcarbamoyl)-2-(1,2,3,4-tetrahydroisoquinoline-2-carbonyl)phenyl)-1H-pyrazole-3-carboxylate (250); ethyl 4-(4-(8-bromo-5-chloronaphthalen-2-ylsulfonylcarbamoyl)-2-(1,2,3,4-tetrahydroisoquinoline-2-carbonyl)phenyl)-5-butyl-1-(4-(3-chlorophenoxy)phenyl)-1H-pyrazole-3-carboxylate (251); 4-(5-butyl-1-(4-(3-chlorophenoxy)phenyl)-3-(hydroxymethyl)-1H-pyrazol-4-yl)-N-(8-chloronaphthalen-2-ylsulfonyl)-3-(1,2,3,4-tetrahydroisoquinoline-2-carbonyl)benzamide (252); 4-(5-butyl-1-(4-(3-chlorophenoxy)phenyl)-3-(hydroxymethyl)-1H-pyrazol-4-yl)-N-(ethylsulfonyl)-3-(1,2,3,4-tetrahydroisoquinoline-2-carbonyl)benzamide (253); 4-(5-butyl-1-(4-(3-chlorophenoxy)phenyl)-3-(hydroxymethyl)-1H-pyrazol-4-yl)-N-(pentylsulfonyl)-3-(1,2,3,4-tetrahydroisoquinoline-2-carbonyl)benzamide (254); N-(8-bromo-5-chloronaphthalen-2-ylsulfonyl)-4-(5-butyl-1-(4-(3-chlorophenoxy)phenyl)-3-(hydroxymethyl)-1H-pyrazol-4-yl)-3-(1,2,3,4-tetrahydroisoquinoline-2-carbonyl)benzamide (255); 4-(5-Butyl-3-(hydroxymethyl)-1-(4-hydroxyphenyl)-1H-pyrazol-4-yl)-N-(naphthalen-2-ylsulfonyl)-3-(1,2,3,4-tetrahydroisoquinoline-2-carbonyl)benzamide (256); 4-(5-Butyl-3-(hydroxymethyl)-1-(4-(3-hydroxypropoxy)phenyl)-1H-pyrazol-4-yl)-N-(naphthalen-2-ylsulfonyl)-3-(1,2,3,4-tetrahydroisoquinoline-2-carbonyl)benzamide (257); (±)-4-(5-Butyl-1-(4-(2,3-dihydroxypropoxy)phenyl)-3-(hydroxymethyl)-1H-pyrazol-4-yl)-N-(naphthalen-2-ylsulfonyl)-3-(1,2,3,4-tetrahydroisoquinoline-2-carbonyl)benzamide (258); Ethyl 5-butyl-4-(2-((S)-3-(hydroxymethyl)-1,2,3,4-tetrahydroisoquinoline-2-carbonyl)-4-(naphthalen-2-ylsulfonylcarbamoyl)phenyl)-1-phenyl-1H-pyrazole-3-carboxylate (259); 4-(5-Butyl-3-(hydroxymethyl)-1-phenyl-1H-pyrazol-4-yl)-3-((S)-3-(hydroxymethyl)-1,2,3,4-tetrahydroisoquinoline-2-carbonyl)-N-(naphthalen-2-ylsulfonyl)benzamide (260); Ethyl 4-(2-((S)-3-(azidomethyl)-1,2,3,4-tetrahydroisoquinoline-2-carbonyl)-4-(naphthalen-2-ylsulfonylcarbamoyl)phenyl)-5-butyl-1-phenyl-1H-pyrazole-3-carboxylate (261);

Ethyl 4-(2-((S)-3-(aminomethyl)-1,2,3,4-tetrahydroisoquinoline-2-carbonyl)-4-(naphthalen-2-ylsulfonylcarbamoyl)phenyl)-5-butyl-1-phenyl-1H-pyrazole-3-carboxylate (262); and 3-((S)-3-(Aminomethyl)-1,2,3,4-tetrahydroisoquinoline-2-carbonyl)-4-(5-butyl-3-(hydroxymethyl)-1-phenyl-1H-pyrazol-4-yl)-N-(naphthalen-2-ylsulfonyl)benzamide (263).

One embodiment provides compounds of Formula (I), pharmaceutically acceptable salts or prodrugs thereof, wherein said compound is selected from N,N-Dibutyl-1-methyl-2-(4-(naphthalen-2-ylsulfonylcarbamoyl)-2-(1,2,3,4-tetrahydroisoquinoline-2-carbonyl)phenyl)-1H-imidazole-4-carboxamide (264); N,N-Dibutyl-1-(2-(methylamino)-2-oxoethyl)-2-(4-(naphthalen-2-ylsulfonylcarbamoyl)-2-(1,2,3,4-tetrahydroisoquinoline-2-carbonyl)phenyl)-1H-imidazole-4-carboxamide (265); N,N-Dibutyl-1-(3-hydroxypropyl)-2-(4-(naphthalen-2-ylsulfonylcarbamoyl)-2-(1,2,3,4-tetrahydroisoquinoline-2-carbonyl)phenyl)-1H-imidazole-4-carboxamide (266); N,N-Dibutyl-1-(3-(dimethylamino)propyl)-2-(4-(naphthalen-2-ylsulfonylcarbamoyl)-2-(1,2,3,4-tetrahydroisoquinoline-2-carbonyl)phenyl)-1H-imidazole-4-carboxamide (267); N,N-Dibutyl-2-(4-(naphthalen-2-ylsulfonylcarbamoyl)-2-(1,2,3,4-tetrahydroisoquinoline-2-carbonyl)phenyl)-1-((2-(trimethylsilyl)ethoxy)methyl)-1H-imidazole-4-carboxamide (268); 2-(4-(Dibutylcarbamoyl)-2-(4-(naphthalen-1-ylsulfonylcarbamoyl)-2-(1,2,3,4-tetrahydroisoquinoline-2-carbonyl)phenyl)-1H-imidazol-1-yl)acetic acid (269); N,N-Dibutyl-2-(4-(8-iodonaphthalen-2-ylsulfonylcarbamoyl)-2-(1,2,3,4-tetrahydroisoquinoline-2-carbonyl)phenyl)-1-methyl-1H-imidazole-4-carboxamide (270); N,N-Dibutyl-2-(4-(8-chloronaphthalen-2-ylsulfonylcarbamoyl)-2-((S)-3-(hydroxymethyl)-1,2,3,4-tetrahydroisoquinoline-2-carbonyl)phenyl)-1-phenethyl-1H-imidazole-4-carboxamide (271); N,N-Dibutyl-2-(4-(8-chloronaphthalen-2-ylsulfonylcarbamoyl)-2-((S)-3-(hydroxymethyl)-1,2,3,4-tetrahydroisoquinoline-2-carbonyl)phenyl)-1-(3-phenylpropyl)-1H-imidazole-4-carboxamide (272); 1-Benzyl-N,N-dibutyl-2-(4-(8-chloronaphthalen-2-ylsulfonylcarbamoyl)-2-((S)-3-(hydroxymethyl)-1,2,3,4-tetrahydroisoquinoline-2-carbonyl)phenyl)-1H-imidazole-4-carboxamide (273); N,N-Dibutyl-1-(2-hydroxyethyl)-2-(2-((S)-3-(hydroxymethyl)-1,2,3,4-tetrahydroisoquinoline-2-carbonyl)-4-(naphthalen-2-ylsulfonylcarbamoyl)phenyl)-1H-imidazole-4-carboxamide (274); N,N-Dibutyl-2-(2-((S)-3-(hydroxymethyl)-1,2,3,4-tetrahydroisoquinoline-2-carbonyl)-4-(naphthalen-2-ylsulfonylcarbamoyl)phenyl)-1-(2-methoxyethyl)-1H-imidazole-4-carboxamide (275); N,N-Dibutyl-1-(2-(2-hydroxyethoxy)ethyl)-2-(2-((S)-3-(hydroxymethyl)-1,2,3,4-tetrahydroisoquinoline-2-carbonyl)-4-(naphthalen-2-ylsulfonylcarbamoyl)phenyl)-1H-imidazole-4-carboxamide (276); N,N-Dibutyl-2-(2-((S)-3-(hydroxymethyl)-1,2,3,4-tetrahydroisoquinoline-2-carbonyl)-4-(naphthalen-2-ylsulfonylcarbamoyl)phenyl)-1-(2-morpholinoethyl)-1H-imidazole-4-carboxamide (277); N,N-Dibutyl-2-(2-((S)-3-(hydroxymethyl)-1,2,3,4-tetrahydroisoquinoline-2-carbonyl)-4-(naphthalen-2-ylsulfonylcarbamoyl)phenyl)-1-(3-morpholinopropyl)-1H-imidazole-4-carboxamide (278); N,N-Dibutyl-2-(2-((S)-3-(hydroxymethyl)-1,2,3,4-tetrahydroisoquinoline-2-carbonyl)-4-(naphthalen-2-ylsulfonylcarbamoyl)phenyl)-1-(3-(4-methylpiperazin-1-yl)propyl)-1H-imidazole-4-carboxamide (279); N,N-Dibutyl-2-(2-((S)-3-(hydroxymethyl)-1,2,3,4-tetrahydroisoquinoline-2-carbonyl)-4-(naphthalen-2-ylsulfonylcarbamoyl)phenyl)-1-(2-(4-methylpiperazin-1-yl)ethyl)-1H-imidazole-4-carboxamide (280); 2-(2-((S)-3-(Aminomethyl)-1,2,3,4-tetrahydroisoquinoline-2-carbonyl)-4-(naphthalen-2-ylsulfonylcarbamoyl)phenyl)-N,N-dibutyl-1-methyl-1H-imidazole-4-carboxamide (281); 2-(2-((S)-3-(Aminomethyl)-1,2,3,4-tetrahydroisoquinoline-2-carbonyl)-4-(8-iodonaphthalen-2-ylsulfonylcarbamoyl)phenyl)-N,N-dibutyl-1-methyl-1H-imidazole-4-carboxamide (282); and N,N-Dibutyl-2-(4-(8-chloronaphthalen-2-ylsulfonylcarbamoyl)-2-((S)-3-(hydroxymethyl)-1,2,3,4-tetrahydroisoquinoline-2-carbonyl)phenyl)-1-methyl-1H-imidazole-4-carboxamide (283).

One embodiment provides compounds of Formula (I), pharmaceutically acceptable salts or prodrugs thereof, wherein said compound is selected from N,N-Dibutyl-5-(4-(8-iodonaphthalen-2-ylsulfonylcarbamoyl)-2-(1,2,3,4-tetrahydroisoquinoline-2-carbonyl)phenyl)-1-methyl-1H-imidazole-4-carboxamide (284); and N,N-Dibutyl-5-(4-(8-chloronaphthalen-2-ylsulfonylcarbamoyl)-2-(1,2,3,4-tetrahydroisoquinoline-2-carbonyl)phenyl)-1-methyl-1H-imidazole-4-carboxamide (285).

One embodiment provides compounds of Formula (I), pharmaceutically acceptable salts or prodrugs thereof, wherein said compound is selected from N,N-Dibutyl-6-(4-(naphthalen-2-ylsulfonylcarbamoyl)-2-(1,2,3,4-tetrahydroisoquinoline-2-carbonyl)phenyl)picolinamide (286); 4-(6-(Dibutylamino)pyridin-2-yl)-N-(naphthalen-2-ylsulfonyl)-3-(1,2,3,4-tetrahydroisoquinoline-2-carbonyl)benzamide (287); 4-(3-Bromo-6-(dibutylamino)pyridin-2-yl)-N-(7-chloronaphthalen-2-ylsulfonyl)-3-(1,2,3,4-tetrahydroisoquinoline-2-carbonyl)benzamide (288); 4-(3-Bromo-6-(dibutylamino)pyridin-2-yl)-N-(8-chloronaphthalen-2-ylsulfonyl)-3-(1,2,3,4-tetrahydroisoquinoline-2-carbonyl)benzamide (289); and 4-(3-Bromo-6-(dibutylamino)pyridin-2-yl)-N-(1-(3,4-dichlorobenzyl)indolin-5-ylsulfonyl)-3-(1,2,3,4-tetrahydroisoquinoline-2-carbonyl)benzamide (290).

One embodiment provides compounds of Formula (I), pharmaceutically acceptable salts or prodrugs thereof, wherein said compound is selected from 4-(2-(Dibutylamino)pyrimidin-4-yl)-N-(naphthalen-2-ylsulfonyl)-3-(1,2,3,4-tetrahydroisoquinoline-2-carbonyl)benzamide (291); N-(8-chloronaphthalen-2-ylsulfonyl)-4-(2-(dibutylamino)pyrimidin-4-yl)-3-(1,2,3,4-tetrahydroisoquinoline-2-carbonyl)benzamide (292); 4-(2-(dibutylamino)pyrimidin-4-yl)-N-(7-iodonaphthalen-2-ylsulfonyl)-3-(1,2,3,4-tetrahydroisoquinoline-2-carbonyl)benzamide (293); 4-(2-(dibutylamino)pyrimidin-4-yl)-N-(1-ethyl-1H-indol-5-ylsulfonyl)-3-(1,2,3,4-tetrahydroisoquinoline-2-carbonyl)benzamide (294); 4-(2-(dibutylamino)pyrimidin-4-yl)-N-(1-(3,4-dichlorobenzyl)-1H-indol-5-ylsulfonyl)-3-(1,2,3,4-tetrahydroisoquinoline-2-carbonyl)benzamide (295); 4-(2-(dipentylamino)pyrimidin-4-yl)-N-(naphthalen-2-ylsulfonyl)-3-(1,2,3,4-tetrahydroisoquinoline-2-carbonyl)benzamide (296); N-(naphthalen-2-ylsulfonyl)-4-(2-(3-propylpyrrolidin-1-yl)pyrimidin-4-yl)-3-(1,2,3,4-tetrahydroisoquinoline-2-carbonyl)benzamide (297); 4-(2-(butyl(3,4-dichlorobenzyl)amino)pyrimidin-4-yl)-N-(naphthalen-2-ylsulfonyl)-3-(1,2,3,4-tetrahydroisoquinoline-2-carbonyl)benzamide (298); 4-(2-(dipropylamino)pyrimidin-4-yl)-N-(naphthalen-2-ylsulfonyl)-3-(1,2,3,4-tetrahydroisoquinoline-2-carbonyl)benzamide (299); 4-(2-((cyclopropylmethyl)(propyl)amino)pyrimidin-4-yl)-N-(naphthalen-2-ylsulfonyl)-3-(1,2,3,4-tetrahydroisoquinoline-2-carbonyl)benzamide (300); 4-(2-(diethylamino)pyrimidin-4-yl)-N-(naphthalen-2-ylsulfonyl)-3-(1,2,3,4-tetrahydroisoquinoline-2-carbonyl)benzamide (301); N-(naphthalen-2-ylsulfonyl)-4-(2-(3-phenethylpyrrolidin-1-yl)pyrimidin-4-yl)-3-(1,2,3,4- tetrahydroisoquinoline-2-carbonyl)benzamide (302); (S)-4-(2-(Dibutylamino)pyrimidin-4-yl)-3-(3-(hydroxymethyl)-1,2,3,4-tetrahydroisoquinoline-2-carbonyl)-N-(naphthalen-2-ylsulfonyl)benzamide (303); (S)-3-(3-(Aminomethyl)-1,2,3,4-tetrahydroisoquinoline-2-carbonyl)-4-(2-(dibutylamino)pyrimidin-4-yl)-N-(naphthalen-2-ylsulfonyl)benzamide (304); 4-(2-(dibutylamino)pyrimidin-4-yl)-3-(isoindoline-2-carbonyl)-N-(naphthalen-2-ylsulfonyl)benzamide (305); 4-(2-(dibutylamino)pyrimidin-4-yl)-N-(naphthalen-2-ylsulfonyl)-3-(7-(trifluoromethyl)-1,2,3,4-tetrahydroisoquinoline-2-carbonyl)benzamide (306); 4-(2-(dibutylamino)pyrimidin-4-yl)-N3,N3-dimethyl-N1-(naphthalen-2-ylsulfonyl) isophthalamide (307); (S)—N-(8-Chloronaphthalen-2-ylsulfonyl)-4-(2-(dibutylamino)pyrimidin-4-yl)-3-(3-(hydroxymethyl)-1,2,3,4-tetrahydroisoquinoline-2-carbonyl)benzamide (308); (S)-4-(2-(Dibutylamino)pyrimidin-4-yl)-3-(3-(hydroxymethyl)-1,2,3,4-tetrahydroisoquinoline-2-carbonyl)-N-(7-iodonaphthalen-2-ylsulfonyl)benzamide (309); (S)-4-(2-(Dibutylamino)pyrimidin-4-yl)-N-(1-ethylindolin-5-ylsulfonyl)-3-(3-(hydroxymethyl)-1,2,3,4-tetrahydroisoquinoline-2-carbonyl)benzamide (310); 4-(5-Chloro-2-(dibutylamino)pyrimidin-4-yl)-N-(naphthalen-2-ylsulfonyl)-3-(1,2,3,4-tetrahydroisoquinoline-2-carbonyl)benzamide (311); 4-(2-(Dibutylamino)-5-methylpyrimidin-4-yl)-N-(naphthalen-2-ylsulfonyl)-3-(1,2,3,4-tetrahydroisoquinoline-2-carbonyl) benzamide (312); 4-(5-Chloro-2-(dibutylamino)pyrimidin-4-yl)-N-(8-chloronaphthalen-2-ylsulfonyl)-3-(1,2,3,4-tetrahydroisoquinoline-2-carbonyl)benzamide (313); N-(8-Chloronaphthalen-2-ylsulfonyl)-4-(2-(dibutylamino)-5-methylpyrimidin-4-yl)-3-(1,2,3,4-tetrahydroisoquinoline-2-carbonyl)benzamide (314); 4-(5-Chloro-2-(dibutylamino)pyrimidin-4-yl)-3-((S)-3-(hydroxymethyl)-1,2,3,4-tetrahydroisoquinoline-2-carbonyl)-N-(naphthalen-2-ylsulfonyl)benzamide (315); 4-(5-Bromo-2-(dibutylamino)pyrimidin-4-yl)-3-((S)-3-(hydroxymethyl)-1,2,3,4-tetrahydroisoquinoline-2-carbonyl)-N-(naphthalen-2-ylsulfonyl)benzamide (316); 4-(5-Bromo-2-(dibutylamino)pyrimidin-4-yl)-N-(8-chloronaphthalen-2-ylsulfonyl)-3-(1,2,3,4-tetrahydroisoquinoline-2-carbonyl)benzamide (317); 4-(5-Chloro-2-(dibutylamino)pyrimidin-4-yl)-N-(7-chloronaphthalen-2-ylsulfonyl)-3-(1,2,3,4-tetrahydroisoquinoline-2-carbonyl)benzamide (318); Ethyl 4-(4-(7-chloronaphthalen-2-ylsulfonylcarbamoyl)-2-(1,2,3,4-tetrahydroisoquinoline-2-carbonyl)phenyl)-2-(dibutylamino)pyrimidine-5-carboxylate (319); 4-(4-(7-Chloronaphthalen-2-ylsulfonylcarbamoyl)-2-(1,2,3,4-tetrahydroisoquinoline-2-carbonyl)phenyl)-2-(dibutylamino)pyrimidine-5-carboxylic acid (320); 4-(5-Chloro-2-(dibutylamino)pyrimidin-4-yl)-N-(1-(3,4-dichlorobenzyl)indolin-5-ylsulfonyl)-3-(1,2,3,4-tetrahydroisoquinoline-2-carbonyl)benzamide (321); 4-(2-(Butyl (3,4-dichlorobenzyl)amino)-5-chloropyrimidin-4-yl)-N-(8-chloronaphthalen-2-ylsulfonyl)-3-(1,2,3,4-tetrahydroisoquinoline-2-carbonyl)benzamide (322); 4-(5-Chloro-2-(dipropylamino)pyrimidin-4-yl)-N-(naphthalen-2-ylsulfonyl)-3-(1,2,3,4-tetrahydroisoquinoline-2-carbonyl) benzamide (323); 4-(5-Chloro-2-(dipropylamino)pyrimidin-4-yl)-3-((S)-3-(hydroxymethyl)-1,2,3,4-tetrahydroisoquinoline-2-carbonyl)-N-(naphthalen-2-ylsulfonyl)benzamide (324); 4-(5-Bromo-2-(dipropylamino)pyrimidin-4-yl)-3-((S)-3-(hydroxymethyl)-1,2,3,4-tetrahydroisoquinoline-2-carbonyl)-N-(naphthalen-2-ylsulfonyl)benzamide (325); 4-(5-Chloro-2-((cyclopropylmethyl)(propyl)amino)pyrimidin-4-yl)-3-((S)-3-(hydroxymethyl)-1,2,3,4-tetrahydroisoquinoline-2-carbonyl)-N-(naphthalen-2-ylsulfonyl)benzamide (326); 3-((S)-3-(Aminomethyl)-1,2,3,4-tetrahydroisoquinoline-2-carbonyl)-4-(5-chloro-2-(dipropylamino)pyrimidin-4-yl)-N-(naphthalen-2-ylsulfonyl)benzamide (327); 4-(5-Chloro-2-(dipropylamino)pyrimidin-4-yl)-N-(8-chloronaphthalen-2-ylsulfonyl)-3-((S)-3-(hydroxymethyl)-1,2,3,4-tetrahydroisoquinoline-2-carbonyl)benzamide (328); and 3-((S)-3-(Aminomethyl)-1,2,3,4-tetrahydroisoquinoline-2-carbonyl)-4-(5-chloro-2-(dipropylamino)pyrimidin-4-yl)-N-(8-chloronaphthalen-2-ylsulfonyl)benzamide (329).

The present invention may be embodied in other specific forms without departing from the spirit or essential attributes thereof. This invention encompasses all combinations of the aspects and/or embodiments of the invention noted herein. It is understood that any and all embodiments of the present invention may be taken in conjunction with any other embodiment or embodiments to describe addition more embodiments. It is also to be understood that each individual element of the embodiments is meant to be combined with any and all other elements from any embodiment to describe an additional embodiment.

DEFINITIONS

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The terms "halo" and "halogen", as used herein, refer to F, Cl, Br, and I.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-6}$alkyl" denotes straight and branched chain alkyl groups with one to six carbon atoms.

The term "haloalkyl", as used herein, refers to an alkyl group in which one or more hydrogen atoms are replaced by halogen atom(s), the number of which can range from one up to the total number of hydrogen atoms that could otherwise exist in the parent alkyl group. Representative examples of haloalkyl groups include, but are not limited to, chloromethyl (—$CH_2Cl$), trifluoromethyl (—$CF_3$—, and 2,2,2-trifluoroethyl (—$CH_2CF_3$). When numbers appear in a subscript after the symbol "C", the subscript defines with more specificity the number of carbon atoms that a particular haloalkyl group may contain. For example, "$C_{1-4}$haloalkyl" denotes straight and branched chain haloalkyl groups with one to four carbon atoms.

The term "fluoroalkyl" as used herein is intended to include both branched and straight-chain saturated aliphatic hydrocarbon groups substituted with one or more fluorine atoms. For example, "$C_{1-4}$ fluoroalkyl" is intended to include $C_1$, $C_2$, $C_3$, and $C_4$ alkyl groups substituted with one or more fluorine atoms. Representative examples of fluoroalkyl groups include, but are not limited to, —$CF_3$ and —$CH_2CF_3$.

The term "hydroxyalkyl" includes both branched and straight-chain saturated alkyl groups substituted with one or more hydroxyl groups. For example, "hydroxyalkyl" includes —$CH_2OH$, —$CH_2CH_2OH$, and $C_{1-4}$ hydroxyalkyl.

The term "cyano" refers to the group —CN.

The term "cycloalkyl", as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "$C_3$-$C_6$ cycloalkyl" denotes cycloalkyl groups with three to six carbon atoms.

The term "alkoxy", as used herein, refers to an alkyl group attached to the parent molecular moiety through an oxygen atom, for example, methoxy group (—$OCH_3$).

"Fluoroalkoxy" and "—O(fluoroalkyl)" represent a fluoroalkyl group as defined above attached through an oxygen linkage (—O—). For example, "$C_{1-4}$-fluoroalkoxy" is intended to include $C_1$, $C_2$, $C_3$, and $C_4$ fluoroalkoxy groups.

The term "aryl", as used herein, refers to a group of atoms derived from a molecule containing aromatic ring(s) by removing one hydrogen that is bonded to the aromatic ring(s). Representative examples of aryl groups include, but are not limited to, phenyl, naphthyl, indanyl, indenyl, and 1,2,3,4-tetrahydronaphth-5-yl.

The term "benzyl", as used herein, refers to a methyl group in which one of the hydrogen atoms is replaced by a phenyl group.

The term "heteroatom" refers to oxygen (O), sulfur (S), and nitrogen (N).

The term "heterocyclo" or "heterocyclyl" may be used interchangeably and refer to non-aromatic 3- to 7-membered monocyclic groups and 6- to 11-membered bicyclic groups, in which at least one of the rings has at least one heteroatom (O, S or N), said heteroatom containing ring preferably having 1 to 3 heteroatoms independently selected from O, S, and/or N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic group may contain only carbon atoms and may be saturated, partially saturated, or unsaturated. The heterocyclo group may be attached at any available nitrogen or carbon atom. The heterocyclo ring may be unsubstituted or may contain one or more substituents as valence allows.

Exemplary monocyclic heterocyclyl groups include oxetanyl, azetidinyl, pyrrolidinyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl. Exemplary bicyclic heterocyclo groups include quinuclidinyl.

The term "heteroaryl" refers to substituted and unsubstituted aromatic 5- or 6-membered monocyclic groups and 9- or 10-membered bicyclic groups which have at least one heteroatom (O, S or N) in at least one of the rings, said heteroatom-containing ring preferably having 1, 2, or 3 heteroatoms independently selected from O, S, and/or N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic group may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may be unsubstituted or may contain one or more substituents.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thiophenyl, oxadiazolyl, pyridinyl, pyrazinyl, pyrimidinyl, pyridazinyl, and triazolyl.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, and tetrahydroquinolinyl.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th Edition, p. 1418, Mack Publishing Company, Easton, Pa. (1985), the disclosure of which is hereby incorporated by reference.

Salt(s) of the Formula (I) compounds can be formed by, for example, reacting a Formula (I) compound with, for example, an equivalent amount of acid or base in a medium that allows the newly formed salt to, for example, either be precipitated out, or be isolated via lyophilization. Exemplary acidic salt(s) that the compounds of Formula (I) can form with inorganic and/or organic acids include, but are not limited to, for example, include acetate, ascorbate, benzoate, benzenesulfonate, bisulfate, bitartrate, acid citrate, citrate, ethanesulfonate, formate, fumarate, gentisinate, gluconate, glucaronate, glutamate, hydrochloride, hydrobromide, hydroiodide, isonicotinate, maleate, mesylate, methanesulfonate, nitrate, pantothenate, phosphate, acid phosphate, saccharate, salicylate, succinate, sulfate, tartrate, p-toluenesulfonate, trifluoroacetate, lactate, and pamoate [i.e., 1,1'-methylene-bis-(2-hydroxy-3-naphthoate)] salts. Such salts can be formed in accordance with methods known to a person of ordinary skill in the art.

Exemplary basic salt(s) that the compounds of Formula (I) can form with inorganic and/or organic bases include, but are not limited to, for example, ammonium salts; alkali metal salts, such as, for example, sodium, lithium and potassium salts: alkaline earth metal salts, such as, for example, calcium and magnesium salts; salts formed with organic bases, such as, for example, benzathines, dicyclohexylamines, 2-amino-2-(hydroxymethyl)propane-1,3-diol (trisamine or tris), hydrabamines (such as, for example, N,N-bis(dehydroabietyl)ethylenediamine), N-methyl-D-glucamines, N-methyl-D-glycamides, and t-butyl amines; salts formed with amino acids, such as, for example, arginine and lysine; and salts formed by using agents, such as, for example, lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), and aralkyl halides (e.g., benzyl and phenethyl bromides) to quaternize basic nitrogen-containing groups. Such salts can be formed in accordance with methods known to a person of ordinary skill in the art.

In addition, compounds of Formula (I) are, subsequent to their preparation, preferably isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

Any compound that can be converted in vivo to provide the bioactive agent (i.e., the compound of Formula (I)) is a prodrug within the scope and spirit of the invention.

The term "prodrugs" as employed herein includes amides and carbamates formed by reacting one or more amino groups of compounds of Formula (I) with alkyl, alkoxy, or aryl substituted acylating agents employing procedures known to those skilled in the art to generate amides, ureas, carbamates, and the like.

Various forms of prodrugs are well known in the art and are described in:

a) Wermuth, C. G. et al., *The Practice of Medicinal Chemistry*, Chapter 31, Academic Press (1996);

b) Bundgaard, H. ed., *Design of Prodrugs*, Elsevier (1985);

c) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991); and d) Testa, B. et al., *Hydrolysis in Drug and Prodrug Metabolism*, Wiley-VCH (2003).

In addition, compounds of the Formula (I) are, subsequent to their preparation, preferably isolated and purified to obtain a composition containing an amount by weight equal to or greater than 99% Formula (I) compound ("substantially pure" compound I), which is then used or formulated as described herein. Such "substantially pure" compounds of the Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an antagonist of Bcl, or effective to treat cancer.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

Compounds of the present invention may contain one or more additional asymmetric carbon atoms and therefore exist in two or more stereoisomeric forms. The present invention includes all of the possible individual stereoisomers, the individual tautomeric forms thereof, together with mixtures thereof. Separation of diastereoisomers may be achieved by conventional techniques, e.g., by fractional crystallization, chromatography or HPLC of a stereoisomeric mixture of a compound of the present invention, or a suitable salt or derivative thereof. An individual enantiomer of the compound may also be prepared from a corresponding optically pure intermediate or by resolution, such as by HPLC of the corresponding racemate using a suitable chiral support or by fractional crystallization of the diastereoisomeric salts formed by reaction of the corresponding racemate with a suitable optically active acid or base, as appropriate. All stereoisomers of the compounds of the instant invention are contemplated, either in admixture or in pure or substantially pure form.

The compounds of the present invention are intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Also embraced within this invention is a class of pharmaceutical compositions comprising the compound of Formula (I) or a pharmaceutically acceptable salt thereof in association with one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g., magnesium stearate and a disintegrating agent such as crospovidone. The carrier mixture may be filled into a gelatin capsule or compressed as a tablet.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a tablet, capsule, suspension, or liquid. The pharmaceutical composition is preferably made in the form of a dosage unit containing a particular amount of the active ingredient. Examples of such dosage units are tablets or capsules. For example, these may contain an amount of active ingredient from about 0.5 to 2000 mg, preferably from about 0.5 to 500 mg, more preferably from about 0.5 to 150 mg. A suitable daily dose for a human or other mammal may vary widely depending on the condition of the patient and other factors, but, once again, can be determined using routine methods.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.01 to 100 mg/kg body weight, preferably between about 0.05 and about 50 mg/kg body weight and most preferably between about 0.05 to 20 mg/kg body weight, may be appropriate. The daily dose can be administered in one to four doses per day.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinyl alcohol, and/or polyvinylpyrrolidone, and then tableted or encapsulated for convenient administration. Such capsules or tablets may contain a controlled-release formulation as may be provided in a dispersion of active compound in hydroxypropylmethyl cellulose.

The oily phase of the emulsions comprising compounds of Formula (I) may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e., CAPTISOL®), cosolvent solubilization (i.e., propylene glycol) or micellar solubilization (i.e., Tween 80).

The sterile injectable preparation may also be a sterile injectable solution or suspension in a non-toxic parenterally acceptable diluent or solvent, for example as a solution in propylene glycol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

The pharmaceutical compositions may be subjected to conventional pharmaceutical operations such as sterilization and/or may contain conventional adjuvants, such as preservatives, stabilizers, wetting agents, emulsifiers, and buffers. Tablets and pills can additionally be prepared with enteric coatings. Such compositions may also comprise adjuvants, such as wetting, sweetening, flavoring, and perfuming agents.

Pharmaceutical compositions of this invention comprise the compound of Formula (I), or a pharmaceutically acceptable salt thereof, and optionally an additional agent selected from any pharmaceutically acceptable carrier, adjuvant, and vehicle. Alternate compositions of this invention comprise a compound of the Formula (I) described herein, or a pharmaceutically acceptable salt thereof, and a pharmaceutically acceptable carrier, adjuvant, or vehicle.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

UTILITY

The compounds of Formula (I) are useful as small molecule Bcl-2 family prosurvival protein antagonists for cancer treatment and other diseases caused by impaired apoptosis.

As stated above, the compounds of Formula (I) are of interest for their antiproliferative effects. Such compounds of the invention are expected to be useful in a wide range of disease states including cancer, psoriasis, and rheumatoid arthritis.

Thus, the present invention provides methods for the treatment of a variety of cancers, including, but not limited to, the following:

carcinoma including that of the bladder (including accelerated and metastatic bladder cancer), breast, colon (including colorectal cancer), kidney, liver, lung (including small and non-small cell lung cancer and lung adenocarcinoma), ovary, prostate, testes, genitourinary tract, lymphatic system, rectum, larynx, pancreas (including exocrine pancreatic carcinoma), esophagus, stomach, gall bladder, cervix, thyroid, and skin (including squamous cell carcinoma);

hematopoietic tumors of lymphoid lineage including leukemia, acute lymphocytic leukemia, acute lymphoblastic leukemia, B-cell lymphoma, T-cell lymphoma, Hodgkin's lymphoma, non-Hodgkin's lymphoma, hairy cell lymphoma, histiocytic lymphoma, and Burkett's lymphoma;

hematopoietic tumors of myeloid lineage including acute and chronic myelogenous leukemias, myelodysplastic syndrome, myeloid leukemia, and promyelocytic leukemia;

tumors of the central and peripheral nervous system including astrocytoma, neuroblastoma, glioma, and schwannomas;

tumors of mesenchymal origin including fibrosarcoma, rhabdomyosarcoma, and osteosarcoma; and other tumors including melanoma, xenoderma pigmentosum, keratoactanthoma, seminoma, thyroid follicular cancer, and teratocarcinoma.

The present invention provides methods for the treatment of a variety of non-cancerous proliferative diseases. The invention is useful to treat GIST, Breast cancer, pancreatic cancer, colon cancer, NSCLC, CML, and ALL, sarcoma, and various pediatric cancers.

The present invention provides methods for the treatment of a variety of proliferative diseases, including a method for treating mesothelioma, bladder cancer, pancreatic cancer, skin cancer, cancer of the head or neck, cutaneous or intraocular melanoma, ovarian cancer, breast cancer, uterine cancer, carcinoma of the fallopian tubes, carcinoma of the endometrium, carcinoma of the cervix, carcinoma of the vagina, carcinoma of the vulva, bone cancer, ovarian cancer, cervical cancer, colon cancer, rectal cancer, cancer of the anal region, stomach cancer, gastrointestinal (gastric, colorectal, and duodenal), chronic lymphocytic leukemia, esophageal cancer, cancer of the small intestine, cancer of the endocrine system, cancer of the thyroid gland, cancer of the parathyroid gland, cancer of the adrenal gland, sarcoma of soft tissue, cancer of the urethra, cancer of the penis, testicular cancer, hepatocellular cancer (hepatic and biliary duct), primary or secondary central nervous system tumor, primary or secondary brain tumor, Hodgkin's disease, chronic or acute leukemia, chronic myeloid leukemia, lymphocytic lymphomas, lymphoblastic leukemia, follicular lymphoma, lymphoid malignancies of T-cell or B-cell origin, melanoma, multiple myeloma, oral cancer, small cell lung cancer, cancer of the kidney and ureter, renal cell carcinoma, carcinoma of the renal pelvis, neoplasms of the central nervous system, primary central nervous system lymphoma, non Hodgkin's lymphoma, spinal axis tumors, brain stem glioma, pituitary adenoma, adrenocortical cancer, gall bladder cancer, cancer of the spleen, cholangiocarcinoma, fibrosarcoma, neuroblastoma, retinoblastoma, or a combination thereof.

In one embodiment, a method is provided for treating cancer comprising administering compound of Formula (I) or a pharmaceutically acceptable salt or prodrug thereof to a mammal in need thereof. The method of this embodiment can be used to treat a variety of cancers, including, but not limited to, breast cancer, ovarian cancer, and prostate cancer. Preferably, the method of this embodiment is used to treat prostate cancer or breast cancer. In one method of this embodiment, compound of Formula (I) is administered in a therapeutically effective amount.

The amount of a compound of Formula (I) which is administered and the dosage regimen for treating a particular cancer depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg body weight, preferably between about 0.05 and about 50 mg/kg body weight and most preferably between about 0.05 to 20 mg/kg body weight, may be appropriate may be appropriate. The daily dose can be administered in one to four doses per day.

In treating cancer, a combination of chemotherapeutic agents and/or other treatments (e.g., radiation therapy) is often advantageous. The second (or third) agent may have the same or different mechanism of action than the primary therapeutic agent. It may be especially useful to employ cytotoxic drug combinations wherein the two or more drugs being administered act in different manners or in different phased of the cell cycle, and/or where the two or more drugs have overlapping toxicities or side effects, and/or where the drugs being combined each has a demonstrated efficacy in treating the particular disease state manifested by the patient.

Accordingly, a compound of Formula (I) may be administered in combination with other anti-cancer treatments useful in the treatment of cancer or other proliferative diseases. The invention herein further comprises use of a compound of Formula (I) in preparing medicaments for the treatment of cancer, and/or it comprises the packaging of a compound of Formula (I) herein together with instructions that the compound be used in combination with other anti-cancer or cytotoxic agents and treatments for the treatment of cancer. The present invention further comprises combinations of a compound of Formula (I) and one or more additional agents in kit form, e.g., where they are packaged together or placed in separate packages to be sold together as a kit, or where they are packaged to be formulated together.

The compound of Formula (I) can be formulated or co-administered with other therapeutic agents that are selected for their particular usefulness in addressing side effects associated with the aforementioned conditions. For example, the compound of Formula (I) may be formulated with agents to prevent nausea, hypersensitivity and gastric irritation, such as antiemetics, and $H_1$ and $H_2$ antihistaminics.

The phrase "anti-cancer treatment" includes but is not limited to, for example, radiation therapy and surgery.

The other anti-cancer agents may be selected from any one or more of the following: alkylating agents (including nitrogen mustards, alkyl sulfonates, nitrosoureas, ethylenimine derivatives, and triazenes); anti-angiogenics (including matrix metalloproteinase inhibitors); antimetabolites (including adenosine deaminase inhibitors, folic acid antagonists, purine analogues, and pyrimidine analogues); antibiotics or antibodies (including monoclonal antibodies, CTLA-4 antibodies, anthracyclines); aromatase inhibitors; cell-cycle response modifiers; enzymes; farnesyl-protein transferase inhibitors; hormonal and antihormonal agents and steroids (including synthetic analogs, glucocorticoids, estrogens/anti-estrogens [e.g., SERMs], androgens/anti-androgens, progestins, progesterone receptor agonists, and luteinizing hormone-releasing [LHRH] agonists and antagonists); insulin-like growth factor (IGF)/insulin-like growth factor receptor (IGFR) system modulators (including IGFR1 inhibitors); integrin-signaling inhibitors; kinase inhibitors (including multi-kinase inhibitors and/or inhibitors of Src kinase or Src/abl, cyclin dependent kinase [CDK] inhibitors, panHer, Her-1 and Her-2 antibodies, VEGF inhibitors, including anti-VEGF antibodies, EGFR inhibitors, mitogen-activated protein [MAP] inhibitors, MEK inhibitors, Aurora kinase inhibitors, PDGF inhibitors, and other tyrosine kinase inhibitors or serine/threonine kinase inhibitors; microtubule-disruptor agents, such as ecteinascidins or their analogs and derivatives; microtubule-stabilizing agents such as taxanes, and the naturally-occurring epothilones and their synthetic and semi-synthetic analogs; microtubule-binding, destabilizing agents (including vinca alkaloids); topoisomerase inhibitors; prenyl-protein transferase inhibitors; platinum coordination complexes; signal transduction inhibitors; and other agents used as anti-cancer and cytotoxic agents such as biological response modifiers, growth factors, and immune modulators.

The above other therapeutic agents, when employed in combination with a compound of Formula (I), can be used, for example, in those amounts indicated in the Physicians' Desk Reference (PDR) or as otherwise determined by one of ordinary skill in the art.

In one embodiment, a method is provided for treating cancer comprising administering to a mammal in need thereof a compound of Formula (I) or a pharmaceutically acceptable salt or prodrug thereof; administering a glucocorticoid; and optionally, one or more additional anticancer agent. Examples of suitable glucocorticoids include, but are not limited to, dexamethasone and prednisolone.

In one embodiment, a method is provided for treating cancer comprising administering to a mammal in need thereof a compound of Formula (I) or a pharmaceutically acceptable salt or prodrug thereof; administering a mineralocorticoid receptor antagonist; and optionally, one or more additional anticancer agent. Examples of suitable mineralocorticoid receptor antagonists include, but are not limited to, eplerenone.

In another embodiment, a compound of Formula (I) or a pharmaceutically acceptable salt thereof is used to treat prostate cancer.

In one embodiment, the patient is an animal.

In another embodiment, the patient is a mammalian species including, but not limited to, for example, humans and domestic animals, such as, for example, dogs, cats, and horses.

In one embodiment, the present invention provides a compound of Formula (I) or a pharmaceutically acceptable salt thereof for use in therapy.

In one embodiment, the use of a compound of Formula (I) or a pharmaceutically acceptable salt thereof in the manufacture of a medicament for the treatment of cancer, including prostate cancer, is provided.

In one embodiment, the use of a compound of Formula (I) or a pharmaceutically acceptable salt thereof in the manufacture of a medicament for the treatment of cancer, including breast cancer, is provided.

METHODS OF PREPARATION

The compounds of the present invention may be prepared by synthetic routes that include processes analogous to those well-known in the chemical arts, particularly in light of the description provided herein. For illustrative purposes, general Schemes 1-13 below show general methods for preparing the compounds of the present invention, as well as key intermediates. For a more detailed description of the individual reaction steps, see the Example section below. Those skilled in the art will appreciate that other synthetic routes may be used to synthesize the inventive compounds. Although specific starting materials and reagents are depicted in the Schemes and discussed below, other starting materials and reagents can easily be substituted to provide a variety of compounds of the present invention. In addition, many of the compounds prepared by the methods below can be further modified in light of this disclosure using conventional chemistry well known to those skilled in the art.

General routes to analogues described in the invention are illustrated in Schemes 1-34. The substituted pyrazole and aryl fluoride coupling fragments 3 and 7 can be prepared as shown in Scheme 1. Halogenation of commercially available pyrazole 1 with, for example, NCS or NBS provides derivative 2. Conversion to the amide Intermediate 3 can occur via treatment with a secondary amine in the presence of n-BuLi or through a two-step procedure employing a coupling reagent, such as EDC, after hydrolysis to the carboxylic acid. Synthesis of coupling partner 7 commences from 2-fluoro-5-iodobenzoic acid (Aldrich, 4), which can be converted to either the ethyl ester (6, Y=Et) under acidic conditions or to the tetrahydroisoquinoline derivative (6, Y=1,2,3,4-tetrahydroisoquinoline) via the acid chloride. Palladium-catalyzed carbonylation in the presence of an alcohol, such as ethanol or benzyl alcohol, furnishes the activated phenyl Intermediate 7.

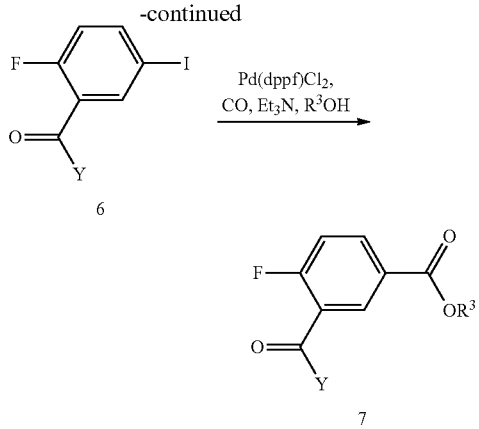

Fully functionalized pyrazole analogues can be prepared using the synthetic routes outlined in Schemes 2-4. Base-mediated coupling of pyrazole 3 and aryl fluoride 7 provides Intermediate 8, which can be hydrolyzed using conditions dependent on the nature of $R^3$. For example, hydrolysis of an ethyl ester can occur using basic conditions, while catalytic hydrogenation with palladium on carbon cleaves a benzyl ester. Treatment with sulfonamide 13 or 14 in the presence of a coupling reagent affords acylsulfonamides 10. For derivatives in which Y=OEt, hydrolysis of the ethyl ester can be followed by coupling with substituted tetrahydroisoquinoline 15 or benzodiazepine 16 to furnish analogue 12.

Scheme 1

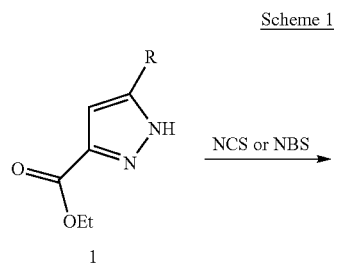

Scheme 2

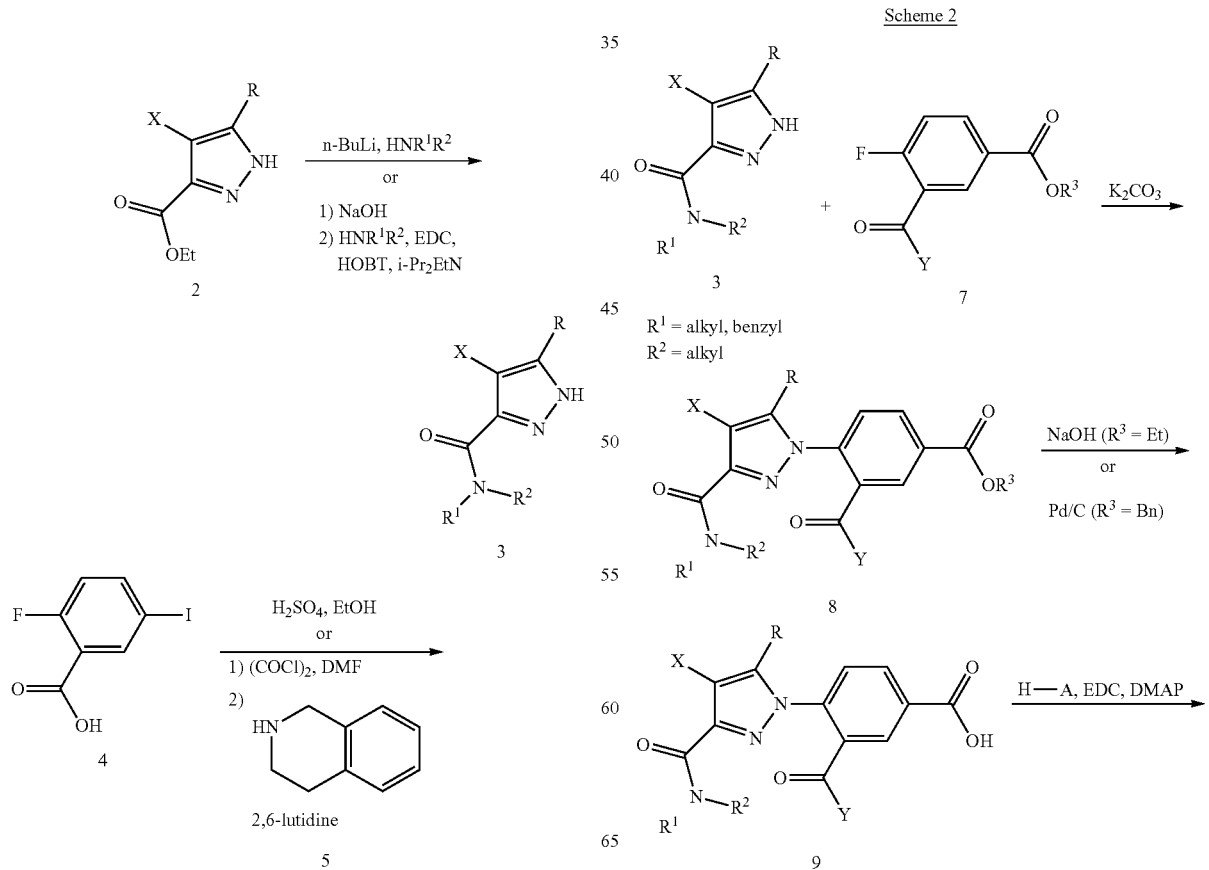

-continued

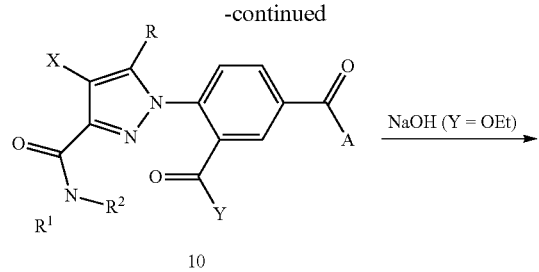

10

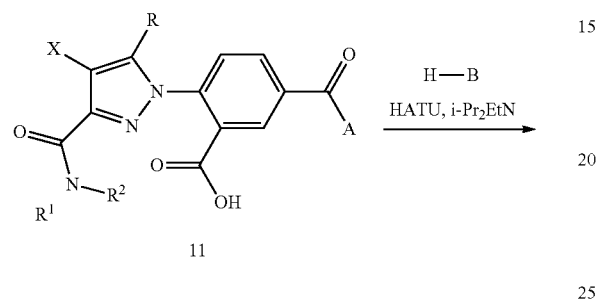

11

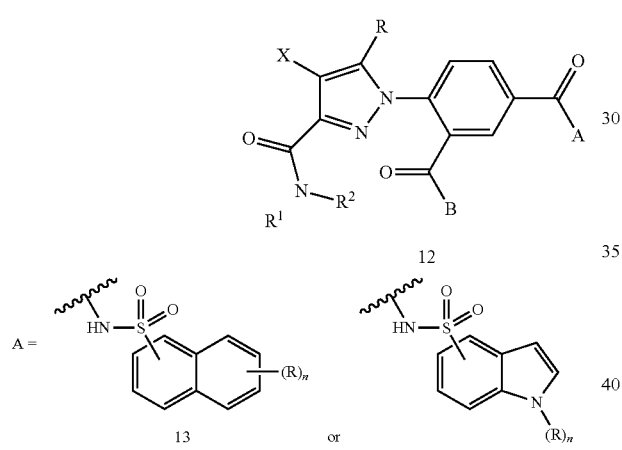

12

A = 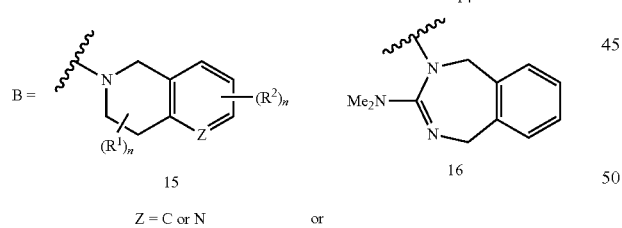

13     or     14

B = 15

Z = C or N     or     16

Similarly, pyrazole Intermediate 2 can be coupled with aryl fluorides 7 (R³=Bn) under basic conditions to give Intermediate 17 (Scheme 3). Hydrogenolysis with palladium on carbon and conversion to the acylsulfonamide in the presence of a coupling reagent, such as EDC, can be followed by hydrolysis to provide the carboxylic acids 20. Conversion to amide 21 can occur via a two-step procedure in which the corresponding acid chloride is subjected to various amines in the presence of base, such as triethylamine or diisopropylethylamine (Hunig's base). Alternatively, the acid chloride can be generated in situ using 1-chloro-N,N-2-trimethyl-1-propenylamine (Ghosez's reagent) and then treated with an amine under basic conditions to afford analogue 21.

Scheme 3

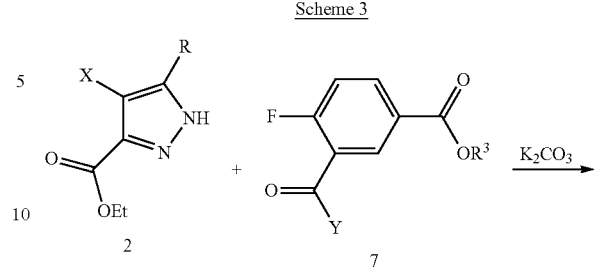

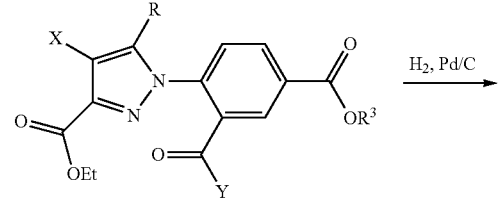

17

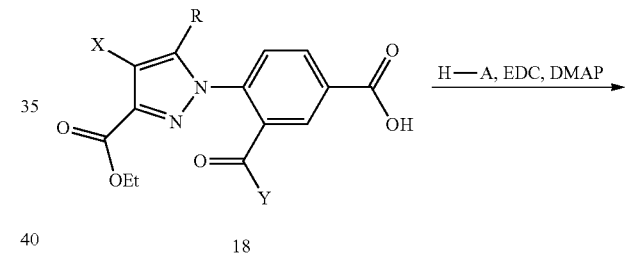

18

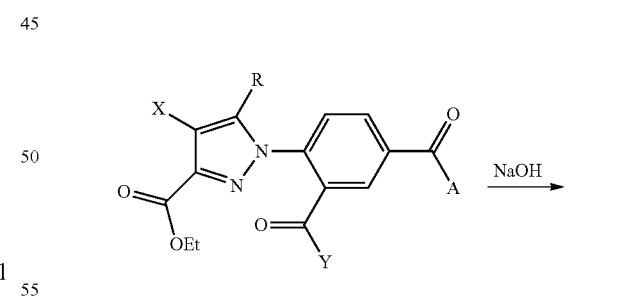

19

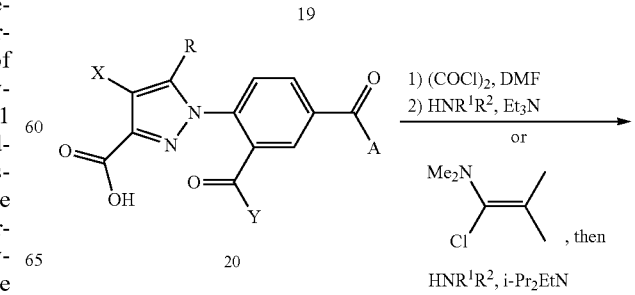

20

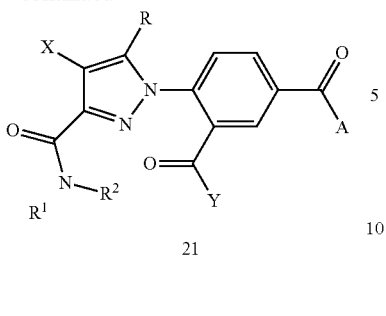

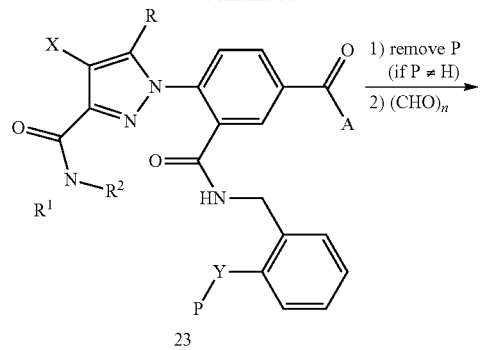

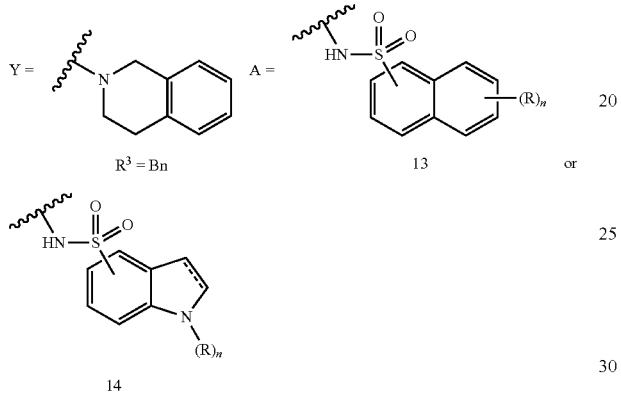

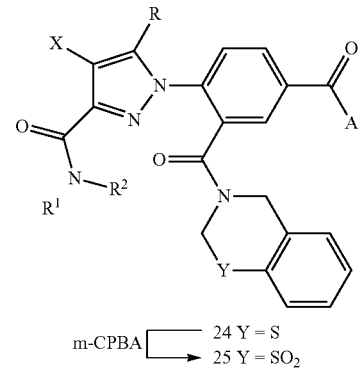

Tetrahydroisoquinoline derivatives such as 24 can be prepared using the synthetic route outlined in Scheme 4, which is based on similar chemistry previously reported. (Goble, S. D. et al., PCT International Application No. 2004/082616). Carboxylic acids (11, Scheme 1) can be converted to benzylic amides 23 in the presence of an appropriate amine 22 and a coupling reagent, such as EDC. The resulting amides are then deprotected in cases where Y has a protecting group. For example, if Y—P is S-t-Bu, 23 could be treated with 2-nitrobenzenesulfenyl chloride in acetic acid, and the resulting disulfide can be reduced with $NaBH_4$ to generate the free thiol. Exposure to paraformaldehyde, in the presence or absence of an acid catalyst such as TsOH, can provide the cyclized Intermediate 24. Subsequent oxidation in cases where Y=S can be achieved using, for example, m-CPBA to give sulfones 25.

Scheme 4

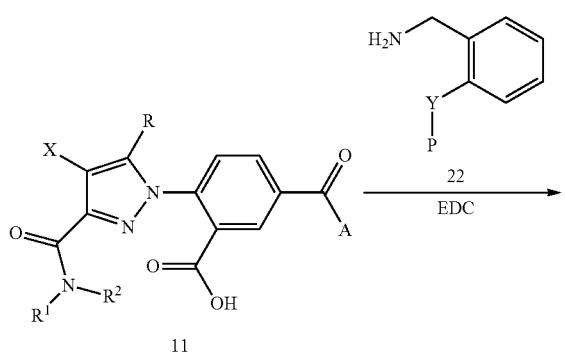

Preparation of pyrazole analogues containing carbamate or carboxylic acid functionality can be achieved using the synthetic route outlined in Scheme 5. Pyrazole starting material 26 can be accessed following a previously published procedure. (Qi, X. et al., *Angew. Chem. Int. Ed.*, 46:3242-3244 (2007)). Conversion to the elaborated Intermediate 29 can be accomplished using chemistry described in Scheme 1, and removal of the protecting group under acidic conditions, (e.g., HCl) provides the primary alcohol 30. Further functionalization to access carbamates such as 31 can occur upon exposure to trichloroacetyl isocyanate followed by treatment with base (e.g., potassium carbonate in MeOH), or 4-nitrophenyl carbonochloridate followed by treatment with a primary or secondary amine in the presence of a base, such as triethylamine Alternatively, primary alcohol 30 can undergo oxidation with, for example, Jones Reagent to give the carboxylic acid 32.

Scheme 5
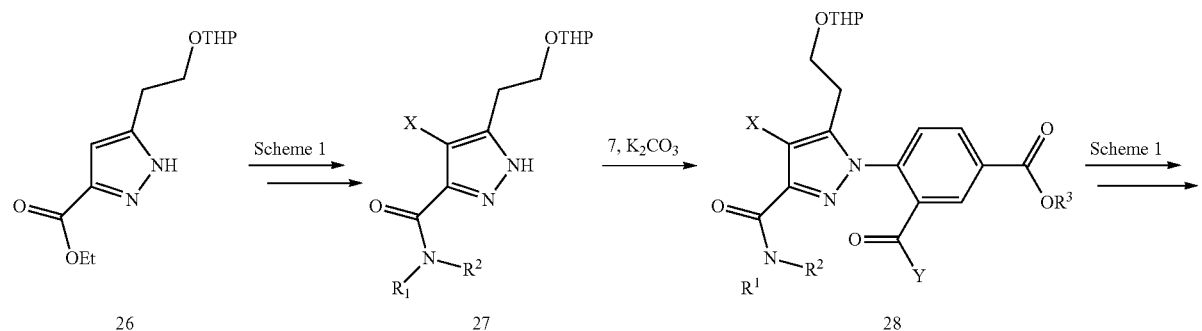
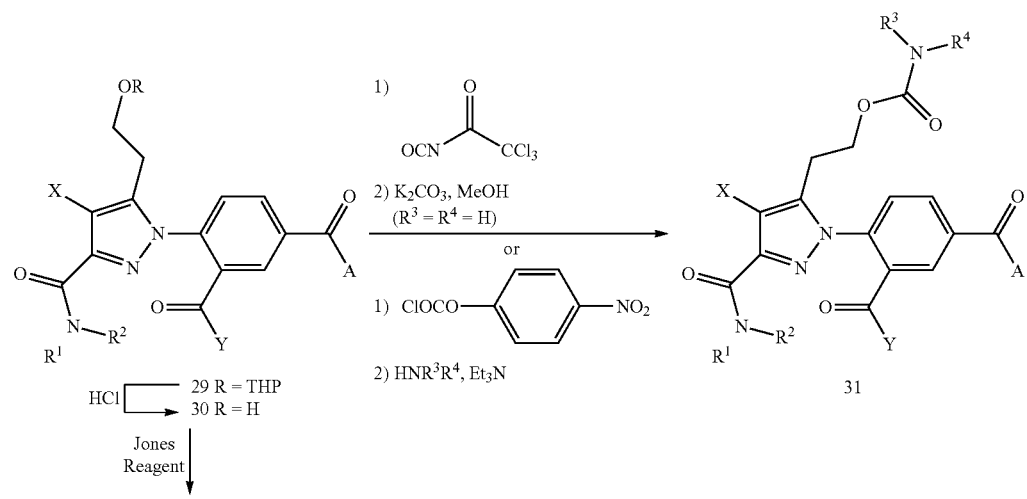
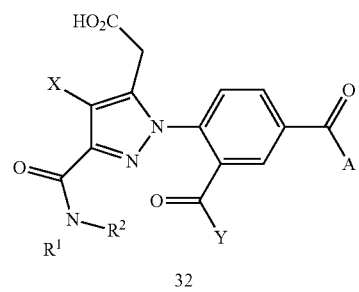
X = H, Cl, Br
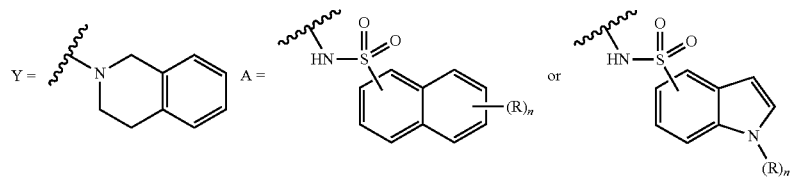

Pyrazole derivatives 36 and 38 may be prepared according to the synthetic sequence outlined in Scheme 6. From Intermediate 33, which can be prepared according to the chemistry described in Scheme 1 (see 8; X=Br, $R^3$=Bn), palladium-catalyzed cross-coupling with t-butyl acrylate can provide the α,β-unsaturated ester 34. Conversion of the benzyl ester to the acyl sulfonamides 35 can occur as outlined in Scheme 1. Deprotection of the t-butyl ester is possible under acidicconditions (e.g., TFA) and subsequent hydrogenation using catalytic palladium on carbon generates the saturated carboxylic acid analogue 36. Following deprotection, Intermediate 35 can also be converted to the primary alcohol 37 via a two-step procedure involving reduction of the acyl imidazole and subsequent hydrogenation. Mesylation of the alcohol followed by displacement with dimethylamine under basic conditions (e.g., diisopropylethylamine) can provide the tertiary amine 36.

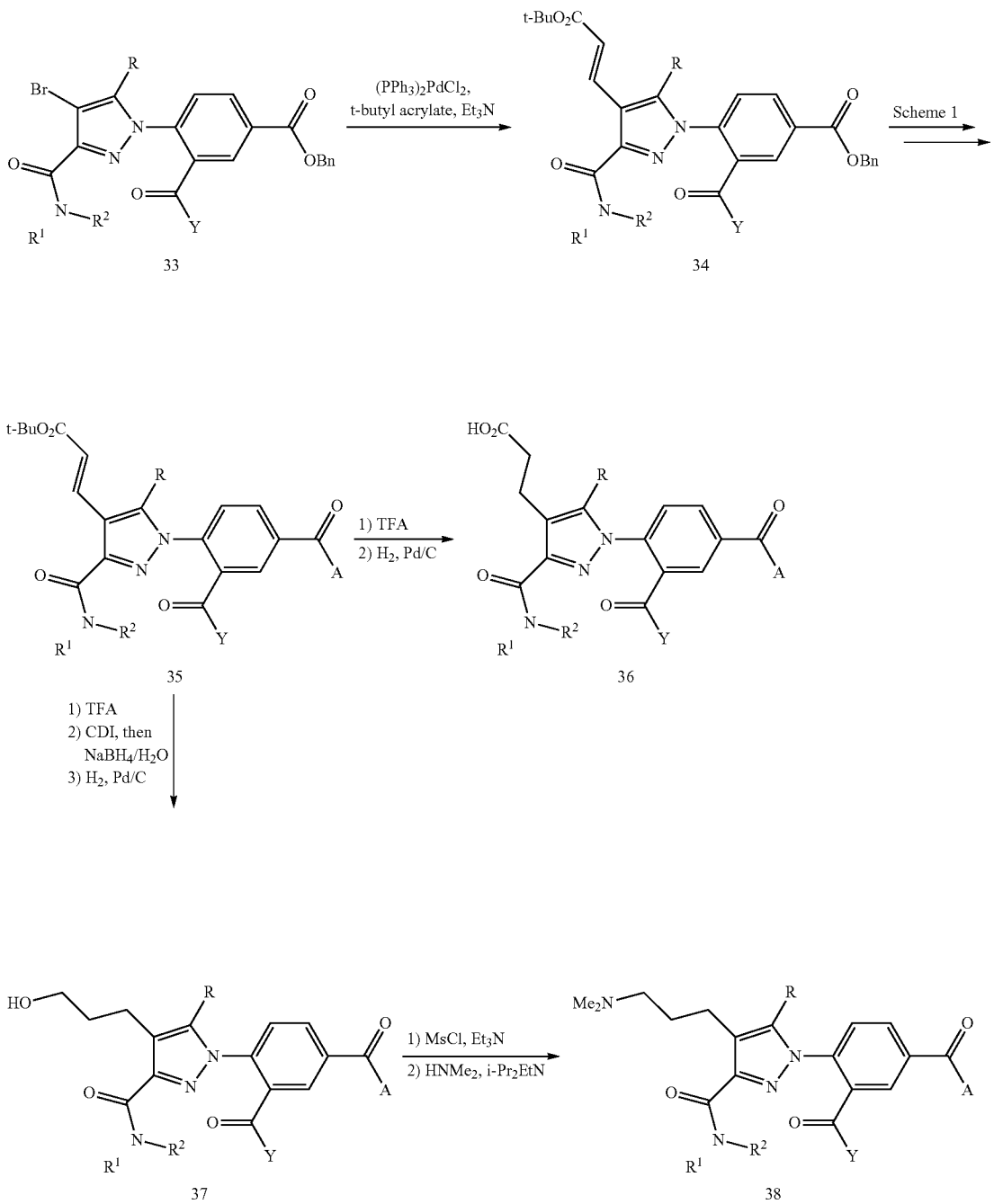

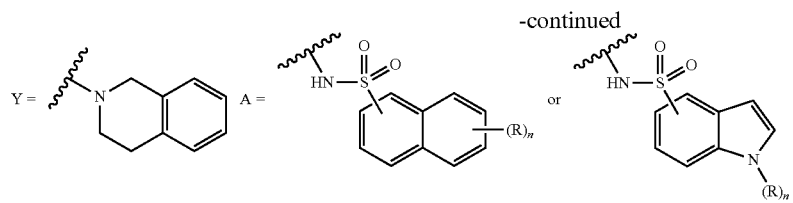

In an alternative approach to compounds related to 37, hydroxymethyl pyrazole 40 can be prepared as demonstrated in Scheme 7. Intermediate 39 can be prepared following the sequence outlined in Scheme 1 (see 9; X=Br, Y=1,2,3,4-tetrahydroisoquinoline). Lithium-halogen exchange with n-BuLi, for example, and quenching with DMF can provide the formylated pyrazole. Conversion to the acylsulfonamide is possible in the presence of coupling reagent such as EDC as previously described in Scheme 2. Finally, reduction of the aldehyde with, for example, NaBH$_4$ provides the primary alcohol 40.

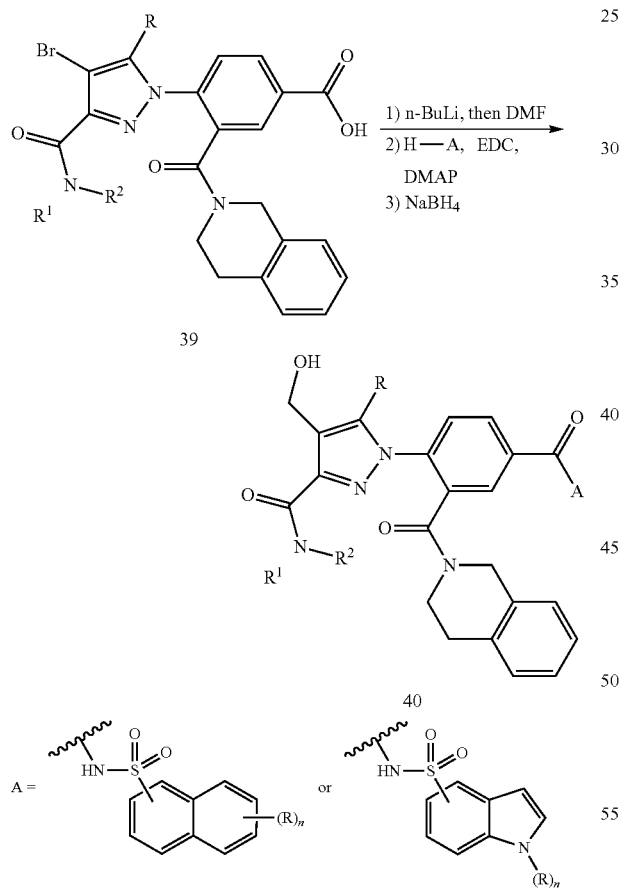

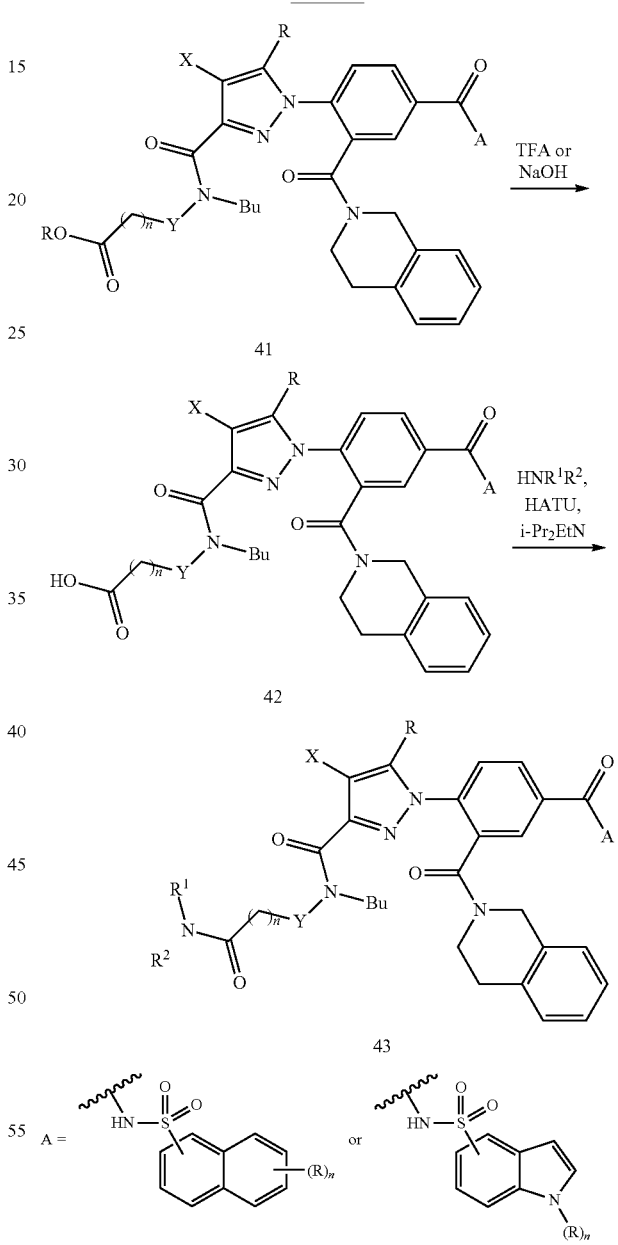

Functionalized amide derivatives, such as 43, may be prepared according to the synthetic route illustrated in Scheme 8. Ester 41, available following the sequence described in Scheme 3, can be hydrolyzed under acidic or basic conditions to give carboxylic acid 42. Coupling with a primary or secondary amine in the presence of a coupling reagent (e.g., EDC or HATU) and a base (e.g., triethylamine or Hunig's base) affords the desired amide 43.

Tetrahydroisoquinoline derivatives 45 and 47 can be prepared using the sequences described in Scheme 9. Alkylation of 44, available following the synthetic route outlined in Scheme 2, in the presence of tetrabutylammonium iodide can provide alkoxy compound 45. Alternatively, functionalized amino derivatives may be prepared via reductive amination of 46 (prepared according to Scheme 2) with various ketones in the presence of, for example, sodium triacetoxyborohydride.

Scheme 9

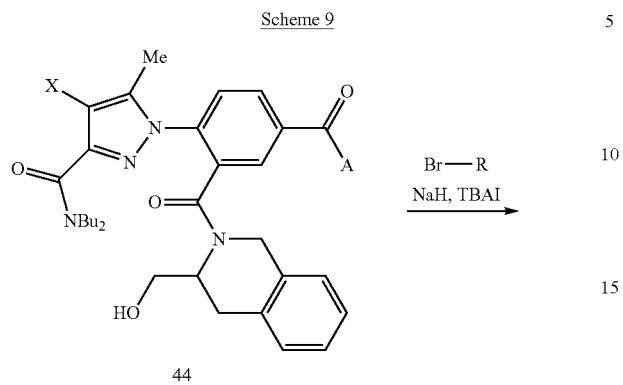

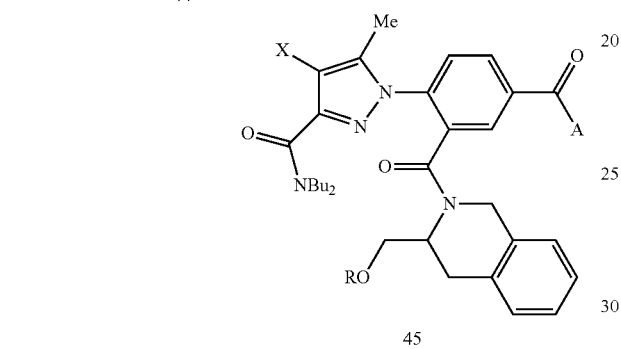

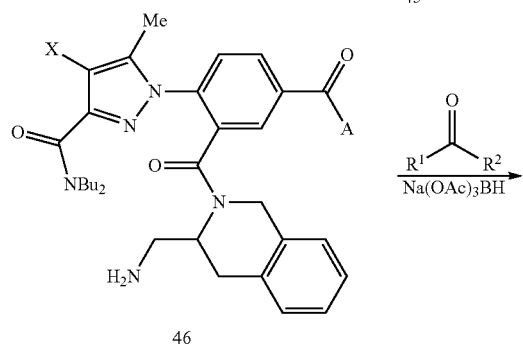

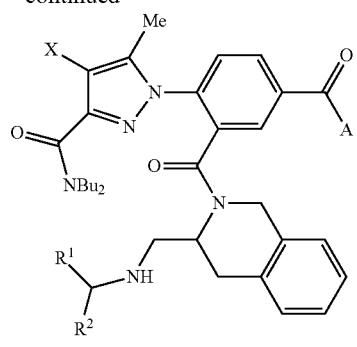

Incorporation of various substituents at the 5-position of the indoline in compound 48, which is prepared as described in Scheme 2, can be accomplished as shown in Scheme 10. Palladium-catalyzed coupling with a range of vinyl boronic acids in the presence of potassium metaphosphate can provide derivatives such as 49. Alternatively, 5-aminoindoline compounds 50 are available through the copper-catalyzed coupling of an amine with 48 in the presence of, for example, potassium carbonate and L-proline.

Scheme 10

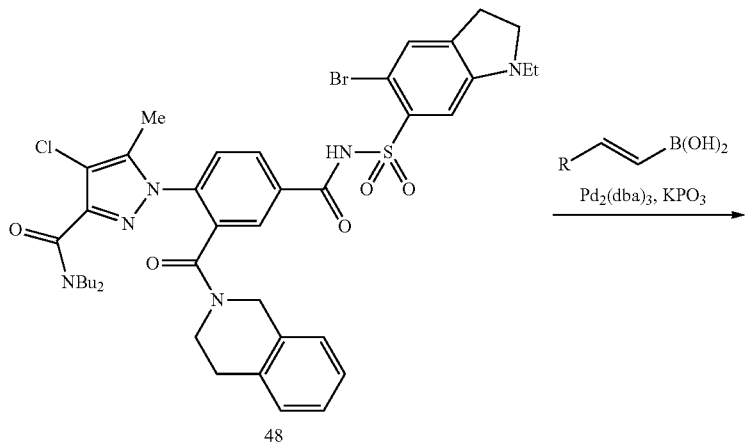

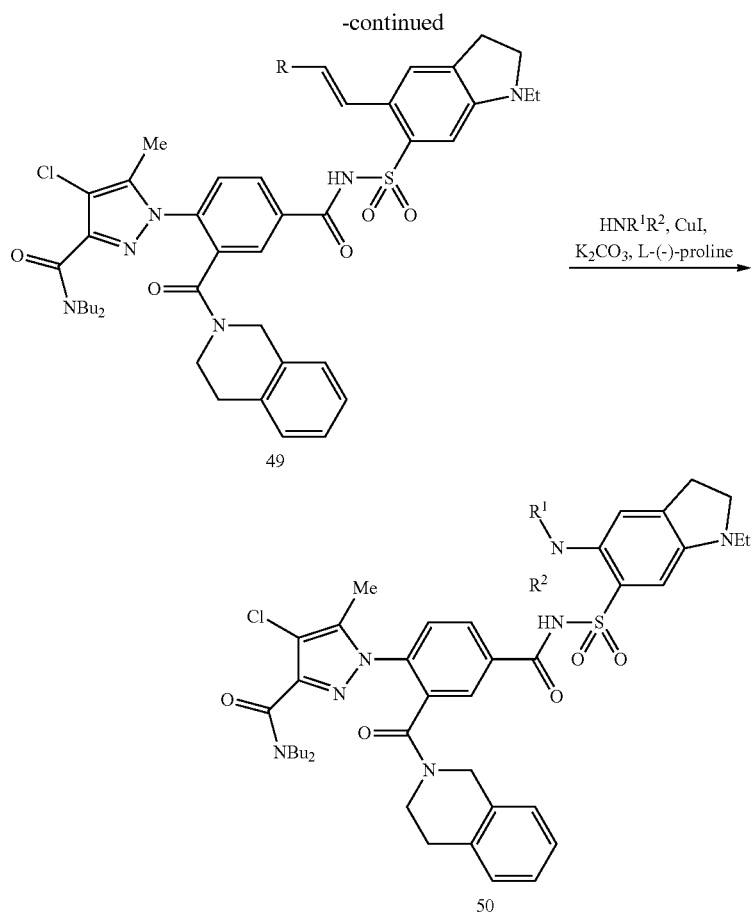

Aminopyrazole derivatives 54 and 60 are available following the synthetic routes outlined in Schemes 11 and 12, respectively. Reductive amination of 3-amino-5-methylpyrazole (Aldrich) with a variety of aldehydes in the presence of sodium triacetoxyborohydride can provide 52 (Scheme 11). Exposure to NCS gives pyrazole Intermediate 53 which can be elaborated to the fully functionalized compound 54 as described previously (Scheme 2, A and B as defined therein).

Scheme 11

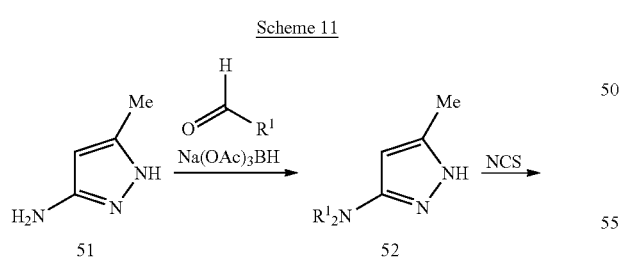

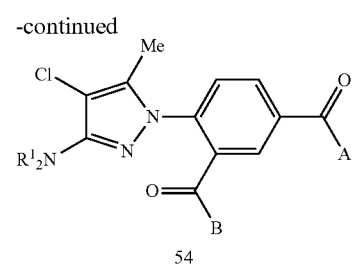

Likewise, compounds such as 60 may be derived from 3-amino-5-trifluoromethylpyrazole (56, Scheme 12). The β-ethoxy-β-enamino ketone 55, prepared as described previously in the literature, (Hojo, M. et al., *Synthesis*, 195-198 (1990)) can undergo cyclocondensation with benzylhydrazine to give 56 (Martins, M. A. P. et al., *Synthesis*, 1485-1493 (2006)) as a mixture of regioisomers. Exposure to propionic acid and sodium borohydride can then provide the dipropylaminopyrazole 57. Removal of the benzyl group using, for example, transfer hydrogenation with formic acid and catalytic palladium on carbon gives 58 which, after chlorination, can be converted to the fully elaborated derivative 60 as previously described in Scheme 2 (A and B as defined therein).

Scheme 12

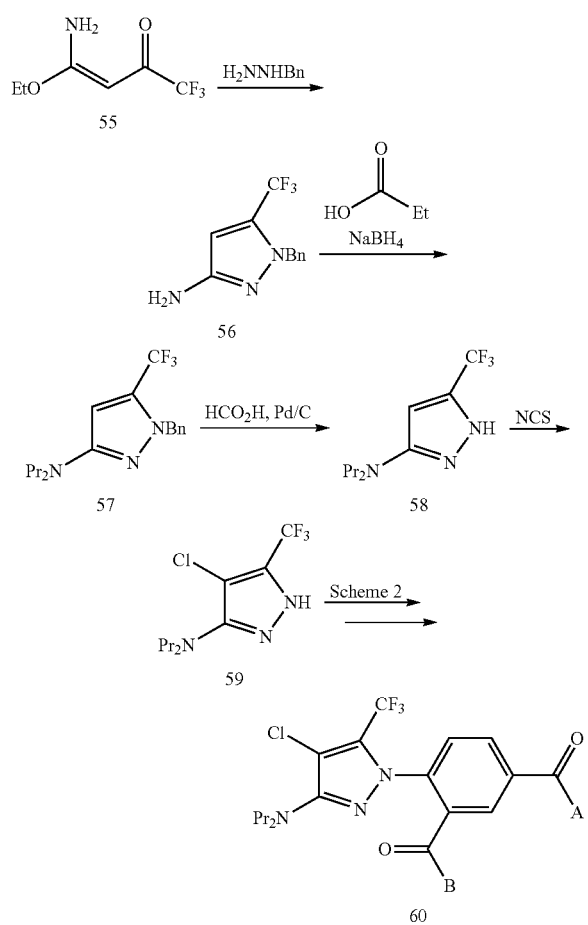

A variety of functionalized naphthalenesulfonamide intermediates may be accessed using the synthetic sequences illustrated in Schemes 13-16. Commercially available naphthalenes such as 61 can be converted to the corresponding sulfonic acids 62 with chlorosulfonic acid (Scheme 13).

Treatment with phosphorus oxychloride followed by exposure to ammonia can generate the sulfonamide products 63.

Scheme 13

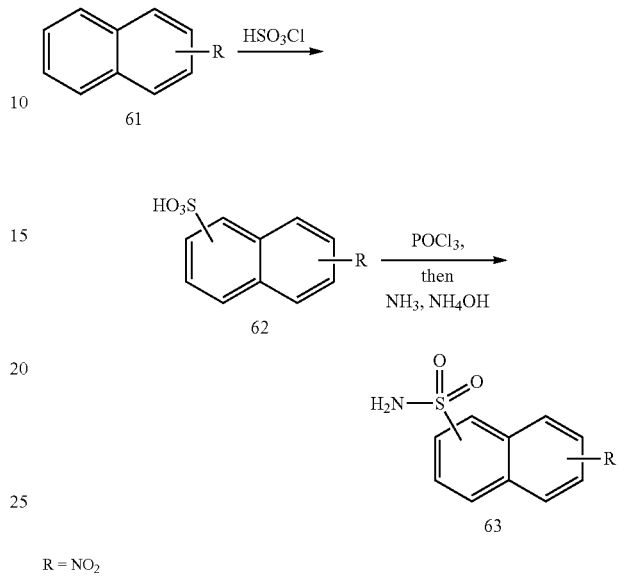

R = NO$_2$

Commercially available aminonaphthalenesulfonic acids 64 can be converted to various functionalized intermediates as shown in Scheme 14. The corresponding naphthyl halides 65 can be generated under acidic conditions by treatment with sodium nitrite and copper (I) chloride (X=Cl), or by treatment with potassium nitrite, potassium hydroxide and potassium iodide (X=I). Conversion to the sulfonamide 66 can occur via the sulfonyl chloride as describe previously in Scheme 13. Palladium-catalyzed reaction of Intermediate 66 with sodium ethanethiolate, zinc cyanide, or carbon monoxide in ethanol can provide sulfonamides 67-69, respectively. Subsequent oxidation of 67 with, for example, m-CPBA provides the analogous sulfonate derivative 70.

Scheme 14

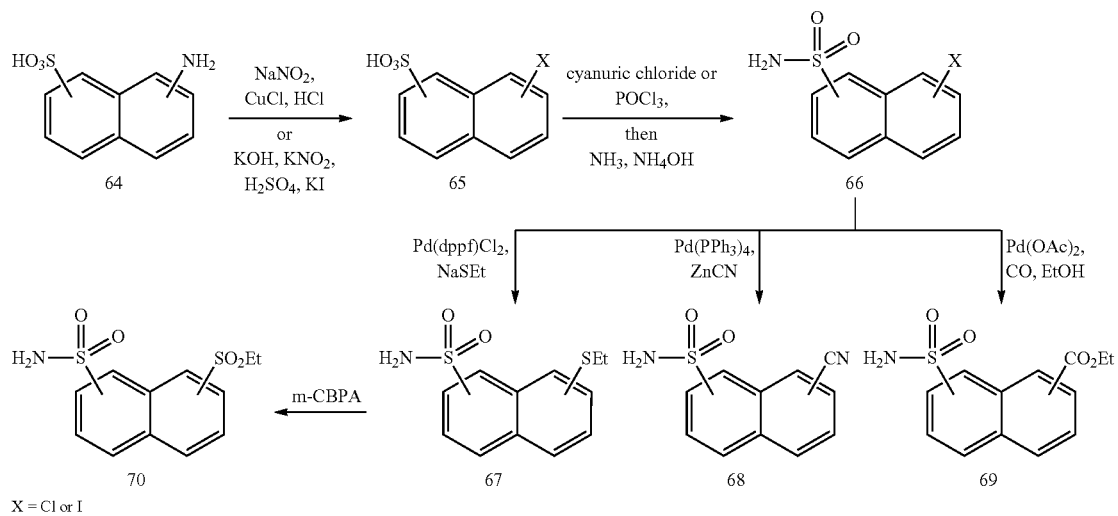

X = Cl or I

Alkoxynaphthalene sulfonamides such as 73 can be prepared as depicted in Scheme 15. Treatment of hydroxynaphthalene sulfonate 71 with a base in the presence of sodium iodide and tetrabutylammonium iodide can effect the displacement of various leaving groups, such as but not limited to mesylate, bromide or iodide, to generate alkoxynaphthalene sulfonic acid 72. Conversion to the corresponding sulfonamide can occur as described previously (Scheme 13).

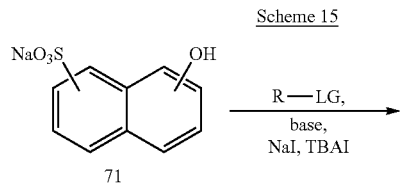

LG = leaving group

5-Aminonaphthalene-2-sulfonic acid (Aldrich) can be converted to a variety of functionalized derivatives as shown in Scheme 16. Following Boc-protection of the amine to give 75, halogenation with NBS or NCS followed by acid-mediated deprotection with, for example, trifluoroacetic acid can generate Intermediate 76. Reductive alkylation with formaldehyde in the presence of triethylsilane, followed by conversion to the sulfonamide (as shown in Scheme 2) can provide 77. Alternatively, Intermediate 78 can be accessed following the sequence previously described in Scheme 14.

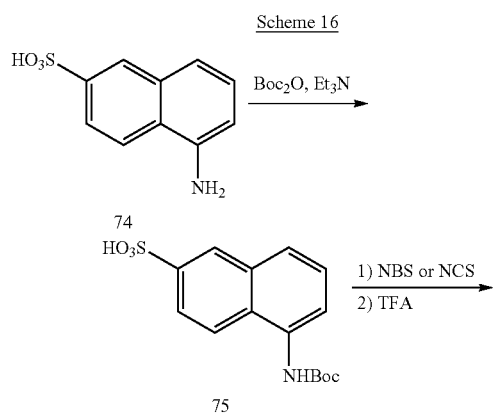

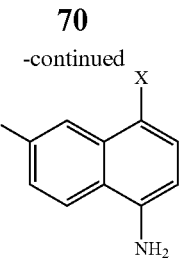

X = Br or Cl

Various indole and indoline intermediates can be prepared following the synthetic sequences outlined in Schemes 17-19. Acetylindoline sulfonyl chlorides such as 79 (Borror, A. L. et al., *J. Org. Chem.*, 53:2047-2052 (1988)) can be converted to sulfonamide 80 using ammonia in the presence of a base, such as triethylamine, followed by treatment with acid (Scheme 17). Exposure to a base (e.g., potassium carbonate) and a variety of acid chlorides then affords the functionalized sulfonamide 81. Reduction of the resulting amide with, for example, a borane-THF complex solution, followed by oxidation with DDQ can generate the alkylindole 85. Alternatively, 85 can be accessed via oxidation of sulfonamide 80 with DDQ, followed by acylation and reduction of the amide as described above. Incorporation of a halogen at the 3-position of the indole can occur through alkylation of Intermediate 83 (as described in Scheme 15), followed by subjection to NCS, NBS or iodine to give compounds such as 87.

Scheme 17

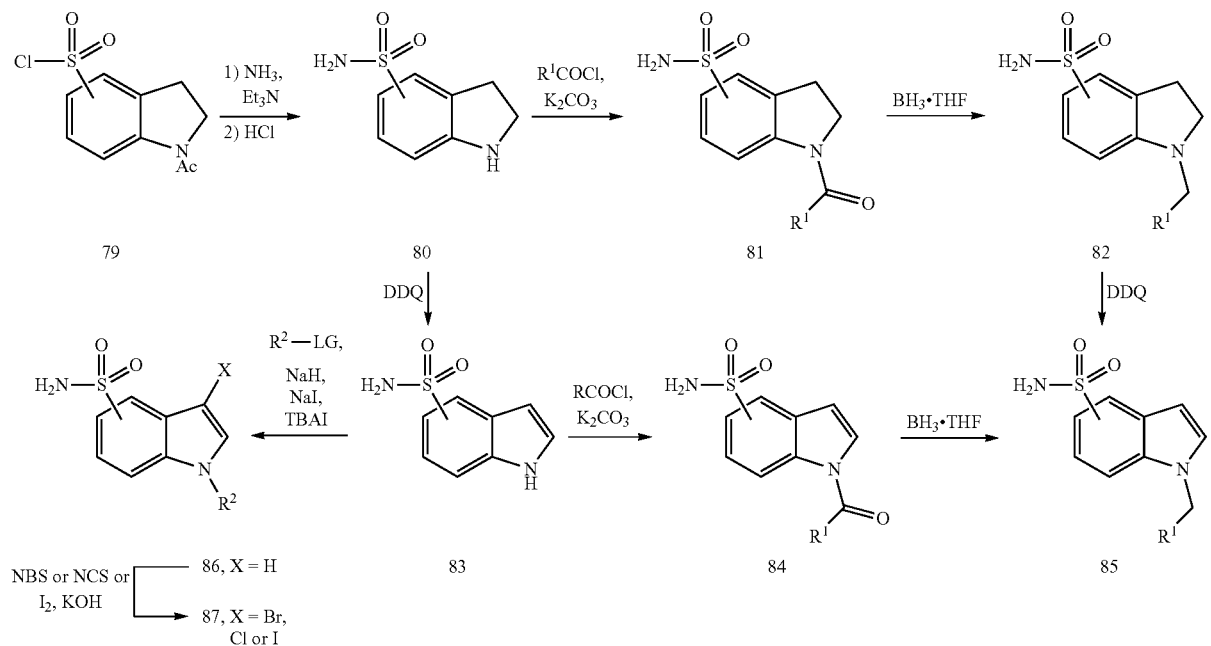

$R^1$ = alkyl, cycloalkyl, benzyl, heteroaromatic
$R^2$ = H, alkyl, heteroalkyl

Functionalized 6-indolinesulfonamides 93 can be prepared as depicted in Scheme 18. Acylation of commercially available indoline (88), as described previously in Scheme 17, can be followed by bromination with, for example, bromine in the presence of acetic acid to give 5-bromoindolines 90. Installation of the sulfonamide moiety can occur using the two-step procedure previously outlined in Scheme 13 to give compound 91. Removal of the bromine using hydrogen and catalytic palladium on carbon can afford Intermediate 92, which then undergoes reduction as previously described in Scheme 17 to give compounds such as 93.

Scheme 18

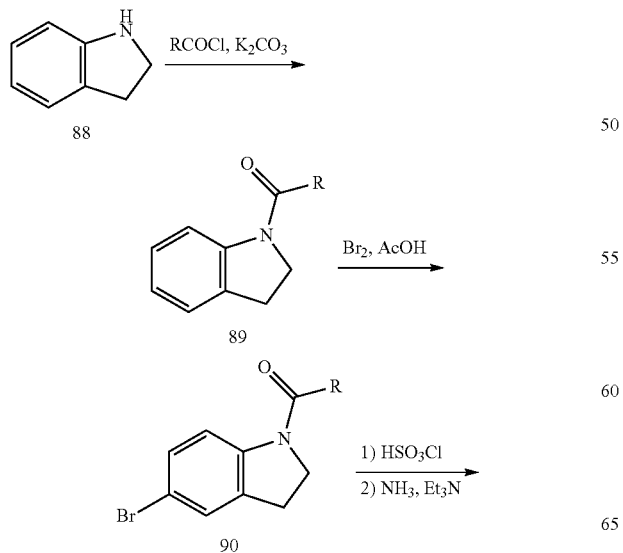

Sulfonamide compound 97 can be prepared from 6-chloronicotinic acid (Aldrich, 94) according to the synthetic route outlined in Scheme 19. Coupling with 2-morpholinoethanol (Aldrich, 95) in the presence of a base, such as potassium t-butoxide can generate Intermediate 96. Following conversion to the acid chloride with oxalyl chloride and catalytic DMF, coupling with indolinesulfonamide 80 (prepared in Scheme 17) in the presence of a base, such as potassium carbonate, can provide the functionalized sulfonamide product 97.

Scheme 19

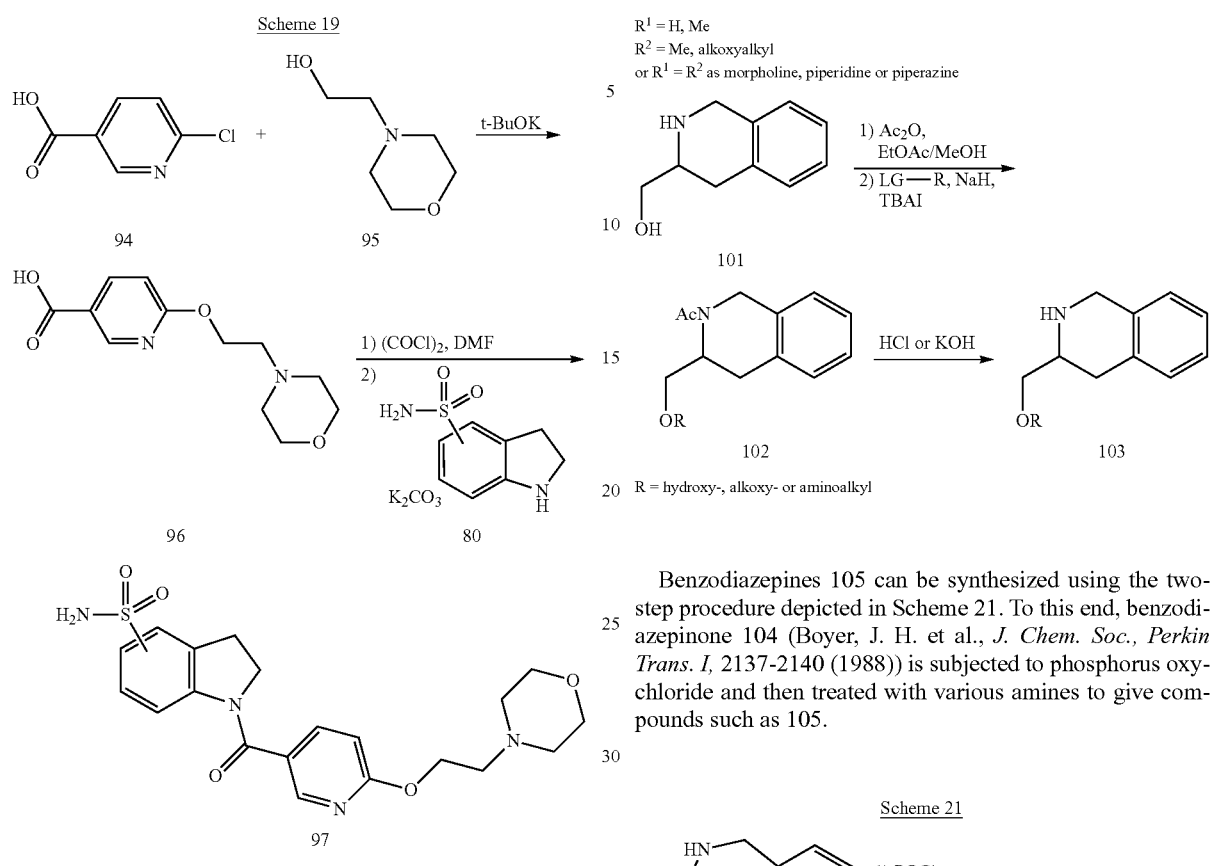

Tetrahydroisoquinoline Intermediates 100 and 103 can be accessed using the synthetic routes shown in Scheme 20. From aldehyde 98, (Schiller, P. W. et al., *J. Med. Chem.*, 36:3182-3187 (1993)) reductive amination as described above can give compound 99, which after Boc-deprotection (described previously) can afford amino derivatives such as 100. Alkoxy derivatives 103 can arise from selective acylation of tetrahydroisoquinoline 101 (Aldrich) with acetic anhydride in ethyl acetate and methanol, followed by alkylation as described in Scheme 15. Deprotection under acidic (e.g., HCl) or basic (e.g., KOH) conditions can then generate products such as 103.

Scheme 20

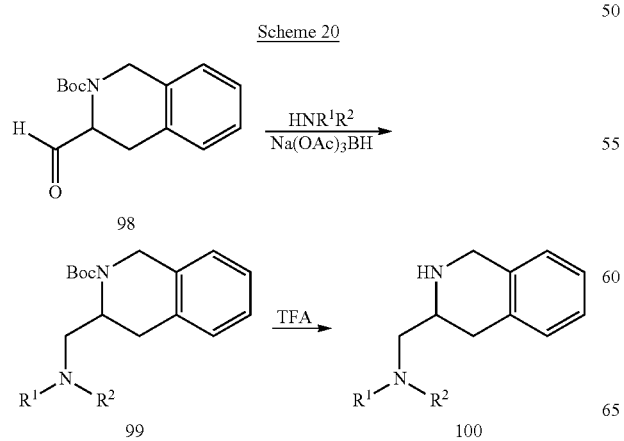

Benzodiazepines 105 can be synthesized using the two-step procedure depicted in Scheme 21. To this end, benzodiazepinone 104 (Boyer, J. H. et al., *J. Chem. Soc., Perkin Trans. I*, 2137-2140 (1988)) is subjected to phosphorus oxychloride and then treated with various amines to give compounds such as 105.

Scheme 21

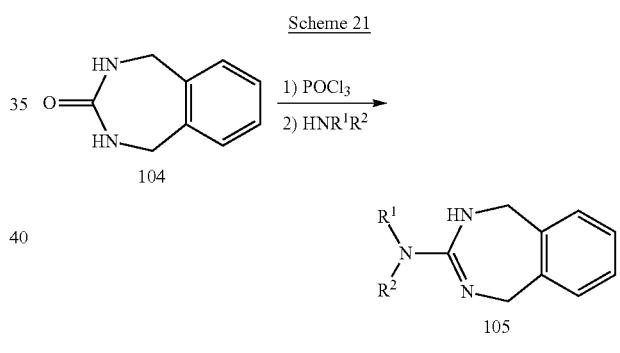

Boronic ester Intermediates 110 and 113 can be prepared using the synthetic routes outlined in Schemes 22 and 23. Commercially available dimethyl 4-hydroxyisophthalate (106, TCI) can undergo selective hydrolysis to give mono-acid 107 by refluxing in pyridine. Esterification of benzoic acid 107 with t-butanol can give bis-ester 108, which reacts with triflic anhydride to give triflate 109. Palladium-catalyzed coupling with bis(pinacolato)diboron then provides Intermediate 110.

Scheme 22

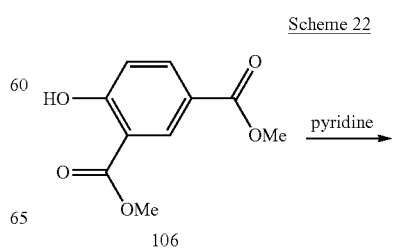

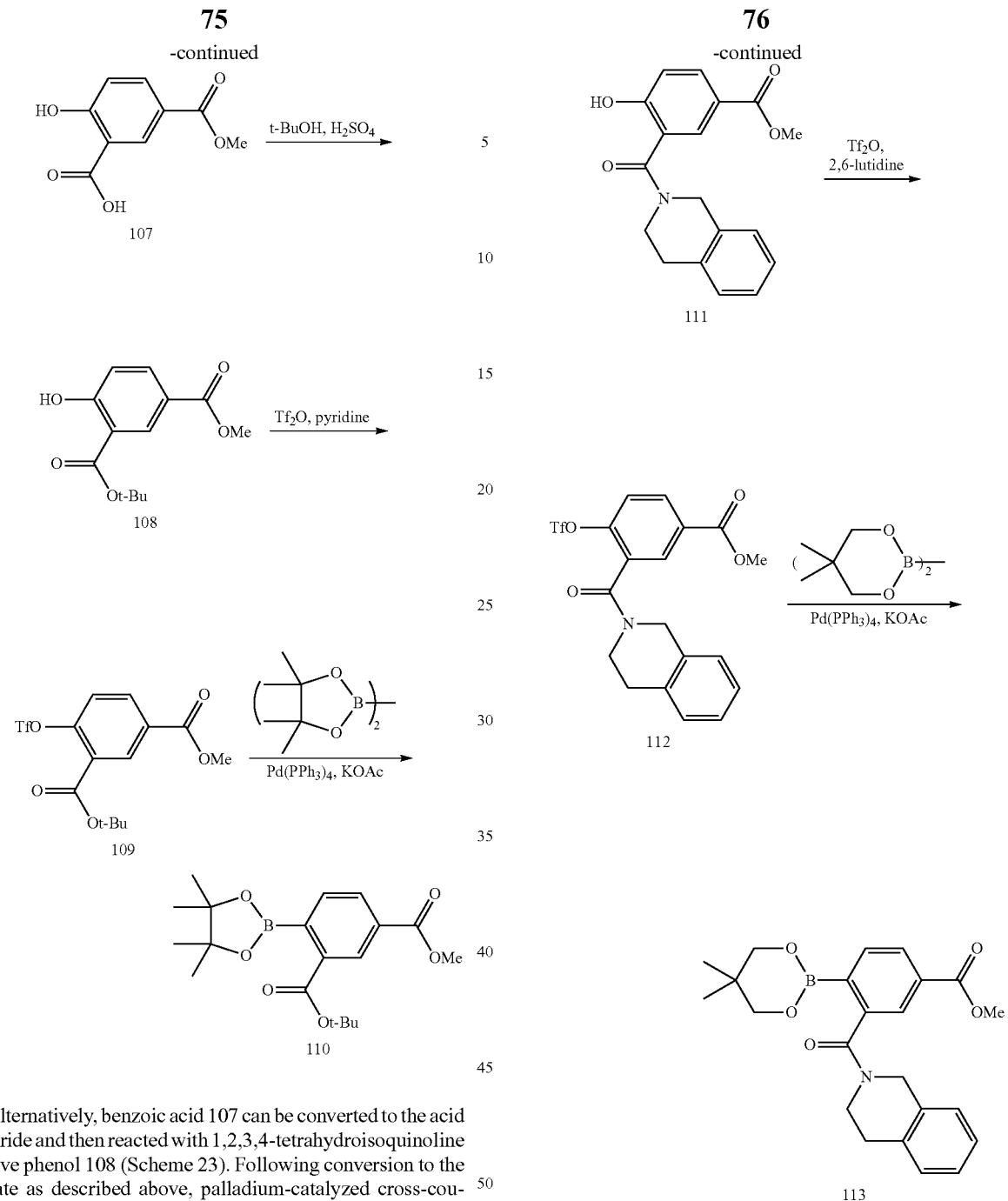

Alternatively, benzoic acid 107 can be converted to the acid chloride and then reacted with 1,2,3,4-tetrahydroisoquinoline to give phenol 108 (Scheme 23). Following conversion to the triflate as described above, palladium-catalyzed cross-coupling with bis(neopentyl glycolato)diboron can afford the functionalized boronic ester 113.

Scheme 23

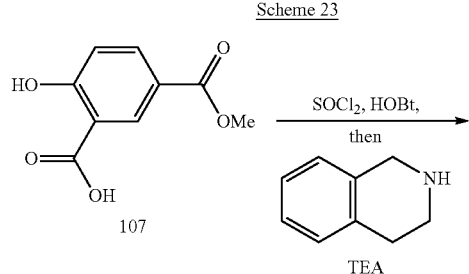

Aminopyridine analogs 120 and 121 can be prepared using the synthetic route outlined in Scheme 24. Commercially available 2,6-dibromopyridines 114 can be converted to 2-aminopyridine 115 upon exposure to dibutylamine in the presence of a base, such as potassium carbonate. Suzuki coupling with Intermediate 110 (prepared in Scheme 22) provides the biaryl compound 116. Selective hydrolysis under basic conditions converts the methyl ester to benzoic acid 117. Compound 117 can react with sulfonamide 118 (prepared according to Scheme 14) to give acylsulfonamide 119 after acid-mediated removal of the t-butylester. Coupling with substituted various tetrahydroisoquinolines forms the desired product 120. When $R^2=N_3$, reduction of the azide can be accomplished using, for example, triphenylphosphine to give compound 121.

Scheme 24

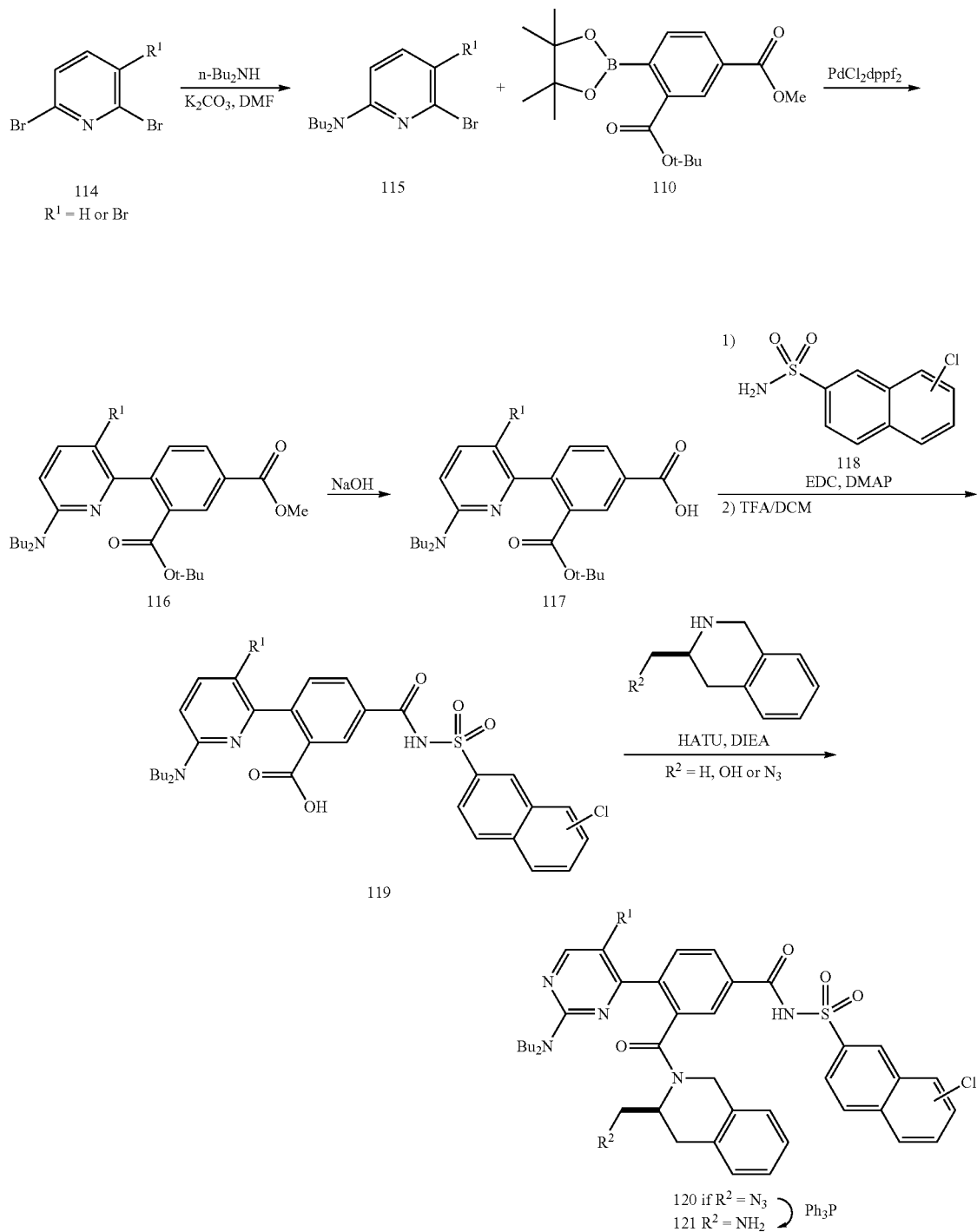

Aminopyrimidine analogs can be prepared using the synthetic routes outlined in Schemes 25 and 26. Commercially available trisubstituted pyrimidines 122 can be converted to biaryl compounds, such as 123, via Suzuki coupling reactions with boronic ester Intermediate 113 (prepared in Scheme 23). Displacement of the chlorine with various amines, followed by hydrolysis of the ester and coupling with substituted sulfonamides can be accomplished using the chemistry previously outlined in Scheme 24.

Scheme 25

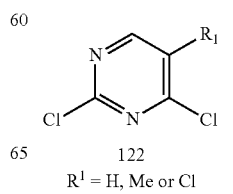

122
$R^1$ = H, Me or Cl

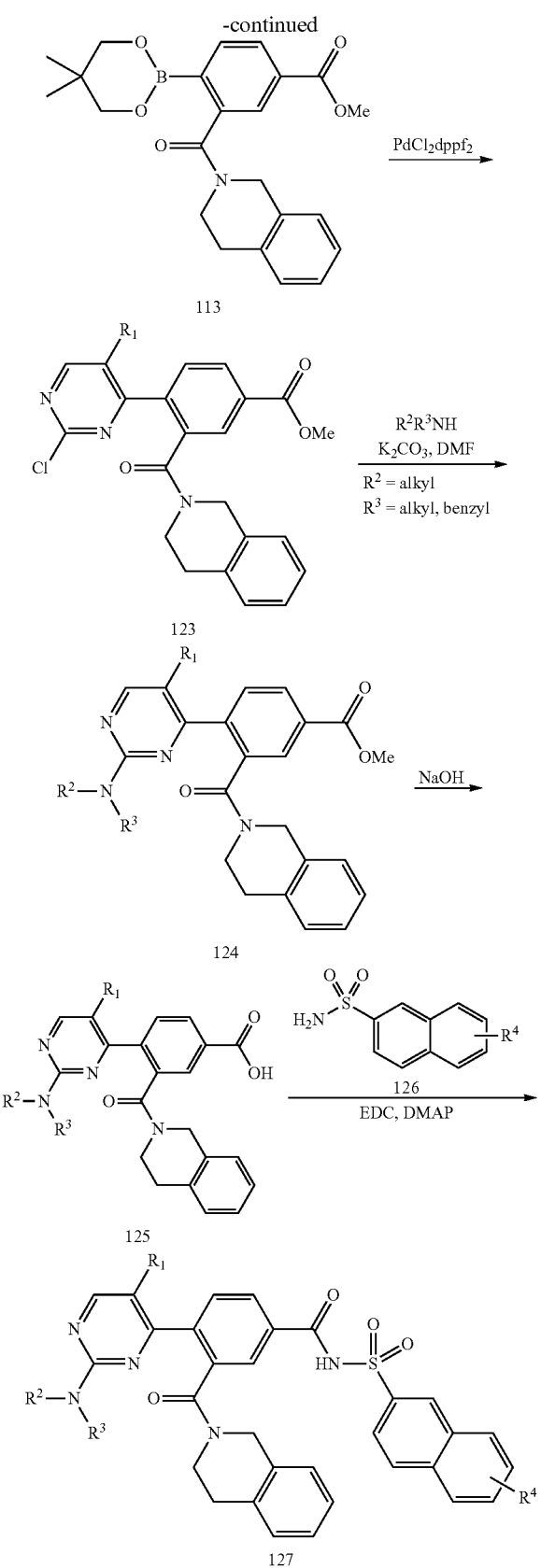

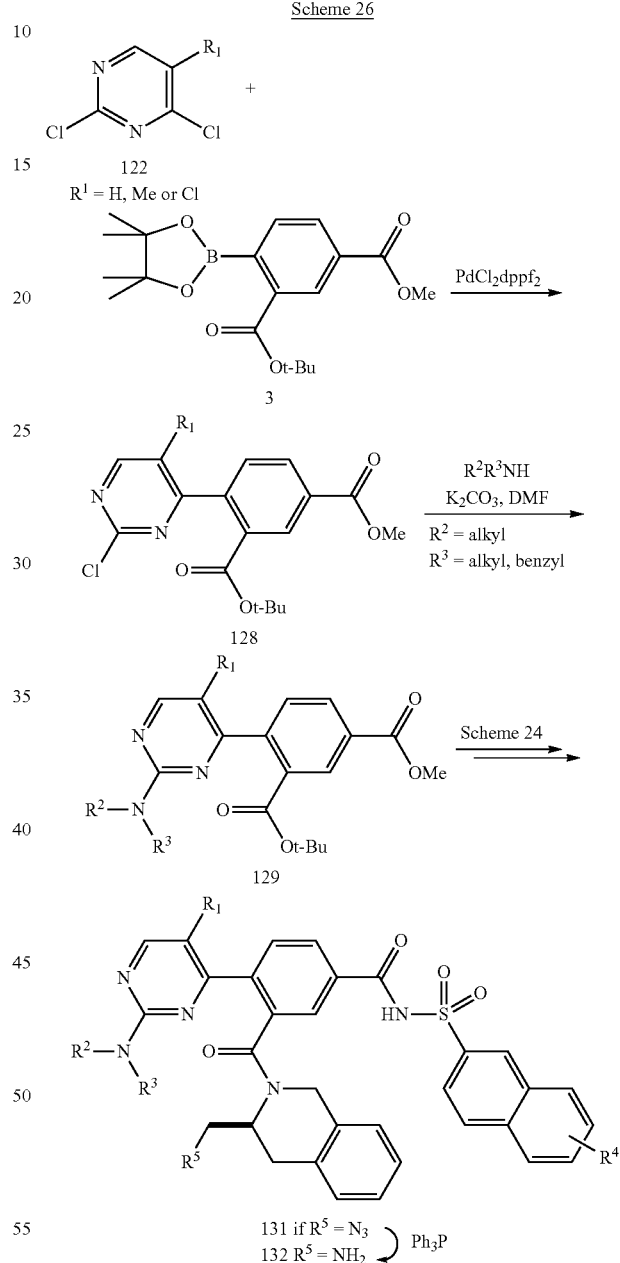

Scheme 26. From dichloropyrimidine 122, Suzuki coupling with boronic ester Intermediate 110 (prepared in Scheme 22) can provide biaryl compound 128. Subsequent conversion to the dialkylamine and elaboration to the final products 130 and 131 can be achieved using chemistry previously described in Scheme 24.

Alternatively, aminopyrimidine compounds such as 130 and 131 can be synthesized according to the route outlined in Trisubstituted imidazole analogs, such as compound 138, can be prepared using the synthetic routes outlined in Schemes 27-31. Commercially available methyl 1H-imidazole-4-carboxylate (132, Maybridge) is SEM protected using an appropriate base such as sodium hydride and selectively brominated using radical bromination methods such as NBS to give bromoimidazole 134. Hydrolysis using aqueous base followed by HATU-mediated amide coupling with suitable amides such as dibutylamine provides imidazole 135. Intermediate 136 is then obtained through Suzuki coupling of imidazole 135 with Intermediate 113 (prepared in Scheme 23). Various alkylations are performed on the imidazole nitrogen by removing the SEM group with suitable reagents such as TFA and coupling a desired alkyl halide such as methyl iodide using an appropriate base such as potassium carbonate to give compound 137. Following procedures previously outlined in Scheme 2, various naphthylsulfonamides 13 can be installed to afford compounds with general structure 138.

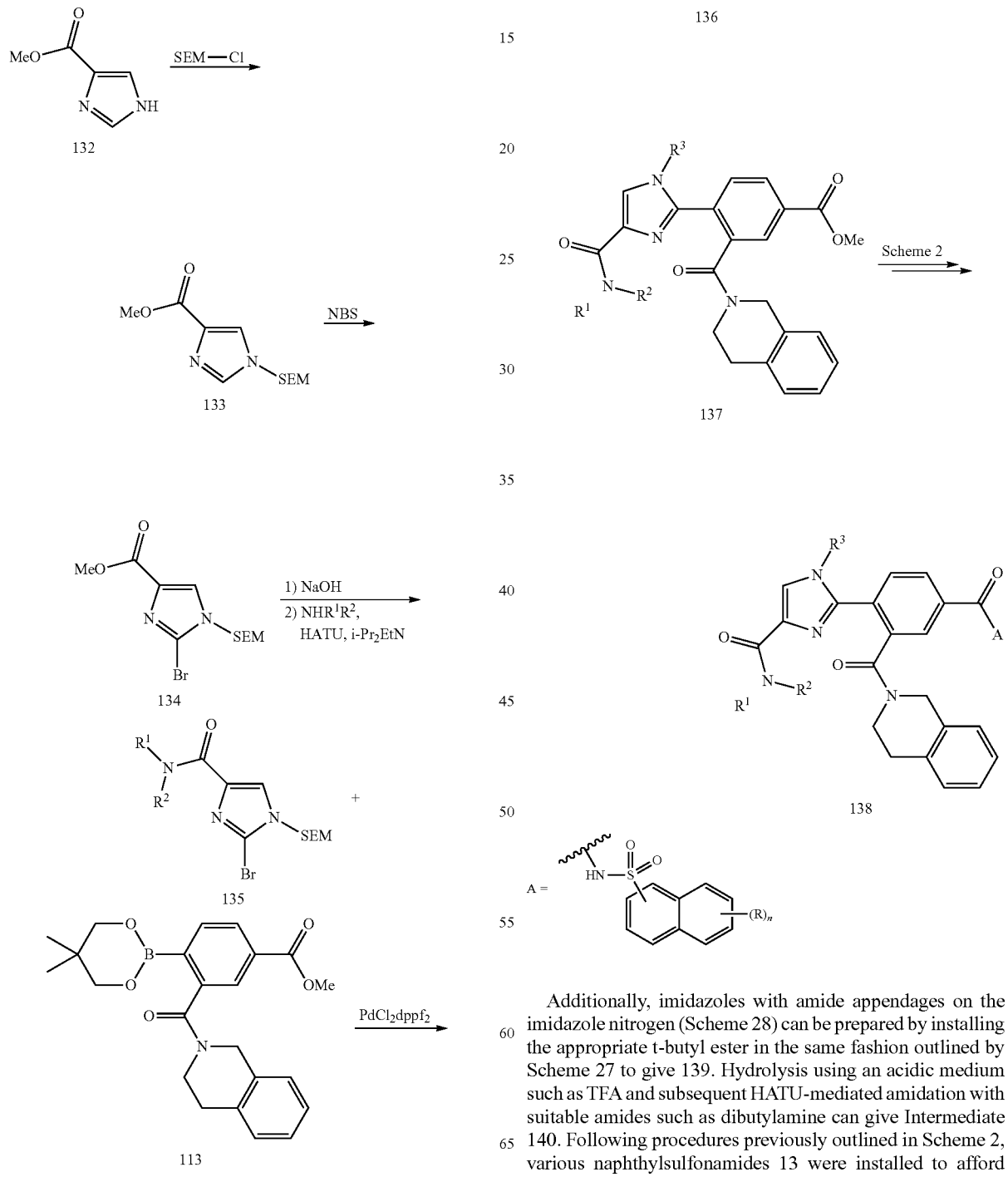

Additionally, imidazoles with amide appendages on the imidazole nitrogen (Scheme 28) can be prepared by installing the appropriate t-butyl ester in the same fashion outlined by Scheme 27 to give 139. Hydrolysis using an acidic medium such as TFA and subsequent HATU-mediated amidation with suitable amides such as dibutylamine can give Intermediate 140. Following procedures previously outlined in Scheme 2, various naphthylsulfonamides 13 were installed to afford compounds of general structure 141.

Scheme 28

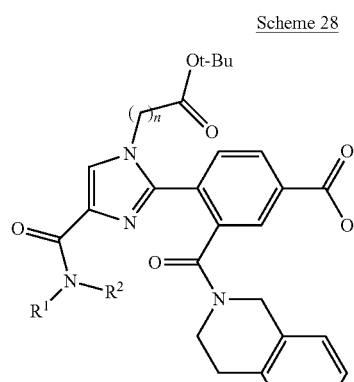

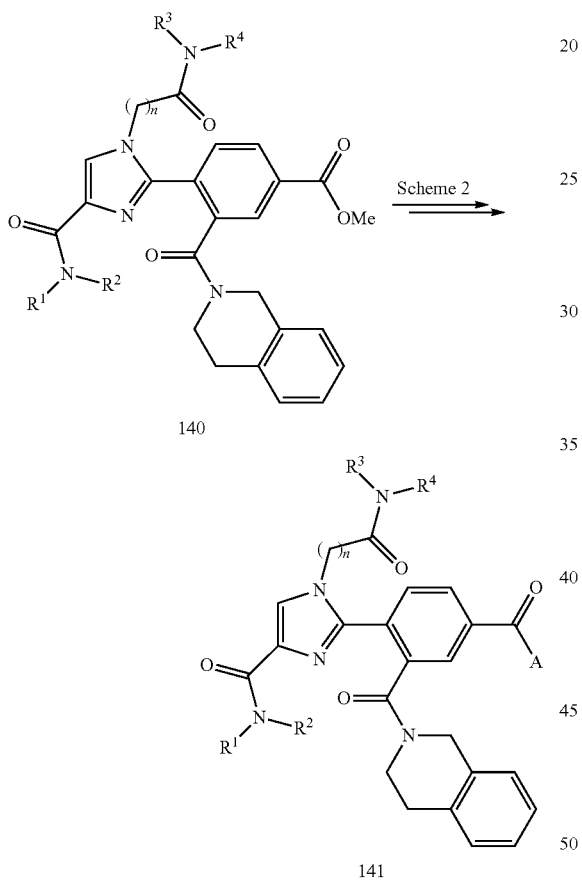

A = 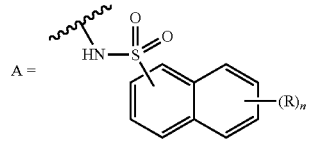

Alternatively, substituted tetrahydroisoquinoline derivatives such as 145 can be synthesized according to the route outlined in Scheme 29. Intermediate 142 is accessed by reacting compound 107 with benzyl bromide and a suitable base such as potassium hydrogen carbonate. Using methods described in Scheme 22, boronic ester 143 is subsequently obtained. Following the procedures for imidazole coupling described in Scheme 27 can afford compounds such as 144. Lastly, using synthetic steps in Scheme 2, substituted tetrahydroisoquinolines and naphthylsulfonamides were installed in the appropriate locations to give compound 145.

Scheme 29

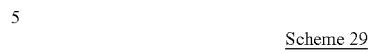

Incorporation of alcohol tethers on the imidazole nitrogen (Scheme 30) can be achieved by installing the desired t-butyl-dimethylsilanol in the same fashion outlined in Scheme 27 to give 146. Leveraging procedures from Scheme 2, substituted tetrahydroisoquinolines and naphthylsulfonamides can be installed in their appropriate locations to afford compound 147. Analogs encompassed by compound 148 may be obtained by removing the silyl protecting groups with a suitable acid such as concentrated hydrochloric acid.

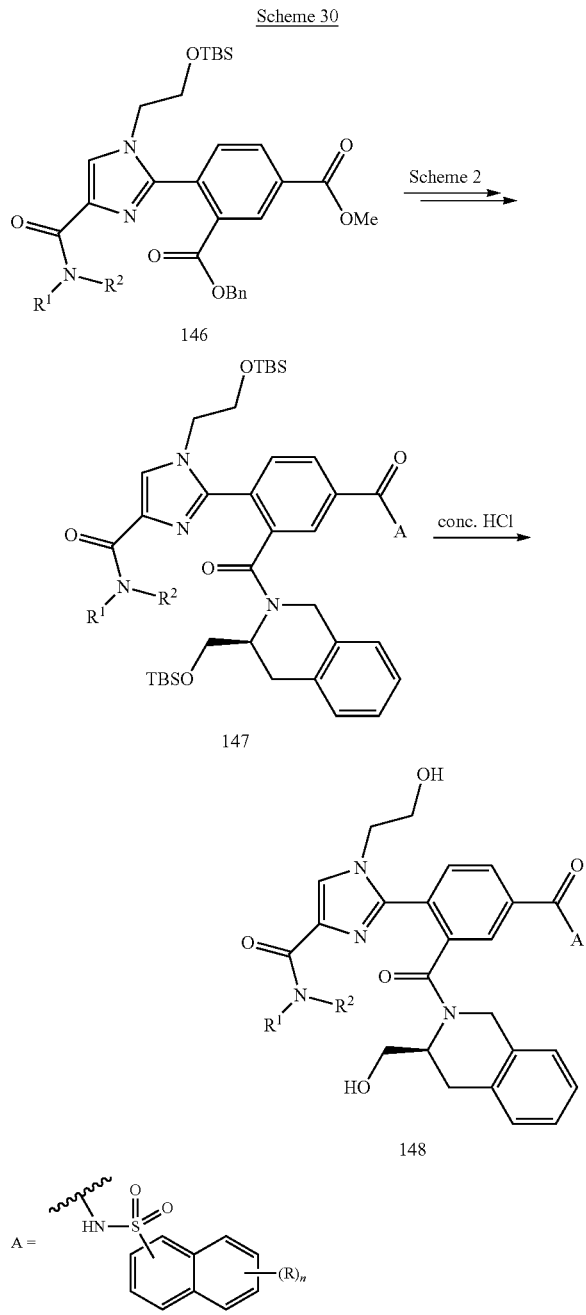

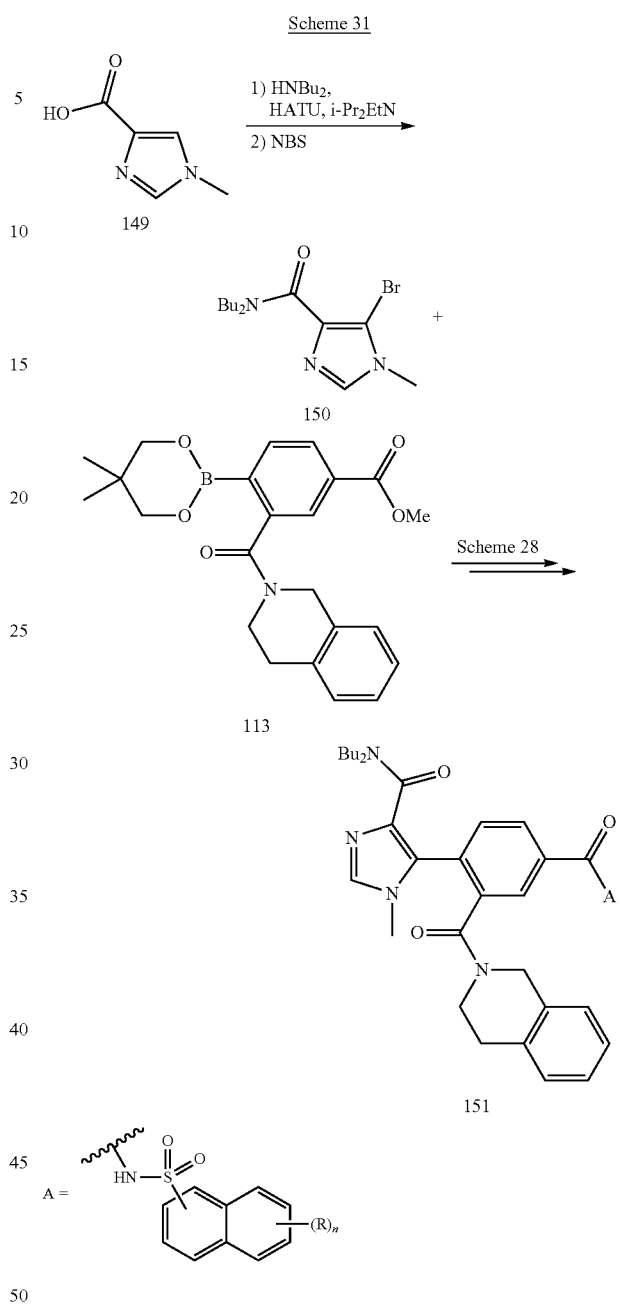

Regioisomeric imidazoles can be accessed through the synthetic route shown in Scheme 31. Amide 150 can be obtained from the commercially available carboxylic acid 149 using similar amide formation and bromination procedures from Scheme 27, where the site of bromination changes as a function of the imidazole substitution. Also, following methods used in Scheme 27, Intermediates 150 and 113 were coupled together and appropriately manipulated to give compounds of structure 151.

Fully functionalized, regioisomeric pyrazole analogs 160 can be accessed through the synthetic routes outlined in Schemes 32-34. Iodination of the commercially available benzoic acid 152 (Matrix) in the presence of iodine, palladium (II) acetate, (diacetoxyiodo)benzene and tetrabutylammonium iodide provides iodide 153. Coupling of Intermediate 153 with substituted tetrahydroisoquinoline derivatives, followed by palladium-mediated carbonylation of the requisite Intermediate 154 furnishes aldehyde 155. Treatment of Intermediate 155 with substituted nitro alkane derivatives gives Intermediate 156. The alcohol of compound 156 can be acetylated with acetic anhydride and upon elimination affords alkene 157. Treatment of 157 with various ethyl 2-(2-phenylhydrazono)acetate derivatives in the presence of potassium t-butoxide provides pyrazoles 158. Hydrolysis of the t-butyl ester moiety of 158, followed by coupling of substituted sulfonamide derivatives in the presence of a coupling reagent, such as EDC furnishes the desired acylsulfonamides 160.
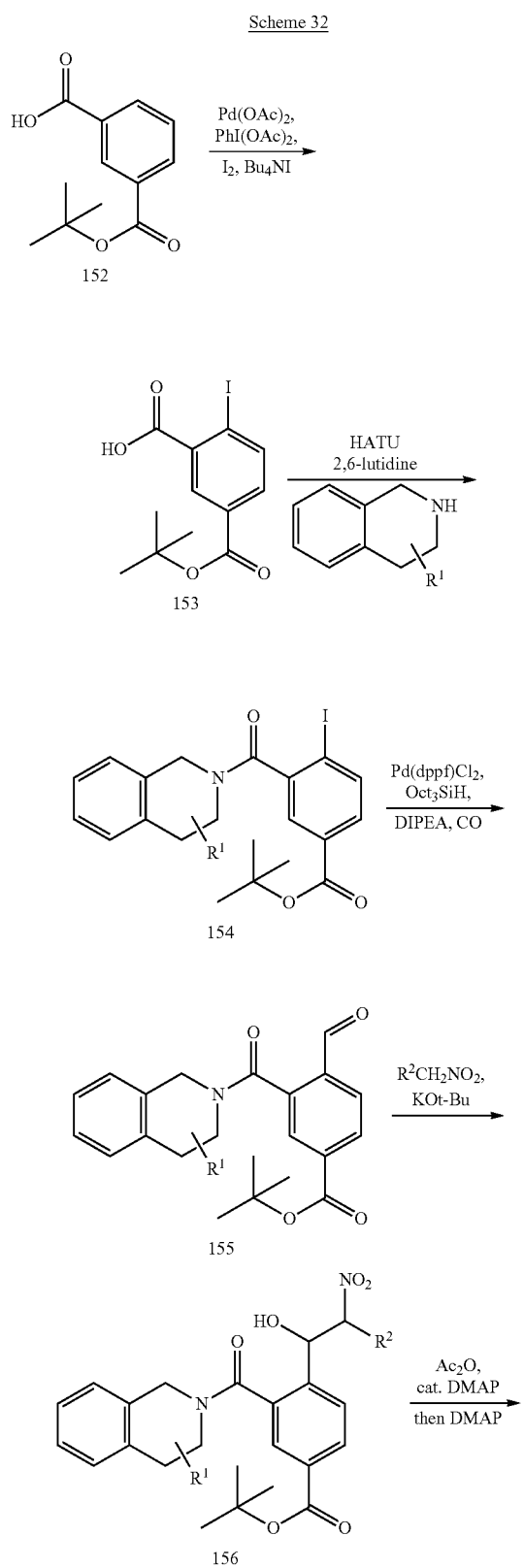
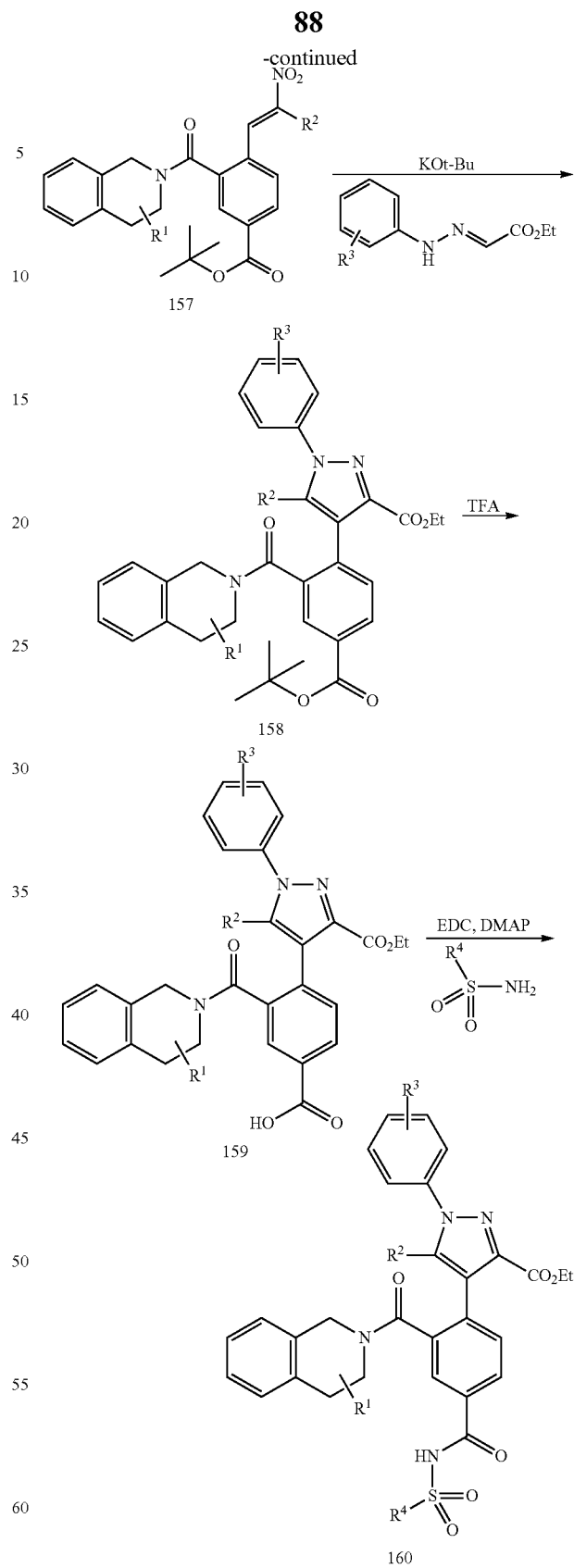
Reduction or base-mediated hydrolysis of the ester moiety of pyrazoles 160 provides the desired alcohols 161 and carboxylic acid derivatives 162, respectively (Scheme 33 and 34).

Scheme 33

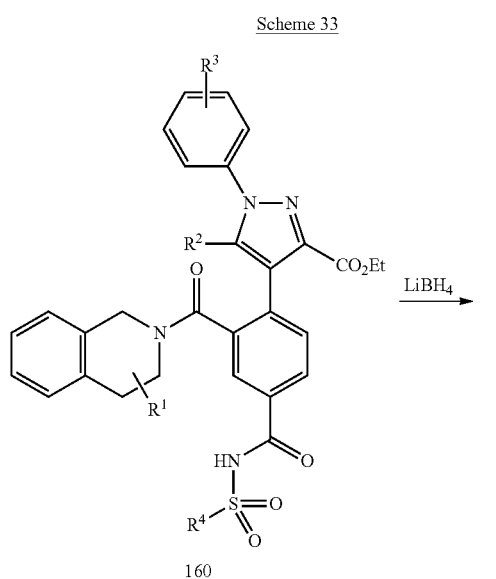

Scheme 34

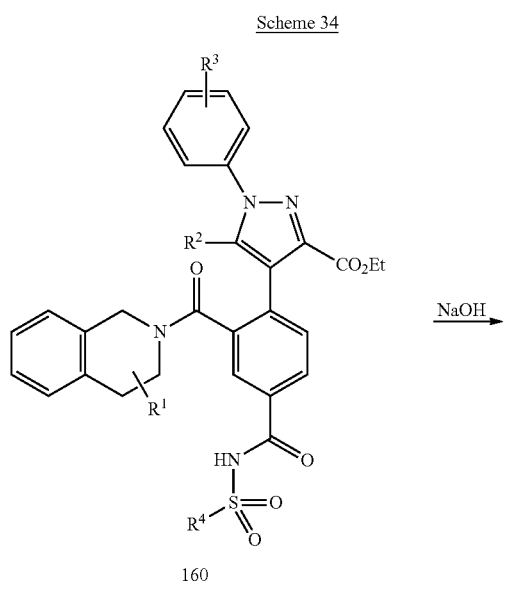

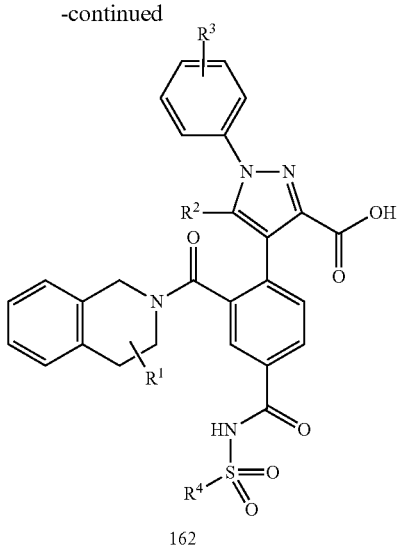

EXAMPLES

All reactions were carried out with continuous magnetic stirring under an atmosphere of dry nitrogen or argon. All evaporations and concentrations were carried out on a rotary evaporator under reduced pressure. Commercial reagents were used as received without additional purification. Solvents were commercial anhydrous grades and were used without further drying or purification. Flash chromatography was performed using prepacked REDISEP® $R_f$ silica gel columns on a CombiFlash Companion machine.

Preparative Reverse Phase (RP) HPLC was performed with a linear gradient elution using $H_2O$/MeOH or $H_2O$/MeCN mixtures buffered with 0.1% trifluoroacetic acid or 10 mM $NH_4OAc$ and detection at 220 nm on one of the following columns: Shimadzu Sunfire S10 30×250 mm (flow rate=40 mL/min), or C18 PHENOMENEX® Luna S5 ODS 21×100 mm (flow rate=20 mL/min), or YMC S5 ODS 20×100 mm (flow rate=20 mL/min) or Waters XBridge C18 19×250 mm (flow rate=20 mL/min).

All final products were characterized by $^1H$ NMR, RP HPLC and electrospray ionization (ESI) or atmospheric pressure ionization (API) mass spectrometry (MS). $^1H$ NMR spectra were obtained a 500 MHz or a 400 MHz Bruker instrument. Field strengths are expressed in units of δ (parts per million, ppm) relative to the solvent peaks, and peak multiplicities are designated as follows: s, singlet; d, doublet; dd, doublet of doublets; t, triplet; q, quartet; sxt, sextet; br s, broad singlet; m, multiplet.

ABBREVIATIONS

Ac acetyl
AcOH acetic acid
$Ac_2O$ acetic anhydride
aq. aqueous
Bn benzyl
Boc t-butyl carbamate
$Boc_2O$ di-t-butyl dicarbonate
Bu butyl
$Bu_4NI$ tetrabutylammonium iodide
CDI 1,1'-carbonyldiimidazole
conc. concentrated DBU 1,8-diazabicyclo[5.4.0]undec-7-ene
DCE dichloroethane
DCM dichloromethane
DDQ 2,3-dichloro-5,6-dicyano-1,4-benzoquinone
DIAD diisopropyl azodicarboxylate
DIEA diisopropylethylamine
DMAP 4-N,N-dimethylaminopyridine
DMF dimethyl formamide
DMSO dimethyl sulfoxide
EDC 1-(dimethylaminopropyl)-3-ethylcarbodiimide hydrochloride
Et ethyl
EtOAc ethyl acetate
EtOH ethanol
$Et_2O$ diethyl ether
$Et_3N$ triethyl amine
h hour(s)
HATU O-(7-azabenzotriazol-1-yl)-N,N,N',N'-tetramethyluronium hexafluorophosphate
$HNBu_2$ dibutyl amine
$H_2NNHBn$ 1-benzylhydrazine
HOBT hydroxybenzotriazole
HPLC high pressure liquid chromatography
i-PrOH isopropanol
i-$Pr_2EtN$ di(isopropyl)ethylamine
KOAc potassium acetate
m minute(s)
m-CPBA m-chloro-3-chloroperbenzoic acid
Me methyl
MeCN acetonitrile
MeOH methanol
$Me_2NH$ dimethyl amine
MTBE methyl tert-butyl ether
Na(OAc)$_3$BH sodium triacetoxyborohydride
NaSEt sodium ethanethiolate
NBS N-bromosuccinimide
n-BuLi n-butyl lithium
NCS N-chlorosuccinimide
NMO N-methylmorpholine-N-oxide
NMP n-methylpyrrolidinone
NMR nuclear magnetic resonance
OTBDPS tert-butyldiphenylsilyloxy
OTf trifluoromethylsulfonyloxy
Pd/C palladium on carbon
Pd(dppf)$_2$Cl$_2$ [1,1'-bis(diphenylphosphino)ferrocene]dichloropalladium(II)
Pd(OAc)$_2$ palladium acetate
Pd(PPh$_3$)$_4$ tetrakis(triphenylphosphine)palladium
Pd$_2$(dba)$_3$ tris(dibenzylideneacetone)dipalladium(0)
Ph phenyl
PhI(OAc)$_2$ phenyl iodoacetate
PhMe toluene
PPh$_3$ triphenyl phosphorus
sat. saturated
SEM (trimethylsilyl)ethoxy)methyl
SEM-Cl (trimethylsilyl)ethoxy)methyl chloride
TBAF tetrabutylammonium fluoride
TBAI tetrabutylammonium iodide
TBSO tert-butyldimethylsilyloxy
t-Bu tertiary butyl
t-BuOH tertiary butanol
t-BuOK potassium tertiary-butoxide
tert-BuOH tertiary butanol
TFA trifluoroacetic acid
Tf$_2$O trifluoromethylsulfonic anhydride
THF tetrahydrofuran
TMS trimethylsilyl
THP tetrahydro-2H-pyran-2-yl
TMS-OTf trimethylsilyl triflate
TsO p-toluenesulfonyl Example 1

N,N-Dibutyl-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide

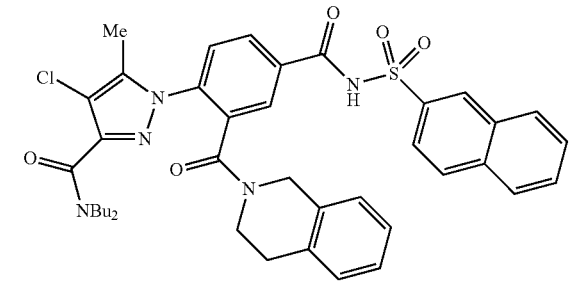

(1)

Intermediate 1A

Ethyl 4-chloro-5-methyl-1H-pyrazole-3-carboxylate

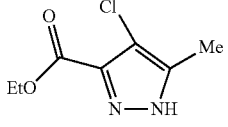

(Int-1A)

To a solution of ethyl 5-methyl-1H-pyrazole-3-carboxylate (Maybridge, 4.41 g, 28.6 mmol) in DMF (14 mL) was added N-chlorosuccinimide (3.86 g, 28.9 mmol). The resulting solution was heated at 60° C. for 3 h and then cooled to room temperature. Water was added until a white precipitate formed, and the solid was collected by filtration washing with water. The solid was dissolved in CH$_2$Cl$_2$, washed with water (2×), dried over MgSO$_4$ and concentrated in vacuo to provide the title compound (5.14 g, 90%) as a white solid. $^1$H NMR (CDCl$_3$) δ 8.03 (s, 1H), 4.42 (q, J=7.0 Hz, 2H), 2.32 (s, 3H), 1.42 (t, J=7.1 Hz, 3H); MS(ESI$^+$) m/z 188.9 (M+H)$^+$.

Intermediate 1B

N,N-Dibutyl-4-chloro-5-methyl-1H-pyrazole-3-carboxamide

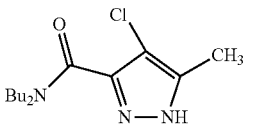

(Int-1B)

To a solution of n-butylamine (900 µL, 5.30 mmol) in THF (4.0 mL) was added n-BuLi (5.0 mL, 7.95 mmol, 2.5M solution in hexanes) at −78° C. After stirring at −78° C. for 30 min, a solution of ethyl 4-chloro-5-methyl-1H-pyrazole-3-carboxylate (500 mg, 2.65 mmol) in 2.0 mL of THF was added dropwise via syringe. The reaction mixture was allowed to warm to room temperature overnight and quenched with sat. aq. NH$_4$Cl solution. The aqueous layer was extracted with CH$_2$Cl$_2$ (3×), and the combined organic extracts were dried over Na$_2$SO$_4$, filtered and concentrated in vacuo to give a crude oil. Purification using flash column chromatography (gradient from 0% to 7% MeOH/CH$_2$Cl$_2$) provided the title compound (589 mg, 82%) as a colorless oil. $^1$H NMR (CD$_3$OD) δ 3.51 (t, J=7.4 Hz, 2H), 3.38-3.32 (m, 2H), 1.68-1.62 (m, 2H), 1.56-1.50 (m, 2H), 1.45-1.38 (m, 2H), 1.22-1.15 (m, 2H) 0.98 (t, J=7.4 Hz, 3H), 0.81 (t, J=7.4 Hz, 3H); MS(ESI$^+$) m/z 272.1 (M+H)$^+$.

Intermediate 1C (3,4-Dihydroisoquinolin-2(1H)-yl)(2-fluoro-5-iodophenyl)methanone (Int-1C)

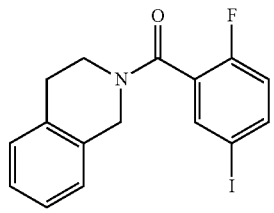

To a suspension of 2-fluoro-5-iodobenzoic acid (Aldrich, 5.27 g, 19.8 mmol) in CH$_2$Cl$_2$ (35.0 mL) was added oxalyl chloride (14.9 mL, 29.7 mmol, 1M solution in CH$_2$Cl$_2$) followed by 2 drops of DMF via syringe. Gas evolution was initiated and the resulting mixture was stirred at room temperature for 2 h. The reaction mixture was then quenched with sat. aq. NH$_4$Cl solution and extracted with EtOAc (3×). The combined organic extracts were dried over Na$_2$SO$_4$, filtered and concentrated in vacuo to give crude 2-fluoro-5-iodobenzoyl chloride which was used directly in the next step.

The crude product obtained above was dissolved in CH$_2$Cl$_2$ (49.6 mL) and cooled to 0° C. To the solution were added 1,2,3,4-tetrahydroisoquinoline (2.7 mL, 21.8 mmol) followed by 2,6-lutidine (4.6 mL, 39.7 mmol). The resulting reaction mixture was stirred at room temperature for 1 h. The reaction mixture was washed 1N HCl (2×) and the organic layer was extracted with CH$_2$Cl$_2$ (2×). The combined organic extracts were washed with sat. aq. NaCl solution and dried over Na$_2$SO$_4$. Filtration and concentration in vacuo provided the title compound (7.55 g, 95%) as a viscous, yellow oil. $^1$H NMR (CDCl$_3$, 1.5:1 mixture of amide rotamers) δ 7.78-7.66 (m, 2H), 7.26-7.12 (m, 3.5H), 6.98-6.86 (m, 1.5H), 4.92 (s, 1.5H), 4.50 (br s, 0.5H), 3.65-3.52 (m, 1.5H), 3.04-2.95 (m, 1H), 2.92-2.82 (m, 1.5H); MS(ESI$^+$) m/z 382.1 (M+H)$^+$.

Intermediate 1D

Ethyl 4-fluoro-3-(1,2,3,4-tetrahydroisoquinoline-2-carbonyl)benzoate (Int-1D)

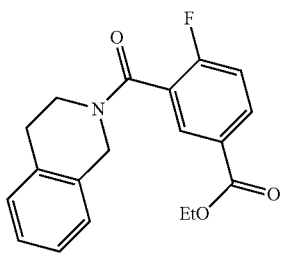

To 2-neck round bottom flask equipped with a reflux condenser was added (3,4-dihydroisoquinolin-2(1H)-yl)(2-fluoro-5-iodophenyl)methanone (8.39 g, 22.0 mmol) and MeCN (65.0 mL). Et$_3$N (6.2 mL, 44.0 mmol), EtOH (6.4 mL, 110 mmol, 200 proof) and Pd(dppf)$_2$Cl$_2$ (1.29 g, 1.76 mmol) were then added, and a 3-way stopcock was attached to the reflux condenser with one outlet connected to a balloon and the other connected to a CO tank. The flask was evacuated and purged with CO from the balloon (3×), and then heated at 75° C. under CO for 7 h. The reaction mixture was then concentrated in vacuo and the residue was purified by flash chromatography (gradient from 0% to 40% EtOAc/hexanes) to afford the title compound (5.52 g, 77%) as a clear, tan oil. $^1$H NMR (CDCl$_3$, 1.5:1 mixture of amide rotamers) δ 8.20-8.07 (m, 1.5H), 7.26-7.10 (m, 5H), 6.92 (d, J=7.3 Hz, 0.5H), 4.95 (s, 2H), 4.50 (br s, 1H), 4.42-4.35 (m, 2H), 3.57 (t, J=5.7 Hz, 1H), 3.00 (t, J=5.9 Hz, 1H), 2.88 (t, J=5.6 Hz, 1H), 1.42-1.36 (m, 3H); MS(ESI$^+$) m/z 328.2 (M+H)$^+$.

Intermediate 1E

Ethyl 4-(4-chloro-3-(dibutylcarbamoyl)-5-methyl-1H-pyrazol-1-yl)-3-(1,2,3,4-tetrahydroisoquinoline-2-carbonyl)benzoate (Int-1E)

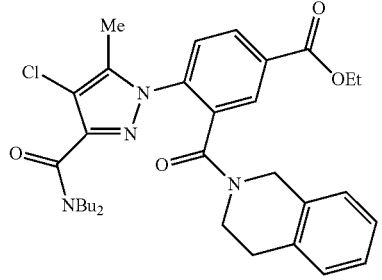

To a solution of ethyl 4-fluoro-3-(1,2,3,4-tetrahydroisoquinoline-2-carbonyl)benzoate (645 mg, 1.97 mmol) and N,N-dibutyl-4-chloro-5-methyl-1H-pyrazole-3-carboxamide (1.07 g, 3.94 mmol) in NMP (9.9 mL) was added K$_2$CO$_3$ (1.09 g, 7.88 mmol). The resulting reaction mixture was stirred at 125° C. for 3 h, cooled to room temperature and quenched with 10% aq. LiCl solution. The solution was extracted with EtOAc (3×) and the combined organic extracts were washed with 10% LiCl (3×), dried over Na$_2$SO$_4$, filtered and concentrated in vacuo. The residue was purified by flash chromatography (25% EtOAc/CHCl$_3$) to afford the title compound (930 mg, 81%). $^1$H NMR (DMSO-d$_6$, 2:1 mixture of amide rotamers) δ 8.32 (s, 0.5H), 8.23-8.13 (m, 1H), 8.11-8.00 (m, 1H), 7.76-7.87 (m, 0.5H), 7.28-7.08 (m, 3.5H), 7.03-6.94 (m, 0.5H), 4.87-4.51 (m, 2H), 4.43-4.27 (m, 2.5H), 3.86-3.75 (m, 0.5H), 3.63-3.32 (m, 3H), 3.23-3.07 (m, 1H), 3.05-2.94 (m, 1H), 2.85-2.62 (m, 2H), 2.27 (s, 2H), 2.22 (s, 1H), 1.48-1.09 (m, 9H), 1.04-0.92 (m, 2H), 0.90-0.82 (m, 3H), 0.70-0.63 (m, 3H); MS(ESI$^+$) m/z 579.4 (M+H)$^+$.

Intermediate 1F 4-(4-Chloro-3-(dibutylcarbamoyl)-5-methyl-1H-pyrazol-1-yl)-3-(1,2,3,4-tetrahydroisoquinoline-2-carbonyl)benzoic acid

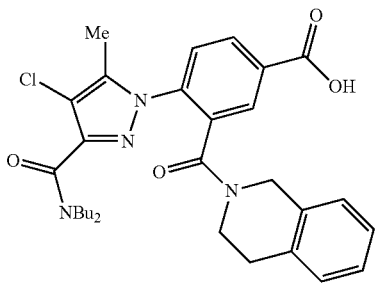
(Int-1F)

To a solution of ethyl 4-(4-chloro-3-(dibutylcarbamoyl)-5-methyl-1H-pyrazol-1-yl)-3-(1,2,3,4-tetrahydroisoquinoline-2-carbonyl)benzoate (930 mg, 1.61 mmol) in EtOH (5.0 mL) and THF (5.0 mL) was added 2N NaOH (4.0 mL, 8.03 mmol). The resulting reaction mixture was stirred at 40° C. for 1 h, cooled to room temperature and quenched with 6N HCl. The solution was extracted with CHCl$_3$ (3×), and the combined organic extracts were dried over Na$_2$SO$_4$, filtered and concentrated in vacuo to afford the title compound (885 mg, 99%), which was used without further purification. $^1$H NMR (DMSO-d$_6$, 2:1 mixture of amide rotamers) δ 8.32 (s, 0.5H), 8.14 (dd, J=8.36, 1.98 Hz, 1H), 8.07-7.98 (m, 1H), 7.83-7.72 (m, 1H), 7.28-7.06 (m, 3H), 7.03-6.93 (m, 0.5H), 4.86-4.68 (m, 0.5H), 4.65-4.47 (m, 1H), 4.42-4.24 (m, 0.5H), 3.88-3.70 (m, 0.5H), 3.66-3.34 (m, 3.5H), 3.23-3.06 (m, 1H), 3.04-2.94 (m, 1H), 2.87-2.70 (m, 2H), 2.26 (s, 2H), 2.21 (s, 1H), 1.47-1.34 (m, 0.5H), 1.33-1.06 (m, 5.5H), 1.01-0.91 (m, 2H), 0.88-0.82 (m, 3H), 0.70-0.62 (m, 3H); MS(ESI$^+$) m/z 551.3 (M+H)$^+$.

Example 1

To a mixture of 4-(4-chloro-3-(dibutylcarbamoyl)-5-methyl-1H-pyrazol-1-yl)-3-(1,2,3,4-tetrahydroisoquinoline-2-carbonyl)benzoic acid (30 mg, 0.054 mmol) and naphthalene-2-sulfonamide (18 mg, 0.087 mmol) in DMF (0.5 mL) and THF (1.0 mL) was added EDC (21 mg, 0.11 mmol) followed by DMAP (20 mg, 0.16 mmol). The resulting reaction mixture was stirred at room temperature for 3 h. The solvents were removed in vacuo and the residue was purified by preparative HPLC to give the title compound (27 mg, 64%). $^1$H NMR (CD$_3$OD, 2:1 mixture of amide rotamers) δ 8.73 (s, 1H), 8.13-8.03 (m, 4H), 8.01 (d, J=8.2 Hz, 1H), 7.99-7.95 (m, 1H), 7.76-7.64 (m, 3H), 7.25-7.05 (m, 3.5H), 6.90 (d, J=7.7 Hz, 0.5H), 5.03-4.87 (m, 1H), 4.68-4.38 (m, 2H), 4.09-3.92 (m, 0.5H), 3.78-3.36 (m, 2.5H), 3.26-2.55 (m, 4H), 2.33 (s, 2H), 2.28 (s, 1H), 1.55-0.86 (m, 12H), 0.76 (t, J=7.4 Hz, 2H), 0.70-0.65 (m, 1H); MS(ESI$^+$) m/z 740.2 (M+H)$^+$.

Intermediate 2

5-Chloronaphthalene-2-sulfonamide

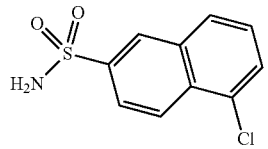
(Int-2)

5-Chloronaphthalene-2-sulfonyl chloride (Toronto, 531 mg, 2.03 mmol) was treated with NH$_3$ (10.2 mL, 5.08 mmol, 0.5M solution in dioxanes) and stirred at room temperature for 1 h. The reaction mixture was concentrated in vacuo, redissolved in sat. aq. NaHCO$_3$ solution and extracted with CHCl$_3$ (3×). The combined organic extracts were dried over Na$_2$SO$_4$, filtered and concentrated in vacuo to give the title compound (200 mg, 37%). $^1$H NMR (DMSO-d$_6$) δ 8.53 (d, J=1.8 Hz, 1H), 8.36 (d, J=9.0 Hz, 1H), 8.18 (d, J=8.6 Hz, 1H), 8.06 (d, J=9.0 Hz, 1H), 7.87 (d, J=7.5 Hz, 1H), 7.70-7.62 (m, 1H); MS(ESI$^-$) m/z 240.3 (M–H)$^-$.

Intermediate 3

6-(Dimethylamino)naphthalene-2-sulfonamide

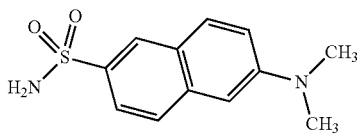
(Int-3)

Following a procedure analogous to the synthesis of Intermediate 2, 6-(dimethylamino)naphthalene-2-sulfonyl chloride (Aldrich, 63 mg, 0.23 mmol) was converted to the title compound (14 mg, 25%). MS(ESI$^-$) m/z 249.4 (M–H)$^-$.

Intermediate 4

5-(Dimethylamino)naphthalene-1-sulfonamide

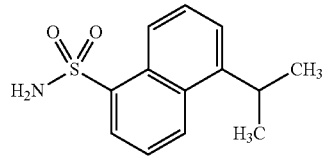
(Int-4)

Following a procedure analogous to the synthesis of Intermediate A in Example 2,5-(dimethylamino)naphthalene-1-sulfonyl chloride (Aldrich, 500 mg, 1.85 mmol) was converted to the title compound (36 mg, 8%). $^1$H NMR (DMSO-d$_6$) δ 8.10 (d, J=8.6 Hz, 1H), 7.96 (d, J=8.6 Hz, 1H), 7.79 (dd, J=13.2, 7.3 Hz, 1H), 7.35-7.13 (m, 4H), 6.93 (d, J=7.3 Hz, 1H), 3.01 (s, 6H); MS(ESI⁻) m/z 249.4 (M−H)⁻.

Intermediate 5

8-Chloronaphthalene-2-sulfonamide

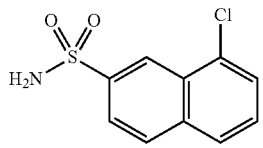

Intermediate 5A

8-Chloronaphthalene-2-sulfonic acid

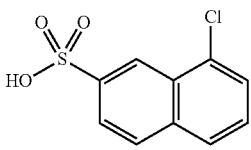

A solution of 8-amino-2-naphthalenesulfonic acid (Aldrich, 1.00 g, 4.48 mmol) in water (3.0 mL) and conc. HCl (7.0 mL) was cooled to 0° C. A solution of NaNO$_2$ (143 μL, 4.48 mmol) in water (3.0 mL) was added dropwise while maintaining the temperature below 5° C. The reaction mixture was stirred at 0° C. for 1 h. In a separate flask, CuCl (214 μL, 8.96 mmol) was dissolved in conc. HCl (7.0 mL) and the solution was cooled to 0° C. The copper solution was added to the diazonium solution at 0° C. in portions to control the gas evolution. The reaction mixture was allowed to stir at 0° C. for 1 h and then at room temperature for 12 h. The reaction mixture was then diluted with 10% aq. NH$_4$Cl solution and extracted with EtOAc (3×). The combined organic extracts were washed again with aq. 10% NH$_4$Cl solution, dried over Na$_2$SO$_4$, filtered and concentrated in vacuo to give the title compound (740 mg, 65%). $^1$H NMR (DMSO-d$_6$) δ 8.43 (s, 1H), 7.95 (dd, J=17.1, 8.5 Hz, 2H), 7.80 (dd, J=8.4, 1.5 Hz, 1H), 7.71 (dd, J=7.5, 1.1 Hz, 1H), 7.57-7.45 (m, 1H); MS(ESI⁻) m/z 241.2 (M−H)⁻.

Intermediate 5

8-Chloronaphthalene-2-sulfonic acid (740 mg, 3.05 mmol) and 2,4,6-trichloro-1,3,5-triazine (562 mg, 3.05 mmol) were stirred in acetone (25.0 mL) at room temperature. Et$_3$N (425 μL, 3.05 mmol) was then added, and the reaction mixture was stirred at reflux overnight. After cooling to room temperature, the reaction mixture was filtered. The filtrate was concentrated in vacuo and used in the next step without further purification.

The crude product obtained above was treated with NH$_3$ (30.3 mL, 0.5M solution in dioxanes) at room temperature. Conc. NH$_4$OH (10.0 mL) was added, and the resulting solution was stirred at room temperature for 1 h. The reaction mixture was concentrated in vacuo to remove the volatiles, and the remaining slurry was treated with water. The solid that precipitated was collected via filtration, washed with water and dried under high vacuum overnight to give the title compound (145 mg, 19%). $^1$H NMR (DMSO-d$_6$) δ 8.66 (br s, 1H), 8.25 (d, J=8.4 Hz, 1H), 8.14-7.93 (m, 2H), 7.87 (d, J=6.8 Hz, 1H), 7.69 (br s, 1H), 7.59 (br s, 2H); MS(ESI⁻) m/z 240.3 (M−H)⁻.

Intermediate 6

6-Chloronaphthalene-2-sulfonamide

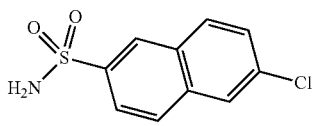

Intermediate 6A

6-Chloronaphthalene-2-sulfonic acid

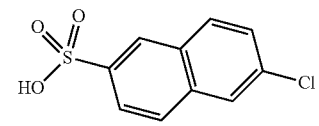

Following a procedure analogous to that for the synthesis of Intermediate 5A, 6-aminonaphthalene-2-sulfonic acid (Aldrich, 2.00 g, 8.96 mmol) was converted to the title compound (760 mg, 33%). $^1$H NMR (DMSO-d$_6$) δ 8.18 (s, 1H), 8.11-7.98 (m, 2H), 7.87 (d, J=8.4 Hz, 1H), 7.76 (d, J=8.4 Hz, 1H), 7.53 (dd, J=8.8, 1.5 Hz, 1H); MS (ESI⁻) m/z 241.2 (M−H)⁻.

Intermediate 6

Following a procedure analogous to that for the synthesis of Intermediate 5, 6-chloronaphthalene-2-sulfonic acid (760 mg, 3.13 mmol) was converted to the title compound (600 mg, 71%). $^1$H NMR (DMSO-d$_6$) δ 8.48 (br s, 1H), 8.37-8.02 (m, 3H), 7.94 (br s, 1H), 7.68 (br s, 1H), 7.60-7.33 (m, 2H).

Intermediate 7

8-Iodonaphthalene-2-sulfonamide

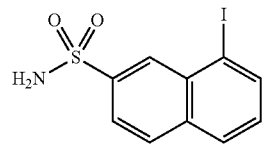

To a solution of KOH (560 mg, 9.99 mmol) in water (16.0 mL) was added 8-amino-2-naphthalenesulfonic acid (Aldrich, 2.23 g, 9.99 mmol) with warming KNO$_2$ (850 mg, 9.99 mmol) was then added. The solution was cooled to room temperature and added dropwise to 1N H$_2$SO$_4$ (14.0 mL, 14.0 mmol) over 35 min at 0° C., keeping the internal temperature at or below 0° C. After stirring for a further 10 min, a solution of KI (2.00 g, 12.1 mmol) in water (10.0 mL) was added dropwise over 5 min. The reaction mixture was then stirred at room temperature for 2 h and then on a steam bath for 1 h. The solution was cooled to room temperature treated with EtOH. The reaction mixture was concentrated to near dryness in vacuo and the remaining slurry was filtered, washing the solids with EtOH. The filtrate was concentrated in vacuo to afford the title compound (2.42 g, 65%) which was used in the next step without further purification. MS(ESI⁻) m/z 333.2 (M−H)⁻.

The crude product obtained above was treated with POCl₃ (30.0 mL, 322 mmol), and the resulting reaction mixture was heated at reflux for 2 h. The reaction mixture was cooled to room temperature and concentrated in vacuo. The residue was azeotroped with PhMe (3×) and then treated with NH₃ (0.5M solution in dioxane) while cooling in an ice bath. Conc. NH₄OH (10.0 mL, 601 mmol) was added, and the reaction mixture was allowed to warm to room temperature. The reaction mixture was concentrated in vacuo, water was added and the solution was acidified with conc. HCl. The solution was saturated with NaCl and extracted with EtOAc (7×). The combined organic extracts were dried over MgSO₄, filtered and concentrated in vacuo to afford the title compound (1.80 g, 71%). $^1$H NMR (DMSO-d₆) δ 8.55-8.51 (m, 1H), 8.28 (dd, J=7.4, 1.0 Hz, 1H), 8.14 (d, J=8.8 Hz, 1H), 8.09 (d, J=8.4 Hz, 1H), 7.94 (dd, J=8.6, 1.8 Hz, 1H), 7.58 (s, 2H), 7.48-7.41 (m, 1H); MS(ESI⁻) m/z 332.3 (M−H)⁻.

Intermediate 8

8-Cyanonaphthalene-2-sulfonamide

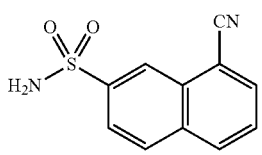

(Int-8)

A solution of 8-iodonaphthalene-2-sulfonamide (Intermediate 7, 100 mg, 0.30 mmol), ZnCN (11 µL, 0.180 mmol) and Pd(PPh₃)₄ (14 mg, 0.012 mmol) in DMF (1.5 mL) was purged with argon for 5 min. The reaction mixture was then heated to 125° C. in a microwave reactor for 30 min. Additional ZnCN (33 µL, 0.54 mmol) and Pd(PPh₃)₄ (280 mg, 0.24 mmol) were added, and the reaction mixture was heated at 125° C. for 12 h. The reaction mixture was cooled to room temperature, diluted with 10% aq. LiCl solution and extracted with EtOAc (3×). The combined organic extracts were dried over Na₂SO₄, filtered and concentrated in vacuo. The residue was purified by preparative HPLC to give the title compound (22 mg, 30%). $^1$H NMR (CD₃OD) δ 8.77 (d, J=0.9 Hz, 1H), 8.35 (d, J=8.4 Hz, 1H), 8.25 (d, J=8.8 Hz, 1H), 8.19 (d, J=7.3 Hz, 1H), 8.14 (d, J=1.8 Hz, 1H), 7.85-7.75 (m, 1H); MS(ESI⁺) m/z 250.1 (M+NH₄)⁺.

Intermediate 9

Ethyl 7-sulfamoyl-1-naphthoate

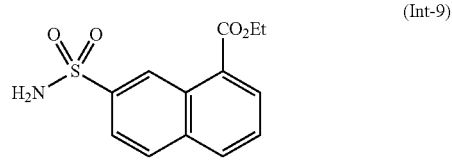 [SMILES: CCOC(=O)c1cccc2ccc(S(N)(=O)=O)cc12]

(Int-9)

To a solution of 8-iodonaphthalene-2-sulfonamide (Intermediate 7, 200 mg, 0.60 mmol) in dioxane (2.0 mL) in a microwave tube was added EtOH (400 µL, 6.00 mmol), molybdenum hexacarbonyl (81 µL, 0.60 mmol) and Pd(OAc)₂ (17 mg, 0.075 mmol). DBU (270 µL, 1.80 mmol) was then added, and the sealed tube was placed in the microwave and heated at 100° C. for 20 min. The reaction mixture was cooled to room temperature and quenched with 10% aq. LiCl solution. The solution was extracted with EtOAc (3×). The combined organic extracts were dried over Na₂SO₄, filtered and concentrated in vacuo. The residue was purified using preparative HPLC to give the title compound (22 mg, 13%). $^1$H NMR (CD₃OD) δ 9.54 (d, J=0.9 Hz, 1H), 8.31 (dd, J=7.4, 1.2 Hz, 1H), 8.20 (d, J=8.4 Hz, 1H), 8.13 (d, J=8.8 Hz, 1H), 8.00 (dd, J=8.7, 1.9 Hz, 1H), 7.72 (dd, J=8.2, 7.4 Hz, 1H), 4.50 (q, J=7.0 Hz, 2H), 1.48 (t, J=7.2 Hz, 3H); MS (ESI⁻) m/z 278.4 (M−H)⁻.

Intermediate 10

7-Chloronaphthalene-2-sulfonamide

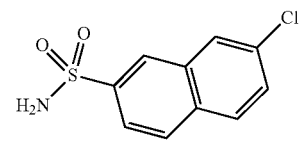

(Int-10)

Intermediate 10A

7-Chloronaphthalene-2-sulfonic acid

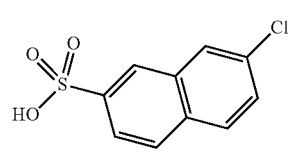

(Int-10A)

A solution of sodium 7-aminonaphthalene-2-sulfonate (Pfaltz and Bauer, 1.00 g, 4.08 mmol) in water (6.0 mL) and conc. HCl (6.0 mL) was cooled to 0° C. A premixed solution of NaNO$_2$ (295 mg, 4.28 mmol) in water (3.0 mL) was added slowly, maintaining the temperature close to 0° C. The resulting reaction mixture was stirred at room temperature for 30 min. A solution of CuCl (807 mg, 8.16 mmol) in water (1.0 mL) and conc. HCl (4.0 mL) was then added dropwise over 30 min, maintaining the temperature close to 0° C. The reaction mixture was stirred at room temperature for 2 h, then concentrated in vacuo and dissolved in a small amount of water. The solids were filtered off and retained. The filtrate was concentrated in vacuo, purified by preparative HPLC and combined with the filtered solids to give the title compound (843 mg, 85%) as a dark grey solid. MS(ESI$^-$) m/z 241.2 (M−H)$^-$.

Intermediate 10

Following a procedure analogous to that for the synthesis of Intermediate 5, 7-chloronaphthalene-2-sulfonic acid (500 mg, 2.06 mmol) was converted to the title compound (84 mg, 17%). MS(ESI$^-$) m/z 240.3 (M−H)$^-$.

Intermediate 11

7-Iodonaphthalene-2-sulfonamide

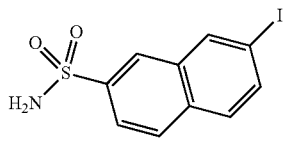

(Int-11)

Intermediate 11A

7-Iodonaphthalene-2-sulfonic acid

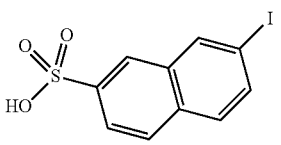

(Int-11A)

A solution of sodium 7-aminonaphthalene-2-sulfonate (Pfaltz and Bauer, 1.00 g, 4.06 mmol) in water (6.0 mL) and conc. HCl (2.0 mL) was cooled to 0° C. A premixed solution of NaNO$_2$ (280 mg, 4.06 mmol) in water (2.0 mL) was added slowly, maintaining the temperature close to 0° C. The reaction mixture was stirred at 0° C. for 1 h. A solution of NaI (609 mg g, 4.06 mmol) in water (3.0 mL) and conc. HCl (1.0 mL) was then added dropwise over 30 min, maintaining a temperature close to 0° C. The reaction mixture was stirred at room temperature for 2 h and then heated to 90° C. for 1 h. The reaction mixture was cooled to room temperature, treated with EtOH (10.0 mL) and concentrated in vacuo. EtOH (10 mL) was added and the mixture was filtered to give the title compound (1.07 g, 79%) as a tan solid. $^1$H NMR (DMSO-d$_6$) δ 8.45 (s, 1H), 8.09 (s, 1H), 8.76 (d, J=8.6 Hz, 1H), 7.80-7.68 (m, 3H); MS(ESI$^-$) m/z 333.2 (M−H)$^-$.

Intermediate 11

7-Iodonaphthalene-2-sulfonic acid (650 mg, 1.95 mmol) was treated with POCl$_3$ (5.0 mL, 53.6 mmol), and the resulting reaction mixture was heated at reflux for 2 h. The reaction mixture was cooled to room temperature and concentrated in vacuo. The residue was azeotroped with PhMe (3×) and then treated with NH$_3$ (6.0 mL, 277.0 mmol, 0.5M solution in dioxane) while cooling in an ice bath. Conc. NH$_4$OH (6.0 mL) was added, and the reaction mixture was allowed to warm to room temperature. The reaction mixture was concentrated in vacuo, water was added and the solution was acidified with conc. HCl (pH=4). The solution was saturated with NaCl and extracted with EtOAc (7×). The combined organic extracts were dried over MgSO$_4$, filtered and concentrated in vacuo to afford the title compound (300 mg, 46%). $^1$H NMR (CDCl$_3$) δ 8.37 (br s, 2H), 7.99-7.85 (m, 3H), 7.66 (d, J=8.6 Hz, 1H); MS(ESI$^-$) m/z 332.2 (M−H)$^-$.

Intermediate 12

5-Nitronaphthalene-1-sulfonamide

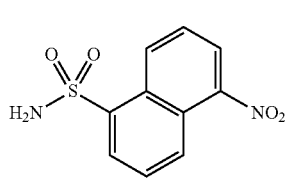

(Int-12)

To a solution of nitronaphthalene (2.1 g, 12.1 mmol) in CH$_2$Cl$_2$ (50.0 mL) at 0° C. was added chlorosulfonic acid (5.0 mL, 75 mmol) dropwise. The resulting red solution was allowed to warm to room temperature overnight and then poured over ice. The layers were separated and the aqueous layer was extracted with EtOAc (3×). The combined organic extracts were washed with sat. aq. NaCl solution, dried over Na$_2$SO$_4$, filtered and concentrated in vacuo. The residue was treated with NH$_3$ (0.5M solution in dioxane) and the resulting solution was stirred at room temperature overnight. The reaction mixture was then treated with EtOH and concentrated in vacuo. The solid was collected via filtration and purified by preparative HPLC to give the title compound (1.00 g, 32%). $^1$H NMR (CD$_3$OD) δ 8.73-8.56 (m, 2H), 8.43 (dd, J=8.1, 1.8 Hz, 2H), 8.19 (dd, J=9.4, 1.8 Hz, 1H), 7.18 (t, J=7.9 Hz, 1H); MS(ESI$^-$) m/z 251.3 (M−H)$^-$.

Intermediate 13

5-Nitronaphthalene-2-sulfonamide

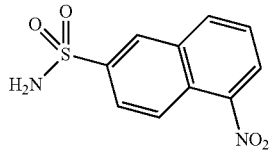

(Int-13)

The filtrate from above (Intermediate 12) was concentrated in vacuo to give the regioisomeric product, 5-nitronaphthalene-2-sulfonamide (1.00 g, 32%). $^1$H NMR (CD$_3$OD) δ 9.12 (d, J=8.8 Hz, 1H), 8.59 (d, J=8.8 Hz, 1H), 8.43 (d, J=7.3 Hz, 1H), 8.30 (d, J=6.8 Hz, 1H), 7.85 (dd, J=8.7, 7.6 Hz, 2H); MS(ESI⁻) m/z 251.3 (M−H)⁻.

Intermediate 14

8-(Ethylsulfonyl)naphthalene-2-sulfonamide

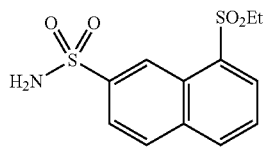

Intermediate 14A 8-(Ethylthio)naphthalene-2-sulfonamide

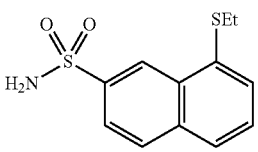

A solution of 8-iodonaphthalene-2-sulfonamide (Intermediate 7, 100 mg, 0.30 mmol), [1,1'-bis(diphenylphosphino)ferrocene]dichloropalladium(II) (12 mg, 0.015 mmol) and sodium ethanethiolate (50 mg, 0.60 mmol) in DMF (2 mL) was purged with argon. The reaction mixture was heated to 50° C. for 12 h. Additional sodium ethanethiolate (25 mg, 0.30 mmol) and [1,1'-bis(diphenylphosphino)ferrocene]dichloropalladium(II) (240 mg, 0.30 mmol) were added, and the reaction mixture was heated at 125° C. for 12 h. The reaction mixture was cooled to room temperature, diluted with 10% aq. LiCl solution and extracted with EtOAc (3×). The combined organic extracts were dried over Na₂SO₄, filtered and concentrated in vacuo. The residue was purified by preparative HPLC to give the title compound (24 mg, 30%). ¹H NMR (CD₃OD) δ 9.02-8.98 (m, 1H), 8.08-8.03 (m, 1H), 8.00-7.95 (m, 1H), 7.86 (d, J=8.4 Hz, 1H), 7.73 (dd, J=7.4, 1.0 Hz, 1H), 7.64-7.57 (m, 1H), 3.09 (q, J=7.3 Hz, 2H), 1.34 (t, J=7.4 Hz, 3H); MS(ESI⁻) m/z 266.2 (M−H)⁻.

Intermediate 14

To a solution of 8-(ethylthio)naphthalene-2-sulfonamide (22 mg, 0.082 mmol) in CH₂Cl₂ (1.0 mL) was added m-CPBA (37 mg, 0.16 mmol). The resulting reaction mixture was stirred overnight at room temperature and then concentrated in vacuo. The residue was dissolved in DMF and purified by preparative HPLC to give the title compound (24 mg, 97%). ¹H NMR (CD₃OD) δ 9.37 (d, J=0.9 Hz, 1H), 8.44-8.36 (m, 2H), 8.29 (d, J=8.6 Hz, 1H), 8.13 (dd, J=8.6, 1.8 Hz, 1H), 7.88 (dd, J=8.3, 7.4 Hz, 1H), 3.45 (q, J=7.5 Hz, 2H), 1.24 (t, J=7.5 Hz, 3H); MS(ESI⁻) m/z 298.3 (M−H)⁻.

Intermediate 15

7-Cyanonaphthalene-2-sulfonamide

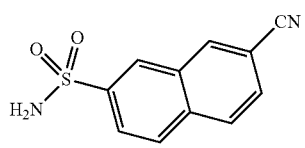

Following a procedure analogous to that for the synthesis of Intermediate 8, 7-iodonaphthalene-2-sulfonamide (Intermediate 11, 75 mg, 0.22 mmol) was converted to the title compound (36 mg, 69%). ¹H NMR (DMSO-d₆) δ 8.63 (s, 1H), 8.38 (d, J=1.7 Hz, 1H), 8.11 (d, J=8.8 Hz, 1H), 7.92 (ddd, J=15.4, 8.6, 1.8 Hz, 2H), 7.83 (d, J=8.6 Hz, 1H), 7.46 (br s, 2H); MS(ESI⁻) m/z 231.3 (M−H)⁻.

Intermediate 16

Ethyl 7-sulfamoyl-2-naphthoate

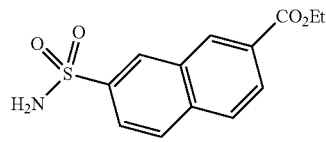

To a solution of 7-iodonaphthalene-2-sulfonamide (Intermediate 11, 70 mg, 0.21 mmol) in DMF (2.0 mL) and EtOH (2.0 mL, 34.2 mmol) was added bis(triphenylphosphine)palladium chloride (74 mg, 0.11 mmol). After purging the solution with nitrogen, the reaction flask was evacuated and refilled with CO. The reaction mixture was heated to 70° C. for 3 h. Pd(OAc)₂ (47 mg, 0.21 mmol) was then added, and the reaction flask was evacuated and refilled with CO. After stirring under CO overnight at 70° C., the reaction mixture was cooled to room temperature, taken up in a biphasic mixture of EtOAc and water, and filtered. The layers were separated and the aqueous layer was extracted with EtOAc (3×). The combined organic fractions were dried over MgSO₄, filtered and concentrated in vacuo. The residue was purified by preparative HPLC to give the title compound (20 mg, 34%) as a white solid. ¹H NMR (MeOD) δ 8.82 (s, 1H), 8.63 (d, J=1.3 Hz, 1H), 8.22 (d, J=8.8 Hz, 1H), 8.17-8.12 (m, 2H), 8.02 (dd, J=8.6, 2.0 Hz, 1H), 7.52 (s, 2H), 4.40 (q, J=7.0 Hz, 2H), 1.38 (t, J=7.2 Hz, 3H); MS(ESI⁻) m/z 278.3 (M−H)⁻.

Intermediate 17

7-(Ethylsulfonyl)naphthalene-2-sulfonamide

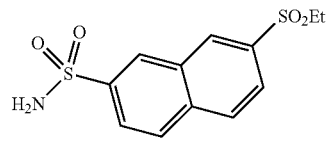

Following a procedure analogous to that for the synthesis of Intermediate 14, 7-iodonaphthalene-2-sulfonamide (Intermediate 11, 100 mg, 0.30 mmol) was converted to the title compound (22 mg, 96%). $^1$H NMR (CD$_3$OD) δ 8.57 (dd, J=2.5, 1.9 Hz, 2H), 8.16-8.08 (m, 2H), 8.05-8.01 (m, 1H), 7.95 (dd, J=8.6, 1.8 Hz, 1H), 3.23 (q, J=7.5 Hz, 2H), 1.16 (J=7.4 Hz, 3H); MS(ESI$^-$) m/z 298.3 (M−H)$^-$.

Intermediate 18

7-(Benzyloxy)naphthalene-2-sulfonamide

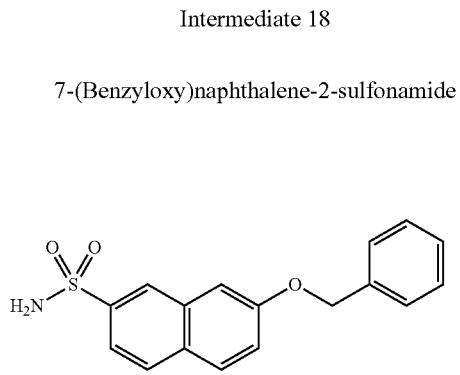

(Int-18)

To a solution of sodium 7-oxidonaphthalene-2-sulfonate (TCI, 100 mg, 0.37 mmol) and (bromomethyl)benzene (89 μL, 0.75 mmol) in DMF (1.0 mL) was added KOH (21 mg, 0.37 mmol), and resulting reaction mixture was stirred at 60° C. for 12 h. The reaction mixture was cooled to room temperature, taken up in a biphasic mixture of EtOAc and water, and filtered to remove any solids. The layers were separated and the aqueous layer was extracted with EtOAc (3×). The aqueous layer was concentrated in vacuo to give the crude sulfonic acid which was used in the next step without further purification.

Following a procedure analogous to that for the synthesis of Intermediate 11, the crude product from above was converted to the title compound (89 mg, 76%). $^1$H NMR (DMSO-d$_6$) δ 8.30 (d, J=1.5 Hz, 1H), 8.03 (d, J=8.6 Hz, 1H), 7.96 (d, J=9.0 Hz, 1H), 7.72 (dd, J=8.6, 2.0 Hz, 1H), 7.66 (d, J=2.4 Hz, 2H), 7.57-7.51 (m, 1H), 7.47-7.28 (m, 6H), 5.27 (s, 2H); MS(ESI$^-$) m/z 312.3 (M−H)$^-$.

Intermediate 19

3,4-Dichloro-N-(7-sulfamoylnaphthalen-1-yl)benzamide

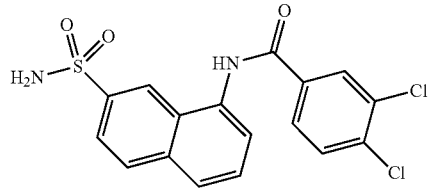

(Int-19)

Intermediate 19A 8-(3,4-Dichlorobenzamido)naphthalene-2-sulfonic acid

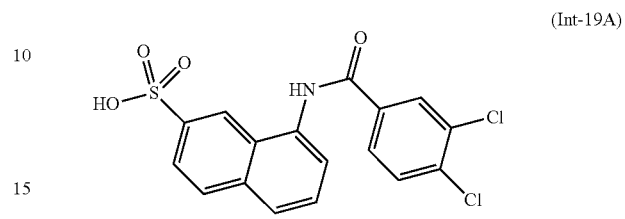

(Int-19A)

8-Amino-2-naphthalenesulfonic acid (Aldrich, 1.00 g, 4.48 mmol) and 3,4-dichlorobenzoyl chloride (938 mg, 4.48 mmol) were dissolved in pyridine (10.0 mL), and the resulting reaction mixture was stirred at room temperature for 12 h. The reaction mixture was then concentrated in vacuo, and the residue was dissolved in 1N HCl. The solution was extracted with EtOAc (5×), and the combined organic extracts were dried over Na$_2$SO$_4$, filtered and concentrated in vacuo to afford the title compound (1.70 g, 91%). $^1$H NMR (DMSO-d$_6$) δ 11.30 (s, 1H), 8.93 (d, J=2.0 Hz, 1H), 8.83 (s, 1H), 8.65 (dd, J=8.0, 1.9 Hz, 1H), 8.58-8.50 (m, 1H), 8.50-8.43 (m, 2H), 8.34 (dd, J=8.6, 1.5 Hz, 1H), 8.19-8.14 (m, 2H), 6.14 (br s, 1H); MS(ESI$^-$) m/z 394.2 (M−H)$^-$.

Intermediate 19

Following a procedure analogous to that for the synthesis of Intermediate 11, 8-(3,4-dichlorobenzamido)naphthalene-2-sulfonic acid was converted to the title compound (1.56 g, 92%). $^1$H NMR (DMSO-d$_6$) δ 8.49-8.29 (m, 1H), 8.14-7.97 (m, 2H), 7.96-7.56 (m, 6H), 7.50-7.44 (m, 1H), 7.39 (s, 1H), 6.77 (br s, 1H); MS(ESI$^-$) m/z 392.2 (M−H)$^-$.

Intermediate 20

7-(4-(Methylsulfonyl)benzyloxy)naphthalene-2-sulfonamide

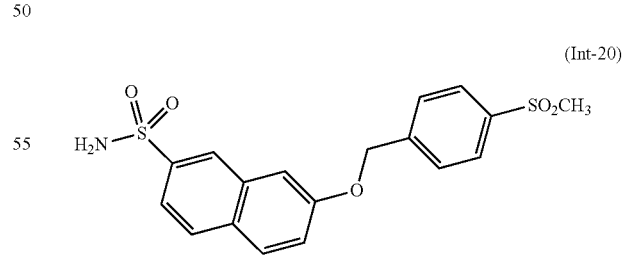

(Int-20)

Following a procedure analogous to that for the synthesis of Intermediate 18, sodium 7-oxidonaphthalene-2-sulfonate (Pfaltz and Bauer, 100 mg, 0.37 mmol) and 1-(bromomethyl)-4-(methylsulfonyl)benzene (186 mg, 0.75 mmol) were converted to the title compound (52 mg, 45%). $^1$H NMR (DMSO-d$_6$) δ 8.29 (s, 1H), 8.01-7.95 (m, 3H), 7.90-7.86 (m, 2H), 7.82-7.78 (m, 2H), 7.74-7.69 (m, 1H), 7.69-7.64 (m, 1H), 7.44-7.39 (m, 2H), 5.41 (s, 2H), 2.64 (s, 3H); MS(ESI⁻) m/z 390.3 (M−H)⁻.

Intermediate 21

8-(3,4-Dichlorobenzyloxy)naphthalene-2-sulfonamide

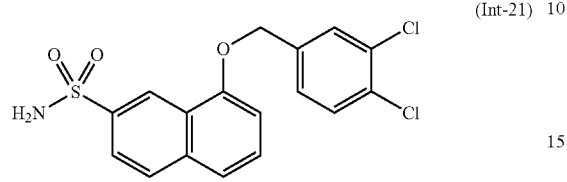

(Int-21)

Following a procedure analogous to that for the synthesis of Intermediate 18, sodium 8-hydroxynaphthalene-2-sulfonic acid (100 mg, 0.37 mmol) and 4-(bromomethyl)-1,2-dichlorobenzene (81 μL, 0.56 mmol) were converted to the title compound (17 mg, 10%). ¹H NMR (DMF-d₇) δ 8.85 (s, 1H), 8.13 (d, J=8.6 Hz, 1H), 8.02 (d, J=2.0 Hz, 1H), 7.91 (d, J=1.8 Hz, 1H), 7.77-7.72 (m, 1H), 7.70-7.59 (m, 3H), 7.47 (br s, 2H), 7.27 (dd, J=7.0, 1.3 Hz, 1H), 5.48 (s, 2H); MS(ESI⁻) m/z 380.2 (M−H)⁻.

Intermediate 22

7-(3,4-Dichlorobenzyloxy)naphthalene-2-sulfonamide

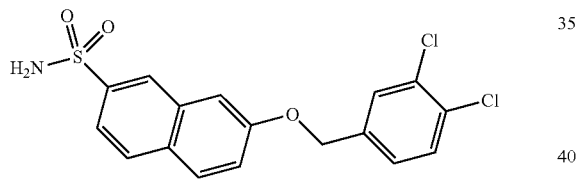

(Int-22)

Following a procedure analogous to that for the synthesis of Intermediate 18, sodium 7-oxidonaphthalene-2-sulfonate (Pfaltz and Bauer, 100 mg, 0.37 mmol) and 4-(bromomethyl)-1,2-dichlorobenzene (108 μL, 0.75 mmol) were converted to the title compound (89 mg, 62%). ¹H NMR (DMSO-d₆) δ 8.30 (s, 1H), 8.03 (d, J=8.6 Hz, 1H), 7.97 (d, J=9.0 Hz, 1H), 7.80 (d, J=2.0 Hz, 1H), 7.73 (dd, J=8.6, 1.8 Hz, 1H), 7.68 (d, J=8.1 Hz, 1H), 7.64 (d, J=2.6 Hz, 1H), 7.52 (dd, J=8.3, 1.9 Hz, 1H), 7.43-7.38 (m, 3H), 5.28 (s, 2H); MS(ESI⁻) m/z 380.2 (M−H)⁻.

Intermediate 23

7-((Tetrahydrofuran-2-yl)methoxy)naphthalene-2-sulfonamide

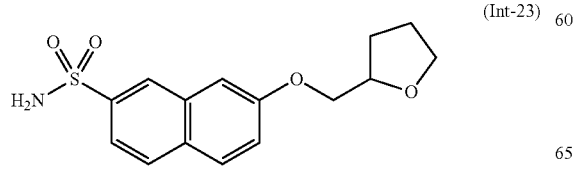

(Int-23)

Following a procedure analogous to that for the synthesis of Intermediate 18, sodium 7-oxidonaphthalene-2-sulfonate (Pfaltz and Bauer, 100 mg, 0.37 mmol) and 2-(bromomethyl)tetrahydrofuran (62 mg, 0.37 mmol) were converted to the title compound (21 mg, 18%). MS(ESI⁻) m/z 306.3 (M−H)⁻.

Intermediate 24

7-Isopropoxynaphthalene-2-sulfonamide

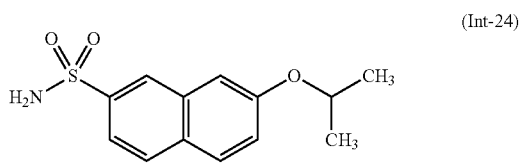 [SMILES: CC(C)Oc1ccc2ccc(S(N)(=O)=O)cc2c1]

(Int-24)

Following a procedure analogous to that for the synthesis of Intermediate 18, sodium 7-oxidonaphthalene-2-sulfonate (Pfaltz and Bauer, 100 mg, 0.37 mmol) and 2-bromopropane (46 mg, 0.37 mmol) were converted to the title compound (98 mg, 98%). ¹H NMR (DMSO-d₆) δ 8.30 (s, 1H), 8.00 (d, J=8.6 Hz, 1H), 7.91 (d, J=9.0 Hz, 1H), 7.69 (dd, J=8.6, 1.8 Hz, 1H), 7.55 (d, J=2.4 Hz, 1H), 7.38 (s, 2H), 7.28 (dd, J=8.9, 2.5 Hz, 1H), 4.81 (quin, J=6.0 Hz, 1H), 1.34 (d, J=5.9 Hz, 6H); MS(ESI⁻) m/z 264.4 (M−H)⁻.

Intermediate 25

7-(2-Phenoxyethoxy)naphthalene-2-sulfonamide

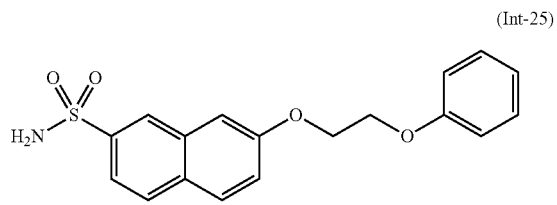 [SMILES: NS(=O)(=O)c1ccc2ccc(OCCOc3ccccc3)cc2c1]

(Int-25)

Following a procedure analogous to that for the synthesis of Intermediate 18, sodium 7-oxidonaphthalene-2-sulfonate (Pfaltz and Bauer, 100 mg, 0.37 mmol) and (2-bromoethoxy)benzene (150 mg, 0.75 mmol) were converted to the title compound (84 mg, 66%). MS(ESI⁻) m/z 342.3 (M−H)⁻.

Intermediate 26

Methyl 4-((7-sulfamoylnaphthalen-1-yloxy)methyl)benzoate

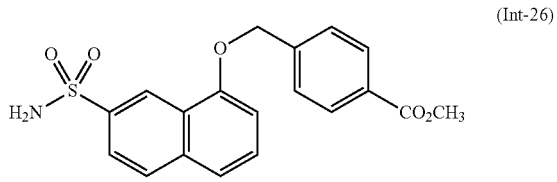 [SMILES: COC(=O)c1ccc(COc2cccc3ccc(S(N)(=O)=O)cc23)cc1]

(Int-26)

Intermediate 26A

8-Hydroxynaphthalene-2-sulfonic acid

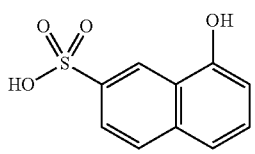
(Int-26A)

A solution of 8-amino-2-naphthalenesulfonic acid (Aldrich, 2.40 g, 10.8 mmol) and 3.9M aq. NaHSO₃ solution (20.0 mL, 77.0 mmol) in water (10.0 mL) was refluxed for 15 h. The reaction mixture was then basified with 30% aq. NaOH solution (430 mg, 10.8 mmol) and refluxed for 4 h. The reaction mixture was neutralized with conc. HCl and then concentrated in vacuo. The remaining solid was azeotroped with 1:1 MeOH/PhMe (3×) to give the title compound (2.41 g, 95%). $^1$H NMR (DMSO-$d_6$) δ 9.43 (br s, 1H), 8.36 (s, 1H), 7.96 d, J=8.4 Hz, 1H), 7.88-7.78 (m, 2H), 7.52 (t, J=7.8 Hz, 1H), 7.43 (d, J=7.3 Hz, 1H); MS(ESI⁻) m/z 222.3 (M–H)⁻.

Intermediate 26B

8-(4-(Methoxycarbonyl)benzyloxy)naphthalene-2-sulfonic acid

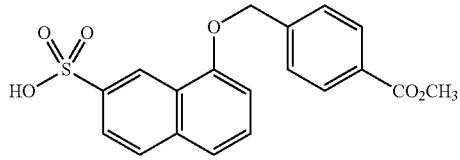
(Int-26B)

8-Hydroxynaphthalene-2-sulfonic acid (110 mg, 0.49 mmol), KOH (110 mg, 1.96 mmol), methyl 4-(bromomethyl) benzoate (112 mg, 0.49 mmol) and NaI (7.4 mg, 0.49 mmol) were stirred in DMF (1.0 mL) at room temperature for 1 h and then at 60° C. for 72 h. The reaction mixture was cooled to room temperature, diluted with water and purified using preparative HPLC to give the title compound (60 mg, 31%). MS(ESI⁻) m/z 371.3 (M–H)⁻.

Intermediate 26

Following a procedure analogous to that for the synthesis of Intermediate 11, 8-(4-(methoxycarbonyl)benzyloxy)naphthalene-2-sulfonic acid (60 mg, 0.16 mmol) was converted to the title compound (48 mg, 72%). $^1$H NMR (CD₃OD) δ 8.95 (t, J=2.5 Hz, 1H), 8.21-8.08 (m, 2H), 8.04-7.92 (m, 2H), 7.74 (dd, J=8.7, 2.8 Hz, 2H), 7.64-7.52 (m, 2H), 7.23-7.07 (m, 1H), 5.51-5.43 (m, 2H), 4.01-3.94 (m, 3H); MS(ESI⁻) m/z 370.3 (M–H)⁻.

Intermediate 27

8-(2-Morpholinoethoxy)naphthalene-2-sulfonamide

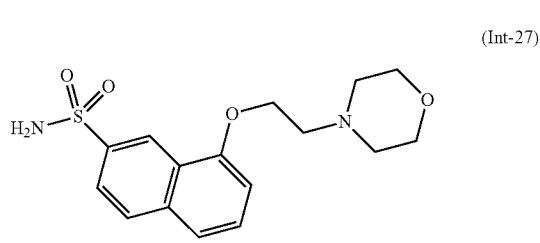 [SMILES: NS(=O)(=O)c1ccc2cccc(OCCN3CCOCC3)c2c1]
(Int-27)

Intermediate 27A

8-(2-Morpholinoethoxy)naphthalene-2-sulfonic acid

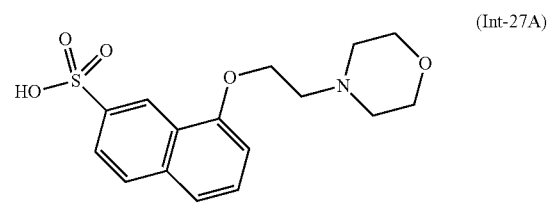 [SMILES: O=S(=O)(O)c1ccc2cccc(OCCN3CCOCC3)c2c1]
(Int-27A)

Following a procedure analogous to that for the synthesis of Intermediate 26B, 8-hydroxynaphthalene-2-sulfonic acid (200 g, 0.89 mmol) and 4-(2-chloroethyl) morpholine, HCl (332 g, 1.78 mmol) were converted to the title compound (100 mg, 32%). MS(ESI⁻) m/z 336.3 (M–H)⁻.

Intermediate 27

8-(2-Morpholinoethoxy)naphthalene-2-sulfonamide

Following a procedure analogous to that for the synthesis of Intermediate 11, 8-(2-morpholinoethoxy)naphthalene-2-sulfonic acid (100 mg, 0.30 mmol) was converted to the title compound (27 mg, 27%). $^1$H NMR (CD₃OD) δ 8.82 (d, J=1.8 Hz, 1H), 8.05-8.01 (m, 1H), 7.99-7.94 (m, 1H), 7.63-7.60 (m, 2H), 7.16 (dd, J=5.3, 3.3 Hz, 1H), 4.70-4.65 (m, 2H), 4.00 (t, J=4.7 Hz, 4H), 3.79-3.74 (m, 2H), 3.49 (d, J=4.2 Hz, 2H), 3.33 (ddd, J=3.2, 1.8, 1.7 Hz, 2H); MS(ESI⁻) m/z 335.3 (M–H)⁻.

Intermediate 28

7-(2-Methoxyethoxy)naphthalene-2-sulfonamide

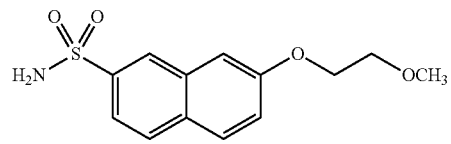
(Int-28)

Following a procedure analogous to that for the synthesis of Intermediate 18, sodium 7-oxidonaphthalene-2-sulfonate (Pfaltz and Bauer, 100 mg, 0.37 mmol) and 1-bromo-2-methoxyethane, HBr (164 mg, 0.75 mmol) were converted to the title compound (30 mg, 29%). $^1$H NMR (CDCl$_3$) δ 7.82-7.75 (m, 5H), 7.27-7.22 (m, 3H), 4.17 (br s, 2H), 3.80 (br s, 2H), 3.47 (s, 3H); MS(ESI$^-$) m/z 280.3 (M–H)$^-$.

Intermediate 29

7-Methoxynaphthalene-2-sulfonamide

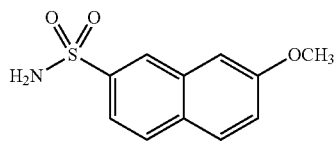
(Int-29)

Following a procedure analogous to that for the synthesis of Intermediate 18, sodium 7-oxidonaphthalene-2-sulfonate (Pfaltz and Bauer, 100 mg, 0.37 mmol) and iodomethane (106 mg, 0.75 mmol) were converted to the title compound (47 mg, 53%). $^1$H NMR (DMSO-d$_6$) δ 8.31 (s, 1H), 8.02 (d, J=8.6 Hz, 1H), 7.93 (d, J=9.0 Hz, 1H), 7.71 (dd, J=8.6, 1.8 Hz, 1H), 7.55 (d, J=2.4 Hz, 1H), 7.40 (s, 2H), 7.32 (dd, J=9.0, 2.6 Hz, 1H), 3.90 (s, 3H); MS(ESI$^-$) m/z 236.3 (M–H)$^-$.

Intermediate 30

7-(2-Ethoxyethoxy)naphthalene-2-sulfonamide

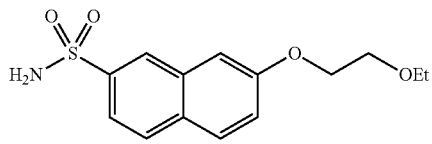
(Int-30)

Following a procedure analogous to that for the synthesis of Intermediate 18, sodium 7-oxidonaphthalene-2-sulfonate (Pfaltz and Bauer, 200 mg, 0.75 mmol) and 1-bromo-2-ethoxyethane (228 mg, 1.49 mmol) were converted to 7-(2-ethoxyethoxy) naphthalene-2-sulfonic acid, which was used in the next step without purification.

Following a procedure analogous to that for the synthesis of Intermediate 11, the crude material from above was converted to the title compound (146 mg, 66%). $^1$H NMR (CDCl$_3$) δ 8.36 (s, 1H), 8.22 (s, 1H), 7.90 (d, J=8.6 Hz, 1H), 7.83-7.79 (m, 1H), 7.76 (dd, J=8.6, 2.0 Hz, 1H), 7.63 (dd, J=8.6, 1.8 Hz, 1H), 7.38-7.34 (m, 1H), 7.24 (d, J=2.2 Hz, 1H), 4.29-4.25 (m, 2H), 3.90-3.87 (m, 2H), 3.65 (q, J=7.04 Hz, 2H), 1.28 (t, J=7.0 Hz, 3H); MS(ESI$^-$) m/z 294.4 (M–H)$^-$.

Intermediate 31

8-Bromo-5-(dimethylamino)naphthalene-2-sulfonamide

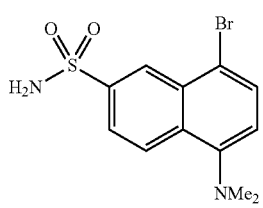
(Int-31)

Intermediate 31A 5-(tert-Butoxycarbonylamino)naphthalene-2-sulfonic acid

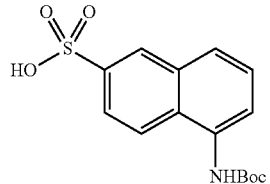
(Int-31A)

A solution of 1-naphthylamine-6-sulfonic acid (Aldrich, 2.50 g, 11.2 mmol), di-tert-butyl dicarbonate (5.7 mL, 24.6 mmol) and Et$_3$N (1.8 mL, 12.9 mmol) was stirred in MeOH (22.0 mL) at room temperature overnight. The reaction mixture was then concentrated in vacuo, and the residue was dissolved in EtOAc. The solution was washed with water, and the aqueous layer was saturated with solid NaCl. The aqueous layer was extracted with EtOAc (2×), followed by a 9:1 EtOAc/MeOH solution (3×). The combined organic extracts were dried over Na$_2$SO$_4$, filtered and concentrated in vacuo to give the title compound (3.60 g, 94%). $^1$H NMR (DMSO-d$_6$) δ 9.21 (s, 1H), 8.10 (d, J=1.3 Hz, 1H), 7.99 (d, J=8.8 Hz, 1H), 7.74 (d, J=8.1 Hz, 1H), 7.69 (dd, J=8.8, 1.5 Hz, 1H), 7.58 (d, J=7.3 Hz, 1H), 7.46 (t, J=7.8 Hz, 1H), 1.49 (s, 9H); MS(ESI$^-$) m/z 322.3 (M–H)$^-$.

Intermediate 31B

5-Amino-8-bromonaphthalene-2-sulfonic acid

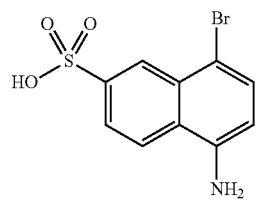
(Int-31B)

To a solution of 5-(tert-butoxycarbonylamino)naphthalene-2-sulfonic acid (2.10 g, 6.49 mmol) in AcOH (53.8 mL) was added N-bromosuccinimide (1.21 g, 6.82 mmol). The resulting reaction mixture was stirred at room temperature for 1 h and then concentrated in vacuo. The residue was dissolved in MeOH, azeotroped with PhMe (3×) and used in the subsequent step without purification.

The crude product from above was dissolved in TFA (10.0 mL, 130 mmol) and CH$_2$Cl$_2$ (10.0 mL). The resulting reaction mixture was stirred at room temperature for 2 h and then concentrated in vacuo to give the title compound (2.17 g, 95%). $^1$H NMR (DMSO-d$_6$) δ 8.37 (br s, 1H), 8.03 (d, J=8.6 Hz, 1H), 7.81 (t, J=8.4 Hz, 2H), 7.15 (d, J=7.5 Hz, 1H), 5.24 (br s, 2H); MS(ESI$^-$) m/z 302.2 (M–H)$^-$.

Intermediate 31C

8-Bromo-5-(dimethylamino)naphthalene-2-sulfonic acid

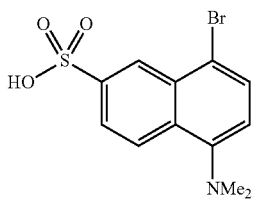
(Int-31C)

A solution of 5-amino-8-bromonaphthalene-2-sulfonic acid (500 mg, 1.66 mmol), formaldehyde (1.3 mL, 16.6 mmol), TFA (1.3 mL, 16.6 mmol) and triethylsilane (577 mg, 4.96 mmol) in DCE (10.0 mL) was heated at 45° C. for 12 h. The reaction mixture was then concentrated in vacuo, and the residue was purified by preparative HPLC to give the title compound (139 mg, 25%). $^1$H NMR (CD$_3$OD) δ 8.89 (d, J=1.1 Hz, 1H), 8.29-8.25 (m, 1H), 8.22-8.17 (m, 1H), 8.10 (d, J=8.1 Hz, 1H), 7.88 (d, J=8.4 Hz, 1H), 3.49 (s, 6H); MS(ESI$^-$) m/z 328.2 (M−H)$^-$.

Intermediate 31

Following a procedure analogous to that for the synthesis of Intermediate 11, 8-bromo-5-(dimethylamino)naphthalene-2-sulfonic acid (50 mg, 0.15 mmol) was converted to the title compound (27 mg, 52%) after purification using preparative HPLC. $^1$H NMR (DMSO-d$_6$) δ 8.59 (d, J=1.5 Hz, 1H), 8.41-8.29 (m, 1H), 7.96 (dd, J=8.9, 1.9 Hz, 1H), 7.90 (d, J=8.1 Hz, 1H), 7.57 (s, 2H), 7.24-7.13 (m, 1H), 2.84 (s, 6H); MS(ESI$^-$) m/z 312.3 (M−H)$^-$.

Intermediate 32

8-(3-Morpholinopropoxy)naphthalene-2-sulfonamide

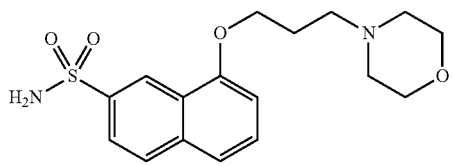
(Int-32)

Intermediate 32A 8-(3-Morpholinopropoxy)naphthalene-2-sulfonic acid

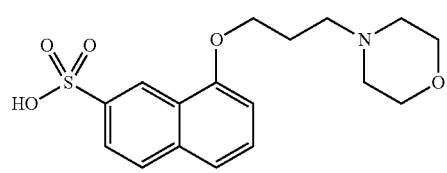
(Int-32A)

To a solution of 8-hydroxynaphthalene-2-sulfonic acid (Intermediate 26A, 300 mg, 1.34 mmol) and pulverized KOH (300 mg, 5.35 mmol) in DMF (2.0 mL) was added 4-(3-chloropropyl)morpholine (438 mg, 2.68 mmol) and NaI (401 mg, 2.68 mmol). The resulting reaction mixture was stirred at 60° C. for 12 h. TBAI (494 mg, 1.34 mmol) was then added followed by 4-(3-chloropropyl)morpholine (438 mg, 2.68 mmol). The reaction mixture was stirred at 60° C. for an additional 12 h, then diluted with water and filtered. The filtrate was purified directly using preparative HPLC to give the title compound (150 mg, 29%). $^1$H NMR (DMSO-d$_6$) δ 8.49-8.34 (m, 1H), 7.80-7.70 (m, 1H), 7.70-7.60 (m, 1H), 7.36-7.19 (m, 2H), 6.89-6.77 (1 H, m), 3.95 (br s, 2H), 3.65 (br s, 4H), 3.48-3.32 (m, 2H), 3.26-3.06 (m, 2H), 2.57-2.44 (m, 2H), 2.37-2.13 (m, 2H); MS(ESI$^-$) m/z 350.4 (M−H)$^-$.

Intermediate 32

Following a procedure analogous to that for the synthesis of Intermediate 11, 8-(3-morpholinopropoxy)naphthalene-2-sulfonic acid (150 mg, 0.43 mmol) was converted to the title compound (38 mg, 25%) after purification using preparative HPLC. $^1$H NMR (DMSO-d$_6$) δ 8.65-8.55 (m, 1H), 8.13-8.02 (m, 1H), 7.93-7.84 (m, 1H), 7.68-7.55 (m, 2H), 7.49-7.39 (m, 2H), 7.14 (dd, J=5.3, 3.5 Hz, 1H), 4.30 (t, J=6.05 Hz, 2H), 3.96 (br s, 2H), 3.74-3.62 (m, 2H), 3.48 (br s, 2H), 3.36 (d, J=15.4 Hz, 2H), 3.16 (br s, 2H), 2.35-2.17 (m, 2H); MS(ESI$^+$) m/z 351.1 (M+H)$^+$.

Intermediate 33

7-(2-Morpholinoethoxy)naphthalene-2-sulfonamide

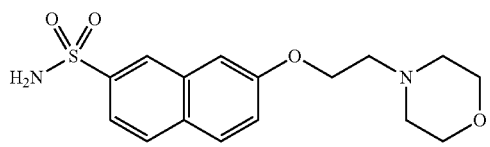
(Int-33)

Intermediate 33A 7-(2-Morpholinoethoxy)naphthalene-2-sulfonic acid

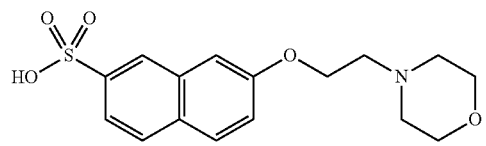
(Int-33A)

Following a procedure analogous to that for the synthesis of Intermediate 26B, sodium 7-oxidonaphthalene-2-sulfonate (Pfaltz and Bauer, 200 mg, 0.75 mmol) and 4-(2-chloroethyl)morpholine (223 g, 1.49 mmol) were converted to the title compound (113 mg, 45%). $^1$H NMR (DMSO-d$_6$) δ 9.90 (br s, 1H), 8.10 (s, 1H), 7.86 (d, J=8.8 Hz, 1H), 7.80 (d, J=8.4 Hz, 1H), 7.58 (dd, J=8.1, 1.3 Hz, 1H), 7.49 (d, J=1.8 Hz, 1H), 7.24 (dd, J=8.7, 2.3 Hz, 1H), 4.48 (br s, 2H), 3.99 (br s, 2H), 3.65 (br s, 4H), 3.26 (br s, 4H); MS (ESI$^+$) m/z 336.3 (M+H)$^+$.

Intermediate 33

Following a procedure analogous to that for the synthesis of Intermediate 11, 7-(2-morpholinoethoxy)naphthalene-2-sulfonic acid (113 mg, 0.34 mmol) was converted to the title compound (78 mg, 69%). ¹H NMR (CDCl₃) δ 8.37 (s, 1H), 7.91 (d, J=8.6 Hz, 1H), 7.81 (d, J=9.0 Hz, 1H), 7.22 (dd, J=8.6, 1.8 Hz, 1H), 7.77 (dd, J=9.0, 2.4 Hz, 1H), 7.24 (d, J=2.2 Hz, 1H), 4.83 (br s, 2H), 4.26 (t, J=5.6 Hz, 2H), 3.78-3.76 (m, 2H), 2.90 (t, J=5.6 Hz, 2H), 2.64 (br s, 2H), 1.55 (br s, 2H); MS(ESI⁻) m/z 335.4 (M–H)⁻.

Intermediate 34

7-(3-Morpholinopropoxy)naphthalene-2-sulfonamide

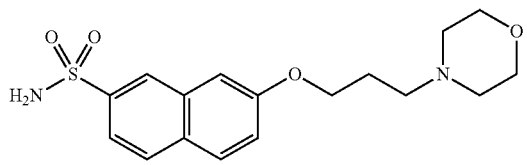
(Int-34)

Intermediate 34A 7-(3-Morpholinopropoxy)naphthalene-2-sulfonic acid

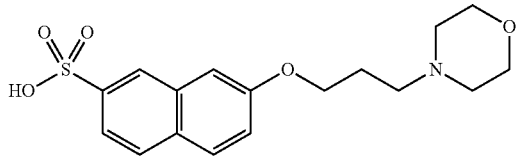
(Int-34A)

Following a procedure analogous to that for the synthesis of Intermediate 26B, sodium 7-oxidonaphthalene-2-sulfonate (Pfaltz and Bauer, 200 mg, 0.75 mmol) and 4-(3-bromopropyl)morpholine (310 mg, 1.49 mmol) were converted to the title compound (180 mg, 69%). ¹H NMR (DMSO-d₆) δ 9.53 (br s, 1H), 8.06 (s, 1H), 7.82 (d, J=9.0 Hz, 1H), 7.77 (d, J=8.6 Hz, 1H), 7.73-7.68 (m, 1H), 7.55 (dd, J=8.4, 1.5 Hz, 1H), 7.40 (d, J=2.2 Hz, 1H), 4.20 (t, J=5.8 Hz, 2H), 4.00 (d, J=11.0 Hz, 2H), 3.65 (t, J=11.6 Hz, 2H), 3.51 (d, J=12.3 Hz, 2H), 3.37-3.32 (m, 2H), 3.17-3.07 (m, 2H), 2.23-2.16 (m, 2H); MS (ESI⁺) m/z 350.3 (M+H)⁺.

Intermediate 34

Following a procedure analogous to that for the synthesis of Intermediate 11, 7-(3-morpholinopropoxy)naphthalene-2-sulfonic acid (113 mg, 0.51 mmol) was converted to the title compound (77 mg, 43%) after purification using flash column chromatography (gradient from 0% to 7% MeOH/CH₂Cl₂). ¹H NMR (CDCl₃) δ 8.37 (d, J=1.5 Hz, 1H), 7.90 (d, J=8.8 Hz, 1H), 7.81 (d, J=9.0 Hz, 1H), 7.76 (dd, J=8.6, 1.8 Hz, 1H), 7.31 (dd, J=9.0, 2.4 Hz, 1H), 7.24 (d, J=2.4 Hz, 1H), 4.82 (br s, 2H), 4.17 (t, J=6.3 Hz, 2H), 3.76-3.74 (m, 4H), 2.56 (t, J=7.3 Hz, 2H), 2.50 (br s, 4H); MS(ESI⁻) m/z 349.4 (M–H)⁻.

Intermediate 35

7-(3-(4-Methylpiperazin-1-yl)propoxy)naphthalene-2-sulfonamide

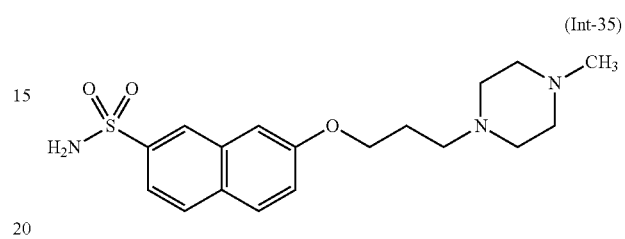
(Int-35)

Intermediate 35A 7-(3-(4-Methylpiperazin-1-yl)propoxy)naphthalene-2-sulfonic acid

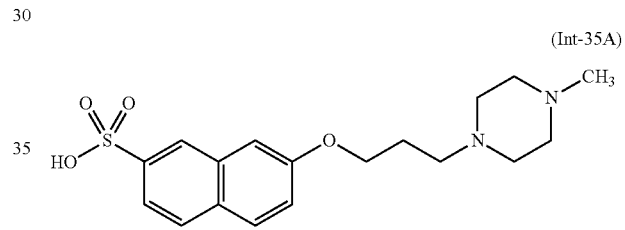
(Int-35A)

Following a procedure analogous to that for the synthesis of Intermediate 26B, sodium 7-oxidonaphthalene-2-sulfonate (Pfaltz and Bauer, 200 mg, 0.75 mmol) and 1-(3-bromopropyl)-4-methylpiperazine, 2HBr (571 mg, 1.49 mmol) were converted to the title compound (192 mg, 71%). ¹H NMR (DMSO-d₆) δ 9.39 (br s, 1H), 8.06 (s, 1H), 7.81 (d, J=9.0 Hz, 1H), 7.77 (d, J=8.6 Hz, 1H), 7.55 (dd, J=8.4, 1.5 Hz, 1H), 7.39 (d, J=2.2 Hz, 1H), 7.15 (dd, J=8.9, 2.5 Hz, 1H), 4.17 (t, J=6.1 Hz, 2H), 3.57-3.29 (m, 5H), 3.16-2.94 (m, 5H), 2.79 (s, 3H), 2.09 (br s, 2H); MS(ESI⁺) m/z 363.4 (M+H)⁺.

Intermediate 35

Following a procedure analogous to that for the synthesis of Intermediate 11, 7-(3-(4-methylpiperazin-1-yl)propoxy)naphthalene-2-sulfonic acid (180 mg, 0.49 mmol) was converted to the title compound (175 mg, 97%) after purification using flash column chromatography (gradient from 0% to 7% MeOH/CH₂Cl₂). ¹H NMR (CDCl₃) δ 8.37 (s, 1H), 7.92 (d, J=8.7 Hz, 1H), 7.81 (d, J=9.1 Hz, 1H), 7.52 (dd, J=8.6, 1.7 Hz, 1H), 7.40 (d, J=2.4 Hz, 1H), 7.19 (dd, J=8.4, 1.6 Hz, 1H), 4.77 (br s, 2H), 4.18 (t, J=6.0 Hz, 2H), 3.68-3.47 (m, 5H), 3.26-3.03 (m, 5H), 2.62 (s, 3H), 2.39 (br s, 2H); MS(ESI⁻) m/z 362.4 (M–H)⁻.

Intermediate 36

7-((1-Methyl-1H-imidazol-2-yl)methoxy)naphthalene-2-sulfonamide

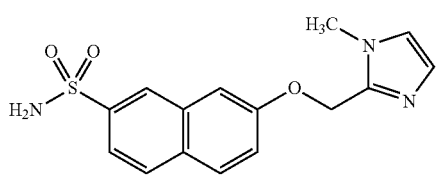
(Int-36)

Intermediate 36A 7-((1-Methyl-1H-imidazol-2-yl)methoxy)naphthalene-2-sulfonic acid

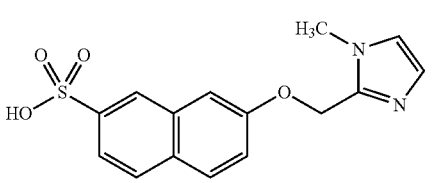
(Int-36A)

Following a procedure analogous to that for the synthesis of Intermediate 26B, sodium 7-oxidonaphthalene-2-sulfonate (Pfaltz and Bauer, 200 mg, 0.75 mmol) and 2-(chloromethyl)-1-methyl-1H-imidazole, HCl (125 mg, 0.75 mmol) were converted to the title compound (129 mg, 54%). MS(ESI$^+$) m/z 317.1 (M+H)$^+$.

Intermediate 36

Following a procedure analogous to that for the synthesis of Intermediate 11, 7-((1-methyl-1H-imidazol-2-yl)methoxy)naphthalene-2-sulfonic acid (129 mg, 0.41 mmol) was converted to the title compound (77 mg, 60%) after purification using flash column chromatography (gradient from 0% to 7% MeOH/CH$_2$Cl$_2$). $^1$H NMR (DMSO-d$_6$) δ 8.37 (d, J=1.5 Hz, 1H), 8.03 (d, J=8.6 Hz, 1H), 7.97-7.95 (m, 1H), 7.76 (d, J=2.4 Hz, 1H), 7.73 (dd, J=8.6, 1.8 Hz, 1H), 7.41 (s, 2H), 7.39 (dd, J=8.9, 2.5 Hz, 1H), 7.21 (d, J=1.1 Hz, 1H), 6.90 (d, J=1.1 Hz, 1H), 5.29 (s, 2H), 3.71 (s, 3H); MS(ESI$^-$) m/z 316.2 (M−H)$^-$.

Intermediate 37

7-(1-(Dimethylamino)propan-2-yloxy)naphthalene-2-sulfonamide

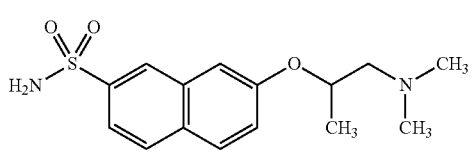
(Int-37)

Intermediate 37A 7-(1-(Dimethylamino)propan-2-yloxy)naphthalene-2-sulfonic acid

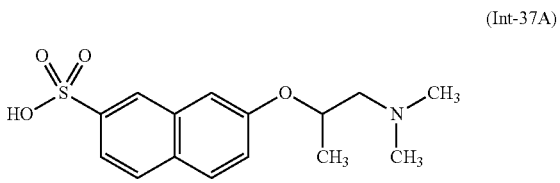 [SMILES: CC(CN(C)C)Oc1ccc2ccc(S(=O)(=O)O)cc2c1]
(Int-37A)

Following a procedure analogous to that for the synthesis of Intermediate 26B, sodium 7-oxidonaphthalene-2-sulfonate (Pfaltz and Bauer, 200 mg, 0.75 mmol) and 2-chloro-N,N-dimethylpropan-1-amine, HCl (118 mg, 0.75 mmol) were converted to the title compound (204 mg, 88%). $^1$H NMR (DMSO-d$_6$) δ 9.48 (br s, 1H), 8.08 (d, J=9.5 Hz, 1H), 7.86 (d, J=9.02 Hz, 1H), 7.79 (dd, J=8.4, 2.0 Hz, 1H), 7.57-7.53 (m, 1H), 7.49 (d, J=2.4 Hz, 1H), 7.25-7.21 (m, 1H), 4.41-4.30 (m, 1H), 3.92-3.81 (m, 1H), 3.53-3.39 (m, 1H), 2.90-2.81 (m, 6H), 1.38-1.31 (m, 3H); MS(ESI$^+$) m/z 310.0 (M+H)$^+$.

Intermediate 37

Following a procedure analogous to that for the synthesis of Intermediate 11, 7-(1-(dimethylamino)propan-2-yloxy)naphthalene-2-sulfonic acid (204 mg, 0.66 mmol) was converted to the title compound (112 mg, 55%) after purification using preparative HPLC. $^1$H NMR (DMSO-d$_6$) δ 8.33 (s, 1H), 8.06-8.03 (m, 1H), 7.99 (d, J=9.0 Hz, 1H), 7.76-7.73 (m, 1H), 7.70 (d, J=2.4 Hz, 1H), 7.43-7.41 (m, 2H), 7.37 (dd, J=8.8, 2.4 Hz, 1H), 5.12-5.07 (m, 1H), 4.43-4.32 (m, 1H), 3.53-3.41 (m, 1H), 2.90-2.82 (m, 6H), 1.38-1.33 (m, 3H); MS(ESI$^+$) m/z 309.1 (M+H)$^+$.

Intermediate 38

7-(2-(1-Methylpyrrolidin-2-yl)ethoxy)naphthalene-2-sulfonamide

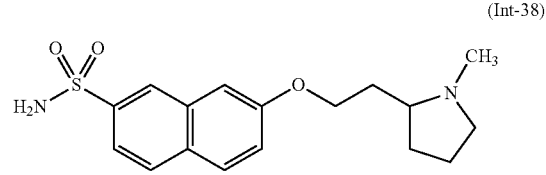 [SMILES: CN1CCCC1CCOc1ccc2ccc(S(N)(=O)=O)cc2c1]
(Int-38)

Intermediate 38A 7-(2-(1-Methylpyrrolidin-2-yl)ethoxy)naphthalene-2-sulfonic acid

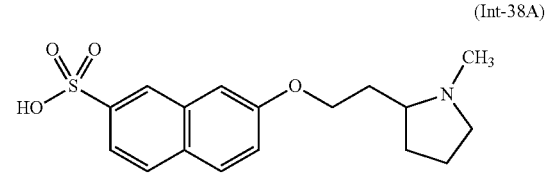 [SMILES: CN1CCCC1CCOc1ccc2ccc(S(=O)(=O)O)cc2c1]
(Int-38A)

Following a procedure analogous to that for the synthesis of Intermediate 26B, sodium 7-oxidonaphthalene-2-sulfonate (Pfaltz and Bauer, 200 mg, 0.75 mmol) and 2-(2-chloroethyl)-1-methylpyrrolidine, HCl (137 mg, 0.75 mmol) were converted to the title compound (173 mg, 69%). MS(ESI⁺) m/z 336.1 (M+H)⁺.

Intermediate 38

Following a procedure analogous to that for the synthesis of Intermediate 11, 7-(2-(1-methylpyrrolidin-2-yl)ethoxy)naphthalene-2-sulfonic acid (173 mg, 0.52 mmol) was converted to the title compound (74 mg, 43%) as an off-white solid after purification using preparative HPLC. ¹H NMR (DMSO-d₆) δ 8.32 (s, 1H), 8.06-8.03 (m, 1H), 7.99-7.95 (m, 1H), 7.76-7.72 (m, 1H), 7.62-7.61 (m, 1H), 7.44-7.43 (m, 2H), 7.36-7.32 (m, 1H), 4.96-4.87 (m, 1H), 4.30-4.21 (m, 2H), 3.67-3.60 (m, 1H), 3.55-3.46 (m, 2H), 3.43-3.39 (m, 1H), 3.28-3.08 (m, 2H), 2.91-2.85 (m, 3H), 2.29-2.22 (m, 1H), 2.17-1.87 (m, 4H), 1.87-1.71 (m, 1H); MS(ESI⁺) m/z 335.2 (M+H)⁺.

Intermediate 39

7-(3-(Dimethylamino)propoxy)naphthalene-2-sulfonamide

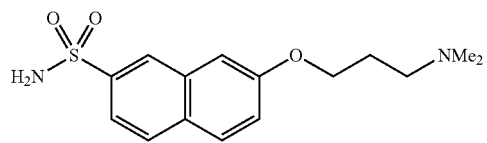

(Int-39)

Intermediate 39A 7-(3-(Dimethylamino)propoxy)naphthalene-2-sulfonic acid

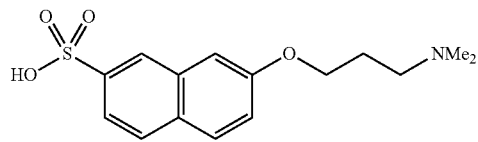

(Int-39A)

Following a procedure analogous to that for the synthesis of Intermediate 26B, sodium 7-oxidonaphthalene-2-sulfonate (Pfaltz and Bauer, 200 mg, 0.75 mmol) and 3-chloro-N,N-dimethylpropan-1-amine, HCl (118 mg, 0.75 mmol) were converted to the title compound (158 mg, 68%). MS(ESI) m/z 310.1 (M+H)⁺.

Intermediate 40

Following a procedure analogous to that for the synthesis of Intermediate 11, 7-(3-(dimethylamino)propoxy)naphthalene-2-sulfonic acid (158 mg, 0.51 mmol) was converted to the title compound (23 mg, 15%) as an off-white solid after purification using preparative HPLC. ¹H NMR (DMSO-d₆) δ 8.33 (s, 1H), 8.04 (s, 1H), 7.87-7.84 (m, 1H), 7.71 (dd, J=8.4, 1.8 Hz, 1H), 7.40 (s, 2H), 7.33 (d, J=2.0, 1H), 7.27 (dd, J=8.6, 2.5, 1H), 4.23-4.20 (m, 2H), 3.66-3.59 (m, 2H), 3.12-3.03 (m, 2H), 2.95 (s, 3H), 2.88 (s, 3H), 1.93-1.85 (m, 2H); MS(ESI⁺) m/z 309.1 (M+H)⁺.

Intermediate 40

7-(3-(Pyrrolidin-1-yl)propoxy)naphthalene-2-sulfonamide

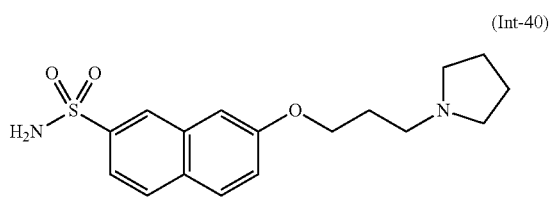 [SMILES: NS(=O)(=O)c1ccc2ccc(OCCCN3CCCC3)cc2c1]

(Int-40)

Intermediate 40A 7-(3-(Pyrrolidin-1-yl)propoxy)naphthalene-2-sulfonic acid

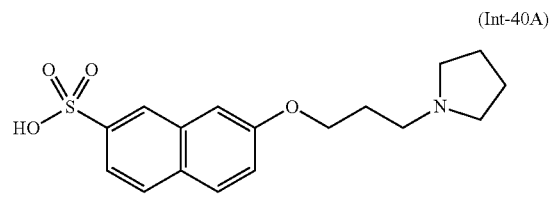 [SMILES: O=S(=O)(O)c1ccc2ccc(OCCCN3CCCC3)cc2c1]

(Int-40A)

Following a procedure analogous to that for the synthesis of Intermediate 26B, sodium 7-oxidonaphthalene-2-sulfonate (Pfaltz and Bauer, 200 mg, 0.75 mmol) and 1-(3-chloropropyl)pyrrolidine (110 mg, 0.75 mmol) were converted to the title compound (138 mg, 55%). MS(ESI⁺) m/z 336.1 (M+H)⁺.

Intermediate 40

Following a procedure analogous to that for the synthesis of Intermediate 11, 7-(3-(pyrrolidin-1-yl)propoxy)naphthalene-2-sulfonic acid (138 mg, 0.41 mmol) was converted to the title compound (34 mg, 24%) as a pale yellow oil after purification using preparative HPLC. ¹H NMR (DMSO-d₆) δ 8.33 (s, 1H), 7.96 (s, 1H), 7.93 (d, J=4.2 Hz, 1H), 7.67 (dd, J=8.5, 1.7 Hz, 1H), 7.42 (s, 2H), 7.36 (d, J=2.2 Hz, 1H), 7.29 (dd, J=8.8, 2.4 Hz, 1H), 4.23-4.20 (m, 2H), 3.66-3.59 (m, 2H), 3.41-3.34 (m, 2H), 3.12-3.03 (m, 2H), 2.22-2.19 (m, 2H), 2.10-2.02 (m, 2H), 1.93-1.85 (m, 2H); MS(ESI⁺) m/z 335.1 (M+H)⁺.

Intermediate 41

7-(3-(Piperidin-1-yl)propoxy)naphthalene-2-sulfonamide

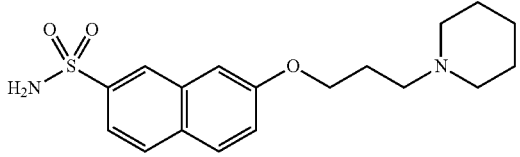

(Int-41)

Intermediate 41A 7-(3-(Piperidin-1-yl)propoxy)naphthalene-2-sulfonic acid (Int-41A)

Following a procedure analogous to that for the synthesis of Intermediate 26B, sodium 7-oxidonaphthalene-2-sulfonate (Pfaltz and Bauer, 200 mg, 0.75 mmol) and 1-(3-chloropropyl)piperidine (121 mg, 0.75 mmol) were converted to the title compound (78 mg, 30%). MS(ESI$^+$) m/z 336.1 (M+H)$^+$.

Intermediate 41

Following a procedure analogous to that for the synthesis of Intermediate 11, 7-(3-(pyrrolidin-1-yl)propoxy)naphthalene-2-sulfonic acid (109 mg, 0.31 mmol) was converted to the title compound (92 mg, 85%) as an off-white solid. $^1$H NMR (DMSO-d$_6$) δ 8.29 (s, 1H), 7.99 (d, J=8.4 Hz, 1H), 7.94-7.90 (m, 1H), 7.77 (dd, J=8.4, 1.5 Hz, 1H), 7.48 (s, 2H), 7.39 (d, J=2.4 Hz, 1H), 7.29 (dd, J=8.7, 2.5, 1H), 4.23-4.20 (m, 2H), 3.66-3.59 (m, 2H), 3.41-3.34 (m, 2H), 3.12-3.03 (m, 2H), 2.22-2.19 (m, 2H), 2.10-2.02 (m, 2H), 1.93-1.85 (m, 2H); MS(ESI$^+$) m/z 349.2 (M+H)$^+$.

Intermediate 42

7-(3-(Pyridin-4-yl)propoxy)naphthalene-2-sulfonamide

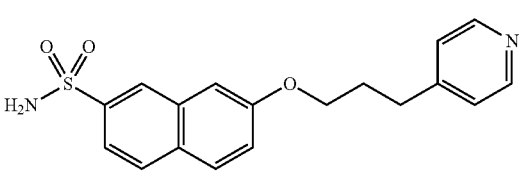

(Int-42)

Intermediate 42A 7-(3-(Pyridin-4-yl)propoxy)naphthalene-2-sulfonic acid

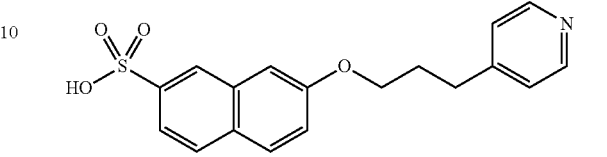

(Int-42A)

Following a procedure analogous to that for the synthesis of Intermediate 26B, sodium 7-oxidonaphthalene-2-sulfonate (Pfaltz and Bauer, 200 mg, 0.75 mmol) and 4-(3-chloropropyl)pyridine (116 mg, 0.75 mmol) were converted to the title compound (109 mg, 43%). $^1$H NMR (DMSO-d$_6$) δ 8.65, (s, 1H), 8.58 (s, 1H), 8.12 (s, 1H), 7.92 (d, J=8.4 Hz, 1H), 7.79 (d, J=8.7 Hz, 1H), 7.62 (d, J=5.7 Hz, 1H), 7.57 (dd, J=8.5, 1.9 Hz, 2H), 7.44 (s, 1H), 7.27 (d, J=8.7, 1H), 4.20 (t, J=6.5 Hz, 2H), 3.10 (t, J=7.7 Hz, 2H), 2.30-2.21 (m, 2H); MS(ESI$^+$) m/z 344.1 (M+H)$^+$.

Intermediate 42

Following a procedure analogous to that for the synthesis of Intermediate 11, 7-(3-(pyridin-4-yl)propoxy)naphthalene-2-sulfonic acid (109 mg, 0.32 mmol) was converted to the title compound (109 mg, 100%). $^1$H NMR (DMSO-d$_6$) δ 8.71 (d, J=6.2 Hz, 2H), 8.31 (s, 1H), 8.04 (d, J=8.6 Hz, 1H), 7.95 (d, J=9.0 Hz, 1H), 7.77 (d, J=5.3 Hz, 1H), 7.73 (dd, J=8.6, 1.8 Hz, 2H), 7.56 (d, J=2.4 Hz, 1H), 7.43 (s, 2H), 7.30 (dd, J=8.9, 2.5 Hz, 1H), 4.18 (t, J=6.2 Hz, 2H), 3.02 (t, J=7.6 Hz, 2H), 2.25-2.18 (m, 2H); MS (ESI$^+$) m/z 343.2 (M+H)$^+$.

Intermediate 43

8-Bromo-5-chloronaphthalene-2-sulfonamide

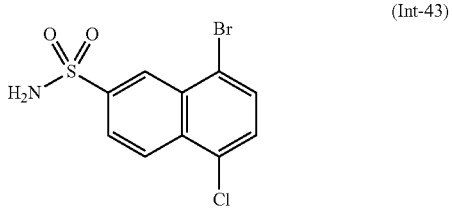 [SMILES: NS(=O)(=O)c1ccc2c(Cl)ccc(Br)c2c1]

(Int-43)

Intermediate 43A

8-Bromo-5-chloronaphthalene-2-sulfonic acid

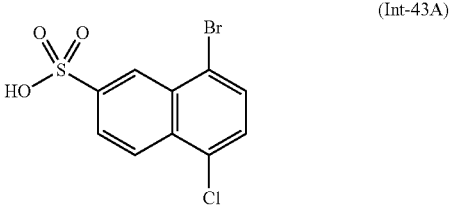 [SMILES: O=S(=O)(O)c1ccc2c(Cl)ccc(Br)c2c1]

(Int-43A)

Following a procedure analogous to that for the synthesis of Intermediate 5A, 5-amino-8-bromonaphthalene-2-sulfonic acid (Example 31B, 1.04 g, 3.46 mmol) was converted to the title compound (740 mg, 63%). $^1$H NMR (DMSO-d$_6$) δ 8.48 (br s, 1H), 8.36-8.12 (m, 1H), 8.12-7.81 (m, 2H), 7.66 (br s, 1H); MS(ESI$^-$) m/z 321.1 (M−H)$^-$.

Intermediate 43

Following a procedure analogous to that for the synthesis of Intermediate 11, 8-bromo-5-chloronaphthalene-2-sulfonic acid (740 mg, 2.30 mmol) was converted to the title compound (319 mg, 41%). $^1$H NMR (DMSO-d$_6$) δ 8.70 (d, J=1.5 Hz, 1H), 8.48-8.44 (m, 1H), 8.15 (dd, J=9.0, 1.8 Hz, 1H), 8.05 (d, J=8.1 Hz, 1H), 7.82 (d, J=8.1 Hz, 1H), 7.68 (s, 2H); MS(ESI$^+$) m/z 321.7 (M+H)$^+$.

Intermediate 44

5,8-Dichloronaphthalene-2-sulfonamide

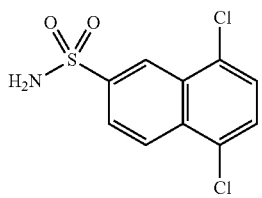

(Int-44)

Intermediate 44A

5-Amino-8-chloronaphthalene-2-sulfonic acid

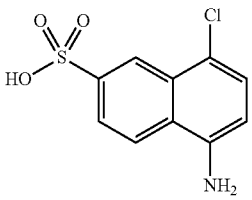

(Int-44A)

Following a procedure analogous to that for the synthesis of Intermediate 31B, 5-(tert-butoxycarbonylamino)naphthalene-2-sulfonic acid (Intermediate 31A, 3.70 g, 11.44 mmol) and N-chlorosuccinimide (1.60 g, 12.01 mmol) were converted to the title compound (2.95 g, 90%). MS(ESI$^+$) m/z 275.1 (M+NH$_4$)$^+$.

Intermediate 44B 5,8-Dichloronaphthalene-2-sulfonamide

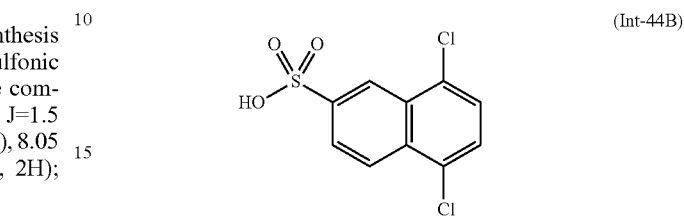

(Int-44B)

Following a procedure analogous to that for the synthesis of Intermediate 5A, 5-amino-8-chloronaphthalene-2-sulfonic acid (765 mg, 2.97 mmol) was converted to the title compound (823 mg, 90%). MS(ESI$^-$) m/z 275.2 (M−H)$^-$.

Intermediate 44

Following a procedure analogous to that for the synthesis of Intermediate 11, 5,8-dichloronaphthalene-2-sulfonic acid (823 mg, 2.97 mmol) was converted to the title compound (220 mg, 27%). $^1$H NMR (DMSO-d$_6$) δ 8.72 (d, J=1.5 Hz, 1H), 8.46 (d, J=8.8 Hz, 1H), 8.16 (dd, J=8.9, 1.6 Hz, 1H), 7.88-7.82 (m, 1H), 7.73-7.64 (m, 1H), 4.49 (br s, 2H); MS(ESI$^-$) m/z 274.3 (M−H)$^-$.

Examples 2 to 44

The following Examples were prepared using 4-(4-chloro-3-(dibutylcarbamoyl)-5-methyl-1H-pyrazol-1-yl)-3-(1,2,3,4-tetrahydroisoquinoline-2-carbonyl)benzoic acid (Intermediate 1F) and the naphthalene sulfonamide intermediates described above according to the procedure for the synthesis of Example 1.

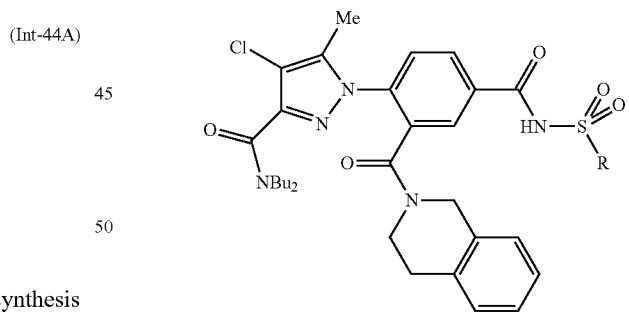

| Ex. No. | R | Name | LCMS (M + H) |
|---|---|---|---|
| 2 | ![naphthalene with Cl] | N,N-dibutyl-4-chloro-1-(4-(5-chloronaphthalen-2-ylsulfonylcarbamoyl)-2-(1,2,3,4-tetrahydroisoquinoline-2-carbonyl)phenyl)-5-methyl-1H-pyrazole-3-carboxamide | 774.7 |

-continued

| Ex. No. | R | Name | LCMS (M + H) |
|---|---|---|---|
| 3 | 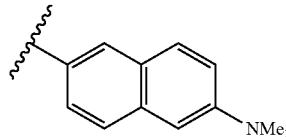 | N,N-dibutyl-4-chloro-1-(4-(6-(dimethylamino)naphthalen-2-ylsulfonylcarbamoyl)-2-(1,2,3,4-tetrahydroisoquinoline-2-carbonyl)phenyl)-5-methyl-1H-pyrazole-3-carboxamide | 783.5 |
| 4 | 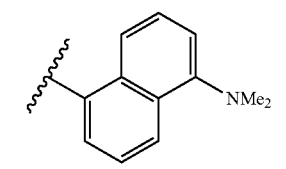 [SMILES: *c1cccc2c(N(C)C)cccc12] | N,N-dibutyl-4-chloro-1-(4-(5-(dimethylamino)naphthalen-1-ylsulfonylcarbamoyl)-2-(1,2,3,4-tetrahydroisoquinoline-2-carbonyl)phenyl)-5-methyl-1H-pyrazole-3-carboxamide | 783.4 |
| 5 | 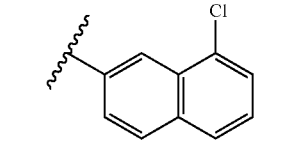 | N,N-dibutyl-4-chloro-1-(4-(8-chloronaphthalen-2-ylsulfonylcarbamoyl)-2-(1,2,3,4-tetrahydroisoquinoline-2-carbonyl)phenyl)-5-methyl-1H-pyrazole-3-carboxamide | 774.3 |
| 6 | 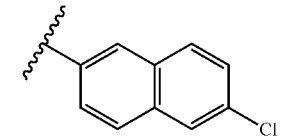 [SMILES: *c1ccc2cc(Cl)ccc2c1] | N,N-dibutyl-4-chloro-1-(4-(6-chloronaphthalen-2-ylsulfonylcarbamoyl)-2-(1,2,3,4-tetrahydroisoquinoline-2-carbonyl)phenyl)-5-methyl-1H-pyrazole-3-carboxamide | 774.3 |
| 7 | 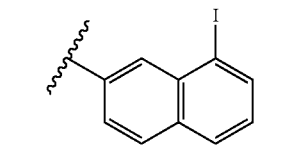 [SMILES: *c1ccc2cccc(I)c2c1] | N,N-dibutyl-4-chloro-1-(4-(8-iodonaphthalen-2-ylsulfonylcarbamoyl)-2-(1,2,3,4-tetrahydroisoquinoline-2-carbonyl)phenyl)-5-methyl-1H-pyrazole-3-carboxamide | 863.9 (M − H) |
| 8 | 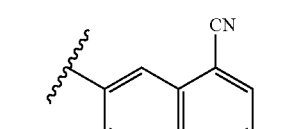 | N,N-dibutyl-4-chloro-1-(4-(8-cyanonaphthalen-2-ylsulfonylcarbamoyl)-2-(1,2,3,4-tetrahydroisoquinoline-2-carbonyl)phenyl)-5-methyl-1H-pyrazole-3-carboxamide | 765.4 |
| 9 | 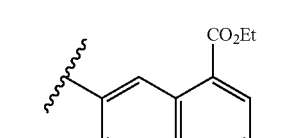 | ethyl 7-(N-(4-(4-chloro-3-(dibutylcarbamoyl)-5-methyl-1H-pyrazol-1-yl)-3-(1,2,3,4-tetrahydroisoquinoline-2-carbonyl)benzoyl)sulfamoyl)-1-naphthoate | 812.4 |
| 10 | 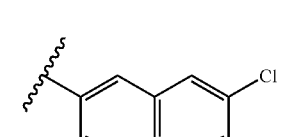 | N,N-dibutyl-4-chloro-1-(4-(7-chloronaphthalen-2-ylsulfonylcarbamoyl)-2-(1,2,3,4-tetrahydroisoquinoline-2-carbonyl)phenyl)-5-methyl-1H-pyrazole-3-carboxamide | 774.2 |
| 11 | 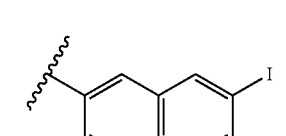 | N,N-dibutyl-4-chloro-1-(4-(7-iodonaphthalen-2-ylsulfonylcarbamoyl)-2-(1,2,3,4-tetrahydroisoquinoline-2-carbonyl)phenyl)-5-methyl-1H-pyrazole-3-carboxamide | 866.2 |

-continued

| Ex. No. | R | Name | LCMS (M + H) |
|---|---|---|---|
| 12 | (5-nitronaphthalen-1-yl, attached at 1-position) | N,N-dibutyl-4-chloro-5-methyl-1-(4-(5-nitronaphthalen-1-ylsulfonylcarbamoyl)-2-(1,2,3,4-tetrahydroisoquinoline-2-carbonyl)phenyl)-1H-pyrazole-3-carboxamide | 785.2 |
| 13 | (5-nitronaphthalen-2-yl) | N,N-dibutyl-4-chloro-5-methyl-1-(4-(5-nitronaphthalen-2-ylsulfonylcarbamoyl)-2-(1,2,3,4-tetrahydroisoquinoline-2-carbonyl)phenyl)-1H-pyrazole-3-carboxamide | 785.1 |
| 14 | (1-(ethylsulfonyl)naphthalen-7-yl) | N,N-dibutyl-4-chloro-1-(4-(6-chloronaphthalen-2-ylsulfonylcarbamoyl)-2-(1,2,3,4-tetrahydroisoquinoline-2-carbonyl)phenyl)-5-methyl-1H-pyrazole-3-carboxamide | 830.6 (M − H) |
| 15 | (7-cyanonaphthalen-2-yl) | N,N-dibutyl-4-chloro-1-(4-(7-cyanonaphthalen-2-ylsulfonylcarbamoyl)-2-(1,2,3,4-tetrahydroisoquinoline-2-carbonyl)phenyl)-5-methyl-1H-pyrazole-3-carboxamide | 765.2 |
| 16 | (7-(ethoxycarbonyl)naphthalen-2-yl) | ethyl 7-(N-(4-(4-chloro-3-(dibutylcarbamoyl)-5-methyl-1H-pyrazol-1-yl)-3-(1,2,3,4-tetrahydroisoquinoline-2-carbonyl)benzoyl)sulfamoyl)-2-naphthoate | 812.3 |
| 17 | (7-(ethylsulfonyl)naphthalen-2-yl) | ethyl 7-(N-(4-(4-chloro-3-(dibutylcarbamoyl)-5-methyl-1H-pyrazol-1-yl)-3-(1,2,3,4-tetrahydroisoquinoline-2-carbonyl)benzoyl)sulfamoyl)-2-naphthoate | 832.1 |
| 18 | (7-(benzyloxy)naphthalen-2-yl) | 1-(4-(7-(benzyloxy)naphthalen-2-ylsulfonylcarbamoyl)-2-(1,2,3,4-tetrahydroisoquinoline-2-carbonyl)phenyl)-N,N-dibutyl-4-chloro-5-methyl-1H-pyrazole-3-carboxamide | 846.1 |
| 19 | (8-(3,4-dichlorobenzamido)naphthalen-2-yl) | N,N-dibutyl-4-chloro-1-(4-(8-(3,4-dichlorobenzamido)naphthalen-2-ylsulfonylcarbamoyl)-2-(1,2,3,4-tetrahydroisoquinoline-2-carbonyl)phenyl)-5-methyl-1H-pyrazole-3-carboxamide | 927.1 |

| Ex. No. | R | Name | LCMS (M + H) |
|---|---|---|---|
| 20 | (7-((4-(methylsulfonyl)benzyl)oxy)naphthalen-2-yl) | N,N-dibutyl-4-chloro-5-methyl-1-(4-(7-(4-(methylsulfonyl)benzyloxy)-naphthalen-2-ylsulfonylcarbamoyl)-2-(1,2,3,4-tetrahydroisoquinoline-2-carbonyl)phenyl)-1H-pyrazole-3-carboxamide | 924.2 |
| 21 | (8-((3,4-dichlorobenzyl)oxy)naphthalen-2-yl) | N,N-dibutyl-4-chloro-1-(4-(8-(3,4-dichlorobenzyloxy)naphthalen-2-ylsulfonylcarbamoyl)-2-(1,2,3,4-tetrahydroisoquinoline-2-carbonyl)phenyl)-5-methyl-1H-pyrazole-3-carboxamide | 914.3 |
| 22 | (7-((3,4-dichlorobenzyl)oxy)naphthalen-2-yl) | N,N-dibutyl-4-chloro-1-(4-(7-(3,4-dichlorobenzyloxy)naphthalen-2-ylsulfonylcarbamoyl)-2-(1,2,3,4-tetrahydroisoquinoline-2-carbonyl)phenyl)-5-methyl-1H-pyrazole-3-carboxamide | 916.3 |
| 23 | (7-((tetrahydrofuran-2-yl)methoxy)naphthalen-2-yl) | N,N-dibutyl-4-chloro-5-methyl-1-(4-(7-((tetrahydrofuran-2-yl)methoxy)naphthalen-2-ylsulfonylcarbamoyl)-2-(1,2,3,4-tetrahydroisoquinoline-2-carbonyl)phenyl)-1H-pyrazole-3-carboxamide | 840.3 |
| 24 | (7-isopropoxynaphthalen-2-yl) | N,N-dibutyl-4-chloro-1-(4-(7-isopropoxynaphthalen-2-ylsulfonylcarbamoyl)-2-(1,2,3,4-tetrahydroisoquinoline-2-carbonyl)phenyl)-5-methyl-1H-pyrazole-3-carboxamide | 798.2 |
| 25 | (7-(2-phenoxyethoxy)naphthalen-2-yl) | N,N-dibutyl-4-chloro-5-methyl-1-(4-(7-(2-phenoxyethoxy)naphthalen-2-ylsulfonylcarbamoyl)-2-(1,2,3,4-tetrahydroisoquinoline-2-carbonyl)phenyl)-1H-pyrazole-3-carboxamide | 876.3 |
| 26 | (8-((4-(methoxycarbonyl)benzyl)oxy)naphthalen-2-yl) | methyl 4-((7-(N-(4-(4-chloro-3-(dibutylcarbamoyl)-5-methyl-1H-pyrazol-1-yl)-3-(1,2,3,4-tetrahydroisoquinoline-2-carbonyl)benzoyl)sulfamoyl)naphthalen-1-yloxy)methyl)benzoate | 904.4 |

-continued

| Ex. No. | R | Name | LCMS (M + H) |
|---|---|---|---|
| 27 | 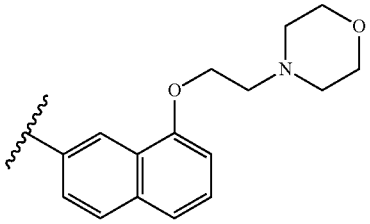 [SMILES: *c1ccc2cccc(OCCN3CCOCC3)c2c1] | N,N-dibutyl-4-chloro-5-methyl-1-(4-(8-(2-morpholinoethoxy)naphthalen-2-ylsulfonylcarbamoyl)-2-(1,2,3,4-tetrahydroisoquinoline-2-carbonyl)phenyl)-1H-pyrazole-3-carboxamide | 869.4 |
| 28 | 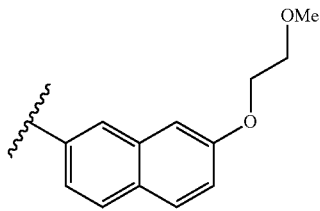 [SMILES: *c1ccc2ccc(OCCOC)cc2c1] | N,N-dibutyl-4-chloro-1-(4-(7-(2-methoxyethoxy)naphthalen-2-ylsulfonylcarbamoyl)-2-(1,2,3,4-tetrahydroisoquinoline-2-carbonyl)phenyl)-5-methyl-1H-pyrazole-3-carboxamide | 814.4 |
| 29 | 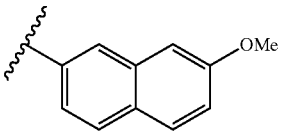 [SMILES: *c1ccc2ccc(OC)cc2c1] | N,N-dibutyl-4-chloro-1-(4-(7-methoxynaphthalen-2-ylsulfonylcarbamoyl)-2-(1,2,3,4-tetrahydroisoquinoline-2-carbonyl)phenyl)-5-methyl-1H-pyrazole-3-carboxamide | 770.2 |
| 30 | 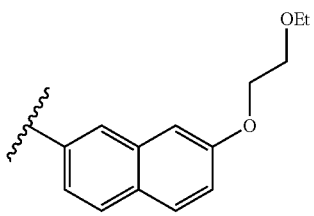 [SMILES: *c1ccc2ccc(OCCOCC)cc2c1] | N,N-dibutyl-4-chloro-1-(4-(7-(2-ethoxyethoxy)naphthalen-2-ylsulfonylcarbamoyl)-2-(1,2,3,4-tetrahydroisoquinoline-2-carbonyl)phenyl)-5-methyl-1H-pyrazole-3-carboxamide | 828.3 |
| 31 | 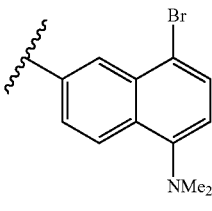 [SMILES: *c1ccc2c(N(C)C)ccc(Br)c2c1] | 1-(4-(8-bromo-5-(dimethylamino)naphthalen-2-ylsulfonylcarbamoyl)-2-(1,2,3,4-tetrahydroisoquinoline-2-carbonyl)phenyl)-N,N-dibutyl-4-chloro-5-methyl-1H-pyrazole-3-carboxamide | 861.3 |
| 32 | 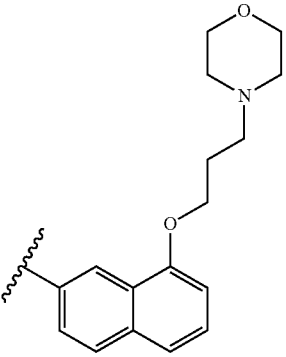 [SMILES: *c1ccc2cccc(OCCCN3CCOCC3)c2c1] | N,N-dibutyl-4-chloro-5-methyl-1-(4-(8-(3-morpholinopropoxy)naphthalen-2-ylsulfonylcarbamoyl)-2-(1,2,3,4-tetrahydroisoquinoline-2-carbonyl)phenyl)-1H-pyrazole-3-carboxamide | 883.4 |

-continued

| Ex. No. | R | Name | LCMS (M + H) |
|---|---|---|---|
| 33 | 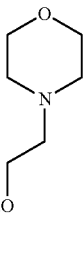 | N,N-dibutyl-4-chloro-5-methyl-1-(4-(7-(2-morpholinoethoxy)naphthalen-2-ylsulfonylcarbamoyl)-2-(1,2,3,4-tetrahydroisoquinoline-2-carbonyl)phenyl)-1H-pyrazole-3-carboxamide | 869.3 |
| 34 | 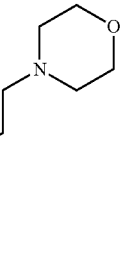 | N,N-dibutyl-4-chloro-5-methyl-1-(4-(7-(3-morpholinopropoxy)naphthalen-2-ylsulfonylcarbamoyl)-2-(1,2,3,4-tetrahydroisoquinoline-2-carbonyl)phenyl)-1H-pyrazole-3-carboxamide | 883.4 |
| 35 |  | N,N-dibutyl-4-chloro-5-methyl-1-(4-(7-(3-(4-methylpiperazin-1-yl)propoxy)naphthalen-2-ylsulfonylcarbamoyl)-2-(1,2,3,4-tetrahydroisoquinoline-2-carbonyl)phenyl)-1H-pyrazole-3-carboxamide | 896.5 |
| 36 | 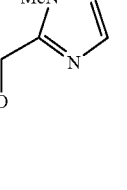 | N,N-dibutyl-4-chloro-5-methyl-1-(4-(7-((1-methyl-1H-imidazol-2-yl)methoxy)naphthalen-2-ylsulfonylcarbamoyl)-2-(1,2,3,4-tetrahydroisoquinoline-2-carbonyl)phenyl)-1H-pyrazole-3-carboxamide | 850.4 |
| 37 |  | N,N-dibutyl-4-chloro-1-(4-(7-(1-(dimethylamino)propan-2-yloxy)naphthalen-2-ylsulfonylcarbamoyl)-2-(1,2,3,4-tetrahydroisoquinoline-2-carbonyl)phenyl)-5-methyl-1H-pyrazole-3-carboxamide | 841.4 |
| 38 | 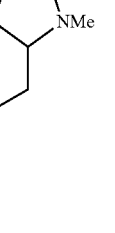 | N,N-dibutyl-4-chloro-5-methyl-1-(4-((7-(2-(1-methylpyrrolidin-2-yl)ethoxy)naphthalene-2-sulfonamido)methyl)-2-(1,2,3,4-tetrahydroisoquinoline-2-carbonyl)phenyl)-1H-pyrazole-3-carboxamide | 867.5 |

-continued

| Ex. No. | R | Name | LCMS (M + H) |
|---|---|---|---|
| 39 | (naphthalene with O-(CH2)3-NMe2 substituent) | N,N-dibutyl-4-chloro-1-(4-(7-(3-(dimethylamino)propoxy)-naphthalen-2-ylsulfonylcarbamoyl)-2-(1,2,3,4-tetrahydroisoquinoline-2-carbonyl)phenyl)-5-methyl-1H-pyrazole-3-carboxamide | 841.4 |
| 40 | (naphthalene with O-(CH2)3-pyrrolidin-1-yl substituent) | N,N-dibutyl-4-chloro-5-methyl-1-(4-(7-(3-(pyrrolidin-1-yl)propoxy)naphthalen-2-ylsulfonylcarbamoyl)-2-(1,2,3,4-tetrahydroisoquinoline-2-carbonyl)phenyl)-1H-pyrazole-3-carboxamide | 867.3 |
| 41 | (naphthalene with O-(CH2)3-piperidin-1-yl substituent) | N,N-dibutyl-4-chloro-5-methyl-1-(4-(7-(3-(piperidin-1-yl)propoxy)naphthalen-2-ylsulfonylcarbamoyl)-2-(1,2,3,4-tetrahydroisoquinoline-2-carbonyl)phenyl)-1H-pyrazole-3-carboxamide | 881.5 |
| 42 | (naphthalene with O-(CH2)3-pyridin-4-yl substituent) | N,N-Dibutyl-4-chloro-5-methyl-1-(4-(7-(3-(pyridin-4-yl)propoxy)naphthalen-2-ylsulfonylcarbamoyl)-2-(1,2,3,4-tetrahydroisoquinoline-2-carbonyl)phenyl)-1H-pyrazole-3-carboxamide | 875.4 |
| 43 | (8-bromo-5-chloronaphthalene) | 1-(4-(8-bromo-5-chloronaphthalen-2-ylsulfonylcarbamoyl)-2-(1,2,3,4-tetrahydroisoquinoline-2-carbonyl)phenyl)-N,N-dibutyl-4-chloro-5-methyl-1H-pyrazole-3-carboxamide | 852.4 (M − H) |
| 44 | (5,8-dichloronaphthalene) | N,N-dibutyl-4-chloro-1-(4-(5,8-dichloronaphthalen-2-ylsulfonylcarbamoyl)-2-(1,2,3,4-tetrahydroisoquinoline-2-carbonyl)phenyl)-5-methyl-1H-pyrazole-3-carboxamide | 806.6 (M − H) |

Example 45

7-(N-(4-(4-Chloro-3-(dibutylcarbamoyl)-5-methyl-1H-pyrazol-1-yl)-3-(1,2,3,4-tetrahydroisoquinoline-2-carbonyl)benzoyl)sulfamoyl)-1-naphthoic acid

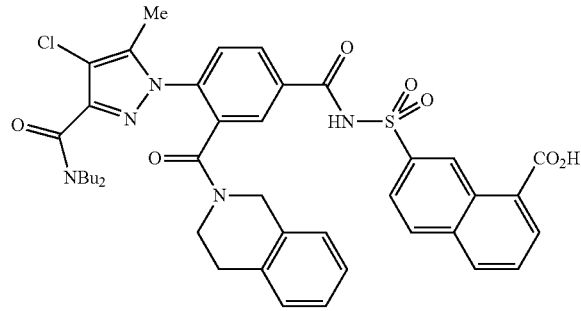

(45)

To a solution of ethyl 7-(N-(4-(4-chloro-3-(dibutylcarbamoyl)-5-methyl-1H-pyrazol-1-yl)-3-(1,2,3,4-tetrahydroisoquinoline-2-carbonyl)benzoyl)sulfamoyl)-1-naphthoate (Example 9, 9.4 mg, 0.012 mmol) in EtOH (0.5 mL) and THF (0.5 mL) was added 2N LiOH (58 μL, 0.12 mmol). The reaction mixture was stirred at room temperature for 30 min and then at 40° C. for 2 h. The reaction mixture was quenched with 6N HCl, and then extracted with CHCl$_3$ (4×). The combined organic extracts were dried over Na$_2$SO$_4$, filtered and concentrated in vacuo to afford the title compound (9.0 mg, 94%). $^1$H NMR (CD$_3$OD, 2:1 mixture of amide rotamers) δ 9.90 (s, 1H), 8.40 (d, J=7.3 Hz, 1H), 8.23 (d, J=8.4 Hz, 1H), 8.17 (d, J=1.1 Hz, 1H), 8.08 (dd, J=8.4, 1.8 Hz, 1H), 7.98 (t, J=2.2 Hz, 1H), 7.79-7.74 (m, 1H), 7.71-7.64 (m, 1H), 7.24-7.04 (m, 4.5H), 6.90-6.88 (m, 0.5H), 4.53 (br s, 2H), 3.58-3.39 (m, 4H), 3.13 (d, J=1.3 Hz, 1H), 3.05-2.94 (m, 1H), 2.82 (br s, 1H), 2.79-2.66 (m, 1H), 2.33 (s, 2H), 2.28 (s, 1H), 1.49-1.20 (m, 6H), 1.13-0.98 (m, 2H), 0.96-0.84 (m, 3H), 0.80-0.64 (m, 3H); MS(ESI$^-$) m/z 782.5 (M–H)$^-$.

Example 46

N,N-Dibutyl-4-chloro-5-methyl-1-(4-(7-(4-methylpiperazine-1-carbonyl)naphthalen-2-ylsulfonylcarbamoyl)-2-(1,2,3,4-tetrahydroisoquinoline-2-carbonyl)phenyl)-1H-pyrazole-3-carboxamide

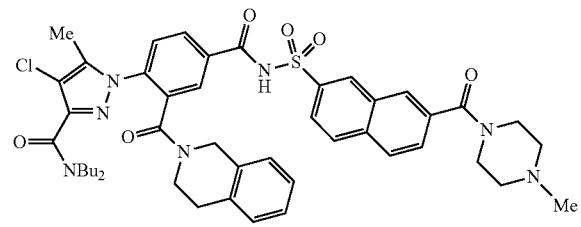

(46)

Intermediate 46A 7-(N-(4-(4-Chloro-3-(dibutylcarbamoyl)-5-methyl-1H-pyrazol-1-yl)-3-(1,2,3,4-tetrahydroisoquinoline-2-carbonyl)benzoyl)sulfamoyl)-2-naphthoic acid

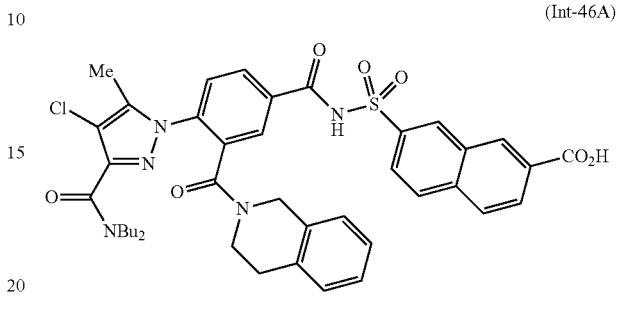

(Int-46A)

To a solution of ethyl 7-(N-(4-(4-chloro-3-(dibutylcarbamoyl)-5-methyl-1H-pyrazol-1-yl)-3-(1,2,3,4-tetrahydroisoquinoline-2-carbonyl)benzoyl)sulfamoyl)-2-naphthoate (Example 16, 84 mg, 0.10 mmol) in EtOH (0.5 mL) and THF (0.5 mL) was added 2N LiOH (0.5 mL, 1.03 mmol). The reaction mixture was stirred for 2 h at 40° C., concentrated to remove volatiles, diluted with water and quenched with 1N HCl. The solution was concentrated in vacuo and purified by preparative HPLC to afford the title compound (57 mg, 68%) as a white solid. $^1$H NMR (DMSO-d$_6$, 2:1 mixture of amide rotamers) δ 8.41 (s, 1H), 8.36 (s, 1H), 8.07 (t, J=7.3 Hz, 2H), 7.99 (d, J=1.3 Hz, 1H), 7.88 (s, 2H), 7.79 (d, J=8.8 Hz, 1H), 7.55-7.51 (m, 1H), 7.20-7.07 (m, 3.5H), 6.97 (d, J=7.5 Hz, 0.5H), 4.10 (br s, 6H), 2.97 (br s, 1.5H), 2.74 (br s, 1.5H), 2.19 (s, 2H), 2.14 (s, 1H), 1.38 (br s, 1H), 1.29-1.12 (m, 6H), 1.01-0.91 (m, 2H), 0.88-0.82 (m, 3H), 0.68-0.61 (m, 3H); MS(ESI$^+$) m/z 784.2 (M+H)$^+$.

Example 46

To a solution of 7-(N-(4-(4-chloro-3-(dibutylcarbamoyl)-5-methyl-1H-pyrazol-1-yl)-3-(1,2,3,4-tetrahydroisoquinoline-2-carbonyl)benzoyl)sulfamoyl)-2-naphthoic acid (12 mg, 0.015 mmol) in DMF (1.0 mL) were added HATU (12 mg, 0.031 mmol), 2,6-lutidine (5 μL, 0.040 mmol) followed by 1-methylpiperazine (4.6 mg, 0.046 mmol). The resulting reaction mixture was heated to 50° C. for 1.5 h, cooled to room temperature and purified directly by preparative HPLC to give the title compound (2 mg, 14%). $^1$H NMR (DMSO-d$_6$, 2:1 mixture of amide rotamers) δ 8.50 (s, 1H), 8.17 (s, 1H), 8.07-8.02 (m, 2H), 7.99-7.98 (m, 2H), 7.95 (m, 1H), 7.60 (dd, J=8.5, 1.5 Hz, 1H), 7.56-7.52 (m, 1H), 7.20-7.07 (m, 3.5H), 6.97 (d, J=7.5 Hz, 0.5H), 4.73 (br s, 1H), 4.56-4.33 (m, 3H), 3.73 (br s, 1H), 3.59-3.40 (m, 3H), 3.50 (br s, 3H), 2.99-2.96 (m, 2H), 2.89 (s, 1H), 2.79-2.63 (m, 5H), 2.53 (br s, 1H), 2.19 (s, 2H), 2.14 (s, 1H), 1.38 (br s, 1H), 1.29-1.14 (m, 6H), 1.01-0.92 (m, 2H), 0.88-0.82 (m, 3H), 0.68-0.61 (m, 3H); MS(ESI⁺) m/z 866.3 (M+H)⁺.

Example 47

N,N-Dibutyl-4-chloro-5-methyl-1-(4-(7-(morpholine-4-carbonyl)naphthalen-2-ylsulfonylcarbamoyl)-2-(1,2,3,4-tetrahydroisoquinoline-2-carbonyl)phenyl)-1H-pyrazole-3-carboxamide (47)

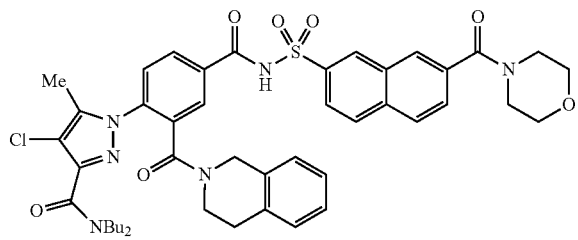

Following a procedure analogous to that for the synthesis of Intermediate 12B of Example 12, 7-(N-(4-(4-chloro-3-(dibutylcarbamoyl)-5-methyl-1H-pyrazol-1-yl)-3-(1,2,3,4-tetrahydroisoquinoline-2-carbonyl)benzoyl)sulfamoyl)-2-naphthoic acid (Intermediate 46A 12 mg, 0.015 mmol) and morpholine (4 mg, 0.046 mmol) were converted to the title compound (3 mg, 20%). ¹H NMR (1:1 CD₃OD:CDCl₃, 2:1 mixture of amide rotamers) δ 8.67 (s, 1H), 8.21 (d, J=8.3 Hz, 1H), 8.14 (dd, J=8.7, 1.5 Hz, 1H), 8.11 (d, J=1.7 Hz, 1H), 8.06 (s, 1H), 7.98 (t, J=7.6 Hz, 2H), 7.60 (d, J=8.3 Hz, 1H), 7.44-7.42 (m, 1H), 7.19-7.09 (m, 3.5H), 6.89 (d, J=7.2 Hz, 0.5H), 4.83 (br s, 1H), 4.50 (s, 1H), 4.36 (br s, 1H), 3.79 (br s, 4H), 3.68 (br s, 3H), 3.54 (br s, 3H), 3.45 (s, 1H), 3.00 (br s, 1.5H), 2.83 (br s, 1.5H), 2.29 (s, 2H), 2.24 (s, 1H), 1.50-1.44 (m, 1H), 1.40-1.35 (m, 2H), 1.32-1.16 (m, 4H), 1.12-0.99 (m, 2H), 0.92-0.86 (m, 3H), 0.75 (t, J=7.4 Hz, 2H), 0.68 (t, J=7.4 Hz, 1H); MS(ESI⁺) m/z 853.3 (M+H)⁺.

Example 48

N,N-Dibutyl-4-chloro-1-(4-(7-(dimethylcarbamoyl) naphthalen-2-ylsulfonylcarbamoyl)-2-(1,2,3,4-tetrahydroisoquinoline-2-carbonyl)phenyl)-5-methyl-1H-pyrazole-3-carboxamide (48)

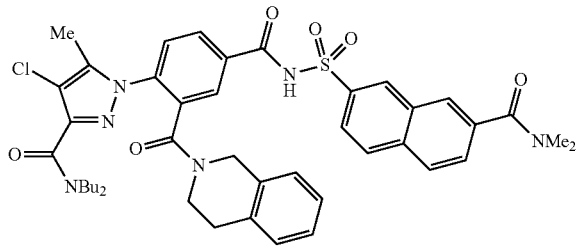

Following a procedure analogous to that for the synthesis of Intermediate 12B of Example 12, 7-(N-(4-(4-Chloro-3-(dibutylcarbamoyl)-5-methyl-1H-pyrazol-1-yl)-3-(1,2,3,4-tetrahydroisoquinoline-2-carbonyl)benzoyl)sulfamoyl)-2-naphthoic acid (Intermediate 46A, 12 mg, 0.015 mmol) and dimethylamine (23 µL, 0.046 mmol, 2M solution in THF) were converted to the title compound (2 mg, 19%). ¹H NMR (1:1 MeOD:CDCl₃, 2:1 mixture of amide rotamers) δ 8.67 (s, 1H), 8.18 (d, J=8.3 Hz, 1H), 8.13 (d, J=8.6 Hz, 1H), 8.07 (s, 1H), 8.05 (s, 1H), 7.97 (d, J=10.3 Hz, 2H), 7.61-7.58 (m, 2H), 7.42 (br s, 1H), 7.20-7.06 (m, 3.5H), 6.87 (d, J=7.2 Hz, 0.5H), 4.80 (br s, 1H), 4.23 (br s, 1H), 3.86 (br s, 1H), 3.64 (br s, 1H), 3.54 (br s, 1H), 3.15 (s, 3H), 3.05 (s, 3H), 2.99 (br s, 1.5H), 2.82 (br s, 1.5H), 2.27 (s, 2H), 2.23 (s, 1H), 1.50-1.43 (m, 1H), 1.39-1.35 (m, 2H), 1.31-1.17 (m, 5H), 1.10-0.98 (m, 2H), 0.91-0.85 (m, 3H), 0.74 (t, J=7.4 Hz, 1.5H), 0.68 (t, J=7.4 Hz, 1.5H); MS(ESI⁺) m/z 811.3 (M+H)⁺.

Example 49

4-((7-(N-(4-(4-Chloro-3-(dibutylcarbamoyl)-5-methyl-1H-pyrazol-1-yl)-3-(1,2,3,4-tetrahydroisoquinoline-2-carbonyl)benzoyl)sulfamoyl)naphthalen-1-yloxy)methyl)benzoic acid (49)

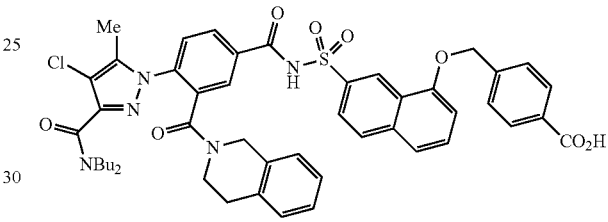

Following a procedure analogous to that for the synthesis of Intermediate 46A, methyl 4-((7-(N-(4-(4-chloro-3-(dibutylcarbamoyl)-5-methyl-1H-pyrazol-1-yl)-3-(1,2,3,4-tetrahydroisoquinoline-2-carbonyl)benzoyl)sulfamoyl)naphthalen-1-yloxy) methyl)benzoate (Example 26, 10 mg, 0.011 mmol) was converted to the title compound (5 mg, 49%). ¹H NMR (CD₃OD, 2:1 mixture of amide rotamers) δ 9.17 (d, J=1.8 Hz, 1H), 8.24-8.00 (m, 6H), 7.81-7.56 (m, 5H), 7.35-7.03 (m, 4.5H), 6.89-6.87 (m, 0.5H), 5.48 (s, 2H), 4.56 (br s, 2H), 3.77-3.42 (m, 4H), 3.24-3.14 (m, 1H), 3.06 (br s, 1H), 2.89 (br s, 2H), 2.37 (s, 2H), 2.32 (s, 1H), 1.63-1.20 (m, 6H), 1.21-1.03 (m, 2H), 1.01-0.88 (m, 3H), 0.86-0.63 (m, 3H); MS(ESI⁺) m/z 890.4 (M+H)⁺.

Example 50

N,N-Dibutyl-4-chloro-1-(4-(7-(2-hydroxyethoxy) naphthalen-2-ylsulfonylcarbamoyl)-2-(1,2,3,4-tetrahydroisoquinoline-2-carbonyl)phenyl)-5-methyl-1H-pyrazole-3-carboxamide (50)

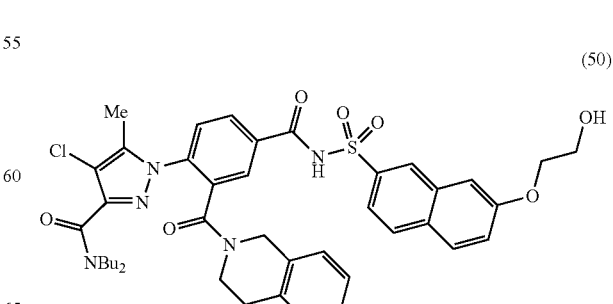

Intermediate 50A

7-Hydroxynaphthalene-2-sulfonamide

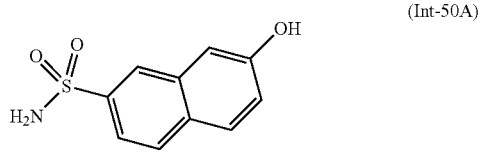 [SMILES: NS(=O)(=O)c1ccc2ccc(O)cc2c1]
(Int-50A)

Following a procedure analogous to that for the synthesis of Intermediate 11, sodium 7-oxidonaphthalene-2-sulfonate (Pfaltz and Bauer, 1.00 g, 3.73 mmol) was converted to the title compound (40 mg, 5%) after purification using preparative HPLC. $^1$H NMR (DMSO-$d_6$) δ 8.17 (s, 1H), 7.95 (d, J=8.6 Hz, 1H), 7.87 (d, J=8.8 Hz, 2H), 7.62 (dd, J=8.6, 1.8 Hz, 1H), 7.35 (s, 2H), 7.28 (d, J=2.2 Hz, 1H), 7.23 (dd, J=8.9, 2.3 Hz, 1H); MS(ESI$^-$) m/z 236.3 (M–H)$^-$.

Intermediate 50B

7-(2-(tert-Butyldimethylsilyloxy)ethoxy)naphthalene-2-sulfonamide

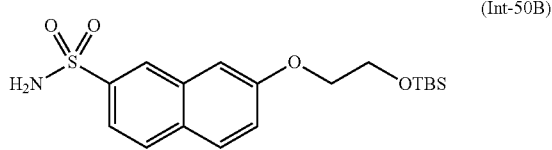 [SMILES: CC(C)(C)[Si](C)(C)OCCOc1ccc2ccc(S(N)(=O)=O)cc2c1]
(Int-50B)

Following a procedure analogous to that for the synthesis of Intermediate 17, 7-hydroxynaphthalene-2-sulfonamide (40 mg, 0.18 mmol) and (2-bromoethoxy)(tert-butyl)dimethylsilane (43 mg, 0.18 mmol) were converted to the title compound (33 mg, 48%) after purification using flash column chromatography (gradient from 0% to 2% MeOH/CH$_2$Cl$_2$). $^1$H NMR (CDCl$_3$) δ 8.31 (s, 1H), 7.84-7.82 (m, 1H), 7.77-7.73 (m, 2H), 7.26 (dd, J=8.9, 2.5 Hz, 1H), 7.19 (d, J=2.2 Hz, 1H), 4.13 (t, J=4.9 Hz, 2H), 4.02 (t, J=4.9 Hz, 2H), 0.90 (s, 9H), 0.10 (s, 6H); MS(ESI$^-$) m/z 380.4 (M–H)$^-$.

Intermediate 50C

N,N-Dibutyl-1-(4-(7-(2-(tert-butyldimethylsilyloxy)ethoxy)naphthalen-2-ylsulfonylcarbamoyl)-2-(1,2,3,4-tetrahydroisoquinoline-2-carbonyl)phenyl)-4-chloro-5-methyl-1H-pyrazole-3-carboxamide

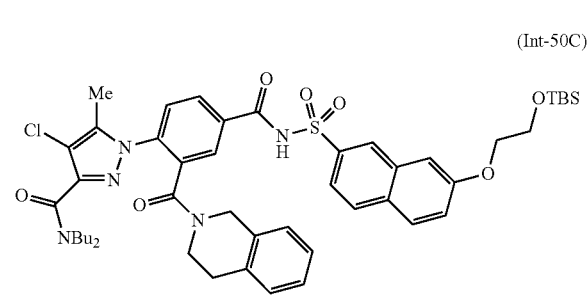
(Int-50C)

Following a procedure analogous to that for the synthesis of Example 1,4-(4-chloro-3-(dibutylcarbamoyl)-5-methyl-1H-pyrazol-1-yl)-3-(1,2,3,4-tetrahydroisoquinoline-2-carbonyl)benzoic acid (Intermediate 1F, 40 mg, 0.073 mmol) and 7-(2-(tert-butyldimethylsilyloxy)ethoxy)naphthalene-2-sulfonamide (Intermediate 50B, 33 mg, 0.087 mmol) were converted to the title compound (31 mg, 47%) after purification using flash column chromatography (gradient from 0% to 3% MeOH/CH$_2$Cl$_2$). $^1$H NMR (CDCl$_3$, 2:1 mixture of amide rotamers) δ 8.62 (s, 1H), 8.11-8.09 (m, 1H), 7.97-7.96 (m, 1H), 7.89-7.88 (m, 2H), 7.84 (d, J=8.9 Hz, 1H), 7.55-7.52 (m, 1H), 7.40-7.38 (m, 2H), 7.23-7.07 (m, 3.5H), 6.85 (d, J=7.4 Hz, 0.5H), 4.75 (br s, 1H), 4.63 (br s, 1H), 4.42 (s, 1H), 4.27-4.24 (m, 2H), 3.85-3.81 (m, 2H), 3.46 (br s, 2H), 3.18-3.15 (m, 2H), 3.02 (br s, 1.5H), 2.84 (br s, 1.5H), 2.29 (s, 2H), 2.24 (s, 1H), 1.50-1.45 (m, 1H), 1.41-1.36 (m, 1H), 1.32-1.20 (m, 6H), 1.12-0.99 (m, 1H), 0.93-0.86 (m, 12H), 0.74 (t, J=7.4 Hz, 2H), 0.68 (t, J=7.2 Hz, 1H), 0.10 (s, 6H); MS(ESI$^+$) m/z 914.3 (M+H)$^+$.

Example 50

To a solution of N,N-dibutyl-1-(4-(7-(2-(tert-butyldimethylsilyloxy)ethoxy)naphthalen-2-ylsulfonylcarbamoyl)-2-(1,2,3,4-tetrahydroisoquinoline-2-carbonyl)phenyl)-4-chloro-5-methyl-1H-pyrazole-3-carboxamide (31 mg, 0.034 mmol) in THF (1.0 mL) was added TBAF (68 μL, 0.068 mmol). The resulting reaction mixture was stirred at room temperature for 1 h, then diluted with EtOAc and washed with sat. aq. NaHCO$_3$ solution. The organic layer was dried (MgSO$_4$), filtered and concentrated in vacuo. The residue was purified using flash column chromatography (gradient from 0% to 10% MeOH/CH$_2$Cl$_2$) to give the title compound (20 mg, 72% yield) as clear, colorless oil. $^1$H NMR (1:1 CD$_3$OD:CDCl$_3$, 2:1 mixture of amide rotamers) δ 8.58 (s, 1H), 8.07-8.05 (m, 1H), 7.92-7.91 (m, 1H), 7.87-7.86 (m, 2H), 7.82 (d, J=9.0 Hz, 1H), 7.50-7.48 (m, 1H), 7.35-7.32 (m, 2H), 7.21-7.08 (m, 3.5H), 6.83 (d, J=7.4 Hz, 0.5H), 4.75 (br s, 1H), 4.62 (br s, 1H), 4.45 (s, 1H), 4.27-4.24 (m, 2H), 3.83-3.80 (m, 2H), 3.45 (br s, 2H), 3.16 (br s, 2H), 3.04-3.03 (m, 1.5H), 2.84 (br s, 1.5H), 2.29 (s, 2H), 2.24 (s, 1H), 1.50-1.45 (m, 1H), 1.41-1.36 (m, 1H), 1.32-1.20 (m, 6H), 1.12-0.99 (m, 1H), 0.91-0.86 (m, 3H), 0.74 (t, J=7.4 Hz, 2H), 0.68 (t, J=7.2 Hz, 1H); MS(ESI$^+$) m/z 800.2 (M+H)$^+$.

Example 51

N,N-Dibutyl-4-chloro-1-(4-(7-hydroxynaphthalen-2-ylsulfonylcarbamoyl)-2-(1,2,3,4-tetrahydroisoquinoline-2-carbonyl)phenyl)-5-methyl-1H-pyrazole-3-carboxamide

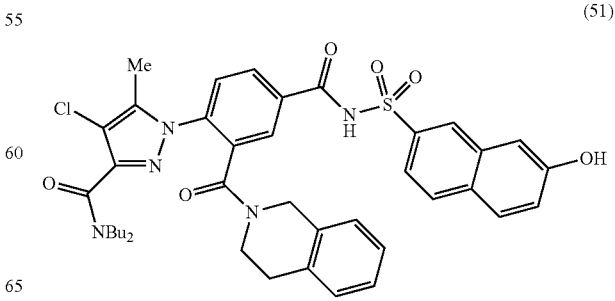
(51)

To a solution of 1-(4-(7-(benzyloxy)naphthalen-2-ylsulfonylcarbamoyl)-2-(1,2,3,4-tetrahydroisoquinoline-2-carbonyl)phenyl)-N,N-dibutyl-4-chloro-5-methyl-1H-pyrazole-3-carboxamide (Example 18, 30 mg, 0.035 mmol) in MeOH (5.0 mL) was added 10% Pd/C (75 mg, 0.71 mmol). The flask was evacuated and purged with H₂ from a balloon (2×), and the reaction mixture was then stirred overnight under an atmosphere of H₂. The reaction mixture was diluted with CH₂Cl₂ and filtered through a pad of CELITE®, washing with CH₂Cl₂. The filtrate was concentrated in vacuo and purified by preparative HPLC to give the title compound (12 mg, 43%). ¹H NMR (1:1 CD₃OD:CDCl₃, 1:1 mixture of amide rotamers) δ 8.37 (s, 1H), 8.17-8.13 (m, 1H), 8.05 (s, 1H), 7.93 (s, 1H), 7.80-7.76 (m, 2H), 7.70 (d, J=8.9 Hz, 1H), 7.34 (dd, J=8.5, 1.3 Hz, 1H), 7.23 (s, 1H), 7.17-7.05 (m, 4.5H), 6.83 (d, J=7.9 Hz, 0.5H), 4.66 (br s, 2H), 4.41 (s, 1H), 3.88 (br s, 1H), 3.51 (br s, 2H), 3.04-3.00 (m, 1H), 2.81-2.78 (m, 1H), 2.24 (s, 1.5H), 2.20 (s, 1.5H), 1.49-1.42 (m, 1H), 1.40-1.33 (m, 2H), 1.30-1.16 (m, 5H), 1.09-0.96 (m, 2H), 0.90-0.84 (m, 3H), 0.72 (t, J=7.4 Hz, 1.5H), 0.67 (t, J=7.4 Hz, 1.5H); MS (ESI⁺) m/z 756.2 (M+H)⁺.

Example 52

N,N-Dibutyl-4-chloro-1-(4-(indolin-5-ylsulfonylcarbamoyl)-2-(1,2,3,4-tetrahydroisoquinoline-2-carbonyl)phenyl)-5-methyl-1H-pyrazole-3-carboxamide

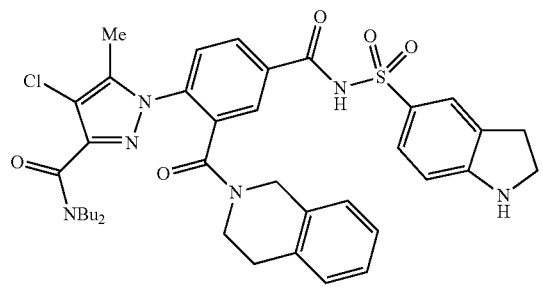

(52)

Intermediate 52A

1-Acetylindoline-5-sulfonamide

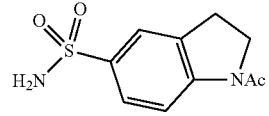

(Int-52A)

To a solution 1-acetylindoline-5-sulfonyl chloride (Borror, A. L. et al., *J. Org. Chem.*, 53:2047-2052 (1988)) (2.00 g, 7.70 mmol) in CH₂Cl₂ (5.0 mL) was added NH₃ (38.5 mL, 19.3 mmol, 0.5M solution in dioxane) and Et₃N (2.2 mL, 15.4 mmol). The resulting reaction mixture was stirred at room temperature for 3 h. The reaction mixture was then concentrated in vacuo, and the residue was triturated with 1N aq. HCl solution (2×) and water (1×) to give the title compound (1.80 g, 97%) as a white solid. ¹H NMR (DMSO-d₆) δ 8.11 (d, J=8.1 Hz, 1H), 7.64-7.62 (m, 2H), 7.20 (br s, 2H), 4.16 (t, J=8.6 Hz, 2H), 3.19 (t, J=8.5 Hz, 2H), 2.19 (s, 3H); MS(ESI⁺) m/z 241.0 (M+H)⁺.

Intermediate 52B 1-(4-(1-Acetylindolin-5-ylsulfonylcarbamoyl)-2-(1,2,3,4-tetrahydroisoquinoline-2-carbonyl)phenyl)-N,N-dibutyl-4-chloro-5-methyl-1H-pyrazole-3-carboxamide

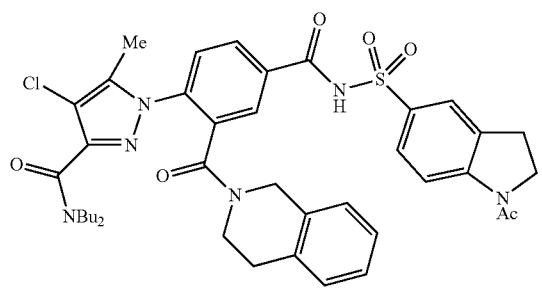

(52B)

To a solution of 4-(4-chloro-3-(dibutylcarbamoyl)-5-methyl-1H-pyrazol-1-yl)-3-(1,2,3,4-tetrahydroisoquinoline-2-carbonyl)benzoic acid (Intermediate 1F, 30 mg, 0.054 mmol) in DMF (2.0 mL) was added HATU (29 mg, 0.076 mmol), 1-acetylindoline-5-sulfonamide (20 mg, 0.082 mmol), DMAP (7 mg, 0.054 mmol) and i-Pr₂EtN (0.029 mL, 0.163 mmol). The resulting reaction mixture was stirred at room temperature for 3 h and then diluted with EtOAc and 1N aq. HCl solution. The organic layer was washed with 1N aq. NaOH solution (2×) followed by 1N aq. HCl solution (1×). The combined aqueous layer was extracted with EtOAc (3×). The combined organic extracts were dried over MgSO₄, filtered and concentrated in vacuo to give a crude oil, which was purified using preparative HPLC to give the title compound (10 mg, 24%). ¹H NMR (CD₃OD, 2:1 mixture of amide rotamers) δ 8.19-8.16 (m, 2H), 8.08-8.06 (m, 1H), 7.89-7.86 (m, 2H), 7.57 (t, J=7.8 Hz, 1H), 7.22-7.10 (m, 3.5H), 6.94 (d, J=7.3 Hz, 0.5H), 4.75-4.50 (m, 2H), 4.22-4.18 (m, 2H), 3.90-3.40 (m, 4H), 3.15-2.65 (m, 4H), 2.33 (s, 2H), 2.28 (s, 1H), 2.25 (s, 3H), 1.52-1.00 (m, 10H), 0.95-0.88 (m, 3H), 0.79-0.75 (m, 2H), 0.71-0.67 (m, 1H); MS(ESI⁺) m/z 773.2 (M+H)⁺.

Example 52

To a solution of 1-(4-(1-acetylindolin-5-ylsulfonylcarbamoyl)-2-(1,2,3,4-tetrahydroisoquinoline-2-carbonyl)phenyl)-N,N-dibutyl-4-chloro-5-methyl-1H-pyrazole-3-carboxamide (70 mg, 0.091 mmol) in MeOH (4.0 mL) was added conc. HCl (151 µL, 1.81 mmol). The resulting reaction mixture was heated at 75° C. for 2 h, then cooled to room temperature and concentrated in vacuo. The crude residue was purified using preparative HPLC to give the title compound (1 mg, 2%). ¹H NMR (CD₃OD, 2:1 mixture of amide rotamers) δ 8.11-8.09 (m, 2H), 8.03-7.99 (m, 1H), 7.72-7.65 (m, 2H), 7.24-7.07 (m, 3.5H), 6.94-6.92 (m, 0.5H), 6.55-6.52 (m, 1H), 4.75-4.50 (m, 2H), 4.16-3.65 (m, 2H), 3.35-3.20 (m, 2H), 3.15-2.65 (m, 6H), 2.32 (s, 2H), 2.27 (s, 1H), 1.52-1.00 (m, 10H), 0.95-0.88 (m, 3H), 0.79-0.75 (m, 2H), 0.70-0.66 (m, 1H); MS(ESI⁺) m/z 731.2 (M+H)⁺.

Intermediate 53

1-Ethylindoline-5-sulfonamide

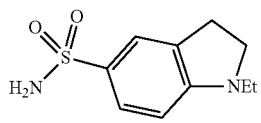
(Int-53)

To a suspension of 1-acetylindoline-5-sulfonamide (Intermediate 52A, 120 mg, 0.50 mmol) in THF (2.0 mL) was added BH₃.THF (5.0 mL, 5.0 mmol, 1.0M solution in THF). The resulting reaction mixture was stirred at room temperature for 1 h, then quenched carefully with MeOH and concentrated in vacuo to give the title compound (115 mg, 100%) as a white solid. ¹H NMR (CD₃OD) δ 7.56 (dd, J=8.4, 2.0 Hz, 1H), 7.48 (d, J=1.6 Hz, 1H), 6.46-6.44 (m, 1H), 3.51 (t, J=8.6 Hz, 2H), 3.24-3.20 (m, 2H), 2.99 (t, J=8.5 Hz, 2H), 1.17-1.13 (m, 3H); MS(ESI⁺) m/z 227.2 (M+H)⁺.

Intermediate 54

1H-Indole-5-sulfonamide

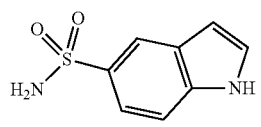
(Int-54)

Intermediate 54A

Indoline-5-sulfonamide

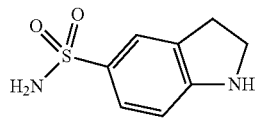
(Int-54A)

To a suspension of 1-acetylindoline-5-sulfonamide (Intermediate 52A, 1.00 g, 4.16 mmol) in MeOH (12.0 mL) was added conc. HCl (1.7 mL, 20.8 mmol). The resulting reaction mixture was stirred at room temperature for 18 h and then at 80° C. for 2 h. The reaction mixture was cooled to room temperature and concentrated in vacuo. The brown residue was dissolved in water and the solution was adjusted to a pH of 7-8 with 1 N aq. NaOH solution. The mixture was then extracted with EtOAc (2×), and the combined organic extracts were dried over Na₂SO₄, filtered and concentrated in vacuo to give the title compound (720 mg, 87%) as a light brown solid. ¹H NMR (DMSO-d₆) δ 7.42-7.38 (m, 2H), 6.86 (s, 2H), 6.47 (d, J=8.1 Hz, 1H), 6.24-6.22 (m, 1H), 3.53-3.50 (m, 2H), 2.98-2.95 (m, 2H); MS(ESI⁺) m/z 199.1 (M+H)⁺.

Intermediate 54

To a suspension of indoline-5-sulfonamide (400 mg, 2.02 mmol) in DCE (12.0 mL) was added DDQ (458 mg, 2.02 mmol). The resulting reaction mixture was stirred at 75° C. for 2 h and then filtered through CELITE®, washing with EtOAc. The filtrate was concentrated in vacuo and purified using preparative HPLC to give the title compound (220 mg, 56%) as a white solid after lyophilization. ¹H NMR (CD₃OD) δ 10.97 (br s, 1H), 8.17 (d, J=1.8 Hz, 1H), 7.66 (dd, J=8.6, 1.8 Hz, 1H), 7.51 (d, J=8.6 Hz, 1H), 7.41-7.39 (m, 1H), 6.61-6.59 (m, 1H); MS(ESI⁺) m/z 197.1 (M+H)⁺.

Intermediate 55

1-(Cyclohexanecarbonyl)indoline-5-sulfonamide

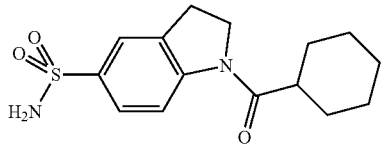
(Int-55)

To a solution of indoline-5-sulfonamide (Intermediate 54A, 100 mg, 0.50 mmol) in MeCN (5.0 mL) was added cyclohexanecarbonyl chloride (0.14 mL, 1.00 mmol) and K₂CO₃ (174 mg, 1.26 mmol). The resulting reaction mixture was stirred at room temperature overnight and then diluted with EtOAc and sat. aq. NaHCO₃ solution. The organic layer was washed with 1 N aq. NaOH solution, followed by 10% aq. LiCl solution. The combined organic extracts were dried over MgSO₄, filtered and concentrated in vacuo. The residue was triturated with CH₂Cl₂ to give the title compound (31 mg, 20%) as a white solid. ¹H NMR (DMSO-d₆) δ 8.16 (d, J=6.8 Hz, 1H), 7.64-7.60 (m, 2H), 7.19 (m, 2H), 4.22 (t, J=8.5 Hz, 2H), 3.21-3.16 (m, 2H), 2.62-2.55 (m, 1H), 1.91-1.65 (m, 5H), 1.45-1.16 (m, 5H); MS(ESI⁺) m/z 309.1 (M+H)⁺.

Intermediate 56

1-Ethyl-1H-indole-5-sulfonamide

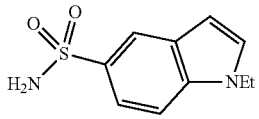
(Int-56)

Following a procedure analogous to that for the synthesis of Intermediate 54, 1-ethylindoline-5-sulfonamide (Intermediate 53, 65 mg, 0.29 mmol) was converted to the title compound (29 mg, 45%). ¹H NMR (CD₃OD) δ 8.16 (d, J=1.3 Hz, 1H), 7.70 (dd, J=8.8, 1.8 Hz, 1H), 7.55 (d, J=8.8 Hz, 1H), 7.40

(d, J=3.3 Hz, 1H), 6.61-6.60 (m, 1H), 4.28 (t, J=7.3 Hz, 2H), 1.45 (t, J=7.3 Hz, 3H); MS(ESI⁺) m/z 225.2 (M+H)⁺.

Intermediate 57

1-(Cyclohexylmethyl)indoline-5-sulfonamide

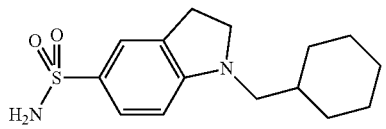
(Int-57)

Following a procedure analogous to that for the synthesis of Intermediate 53, 1-(cyclohexanecarbonyl)indoline-5-sulfonamide (Intermediate 55, 120 mg, 0.39 mmol) was converted to the title compound (65 mg, 57%) after purification using preparative HPLC. ¹H NMR (CD₃OD) δ 7.54 (dd, J=8.4, 2.0 Hz, 1H), 7.45 (d, J=1.5 Hz, 1H), 6.38 (d, J=8.4 Hz, 2H), 3.54 (d, J=8.7 Hz, 2H), 3.04-2.96 (m, 4H), 1.80-1.68 (m, 6H), 1.31-1.23 (m, 3H), 1.05-0.96 (m, 2H); MS(ESI⁺) m/z 295.1 (M+H)⁺.

Intermediate 58

1-(3,4-Dichlorobenzoyl)indoline-5-sulfonamide

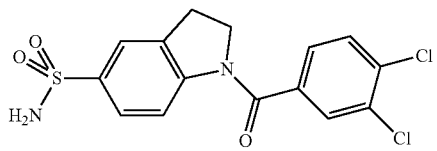
(Int-58)

Following a procedure analogous to that for the synthesis of Intermediate 55, indoline-5-sulfonamide (Intermediate 54A, 195 mg, 0.98 mmol) and 3,4-dichlorobenzoyl chloride (412 mg, 1.97 mmol) were converted to the title compound (132 mg, 36%) after purification using preparative HPLC. ¹H NMR (DMSO-d₆) δ 7.92 (d, J=1.1 Hz, 1H), 7.78 (d, J=8.1 Hz, 1H), 7.71-7.61 (m, 3H), 7.26 (s, 2H), 4.07 (t, J=8.3 Hz, 2H), 3.16 (t, J=8.2 Hz, 2H); MS(ESI⁺) m/z 370.8 (M+H)⁺.

Intermediate 59

1-(3,4-Dichlorobenzyl)indoline-5-sulfonamide

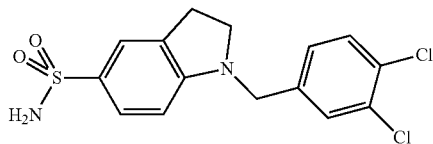
(Int-59)

Following a procedure analogous to that for the synthesis of Intermediate 53, 1-(3,4-dichlorobenzoyl)indoline-5-sulfonamide (Intermediate 58, 70 mg, 0.19 mmol) was converted to the title compound (41 mg, 61%) after purification using preparative HPLC. ¹H NMR (DMSO-d₆) δ 7.63-7.58 (m, 2H), 7.48-7.43 (m, 2H), 7.31 (dd, J=8.3, 2.1 Hz, 1H), 6.91 (s, 2H), 6.60 (d, J=8.1 Hz, 1H), 4.41 (s, 2H), 3.46 (t, J=8.7 Hz, 2H), 3.03-2.98 (m, 2H); MS(ESI⁺) m/z 356.9 (M+H)⁺.

Intermediate 60

1-Acetylindoline-6-sulfonamide

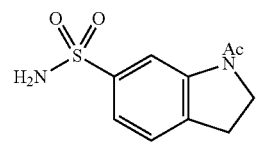
(Int-60)

Intermediate 60A

1-Acetyl-5-bromoindoline-6-sulfonamide

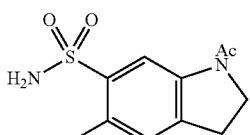
(Int-60A)

A solution of 1-acetyl-5-bromoindoline-6-sulfonyl chloride (2.30 g, 6.79 mmol) in NH₃ (54.3 mL, 27.2 mmol, 0.5M solution in dioxane) was stirred at room temperature overnight. The reaction mixture was then concentrated in vacuo, and the residue was triturated with CH₂Cl₂ to give the title compound (1.40 g, 65%) as a brown solid. ¹H NMR (DMSO-d₆) δ 8.73 (s, 1H), 7.63 (s, 1H), 7.15 (s, 2H), 4.15 (t, J=8.5 Hz, 2H), 3.19 (t, J=8.6 Hz, 2H), 2.17 (s, 3H); MS(ESI⁺) m/z 321.1 (M+H)⁺.

Intermediate 60

To a suspension of 1-acetyl-5-bromoindoline-6-sulfonamide (650 mg, 2.04 mmol) in EtOH (10.0 mL) was added 10% Pd/C (433 mg, 0.41 mmol) and Et₃N (852 μL, 6.11 mmol). The reaction mixture was evacuated and purged with H₂ from a balloon (2×) and allowed to stir under H₂ for 22 h. The reaction mixture then was filtered through a pad of CELITE®, washing with EtOAc. The filtrate was concentrated in vacuo to give the title compound (450 mg, 92%) as a white solid. ¹H NMR (DMSO-d₆) δ 8.49 (s, 1H), 7.46-7.44 (m, 1H), 7.38-7.36 (m, 1H), 7.29 (br s, 2H), 4.15 (t, J=8.6 Hz, 2H), 3.19 (t, J=8.5 Hz, 2H), 2.18 (s, 3H); MS(ESI⁺) m/z 241.1 (M+H)⁺.

Intermediate 61

1-Benzylindoline-5-sulfonamide (61)

Intermediate 61A

1-Benzoylindoline-5-sulfonamide

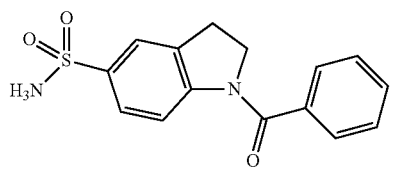
(Int-61A)

Following a procedure analogous to that for the synthesis of Intermediate 55, indoline-5-sulfonamide (Intermediate 54A, 100 mg, 0.50 mmol) and benzoyl chloride (64 μL, 0.56 mmol) were converted to the title compound (120 mg, 79%). $^1$H NMR (DMSO-$d_6$) δ 7.70 (s, 1H), 7.65-7.60 (m, 3H), 7.57-7.49 (m, 4H), 7.24 (s, 2H), 4.07 (t, J=8.5 Hz, 2H), 3.15 (t, J=8.4 Hz, 2H); MS(ESI$^+$) m/z 303.2 (M+H)$^+$.

Intermediate 61

Following a procedure analogous to that for the synthesis of Intermediate 45, 1-benzoylindoline-5-sulfonamide (120 mg, 0.40 mmol) was converted to the title compound (100 mg, 87%) after purification using preparative HPLC. $^1$H NMR (CD$_3$OD) δ 7.56 (dd, J=8.4, 2.0 Hz, 1H), 7.52-7.51 (m, 1H), 7.35-7.25 (m, 5H), 6.52 (d, J=8.4 Hz, 1H), 4.38 (s, 2H), 3.49 (t, J=8.7 Hz, 2H), 3.03 (t, J=8.6 Hz, 2H); MS(ESI$^+$) m/z 289.2 (M+H)$^+$.

Intermediate 62

1-(3,4-Difluorobenzyl)indoline-5-sulfonamide

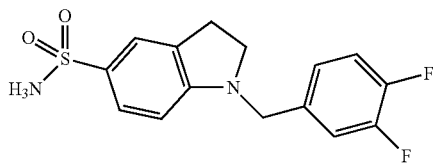
(Int-62)

Intermediate 62A 1-(3,4-Difluorobenzoyl)indoline-5-sulfonamide

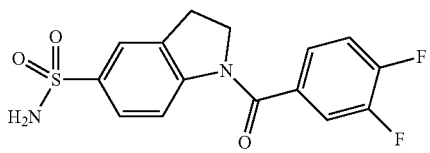
(Int-62A)

Following a procedure analogous to that for the synthesis of Intermediate 55, indoline-5-sulfonamide (Intermediate 54A, 90 mg, 0.45 mmol) and 3,4-difluorobenzoyl chloride (69 μL, 0.54 mmol) were converted to the title compound (120 mg, 78%). $^1$H NMR (DMSO-$d_6$) δ 7.60-7.21 (m, 6H), 7.01 (s, 2H), 3.85 (t, J=8.6 Hz, 2H), 2.92 (t, J=8.6 Hz, 2H); MS(ESI$^+$) m/z 338.9 (M+H)$^+$.

Intermediate 62B 1-(3,4-Difluorobenzyl)indoline-5-sulfonamide

Following a procedure analogous to that for the synthesis of Intermediate 53, 1-benzoylindoline-5-sulfonamide (100 mg, 0.30 mmol) was converted to the title compound (58 mg, 60%) after purification using preparative HPLC. $^1$H NMR (DMSO-$d_6$) δ 7.46-7.35 (m, 4H), 7.18-7.15 (m, 1H), 6.92 (s, 2H), 6.60 (d, J=8.1 Hz, 1H), 4.39 (s, 2H), 3.46 (t, J=8.6 Hz, 2H), 3.00 (t, J=8.6 Hz, 2H); MS(ESI$^+$) m/z 325.1 (M+H)$^+$.

Intermediate 63

1-Ethylindoline-6-sulfonamide

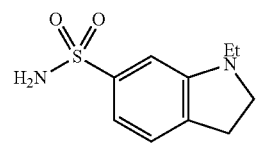
(Int-63)

Following a procedure analogous to that for the synthesis of Intermediate 53, 1-acetylindoline-6-sulfonamide (Intermediate 60, 200 mg, 0.83 mmol) was converted to the title compound (50 mg, 27%) after purification using preparative HPLC. $^1$H NMR (CDCl$_3$) δ 7.37 (d, J=7.5 Hz, 1H), 7.21 (d, J=9.7 Hz, 2H), 3.59 (t, J=8.1 Hz, 2H), 3.28 (q, J=8.1 Hz, 2H), 3.10 (t, J=8.1 Hz, 2H), 1.26-1.22 (m, 3H); MS(ESI$^+$) m/z 227.1 (M+H)$^+$.

Intermediate 64

1-(2-(3,4-Dichlorophenyl)acetyl)indoline-5-sulfonamide

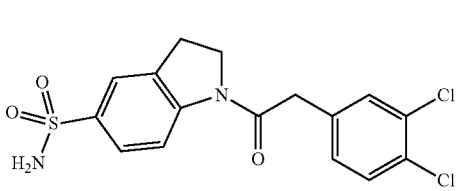
(Int-64)

To a suspension of 2-(3,4-dichlorophenyl)acetic acid (137 mg, 0.67 mmol) in DCE (2.0 mL) was added oxalyl chloride (908 μL, 1.82 mmol, 2.0M solution in CH$_2$Cl$_2$) (0.908 mL, 1.816 mmol) followed by one drop of DMF. The resulting reaction mixture was stirred at room temperature for 40 min and then concentrated in vacuo. To a solution of the crude residue in MeCN (4.0 mL) was added indoline-5-sulfonamide (120 mg, 0.61 mmol) and K$_2$CO$_3$ (167 mg, 1.21 mmol). The reaction mixture was stirred at room temperature for 1 h. Additional indoline-5-sulfonamide (40 mg, 0.20 mmol) was added, and the reaction mixture was allowed to stir at room temperature overnight. The reaction mixture was then diluted with EtOAc and sat. aq. NaHCO$_3$ solution. The organic layer was washed with 10% aq. LiCl solution and then dried over MgSO$_4$, filtered and concentrated in vacuo. The residue was triturated with CH$_2$Cl$_2$ to give the title compound (180 mg, 77%) as a pale yellow solid. $^1$H NMR (DMSO-d$_6$) δ 8.11 (d, J=8.4 Hz, 1H), 7.59 (m, 4H), 7.29 (dd, J=8.1, 2.0 Hz, 1H), 7.22 (s, 2H), 4.26 (t, J=8.5 Hz, 2H), 3.94 (s, 2H), 3.24 (t, J=8.5 Hz, 2H); MS(ESI$^+$) m/z 385.0 (M+H)$^+$.

Intermediate 65

1-(3,4-Dichlorophenethyl)indoline-5-sulfonamide

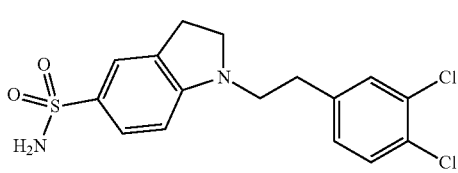
(Int-65)

Following a procedure analogous to that for the synthesis of Intermediate 53, 1-(2-(3,4-dichlorophenyl)acetyl)indoline-5-sulfonamide (Intermediate 64, 140 mg, 0.363 mmol) was converted to the title compound (89 mg, 66%) after purification using preparative HPLC. $^1$H NMR (DMSO-d$_6$) δ 7.64-7.63 (m, 1H), 7.54 (d, J=8.1 Hz, 1H), 7.43 (dd, J=8.4, 2.0 Hz, 1H), 7.39 (d, J=1.5 Hz, 1H), 7.33 (dd, J=8.3 Hz, 2.1 Hz, 1H), 6.90 (s, 2H), 6.56 (d, J=8.4 Hz, 1H), 3.49 (t, J=8.7 Hz, 2H), 3.42-3.38 (m, 2H), 2.95 (t, J=8.5 Hz, 2H), 2.84 (t, J=7.5 Hz, 2H); MS(ESI$^+$) m/z 371.0 (M+H)$^+$.

Intermediate 66

1-(2-(Phenylthio)acetyl)indoline-5-sulfonamide

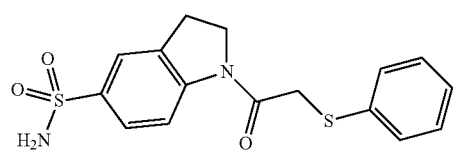
(Int-66)

Following a procedure analogous to that for the synthesis of Intermediate 64, indoline-5-sulfonamide (Intermediate 54A, 120 mg, 0.60 mmol) and 2-(phenylthio)acetic acid (117 mg, 0.70 mmol) were converted to the title compound (100 mg, 45%). $^1$H NMR (DMSO-d$_6$) δ 8.09 (d, J=8.4 Hz, 1H), 7.67-7.62 (m, 2H), 7.43-7.40 (m, 2H), 7.34-7.30 (m, 2H), 7.22-7.19 (m, 3H), 4.29 (t, J=8.6 Hz, 2H), 4.17 (s, 2H), 3.23 (t, J=8.5 Hz, 2H); MS(ESI$^+$) m/z 348.9 (M+H)$^+$.

Intermediate 67

1-(2-(Phenylthio)ethyl)indoline-5-sulfonamide

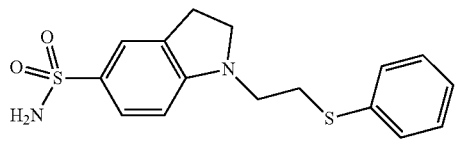
(Int-67)

Following a procedure analogous to that for the synthesis of Intermediate 53, 1-(2-(phenylthio)acetyl)indoline-5-sulfonamide (Intermediate 66, 74 mg, 0.21 mmol) was converted to the title compound (40 mg, 52%) after purification using preparative HPLC. $^1$H NMR (DMSO-d$_6$) δ 7.43-7.33 (m, 6H), 7.21 (t, J=7.2 Hz, 1H), 6.90 (s, 2H), 6.36 (d, J=8.4 Hz, 1H), 3.53 (t, J=8.6 Hz, 2H), 3.39 (t, J=6.8 Hz, 2H), 3.19 (t, J=6.9 Hz, 2H), 2.94 (t, J=8.6 Hz, 2H); MS(ESI$^+$) m/z 335.1 (M+H)$^+$.

Intermediate 68

1-(3,4-Dichlorobenzyl)-1H-indole-5-sulfonamide

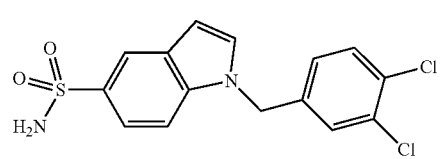
(Int-68)

Following a procedure analogous to that for the synthesis of Intermediate 54, 1-(3,4-dichlorobenzyl)indoline-5-sulfonamide (Intermediate 59, 60 mg, 0.17 mmol) was converted to the title compound (52 mg, 87%). $^1$H NMR (DMSO-d$_6$) δ 8.08 (d, J=1.3 Hz, 1H), 7.70 (d, J=3.1 Hz, 1H), 7.66-7.64 (m, 1H), 7.70 (m, 1H), 7.60-7.56 (m, 2H), 7.50 (d, J=2.0 Hz, 1H), 7.12-7.09 (m, 3H), 6.70 (d, J=2.6 Hz, 1H), 5.50 (s, 2H); MS (ESI$^+$) m/z 354.8 (M+H)$^+$.

Intermediate 69

1-((6-Chloropyridin-2-yl)methyl)indoline-5-sulfonamide

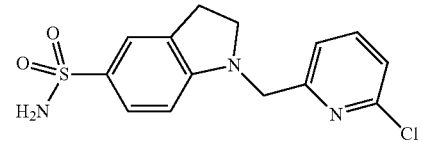
(Int-69)

Intermediate 69A 1-(6-Chloropicolinoyl)indoline-5-sulfonamide

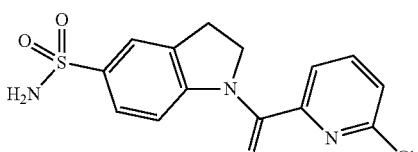
(Int-69A)

Following a procedure analogous to that for the synthesis of Intermediate 64, indoline-5-sulfonamide (Intermediate 54A, 300 mg, 1.51 mmol) and 6-chloropicolinic acid (262 mg, 1.66 mmol) were converted to the title compound (250 mg, 49%). $^1$H NMR (DMSO-d$_6$) δ 8.69 (d, J=2.0 Hz, 1H), 8.15-8.13 (m, 2H), 7.72-7.67 (m, 3H), 7.27 (s, 2H), 4.11 (t, J=8.4 Hz, 2H), 3.17 (t, J=8.4 Hz, 2H); MS(ESI$^+$) m/z 338.1 (M+H)$^+$.

Intermediate 69

Following a procedure analogous to that for the synthesis of Intermediate 53, 1-(6-chloropicolinoyl)-1H-indole-5-sulfonamide (60 mg, 0.18 mmol) was converted to the title compound (29 mg, 50%) after purification using preparative HPLC. $^1$H NMR (DMSO-d$_6$) δ 8.40 (d, J=2.0 Hz, 1H), 7.80 (dd, J=8.1, 2.6 Hz, 1H), 7.52-7.43 (m, 3H), 6.93 (br s, 2H), 6.66 (d, J=8.4 Hz, 1H), 4.44 (s, 2H), 3.45 (t, J=8.6 Hz, 2H), 2.99 (t, J=8.5 Hz, 2H); MS(ESI$^+$) m/z 324.1 (M+H)$^+$.

Intermediate 70

1-((1-Methyl-1H-indol-6-yl)methyl)indoline-5-sulfonamide

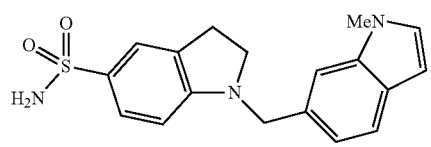
(Int-70)

Intermediate 70A

1-(1-Methyl-1H-indole-6-carbonyl)indoline-5-sulfonamide

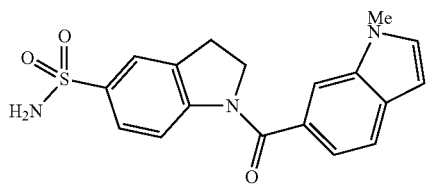
(Int-70A)

Following a procedure analogous to that for the synthesis of Intermediate 56, indoline-5-sulfonamide (Intermediate 54A, 130 mg, 0.66 mmol) and 1-methyl-1H-indole-3-carboxylic acid (Aldrich, 126 mg, 0.721 mmol) were converted to the title compound (21 mg, 9%) after purification using preparative HPLC. $^1$H NMR (DMSO-d$_6$) δ 7.79 (m, 2H), 7.70 (m, 1H), 7.65-7.61 (m, 2H), 7.50 (d, J=3.1 Hz, 1H), 7.27 (dd, J=8.3, 1.4 Hz, 1H), 7.23 (s, 2H), 6.52 (d, J=2.4 Hz, 1H), 4.17 (t, J=8.4 Hz, 2H), 3.84 (s, 3H), 3.16 (t, J=8.3 Hz, 2H); MS(ESI$^+$) m/z 356.1 (M+H)$^+$.

Intermediate 70

Following a procedure analogous to that for the synthesis of Intermediate 53, 1-(1-methyl-1H-indole-6-carbonyl)indoline-5-sulfonamide (40 mg, 0.11 mmol) was converted to the title compound (20 mg, 52%) after purification using preparative HPLC. $^1$H NMR (DMSO-d$_6$) δ 7.55-7.43 (m, 4H), 7.32 (d, J=2.0 Hz, 1H), 7.02 (dd, J=8.3, 1.4 Hz, 1H), 6.95 (s, 2H), 6.72 (d, J=8.3 Hz, 1H), 6.42 (d, J=2.4 Hz, 1H), 4.50 (s, 2H), 3.84 (s, 3H), 3.48 (t, J=8.4 Hz, 2H), 3.00 (t, J=8.3 Hz, 2H); MS(ESI$^+$) m/z 341.1 (M+H)$^+$.

Intermediate 71

5-Bromo-1-ethylindoline-6-sulfonamide

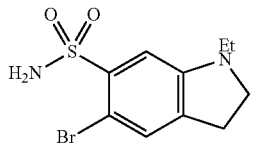
(Int-71)

Following a procedure analogous to that for the synthesis of Intermediate 53, 1-acetyl-5-bromoindoline-6-sulfonamide (Intermediate 60A, 110 mg, 0.34 mmol) was converted to the title compound (53 mg, 50%). $^1$H NMR (DMSO-d$_6$) δ 7.34 (s, 1H), 7.32 (s, 2H), 7.00 (s, 1H), 3.41 (t, J=8.5 Hz, 2H), 3.14 (q, J=7.1 Hz, 2H), 2.95 (t, J=8.5 Hz, 2H), 1.10 (t, J=7.2 Hz, 3H); MS(ESI$^+$) m/z 307.1 (M+H)$^+$.

Intermediate 72

5-Bromo-1-(3,4-dichlorobenzyl)indoline-6-sulfonamide

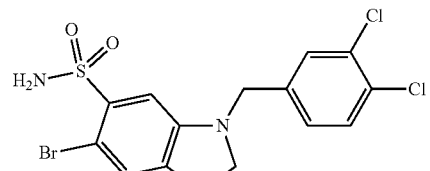
(Int-72)

Intermediate 72A

(3,4-Dichlorophenyl)(indolin-1-yl)methanone

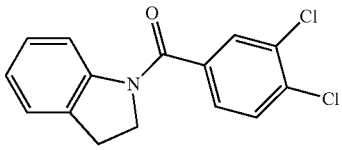
(Int-72A)

To a solution of indoline (2.0 mL, 17.8 mmol) in MeCN (45.0 mL) was added 3,4-dichlorobenzoyl chloride (4.11 g, 19.6 mmol) followed by Et$_3$N (7.5 mL, 53.5 mmol) at 0° C. The reaction mixture was stirred at room temperature for 1 h and then concentrated in vacuo. The residue was triturated with water and dried under high vacuum to give the title compound (5.2 g, 100%) as a light brown solid. $^1$H NMR (DMSO-d$_6$) δ 7.89 (d, J=1.1 Hz, 1H), 7.77 (d, J=8.1 Hz, 1H), 7.60 (d, J=8.1 Hz, 1H), 7.29 (d, J=7.3 Hz, 1H), 7.19 (m, 1H), 7.06 (t, J=7.2 Hz, 1H), 4.00 (t, J=8.3 Hz, 2H), 3.09 (t, J=8.3 Hz, 2H); MS(ESI+) m/z 292.1 (M+H)+.

Intermediate 72B (5-Bromoindolin-1-yl)(3,4-dichlorophenyl)methanone

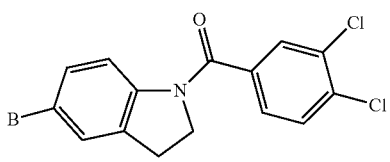

To a solution of (3,4-dichlorophenyl)(indolin-1-yl)methanone (2.6 g, 8.90 mmol) in AcOH (8.2 mL, 142 mmol) was added bromine (504 µL, 9.79 mmol) dropwise via syringe at 0° C. Additional AcOH (6.0 mL) was added, and the reaction mixture was stirred at room temperature for 1 h. Cold water was added to the reaction mixture followed by sat. aq. NaHSO$_3$ solution. The resulting mixture was stirred for 10 min, and the precipitate was collected via filtration to give the title compound (3.30 g, 100%) as a light brown solid. $^1$H NMR (DMSO-d$_6$) δ 7.90 (d, J=1.5 Hz, 1H), 7.77 (d, J=8.4 Hz, 1H), 7.60 (d, J=8.1 Hz, 1H), 7.49 (s, 1H), 7.38 (br s, 1H), 4.02 (t, J=8.3 Hz, 2H), 3.10 (t, J=8.3 Hz, 2H); MS(ESI+) m/z 371.9 (M+H)+.

Intermediate 72C

5-Bromo-1-(3,4-dichlorobenzoyl)indoline-6-sulfonamide

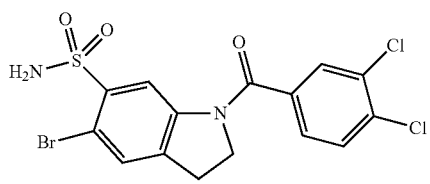

To sulfurochloridic acid (2.9 mL, 43.1 mmol) was added (5-bromoindolin-1-yl)(3,4-dichlorophenyl)methanone (2.00 g, 5.39 mmol) portionwise at 0° C. The reaction mixture was stirred at 65° C. for 6 h and then at room temperature overnight. The reaction mixture poured slowly into ice water and then extracted with CH$_2$Cl$_2$. The organic layer was washed with sat. aq. NaCl solution, dried over MgSO$_4$, filtered and concentrated in vacuo to give a brown solid, which was used in the subsequent step without purification.

Following a procedure analogous to that for the synthesis of Compound A of Example 52, the crude solid from above was converted to the title compound (310 mg, 16% over two steps) after purification using preparative HPLC. $^1$H NMR (DMSO-d$_6$) δ 8.65 (br s, 1H), 7.91 (d, J=1.8 Hz, 1H), 7.78 (d, J=8.4 Hz, 1H), 7.72 (s, 1H), 7.62 (dd, J=8.3, 1.9 Hz, 1H), 7.53 (s, 2H), 4.07 (t, J=8.4 Hz, 2H), 3.16 (t, J=8.3 Hz, 2H); MS (ESI+) m/z 450.9 (M+H)+.

Intermediate 72

Following a procedure analogous to that for the synthesis of Intermediate 53, 5-bromo-1-(3,4-dichlorobenzoyl)indoline-6-sulfonamide (240 mg, 0.53 mmol) was converted to the title compound (160 mg, 69%) after purification using preparative HPLC. $^1$H NMR (DMSO-d$_6$) δ 7.63 (d, J=8.1 Hz, 1H), 7.60 (d, J=2.0 Hz, 1H), 7.93 (s, 1H), 7.34-7.31 (m, 3H), 7.07 (s, 1H), 4.33 (s, 2H), 3.43 (t, J=8.6 Hz, 2H), 3.02 (t, J=8.5 Hz, 2H); MS(ESI+) m/z 436.9 (M+H)+.

Intermediate 73

Methyl 1-(3,4-dichlorobenzyl)-5-sulfamoylindoline-2-carboxylate

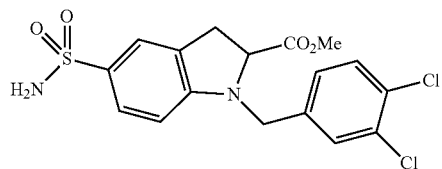

Intermediate 73A

Methyl 1-(3,4-dichlorobenzoyl)indoline-2-carboxylate

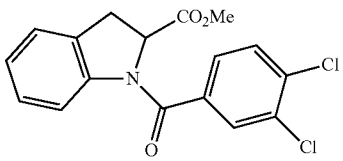

Following a procedure analogous to that for the synthesis of Intermediate 72A, methyl indoline-2-carboxylate (Lee, S. et al., Eur. J. Org. Chem., 38:459-471 (2003)) (3.23 g, 18.3 mmol) and 3,4-dichlorobenzoyl chloride (4.21 g, 20.1 mmol) were converted to the title compound (5.30 g, 83%) after purification using flash column chromatography (gradient from 0% to 5% EtOAc/CH$_2$Cl$_2$). $^1$H NMR (CDCl$_3$, 1:1 mixture of amide rotamers) δ 7.67 (s, 1H), 7.55 (d, J=8.4 Hz, 1H), 7.41-7.37 (m, 1.5H), 7.23-7.20 (m, 1.5H), 7.04-7.01 (m, 2H), 5.31-5.08 (m, 1H), 3.77-3.75 (m, 3H), 3.62-3.55 (m, 1H), 3.24-3.19 (m, 1H); MS(ESI+) m/z 350.1 (M+H)+.

Intermediate 73B

Methyl 1-(3,4-dichlorobenzoyl)-5-sulfamoylindoline-2-carboxylate

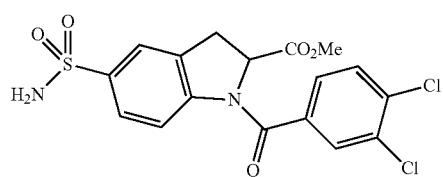

Following a procedure analogous to that for the synthesis of Intermediate 72C, methyl 1-(3,4-dichlorobenzoyl)indoline-2-carboxylate (2.00 g, 5.71 mmol) was converted to the title compound (200 mg, 14% over two steps). ¹H NMR (CDCl₃) δ 8.19 (d, J=2.0 Hz, 1H), 7.93 (dd, J=8.4, 2.0 Hz, 1H), 7.76 (s, 1H), 7.72-7.67 (m, 2H), 7.59-7.56 (m, 2H), 7.41-7.39 (m, 1H), 5.14-5.11 (m, 1H), 3.75-3.73 (m, 3H), 3.67-3.60 (m, 1H), 3.29-3.24 (m, 1H); MS(ESI⁺) m/z 428.9 (M+H)⁺.

Intermediate 73

Following a procedure analogous to that for the synthesis of Intermediate 53, methyl 1-(3,4-dichlorobenzoyl)-5-sulfamoylindoline-2-carboxylate (200 mg, 0.47 mmol) was converted to the title compound (44 mg, 22%) after purification using preparative HPLC. ¹H NMR (DMSO-d₆) δ 7.61 (dd, J=5.1, 3.1 Hz, 2H), 7.46-7.44 (m, 2H), 7.32 (dd, J=8.4, 2.0 Hz, 1H), 6.98 (s, 2H), 6.43 (d, J=8.8 Hz, 1H), 4.61-4.58 (m, 2H), 4.37 (d, J=16.3 Hz, 1H), 3.63-3.62 (m, 3H), 3.54-3.47 (m, 1H), 3.13 (dd, J=16.6, 6.1 Hz, 1H); MS(ESI⁺) m/z 415.1 (M+H)⁺.

Intermediate 74

1-(Morpholine-4-carbonyl)indoline-5-sulfonamide

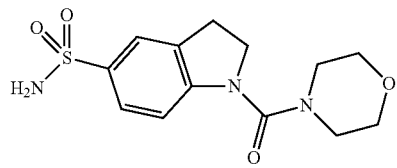

(Int-74)

Following a procedure analogous to that for the synthesis of Intermediate 55, indoline-5-sulfonamide (Intermediate 54A, 250 mg, 1.26 mmol) and morpholine-4-carbonyl chloride (206 µL, 1.77 mmol) were converted to the title compound (230 mg, 59%) after purification using preparative HPLC. ¹H NMR (DMSO-d₆) δ 7.61-7.58 (m, 2H), 7.15-7.12 (m, 3H), 3.92 (t, J=6.5 Hz, 2H), 3.78-3.75 (m, 2H), 3.66-3.63 (m, 4H), 3.10-3.07 (m, 4H); MS(ESI⁺) m/z 312.2 (M+H)⁺.

Intermediate 75

1-(2-Morpholinoacetyl)indoline-5-sulfonamide

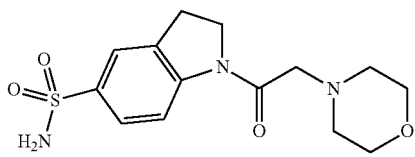

(Int-75)

Intermediate 75A 1-(2-Chloroacetyl)indoline-5-sulfonamide

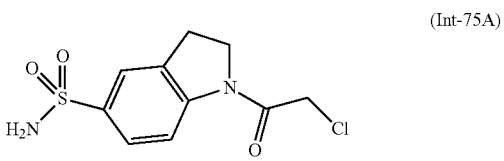 [SMILES: NS(=O)(=O)c1ccc2c(c1)CCN2C(=O)CCl]

(Int-75A)

Following a procedure analogous to that for the synthesis of Intermediate 55, indoline-5-sulfonamide (Intermediate 54A, 500 mg, 2.52 mmol) and 2-chloroacetyl chloride (221 µL, 2.77 mmol) were converted to the title compound (160 mg, 23%). ¹H NMR (DMSO-d₆) δ 8.13 (d, J=8.1 Hz, 1H), 7.68-7.66 (m, 2H), 7.24 (s, 2H), 4.58 (s, 2H), 4.20 (t, J=8.5 Hz, 2H), 3.24 (t, J=8.5 Hz, 2H); MS(ESI⁺) m/z 275.0 (M+H)⁺.

Intermediate 75

Following a procedure analogous to that for the synthesis of Intermediate 55, 1-(2-chloroacetyl)indoline-5-sulfonamide (160 mg, 0.58 mmol) and morpholine (221 µL, 2.77 mmol) were converted to the title compound (86 mg, 45%). ¹H NMR (DMSO-d₆) δ 8.12 (br s, 1H), 7.65-7.62 (m, 2H), 7.21 (s, 2H), 4.23 (t, J=8.6 Hz, 2H), 3.60-3.58 (m, 4H), 3.32-3.30 (m, 6H), 3.22-3.16 (m, 2H); MS(ESI⁺) m/z 326.1 (M+H)⁺.

Intermediate 76

7-Bromo-1-ethylindoline-5-sulfonamide

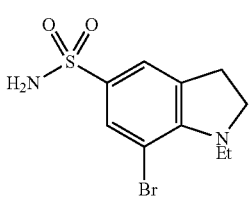

(Int-76)

Following a procedure analogous to that for the synthesis of Intermediate 72B, 1-ethylindoline-5-sulfonamide (Intermediate 53, 230 mg, 1.02 mmol) was converted to the title compound (225 mg, 72%). ¹H NMR (DMSO-d₆) δ 7.56 (d, J=1.8 Hz, 1H), 7.36 (d, J=1.5 Hz, 1H), 7.08 (s, 2H), 3.65-3.55

(m, 4H), 2.99 (t, J=8.9 Hz, 2H), 1.09 (t, J=7.0 Hz, 3H); MS(ESI⁺) m/z 307.1 (M+H)⁺.

Intermediate 77

1-(2-Morpholinoethyl)indoline-5-sulfonamide

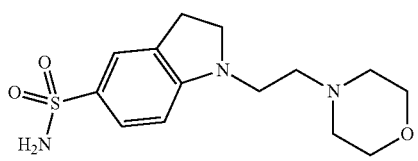

(Int-77)

Intermediate 77A 1-(2-Chloroethyl)indoline-5-sulfonamide

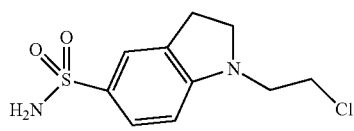

(Int-77A)

Following a procedure analogous to that for the synthesis of Intermediate 53, 1-(2-chloroacetyl)indoline-5-sulfonamide (Intermediate 75A, 400 mg, 1.46 mmol) was converted to the title compound (300 mg, 79%). ¹H NMR (DMSO-d₆) δ 7.45 (dd, J=8.3, 1.9 Hz, 1H), 7.41 (br s, 1H), 6.91 (s, 2H), 6.56 (d, J=8.4 Hz, 1H), 3.83-3.80 (m, 2H), 3.60-3.51 (m, 4H), 2.99 (t, J=8.7 Hz, 2H); MS(ESI⁺) m/z 261.2 (M+H)⁺.

Intermediate 75

To a solution of 1-(2-chloroethyl)indoline-5-sulfonamide (100 mg, 0.38 mmol) in DMF (2.0 mL) were added NaI (86 mg, 0.58 mmol), KOH (108 mg, 1.92 mmol) and morpholine (201 μL, 2.30 mmol). The resulting reaction mixture was stirred at 72° C. overnight. The reaction mixture was then filtered and purified by preparative HPLC to give the title compound (26 mg, 22%) as a white solid after lyophilization. ¹H NMR (DMSO-d₆) δ 7.45-7.38 (m, 2H), 6.90 (br s, 2H), 6.49 (d, J=8.6 Hz, 1H), 3.57-3.52 (m, 6H), 3.28 (t, J=6.8 Hz, 2H), 2.44-2.42 (m, 4H), 2.96 (t, J=8.6 Hz, 4H); MS (ESI⁺) m/z 312.0 (M+H)⁺.

Intermediate 78

1-(6-(2-Morpholinoethoxy)nicotinoyl)indoline-5-sulfonamide

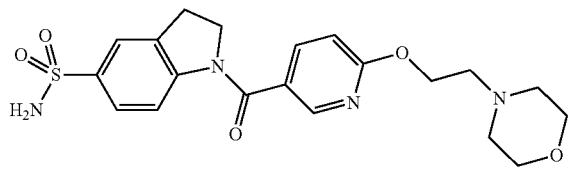

(Int-78)

Intermediate 78A 6-(2-Morpholinoethoxy)nicotinic acid

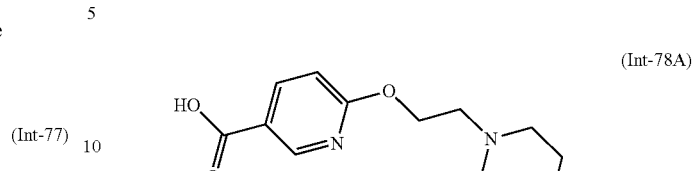

(Int-78A)

To a solution of 6-chloronicotinic acid (Aldrich, 1.00 g, 6.35 mmol) and t-BuOK (1.42 g, 12.7 mmol) in DMSO (10.0 mL) was added 2-morpholinoethanol (1.5 mL, 12.7 mmol) at room temperature. The reaction mixture was then heated at 95° C. for 16 h. Additional t-BuOK (1.42 g, 12.7 mmol), 2-morpholinoethanol (1.54 mL, 12.7 mmol) and DMSO (10.0 mL) were added, and the reaction mixture was heated at 95° C. for another 24 h. The reaction mixture was then cooled to room temperature, poured into ice cold 4N aq. HCl solution and extracted with EtOAc (3×). The aqueous layer was concentrated in vacuo to near dryness and purified using preparative HPLC to give the title compound (150 mg, 9%) as a white solid after lyophilization. ¹H NMR (DMSO-d₆) δ 13.1 (br s, 1H), 8.74 (d, J=1.8 Hz, 1H), 8.21 (dd, J=8.6, 2.2 Hz, 1H), 6.98 (d, J=8.6 Hz, 1H), 4.69 (br s, 4H), 3.96 (br s, 2H), 3.75-3.70 (m, 2H), 3.19 (br s, 4H); MS(ESI⁺) m/z 253.2 (M+H)⁺.

Intermediate 78

Following a procedure analogous to that for the synthesis of Intermediate 64, indoline-5-sulfonamide (Intermediate 54A, 110 mg, 0.56 mmol) and 6-(2-morpholinoethoxy)nicotinic acid (147 mg, 0.58 mmol) were converted to the title compound (51 mg, 21%). ¹H NMR (DMSO-d₆) δ 8.52 (d, J=2.0 Hz, 1H), 8.05 (dd, J=8.6, 2.4 Hz, 1H), 7.95 (br s, 1H), 7.71-7.66 (m, 2H), 7.26 (s, 2H), 7.02-6.98 (m, 1H), 4.74-4.68 (m, 2H), 4.14 (t, J=8.4 Hz, 2H), 3.97 (br s, 2H), 3.75-3.49 (m, 6H), 3.17 (t, J=8.5 Hz, 4H); MS(ESI⁺) m/z 433.2 (M+H)⁺.

Intermediate 79

3-Bromo-1H-indole-5-sulfonamide

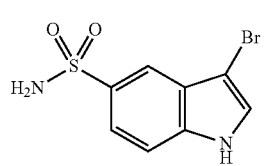

(Int-79)

To a solution of 1H-indole-5-sulfonamide (Intermediate 54, 100 mg, 0.51 mmol) in DMF (2.0 mL) was added N-bromosuccinimide (91 mg, 0.51 mmol) at 0° C. The resulting reaction mixture was stirred at room temperature for 30 min and then diluted with sat. aq. NaHSO₃ solution and EtOAc. The organic layer was washed with sat. aq. NaCl solution, dried over MgSO₄, filtered and concentrated in vacuo. The residue was purified using preparative HPLC to give the title compound (90 mg, 61%) as a white solid after lyophilization. ¹H NMR (DMSO-d₆) δ 11.88 (br s, 1H), 7.94 (d, J=8.1 Hz, 1H), 7.75 (d, J=2.6 Hz, 1H), 7.65-7.63 (m, 1H), 7.59-7.57 (m, 1H), 7.21 (s, 2H); MS (ESI⁺) m/z 277.1 (M+H)⁺.

Intermediate 80

3-Bromo-1-ethyl-1H-indole-5-sulfonamide

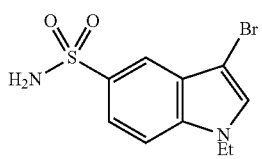
(Int-80)

Following a procedure analogous to that for the synthesis of Intermediate 77, 1-ethyl-1H-indole-5-sulfonamide (Intermediate 56, 70 mg, 0.31 mmol) was converted to the title compound (56 mg, 59%). $^1$H NMR (DMSO-$d_6$) δ 7.93 (d, J=1.3 Hz, 1H), 7.84 (s, 1H), 7.76-7.74 (m, 1H), 7.69-7.66 (m, 1H), 7.23 (s, 2H), 4.28 (q, J=7.3 Hz, 2H), 1.37 (t, J=7.3 Hz, 3H); MS(ESI$^+$) m/z 305.2 (M+H)$^+$.

Intermediate 81

1-(3-Morpholinopropanoyl)indoline-5-sulfonamide

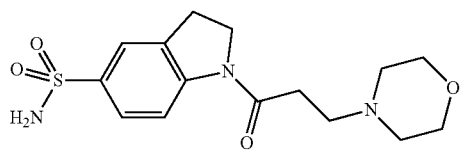
(Int-81)

Intermediate 81A

1-(3-Chloropropanoyl)indoline-5-sulfonamide

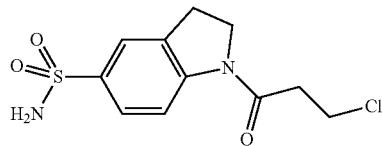
(Int-81A)

Following a procedure analogous to that for the synthesis of Intermediate 55, indoline-5-sulfonamide (Intermediate 54A, 300 mg, 1.51 mmol) and 3-chloropropanoyl chloride (189 µL, 1.97 mmol) were converted to the title compound (430 mg, 98%). $^1$H NMR (DMSO-$d_6$) δ 8.16 (d, J=8.1 Hz, 1H), 7.66-7.63 (m, 2H), 7.22 (s, 2H), 4.18 (t, J=8.6 Hz, 2H), 3.89-3.86 (m, 2H), 3.21 (t, J=8.5 Hz, 2H), 3.03 (t, J=6.4 Hz, 2H); MS (ESI$^+$) m/z 289.2 (M+H)$^+$.

Intermediate 81

To a solution of 1-(3-chloropropanoyl)indoline-5-sulfonamide (210 mg, 0.73 mmol) in DMF (2.0 mL) were added morpholine (509 µL, 5.82 mmol), KOH (82 mg, 1.46 mmol) and TBAI (107 mg, 0.29 mmol). The resulting reaction mixture was stirred at 75° C. for 4 h and then diluted with EtOAc and sat. aq. NaHCO$_3$ solution. The organic layer washed with sat. aq. NaCl solution, dried over MgSO$_4$, filtered and concentrated in vacuo to give the title compound (185 mg, 75%) as a white solid. $^1$H NMR (DMSO-$d_6$) δ 8.14 (d, J=8.1 Hz, 1H), 7.64-7.61 (m, 2H), 7.20 (s, 2H), 4.18 (t, J=8.5 Hz, 2H), 3.58-3.53 (m, 4H), 3.22-3.18 (m, 2H), 2.67-2.62 (m, 4H), 2.41-2.40 (m, 4H); MS(ESI$^+$) m/z 340.3 (M+H)$^+$.

Intermediate 82

1-(3-Morpholinopropyl)-1H-indole-5-sulfonamide, TFA

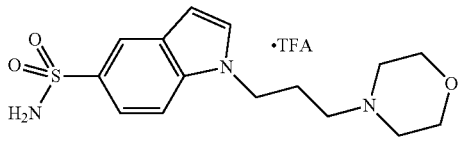
(Int-82)

To a solution of NaH (163 mg, 4.08 mmol, 60% suspension in mineral oil) in DMF (1.5 mL) at 0° C. were added 1H-indole-5-sulfonamide (Intermediate 54, 80 mg, 0.41 mmol), TBAI (60 mg, 0.16 mmol) and 4-(3-chloropropyl)morpholine (667 mg, 4.08 mmol). The resulting reaction mixture was stirred at 0° C. for 2 h, then quenched with MeOH and concentrated in vacuo. The residue was purified by preparative HPLC (H$_2$O/MeOH/0.1% TFA) to give the title compound (178 mg, 100%) as a white solid after lyophilization. $^1$H NMR (DMSO-$d_6$) δ 8.08 (d, J=1.3 Hz, 1H), 7.72-7.67 (m, 1H), 7.65-7.60 (m, 1H), 7.58 (d, J=3.1 Hz, 1H), 7.14 (s, 2H), 6.67 (dd, J=3.2, 0.6 Hz, 1H), 4.34 (t, J=7.0 Hz, 2H), 4.30-4.23 (m, 1H), 4.12-3.09 (m, 9H), 2.24-2.07 (m, 2H); MS(ESI$^+$) m/z 324.3 (M+H)$^+$.

Intermediate 83

3-Chloro-1-ethyl-1H-indole-5-sulfonamide

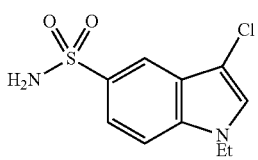
(Int-83)

Following a procedure analogous to that for the synthesis of Intermediate 77, 1-ethyl-1H-indole-5-sulfonamide (Intermediate 56, 50 mg, 0.22 mmol) and N-chlorosuccinimide (36 mg, 0.27 mmol) were converted to the title compound (21 mg, 35%). $^1$H NMR (DMSO-$d_6$) δ 7.99 (d, J=1.3 Hz, 1H), 7.81 (s, 1H), 7.77-7.71 (m, 1H), 7.70-7.64 (m, 1H), 7.22 (s, 2H), 4.26 (q, J=7.3 Hz, 2H), 1.36 (t, J=7.2 Hz, 3H); MS (ESI$^+$) m/z 259.2 (M+H)$^+$.

Intermediate 84

1-Ethyl-3-iodo-1H-indole-5-sulfonamide

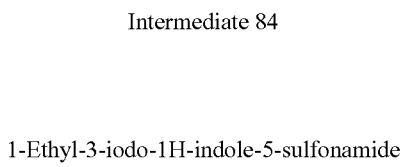
(Int-84)

To a solution of 1-ethyl-1H-indole-5-sulfonamide (Intermediate 56, 175 mg, 0.78 mmol) in DMF (5.0 mL) was added a solution of iodine (218 mg, 0.86 mmol) in DMF (5.0 mL). KOH (109 mg, 1.95 mmol) was then added, and the resulting reaction mixture was stirred at room temperature for 24 h. The reaction mixture was then diluted with EtOAc and sat. aq. NaHSO$_3$ solution. The organic layer was washed with sat. aq. NaCl solution, dried over MgSO$_4$, filtered and concentrated in vacuo. The residue was purified by preparative HPLC to give the title compound (95 mg, 35%) as a pale yellow solid after lyophilization. $^1$H NMR (DMSO-d$_6$) δ 7.86-7.76 (m, 2H), 7.74-7.61 (m, 2H), 7.21 (s, 2H), 4.28 (q, J=7.2 Hz, 2H), 1.36 (t, J=7.3 Hz, 3H); MS(ESI$^+$) m/z 351.1 (M+H)$^+$.

Intermediate 85

3,7-Dibromo-1-ethyl-1H-indole-5-sulfonamide

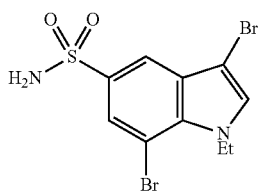
(Int-85)

Intermediate 85A

7-Bromo-1-ethyl-1H-indole-5-sulfonamide

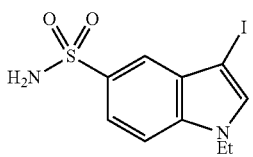
(Int-85A)

Following a procedure analogous to that for the synthesis of Intermediate 54, 7-bromo-1-ethylindoline-5-sulfonamide (Intermediate 76, 140 mg, 0.46 mmol) was converted to the title compound (45 mg, 31%). $^1$H NMR (DMSO-d$_6$) δ 8.04 (d, J=1.8 Hz, 1H), 7.77 (d, J=1.5 Hz, 1H), 7.63 (d, J=3.1 Hz, 1H), 7.26 (s, 2H), 6.72 (d, J=3.3 Hz, 1H), 4.60 (q, J=7.1 Hz, 2H), 1.38 (t, J=7.2 Hz, 3H); MS(ESI$^+$) m/z 305.2 (M+H)$^+$.

Intermediate 85

Following a procedure analogous to that for the synthesis of Intermediate 79, 7-bromo-1-ethyl-1H-indole-5-sulfonamide (45 mg, 0.15 mmol) was converted to the title compound (57 mg, 100%). $^1$H NMR (DMSO-d$_6$) δ 7.94 (s, 1H), 7.90 (d, J=1.8 Hz, 1H), 7.85 (d, J=1.5 Hz, 1H), 7.38 (s, 2H), 4.61 (q, J=7.1 Hz, 2H), 1.39 (t, J=7.2 Hz, 3H).

Examples 53 to 85

The following Examples were prepared using 4-(4-chloro-3-(dibutylcarbamoyl)-5-methyl-1H-pyrazol-1-yl)-3-(1,2,3,4-tetrahydroisoquinoline-2-carbonyl)benzoic acid (Intermediate 1F) and the indole/indoline sulfonamide intermediates described above according to the general procedure for the synthesis of Intermediate 56.

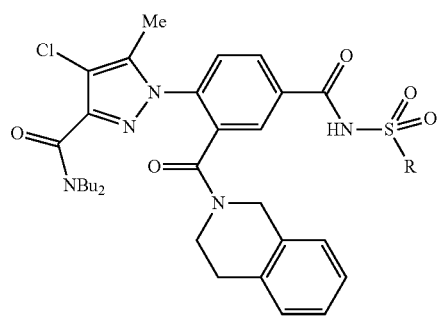

| Ex. No. | R | Name | LCMS (M + H) |
|---|---|---|---|
| 53 | 5-(1-ethylindolin-yl) | N,N-dibutyl-4-chloro-1-(4-(1-ethylindolin-5-ylsulfonylcarbamoyl)-2-(1,2,3,4-tetrahydroisoquinoline-2-carbonyl)phenyl)-5-methyl-1H-pyrazole-3-carboxamide | 759.3 |
| 54 | 5-(1H-indol-yl) | 1-(4-(1H-indol-5-ylsulfonylcarbamoyl)-2-(1,2,3,4-tetrahydroisoquinoline-2-carbonyl)phenyl)-N,N-dibutyl-4-chloro-5-methyl-1H-pyrazole-3-carboxamide | 729.3 |
| 55 | 5-(1-(cyclohexanecarbonyl)indolin-yl) | N,N-dibutyl-4-chloro-1-(4-(1-(cyclohexanecarbonyl)indolin-5-ylsulfonylcarbamoyl)-2-(1,2,3,4-tetrahydroisoquinoline-2-carbonyl)phenyl)-5-methyl-1H-pyrazole-3-carboxamide | 841.3 |
| 56 | 5-(1-ethyl-1H-indol-yl) | N,N-dibutyl-4-chloro-1-(4-(1-ethyl-1H-indol-5-ylsulfonylcarbamoyl)-2-(1,2,3,4-tetrahydroisoquinoline-2-carbonyl)phenyl)-5-methyl-1H-pyrazole-3-carboxamide | 757.3 |
| 57 | 5-(1-(cyclohexylmethyl)indolin-yl) | N,N-dibutyl-4-chloro-1-(4-(1-(cyclohexylmethyl)indolin-5-ylsulfonylcarbamoyl)-2-(1,2,3,4-tetrahydroisoquinoline-2-carbonyl)phenyl)-5-methyl-1H-pyrazole-3-carboxamide | 827.2 |
| 58 | 5-(1-(3,4-dichlorobenzoyl)indolin-yl) | N,N-dibutyl-4-chloro-1-(4-(1-(3,4-dichlorobenzoyl)indolin-5-ylsulfonylcarbamoyl)-2-(1,2,3,4-tetrahydroisoquinoline-2-carbonyl)phenyl)-5-methyl-1H-pyrazole-3-carboxamide | 905.2 |
| 59 | 5-(1-(3,4-dichlorobenzyl)indolin-yl) | N,N-dibutyl-4-chloro-1-(4-(1-(3,4-dichlorobenzyl)indolin-5-ylsulfonylcarbamoyl)-2-(1,2,3,4-tetrahydroisoquinoline-2-carbonyl)phenyl)-5-methyl-1H-pyrazole-3-carboxamide | 891.1 |

-continued

| Ex. No. | R | Name | LCMS (M + H) |
|---|---|---|---|
| 60 | (6-indolinyl with N-Ac) | 1-(4-(1-acetylindolin-6-ylsulfonylcarbamoyl)-2-(1,2,3,4-tetrahydroisoquinoline-2-carbonyl)phenyl)-N,N-dibutyl-4-chloro-5-methyl-1H-pyrazole-3-carboxamide | 773.1 |
| 61 | (5-indolinyl with N-benzyl) | 1-(4-(1-benzylindolin-5-ylsulfonylcarbamoyl)-2-(1,2,3,4-tetrahydroisoquinoline-2-carbonyl)phenyl)-N,N-dibutyl-4-chloro-5-methyl-1H-pyrazole-3-carboxamide | 821.3 |
| 62 | (5-indolinyl with N-(3,4-difluorobenzyl)) | N,N-dibutyl-4-chloro-1-(4-(1-(3,4-difluorobenzyl)indolin-5-ylsulfonylcarbamoyl)-2-(1,2,3,4-tetrahydroisoquinoline-2-carbonyl)phenyl)-5-methyl-1H-pyrazole-3-carboxamide | 857.1 |
| 63 | (6-indolinyl with N-Et) | N,N-dibutyl-4-chloro-1-(4-(1-ethylindolin-6-ylsulfonylcarbamoyl)-2-(1,2,3,4-tetrahydroisoquinoline-2-carbonyl)phenyl)-5-methyl-1H-pyrazole-3-carboxamide | 759.1 |
| 64 | (5-indolinyl with N-(2-(3,4-dichlorophenyl)acetyl)) | N,N-dibutyl-4-chloro-1-(4-(1-(2-(3,4-dichlorophenyl)acetyl)indolin-5-ylsulfonylcarbamoyl)-2-(1,2,3,4-tetrahydroisoquinoline-2-carbonyl)phenyl)-5-methyl-1H-pyrazole-3-carboxamide | |
| 65 | (5-indolinyl with N-(3,4-dichlorophenethyl)) | N,N-dibutyl-4-chloro-1-(4-(1-(3,4-dichlorophenethyl)indolin-5-ylsulfonylcarbamoyl)-2-(1,2,3,4-tetrahydroisoquinoline-2-carbonyl)phenyl)-5-methyl-1H-pyrazole-3-carboxamide | |

-continued

| Ex. No. | R | Name | LCMS (M + H) |
|---|---|---|---|
| 66 | | N,N-dibutyl-4-chloro-5-methyl-1-(4-(1-(2-(phenylthio)acetyl)indolin-5-ylsulfonylcarbamoyl)-2-(1,2,3,4-tetrahydroisoquinoline-2-carbonyl)phenyl)-1H-pyrazole-3-carboxamide | 881.3 |
| 67 | | N,N-dibutyl-4-chloro-5-methyl-1-(4-(1-(2-(phenylthio)ethyl)indolin-5-ylsulfonylcarbamoyl)-2-(1,2,3,4-tetrahydroisoquinoline-2-carbonyl)phenyl)-1H-pyrazole-3-carboxamide | 867.0 |
| 68 | | N,N-dibutyl-4-chloro-1-(4-(1-(3,4-dichlorobenzyl)-1H-indol-5-ylsulfonylcarbamoyl)-2-(1,2,3,4-tetrahydroisoquinoline-2-carbonyl)phenyl)-5-methyl-1H-pyrazole-3-carboxamide | 889.3 |
| 69 | | N,N-dibutyl-4-chloro-1-(4-(1-((6-chloropyridin-2-yl)methyl)indolin-5-ylsulfonylcarbamoyl)-2-(1,2,3,4-tetrahydroisoquinoline-2-carbonyl)phenyl)-5-methyl-1H-pyrazole-3-carboxamide | 856.0 |
| 70 | | N,N-dibutyl-4-chloro-5-methyl-1-(4-(1-((1-methyl-1H-indol-6-yl)methyl)indolin-5-ylsulfonylcarbamoyl)-2-(1,2,3,4-tetrahydroisoquinoline-2-carbonyl)phenyl)-1H-pyrazole-3-carboxamide | 874.1 |

-continued

| Ex. No. | R | Name | LCMS (M + H) |
|---|---|---|---|
| 71 | (5-bromo-1-ethylindolin-6-yl, attached at 6) | 1-(4-(5-bromo-1-ethylindolin-6-ylsulfonylcarbamoyl)-2-(1,2,3,4-tetrahydroisoquinoline-2-carbonyl)phenyl)-N,N-dibutyl-4-chloro-5-methyl-1H-pyrazole-3-carboxamide | 839.2 |
| 72 | (5-bromo-1-(3,4-dichlorobenzyl)indolin-6-yl) | 1-(4-(5-bromo-1-(3,4-dichlorobenzyl)indolin-6-ylsulfonylcarbamoyl)-2-(1,2,3,4-tetrahydroisoquinoline-2-carbonyl)phenyl)-N,N-dibutyl-4-chloro-5-methyl-1H-pyrazole-3-carboxamide | 969.2 |
| 73 | (1-(3,4-dichlorobenzyl)-2-(methoxycarbonyl)indolin-5-yl) | methyl 5-(N-(4-(4-chloro-3-(dibutylcarbamoyl)-5-methyl-1H-pyrazol-1-yl)-3-(1,2,3,4-tetrahydroisoquinoline-2-carbonyl)benzoyl)sulfamoyl)-1-(3,4-dichlorobenzyl)indoline-2-carboxylate | 949.3 |
| 74 | (1-(morpholine-4-carbonyl)indolin-5-yl) | N,N-dibutyl-4-chloro-5-methyl-1-(4-(1-(morpholine-4-carbonyl)indolin-5-ylsulfonylcarbamoyl)-2-(1,2,3,4-tetrahydroisoquinoline-2-carbonyl)phenyl)-1H-pyrazole-3-carboxamide | 844.4 |
| 75 | (1-(2-morpholinoacetyl)indolin-5-yl) | N,N-dibutyl-4-chloro-5-methyl-1-(4-(1-(2-morpholinoacetyl)indolin-5-ylsulfonylcarbamoyl)-2-(1,2,3,4-tetrahydroisoquinoline-2-carbonyl)phenyl)-1H-pyrazole-3-carboxamide | 858.5 |
| 76 | (7-bromo-1-ethylindolin-5-yl) | 1-(4-(7-bromo-1-ethylindolin-5-ylsulfonylcarbamoyl)-2-(1,2,3,4-tetrahydroisoquinoline-2-carbonyl)phenyl)-N,N-dibutyl-4-chloro-5-methyl-1H-pyrazole-3-carboxamide | 839.4 |

-continued

| Ex. No. | R | Name | LCMS (M + H) |
|---|---|---|---|
| 77 | (5-indolin-yl with N-(2-morpholinoethyl)) | N,N-dibutyl-4-chloro-5-methyl-1-(4-(1-(2-morpholinoethyl)indolin-5-ylsulfonylcarbamoyl)-2-(1,2,3,4-tetrahydroisoquinoline-2-carbonyl)phenyl)-1H-pyrazole-3-carboxamide | 844.4 |
| 78 | (5-indolin-yl with N-acyl-pyridinyl-O-ethyl-morpholine) | N,N-dibutyl-4-chloro-5-methyl-1-(4-(1-((2-(2-morpholinoethoxy)pyridin-3-yl)methyl)indolin-5-ylsulfonylcarbamoyl)-2-(1,2,3,4-tetrahydroisoquinoline-2-carbonyl)phenyl)-1H-pyrazole-3-carboxamide | 965.6 |
| 79 | (3-bromo-1H-indol-5-yl) | 1-(4-(3-bromo-1H-indol-5-ylsulfonylcarbamoyl)-2-(1,2,3,4-tetrahydroisoquinoline-2-carbonyl)phenyl)-N,N-dibutyl-4-chloro-5-methyl-1H-pyrazole-3-carboxamide | 809.2 |
| 80 | (3-bromo-1-ethyl-1H-indol-5-yl) | 1-(4-(3-bromo-1-ethyl-1H-indol-5-ylsulfonylcarbamoyl)-2-(1,2,3,4-tetrahydroisoquinoline-2-carbonyl)phenyl)-N,N-dibutyl-4-chloro-5-methyl-1H-pyrazole-3-carboxamide | 837.2 |
| 81 | (5-indolin-yl with N-(3-morpholinopropanoyl)) | N,N-dibutyl-4-chloro-5-methyl-1-(4-(1-(3-morpholinopropanoyl)indolin-5-ylsulfonylcarbamoyl)-2-(1,2,3,4-tetrahydroisoquinoline-2-carbonyl)phenyl)-1H-pyrazole-3-carboxamide | 872.4 |

| Ex. No. | R | Name | LCMS (M + H) |
|---|---|---|---|
| 82 | ![5-indolyl with N-(3-morpholinopropyl)] | N,N-dibutyl-4-chloro-5-methyl-1-(4-(1-(3-morpholinopropyl)-1H-indol-5-ylsulfonylcarbamoyl)-2-(1,2,3,4-tetrahydroisoquinoline-2-carbonyl)phenyl)-1H-pyrazole-3-carboxamide | 856.3 |
| 83 | ![3-chloro-1-ethyl-5-indolyl] | N,N-dibutyl-4-chloro-1-(4-(3-chloro-1-ethyl-1H-indol-5-ylsulfonylcarbamoyl)-2-(1,2,3,4-tetrahydroisoquinoline-2-carbonyl)phenyl)-5-methyl-1H-pyrazole-3-carboxamide | 791.4 |
| 84 | ![1-ethyl-3-iodo-5-indolyl] | N,N-dibutyl-4-chloro-1-(4-(1-ethyl-3-iodo-1H-indol-5-ylsulfonylcarbamoyl)-2-(1,2,3,4-tetrahydroisoquinoline-2-carbonyl)phenyl)-5-methyl-1H-pyrazole-3-carboxamide | 883.2 |
| 85 | ![3,7-dibromo-1-ethyl-5-indolyl] | N,N-dibutyl-4-chloro-1-(4-(3,7-dibromo-1-ethyl-1H-indol-5-ylsulfonylcarbamoyl)-2-(1,2,3,4-tetrahydroisoquinoline-2-carbonyl)phenyl)-5-methyl-1H-pyrazole-3-carboxamide | 915.2 |

Example 86

N,N-Dibutyl-4-chloro-1-(4-(indolin-6-ylsulfonylcarbamoyl)-2-(1,2,3,4-tetrahydroisoquinoline-2-carbonyl)phenyl)-5-methyl-1H-pyrazole-3-carboxamide (86)

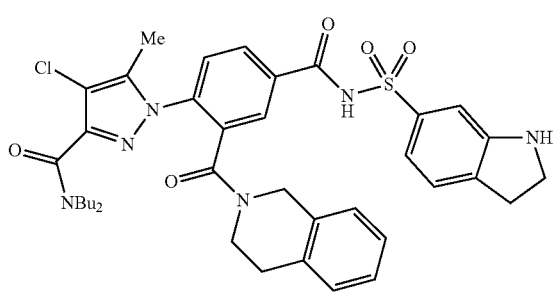

Following a procedure analogous to that for the synthesis of Example 52, 1-(4-(1-acetylindolin-6-ylsulfonylcarbamoyl)-2-(1,2,3,4-tetrahydroisoquinoline-2-carbonyl) phenyl)-N,N-dibutyl-4-chloro-5-methyl-1H-pyrazole-3-carboxamide (Example 60, 25 mg, 0.032 mmol) was converted to the title compound (18 mg, 63%) after preparative HPLC. $^1$H NMR (CD$_3$OD, 2:1 mixture of amide rotamers) δ 8.08-8.06 (m, 1H), 7.97-7.95 (m, 1H), 7.71-7.67 (m, 1H), 7.49 (dd, J=7.7, 1.8 Hz, 1H), 7.40 (s, 1H), 7.32 (d, J=7.9 Hz, 1H), 7.26-7.09 (m, 3.5H), 6.93 (d, J=7.5 Hz, 0.5H), 4.85-4.40 (m, 2H), 4.00-3.50 (m, 2H), 3.64 (t, J=8.5 Hz, 2H), 3.14-3.10 (m, 2H), 3.16-2.55 (m, 4H), 2.34 (s, 2H), 2.29 (s, 1H), 1.52-1.00 (m, 10H), 0.95-0.87 (m, 3H), 0.79-0.75 (m, 2H), 0.70-0.67 (m, 1H); MS (ESI$^+$) m/z 731.3 (M+H)$^+$.

Example 87

(E)-1-(4-(5-(But-1-enyl)-1-ethylindolin-6-ylsulfonylcarbamoyl)-2-(1,2,3,4-tetrahydroisoquinoline-2-carbonyl)phenyl)-N,N-dibutyl-4-chloro-5-methyl-1H-pyrazole-3-carboxamide (87)

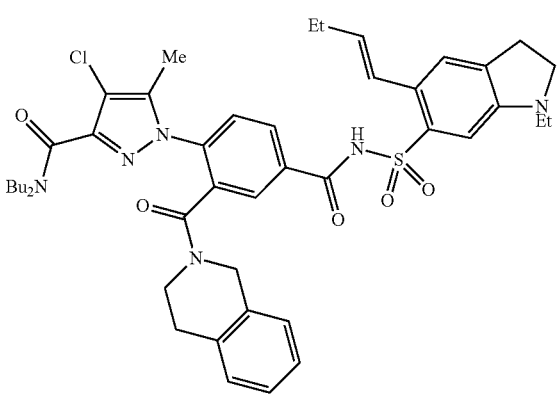

To a sealed tube containing 1-(4-(5-bromo-1-ethylindolin-6-ylsulfonylcarbamoyl)-2-(1,2,3,4-tetrahydroisoquinoline-2-carbonyl)phenyl)-N,N-dibutyl-4-chloro-5-methyl-1H-pyrazole-3-carboxamide (Example 71, 16 mg, 0.019 mmol) in dioxane (1.0 mL) was added (E)-but-1-enylboronic acid (8 mg, 0.076 mmol), Pd$_2$(dba)$_3$ (9 mg, 10 μmol), 1,1'-bis(di-tert-butylphosphino)ferrocene (9 mg, 0.019 mmol) and potassium metaphosphate (5 mg, 0.038 mmol). The reaction mixture was purged with nitrogen for 1 min and then heated at 90° C. for 16 h. The reaction mixture was then diluted with EtOAc and 1N aq. HCl solution. The organic layer was separated, dried over MgSO$_4$ and concentrated in vacuo. The residue was purified by preparative HPLC to give the title compound (11 mg, 64%) as a pale yellow solid after lyophilization. $^1$H NMR (CD$_3$OD, 2:1 mixture of amide rotamers) δ 8.06-8.05 (m, 1H), 7.94 (br s, 1H), 7.65-7.63 (m, 1H), 7.30-7.11 (m, 6.5H), 6.93 (d, J=7.0 Hz, 0.5H), 6.05-5.95 (m, 1H), 4.75-4.50 (m, 2H), 3.95-3.55 (m, 1H), 3.49-3.41 (m, 2H), 3.25 (t, J=6.8 Hz, 2H), 3.15-3.10 (m, 2H), 3.00-2.96 (m, 3H), 2.90-2.65 (m, 2H), 2.33 (s, 2H), 2.28 (s, 1H), 2.21-2.18 (m, 2H), 1.58-1.02 (m, 11 H), 1.03-0.95 (m, 5H), 0.93-0.87 (m, 3H), 0.77 (t, J=7.3 Hz, 2H), 0.69 (t, J=7.4 Hz, 1H); MS(ESI$^+$) m/z 813.3 (M+H)$^+$.

Example 88

N,N-Dibutyl-4-chloro-1-(4-(1-ethyl-5-morpholinoindolin-6-ylsulfonylcarbamoyl)-2-(1,2,3,4-tetrahydroisoquinoline-2-carbonyl)phenyl)-5-methyl-1H-pyrazole-3-carboxamide (88)

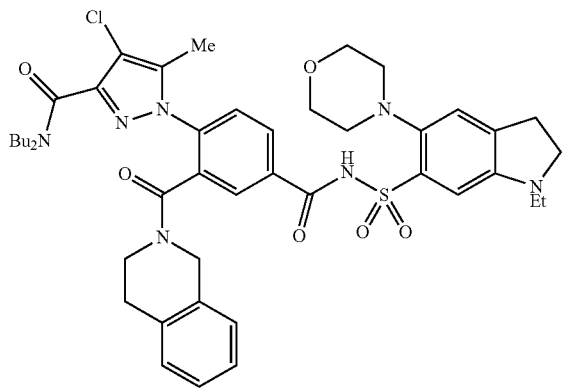

A solution of 1-(4-(5-bromo-1-ethylindolin-6-ylsulfonylcarbamoyl)-2-(1,2,3,4-tetrahydroisoquinoline-2-carbonyl)phenyl)-N,N-dibutyl-4-chloro-5-methyl-1H-pyrazole-3-carboxamide (Example 71, 35 mg, 0.042 mmol), L-(−)-proline (5 mg, 0.042 mmol), K$_2$CO$_3$ (12 mg, 0.084 mmol) and CuI (4 mg, 0.021 mmol) in DMSO (1.5 mL) was purged with air for 1 min. The resulting mixture was heated at 102° C. open to air for 20 h. The reaction mixture was then diluted with 1N aq. HCl solution and EtOAc. The organic layer was separated, dried over MgSO$_4$ and concentrated in vacuo. The residue was purified by preparative HPLC to give the title compound (6 mg, 16%) as a white solid after lyophilization. $^1$H NMR (CD$_3$OD, 2:1 mixture of amide rotamers) δ 8.24 (dd, J=8.3, 1.9 Hz, 1H), 8.13-8.10 (m, 1H), 7.60-7.50 (m, 1H), 7.48 (s, 1H), 7.25-7.09 (m, 3.5H), 6.95 (s, 1H), 6.93 (d, J=7.5 Hz, 0.5H), 4.90-4.50 (m, 2H), 4.20-3.99 (m, 4H), 3.71-3.60 (m, 4H), 3.55-3.49 (m, 2H), 3.26-3.20 (m, 4H), 3.09-3.03 (m, 2H), 2.90-2.60 (m, 4H), 2.33 (s, 2H), 2.28 (s, 1H), 1.55-1.00 (m, 13H), 0.95-0.88 (m, 3H), 0.79-0.75 (m, 2H), 0.72-0.68 (m, 1H); MS(ESI$^+$) m/z 844.5 (M+H)$^+$.

Example 89

(E)-N,N-Dibutyl-4-chloro-1-(4-(1-ethyl-5-(prop-1-enyl)indolin-6-ylsulfonylcarbamoyl)-2-(1,2,3,4-tetrahydroisoquinoline-2-carbonyl)phenyl)-5-methyl-1H-pyrazole-3-carboxamide (89)

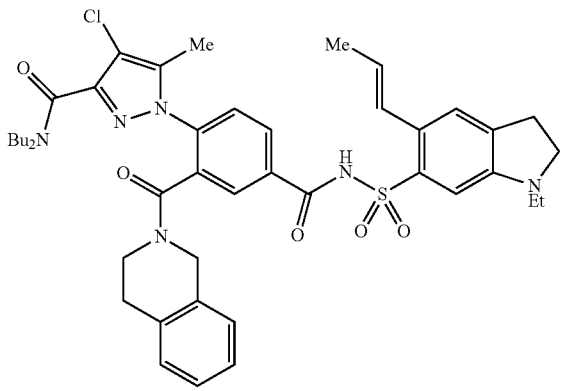

Following a procedure analogous to that for the synthesis of Example 87, 1-(4-(5-bromo-1-ethylindolin-6-ylsulfonylcarbamoyl)-2-(1,2,3,4-tetrahydroisoquinoline-2-carbonyl)phenyl)-N,N-dibutyl-4-chloro-5-methyl-1H-pyrazole-3-carboxamide (Example 71, 35 mg, 0.042 mmol) and (E)-prop-1-enylboronic acid (14 mg, 0.17 mmol) were converted to the title compound (8 mg, 22%) as a white solid. $^1$H NMR (CD$_3$OD, 2:1 mixture of amide rotamers) δ 8.03-7.99 (m, 1H), 7.88-7.87 (m, 1H), 7.72-7.67 (m, 1H), 7.31-7.12 (m, 6.5H), 6.94-6.93 (m, 0.5H), 6.05-5.90 (m, 1H), 4.75-4.40 (m, 2H), 3.95-3.55 (m, 1H), 3.47 (t, J=8.4 Hz, 2H), 3.27-3.15 (m, 2H), 3.26 (q, J=7.0 Hz, 2H), 3.01 (t, J=7.9 Hz, 2H), 2.80-2.60 (m, 2H), 2.34 (s, 2H), 2.30 (s, 1H), 2.09-2.07 (m, 1H), 1.85-1.83 (m, 2H), 1.55-0.90 (m, 14H), 0.95-0.87 (m, 3H), 0.77 (t, J=7.3 Hz, 2H), 0.70 (t, J=7.4 Hz, 1H); MS(ESI$^+$) m/z 799.4 (M+H)$^+$.

Example 90

N,N-Dibutyl-4-chloro-1-(4-(1-(3,4-dichlorobenzyl)indolin-6-ylsulfonylcarbamoyl)-2-(1,2,3,4-tetrahydroisoquinoline-2-carbonyl)phenyl)-5-methyl-1H-pyrazole-3-carboxamide (90)

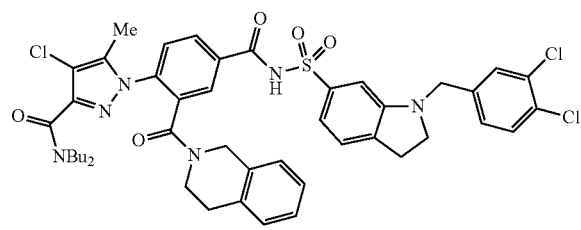

To a solution of 1-(4-(5-bromo-1-(3,4-dichlorobenzyl)indolin-6-ylsulfonylcarbamoyl)-2-(1,2,3,4-tetrahydroisoquinoline-2-carbonyl)phenyl)-N,N-dibutyl-4-chloro-5-methyl-1H-pyrazole-3-carboxamide (Example 72, 30 mg, 0.031 mmol) in i-PrOH (4.0 mL) were added Pd$_2$(dba)$_3$ (23 mg, 0.025 mmol), tris(2,4-di-tert-butylphenyl)phosphite (10 mg, 0.015 mmol) and Cs$_2$CO$_3$ (13 mg, 0.040 mmol). The resulting reaction mixture was heated at 80° C. for 20 h, then cooled to room temperature and filtered. The filtrate was concentrated in vacuo, and the residue was purified by preparative HPLC to give the title compound (15 mg, 52%) as a pale yellow solid after lyophilization. $^1$H NMR (CD$_3$OD, 2:1 mixture of amide rotamers) δ 8.05 (dd, J=8.4, 2.2 Hz, 1H), 7.97-7.96 (m, 1H), 7.71-7.67 (m, 1H), 7.52 (d, J=2.0 Hz, 1H), 7.46 (d, J=8.1 Hz, 1H), 7.38 (dd, J=7.7, 1.5 Hz, 1H), 7.31 (dd, J=8.4, 2.0 Hz, 1H), 7.25-7.10 (m, 5.5H), 6.93 (d, J=7.5 Hz, 0.5H), 4.88-4.60 (m, 2H), 4.36 (s, 2H), 4.10-3.50 (m, 2H), 3.48 (t, J=8.5 Hz, 2H), 3.15-3.05 (m, 2H), 3.08 (t, J=8.5 Hz, 2H), 2.90-2.70 (m, 2H), 2.35 (s, 2H), 2.30 (s, 1H), 1.53-0.98 (m, 10H), 0.95-0.88 (m, 3H), 0.79-0.75 (m, 2H), 0.70 (t, J=7.3 Hz, 1H); MS(ESI$^+$) m/z 891.4 (M+H)$^+$.

Example 91

N,N-Dibutyl-4-chloro-1-(2-((S)-3-(hydroxymethyl)-1,2,3,4-tetrahydroisoquinoline-2-carbonyl)-4-(naphthalen-2-ylsulfonylcarbamoyl)phenyl)-5-methyl-1H-pyrazole-3-carboxamide (91)

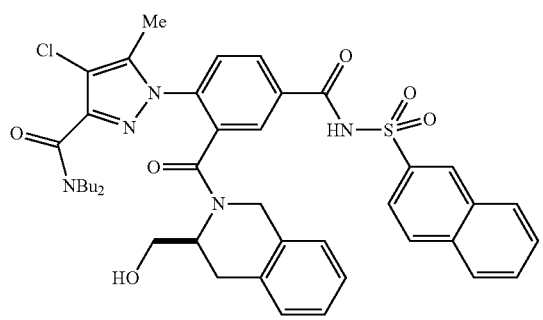

Intermediate 91A

Ethyl 2-fluoro-5-iodobenzoate (Int-91A)

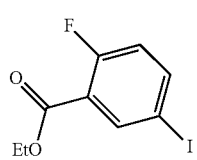

To a solution of 2-fluoro-5-iodobenzoic acid (Oakwood, 0.99 g, 3.72 mmol) in EtOH (7.4 mL) was added H$_2$SO$_4$ (198 µL, 3.72 mmol). The resulting reaction mixture was stirred at 100° C. overnight and then concentrated in vacuo. The crude oil was purified using flash column chromatography (gradient from 0% to 10% EtOAc/hexanes) to give the title compound (916 mg, 84%) as a colorless oil. $^1$H NMR (CDCl$_3$) δ 8.24 (dd, J=6.8, 2.4 Hz, 1H), 7.81 (ddd, J=8.8, 4.5, 2.4 Hz, 1H), 6.93 (dd, J=10.3, 8.6 Hz, 1H), 4.41 (q, J=7.0 Hz, 2H), 1.42 (t, J=7.2 Hz, 3H).

Intermediate 91B

1-Benzyl 3-ethyl 4-fluoroisophthalate (Int-91B)

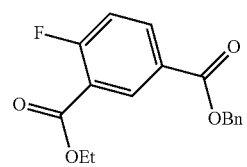

Following a procedure analogous to that for the synthesis of Intermediate 1D, ethyl 2-fluoro-5-iodobenzoate (916 mg, 3.11 mmol) and benzyl alcohol (389 µL, 3.74 mmol) were converted to the title compound (871 mg, 92%). $^1$H NMR (CDCl$_3$) δ 8.65 (dd, J=6.9, 2.3 Hz, 1H), 8.23 (ddd, J=8.7, 4.6, 2.3 Hz, 1H), 7.51-7.32 (m, 5H), 7.20 (dd, J=10.1, 8.6 Hz, 1H), 5.39 (s, 2H), 4.42 (q, J=7.0 Hz, 2H), 1.41 (t, J=7.2 Hz, 3H).

Intermediate 91C

1-Benzyl 3-ethyl 4-(4-chloro-3-(dibutylcarbamoyl)-5-methyl-1H-pyrazol-1-yl)isophthalate (Int-91C)

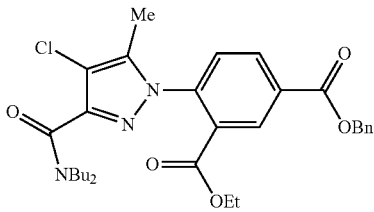

Following a procedure analogous to that for the synthesis of Intermediate 1E, 1-benzyl 3-ethyl 4-fluoroisophthalate (1.50 g, 4.96 mmol) and N,N-dibutyl-4-chloro-5-methyl-1H-pyrazole-3-carboxamide (Intermediate 1B, 2.02 g, 7.44 mmol) were converted to the title compound (2.15 g, 78%). $^1$H NMR (CDCl$_3$) δ 8.69 (d, J=2.0 Hz, 1H), 8.33 (dd, J=8.1, 2.0 Hz, 1H), 7.51-7.36 (m, 6H), 5.43 (s, 2H), 4.19 (d, J=7.0 Hz, 2H), 3.50 (s, 2H), 3.41 (s, 2H), 2.15 (s, 3H), 1.70-1.60 (m, 2H), 1.58-1.50 (m, 2H), 1.46-1.34 (m, 2H), 1.25-1.16 (m, 5H), 0.96 (t, J=7.4 Hz, 3H), 0.83 (t, J=7.3 Hz, 3H); MS(ESI$^+$) m/z 554.2 (M+H)$^+$.

Intermediate 91D 4-(4-Chloro-3-(dibutylcarbamoyl)-5-methyl-1H-pyrazol-1-yl)-3-(ethoxycarbonyl)benzoic acid (Int-91D)

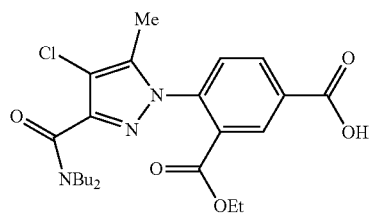

To a 30 mL pressure flask containing 10% Pd/C (59 mg, 0.055 mmol) was added a solution of 1-benzyl 3-ethyl 4-(4-chloro-3-(dibutylcarbamoyl)-5-methyl-1H-pyrazol-1-yl) isophthalate (153 mg, 0.28 mmol) in MeOH (5.0 mL). The reaction mixture was stirred under $H_2$ at 5 psi for 1 h, then filtered through a pipette containing a plug of CELITE® and concentrated in vacuo to give the title compound (110 mg, 85%) as a colorless oil. $^1$H NMR (CDCl$_3$) δ 8.72 (d, J=2.0 Hz, 1H), 8.35 (dd, J=8.1, 2.0 Hz, 1H), 7.49 (d, J=8.1 Hz, 1H), 4.21 (q, J=7.3 Hz, 2H), 3.56-3.49 (m, 2H), 3.46-3.38 (m, 2H), 2.20-2.13 (m, 3H), 1.71-1.60 (m, 2H), 1.59-1.50 (m, 1H), 1.47-1.33 (m, 2H), 1.30-1.15 (m, 5H), 0.96 (t, J=7.3 Hz, 3H), 0.83 (t, J=7.4 Hz, 3H); MS(ESI$^+$) m/z 464.2 (M+H)$^+$.

Intermediate 91E

Ethyl 2-(4-chloro-3-(dibutylcarbamoyl)-5-methyl-1H-pyrazol-1-yl)-5-(naphthalen-2-ylsulfonylcarbamoyl)benzoate (Int-91E)

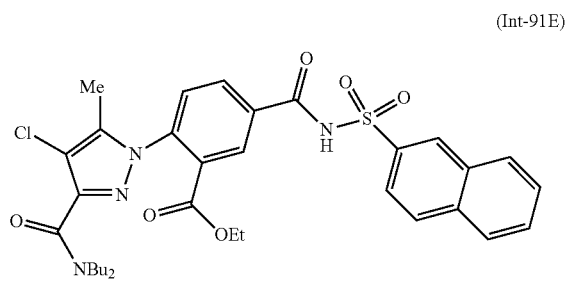

Following a procedure analogous to that for the synthesis of Example 1,4-(4-chloro-3-(dibutylcarbamoyl)-5-methyl-1H-pyrazol-1-yl)-3-(ethoxycarbonyl)benzoic acid (230 g, 0.50 mmol) was converted to the title compound (188 mg, 58%) after purification by flash column chromatography (20% EtOAc/hexanes). $^1$H NMR (DMSO-d$_6$) δ 8.65 (s, 1H), 8.40 (d, J=2.0 Hz, 1H), 8.25-8.16 (m, 2H), 8.12 (d, J=8.6 Hz, 1H), 8.05 (d, J=7.9 Hz, 1H), 7.97 (dd, J=8.8, 1.8 Hz, 1H), 7.77-7.62 (m, 3H), 4.10 (q, J=7.2 Hz, 2H), 3.38 (t, J=7.4 Hz, 1H), 3.29 (t, J=7.4 Hz, 1H), 2.12 (s, 3H), 1.62-1.40 (m, 4H), 1.36-1.26 (m, 2H), 1.36-1.22 (m, 2H), 1.18-1.04 (m, 5H), 0.90 (t, J=7.3 Hz, 3H), 0.74 (t, J=7.4 Hz, 3H); MS(ESI$^+$) m/z 653.3 (M+H)$^+$.

Intermediate 91F 2-(4-Chloro-3-(dibutylcarbamoyl)-5-methyl-1H-pyrazol-1-yl)-5-(naphthalen-2-ylsulfonylcarbamoyl) benzoic acid (Int-91F)

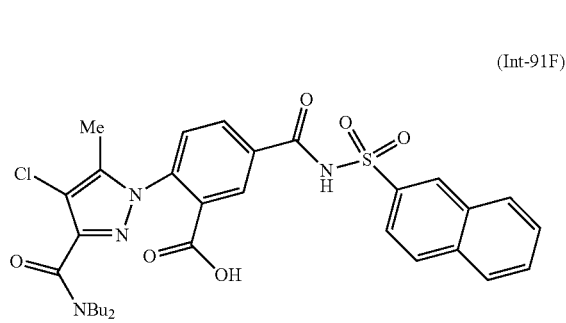

To ethyl 2-(4-chloro-3-(dibutylcarbamoyl)-5-methyl-1H-pyrazol-1-yl)-5-(naphthalen-2-ylsulfonylcarbamoyl)benzoate (1.39 g, 2.13 mmol) in THF (12.0 mL) and MeOH (4.0 mL) was added 0.5N aq. NaOH solution (21.3 mL, 10.7 mmol). The resulting reaction mixture was stirred at room temperature for 1.5 h. The mixture was then neutralized with 1N aq. HCl solution (pH=7) and extracted with EtOAc (3×). The combined organic extracts were dried over Na$_2$SO$_4$, filtered and concentrated in vacuo. The crude oil was triturated with CH$_2$Cl$_2$ (3×) to give the title compound (1.04 g, 78%) as a white solid. $^1$H NMR (DMSO-d$_6$) δ 13.36 (br s, 1H), 8.71 (s, 1H), 8.43 (d, J=2.0 Hz, 1H), 8.26 (d, J=8.1 Hz, 1H), 8.17 (dd, J=8.4, 2.2 Hz, 2H), 8.07 (d, J=8.1 Hz, 1H), 7.99 (dd, J=8.7, 1.9 Hz, 1H), 7.78-7.64 (m, 3H), 3.38 (t, J=7.4 Hz, 2H), 3.29 (t, J=7.4 Hz, 2H), 2.10 (s, 3H), 1.58-1.38 (m, 4H), 1.36-1.22 (m, 2H), 1.13 (dq, J=14.8, 7.4 Hz, 2H), 0.90 (t, J=7.4 Hz, 3H), 0.74 (t, J=7.4 Hz, 3H); MS(ESI$^+$) m/z 625.2 (M+H)$^+$.

Example 91

To 2-(4-chloro-3-(dibutylcarbamoyl)-5-methyl-1H-pyrazol-1-yl)-5-(naphthalen-2-ylsulfonylcarbamoyl)benzoic acid (50 mg, 0.080 mmol) in DMF (800 μL) and THF (800 μL) were added (S)-(1,2,3,4-tetrahydroisoquinolin-3-yl)methanol (Aldrich, 20 mg, 0.12 mmol), HATU (55 mg, 0.14 mmol) and i-Pr$_2$EtN (70 μl, 0.40 mmol). The resulting reaction mixture was stirred at room temperature for 1.5 h, then concentrated in vacuo and purified by preparative HPLC to give the title compound (44 mg, 70%). $^1$H NMR (1:1 CD$_3$OD:CDCl$_3$, mixture of amide rotamers) δ 8.63 (s, 1H), 8.30-8.15 (m, 1.5H), 8.10-7.84 (m, 5H), 7.65-7.52 (m, 1H), 7.52-7.36 (m, 1H), 7.27-7.04 (m, 4H), 6.91 (br s, 0.5H), 5.25 (d, J=18.0 Hz, 0.5H), 4.42-4.10 (m, 2.5H), 3.70-3.37 (m, 2H), 3.26 (dd, J=16.4, 5.4 Hz, 1H), 3.14-2.74 (m, 5H), 2.31-2.22 (m, 3H), 1.60-0.59 (m, 14H); MS (ESI$^+$) m/z 770.3 (M+H)$^+$.

Example 92

1-(2-((S)-3-(Aminomethyl)-1,2,3,4-tetrahydroisoquinoline-2-carbonyl)-4-(naphthalen-2-ylsulfonylcarbamoyl)phenyl)-N,N-dibutyl-4-chloro-5-methyl-1H-pyrazole-3-carboxamide (92)

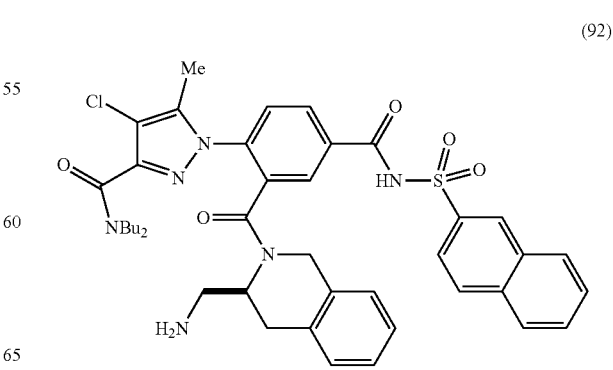

Intermediate 92A (S)-3-(Azidomethyl)-1,2,3,4-tetrahydroisoquinoline

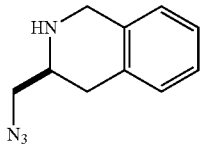
(Int-92A)

To a solution of (S)-tert-butyl 3-(azidomethyl)-3,4-dihydroisoquinoline-2(1H)-carboxylate (Page, D. et al., *J. Med. Chem.*, 44:2387-2390 (2001)) (509 mg, 1.77 mmol) in CH$_2$Cl$_2$ (8.0 mL) was added TFA (2.7 mL, 35.3 mmol). The resulting reaction mixture was stirred at room temperature for 1 h and then concentrated in vacuo. The residue was dissolved in CH$_2$Cl$_2$ and washed with sat. aq. NaHCO$_3$ solution (2×). The aqueous layer was extracted with CH$_2$Cl$_2$ (2×), and the combined organic extracts were dried over Na$_2$SO$_4$, filtered and concentrated in vacuo to provide the title compound (302 mg, 91%) as a clear, colorless oil. $^1$H NMR (CDCl$_3$) δ 7.17-7.13 (m, 2H), 7.12-7.08 (m, 1H), 7.07-7.02 (m, 1H), 4.14-4.05 (m, 2H), 3.55 (dd, J=12.2, 4.4 Hz, 1H), 3.45-3.39 (m, 1H), 3.16-3.09 (m, 1H), 2.82-2.75 (m, 1H), 2.70-2.60 (m, 1H), 2.02 (br s, 1H); MS(ESI$^+$) m/z 189.1 (M+H)$^+$.

Example 92

Following a procedure analogous to that for the synthesis of Example 91, 2-(4-chloro-3-(dibutylcarbamoyl)-5-methyl-1H-pyrazol-1-yl)-5-(naphthalen-2-ylsulfonylcarbamoyl)benzoic acid (Intermediate 91F, 50 mg, 0.080 mmol) was reacted with (S)-3-(azidomethyl)-1,2,3,4-tetrahydroisoquinoline (18 mg, 0.10 mmol) to give a crude oil which was used in the subsequent step without purification.

The crude oil from above was dissolved in THF (1.1 mL), and PPh$_3$ (63 mg, 0.24 mmol) was added followed by 0.5N NaOH (200 μL). The resulting reaction mixture was stirred at 50° C. for 1.5 h, then neutralized with 1N aq. HCl solution (100 μL). The volatiles were removed in vacuo, and the residue was purified by preparative HPLC to give the title compound (18 mg, 29%). $^1$H NMR (1:1 CD$_3$OD:CDCl$_3$, mixture of amide rotamers) δ 8.60 (br s, 1H), 8.38-8.11 (m, 2H), 8.11-8.04 (m, 1H), 7.97 (d, J=7.2 Hz, 1H), 7.92-7.83 (m, 2H), 7.58-7.36 (m, 3H), 7.31-7.10 (m, 3H), 7.07-6.92 (m, 1H), 5.10-4.97 (m, 0.5H), 4.87 (br s, 0.5H), 4.50-4.44 (m, 1.5H), 4.26 (d, J=18.6 Hz, 0.5H), 3.48 (br s, 1H), 3.33-3.04 (m, 3.5H), 2.98-2.83 (m, 2H), 2.80-2.60 (m, 1H), 2.43-2.19 (m, 3.5H), 1.28 (br s, 2.5H), 1.38-1.30 (m, 4.5H), 1.02-0.72 (m, 6H), 0.62 (br s, 1H); MS (ESI$^+$) m/z 769.4 (M+H)$^+$.

Example 93

(3R)-2-(2-(4-Chloro-3-(dibutylcarbamoyl)-5-methyl-1H-pyrazol-1-yl)-5-(naphthalen-2-ylsulfonylcarbamoyl)benzoyl)-1,2,3,4-tetrahydroisoquinoline-3-carboxylic acid (93)

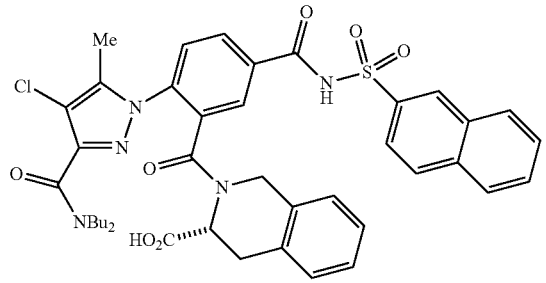

Intermediate 93A (R)-Methyl 1,2,3,4-tetrahydroisoquinoline-3-carboxylate hydrochloride

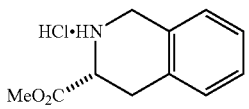
(Int-93A)

To (S)-1,2,3,4-tetrahydroisoquinoline-3-carboxylic acid (Aldrich, 500 mg, 2.82 mmol) in MeOH (2.8 mL) was added SOCl$_2$ (824 μL, 11.3 mmol) at 0° C. The resulting reaction mixture was allowed to warm to room temperature over 5 h and then stirred at 50° C. overnight. The reaction mixture was then concentrated in vacuo to give the title compound (457 mg, 71%) as a white solid. $^1$H NMR (CDCl$_3$) δ 7.30-7.23 (m, 2H), 7.20-7.13 (m, 2H), 4.78-4.69 (m, 1H), 4.56-4.45 (m, 1H), 4.43-4.35 (m, 1H), 3.87 (s, 3H), 3.49-3.43 (m, 2H); MS(ESI$^+$) m/z 192.1 (M+H)$^+$.

Intermediate 93B (3R)-Methyl 2-(2-(4-chloro-3-(dibutylcarbamoyl)-5-methyl-1H-pyrazol-1-yl)-5-(naphthalen-2-ylsulfonylcarbamoyl)benzoyl)-1,2,3,4-tetrahydroisoquinoline-3-carboxylate (Int-93B)

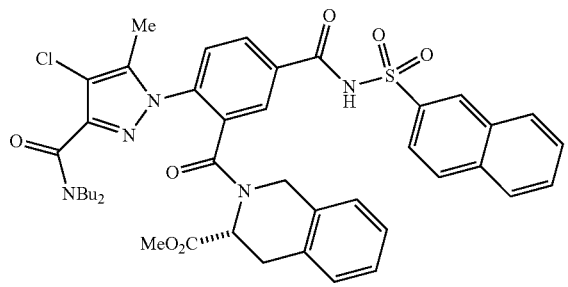

To 2-(4-chloro-3-(dibutylcarbamoyl)-5-methyl-1H-pyrazol-1-yl)-5-(naphthalen-2-ylsulfonylcarbamoyl)benzoic acid (Intermediate 91F, 50 mg, 0.080 mmol) in CH$_2$Cl$_2$ (890 μL) was added 1-chloro-N,N-2-trimethylprop-1-en-1-amine (21 μL, 0.16 mmol). After stirring for 30 min at room temperature, (R)-methyl 1,2,3,4-tetrahydroisoquinoline-3-carboxylate hydrochloride (20 mg, 0.088 mmol) in THF (900 μL) was added followed by i-Pr$_2$EtN (42 μL, 0.24 mmol). The resulting reaction mixture was stirred at room temperature for 1 h, then quenched with sat. aq. NH$_4$Cl solution and extracted with EtOAc (1×). The organic layer was washed with 1N aq. HCl solution, and the combined aqueous layer was extracted with EtOAc (2×). The combined organic extracts were dried over Na$_2$SO$_4$, filtered and concentrated in vacuo. The residue was purified by preparative HPLC to give the title compound (24 mg, 37%). $^1$H NMR (1:1 CD$_3$OD:CDCl$_3$, 1:1 mixture of amide rotamers) δ 8.62 (d, J=15.9 Hz, 1H), 8.20 (dd, J=13.9, 9.0 Hz, 1.5H), 8.13-7.85 (m, 5H), 7.63-7.52 (m, 1.5H), 7.47 (d, J=8.4 Hz, 1H), 7.24-7.06 (m, 3.5H), 6.93 (d, J=6.8 Hz, 0.5H), 5.17 (t, J=5.4 Hz, 0.5H), 5.02 (d, J=17.6 Hz, 0.5H), 4.75 (d, J=5.9 Hz, 1H), 4.49 (d, J=18.0 Hz, 1.5H), 3.64 (br s, 1.5H), 3.55-3.41 (m, 2.5H), 3.27-3.09 (m, 4H), 3.05-2.99 (m, 0.5H), 2.31 (s, 1.5H), 2.24 (s, 1.5H), 1.50-0.95 (m, 8H), 0.95-0.82 (m, 3H), 0.74 (t, J=7.5 Hz, 1.5H), 0.71-0.63 (m, 1.5H); MS(ESI$^+$) m/z 798.3 (M+H)$^+$.

Example 93

To (3R)-methyl 2-(2-(4-chloro-3-(dibutylcarbamoyl)-5-methyl-1H-pyrazol-1-yl)-5-(naphthalen-2-ylsulfonylcarbamoyl)benzoyl)-1,2,3,4-tetrahydroisoquinoline-3-carboxylate (38 mg, 0.048 mmol) in MeOH (500 μL) was added 1N aq. NaOH solution (480 μL, 0.48 mmol). The resulting reaction mixture was stirred at 40° C. for 1 h, then acidified (pH=2) with 1N aq. HCl solution and extracted EtOAc (3×). The combined organic extracts were dried over $Na_2SO_4$, filtered and concentrated in vacuo. The crude oil was purified by preparative HPLC to give the title compound (16 mg, 41%). $^1$H NMR (1:1 $CD_3OD$:$CDCl_3$, 1.5:1 mixture of amide rotamers) δ 8.65-8.54 (m, 1H), 8.23-8.12 (m, 1.5H), 8.08-7.82 (m, 5H), 7.61-7.50 (m, 1H), 7.42-7.34 (m, 1H), 7.21-7.04 (m, 4H), 6.89 (d, J=6.8 Hz, 0.5H), 5.19 (t, J=5.2 Hz, 0.5H), 4.98 (d, J=17.6 Hz, 0.5H), 4.69-4.62 (m, 1H), 3.54-3.40 (m, 1H), 3.25-2.80 (m, 5.5H), 2.58 (dt, J=14.2, 7.1 Hz, 0.5H), 2.27 (s, 2H), 2.22 (s, 1H), 1.55-0.77 (m, 11H), 0.76-0.60 (m, 3H); MS(ESI$^+$) m/z 784.4 (M+H)$^+$.

Example 94

(3S)-2-(2-(4-Chloro-3-(dibutylcarbamoyl)-5-methyl-1H-pyrazol-1-yl)-5-(naphthalen-2-ylsulfonylcarbamoyl)benzoyl)-1,2,3,4-tetrahydroisoquinoline-3-carboxylic acid

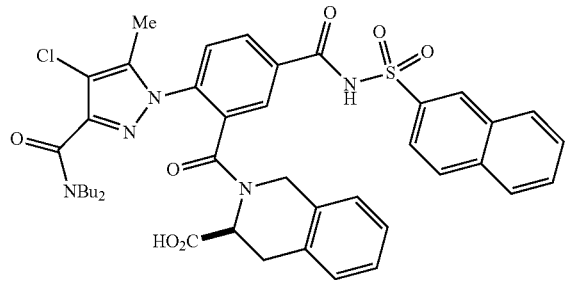

(94)

Intermediate 94A (S)-Methyl 1,2,3,4-tetrahydroisoquinoline-3-carboxylate hydrochloride

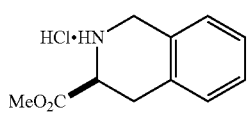

(Int-94A)

Following a procedure analogous to that for the synthesis of Intermediate 93A, (S)-1,2,3,4-tetrahydroisoquinoline-3-carboxylic acid (Aldrich, 500 mg, 2.82 mmol) was converted to the title compound (526 mg, 82%). $^1$H NMR (CDCl$_3$) δ 7.30-7.23 (m, 2H), 7.20-7.13 (m, 2H), 4.78-4.69 (m, 1H), 4.56-4.45 (m, 1H), 4.43-4.35 (m, 1H), 3.87 (s, 3H), 3.49-3.43 (m, 2H); MS(ESI$^+$) m/z 192.1 (M+H)$^+$.

Following a procedure analogous to that for the synthesis of Intermediate 85, 2-(4-chloro-3-(dibutylcarbamoyl)-5-methyl-1H-pyrazol-1-yl)-5-(naphthalen-2-ylsulfonylcarbamoyl)benzoic acid (Intermediate 91F, 30 mg, 0.048 mmol) was reacted with (S)-methyl 1,2,3,4-tetrahydroisoquinoline-3-carboxylate hydrochloride (12 mg, 0.053 mmol) to give a crude oil which was used in the subsequent step without purification.

The crude oil from above was converted to the title compound (19 mg, 51%) following a procedure analogous to that for the synthesis of Example 93. $^1$H NMR (1:1 $CD_3OD$:$CDCl_3$, 1.5:1 mixture of amide rotamers) δ 8.65-8.54 (m, 1H), 8.23-8.12 (m, 1.5H), 8.08-7.82 (m, 5H), 7.61-7.50 (m, 1H), 7.42-7.34 (m, 1H), 7.21-7.04 (m, 4H), 6.89 (d, J=6.8 Hz, 0.5H), 5.19 (t, J=5.2 Hz, 0.5H), 4.98 (d, J=17.6 Hz, 0.5H), 4.69-4.62 (m, 1H), 3.54-3.40 (m, 1H), 3.25-2.80 (m, 5.5H), 2.58 (dt, J=14.2, 7.1 Hz, 0.5H), 2.27 (s, 2H), 2.22 (s, 1H), 1.55-0.77 (m, 11H), 0.76-0.60 (m, 3H); MS(ESI$^+$) m/z 784.4 (M+H)$^+$.

Example 95

N,N-Dibutyl-4-chloro-1-(2-((R)-3-(hydroxymethyl)-1,2,3,4-tetrahydroisoquinoline-2-carbonyl)-4-(naphthalen-2-ylsulfonylcarbamoyl)phenyl)-5-methyl-1H-pyrazole-3-carboxamide

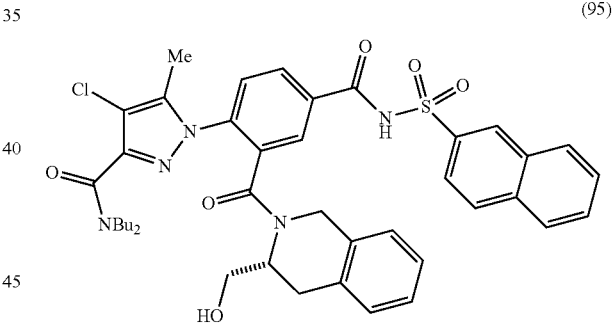

(95)

To a solution of (3R)-methyl 2-(2-(4-chloro-3-(dibutylcarbamoyl)-5-methyl-1H-pyrazol-1-yl)-5-(naphthalen-2-ylsulfonylcarbamoyl)benzoyl)-1,2,3,4-tetrahydroisoquinoline-3-carboxylate (Intermediate 85, 40 mg, 0.050 mmol) in THF (835 μL) and MeOH (170 μL) was added NaBH$_4$ (4 mg, 0.10 mmol). The resulting reaction mixture was stirred at room temperature for 1 h. Additional NaBH$_4$ (20 mg, 0.50 mmol) was added and stirring was continued at room temperature for 30 min. The reaction mixture was then quenched with water, poured into sat. aq. NH$_4$Cl solution and extracted with EtOAc (3×). The combined organic extracts were dried over Na$_2$SO$_4$, filtered, concentrated in vacuo and purified by preparative HPLC to give the title compound (13 mg, 34%). $^1$H NMR (1:1 CD$_3$OD:CDCl$_3$, mixture of amide rotamers) δ 8.68-8.77 (m, 1H), 8.23 (s, 0.5H), 8.13-7.99 (m, 4.5H), 7.95 (d, J=7.0 Hz, 1.5H), 7.72-7.61 (m, 1H), 7.58-7.45 (m, 1H), 7.23-7.03 (m, 4H), 6.87 (br s, 0.5H), 5.24 (d, J=18.0 Hz, 0.5H), 4.87 (br s, 0.5H), 4.49 (br s, 0.5H), 4.28 (d, J=17.4 Hz, 1H), 4.12 (br s, 1H), 3.63-3.52 (m, 1H), 3.51-3.34 (m, 1.5H), 3.27-2.92 (m, 4H), 2.83-2.53 (m, 1H), 2.28-2.25 (m, 3H), 1.62-0.83 (m, 11H), 0.77-0.69 (m, 2H), 0.64 (br s, 1H); MS(ESI$^+$) m/z 770.3 (M+H)$^+$.

Example 96

N,N-Dibutyl-4-chloro-1-(2-(3,4-dihydro-2H-benzo[e][1,3]oxazine-3-carbonyl)-4-(naphthalen-2-ylsulfonylcarbamoyl)phenyl)-5-methyl-1H-pyrazole-3-carboxamide (96)

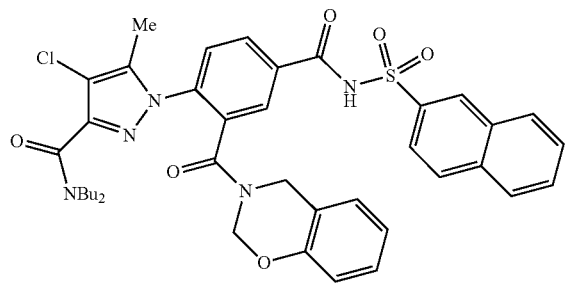

Intermediate 96A 4-(4-Chloro-3-(dibutylcarbamoyl)-5-methyl-1H-pyrazol-1-yl)-N3-(2-hydroxybenzyl)-N1-(naphthalen-2-ylsulfonyl)isophthalamide (Int-96A)

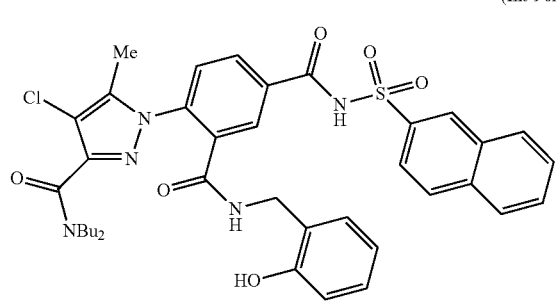

Following a procedure analogous to that for the synthesis of Intermediate 93B, 2-(4-chloro-3-(dibutylcarbamoyl)-5-methyl-1H-pyrazol-1-yl)-5-(naphthalen-2-ylsulfonylcarbamoyl)benzoic acid (Intermediate 91F, 21 mg, 0.034 mmol) and 2-(aminomethyl)phenol, HCl (27 mg, 0.17 mmol) were converted to the title compound (12 mg, 44%) following purification by preparative HPLC. $^1$H NMR (CDCl$_3$) δ 8.78 (d, J=1.5 Hz, 1H), 8.46 (d, J=2.0 Hz, 1H), 8.11-8.07 (m, 2H), 8.04 (d, J=7.9 Hz, 1H), 7.98 (d, J=8.8 Hz, 1H), 7.91 (d, J=7.9 Hz, 1H), 7.71-7.60 (m, 2H), 7.24 (d, J=8.1 Hz, 1H), 7.14-7.07 (m, 2H), 6.98-6.94 (m, 1H), 6.82 (d, J=7.5 Hz, 1H), 6.75 (t, J=7.5 Hz, 1H), 4.40 (d, J=5.9 Hz, 2H), 3.60 (t, J=7.5 Hz, 2H), 3.34-3.30 (m, 2H), 1.74-1.70 (m, 5H), 1.59 (dt, J=15.0, 7.6 Hz, 2H), 1.46 (dq, J=15.1, 7.4 Hz, 2H), 1.25 (dq, J=14.8, 7.4 Hz, 2H), 1.02 (t, J=7.4 Hz, 3H), 0.85 (t, J=7.4 Hz, 3H); MS(ESI$^+$) m/z 730.7 (M+H)$^+$.

Example 96

A solution of 4-(4-chloro-3-(dibutylcarbamoyl)-5-methyl-1H-pyrazol-1-yl)-N3-(2-hydroxybenzyl)-N1-(naphthalen-2-ylsulfonyl)isophthalamide (10 mg, 0.014 mmol), paraformaldehyde (40 mg), 4 Å molecular sieves (100 mg) and 4-methylbenzenesulfonic acid monohydrate (10 mg, 0.058 mmol) in PhMe (1.2 mL) was heated in a sealed tube at 100° C. for 30 min. Additional paraformaldehyde (14 mg) was added, and the reaction mixture was heated at 105° C. for 5 h. The solution was then filtered, and the filtrate was concentrated in vacuo and purified by preparative HPLC to give the title compound (2 mg, 18%) as a white solid. $^1$H NMR (CD$_3$OD, 2:1 mixture of amide rotamers) δ 8.67 (s, 1H), 8.23-7.92 (m, 7H), 7.73-7.57 (m, 3H), 7.22-7.10 (m, 1.5H), 7.04-6.71 (m, 1.5H), 5.15 (br s, 2H), 3.60-2.99 (m, 6H), 2.32 (s, 2H), 2.29 (s, 1H), 1.72-1.04 (m, 7H), 1.02-0.72 (m, 7H); MS(ESI$^+$) m/z 742.6 (M+H)$^+$.

Example 97

N,N-Dibutyl-4-chloro-5-methyl-1-(2-(1-methyl-1,2,3,4-tetrahydroisoquinoline-2-carbonyl)-4-(naphthalen-2-ylsulfonylcarbamoyl)phenyl)-1H-pyrazole-3-carboxamide (97)

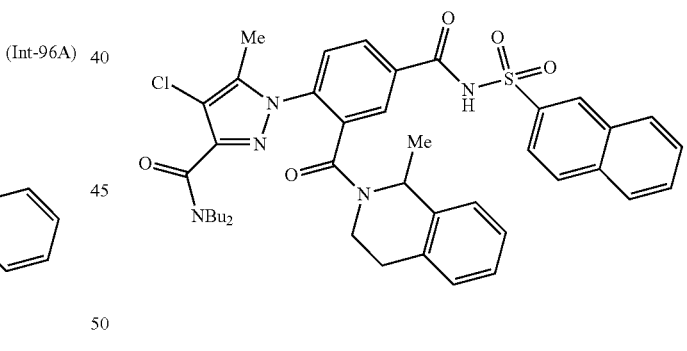

Following a procedure analogous to that for the synthesis of Intermediate 93B, 2-(4-chloro-3-(dibutylcarbamoyl)-5-methyl-1H-pyrazol-1-yl)-5-(naphthalen-2-ylsulfonylcarbamoyl)benzoic acid (Intermediate 91F, 32 mg, 0.051 mmol) and 1-methyl-1,2,3,4-tetrahydroisoquinoline (Parkway Scientific, 8 mg, 0.056 mmol) were converted to the title compound (12 mg, 31%) following purification by preparative HPLC. $^1$H NMR (DMSO-d$_6$, mixture of amide rotamers) δ 8.65 (s, 1H), 8.21 (d, J=8.1 Hz, 2H), 8.16-8.03 (m, 4H), 8.01-7.94 (m, 1.5H), 7.91 (br s, 0.5H), 7.77-7.61 (m, 3H), 7.27-6.93 (m, 2H), 5.48-5.31 (m, 0.5H), 3.68-3.55 (m, 1H), 3.17-2.57 (m, 4.5H), 2.55 (t, J=5.5 Hz, 3H), 2.20 (s, 3H), 1.53-1.36 (3.5H), 1.29-1.23 (m, 2.5H), 1.21-1.12 (m, 4H), 0.95-0.82 (m, 3.5H), 0.66 (d, J=7.3 Hz, 3H), 0.56 (br s, 0.5H); MS(ESI⁺) m/z 754.3 (M+H)⁺.

Example 98

N,N-Dibutyl-4-chloro-1-(2-(4,4-dimethyl-1,2,3,4-tetrahydroisoquinoline-2-carbonyl)-4-(naphthalen-2-ylsulfonylcarbamoyl)phenyl)-5-methyl-1H-pyrazole-3-carboxamide (98)

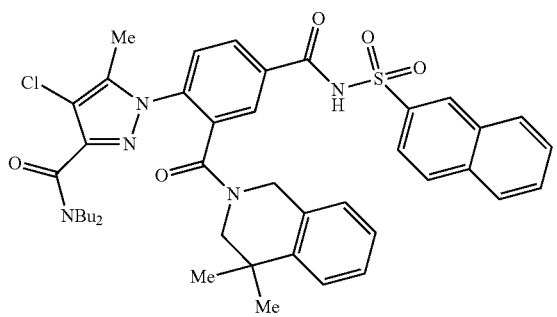

Following a procedure analogous to that for the synthesis of Intermediate 93B, 2-(4-chloro-3-(dibutylcarbamoyl)-5-methyl-1H-pyrazol-1-yl)-5-(naphthalen-2-ylsulfonylcarbamoyl)benzoic acid (Intermediate 91F, 32 mg, 0.051 mmol) and 4,4-dimethyl-1,2,3,4-tetrahydroisoquinoline (Milestone Pharmtech, 9 mg, 0.056 mmol) were converted to the title compound (14 mg, 34%) following purification by preparative HPLC. $^1$H NMR (DMSO-$d_6$, 1:1 mixture of amide rotamers) δ 8.64 (s, 1H), 8.20 (d, J=7.7 Hz, 1H), 8.14-7.90 (m, 5H), 7.78-7.59 (m, 3H), 7.36 (t, J=7.7 Hz, 1H), 7.26-7.13 (m, 2H), 7.11-7.02 (m, 0.5H), 6.99-6.89 (m, 0.5H), 4.85-4.20 (m, 2H), 3.58 (br s, 0.5H), 3.51-2.98 (m, 5H), 2.57-2.52 (m, 0.5H), 2.24 (s, 1.5H), 2.18 (s, 1.5H), 1.43-0.94 (m, 14H), 0.82 (t, J=7.3 Hz, 1H), 0.74 (t, J=7.3 Hz, 2H), 0.69 (t, J=7.4 Hz, 1.5H), 0.64 (t, J=7.4 Hz, 1.5H); MS(ESI⁺) m/z 768.3 (M+H)⁺.

Example 99

1-(2-(7-Bromo-1,2,3,4-tetrahydroisoquinoline-2-carbonyl)-4-(naphthalen-2-ylsulfonylcarbamoyl)phenyl)-N,N-dibutyl-4-chloro-5-methyl-1H-pyrazole-3-carboxamide (99)

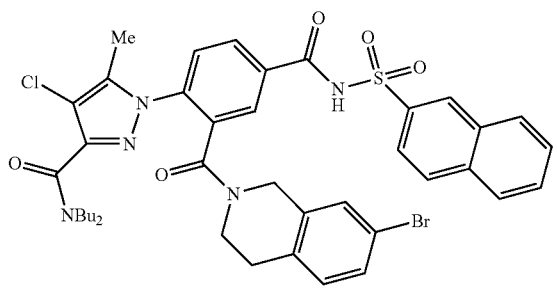

Following a procedure analogous to that for the synthesis of Intermediate 93B, 2-(4-chloro-3-(dibutylcarbamoyl)-5-methyl-1H-pyrazol-1-yl)-5-(naphthalen-2-ylsulfonylcarbamoyl)benzoic acid (Intermediate 91F, 35 mg, 0.056 mmol) and 7-bromo-1,2,3,4-tetrahydroisoquinoline, HCl (Arch, 15 mg, 0.062 mmol) were converted to the title compound (18 mg, 39%) following purification by preparative HPLC. $^1$H NMR (1:1 CD$_3$OD:CDCl$_3$, 1.5:1 mixture of amide rotamers) δ 8.64 (br s, 1H), 8.14 (d, J=8.6 Hz, 1H), 8.09-7.82 (m, 5.5H), 7.66-7.52 (m, 1.5H), 7.49-7.35 (m, 1H), 7.32-7.18 (m, 1.5H), 7.06-6.94 (m, 1.5H), 4.73 (br s, 0.5H), 4.43 (s, 1H), 3.99 (br s, 0.5H), 3.69-3.34 (m, 3H), 3.24-2.65 (m, 5H), 2.27 (s, 2H), 2.23 (s, 1H), 1.58-0.95 (m, 8H), 0.91 (t, J=7.3 Hz, 1.5H), 0.88 (t, J=7.3 Hz, 1.5H), 0.76 (t, J=7.4 Hz, 2H), 0.68 (t, J=7.4 Hz, 1H); MS (ESI⁺) m/z 820.2 (M+H)⁺.

Example 100

2-(2-(4-Chloro-3-(dibutylcarbamoyl)-5-methyl-1H-pyrazol-1-yl)-5-(naphthalen-2-ylsulfonylcarbamoyl)benzoyl)-1,2,3,4-tetrahydroisoquinoline-7-carboxylic acid (100)

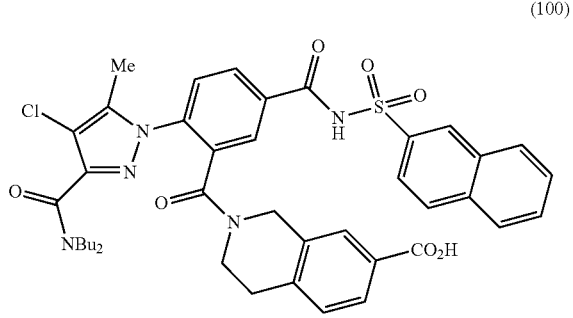

Following a procedure analogous to that for the synthesis of Intermediate 93B, 2-(4-chloro-3-(dibutylcarbamoyl)-5-methyl-1H-pyrazol-1-yl)-5-(naphthalen-2-ylsulfonylcarbamoyl)benzoic acid (Intermediate 91F, 35 mg, 0.056 mmol) was reacted with methyl 1,2,3,4-tetrahydroisoquinoline-7-carboxylate, HCl (14 mg, 0.062 mmol) to give a crude oil which was used in the subsequent step without purification.

The crude oil from above was converted to the title compound (7 mg, 16%) following a procedure analogous to that for the synthesis of Example 93. $^1$H NMR (DMSO-$d_6$, 1.5:1 mixture of amide rotamers) δ 8.70-8.62 (m, 1H), 8.26-8.18 (m, 1H), 8.15-8.09 (m, 1H), 8.09-8.02 (m, 3H), 7.95 (s, 1.5H), 7.80-7.77 (m, 0.5H), 7.76-7.65 (m, 4H), 7.57-7.54 (m, 0.5H), 7.29-7.21 (m, 1H), 4.88-4.75 (m, 0.5H), 4.67-4.54 (m, 1H), 4.45-4.31 (m, 0.5H), 3.99-3.88 (m, 0.5H), 3.57-3.44 (m, 2H), 3.26-2.94 (m, 2H), 2.89 (s, 3H), 2.59-2.53 (m, 0.5H), 2.22 (s, 2H), 2.18 (s, 1H), 1.40-1.30 (m, 0.5H), 1.28-0.78 (m, 10H), 0.67 (t, J=7.4 Hz, 2H), 0.58 (t, J=7.2 Hz, 1H); MS(ESI⁺) m/z 784.3 (M+H)⁺.

Example 101

N,N-Dibutyl-4-chloro-5-methyl-1-(4-(naphthalen-2-ylsulfonylcarbamoyl)-2-(7-(trifluoromethyl)-1,2,3,4-tetrahydroisoquinoline-2-carbonyl)phenyl)-1H-pyrazole-3-carboxamide

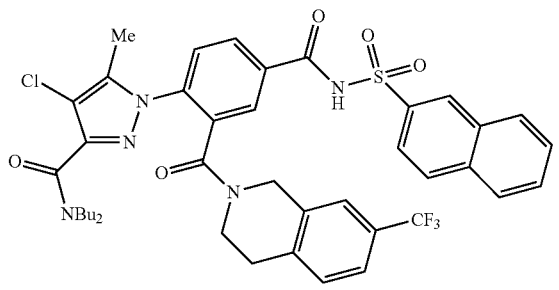

(101)

Following a procedure analogous to that for the synthesis of Intermediate 93B, 2-(4-chloro-3-(dibutylcarbamoyl)-5-methyl-1H-pyrazol-1-yl)-5-(naphthalen-2-ylsulfonylcarbamoyl)benzoic acid (Intermediate 91F, 21 mg, 0.034 mmol) and 7-(trifluoromethyl)-1,2,3,4-tetrahydroisoquinoline (7 mg, 0.037 mmol) were converted to the title compound (20 mg, 71%) following purification by preparative HPLC. ¹H NMR (1:1 CD₃OD:CDCl₃, 1.5:1 mixture of amide rotamers) δ 8.69-8.58 (m, 1H), 8.19-8.13 (m, 1H), 8.08-8.02 (m, 2H), 8.01-7.97 (m, 1H), 7.95-7.91 (m, 1H), 7.90-7.86 (m, 1H), 7.60-7.54 (m, 2H), 7.45-7.34 (m, 2.5H), 7.28-7.23 (m, 1H), 7.17-7.14 (m, 0.5H), 4.89-4.64 (m, 1.5H), 4.52 (s, 1H), 4.16-4.02 (m, 0.5H), 3.70-3.34 (m, 2.5H), 3.24-2.75 (m, 4.5H), 2.28 (s, 2H), 2.23 (s, 1H), 1.51-0.93 (m, 8H), 0.87 (dt, J=17.8, 7.4 Hz, 3H), 0.75 (t, J=7.4 Hz, 2H), 0.64 (t, J=7.4 Hz, 1H); MS(ESI⁺) m/z 808.3 (M+H)⁺.

Example 102

1-(2-(3-Bromo-5,6,7,8-tetrahydro-1,6-naphthyridine-6-carbonyl)-4-(naphthalen-2-ylsulfonylcarbamoyl)phenyl)-N,N-dibutyl-4-chloro-5-methyl-1H-pyrazole-3-carboxamide

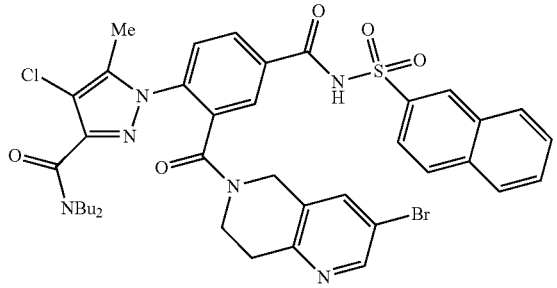

(102)

Following a procedure analogous to that for the synthesis of Intermediate 93B, 2-(4-chloro-3-(dibutylcarbamoyl)-5-methyl-1H-pyrazol-1-yl)-5-(naphthalen-2-ylsulfonylcarbamoyl)benzoic acid (Intermediate 91F, 25 mg, 0.040 mmol) and 3-bromo-5,6,7,8-tetrahydro-1,6-naphthyridine (D-L Chiral, 9 mg, 0.044 mmol) were converted to the title compound (16 mg, 45%) following purification by preparative HPLC. ¹H NMR (1:1 CD₃OD:CDCl₃, 1.5:1 mixture of amide rotamers) δ ppm 8.69-8.65 (m, 1H), 8.47-8.41 (m, 1H), 8.21-8.16 (m, 1H), 8.09-8.05 (m, 2H), 8.04-8.00 (m, 1H), 7.99-7.95 (m, 1.5H), 7.94-7.90 (m, 1H), 7.78-7.74 (m, 0.5H), 7.66-7.57 (m, 1.5H), 7.53-7.43 (m, 1.5H), 4.79-4.73 (m, 1H), 4.57-4.51 (m, 1H), 3.71-3.61 (m, 1.5H), 3.58-3.39 (m, 1H), 3.31-2.85 (m, 5.5H), 2.31 (s, 1.5H), 2.28 (s, 1.5H), 1.57-1.02 (m, 8H), 0.93 (dt, J=14.4, 7.4 Hz, 3H), 0.79 (t, J=7.4 Hz, 1.5H), 0.74 (t, J=7.4 Hz, 1.5H); MS(ESI⁺) m/z 821.0 (M+H)⁺.

Example 103

N,N-Dibutyl-4-chloro-5-methyl-1-(4-(naphthalen-2-ylsulfonylcarbamoyl)-2-(1,2,3,4-tetrahydroquinazoline-3-carbonyl)phenyl)-1H-pyrazole-3-carboxamide

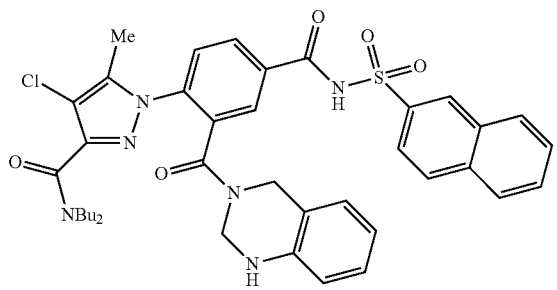

(103)

Intermediate 103A

N³-(2-Aminobenzyl)-4-(4-chloro-3-(dibutylcarbamoyl)-5-methyl-1H-pyrazol-1-yl)-N¹-(naphthalen-2-ylsulfonyl)isophthalamide

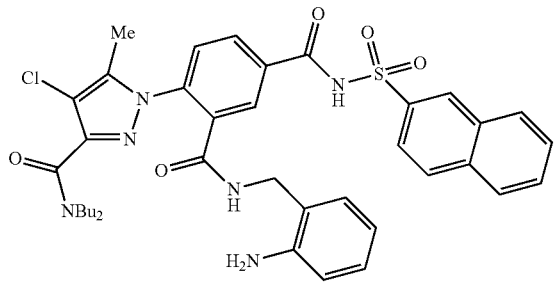

(103A)

To a solution of 2-(4-chloro-3-(dibutylcarbamoyl)-5-methyl-1H-pyrazol-1-yl)-5-(naphthalen-2-ylsulfonylcarbamoyl)benzoic acid (Intermediate 91F, 50 mg, 0.080 mmol) in CH₂Cl₂ (1.1 mL) and DMF (0.2 mL) was added 2-(aminomethyl)aniline (20 mg, 0.16 mmol) followed by EDC (34 mg, 0.18 mmol) and 1-hydroxy-7-azabenzo-triazole (290 μL, 0.18 mmol, 0.6M solution in DMF). The resulting reaction mixture was stirred at room temperature overnight, then quenched with sat. aq. NH₄Cl solution and extracted with EtOAc (3×). The combined organic extracts were dried over Na₂SO₄, filtered and concentrated in vacuo. Purification by flash column chromatography (gradient from 0% to 10% MeOH/CH₂Cl₂) provided the title compound (35 mg, 60%) as a pale yellow, oily solid. MS(ESI⁺) m/z 729.2 (M+H)⁺.

Example 103

A solution of N³-(2-aminobenzyl)-4-(4-chloro-3-(dibutyl-carbamoyl)-5-methyl-1H-pyrazol-1-yl)-N¹-(naphthalen-2-ylsulfonyl)isophthalamide (35 mg, 0.048 mmol), oven-dried 4 Å molecular sieves (100 mg) and paraformaldehyde (52 mg, 1.73 mmol) in PhMe (807 μL) was heated at 110° C. for 2 h. The reaction mixture was then concentrated in vacuo and purified by preparative HPLC to give the title compound (8 mg, 22%) as a white solid after lyophilization. ¹H NMR (CD₃OD, 2:1 mixture of amide rotamers) δ 8.63-8.56 (m, 1H), 8.24-8.15 (m, 1H), 8.13-8.07 (m, 1H), 8.05-7.89 (m, 4H), 7.64-7.50 (m, 3H), 7.09-6.98 (m, 2H), 6.83-6.76 (m, 1H), 6.72-6.65 (m, 1H), 4.98-4.90 (m, 1.5H), 4.74-4.65 (m, 1H), 4.59-4.39 (m, 2H), 3.51-3.12 (m, 3H), 2.99-2.86 (m, 0.5H), 2.30 (s, 2H), 2.23 (s, 1H), 1.57-1.43 (m, 2H), 1.40-1.20 (m, 4H), 1.16-1.04 (m, 2H), 0.97-0.86 (m, 3H), 0.78 (t, J=7.3 Hz, 2H), 0.75-0.70 (m, 1H); MS(ESI⁺) m/z 741.2 (M+H)⁺.

Example 104

N,N-Dibutyl-4-chloro-1-(2-(1,1-dioxido-3,4-dihydro-2H-benzo[e][1,3]thiazine-3-carbonyl)-4-(naphthalen-2-ylsulfonylcarbamoyl)phenyl)-5-methyl-1H-pyrazole-3-carboxamide (104)

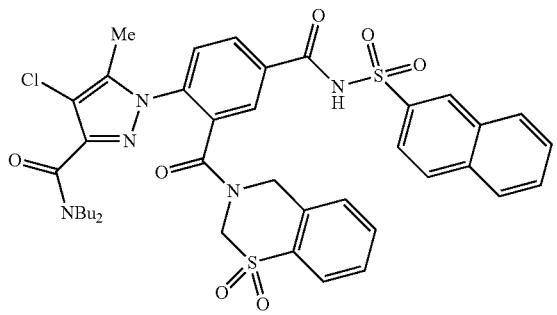

Intermediate 104A (2-(tert-Butylthio)phenyl)methanamine

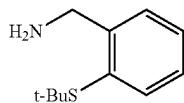

(Int-104A)

To a solution of 2-(tert-butylthio)benzonitrile (Guiu, E. et al., *J. Organomet. Chem.*, 689:1911-1918 (2004)) (1.00 g, 5.23 mmol) in THF (10.5 mL) was added BH₃.THF (10.5 mL, 10.5 mmol, 1.0M solution in THF) via syringe. The resulting clear, colorless solution was stirred at room temperature for 1.5 h and then at 50° C. for 2 h. The reaction mixture was cooled to room temperature, and MeOH (2.5 mL) was added carefully via syringe (gas evolution) followed by 1N aq. HCl solution (12.0 mL). The mixture was poured into EtOAc and the layers were separated. The aqueous layer was basified with 1N aq. NaOH solution (pH=12) and then extracted with CH₂Cl₂ (5×). The combined CH₂Cl₂ extracts were dried over MgSO₄, filtered and concentrated in vacuo to give the title compound (288 mg, 28%) as a colorless oil. ¹H NMR (CDCl₃) δ 7.57-7.53 (m, 1H), 7.44-7.40 (m, 1H), 7.37-7.32 (m, 1H), 7.25-7.19 (m, 1H), 4.07 (s, 2H), 1.30 (s, 9H); MS(ESI⁺) m/z 196.2 (M+H)⁺.

Intermediate 104B

N,N-Dibutyl-4-chloro-1-(2-(3,4-dihydro-2H-benzo[e][1,3]thiazine-3-carbonyl)-4-(naphthalen-2-ylsulfonylcarbamoyl)phenyl)-5-methyl-1H-pyrazole-3-carboxamide (Int-104B)

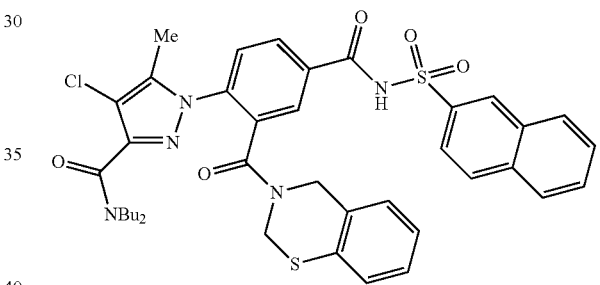

To a solution of 2-(4-chloro-3-(dibutylcarbamoyl)-5-methyl-1H-pyrazol-1-yl)-5-(naphthalen-2-ylsulfonylcarbamoyl)benzoic acid (Intermediate 91F, 50 mg, 0.080 mmol) in CH₂Cl₂ (1.3 mL) was added (2-(tert-butylthio)phenyl)methanamine (23 mg, 0.12 mmol) followed by EDC (31 mg, 0.16 mmol) and DMAP (5 mg, 0.040 mmol). The resulting reaction mixture was stirred at room temperature for 1.5 h, then quenched with sat. aq. NH₄Cl solution, washed with 1N aq. HCl solution and extracted with EtOAc (3×). The combined organic extracts were dried over Na₂SO₄, filtered and concentrated in vacuo to provide a crude oil which was used in the subsequent step without purification.

The crude oil from above (36 mg, 0.040 mmol) was dissolved in AcOH (1.0 mL) and 2-nitrophenyl hypochlorothioite (8 mg, 0.044 mmol) was added. The resulting reaction mixture was stirred at room temperature overnight and then concentrated in vacuo to give a crude oil which was used in the subsequent step without purification.

The crude oil from above was dissolved in EtOH (1.0 mL) and NaBH₄ (3 mg, 0.089 mmol) was added. The resulting reaction mixture was stirred for 5 min, and then HCl (4N solution in dioxane) was added until the color changed to pale yellow. The reaction mixture was concentrated in vacuo and redissolved in PhMe (2.0 mL). To the solution were added 4 Å molecular sieves followed by TsOH (2 mg, 11 μmol). The reaction mixture was stirred at 81° C. for 4 h, then filtered through a pipette containing a plug of cotton. The filtrate was concentrated in vacuo, redissolved in CH$_2$Cl$_2$ and passed through a syringe filter to remove the remaining paraformaldehyde. Purification using preparative HPLC provided the title compound (10 mg, 31%) as a white solid after lyophilization. $^1$H NMR (CD$_3$OD, 1:1 mixture of amide rotamers) δ ppm 8.56 (s, 1H), 8.30-8.19 (m, 1.5H), 8.10 (d, J=1.8 Hz, 0.5H), 8.04-7.97 (m, 2H), 7.96-7.87 (m, 2H), 7.66-7.49 (m, 3H), 7.27-7.08 (m, 3H), 7.06-6.99 (m, 0.5H), 6.96-6.88 (m, 0.5H), 4.78-4.55 (m, 3H), 3.60-3.36 (m, 3H), 3.21-3.17 (m, 2H), 2.31 (s, 1.5H), 2.24 (s, 1.5H), 1.63-1.47 (m, 2.5H), 1.45-1.25 (m, 3H), 1.20-1.03 (m, 2.5H), 0.99-0.87 (m, 3H), 0.84-0.68 (m, 3H); MS(ESI$^+$) m/z 758.1 (M+H)$^+$.

Example 104

To a solution of N,N-dibutyl-4-chloro-1-(2-(3,4-dihydro-2H-benzo[e][1,3]thiazine-3-carbonyl)-4-(naphthalen-2-ylsulfonylcarbamoyl)phenyl)-5-methyl-1H-pyrazole-3-carboxamide (32 mg, 0.042 mmol) in CH$_2$Cl$_2$ (1.0 mL) was added m-CPBA (47 mg, 0.21 mmol). The resulting reaction mixture was stirred at room temperature for 2 h 15 min. Additional m-CPBA (47 mg, 0.21 mmol) was added, and stirring was continued at room temperature for 1 h. The reaction mixture was then diluted with EtOAc and washed with 20% aq. NaHSO$_3$ solution, followed by sat. aq. NaHCO$_3$ solution and sat. aq. NaCl solution. The organic layer was dried over NaSO$_4$, filtered and concentrated in vacuo. Purification using preparative HPLC provided the title compound (11.2 mg, 33%) as a white solid after lyophilization. $^1$H NMR (CD$_3$OD, 2:1 mixture of amide rotamers) δ 8.61-8.49 (m, 1H), 8.36-8.22 (m, 1.5H), 8.08-7.82 (m, 5.5H), 7.68-7.43 (m, 5.5H), 7.25-7.16 (m, 0.5H), 5.63-5.59 (m, 0.5H), 5.40-5.05 (m, 1.5H), 5.02-4.90 (m, 1H), 4.79-4.56 (m, 1H), 3.71-3.55 (m, 0.5H), 3.55-3.38 (m, 2H), 3.27-3.19 (m, 1.5H), 2.30 (s, 1H), 2.24 (s, 2H), 1.66-1.52 (m, 2H), 1.50-1.25 (m, 3.5H), 1.22-1.08 (m, 2.5H), 0.99-0.86 (m, 3H), 0.85-0.72 (m, 3H); MS(ESI$^+$) m/z 790.2 (M+H)$^+$.

Example 105

N,N-Dibutyl-4-chloro-1-(2-((S)-3-((3-methoxypropoxy)methyl)-1,2,3,4-tetrahydroisoquinoline-2-carbonyl)-4-(naphthalen-2-ylsulfonylcarbamoyl)phenyl)-5-methyl-1H-pyrazole-3-carboxamide (105)

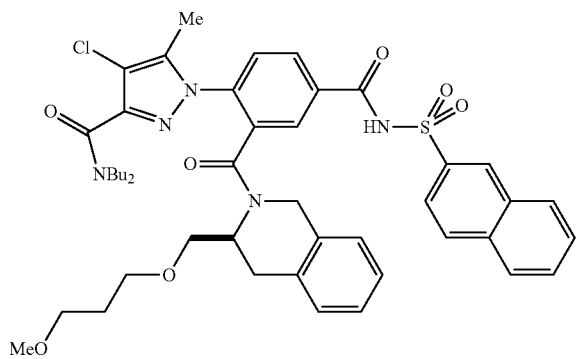

A solution of (S)—N,N-dibutyl-4-chloro-1-(2-(3-(hydroxymethyl)-1,2,3,4-tetrahydroisoquinoline-2-carbonyl)-4-(naphthalen-2-ylsulfonylcarbamoyl)phenyl)-5-methyl-1H-pyrazole-3-carboxamide (Example 91, 21 mg, 0.028 mmol) in DMF (900 μL) was cooled to 0° C., and NaH (2 mg, 0.061 mmol, 60% suspension in mineral oil) was added followed by 1-bromo-3-methoxypropane (9 mg, 0.061 mmol). The resulting reaction mixture was stirred warming to room temperature over 1 h and then heated at 130° C. for 3 h. Additional NaH (2 mg, 0.061 mmol, 60% suspension in mineral oil) and 1-bromo-3-methoxypropane (9 mg, 0.061 mmol) were added, and stirring was continued overnight at 130° C. Additional NaH (2 mg, 0.061 mmol, 60% suspension in mineral oil) and 1-bromo-3-methoxypropane (9 mg, 0.061 mmol) were added, and the reaction mixture was stirred at 135° C. for 24 h. TBAI (10 mg, 0.027 mmol) was then added, and stirring was continued at 140° C. for 72 h. After quenching with sat. aq. NH$_4$Cl solution, the reaction mixture was diluted with EtOAc. The layers were separated, and the aqueous layer was extracted with EtOAc (3×). The combined organic extracts were dried over Na$_2$SO$_4$, filtered and concentrated in vacuo. Purification using preparative HPLC provided the title compound (4 mg, 18%) as an off-white solid after lyophilization. $^1$H NMR (CD$_3$OD, mixture of amide rotamers) δ 8.82-8.69 (m, 1H), 8.29-8.20 (m, 1H), 8.16-7.92 (m, 5.5H), 7.78-7.57 (m, 3H), 7.31-7.05 (m, 3H), 6.94-6.85 (m, 0.5H), 5.24-5.36 (m, 1H), 5.09-4.91 (m, 1H), 4.53-4.47 (m, 0.5H), 4.30-4.16 (m, 1.5H), 3.64-2.73 (m, 12H), 2.62-2.49 (m, 1H), 2.38-2.24 (m, 4H), 1.83-0.86 (m, 13H), 0.80-0.70 (m, 2.5H), 0.67-0.60 (m, 0.5H); MS(ESI$^+$) m/z 842.3 (M+H)$^+$.

Example 106

N,N-Dibutyl-4-chloro-5-methyl-1-(2-((S)-3-((1-methylpiperidin-4-ylamino)methyl)-1,2,3,4-tetrahydroisoquinoline-2-carbonyl)-4-(naphthalen-2-ylsulfonylcarbamoyl)phenyl)-1H-pyrazole-3-carboxamide (106)

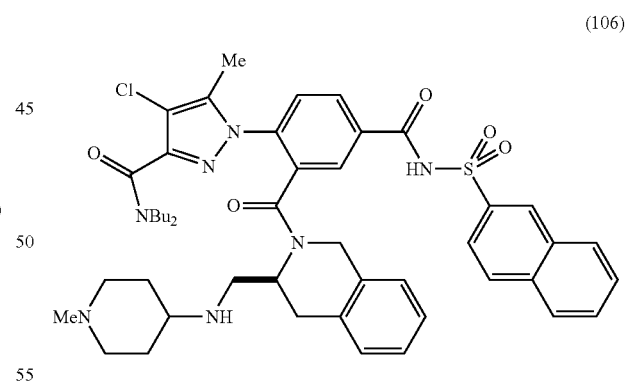

To a solution of 1-(2-((S)-3-(aminomethyl)-1,2,3,4-tetrahydroisoquinoline-2-carbonyl)-4-(naphthalen-2-ylsulfonylcarbamoyl)phenyl)-N,N-dibutyl-4-chloro-5-methyl-1H-pyrazole-3-carboxamide (Example 92, 25 mg, 0.032 mmol) in CH$_2$Cl$_2$ (500 μL) and i-PrOH (500 μL) was added 1-methylpiperidin-4-one (4 μL, 0.032 mmol) followed by Na(OAc)$_3$BH (10 mg, 0.049 mmol). The resulting reaction mixture was stirred at room temperature overnight, then quenched with 2 mL of MeOH followed by 2 mL of 1N aq. NaOH solution. The mixture was poured in sat. aq. NH$_4$Cl solution, and the aqueous layer was extracted with EtOAc (3×). The combined organic extracts were dried over Na₂SO₄, filtered and concentrated in vacuo. The residue was purified using preparative HPLC to give the title compound (10 mg, 31%) as a white solid after lyophilization. ¹H NMR (CD₃OD, mixture of amide rotamers) δ 8.59-8.52 (m, 1H), 8.51-8.45 (m, 0.5H), 8.40-8.34 (m, 0.5H), 8.26-8.12 (m, 1H), 8.06-7.86 (m, 4H), 7.69-7.45 (m, 3H), 7.29-7.20 (m, 3.5H), 7.04-6.91 (m, 0.5H), 5.33-5.21 (m, 0.5H), 5.08-4.94 (m, 0.5H), 4.63-4.53 (m, 0.5H), 4.34-4.23 (m, 1H), 4.17-4.03 (m, 0.5H), 3.54-3.34 (m, 3.5H), 3.22-2.51 (m, 11.5H), 2.43-2.32 (m, 1H), 2.29 (s, 3H), 2.18-1.99 (m, 1H), 1.84-1.67 (m, 1.5H), 1.65-0.85 (m, 12H), 0.81-0.70 (m, 2.5H), 0.69-0.58 (m, 1H); MS(ESI⁺) m/z 866.4 (M+H)⁺.

Example 107

N,N-Dibutyl-4-chloro-5-methyl-1-(4-(naphthalen-2-ylsulfonylcarbamoyl)-2-((S)-3-((piperidin-4-ylamino)methyl)-1,2,3,4-tetrahydroisoquinoline-2-carbonyl)phenyl)-1H-pyrazole-3-carboxamide (107)

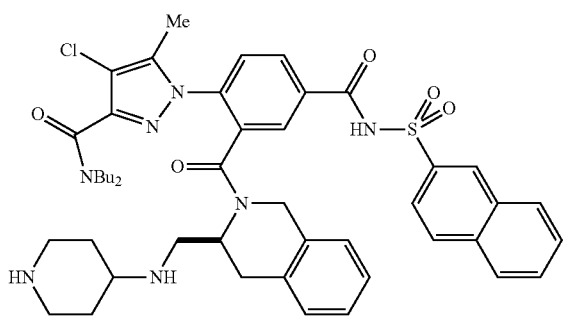

Following a procedure analogous to that for the synthesis of Example 106, (S)-1-(2-(3-(aminomethyl)-1,2,3,4-tetrahydroisoquinoline-2-carbonyl)-4-(naphthalen-2-ylsulfonylcarbamoyl)phenyl)-N,N-dibutyl-4-chloro-5-methyl-1H-pyrazole-3-carboxamide (30 mg, 0.039 mmol) was reacted with tert-butyl 4-oxopiperidine-1-carboxylate (9 mg, 0.047 mmol) to give a crude oil which was used in the subsequent step without purification.

The crude oil from above was dissolved in CH₂Cl₂ (1.0 mL) and TFA (240 µL, 3.12 mmol) was added. The resulting reaction mixture was stirred at room temperature for 1.5 h and then concentrated in vacuo. The residue was purified by preparative HPLC to give the title compound (10 mg, 26%) as a white solid after lyophilization. ¹H NMR (CD₃OD, mixture of amide rotamers) δ 8.79-8.69 (m, 1H), 8.59-8.48 (m, 0.5H), 8.21-7.96 (m, 5H), 7.85-7.55 (m, 4.5H), 7.43-7.09 (m, 2.5H), 7.04-6.90 (m, 0.5H), 5.26-5.10 (m, 0.5H), 4.73-4.34 (m, 2H), 4.25-4.13 (m, 2H), 3.52-2.79 (m, 10H), 2.44-2.14 (m, 4.5H), 2.11-1.74 (m, 1.5H), 1.72-0.69 (m, 15H), 0.63-0.46 (m, 1.5H); MS(ESI⁺) m/z 852.5 (M+H)⁺.

Intermediate 108

(S)—N,N-Dimethyl-1-(1,2,3,4-tetrahydroisoquinolin-3-yl)methanamine hydrochloride (Int-108)

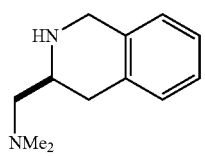

To a solution of (S)-tert-butyl 3-((dimethylamino)methyl)-3,4-dihydroisoquinoline-2(1H)-carboxylate (Edwards, P. J., European Patent Application No. 1598341 (2005)) (66 mg, 0.23 mmol) in CH₂Cl₂ (2.3 mL) was added TFA (1.4 mL, 18.1 mmol). After stirring for 3 h at room temperature, the reaction mixture was concentrated in vacuo. Next, HCl (1N solution in Et₂O) was added and the mixture was concentrated in vacuo (3×) to give a crude oil which was used without purification in the preparation of Example 108. MS(ESI⁺) m/z 790.2 (M+H)⁺.

Intermediate 109

(S)-4-((1,2,3,4-Tetrahydroisoquinolin-3-yl)methyl)morpholine (Int-109)

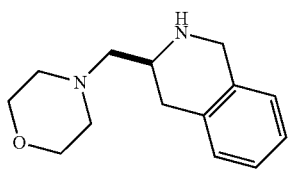

Intermediate 109A (S)-tert-Butyl 3-(morpholinomethyl)-3,4-dihydroisoquinoline-2(1H)-carboxylate (Int-109A)

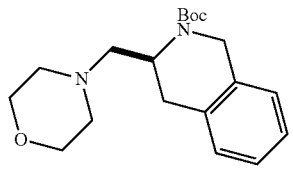

Following a procedure analogous to that for the synthesis of Example 106, (S)-tert-butyl 3-formyl-3,4-dihydroisoquinoline-2(1H)-carboxylate (Aubry, S. et al., *Tetrahedron Lett.*, 47:1319-1323 (2006)) (71 mg, 0.27 mmol) and morpholine (28 µL, 0.33 mmol) were converted to the title compound (80 mg, 89%). ¹H NMR (CDCl₃, mixture of rotamers)

δ 7.24-7.20 (m, 4H), 4.85-4.66 (m, 1H), 4.54-4.42 (m, 1H), 4.30-4.17 (m, 1H), 3.67 (br s, 4H), 3.13-2.96 (m, 1H), 2.93-2.69 (m, 1H), 2.62-2.29 (m, 5H), 2.18-2.01 (m, 1H), 1.51 (s, 9H); MS(ESI$^+$) m/z 333.2 (M+H)$^+$.

Intermediate 109

To a solution of (S)-tert-butyl 3-(morpholinomethyl)-3,4-dihydroisoquinoline-2(1H)-carboxylate (80 mg, 0.24 mmol) in CH$_2$Cl$_2$ (2.0 mL) was added TFA (1.5 mL, 19.3 mmol). The resulting reaction mixture was stirred at room temperature for 2 h, then concentrated in vacuo and used without purification in the preparation of Example 109. MS (ESI$^+$) m/z 233.2 (M+H)$^+$.

Intermediate 110

(S)-1-((1,2,3,4-Tetrahydroisoquinolin-3-yl)methyl)piperidin-4-ol

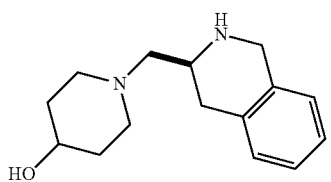
(Int-110)

Following a procedure analogous to that for the synthesis of Example 107, (S)-tert-butyl 3-formyl-3,4-dihydroisoquinoline-2(1H)-carboxylate (57 mg, 0.22 mmol) and piperidin-4-ol (26 mg, 0.26 mmol) provided a crude oil which was used without purification in the preparation of Example 110. MS(ESI$^+$) m/z 247.2 (M+H)$^+$.

Intermediate 111

(S)-3-(Pyrrolidin-1-ylmethyl)-1,2,3,4-tetrahydroisoquinoline

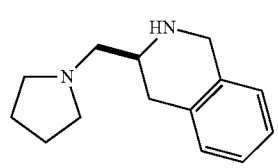
(Int-111)

Following a procedure analogous to that for the synthesis of Example 107, (S)-tert-butyl 3-formyl-3,4-dihydroisoquinoline-2(1H)-carboxylate (57 mg, 0.22 mmol) and pyrrolidine (16 mg, 0.22 mmol) provided a crude oil which was used without purification in preparation of Example 111. MS(ESI$^+$) m/z 217.1 (M+H)$^+$.

Intermediate 112

(S)-3-((4-Methylpiperazin-1-yl)methyl)-1,2,3,4-tetrahydroisoquinoline

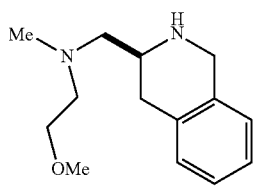
(Int-112)

Following a procedure analogous to that for the synthesis of Example 107, (S)-tert-butyl 3-formyl-3,4-dihydroisoquinoline-2(1H)-carboxylate (57 mg, 0.22 mmol) and 1-methylpiperazine (26 mg, 0.26 mmol) provided a crude oil which was used without purification in the preparation of Example 112. MS(ESI$^+$) m/z 246.1 (M+H)$^+$.

Intermediate 113

(S)-2-Methoxy-N-methyl-N-((1,2,3,4-tetrahydroisoquinolin-3-yl)methyl)ethanamine

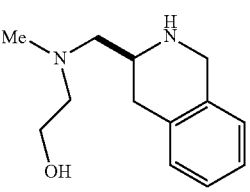
(Int-113)

Following a procedure analogous to that for the synthesis of Example 107, (S)-tert-butyl 3-formyl-3,4-dihydroisoquinoline-2(1H)-carboxylate (58 mg, 0.22 mmol) and 2-(methylamino)ethanol (21 µL, 0.27 mmol) provided a crude oil which was used without purification in the preparation of Example 113. MS(ESI$^+$) m/z 235.2 (M+H)$^+$.

Intermediate 114

(S)-2-(Methyl((1,2,3,4-tetrahydroisoquinolin-3-yl)methyl)amino)ethanol (Int-114)

Following a procedure analogous to that for the synthesis of Example 107, (S)-tert-butyl 3-formyl-3,4-dihydroisoquinoline-2(1H)-carboxylate (58 mg, 0.22 mmol) and 2-(methylamino)ethanol (21.4 µL, 0.27 mmol) provided a crude oil which was used without purification in the preparation of Example 114. MS(ESI⁺) m/z 221.1 (M+H)⁺.

Intermediate 115

(S)-2-(4-((1,2,3,4-Tetrahydroisoquinolin-3-yl)methyl)piperazin-1-yl)ethanol

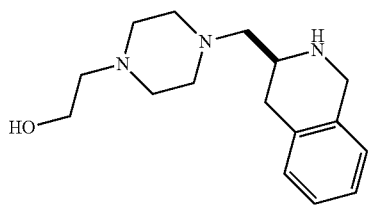
(Int-115)

Following a procedure analogous to that for the synthesis of Example 107, (S)-tert-butyl 3-formyl-3,4-dihydroisoquinoline-2(1H)-carboxylate (58 mg, 0.22 mmol) and 2-(piperazin-1-yl)ethanol (33 µL, 0.267 mmol) provided a crude oil which was used without purification in the preparation of Example 115. MS(ESI⁺) m/z 276.2 (M+H)⁺.

Intermediate 116

(S)—N,N-Dimethyl-2-((1,2,3,4-tetrahydroisoquinolin-3-yl)methoxy)ethanamine

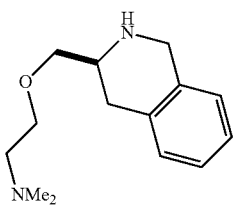
(Int-116)

Intermediate 116A (S)-1-(3-(Hydroxymethyl)-3,4-dihydroisoquinolin-2(1H)-yl)ethanone

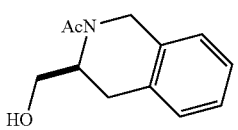
(Int-116A)

To (S)-(1,2,3,4-tetrahydroisoquinolin-3-yl)methanol (Aldrich, 350 mg, 2.14 mmol) in EtOAc (4.3 mL) and MeOH (1.1 mL) was added Ac₂O (243 µL, 2.57 mmol). The resulting reaction mixture was stirred at room temperature for 2 h. K₂CO₃ was then added to neutralize the AcOH, and the reaction mixture was filtered through a pad of CELITE®, washing with EtOAc. The filtrate was concentrated in vacuo to give the title compound (316 mg, 72%) as a white solid. ¹H NMR (CDCl₃, 1.5:1 mixture of amide rotamers) δ 7.26-7.10 (m, 4H), 5.17 (d, J=18.0 Hz, 0.5H), 4.90 (dt, J=5.1, 9.4 Hz, 0.5H), 4.66-4.44 (m, 1H), 4.39-4.23 (m, 1H), 3.66-3.55 (m, 1H), 3.55-3.45 (m, 1H), 3.14 (dd, J=5.9, 16.3 Hz, 0.5H), 3.02 (dd, J=6.2, 15.8 Hz, 0.5H), 2.92-2.76 (m, 1H), 2.27 (s, 1H), 2.24 (s, 2H); MS(ESI⁺) m/z 206.1 (M+H)⁺.

Intermediate 116B (S)-1-(3-((2-(Dimethylamino)ethoxy)methyl)-3,4-dihydroisoquinolin-2(1H)-yl)ethanone

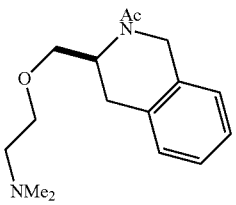
(Int-116B)

To 2-chloro-N,N-dimethylethanamine (63 mg, 0.59 mmol) in DMF (1.0 mL) was added NaH (156 mg, 3.90 mmol, 60% suspension in mineral oil) at 0° C. After stirring for 20 min at 0° C., (S)-1-(3-(hydroxymethyl)-3,4-dihydroisoquinolin-2(1H)-yl)ethanone (40 mg, 0.20 mmol) was added, and the resulting suspension was stirred at room temperature for 10 min. TBAI (7 mg, 0.019 mmol) was then added, and the reaction mixture was heated at 70° C. for 1.5 h. The mixture was then poured into sat. aq. NH₄Cl solution and EtOAc. The layers were separated, and the organic layer was washed with sat. aq. NH₄Cl solution. The aqueous layer was extracted with EtOAc (3×), and the combined organics were washed with sat. aq. NaCl solution and dried over Na₂SO₄. Filtration and concentration in vacuo provided a crude oil which was triturated with hexanes (3×) to give the title compound (29 mg, 54%) as a pale yellow oil. MS(ESI⁺) m/z 206.1 (M+H)⁺.

Intermediate 116

To a solution of (S)-1-(3-((2-(dimethylamino)ethoxy)methyl)-3,4-dihydroisoquinolin-2(1H)-yl)ethanone (29 mg, 0.11 mmol) in EtOH (1.0 mL) and water (125 µL) was added conc. HCl (160 µL, 5.30 mmol). The resulting reaction mixture was stirred at 70° C. overnight. Additional MeOH (1.0 mL) and conc. HCl (260 µL, 7.85 mmol) were added, and the solution was heated at 100° C. for 4 h. Conc. HCl (160 µL, 5.30 mmol) was again added, and after stirring at 100° C. for 3 h, an additional 1 mL of conc. HCl was added The reaction mixture was stirred at 100° C. for 36 h, then cooled to room temperature and concentrated in vacuo to give a crude brown oil which was used without purification in the preparation of Example 116.

Intermediate 117

(S)-3-((2-(Benzyloxy)ethoxy)methyl)-1,2,3,4-tetrahydroisoquinoline

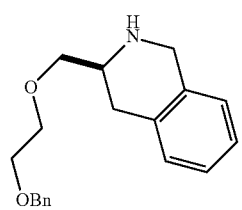
(Int-117)

Intermediate 117A (S)-1-(3-((2-(Benzyloxy)ethoxy)methyl)-3,4-dihydroisoquinolin-2(1H)-yl)ethanone

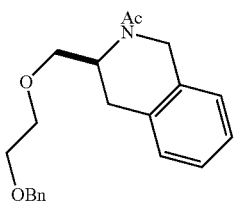

(Int-117A)

Following a procedure analogous to that for the synthesis of Intermediate 116B, (S)-1-(3-(hydroxymethyl)-3,4-dihydroisoquinolin-2(1H)-yl)ethanone (Intermediate 116A, 40.0 mg, 0.20 mmol) and ((2-bromoethoxy)methyl)benzene (92 µl, 0.58 mmol) were converted to the title compound (43 mg, 65%) after purification by flash column chromatography (gradient from 0% to 50% EtOAc/hexanes). $^1$H NMR (CDCl$_3$, 2:1 mixture of amide rotamers) δ 7.41-7.25 (m, 5H), 7.24-7.06 (m, 4H), 5.10 (d, J=18.0 Hz, 1H), 4.66-4.44 (m, 3H), 4.39 (q, J=5.9 Hz, 0.5H), 4.26 (d, J=17.8 Hz, 0.5H), 3.68-3.47 (m, 5H), 3.44-3.27 (m, 1.5H), 3.10 (dd, J=5.8, 16.0 Hz, 0.5H), 3.01-2.80 (m, 1H), 2.24 (s, 2H), 2.19 (s, 1H); MS(ESI$^+$) m/z 340.2 (M+H)$^+$.

Intermediate 117

To a solution of (S)-1-(3-((2-(benzyloxy)ethoxy)methyl)-3,4-dihydroisoquinolin-2(1H)-yl)ethanone (29 mg, 0.086 mmol) in EtOH (1.3 mL) and water (0.4 mL) was added KOH (77 mg, 1.38 mmol). The resulting reaction mixture was stirred at 78° C. for 4 h. Additional KOH (400 mg, 7.17 mmol) was added, and the reaction mixture was stirred at 95° C. overnight. The reaction mixture was then transferred to a pressure vial, rinsing with EtOH (1 mL), and additional KOH (400 mg, 7.17 mmol) was added. The vial was sealed with a Teflon cap and heated at 100° C. for 8 h. The reaction mixture was then quenched with water and extracted CH$_2$Cl$_2$ (3×). The combined organic extracts were dried over Na$_2$SO$_4$, filtered and concentrated in vacuo to give a crude oil which was used without purification in the preparation of Example 117.

Intermediate 118

3-((4-Methylpiperazin-1-yl)methyl)-1,2,3,4-tetrahydroisoquinoline

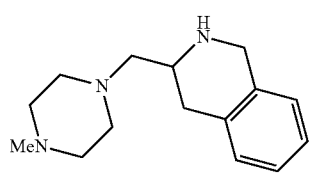

(Int-118)

Intermediate 118A tert-Butyl 3-((4-methylpiperazin-1-yl)methyl)-3,4-dihydroisoquinoline-2(1H)-carboxylate

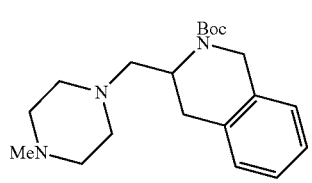

(Int-118A)

Following a procedure analogous to that for the synthesis of Example 106, tert-butyl 3-formyl-3,4-dihydroisoquinoline-2(1H)-carboxylate (Molander, G. A. et al., *Tetrahedron*, 61:2631-2643 (2005)) (95 mg, 0.36 mmol) and 1-methylpiperazine (44 mg, 0.44 mmol) were converted to the title compound (110 mg, 88%), which was used in the subsequent step without purification. MS(ESI$^+$) m/z 346.3 (M+H)$^+$.

Intermediate 118

Following a procedure analogous to that for the synthesis of Intermediate 109B, tert-butyl 3-((4-methylpiperazin-1-yl)methyl)-3,4-dihydroisoquinoline-2(1H)-carboxylate (110 mg, 0.32 mmol) provided a crude oil which was used without purification in the preparation of Example 118.

Examples 108 to 118

The following Examples were prepared using 2-(4-chloro-3-(dibutylcarbamoyl)-5-methyl-1H-pyrazol-1-yl)-5-(naphthalen-2-ylsulfonylcarbamoyl)benzoic acid (Intermediate 91F) and the tetrahydroisoquinoline intermediates described above according to the general procedure for the synthesis of Example 91.

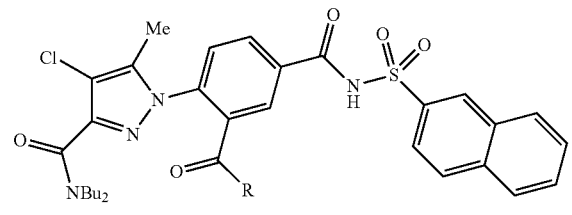

| Ex. No. | R | Name | LCMS (M + H) |
|---|---|---|---|
| 108 | 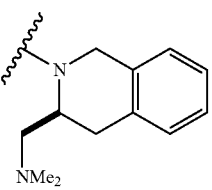 [SMILES: *N1Cc2ccccc2C[C@H]1CN(C)C] | N,N-dibutyl-4-chloro-1-(2-((S)-3-((dimethylamino)methyl)-1,2,3,4-tetrahydroisoquinoline-2-carbonyl)-4-(naphthalen-2-ylsulfonylcarbamoyl)phenyl)-5-methyl-1H-pyrazole-3-carboxamide | 797.3 |
| 109 | 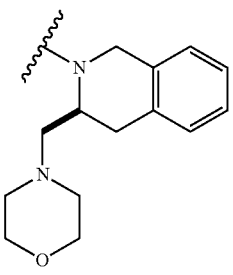 [SMILES: *N1Cc2ccccc2C[C@H]1CN1CCOCC1] | N,N-dibutyl-4-chloro-5-methyl-1-(2-((S)-3-(morpholinomethyl)-1,2,3,4-tetrahydroisoquinoline-2-carbonyl)-4-(naphthalen-2-ylsulfonylcarbamoyl)phenyl)-1H-pyrazole-3-carboxamide | 839.3 |
| 110 | 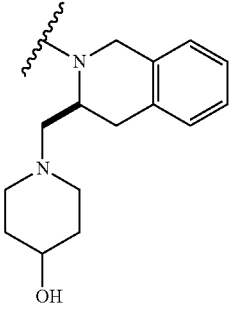 [SMILES: *N1Cc2ccccc2C[C@H]1CN1CCC(O)CC1] | N,N-dibutyl-4-chloro-1-(2-((S)-3-((4-hydroxypiperidin-1-yl)methyl)-1,2,3,4-tetrahydroisoquinoline-2-carbonyl)-4-(naphthalen-2-ylsulfonylcarbamoyl)phenyl)-5-methyl-1H-pyrazole-3-carboxamide | 853.3 |
| 111 | 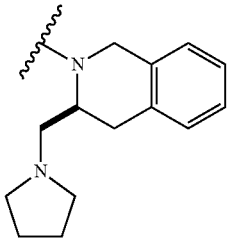 [SMILES: *N1Cc2ccccc2C[C@H]1CN1CCCC1] | N,N-dibutyl-4-chloro-5-methyl-1-(4-(naphthalen-2-ylsulfonylcarbamoyl)-2-((S)-3-(pyrrolidin-1-ylmethyl)-1,2,3,4-tetrahydroisoquinoline-2-carbonyl)phenyl)-1H-pyrazole-3-carboxamide | 823.2 |
| 112 | 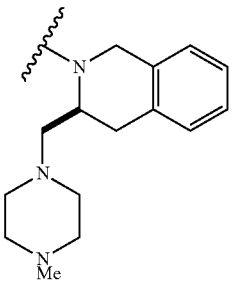 [SMILES: *N1Cc2ccccc2C[C@H]1CN1CCN(C)CC1] | N,N-dibutyl-4-chloro-5-methyl-1-(2-((S)-3-((4-methylpiperazin-1-yl)methyl)-1,2,3,4-tetrahydroisoquinoline-2-carbonyl)-4-(naphthalen-2-ylsulfonylcarbamoyl)phenyl)-1H-pyrazole-3-carboxamide | 852.3 |
| 113 | 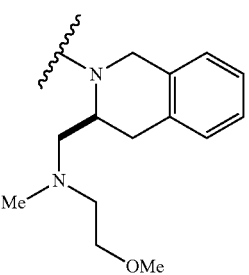 [SMILES: *N1Cc2ccccc2C[C@H]1CN(C)CCOC] | N,N-dibutyl-4-chloro-1-(2-((S)-3-(((2-methoxyethyl)(methyl)amino)-methyl)-1,2,3,4-tetrahydroisoquinoline-2-carbonyl)-4-(naphthalen-2-ylsulfonylcarbamoyl)phenyl)-5-methyl-1H-pyrazole-3-carboxamide | 841.2 |

-continued

| Ex. No. | R | Name | LCMS (M + H) |
|---|---|---|---|
| 114 | (tetrahydroisoquinoline with CH2-N(Me)-CH2CH2-OH substituent) | N,N-dibutyl-4-chloro-1-(2-((S)-3-(((2-hydroxyethyl)(methyl)amino)-methyl)-1,2,3,4-tetrahydroisoquinoline-2-carbonyl)-4-(naphthalen-2-ylsulfonylcarbamoyl)phenyl)-5-methyl-1H-pyrazole-3-carboxamide | 827.2 |
| 115 | (tetrahydroisoquinoline with CH2-piperazine-CH2CH2-OH substituent) | N,N-dibutyl-4-chloro-1-(2-((S)-3-((4-(2-hydroxyethyl)piperazin-1-yl)methyl)-1,2,3,4-tetrahydroisoquinoline-2-carbonyl)-4-(naphthalen-2-ylsulfonylcarbamoyl)phenyl)-5-methyl-1H-pyrazole-3-carboxamide | 882.3 |
| 116 | (tetrahydroisoquinoline with CH2-O-CH2CH2-NMe2 substituent) | N,N-dibutyl-4-chloro-1-(2-((S)-3-((2-(dimethylamino)ethoxy)methyl)-1,2,3,4-tetrahydroisoquinoline-2-carbonyl)-4-(naphthalen-2-ylsulfonylcarbamoyl)phenyl)-5-methyl-1H-pyrazole-3-carboxamide | 841.3 |
| 117 | (tetrahydroisoquinoline with CH2-O-CH2CH2-OBn substituent) | 1-(2-((S)-3-((2-(benzyloxy)ethoxy)methyl)-1,2,3,4-tetrahydroisoquinoline-2-carbonyl)-4-(naphthalen-2-ylsulfonylcarbamoyl)phenyl)-N,N-dibutyl-4-chloro-5-methyl-1H-pyrazole-3-carboxamide | 904.3 |
| 118 | (tetrahydroisoquinoline with CH2-N-methylpiperazine substituent) | N,N-dibutyl-4-chloro-5-methyl-1-(2-(3-((4-methylpiperazin-1-yl)methyl)-1,2,3,4-tetrahydroisoquinoline-2-carbonyl)-4-(naphthalen-2-ylsulfonylcarbamoyl)phenyl)-1H-pyrazole-3-carboxamide | 852.3 |

Example 119

N,N-Dibutyl-4-chloro-1-(2-((S)-3-((2-hydroxyethoxy)methyl)-1,2,3,4-tetrahydroisoquinoline-2-carbonyl)-4-(naphthalen-2-ylsulfonylcarbamoyl)phenyl)-5-methyl-1H-pyrazole-3-carboxamide (119)

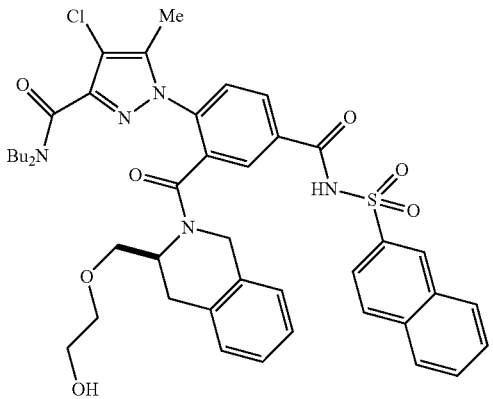

A solution of (S)-1-(2-(3-((2-(benzyloxy)ethoxy)methyl)-1,2,3,4-tetrahydroisoquinoline-2-carbonyl)-4-(naphthalen-2-ylsulfonylcarbamoyl)phenyl)-N,N-dibutyl-4-chloro-5-methyl-1H-pyrazole-3-carboxamide (Example 117, 35 mg, 0.039 mmol) in CH$_2$Cl$_2$ (1.0 mL) was cooled to −78° C., and boron trichloride (270 µL, 0.27 mmol) was added dropwise via syringe. The resulting solution was stirred at −78° C. for 1 h and then at room temperature overnight. Additional boron trichloride (270 µL, 0.27 mmol) was added, and the reaction mixture was stirred at room temperature for 5 h. After quenching with sat. aq. NH$_4$Cl, the solution was extracted with EtOAc (3×). The combined organic extracts were dried over Na$_2$SO$_4$, filtered and concentrated in vacuo. The crude residue was purified by preparative HPLC to give the title compound (10 mg, 31%). $^1$H NMR (1:1 CD$_3$OD:CDCl$_3$, mixture of amide rotamers) δ 8.65 (s, 1H), 8.40 (s, 0.5H), 8.19-8.11 (m, 1H), 8.09-7.83 (m, 4H), 7.63-7.52 (m, 2.5H), 7.47-7.30 (m, 1H), 7.26-6.98 (m, 3.5H), 6.88 (br s, 0.5H), 5.25 (d, J=18.3 Hz, 0.5H), 4.36-4.07 (m, 3H), 3.75-3.17 (m, 6.5H), 3.12-2.61 (m, 4H), 2.51 (d, J=16.4 Hz, 0.5H), 2.35-2.17 (m, 3.5H), 1.68-0.79 (m, 11.5H), 0.75-0.56 (m, 2.5H); MS(ESI$^+$) m/z 814.2 (M+H)$^+$.

Example 120

N,N-Dibutyl-4-chloro-1-(2-(3-(dimethylamino)-2,5-dihydro-1H-benzo[e][1,3]diazepine-2-carbonyl)-4-(naphthalen-2-ylsulfonylcarbamoyl)phenyl)-5-methyl-1H-pyrazole-3-carboxamide (120)

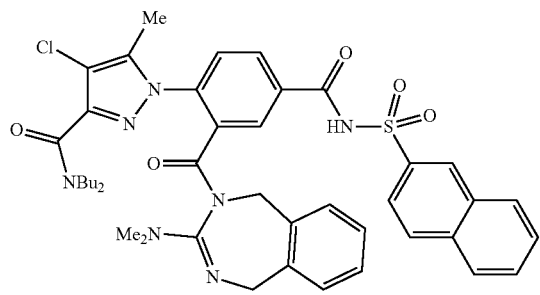

To a solution of 2-(4-chloro-3-(dibutylcarbamoyl)-5-methyl-1H-pyrazol-1-yl)-5-(naphthalen-2-ylsulfonylcarbamoyl)benzoic acid (Intermediate 91F, 36 mg, 0.058 mmol) in DCE (1.0 mL) was added 1-chloro-N,N-2-trimethylprop-1-en-1-amine (15 µL, 0.12 mmol). The resulting reaction mixture was stirred at room temperature for 1.5 h. A solution of N,N-dimethyl-2,5-dihydro-1H-benzo[e][1,3]diazepin-3-amine (Rodriguez, H. R. et al., *J. Org. Chem.*, 33:670-676 (1968)) (11 mg, 0.058 mmol) in THF (1.0 mL) was then added, followed by DMAP (7 mg, 0.058 mmol) and i-Pr$_2$EtN (50 µL, 0.29 mmol). The resulting reaction mixture was stirred at room temperature for 12 h, then concentrated in vacuo and purified by preparative HPLC to give the title compound (11 mg, 24%). $^1$H NMR (DMSO-d$_6$, mixture of amide rotamers) δ 10.31 (br s, 1H), 8.56 (br s, 1H), 8.32-7.87 (m, 7H), 7.77-7.57 (m, 2.5H), 7.33-7.05 (m, 3H), 6.98 (br s, 0.5H), 5.09-4.53 (m, 3H), 4.08 (br s, 2H), 3.86-2.85 (m, 9H), 2.14 (s, 3H), 1.71-1.41 (m, 3H), 1.36-1.07 (m, 3H), 0.99-0.80 (m, 4.5H), 0.54 (br s, 3.5H); MS(ESI$^+$) m/z 796.8 (M+H)$^+$.

Example 121

(Z)—N,N-Dibutyl-4-chloro-1-(2-(3-((2-methoxyethyl)(methyl)amino)-2,5-dihydro-1H-benzo[e][1,3]diazepine-2-carbonyl)-4-(naphthalen-2-ylsulfonylcarbamoyl)phenyl)-5-methyl-1H-pyrazole-3-carboxamide (121)

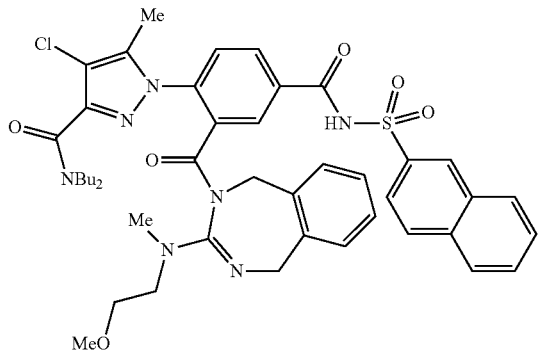

Intermediate 121A (E)-N-(2-Methoxyethyl)-N-methyl-2,5-dihydro-1H-benzo[e][1,3]diazepin-3-amine (Int-121A)

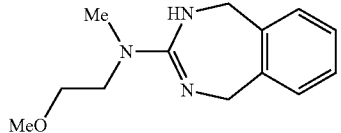

A mixture of 4,5-dihydro-1H-benzo[e][1,3]diazepin-3(2H)-one (Boyer, J. H. et al., *J. Chem. Soc., Perkin Trans. I*, 2137-2140 (1988)) (70 mg, 0.43 mmol) and POCl$_3$ (805 µL, 8.63 mmol) was heated at 106° C. for 2 h. The reaction mixture was then concentrated in vacuo, dissolved in CHCl$_3$ and azeotroped with PhMe. The residue was dissolved in THF (1.0 mL) and treated with 2-methoxy-N-methylethanamine (70 µl, 0.65 mmol). The resulting reaction mixture was stirred at room temperature overnight and then concentrated in vacuo. The residue was purified by preparative HPLC to give the title compound (29 mg, 28%). $^1$H NMR (CDCl$_3$) δ 7.38-7.31 (m, 2H), 7.31-7.21 (m, 2H), 5.95 (br s, 1H), 4.61 (d, J=4.6 Hz, 2H), 4.39 (d, J=4.6 Hz, 2H), 3.56-3.51 (m, 2H), 3.42 (s, 3H), 3.40-3.36 (m, 2H), 3.10 (s, 3H); MS(ESI$^+$) m/z 234.1 (M+H)$^+$.

Example 121

Following a procedure analogous to that for the synthesis of Example 91, 2-(4-chloro-3-(dibutylcarbamoyl)-5-methyl-1H-pyrazol-1-yl)-5-(naphthalen-2-ylsulfonylcarbamoyl)benzoic acid (Intermediate 91F, 30 mg, 0.048 mmol) and (E)-N-(2-methoxyethyl)-N-methyl-2,5-dihydro-1H-benzo[e][1,3]diazepin-3-amine (17 mg, 0.072 mmol) were converted to the title compound (18 mg, 44%). $^1$H NMR (DMSO, 1:1 mixture of amide rotamers) δ 8.55 (br s, 1H), 8.25-8.15 (m, 2H), 8.12-8.03 (m, 2H), 8.00-7.86 (m, 2H), 7.77-7.61 (m, 3H), 7.39-7.27 (m, 1H), 7.23-7.11 (m, 2H), 6.99 (br s, 1H), 5.48 (br s, 0.5H), 5.31 (br s, 0.5H), 5.05-4.81 (m, 2H), 4.72 (br s, 1H), 4.46 (br s, 1H), 4.14 (br s, 2H), 3.82 (br s, 1H), 3.70 (br s, 1H), 3.63-3.54 (m, 2H), 3.48 (br s, 1H), 3.24 (t, 7.5 Hz, 4H), 2.99 (br s, 1H), 2.16 (br s, 3H), 1.58-1.46 (m, 3H), 1.35-1.06 (m, 6H), 0.95-0.80 (m, 6H); MS(ESI$^+$) m/z 840.4 (M+H)$^+$.

Example 122

3-(4-(N-Butyl-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamido)phenyl)propanoic acid

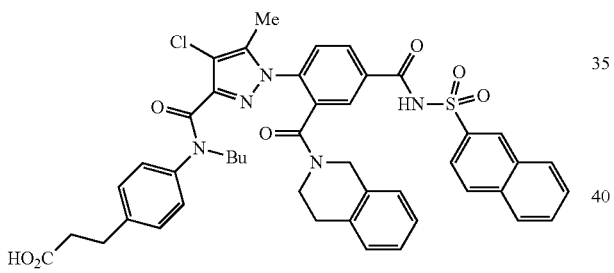

(122)

Intermediate 122A

Methyl 3-(4-(butylamino)phenyl)propanoate

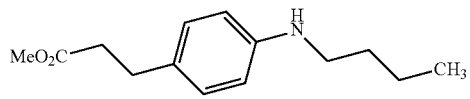

(Int-122A)

Following a procedure analogous to that for the synthesis Example 106, methyl 3-(4-aminophenyl)propanoate (Jakobsen, C. M. et al., *J. Med. Chem.*, 44:4696-4703 (2001)) (896 mg, 5.00 mmol) and butyraldehyde (397 mg, 5.50 mmol) were converted to the title compound (420 mg, 44%). $^1$H NMR (CDCl$_3$) δ 7.01 (d, J=8.4 Hz, 2H), 6.60-6.47 (m, 2H), 3.68 (s, 3H), 3.10 (t, J=7.2 Hz, 2H), 2.89-2.77 (m, 2H), 2.62-2.46 (m, 2H), 1.66-1.53 (m, 2H), 1.43 (qd, J=15.0, 7.3 Hz, 2H), 0.96 (t, J=7.3 Hz, 3H); MS (ESI$^+$) m/z 236.0 (M+H)$^+$.

Intermediate 122B

Benzyl 4-fluoro-3-(1,2,3,4-tetrahydroisoquinoline-2-carbonyl)benzoate

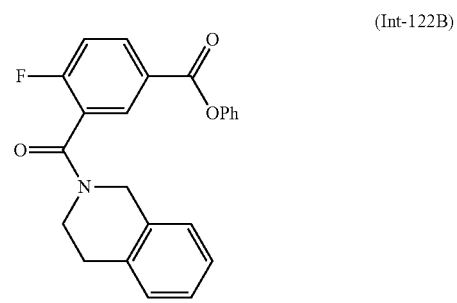 [SMILES: O=C(Oc1ccccc1)c1ccc(F)c(C(=O)N2CCc3ccccc3C2)c1]

(Int-122B)

Following a procedure analogous to that for the synthesis of Intermediate 1D, (3,4-dihydroisoquinolin-2(1H)-yl)(2-fluoro-5-iodophenyl)methanone (1.25 g, 3.28 mmol) and benzyl alcohol (410 µL, 3.94 mmol) were converted to the title compound (1.03 g, 81%). $^1$H NMR (CDCl$_3$, 2:1 mixture of amide rotamers) δ 8.23-8.11 (m, 3H), 7.52-7.34 (m, 4.5H), 7.30-7.11 (m, 4H), 6.91 (d, J=7.5 Hz, 0.5H), 4.94 (s, 1.5H), 4.72 (s, 0.5H), 4.48 (br s, 1H), 4.03 (br s, 0.5H), 3.56 (t, J=5.7 Hz, 1.5H), 3.00 (t, J=5.9 Hz, 1H), 2.87 (t, J=5.5 Hz, 2H); MS(ESI$^+$) m/z 390.2 (M+H)$^+$.

Intermediate 122C

Ethyl 1-(4-(benzyloxycarbonyl)-2-(1,2,3,4-tetrahydroisoquinoline-2-carbonyl)phenyl)-4-chloro-5-methyl-1H-pyrazole-3-carboxylate

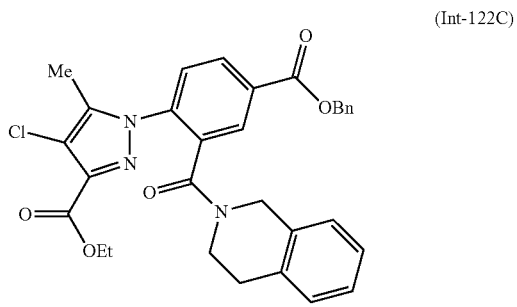 [SMILES: CCOC(=O)c1nn(-c2ccc(C(=O)OCc3ccccc3)cc2C(=O)N2CCc3ccccc3C2)c(C)c1Cl]

(Int-122C)

Following a procedure analogous to that for the synthesis of Intermediate 1E, ethyl 4-chloro-5-methyl-1H-pyrazole-3-carboxylate (Intermediate 1A, 509 mg, 2.70 mmol) and benzyl 4-fluoro-3-(1,2,3,4-tetrahydroisoquinoline-2-carbonyl)benzoate (1.00 g, 2.57 mmol) were converted to the title compound (690 mg, 48%). $^1$H NMR (CDCl$_3$, 1.5:1 mixture of amide rotamers) δ 8.35-8.28 (m, 1H), 8.18 (t, J=1.9 Hz, 1H), 7.76 (d, J=8.4 Hz, 0.5H), 7.70 (d, J=8.4 Hz, 0.5H), 7.50-7.45 (m, 2H), 7.43-7.31 (m, 3H), 7.23-7.07 (m, 3.5H), 6.90 (d, J=7.9 Hz, 0.5H), 5.42 (s, 2H), 4.76-4.54 (m, 1H), 4.47 (s, 1H), 4.16 (q, J=7.0 Hz, 2.5H), 3.64 (br s, 1.5H), 3.13-3.02

(m, 0.5H), 2.81 (t, J=6.1 Hz, 1H), 2.34 (s, 2H), 2.26 (s, 1H), 1.21 (t, J=7.0 Hz, 1H), 1.12 (t, J=7.2 Hz, 2H); MS(ESI⁺) m/z 558.4 (M+H)⁺.

Intermediate 122D 4-(4-Chloro-3-(ethoxycarbonyl)-5-methyl-1H-pyrazol-1-yl)-3-(1,2,3,4-tetrahydroisoquinoline-2-carbonyl)benzoic acid

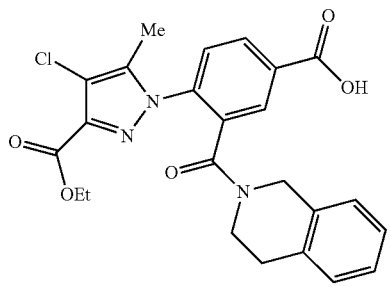

(Int-122D)

Following a procedure analogous to that for the synthesis of Intermediate 91D, ethyl 1-(4-(benzyloxycarbonyl)-2-(1,2,3,4-tetrahydroisoquinoline-2-carbonyl)phenyl)-4-chloro-5-methyl-1H-pyrazole-3-carboxylate (690 mg, 1.24 mmol) was converted to the title compound (500 mg, 86%). ¹H NMR (DMSO-d₆, 1.5:1 mixture of amide rotamers) δ 8.17 (dd, J=2.0, 8.4 Hz, 1H), 8.06 (s, 1H), 7.86 (d, J=8.1 Hz, 0.5H), 7.80 (d, J=8.1 Hz, 0.5H), 7.23-7.06 (m, 3.5H), 6.98 (d, J=6.8 Hz, 0.5H), 4.67-4.34 (m, 2H), 4.12 (q, J=7.1 Hz, 2H), 3.95 (br s, 0.5H), 3.53 (t, J=5.5 Hz, 1.5H), 3.01-2.61 (m, 2H), 2.26 (s, 2H), 2.21 (s, 1H), 1.11 (t, J=7.2 Hz, 1H), 1.07 (t, J=7.0 Hz, 2H); MS(ESI⁺) m/z 468.1 (M+H)⁺.

Intermediate 122E

Ethyl 4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxylate

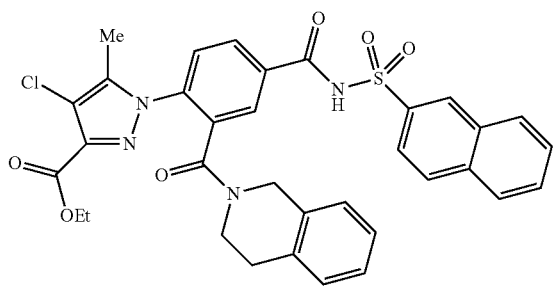

(Int-122E)

Following a procedure analogous to that for the synthesis of Example 1, 4-(4-chloro-3-(ethoxycarbonyl)-5-methyl-1H-pyrazol-1-yl)-3-(1,2,3,4-tetrahydroisoquinoline-2-carbonyl)benzoic acid (800 mg, 1.71 mmol) and naphthalene-2-sulfonamide (372 g, 1.80 mmol) were converted to the title compound (1.10 g, 93%) after purification using flash column chromatography (3% MeOH/CHCl₃ with 0.1% AcOH). ¹H NMR (DMSO-d₆, 2:1 mixture of amide rotamers) δ 8.57 (br s, 1H), 8.42 (d, J=1.3 Hz, 0.5H), 8.30 (s, 0.5H), 8.24-7.85 (m, 5H), 7.75-7.58 (m, 2.5H), 7.42 (s, 1.5H), 7.22-7.05 (m, 2.5H), 6.96 (d, J=7.3 Hz, 0.5H), 4.69-3.66 (m, 4H), 3.60-3.11 (m, 2H), 3.04-2.62 (m, 2H), 2.23-2.18 (m, 2H), 2.15 (s, 1H), 1.16-0.98 (m, 3H); MS(ESI⁺) m/z 657.2 (M+H)⁺.

Intermediate 122F

4-Chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxylic acid

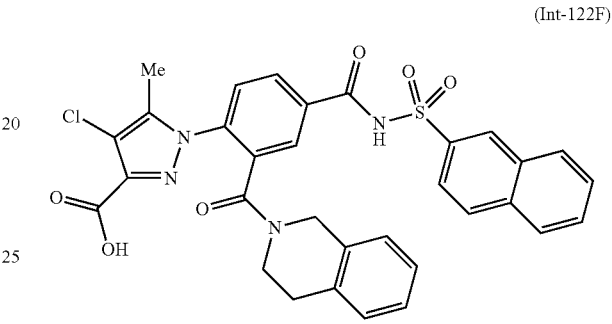

(Int-122F)

Following a procedure analogous to that for the synthesis of Example 45, ethyl 4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxylate (125 mg, 0.19 mmol) was converted to the title compound (120 g, 97%). ¹H NMR (DMSO-d₆, 2:1 mixture of amide rotamers) δ 8.70 (s, 1H), 8.24 (d, J=7.9 Hz, 1H), 8.16 (d, J=8.6 Hz, 1H), 8.11-8.04 (m, 3H), 8.02-7.95 (m, 1H), 7.84-7.64 (m, 3H), 7.22-7.04 (m, 3.5H), 6.95 (d, J=7.0 Hz, 0.5H), 4.82-4.18 (m, 2H), 3.96-3.56 (m, 2H), 3.05-2.64 (m, 2H), 2.21 (s, 2H), 2.16 (s, 1H); MS(ESI⁺) m/z 629.2 (M+H)⁺.

Intermediate 122G

Methyl 3-(4-(N-butyl-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamido)phenyl)propanoate

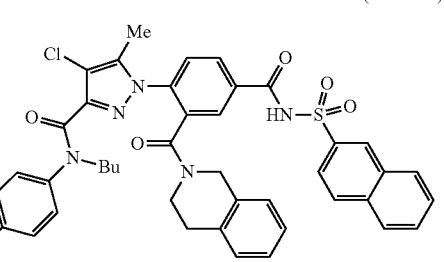

(Int-122G)

To a solution of 4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxylic acid (116 mg, 0.18 mmol) in CH₂Cl₂ (1.0 mL) was added oxalyl chloride (48 μL, 0.55 mmol) followed by 1 drop of DMF. The resulting reaction mixture was stirred at room temperature for 1 h and then concentrated in vacuo. The residue was dissolved in CH₂Cl₂ (1.0 mL), and methyl 3-(4-(butylamino)phenyl)propanoate (Intermediate 122A, 17 mg, 0.074 mmol) and i-Pr₂EtN (32 µL, 0.18 mmol) were added. The reaction mixture was stirred at room temperature for 2 h and then concentrated in vacuo. The crude oil was purified by preparative HPLC to give the title compound (30 mg, 57%). ¹H NMR (CD₃OD, 1:1 mixture of amide rotamers) δ 8.73 (s, 1H), 8.10 (d, J=9.0 Hz, 1H), 8.07-8.06 (m, 1H), 8.04-8.00 (m, 2H), 7.94-7.91 (m, 1H), 7.74-7.66 (m, 2H), 7.48 (br s, 1H), 7.39 (br s, 1H), 7.21-7.19 (m, 3.5H), 7.03 (br s, 1H), 6.98-6.96 (m, 0.5H), 6.90 (br s, 1H), 6.70 (d, J=8.6 Hz, 1H), 6.43 (br s, 1H), 4.73 (br s, 1H), 4.44 (br s, 1H), 4.26 (br s, 1H), 4.10 (br s, 1H), 3.90 (br s, 1H), 3.60-3.56 (m, 3H), 3.48 (br s, 2H), 2.94 (br s, 1H), 2.79-2.71 (m, 2H), 2.54-2.46 (m, 2H), 2.12 (s, 3H), 1.43-1.24 (m, 4H), 0.89-0.83 (m, 3H); MS (ESI⁺) m/z 847.0 (M+H)⁺.

Example 122

Following a procedure analogous to that for the synthesis Example 1F, ethyl 3-(4-(N-butyl-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamido)phenyl) propanoate (20 mg, 0.024 mmol) was converted to the title compound (12 mg, 64%). ¹H NMR (CD₃OD, 1:1 mixture of amide rotamers) δ 8.72 (s, 1H), 8.10 (d, J=8.4 Hz, 1.5H), 8.07-8.03 (m, 2H), 8.00 (d, J=7.9 Hz, 1.5H), 7.94-7.90 (m, 1H), 7.73-7.65 (m, 2H), 7.47 (br s, 0.5H), 7.36 (br s, 0.5H), 7.20-7.19 (m, 4H), 7.05 (br s, 1H), 6.96-6.91 (m, 1H), 6.85 (d, J=8.4 Hz, 1H), 6.55 (br s, 1H), 4.73 (br s, 0.5H), 4.45 (br s, 0.5H), 4.24 (br s, 0.5H), 4.09 (br s, 0.5H), 3.89 (br s, 0.5H), 3.64 (br s, 0.5H), 3.49 (br s, 2H), 3.08 (br s, 0.5H), 2.95 (br s, 0.5H), 2.82-2.71 (m, 2H), 2.51-2.43 (m, 2H), 2.11 (s, 3H), 1.41-1.23 (m, 4H), 0.89-0.83 (m, 3H); MS(ESI⁺) m/z 832.8 (M+H)⁺.

Example 123

N-Butyl-4-chloro-N-(4-iodophenyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide

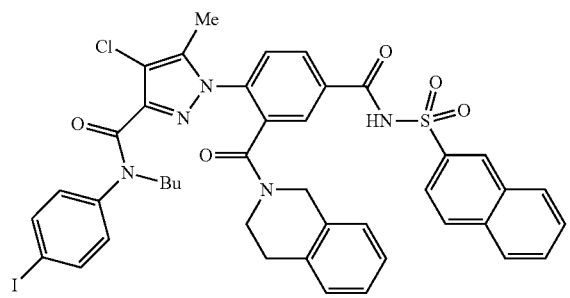

(123)

Following a procedure analogous to that for the synthesis Intermediate 122G, 4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxylic acid (Intermediate 122F, 116 mg, 0.18 mmol) and N-butyl-4-iodoaniline (Okano, K. et al., *Org. Lett.*, 5:4987-4990 (2003)) (59 mg, 0.22 mmol) were converted to the title compound (7 mg, 41%). ¹H NMR (MeOD, 1:1 mixture of amide rotamers) δ 8.65 (s, 1H), 8.15-8.07 (m, 1.5H), 8.05-8.00 (m, 3.5H), 7.95 (d, J=8.0 Hz, 1H), 7.69-7.54 (m, 3H), 7.45-7.31 (m, 2H), 7.20-7.17 (m, 4H), 7.03-7.00 (m, 0.5H), 6.97-6.96 (m, 0.5H), 6.70 (d, J=8.6 Hz, 1H), 6.43 (br s, 1H), 4.93 (br s, 0.5H), 4.68 (br s, 0.5H), 4.48 (br s, 0.5H), 4.35 (br s, 0.5H), 3.83 (br s, 1H), 3.71 (br s, 1H), 3.61-3.45 (m, 2H), 3.11-3.01 (m, 1H), 2.92-2.78 (m, 1H), 2.16 (s, 3H), 1.41-1.22 (m, 4H), 0.91-0.80 (m, 3H); MS(ESI⁺) m/z 886.8 (M+H)⁺.

Example 124

1-(3-(4-(N-Butyl-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamido)phenyl)propanoyl)piperidine-4-carboxylic acid

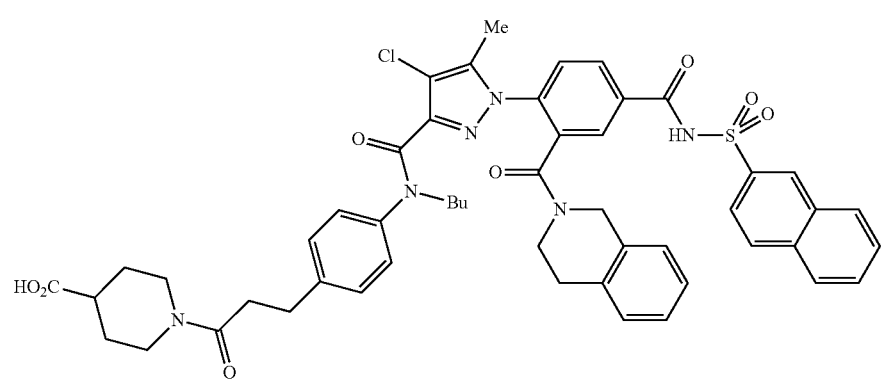

(124)

To a solution of 3-(4-(N-butyl-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamido)phenyl)propanoic acid (Example 122, 5 mg, 0.006 mmol) in DMF were added ethyl piperidine-4-carboxylate (2 mg, 0.012 mmol), HATU (5 mg, 0.012 mmol) and i-Pr$_2$EtN (3 µL, 0.018 mmol). The reaction mixture was stirred at room temperature for 1 h, then quenched with cold water and extracted with CH$_2$Cl$_2$ (3×). The combined organic extracts were dried over MgSO$_4$, filtered and concentrated in vacuo to give a crude oil which was used in the subsequent step without purification.

Following a procedure analogous to that for the synthesis Intermediate 1F, the crude oil from above was converted to the title compound (7 mg, 72%). $^1$H NMR (CD$_3$OD, 1:1 mixture of amide rotamers) δ 8.72 (s, 1H), 8.10 (d, J=8.4 Hz, 1H), 8.07-8.06 (m, 1H), 8.04-8.00 (m, 2H), 7.95-7.92 (m, 1H), 7.73-7.65 (m, 2H), 7.48 (br s, 1H), 7.39 (br s, 1H), 7.21-7.19 (m, 4H), 7.06 (br s, 1H), 6.98 (br s, 0.5H), 6.93 (br s, 0.5H), 6.86 (d, J=8.1 Hz, 1H), 6.54 (br s, 1H), 4.46 (br s, 1H), 4.29 (br s, 2H), 4.09 (br s, 1H), 3.89 (br s, 1H), 3.78 (br s, 1H), 3.64 (br s, 1H), 3.48 (br s, 2H), 3.24-3.19 (m, 1H), 3.05 (br s, 2H), 2.94 (br s, 1H), 2.85-2.70 (m, 4H), 2.61-2.51 (m, 2H), 2.12 (s, 3H), 1.90-1.82 (m, 2H), 1.51-1.21 (m, 6H), 0.89-0.83 (m, 3H); MS(ESI$^+$) m/z 944.2 (M+H)$^+$.

Example 125

4-Chloro-N-(3,4-dichlorobenzyl)-N,5-dimethyl-1-(4-(naphthalen-2-ylsulfonylcarbamoyl)-2-(1,2,3,4-tetrahydroisoquinoline-2-carbonyl)phenyl)-1H-pyrazole-3-carboxamide (125)

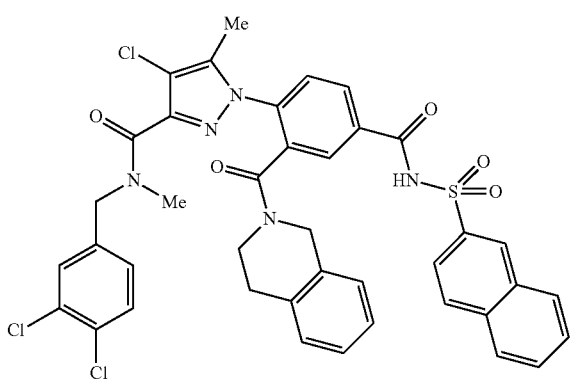

To a solution of 4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxylic acid (Intermediate 122F, 25 mg, 0.040 mmol) in CH$_2$Cl$_2$ (0.5 mL) was added 1-chloro-N,N-2-trimethylprop-1-en-1-amine (11 µL, 0.079 mmol) via syringe. The resulting reaction mixture was stirred at room temperature for 30 min. 1-(3,4-Dichlorophenyl)-N-methylmethanamine (Maybridge, 8 mg, 0.044 mmol) and THF (0.5 mL) were added followed by i-Pr$_2$EtN (14 µL, 0.079 mmol). The reaction mixture was stirred at room temperature for 10 min, then concentrated in vacuo and purified by preparative HPLC to give the title compound (6 mg, 19%). $^1$H NMR (1:1 CD$_3$OD:CDCl$_3$, 2:1 mixture of amide rotamers) δ 8.58 (s, 1H), 8.12 (s, 1H), 8.03 (d, J=8.6 Hz, 1H), 7.98-7.94 (m, 1.5H), 7.91-7.83 (m, 2H), 7.59-7.48 (m, 2H), 7.43-7.23 (m, 3H), 7.21-6.95 (m, 4.5H), 6.90-6.75 (m, 1H), 4.50 (d, J=11.7 Hz, 2.5H), 4.30-4.10 (m, 1H), 3.82 (br s, 1H), 3.63-3.43 (m, 1.5H), 2.84-2.67 (m, 3.5H), 2.60 (s, 1H), 2.57 (s, 0.5H), 2.28-2.22 (m, 2.5H), 2.20 (s, 0.5H); MS(ESI$^+$) m/z 802.0 (M+H)$^+$.

Intermediate 126

N-(3,4-Dichlorobenzyl)butan-1-amine

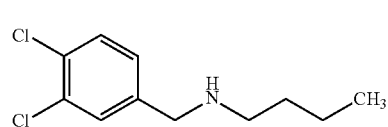

(Int-126)

Following a procedure analogous to that for the synthesis of Example 106, 3,4-dichlorobenzaldehyde (10.0 g, 57.1 mmol) and butan-1-amine (4.18 g, 57.1 mmol) were converted to the title compound (7.09 g, 53%). $^1$H NMR (CDCl$_3$) δ 7.45 (d, J=2.0 Hz, 1H), 7.40 (d, J=8.1 Hz, 1H), 7.19 (dd, J=2.0, 8.1 Hz, 1H), 3.79 (s, 2H), 2.68-2.59 (m, 2H), 1.59-1.45 (m, 2H), 1.36 (qd, J=7.3, 15.0 Hz, 2H), 0.92 (t, J=7.4 Hz, 3H); MS (ESI$^+$) m/z 232.1 (M+H)$^+$.

Intermediate 127

N-(3,4-Dichlorophenethyl)butan-1-amine

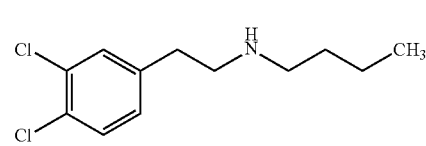

(Int-127)

Following a procedure analogous to that for the synthesis of Example 106, 2-(3,4-dichlorophenyl)ethanamine (1.27 g, 6.68 mmol) and butyraldehyde (600 µL, 6.68 mmol) were converted to the title compound (390 mg, 24%). $^1$H NMR (CDCl$_3$) δ 7.37 (d, J=8.1 Hz, 1H), 7.32 (d, J=2.0 Hz, 1H), 7.06 (dd, J=2.1, 8.3 Hz, 1H), 2.97-2.90 (m, 2H), 2.88-2.81 (m, 2H), 2.75-2.66 (m, 2H), 1.53 (quin, J=7.5 Hz, 2H), 1.34 (qd, J=7.4, 15.0 Hz, 2H), 0.92 (t, J=7.3 Hz, 3H); MS(ESI$^+$) m/z 246.1 (M+H)$^+$.

Intermediate 128

N-Butyl-4,4,4-trifluorobutan-1-amine

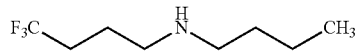

(Int-128)

Following a procedure analogous to that for the synthesis of Example 106, butan-1-amine (293 mg, 4.00 mmol) and 4,4,4-trifluorobutanal (504 mg, 4.00 mmol) were converted to a crude oil which was used without purification. MS(ESI⁺) m/z 184.1 (M+H)⁺.

Intermediate 129

Bis(4,4,4-trifluorobutyl)amine

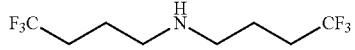

(Int-129)

Following a procedure analogous to that for the synthesis of Example 106, 4,4,4-trifluorobutan-1-amine, HCl (598 mg, 4.00 mmol), Et₃N (550 µL, 4.00 mmol) and 4,4,4-trifluorobutanal (504 mg, 4.00 mmol) provided a colorless oil which was used directly in the preparation of Example 129. MS(ESI⁺) m/z 192.1 (M+H)⁺.

Intermediate 130

Bis(3,3,3-trifluoropropyl)amine

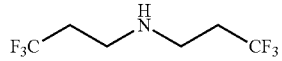

(Int-130)

The title compound was prepared as previously described: PCT International Application No. WO 2008/156614.

Intermediate 131

N-(3-Isopropoxybenzyl)butan-1-amine

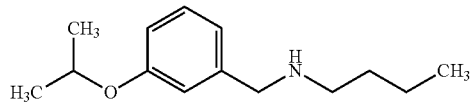

(Int-131)

Following a procedure analogous to that for the synthesis of Example 106, (3-isopropoxyphenyl)methanamine (Matrix, 200 mg, 1.21 mmol) and butyraldehyde (110 µL, 1.21 mmol) were converted to the title compound (43 mg, 16%). ¹H NMR (CDCl₃) δ 7.29-7.17 (m, 1H), 6.99-6.74 (m, 3H), 4.57 (td, J=6.1, 12.1 Hz, 1H), 3.80 (s, 2H), 2.65 (t, J=7.3 Hz, 2H), 1.63-1.50 (m, 2H), 1.40-1.24 (m, 8H), 0.90 (t, J=7.3 Hz, 3H); MS (ESI⁺) m/z 222.2 (M+H)⁺.

Intermediate 132

N-(3-(4-Chlorophenoxy)benzyl)butan-1-amine

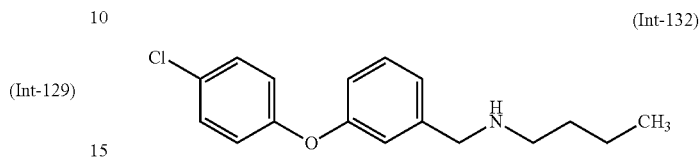

(Int-132)

Following a procedure analogous to that for the synthesis of Example 106, (3-(4-chlorophenoxy)phenyl)methanamine (ASDI, 533 mg, 2.28 mmol) and butyraldehyde (210 µL, 2.28 mmol) were converted to the title compound (211 mg, 32%). ¹H NMR (CDCl₃) δ 7.41-7.19 (m, 4H), 7.14-7.06 (m, 1H), 6.99-6.87 (m, 3H), 3.98-3.86 (m, 2H), 2.80-2.66 (m, 2H), 1.66 (quin, J=7.5 Hz, 2H), 1.42-1.24 (m, 2H), 1.00-0.81 (m, 3H); MS (ESI⁺) m/z 290.1 (M+H)⁺.

Intermediate 133

N-(4-Butoxybenzyl)butan-1-amine

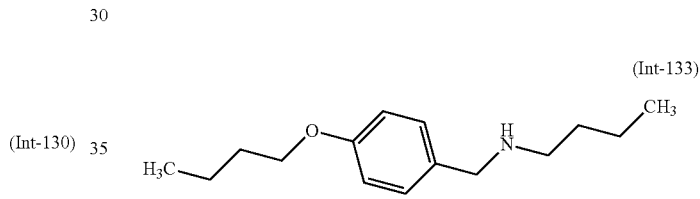

(Int-133)

Following a procedure analogous to that for the synthesis of Example 106, (4-butoxyphenyl)methanamine, HCl (500 mg, 2.79 mmol), i-Pr₂EtN (490 µL, 2.79 mmol) and butyraldehyde (250 µL, 2.79 mmol) were converted to the title compound (466 mg, 71%). ¹H NMR (CDCl₃) δ 7.47 (d, J=8.4 Hz, 2H), 6.89 (d, J=8.6 Hz, 2H), 3.95 (s, 2H), 3.89 (t, J=6.6 Hz, 2H), 2.79-2.70 (m, 2H), 1.85-1.65 (m, 4H), 1.50-1.40 (m, 2H), 1.37-1.27 (m, 2H), 0.96 (t, J=7.4 Hz, 3H), 0.89 (t, J=7.3 Hz, 3H); MS(ESI⁺) m/z 236.2 (M+H)⁺.

Intermediate 134

N-Butyl-3,4-dichloroaniline

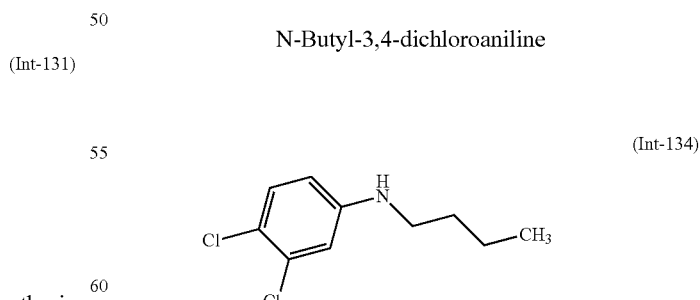

(Int-134)

Following a procedure analogous to that for the synthesis of Example 106, 3,4-dichloroaniline (1.62 g, 10.0 mmol) and butyraldehyde (721 mg, 10.0 mmol) were converted to the title compound (1.24 g, 57%). ¹H NMR (CDCl₃) δ 7.17 (d, J=8.8 Hz, 1H), 6.65 (d, J=2.9 Hz, 1H), 6.41 (dd, J=2.8, 8.7 Hz, 1H), 3.05 (t, J=7.0 Hz, 2H), 1.65-1.53 (m, 2H), 1.43 (qd, J=7.3, 15.0 Hz, 2H), 0.98 (t, J=7.4 Hz, 3H); MS(ESI⁺) m/z 218.1 (M+H)⁺.

Intermediate 135

N-(3-Chlorobenzyl)butan-1-amine

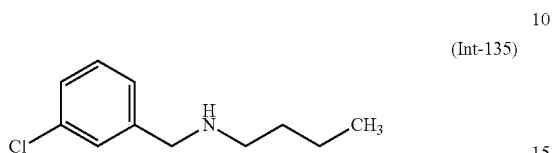
(Int-135)

Following a procedure analogous to that for the synthesis of Example 106, (3-chlorophenyl)methanamine (750 mg, 5.30 mmol) and butyraldehyde (480 µL, 5.30 mmol) were converted to the title compound (331 mg, 32%). ¹H NMR (CDCl₃) δ 7.64-7.55 (m, 2H), 7.44-7.33 (m, 2H), 4.02 (s, 2H), 2.84-2.72 (m, 2H), 1.84 (td, J=7.8, 15.8 Hz, 2H), 1.38 (sxt, J=7.5 Hz, 2H), 0.91 (t, J=7.4 Hz, 3H); MS(ESI⁺) m/z 198.1 (M+H)⁺.

Intermediate 136

N-(4-Chlorobenzyl)butan-1-amine

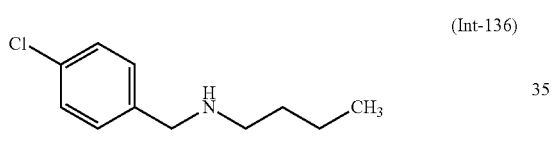
(Int-136)

Following a procedure analogous to that for the synthesis of Example 106, (4-chlorophenyl)methanamine (750 mg, 5.30 mmol) and butyraldehyde (480 µL, 5.30 mmol) were converted to the title compound (421 mg, 40%). ¹H NMR (CDCl₃) δ 7.55 (d, J=8.4 Hz, 2H), 7.41-7.34 (m, 2H), 3.98 (s, 2H), 2.78-2.70 (m, 2H), 1.79 (td, J=7.7, 15.6 Hz, 2H), 1.36 (qd, J=7.4, 15.1 Hz, 2H), 0.95-0.88 (m, 4H); MS(ESI⁺) m/z 198.1 (M+H)⁺.

Intermediate 137

N-Butyl-4-(4-fluorophenoxy)aniline

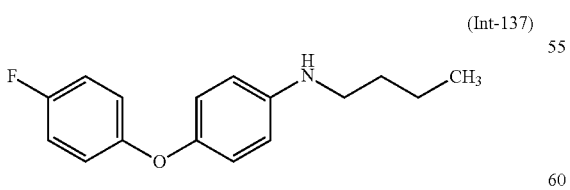
(Int-137)

To a solution of 4-(4-fluorophenoxy)aniline (Apollo, 500 mg, 2.46 mmol) and butyraldehyde (240 µL, 2.71 mmol) in DCE (5.0 mL) were added 4 Å molecular sieves. The resulting reaction mixture was stirred at room temperature for 1 h. Next, Na(OAc)₃BH (782 mg, 3.69 mmol) was added, and the reaction mixture was stirred at room temperature overnight. Concentration in vacuo afforded a crude residue which was purified by flash column chromatography (10% EtOAc/hexanes) to give the title compound (400 mg, 62%). ¹H NMR (CDCl₃) δ 7.28-7.21 (m, 2H), 7.20-7.13 (m, 4H), 6.91-6.85 (m, 2H), 3.82 (br s, 1H), 3.39 (t, J=7.0 Hz, 2H), 1.96-1.85 (m, 2H), 1.79-1.67 (m, 2H), 1.26 (t, J=7.4 Hz, 3H); MS(ESI⁺) m/z 260.1 (M+H)⁺.

Intermediate 138

N-Butyl-4-(4-chlorophenoxy)aniline

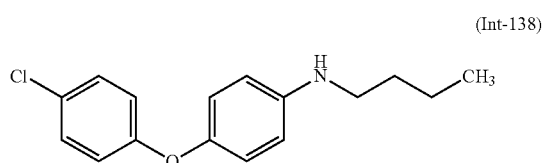
(Int-138)

Following a procedure analogous to that for the synthesis of Intermediate 137, 4-(4-chlorophenoxy)aniline (Aldrich, 500 mg, 2.28 mmol) and butyraldehyde (230 mL, 2.50 mmol) were converted to the title compound (450 mg, 71%). ¹H NMR (CDCl₃) δ 7.34-7.16 (m, 2H), 6.99-6.84 (m, 4H), 6.72-6.62 (m, 2H), 4.19 (br s, 1H), 3.17 (t, J=7.2 Hz, 2H), 1.75-1.61 (m, 2H), 1.60-1.42 (m, 2H), 1.03 (t, J=7.4 Hz, 3H); MS(ESI⁺) m/z 275.8 (M+H)⁺.

Intermediate 139

N-((1-Methyl-1H-indol-2-yl)methyl)butan-1-amine

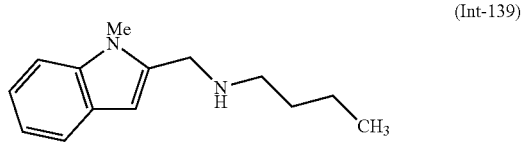 [SMILES: CCCCNCc1cc2ccccc2n1C]
(Int-139)

Following a procedure analogous to that for the synthesis of Intermediate 137, (1-methyl-1H-indol-2-yl)methanamine (500 mg, 3.12 mmol) and butyraldehyde (310 µL, 3.43 mmol) were converted to the title compound (70 mg, 6%). ¹H NMR (CDCl₃) δ 7.62-7.54 (m, 1H), 7.36-7.27 (m, 1H), 7.27-7.16 (m, 1H), 7.17-7.03 (m, 1H), 6.50 (s, 1H), 4.05 (s, 2H), 3.77 (s, 3H), 2.82-2.70 (m, 2H), 1.60 (ddd, J=15.1, 7.5, 7.4 Hz, 2H), 1.45-1.16 (m, 2H), 0.96-0.87 (m, 3H).

Intermediate 140

N-Butyl-3,4-dimethoxyaniline

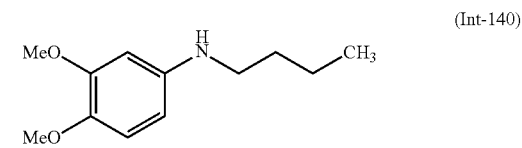
(Int-140)

Following a procedure analogous to that for the synthesis of Intermediate 137, 3,4-dimethoxyaniline (500 mg, 3.26 mmol) and butyraldehyde (290 μL, 3.26 mmol) were converted to the title compound (600 mg, 83%). $^1$H NMR (CDCl$_3$) δ 6.81-6.70 (m, 1H), 6.27-6.21 (m, 1H), 6.16 (dd, J=8.5, 2.5 Hz, 1H), 3.85 (s, 3H), 3.81 (s, 3H), 3.08 (t, J=7.0 Hz, 2H), 1.56-1.40 (m, 4H), 0.99-0.93 (m, 3H); MS(ESI$^+$) m/z 210.2 (M+H)$^+$.

Intermediate 141

N-Butyl-4-isopropoxyaniline

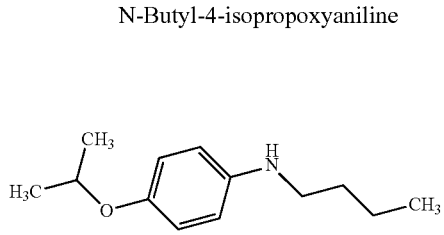

Following a procedure analogous to that for the synthesis of Intermediate 137, 4-isopropoxyaniline (500 mg, 3.31 mmol) and butyraldehyde (300 μL, 3.31 mmol) were converted to the title compound (600 mg, 83%). $^1$H NMR (CDCl$_3$) δ 6.88-6.74 (m, 2H), 6.67-6.51 (m, 2H), 4.41-4.30 (m, 1H), 3.08 (t, J=7.0 Hz, 2H), 1.66-1.37 (m, 4H), 1.30 (s, 3H), 1.29 (s, 3H), 0.99-0.87 (m, 3H); MS(ESI$^+$) m/z 208.2 (M+H)$^+$.

Intermediate 142

N-Butyl-3-chloro-4-methylaniline

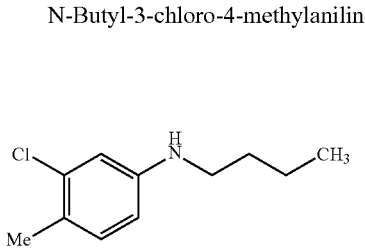

Following a procedure analogous to that for the synthesis of Intermediate 137, 3-chloro-p-toluidine (Aldrich, 430 μL, 3.53 mmol) and butyraldehyde (320 μL, 3.13 mmol) were converted to the title compound (600 mg, 79%). $^1$H NMR (CDCl$_3$) δ 7.06-6.93 (m, 1H), 6.62 (d, J=2.4 Hz, 1H), 6.43 (dd, J=8.1, 2.4 Hz, 1H), 3.56 (br s, 1H), 3.08 (t, J=7.2 Hz, 2H), 2.26 (s, 3H), 1.66-1.50 (m, 2H), 1.49-1.33 (m, 2H), 1.00-0.89 (m, 3H).

Intermediate 143

N-Butylbiphenyl-4-amine

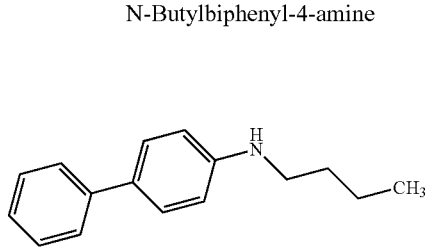

Following a procedure analogous to that for the synthesis of Intermediate 137, 4-aminodiphenyl (500 mg, 2.95 mmol) and butyraldehyde (280 μL, 3.10 mmol) were converted to the title compound (610 mg, 84%). $^1$H NMR (CDCl$_3$) δ 7.62-7.53 (m, 2H), 7.52-7.35 (m, 4H), 7.35-7.16 (m, 1H), 6.75-6.60 (m, 2H), 3.71 (br s, 1H), 3.17 (t, J=7.0 Hz, 2H), 1.68-1.57 (m, 2H), 1.52-1.39 (m, 2H), 1.00 (t, J=7.4 Hz, 3H).

Intermediate 144

N-Butyl-4-methoxyaniline

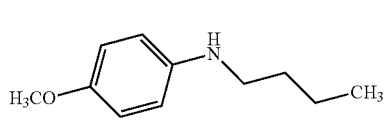

Following a procedure analogous to that for the synthesis of Intermediate 137, 4-methoxyaniline (500 mg, 4.06 mmol) and butyraldehyde (360 μL, 4.06 mmol) were converted to the title compound (700 mg, 88%). $^1$H NMR (CDCl$_3$) δ 6.89-6.73 (m, 2H), 6.69-6.50 (m, 2H), 3.76 (s, 3H), 3.10 (t, J=7.2 Hz, 2H), 1.70-1.28 (m, 4H), 1.02-0.90 (m, 3H); MS(ESI$^+$) m/z 180.1 (M+H)$^+$.

Intermediate 145

N-Butyl-3-methoxyaniline

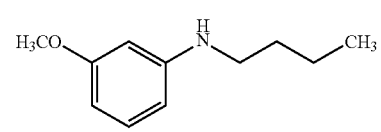

Following a procedure analogous to that for the synthesis of Intermediate 137, 3-methoxyaniline (460 μl, 4.06 mmol) and butyraldehyde (360 μL, 4.06 mmol) were converted to the title compound (700 mg, 88%). $^1$H NMR (CDCl$_3$) δ 7.36-7.20 (m, 1H), 6.56-6.32 (m, 3H), 4.02-3.95 (m, 3H), 3.87 (br s, 1H), 3.30 (t, J=7.0 Hz, 2H), 1.86-1.71 (m, 2H), 1.71-1.58 (m, 2H), 1.19-1.10 (m, 3H); MS(ESI$^+$) m/z 179.9 (M+H)$^+$.

Intermediate 146

3-tert-Butyl-N-butylaniline

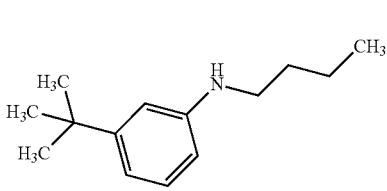

Following a procedure analogous to that for the synthesis of Intermediate 137, 3-tert-butylaniline (500 mg, 3.35 mmol) and butyraldehyde (300 μL, 3.35 mmol) were converted to the title compound (600 mg, 80%). $^1$H NMR (CDCl$_3$) δ 7.15 (t, J=7.8 Hz, 1H), 6.79-6.74 (m, 1H), 6.66 (t, J=2.1 Hz, 1H), 6.47

(ddd, J=8.0, 2.3, 0.7 Hz, 1H), 3.61 (br s, 1H), 3.14 (t, J=7.0 Hz, 2H), 1.69-1.55 (m, 2H), 1.53-1.42 (m, 2H), 1.32 (s, 9H), 0.99 (t, J=7.3 Hz, 3H).

Intermediate 147

N-Butylbiphenyl-3-amine

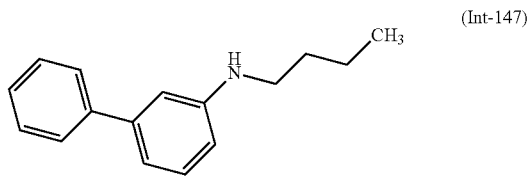 [SMILES: CCCCNc1cccc(-c2ccccc2)c1]
(Int-147)

Following a procedure analogous to that for the synthesis of Intermediate 137, biphenyl-3-amine (500 mg, 2.95 mmol) and butyraldehyde (265 µL, 2.95 mmol) were converted to the title compound (600 mg, 83%). $^1$H NMR (CDCl$_3$) δ 7.65-7.57 (m, 2H), 7.55-7.41 (m, 2H), 7.40-7.32 (m, 1H), 7.31-7.23 (m, 1H), 6.99-6.90 (m, 1H), 6.85 (t, J=2.0 Hz, 1H), 6.64 (ddd, J=8.0, 2.4, 0.9 Hz, 1H), 3.78 (br s, 1H), 3.21 (t, J=7.2 Hz, 2H), 1.75-1.59 (m, 2H), 1.54-1.44 (m, 2H), 1.01 (t, J=7.4 Hz, 3H); MS(ESI$^+$) m/z 226.1 (M+H)$^+$.

Intermediate 148

4-tert-Butyl-N-butylaniline

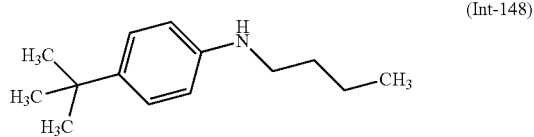
(Int-148)

Following a procedure analogous to that for the synthesis of Intermediate 137, 4-tert-butylaniline (400 mg, 2.68 mmol) and butyraldehyde (240 µL, 2.68 mmol) were converted to the title compound (500 mg, 84%). $^1$H NMR (CDCl$_3$) δ 7.27-7.19 (m, 2H), 6.60 (d, J=8.8 Hz, 2H), 3.61 (br s, 1H), 3.13 (t, J=7.0 Hz, 2H), 1.68-1.53 (m, 2H), 1.50-1.40 (m, 2H), 1.32 (s, 9H), 0.99 (t, J=7.3 Hz, 3H); MS(ESI$^+$) m/z 206.1 (M+H)$^+$.

Intermediate 149

N-Butyl-2,3-dihydrobenzo[b][1,4]dioxin-6-amine

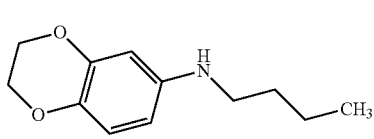
(Int-149)

Following a procedure analogous to that for the synthesis of Intermediate 137, 1,4-benzodioxan-6-amine (410 µL, 3.31 mmol) and butyraldehyde (300 µL, 3.31 mmol) were converted to the title compound (620 mg, 83%). $^1$H NMR (CDCl$_3$) δ 6.77-6.58 (m, 1H), 6.28-5.96 (m, 2H), 4.30-4.12 (m, 4H), 3.04 (t, J=7.2 Hz, 2H), 1.65-1.49 (m, 2H), 1.49-1.37 (m, 2H), 0.95 (t, J=7.4 Hz, 3H); MS(ESI$^+$) m/z 208.3 (M+H)$^+$.

Intermediate 150

N-Butyl-3-isopropoxyaniline

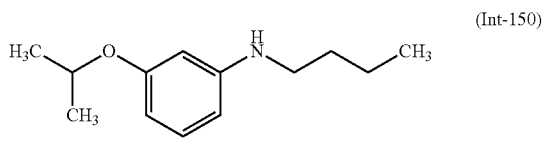
(Int-150)

Following a procedure analogous to that for the synthesis of Intermediate 137, 3-isopropoxyaniline (485 µL, 3.31 mmol) and butyraldehyde (310 µL, 3.47 mmol) were converted to the title compound (610 mg, 84%). $^1$H NMR (CDCl$_3$) δ 7.15-6.96 (m, 1H), 6.37-6.01 (m, 2H), 4.60-4.39 (m, 1H), 3.75 (br s, 1H), 3.10 (t, J=7.0 Hz, 2H), 1.68-1.52 (m, 2H), 1.50-1.38 (m, 2H), 1.34 (s, 3H), 1.33 (s, 3H), 0.97 (t, J=7.4 Hz, 3H).

Intermediate 151

N-(Naphthalen-2-ylmethyl)butan-1-amine

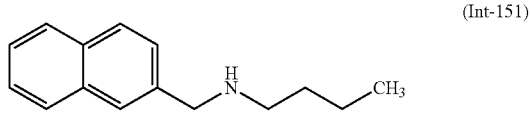 [SMILES: CCCCNCc1ccc2ccccc2c1]
(Int-151)

Following a procedure analogous to that for the synthesis of Intermediate 137, 2-naphthalenemethanamine (500 mg, 3.18 mmol) and butyraldehyde (315 µL, 3.50 mmol) were converted to the title compound (100 mg, 15%). $^1$H NMR (CDCl$_3$) δ 7.87-7.78 (m, 4H), 7.78-7.69 (br s, 1H), 7.56 (dd, J=8.4, 1.5 Hz, 1H), 7.52-7.43 (m, 2H), 4.06 (s, 2H), 2.78-2.69 (m, 2H), 1.65 (dt, J=15.4, 7.6 Hz, 2H), 1.38-1.23 (m, 2H), 0.88 (t, J=7.4 Hz, 3H); MS(ESI$^+$) m/z 214.1 (M+H)$^+$.

Intermediate 152

N-Butyl-3'-chlorobiphenyl-3-amine

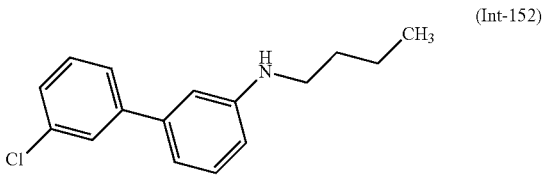 [SMILES: CCCCNc1cccc(-c2cccc(Cl)c2)c1]
(Int-152)

Following a procedure analogous to that for the synthesis of Intermediate 137, 3'-chlorobiphenyl-3-amine (Oakwood, 15 mg, 0.074 mmol) and butyraldehyde (7 µL, 0.074 mmol)

were converted to a crude oil which was used without purification in the preparation of Example 143. $^1$H NMR (CDCl$_3$) δ 8.17 (d, J=0.9 Hz, 1H), 7.86-7.42 (m, 3H), 7.41-7.07 (m, 3H), 6.78-6.57 (m, 1H), 3.00-2.87 (m, 2H), 1.63-1.46 (m, 2H), 1.47-1.34 (m, 2H), 1.02 (t, J=7.4 Hz, 3H); MS(ESI$^+$) m/z 260.2 (M+H)$^+$.

Intermediate 153

N-Butyl-4'-chlorobiphenyl-3-amine

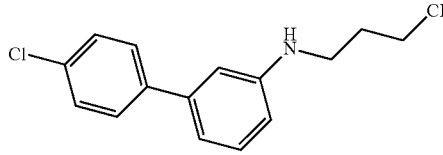
(Int-153)

Following a procedure analogous to that for the synthesis of Intermediate 137, 4'-chlorobiphenyl-3-amine (ChemBridge, 285 mg, 1.40 mmol) and butyraldehyde (125 μL, 1.40 mmol) were converted to the title compound (300 mg, 74%). $^1$H NMR (CDCl$_3$) δ 7.73-7.62 (m, 2H), 7.57-7.44 (m, 3H), 7.43-7.34 (m, 2H), 7.29-7.19 (m, 1H), 3.04-2.96 (m, 2H), 1.67-1.59 (m, 2H), 1.47 (dd, J=15.1, 7.4 Hz, 2H), 0.99 (t, J=7.3 Hz, 3H); MS (ESI$^+$) m/z 260.2 (M+H)$^+$.

Intermediate 154

Methyl 4-(butylamino)benzoate

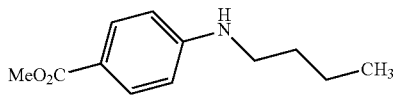
(Int-154)

Following a procedure analogous to that for the synthesis of Intermediate 137, 4-aminobenzoic acid methyl ester (Aldrich, 500 mg, 3.31 mmol) and butyraldehyde (300 μL, 3.31 mmol) were converted to the title compound (600 mg, 82%). $^1$H NMR (CDCl$_3$) δ 7.91-7.80 (m, 2H), 6.59-6.46 (m, 2H), 3.86 (s, 3H), 3.18 (t, J=7.0 Hz, 2H), 1.67-1.58 (m, 2H), 1.48-1.37 (m, 2H), 0.98 (t, J=7.4 Hz, 3H); MS(ESI$^+$) m/z 208.1 (M+H)$^+$.

Intermediate 155

Ethyl 2-(4-(butylamino)phenyl)acetate

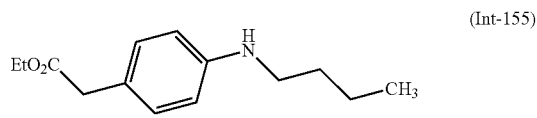 [SMILES: CCCCNc1ccc(CC(=O)OCC)cc1]
(Int-155)

Following a procedure analogous to that for the synthesis of Intermediate 137, ethyl 2-(4-aminophenyl)acetate (500 mg, 2.79 mmol) and butyraldehyde (250 μL, 2.79 mmol) were converted to the title compound (600 mg, 87%). $^1$H NMR (CDCl$_3$) δ 7.12-7.04 (m, 2H), 6.60-6.52 (m, 2H), 4.14 (q, J=7.0 Hz, 2H), 3.49 (s, 2H), 3.11 (t, J=7.0 Hz, 2H), 1.66-1.50 (m, 2H), 1.50-1.36 (m, 2H), 1.25 (t, J=7.0 Hz, 3H), 0.96 (t, J=7.3 Hz, 3H); MS(ESI$^+$) m/z 236.3 (M+H)$^+$.

Examples 126 to 155

The following Examples were prepared using 4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxylic acid (Intermediate 122F) and the amine intermediates described above according to the procedure for the synthesis of Example 125.

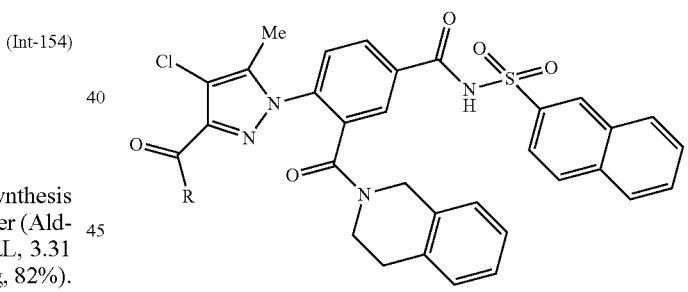

| Ex. No. | R | Name | LCMS (M + H) |
|---|---|---|---|
| 126 |  | N-butyl-4-chloro-N-(3,4-dichlorobenzyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide | 844.0 |

-continued

| Ex. No. | R | Name | LCMS (M + H) |
|---|---|---|---|
| 127 | (CH₂CH₂-3,4-dichlorophenyl)(Bu)N- | N-butyl-4-chloro-N-(3,4-dichlorophenethyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide | 858.1 |
| 128 | (CH₂CH₂CH₂CF₃)(Bu)N- | N-butyl-4-chloro-5-methyl-1-(4-(naphthalen-2-ylsulfonylcarbamoyl)-2-(1,2,3,4-tetrahydroisoquinoline-2-carbonyl)phenyl)-N-(4,4,4-trifluorobutyl)-1H-pyrazole-3-carboxamide | 794.1 |
| 129 | N(CH₂CH₂CH₂CF₃)₂- | 4-chloro-5-methyl-1-(4-(naphthalen-2-ylsulfonylcarbamoyl)-2-(1,2,3,4-tetrahydroisoquinoline-2-carbonyl)phenyl)-N,N-bis(4,4,4-trifluorobutyl)-1H-pyrazole-3-carboxamide | 834.1 |
| 130 | N(CH₂CH₂CF₃)₂- | 4-chloro-5-methyl-1-(4-(naphthalen-2-ylsulfonylcarbamoyl)-2-(1,2,3,4-tetrahydroisoquinoline-2-carbonyl)phenyl)-N,N-bis(3,3,3-trifluoropropyl)-1H-pyrazole-3-carboxamide | 820.1 |
| 131 | (3-iPrO-benzyl)(Bu)N- | N-butyl-4-chloro-N-(3-isopropoxybenzyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide | 832.2 |
| 132 | (3-(4-chlorophenoxy)benzyl)(Bu)N- | N-butyl-4-chloro-N-(3-(4-chlorophenoxy)benzyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide | 900.2 |

-continued

| Ex. No. | R | Name | LCMS (M + H) |
|---|---|---|---|
| 133 | (4-butoxybenzyl)(butyl)N– | N-(4-butoxybenzyl)-N-butyl-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide | 846.2 |
| 134 | (3,4-dichlorophenyl)(butyl)N– | N-butyl-4-chloro-N-(3,4-dichlorophenyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide | 828.2 |
| 135 | (3-chlorobenzyl)(butyl)N– | N-butyl-4-chloro-N-(3-chlorobenzyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide | 808.1 |
| 136 | (4-chlorobenzyl)(butyl)N– | N-butyl-4-chloro-N-(4-chlorobenzyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide | 808.1 |
| 137 | (4-(4-fluorophenoxy)phenyl)(butyl)N– | N-butyl-4-chloro-N-(4-(4-fluorophenoxy)phenyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide | 868.5 (M − H) |

-continued

| Ex. No. | R | Name | LCMS (M + H) |
|---|---|---|---|
| 138 | 4-(4-chlorophenoxy)phenyl-N(Bu)- | N-butyl-4-chloro-N-(4-(4-chlorophenoxy)phenyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide | 886.3 |
| 139 | (1-methyl-1H-indol-2-yl)-N(Bu)- | N-butyl-4-chloro-5-methyl-N-(1-methyl-1H-indol-2-yl)-1-(4-(naphthalen-2-ylsulfonylcarbamoyl)-2-(1,2,3,4-tetrahydroisoquinoline-2-carbonyl)phenyl)-1H-pyrazole-3-carboxamide | 827.1 |
| 140 | (3,4-dimethoxyphenyl)-N(Bu)- | N-butyl-4-chloro-N-(3,4-dimethoxyphenyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide | 818.6 (M − H) |
| 141 | (4-isopropoxyphenyl)-N(Bu)- | N-butyl-4-chloro-N-(4-isopropoxyphenyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide | 816.5 (M − H) |
| 142 | (3-chloro-4-methylphenyl)-N(Bu)- | N-butyl-4-chloro-N-(3-chloro-4-methylphenyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide | 808.1 |
| 143 | (biphenyl-4-yl)-N(Bu)- | N-(biphenyl-4-yl)-N-butyl-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide | 834.4 (M − H) |
| 144 | (4-methoxyphenyl)-N(Bu)- | N-butyl-4-chloro-N-(4-methoxyphenyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide | 790.1 |

-continued

| Ex. No. | R | Name | LCMS (M + H) |
|---|---|---|---|
| 145 | 3-methoxyphenyl, N-Bu | N-butyl-4-chloro-N-(3-methoxyphenyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide | 790.3 |
| 146 | 3-tert-butylphenyl, N-Bu | N-butyl-N-(3-tert-butylphenyl)-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide | 816.3 |
| 147 | biphenyl-3-yl, N-Bu | N-(biphenyl-3-yl)-N-butyl-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide | 836.3 |
| 148 | 4-tert-butylphenyl, N-Bu | N-butyl-N-(4-tert-butylphenyl)-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide | 816.4 |
| 149 | 2,3-dihydrobenzo[b][1,4]dioxin-6-yl, N-Bu | N-butyl-4-chloro-N-(2,3-dihydrobenzo[b][1,4]dioxin-6-yl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide | 818.3 |
| 150 | 3-isopropoxyphenyl, N-Bu | N-butyl-4-chloro-N-(3-isopropoxyphenyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide | 818.2 |

| Ex. No. | R | Name | LCMS (M + H) |
|---|---|---|---|
| 151 | 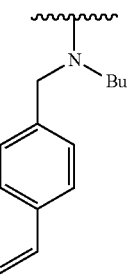 | N-butyl-4-chloro-5-methyl-N-(naphthalen-2-ylmethyl)-1-(4-(naphthalen-2-ylsulfonylcarbamoyl)-2-(1,2,3,4-tetrahydroisoquinoline-2-carbonyl)phenyl)-1H-pyrazole-3-carboxamide | 824.1 |
| 152 | 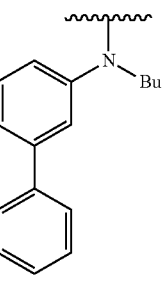 | N-butyl-4-chloro-N-(3'-chlorobiphenyl-3-yl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide | 870.1 |
| 153 | 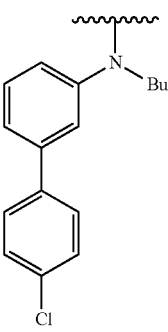 | N-butyl-4-chloro-N-(4'-chlorobiphenyl-3-yl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide | 870.4 |
| 154 | 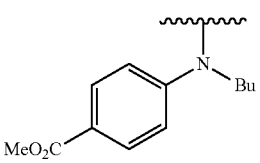 | methyl 4-(N-butyl-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamido)benzoate | 818.1 |

| Ex. No. | R | Name | LCMS (M + H) |
|---|---|---|---|
| 155 | 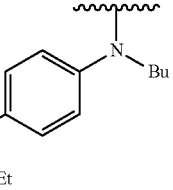 | 4-(N-butyl-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamido)benzyl propionate | 818.1 |

Example 156

N-Butyl-4-chloro-5-methyl-1-(4-(naphthalen-2-ylsulfonylcarbamoyl)-2-(1,2,3,4-tetrahydroisoquinoline-2-carbonyl)phenyl)-N-phenyl-1H-pyrazole-3-carboxamide (156)

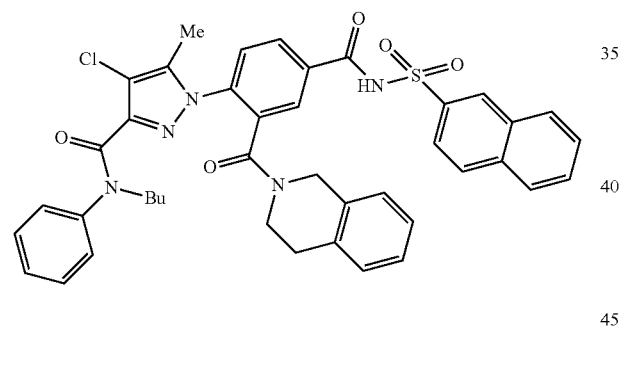

Following a procedure analogous to that for the synthesis of Intermediate 122G, 4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxylic acid (Intermediate 122F, 50 mg, 0.079 mmol) and N-butyl-3,4-dichloroaniline (Aldrich, 10 mg, 0.046 mmol) were converted to the title compound. $^1$H NMR (1:1 CD$_3$OD:CDCl$_3$, mixture of amide rotamers) δ 8.73 (s, 1H), 8.12-8.00 (m, 4H), 7.97-7.94 (m, 1H), 7.74-7.66 (m, 2H), 7.57 (br s, 1H), 7.46 (br s, 1H), 7.36 (br s, 1H), 7.26-7.19 (m, 4.5H), 7.12-7.10 (m, 0.5H), 7.00 (br s, 1H), 6.73 (br s, 1H), 6.66 (br s, 0.5H), 6.50 (br s, 0.5H), 4.66 (br s, 0.5H), 4.51 (br s, 0.5H), 4.39 (br s, 0.5H), 4.25 (br s, 0.5H), 3.85 (br s, 2H), 3.58 (br s, 2H), 3.13 (br s, 1H), 2.81 (br s, 1H), 2.20-2.16 (m, 3H), 1.38-1.21 (m, 4H), 0.93-0.83 (m, 3H); MS(ESI$^+$) m/z 760.2 (M+H)$^+$.

Example 157

N-Benzyl-N-butyl-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (157)

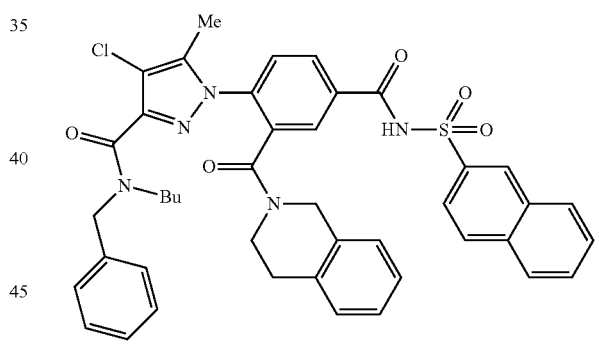

Following a procedure analogous to that for the synthesis of Example 125, 4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxylic acid (Intermediate 122F, 25 mg, 0.040 mmol) and N-benzylbutan-1-amine (Aldrich, 11 μL, 0.064 mmol) were converted to the title compound (21 mg, 68%). $^1$H NMR (1:1 CD$_3$OD:CDCl$_3$) δ 8.62 (br s, 1H), 8.15 (d, J=7.9 Hz, 1H), 8.07-7.82 (m, 5H), 7.64-7.50 (m, 1H), 7.46-7.36 (m, 1.5H), 7.28-6.93 (m, 9H), 6.86 (d, J=7.3 Hz, 0.5H), 4.62 (d, J=5.9 Hz, 1H), 4.47-4.11 (m, 2.5H), 3.77-3.36 (m, 2.5H), 3.21-2.94 (m, 1.5H), 2.81-2.65 (m, 2.5H), 2.35-2.14 (m, 3H), 1.74-1.13 (m, 3H), 1.08-0.77 (m, 3H), 0.72-0.58 (m, 1H); MS(ESI$^+$) m/z 774.1 (M+H)$^+$.

Example 158

N-Butyl-4-chloro-5-methyl-N-(3-(2-(4-methylpiper-azin-1-yl)ethylamino)-3-oxopropyl)-1-(4-(naphtha-len-2-ylsulfonylcarbamoyl)-2-(1,2,3,4-tetrahydroiso-quinoline-2-carbonyl)phenyl)-1H-pyrazole-3-carboxamide

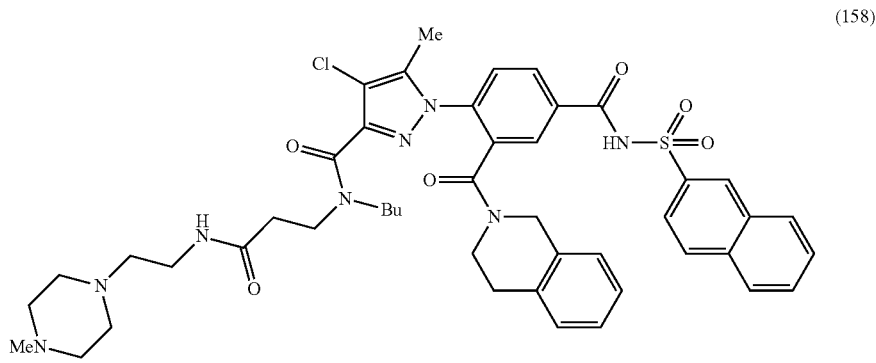

(158)

Intermediate 158A tert-Butyl 3-(butylamino)propanoate

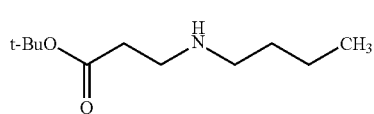

(Int-158A)

Intermediate 158B 3-(N-Butyl-4-chloro-5-methyl-1-(4-(naphthalen-2-ylsulfonylcarbamoyl)-2-(1,2,3,4-tetrahydroisoquino-line-2-carbonyl)phenyl)-1H-pyrazole-3-carboxa-mido)propanoic acid

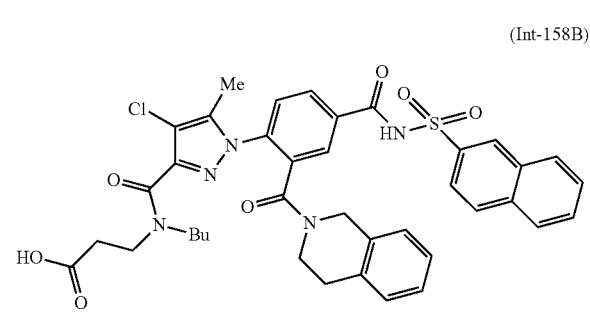

(Int-158B)

To a solution of tert-butyl 3-aminopropanoate, HCl (Bachem, 1.59 g, 8.77 mmol) and butyraldehyde (790 µL, 8.77 mmol) in THF (20.0 mL) was added AcOH (1.0 mL, 17.5 mmol). The resulting reaction mixture was stirred at room temperature for 1.5 h. Na(OAc)$_3$BH (2.60 g, 12.3 mmol) was added portionwise and stirring was continued at room temperature overnight. The reaction mixture was then quenched with 1N aq. NaOH (pH=8-9), and the aqueous layer was extracted with CHCl$_3$ (3×). The combined organic extracts were dried over Na$_2$SO$_4$, filtered and concentrated in vacuo to afford a crude oil. Purification by flash column chromatography (gradient from 0% to 100% EtOAc/hexanes) provided the title compound (944 mg, 53%) as a colorless oil. $^1$H NMR (CDCl$_3$) δ 2.85 (t, J=6.6 Hz, 2H), 2.67-2.58 (m, 2H), 2.45 (t, J=6.5 Hz, 2H), 1.55-1.42 (m, 11H), 1.41-1.30 (m, 2H), 0.92 (t, J=7.3 Hz, 3H); MS(ESI$^+$) m/z 202.3 (M+H)$^+$.

Following a procedure analogous to that for the synthesis of Example 125, 4-chloro-5-methyl-1-(4-(naphthalen-2-yl-sulfonylcarbamoyl)-2-(1,2,3,4-tetrahydroisoquinoline-2-carbonyl)phenyl)-1H-pyrazole-3-carboxylic acid (Intermediate 122F, 199 mg, 0.32 mmol) and tert-butyl 3-(butylamino) propanoate (318 mg, 1.58 mmol) provided a yellow oil which was used without purification in the subsequent step.

The crude oil from above was dissolved in CH$_2$Cl$_2$ (5.0 mL) and TFA (4.0 mL, 51.9 mmol) was added. The resulting reaction mixture was stirred at room temperature for 2 h and then concentrated in vacuo. The residue was purified by preparative HPLC to give the title compound (107 mg, 43%) as a white solid after lyophilization. $^1$H NMR (CD$_3$OD, mixture of amide rotamers) δ 8.73 (br s, 1H), 8.15-7.94 (m, 6.5H), 7.75-7.63 (m, 3H), 7.25-7.05 (m, 4H), 6.93-6.87 (m, 0.5H), 5.03-4.86 (m, 1H), 4.71-4.42 (m, 1H), 4.20-4.00 (m, 0.5H), 3.67-3.40 (m, 4H), 3.28-3.05 (m, 1H), 2.90-2.77 (m, 1H), 2.58-2.38 (m, 1H), 2.32 (s, 2H), 2.28-2.24 (m, 1H), 2.18-2.06 (m, 0.5H), 1.28 (s, 4H), 1.15-0.85 (m, 3H), 0.76 (t, J=7.5 Hz, 1H), 0.68 (t, J=7.5 Hz, 1H); MS (ESI⁺) m/z 756.3 (M+H)⁺.

Example 158

Following a procedure analogous to that for the synthesis of Example 124, 3-(N-butyl-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamido) propanoic acid (20 mg, 0.026 mmol) and 2-(4-methylpiperazin-1-yl)-ethylamine (Aldrich, 12 mg, 0.084 mmol) were converted to the title compound (10 mg, 37%). ¹H NMR (CD₃OD, mixture of amide rotamers) δ 8.73 (br s, 1H), 8.15-7.95 (m, 6.5H), 7.77-7.64 (m, 3.5H), 7.25-7.04 (m, 3.5H), 6.93-6.80 (m, 0.5H), 4.77-4.04 (m, 2H), 3.62-3.52 (m, 2H), 3.48-3.44 (m, 1H), 3.42-3.33 (m, 3H), 3.24 (m, 6H), 2.94-2.61 (m, 9.5H), 2.58-2.39 (m, 1.5H), 2.38-2.31 (m, 2.5H), 2.30-2.20 (m, 1.5H), 1.62-1.13 (m, 4H), 1.13-0.85 (m, 3H), 0.75 (t, J=7.3 Hz, 1H), 0.68 (t, J=7.5 Hz, 1H); MS(ESI⁺) m/z 881.5 (M+H)⁺.

Example 159

N-Butyl-4-chloro-N-(3-(1,3-dihydroxypropan-2-ylamino)-3-oxopropyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (159)

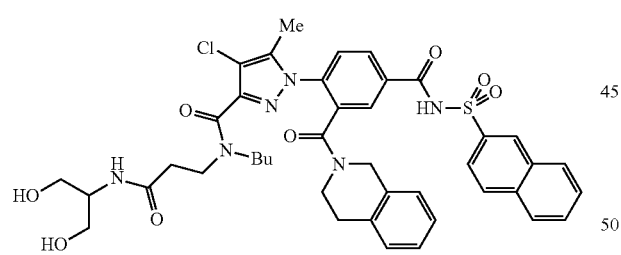

Following a procedure analogous to that for the synthesis of Example 124, 3-(N-butyl-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamido) propanoic acid (Intermediate 158B, 20 mg, 0.026 mmol) and 2-amino-1,3-propanediol (Aldrich, 8 mg, 0.088 mmol) were converted to the title compound (5 mg, 21%). ¹H NMR (CD₃OD, 1:1 mixture of amide rotamers) δ 8.72 (br s, 1H), 8.15-7.94 (m, 6.5H), 7.76-7.62 (m, 3.5H), 7.25-7.03 (m, 3.5H), 6.94-6.81 (m, 0.5H), 4.75-4.00 (m, 2H), 3.97-3.70 (m, 2H), 3.65-3.43 (m, 7H), 2.94-2.64 (m, 3H), 2.58-2.12 (m, 5H), 1.58-1.14 (m, 4H), 1.13-0.85 (m, 3H), 0.76 (t, J=7.3 Hz, 1H), 0.68 (t, J=7.5 Hz, 1H); MS(ESI⁺) m/z 829.4 (M+H)⁺.

Example 160

N-Butyl-4-chloro-N-(3-(1,3-dihydroxy-2-(hydroxymethyl)propan-2-ylamino)-3-oxopropyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (160)

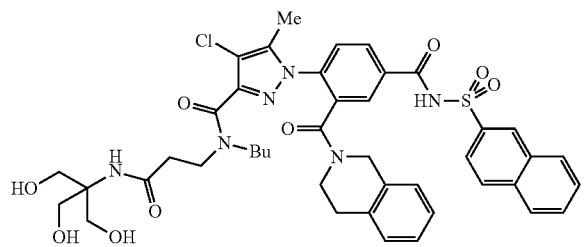

Following a procedure analogous to that for the synthesis of Example 124, 3-(N-butyl-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamido) propanoic acid (Intermediate 158B, 20 mg, 0.026 mmol) and 2-amino-2-(hydroxymethyl) propane-1,3-diol (J. T. Baker, 10 mg, 0.083 mmol) were converted to the title compound (4 mg, 18%). ¹H NMR (CD₃OD, 1.5:1 mixture of amide rotamers) δ 8.73 (br s, 1H), 8.17-7.94 (m, 7H), 7.75-7.65 (m, 3H), 7.23-7.09 (m, 3.5H), 6.96-6.83 (m, 0.5H), 4.61-4.40 (m, 1H), 4.38-3.91 (m, 3H), 3.73-3.66 (m, 3H), 3.66-3.49 (m, 4H), 3.02-2.97 (m, 1H), 2.89-2.79 (m, 2H), 2.75-2.60 (m, 2H), 2.56 (t, J=6.9 Hz, 0.5H), 2.38-2.31 (m, 2H), 2.28-2.23 (m, 1.5H), 1.57-1.18 (m, 4H), 1.14-0.84 (m, 3H), 0.76 (t, J=7.3 Hz, 1H), 0.68 (t, J=7.3 Hz, 1H); MS(ESI⁺) m/z 859.4 (M+H).

Example 161

4-(N-Butyl-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamido)benzoic acid (161)

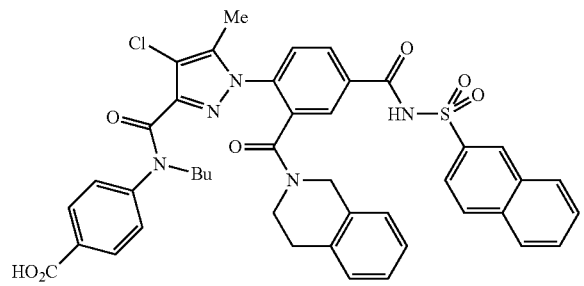

Following a procedure analogous to that for the synthesis of Intermediate 91F, methyl 4-(N-butyl-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamido)benzoate (Example 154, 2 mg, 2.0 µmol) was converted to the title compound (2 mg, 94%). ¹H NMR (CD₃OD, 2:1 mixture of amide rotamers) δ 8.71 (s, 1H), 8.10 (d, J=8.1 Hz, 1H), 8.06 (s, 2H), 8.04-7.97 (m, 2.5H), 7.93 (d, J=2.0 Hz, 0.5H), 7.87 (d, J=8.6 Hz, 1H), 7.75-7.64 (m, 3H), 7.54 (d, J=8.1 Hz, 0.5H), 7.41 (d, J=8.8 Hz, 0.5H), 7.22-7.18 (m, 3.5H), 7.01-6.99 (m, 1.5H), 6.73 (d, J=7.0 Hz, 1H), 4.97 (br s, 1H), 4.69 (br s, 1H), 4.52-4.31 (m, 2H), 4.17 (br s, 1H), 3.93 (br s, 1H), 3.64-3.43 (m, 1H), 2.94-2.78 (m, 1H), 2.21-2.17 (m, 1H), 2.16 (s, 2H), 2.14 (s, 1H), 2.06-2.00 (m, 1H), 1.64-1.56 (m, 1H), 1.44-1.20 (m, 3H), 0.93-0.81 (m, 3H); MS(ESI⁺) m/z 804.3 (M+H)⁺.

Example 162

2-(4-(N-Butyl-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamido)phenyl)acetic acid

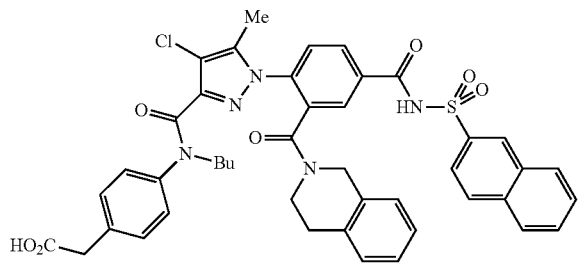

(162)

Following a procedure analogous to that for the synthesis of Intermediate 1F, ethyl 2-(4-(N-butyl-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamido)phenyl)acetate (Example 155, 1 mg, 9.9 µmol) was converted to the title compound (0.5 mg, 53%). ¹H NMR (CD₃OD, 2:1 mixture of amide rotamers) δ 8.71 (s, 1H), 8.10 (d, J=9.2 Hz, 1H), 8.06 (s, 2H), 8.03-7.97 (m, 2.5H), 7.94-7.91 (m, 0.5H), 7.73-7.65 (m, 2H), 7.41 (br s, 0.5H), 7.30 (br s, 0.5H), 7.23-7.10 (m, 5H), 7.03-6.96 (m, 1H), 6.90 (d, J=8.4 Hz, 1H), 6.61 (br s, 1H), 4.73 (br s, 1H), 4.48-4.19 (m, 2H), 4.07 (br s, 1H), 3.91 (br s, 1H), 3.54-3.39 (m, 2H), 2.95-2.75 (m, 2H), 2.10 (s, 2H), 2.01 (s, 1H), 1.65-1.55 (m, 1H), 1.40-1.18 (m, 5H), 0.92-0.80 (m, 3H); MS(ESI⁺) m/z 818.3 (M+H)⁺.

Example 163

4-Bromo-N,N-dibutyl-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide

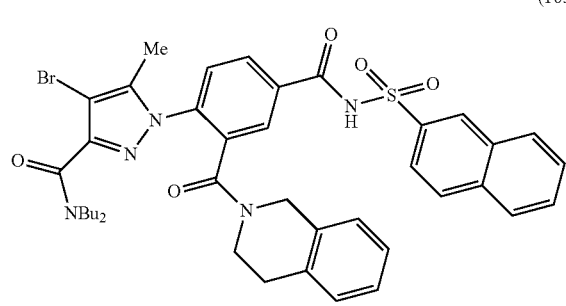

(163)

Intermediate 163A

4-Bromo-N,N-dibutyl-5-methyl-1H-pyrazole-3-carboxamide

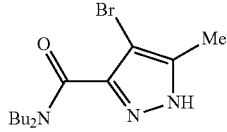

(Int-163A)

Following a procedure analogous to that for the synthesis of Intermediate 1B, ethyl 4-bromo-5-methyl-1H-pyrazole-3-carboxylate (Tabrizi, M. A. et al., Bioorg. Med. Chem., 16:2419-2430 (2008)) (5.68 g, 24.4 mmol) was converted to the title compound (5.79 g, 75%). ¹H NMR (CDCl₃) δ 3.51 (t, J=7.4 Hz, 2H), 3.38-3.26 (m, 2H), 2.34 (s, 3H), 1.73-1.34 (m, 6H), 1.22-1.13 (m, 2H), 1.03-0.75 (m, 6H); MS(ESI⁺) m/z 316.2 (M+H)⁺.

Intermediate 163B

Ethyl 4-(4-bromo-3-(dibutylcarbamoyl)-5-methyl-1H-pyrazol-1-yl)-3-(1,2,3,4-tetrahydroisoquinoline-2-carbonyl)benzoate

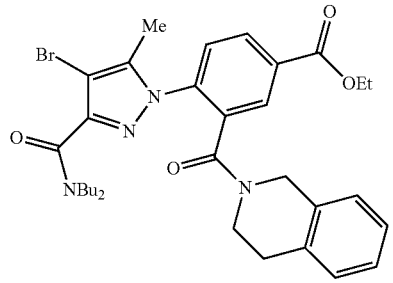

(Int-163B)

Following a procedure analogous to that for the synthesis of Intermediate 1E, 4-bromo-N,N-dibutyl-5-methyl-1H-pyrazole-3-carboxamide (646 mg, 2.04 mmol) and ethyl 4-fluoro-3-(1,2,3,4-tetrahydroisoquinoline-2-carbonyl)benzoate (Intermediate 1D, 1.07 g, 3.27 mmol) were converted to the title compound (660 mg, 48%). ¹H NMR (CDCl₃, 2:1 mixture of amide rotamers) δ 8.24-8.19 (m, 1H), 8.14-8.10 (m, 1H), 7.45-7.39 (m, 1H), 7.25-7.09 (m, 3.5H), 6.88 (d, J=7.3 Hz, 0.5H), 4.78 (d, J=8.8 Hz, 1H), 4.49-4.36 (m, 3H), 3.71-2.69 (m, 8H), 2.32 (s, 2H), 2.28 (s, 1H), 1.54-1.27 (m, 8.5H), 1.11 (d, J=7.7 Hz, 2H), 0.92 (q, J=7.2 Hz, 3.5H), 0.79 (t, J=8.0 Hz, 3H); MS(ESI⁺) m/z 625.3 (M+H)⁺.

Example 163

To a solution of ethyl 4-(4-bromo-3-(dibutylcarbamoyl)-5-methyl-1H-pyrazol-1-yl)-3-(1,2,3,4-tetrahydroisoquinoline-2-carbonyl)benzoate (89 mg, 0.14 mmol) in THF (1.4 mL) was added 1N aq. NaOH solution (2.1 mL, 2.14 mmol). The resulting reaction mixture was stirred at room temperature for 2 h, then neutralized with 1N aq. HCl solution (pH=6) and extracted with EtOAc (3×). The combined organic extracts were dried over $Na_2SO_4$, filtered and concentrated in vacuo to provide a clear, colorless oil which was used in the subsequent step without purification.

Following a procedure analogous to that for the synthesis of Example 1, the crude oil from above was converted to the title compound (70 mg, 61%). $^1$H NMR (DMSO-$d_6$, 2:1 mixture of amide rotamers) δ 8.73 (s, 1H), 8.27 (d, J=7.9 Hz, 1H), 8.18 (d, J=8.8 Hz, 1H), 8.12-8.03 (m, 3H), 8.02-7.96 (m, 1H), 7.82-7.67 (m, 3H), 7.25-7.05 (m, 3.5H), 6.98 (d, J=7.7 Hz, 0.5H), 4.80-3.32 (m, 7H), 3.18-2.57 (m, 3H), 2.23 (s, 2H), 2.19 (s, 1H), 1.42-0.79 (m, 11H), 0.72-0.64 (m, 2H), 0.63-0.58 (m, 1H); MS(ESI$^+$) m/z 803.4 (M+H)$^+$.

Example 164

N,N-Dibutyl-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide

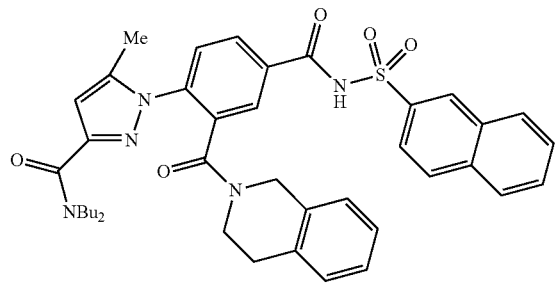

(164)

Intermediate 164A

Benzyl 4-(4-bromo-3-(dibutylcarbamoyl)-5-methyl-1H-pyrazol-1-yl)-3-(1,2,3,4-tetrahydroisoquinoline-2-carbonyl)benzoate

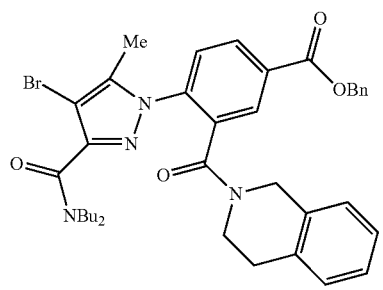

(Int-164A)

Following a procedure analogous to that for the synthesis of Intermediate 1E, 4-bromo-N,N-dibutyl-5-methyl-1H-pyrazole-3-carboxamide (Intermediate 163A, 268 mg, 0.85 mmol) and benzyl 4-fluoro-3-(1,2,3,4-tetrahydroisoquinoline-2-carbonyl)benzoate (Intermediate 122B, 300 mg, 0.77 mmol) were converted to the title compound (215 mg, 41%). $^1$H NMR (DMSO-$d_6$, 2:1 mixture of amide rotamers) δ 8.21 (dd, J=8.3, 1.9 Hz, 1H), 8.11 (d, J=2.0 Hz, 0.5H), 8.08-8.03 (m, 0.5H), 7.85-7.78 (m, 1H), 7.55-7.33 (m, 5.5H), 7.25-7.06 (m, 3H), 7.05-6.96 (m, 0.5H), 5.47-5.32 (m, 2H), 4.82-4.42 (m, 2H), 3.92-3.71 (m, 0.5H), 3.58-3.34 (m, 3H), 3.23-2.91 (m, 2.5H), 2.82-2.74 (m, 2H), 2.27 (s, 2H), 2.22 (s, 1 H), 1.59-1.13 (m, 4H), 1.07-0.80 (m, 7H), 0.72-0.59 (m, 3H); MS(ESI$^+$) m/z 687.5 (M+H)$^+$.

Intermediate 164B 4-(4-Bromo-3-(dibutylcarbamoyl)-5-methyl-1H-pyrazol-1-yl)-3-(1,2,3,4-tetrahydroisoquinoline-2-carbonyl)benzoic acid

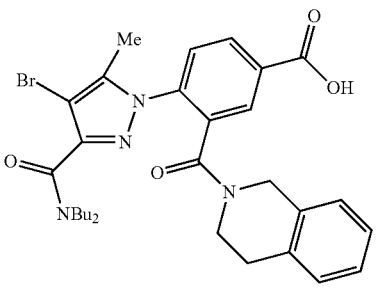

(Int-164B)

To benzyl 4-(4-bromo-3-(dibutylcarbamoyl)-5-methyl-1H-pyrazol-1-yl)-3-(1,2,3,4-tetrahydroisoquinoline-2-carbonyl)benzoate (55 mg, 0.080 mmol) in THF (1.0 mL) was added 1N aq. NaOH solution (802 µL, 0.80 mmol). The resulting biphasic mixture was stirred vigorously at room temperature for 2.5 h, then acidified with 1N aq. HCl solution (pH=3) and extracted with EtOAc (3×). The combined organic extracts were dried over $Na_2SO_4$, filtered and concentrated in vacuo to give the title compound (46 mg, 96%) as a clear, colorless oil. MS(ESI$^+$) m/z 597.3 (M+H)$^+$.

Example 164

To a solution of 4-(4-bromo-3-(dibutylcarbamoyl)-5-methyl-1H-pyrazol-1-yl)-3-(1,2,3,4-tetrahydroisoquinoline-2-carbonyl)benzoic acid (26 mg, 0.043 mmol) in THF (1.0 mL) at −78° C. was added t-BuLi (25 µL, 0.043 mmol, 1.7M in pentane) dropwise via gas-tight syringe. The resulting solution was stirred at −78° C. for 5 min. Additional t-BuLi (50 µL, 0.086 mmol, 1.7M in pentane) was added dropwise and the clear, yellow solution was stirred for 15 min. Additional t-BuLi (25 µL, 0.043 mmol, 1.7M in pentane) was then added until the dark green color persisted. The reaction mixture was stirred at −78° C. for 30 min and then at room temperature for 1 h. After quenching slowly with water, the reaction mixture was extracted with EtOAc (3×). The combined organics were dried over $Na_2SO_4$, filtered and concentrated in vacuo to give a crude oil that was used in the subsequent step without purification.

Following a procedure analogous to that for the synthesis of Example 1, the crude oil from above was converted to the title compound (9 mg, 26%). $^1$H NMR (CD$_3$OD, 1.5:1 mixture of amide rotamers) δ 8.74 (s, 0.5H), 8.17-7.94 (m, 7.5H), 7.76-7.62 (m, 3H), 7.29-7.04 (m, 3.5H), 6.90 (d, J=7.7 Hz, 0.5H), 6.42 (dd, J=4.8, 0.9 Hz, 0.5H), 4.80-4.59 (m, 1.5H), 4.57-4.33 (m, 1H), 4.08 (d, J=12.1 Hz, 0.5H), 3.70-2.66 (m, 7.5H), 2.35 (d, J=0.7 Hz, 1.5H), 2.29 (d, J=0.7 Hz, 1.5H), 1.64-0.85 (m, 10H), 0.80-0.73 (m, 2.5H), 0.71-0.65 (m, 1.5H); MS(ESI⁺) m/z 706.4 (M+H)⁺.

Example 165

N,N-Dibutyl-4-(hydroxymethyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (165)

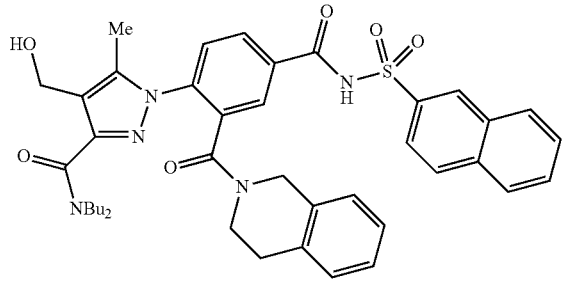

To 4-(4-bromo-3-(dibutylcarbamoyl)-5-methyl-1H-pyrazol-1-yl)-3-(1,2,3,4-tetrahydroisoquinoline-2-carbonyl)benzoic acid (Intermediate 164B, 52 mg, 0.087 mmol) in THF (1.0 mL) was added NaH (6 mg, 0.26 mmol, 60% suspension in mineral oil) at 0° C. The suspension was stirred for 15 min at 0° C. and then cooled to −78° C. n-BuLi (100 µL, 0.25 mmol, 2.5M solution in hexane) was added dropwise via syringe until the dark green color persisted. The reaction mixture was stirred at −78° C. for 15 min and then DMF (68 µL, 0.87 mmol) was added via syringe. The resulting mixture was stirred at −78° C. for 30 min, then quenched with water, warmed to room temperature and transferred to a sep funnel containing sat. aq. NH₄Cl solution and 1N aq. HCl solution (1:1). The aqueous layer was extracted with EtOAc (3×) and the combined organics were dried over Na₂SO₄. Concentration in vacuo provided a crude oil which was used in the next step without purification.

The crude oil from above was subjected to a procedure analogous to that for the synthesis of Example 1. The resulting crude product was dissolved in THF (880 µL) and MeOH (175 µL). NaBH₄ (7 mg, 0.18 mmol) was added, and the reaction mixture was stirred at room temperature for 30 min. The reaction mixture was then quenched with sat. aq. NH₄Cl solution, washed with 1N aq. HCl solution and extracted with EtOAc (3×). The combined organic extracts were dried over Na₂SO₄, filtered and concentrated in vacuo. The residue was purified by preparative HPLC to give the title compound (6 mg, 10%) as a white solid after lyophilization. ¹H NMR (CD₃OD, 1.5:1 mixture of amide rotamers) δ 8.57 (s, 1H), 8.22 (td, J=8.3, 1.9 Hz, 1H), 8.14 (t, J=1.9 Hz, 1H), 8.05-7.98 (m, 2H), 7.97-7.89 (m, 2H), 7.63-7.54 (m, 2H), 7.48 (dd, J=8.3, 4.1 Hz, 1H), 7.24-7.06 (m, 3.5H), 6.93 (d, J=7.3 Hz, 0.5H), 4.84-4.41 (m, 2.5H), 4.09 (br s, 0.5H), 3.70-2.69 (m, 9H), 2.34 (s, 1.5H), 2.28 (s, 1.5H), 1.55-0.86 (m, 11H), 0.78-0.72 (m, 2H), 0.68-0.61 (m, 1H); MS(ESI⁺) m/z 736.5 (M+H)⁺.

Example 166

3-(3-(Dibutylcarbamoyl)-5-methyl-1-(4-(naphthalen-2-ylsulfonylcarbamoyl)-2-(1,2,3,4-tetrahydroisoquinoline-2-carbonyl)phenyl)-1H-pyrazol-4-yl)propanoic acid (166)

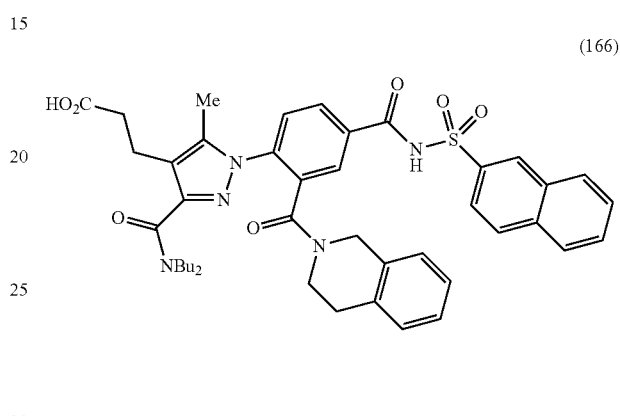

Intermediate 166A (E)-Benzyl 4-(4-(3-tert-butoxy-3-oxoprop-1-enyl)-3-(dibutylcarbamoyl)-5-methyl-1H-pyrazol-1-yl)-3-(1,2,3,4-tetrahydroisoquinoline-2-carbonyl)benzoate (Int-166A)

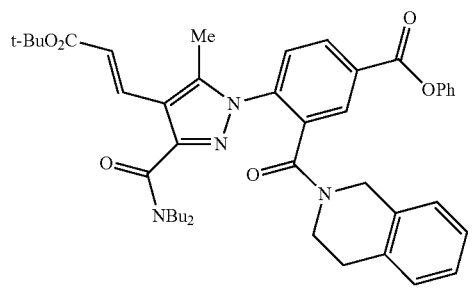

To a solution of benzyl 4-(4-bromo-3-(dibutylcarbamoyl)-5-methyl-1H-pyrazol-1-yl)-3-(1,2,3,4-tetrahydroisoquinoline-2-carbonyl)benzoate (Intermediate 164A, 80 mg, 0.12 mmol) in DMF (580 µL) and Et₃N (580 µL) was added (PPh₃)₂PdCl₂ (8 mg, 0.012 mmol) followed by tert-butyl acrylate (58 µL, 0.40 mmol). The reaction mixture was purged with N₂ for 5 min and then heated at 140° C. overnight. The reaction mixture was poured into a separatory funnel containing 1N aq. HCl solution and EtOAc. The organic layer was washed 1N aq. HCl solution (2×) and the aqueous layer was extracted with EtOAc (3×). The combined organic extracts were washed with sat. aq. NaHCO₃ solution, dried over Na₂SO₄ and concentrated in vacuo. The residue was purified by flash chromatography (gradient from 0% to 35%

EtOAc/hexanes) to provide the title compound (42 mg, 50%) as a colorless oil. MS(ESI+) m/z 733.5 (M+H)+.

Intermediate 166B (E)-4-(4-(3-tert-Butoxy-3-oxoprop-1-enyl)-3-(dibutylcarbamoyl)-5-methyl-1H-pyrazol-1-yl)-3-(1,2,3,4-tetrahydroisoquinoline-2-carbonyl)benzoic acid

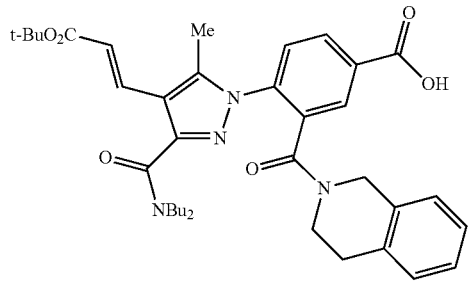

(Int-166B)

Following a procedure analogous to that for the synthesis of Intermediate 91D, (E)-benzyl 4-(4-(3-tert-butoxy-3-oxoprop-1-enyl)-3-(dibutylcarbamoyl)-5-methyl-1H-pyrazol-1-yl)-3-(1,2,3,4-tetrahydroisoquinoline-2-carbonyl)benzoate (71 mg, 0.096 mmol) was converted to the title compound (59 mg, 94%). MS(ESI+) m/z 643.4 (M+H)+.

Intermediate 166C (E)-tert-Butyl 3-(3-(dibutylcarbamoyl)-5-methyl-1-(4-(naphthalen-2-ylsulfonylcarbamoyl)-2-(1,2,3,4-tetrahydroisoquinoline-2-carbonyl)phenyl)-1H-pyrazol-4-yl)acrylate

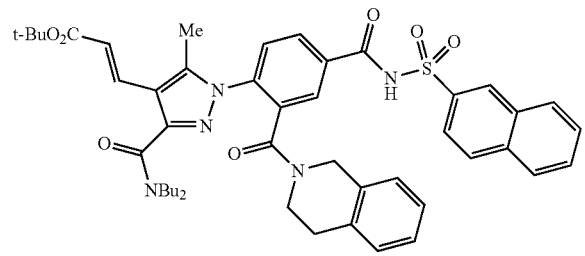

(Int-166C)

Following a procedure analogous to that for the synthesis of Example 1, (E)-benzyl 4-(4-(3-tert-butoxy-3-oxoprop-1-enyl)-3-(dibutylcarbamoyl)-5-methyl-1H-pyrazol-1-yl)-3-(1,2,3,4-tetrahydroisoquinoline-2-carbonyl)benzoate (84 mg, 0.13 mmol) was converted to the title compound (49 mg, 45%). MS(ESI+) m/z 832.5 (M+H)+.

Example 166

To a solution of (E)-tert-butyl 3-(3-(dibutylcarbamoyl)-5-methyl-1-(4-(naphthalen-2-ylsulfonylcarbamoyl)-2-(1,2,3,4-tetrahydroisoquinoline-2-carbonyl)phenyl)-1H-pyrazol-4-yl)acrylate (49 mg, 0.059 mmol) in CH$_2$Cl$_2$ (1.2 mL) was added TFA (340 μL, 4.39 mmol). The resulting reaction mixture was stirred at room temperature for 3.5 h and then concentrated in vacuo to provide a crude oil which was used in the subsequent step without purification.

Following a procedure analogous to that for the synthesis of Intermediate Example 91D, the crude oil from above was converted to the title compound (7 mg, 18%) after purification by preparative HPLC. $^1$H NMR (CDCl$_3$, 1.5:1 mixture of amide rotamers) δ 8.77 (d, J=5.5 Hz, 1H), 8.11-8.02 (m, 2H), 8.02-7.87 (m, 4.5H), 7.71-7.60 (m, 1.5H), 7.44-7.35 (m, 1H), 7.24-7.06 (m, 3.5H), 6.79 (d, J=7.2 Hz, 0.5H), 4.91-4.59 (m, 1.5H), 4.31-4.07 (m, 1H), 3.90-3.65 (m, 1H), 3.56-2.58 (m, 10.5H), 2.20 (s, 1.5H), 2.15 (s, 1.5H), 1.59-1.01 (m, 7H), 0.98-0.81 (m, 4H), 0.80-0.69 (m, 3H); MS(ESI+) m/z 778.4 (M+H)+.

Example 167

N,N-Dibutyl-4-(3-(dimethylamino)propyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide

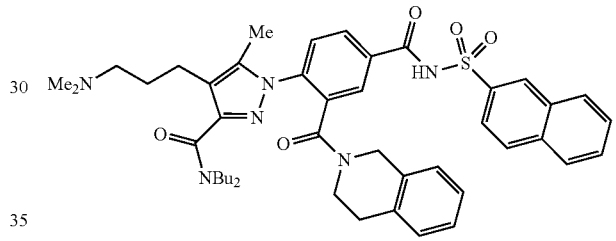

(167)

Intermediate 167A

N,N-Dibutyl-4-(3-hydroxypropyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide

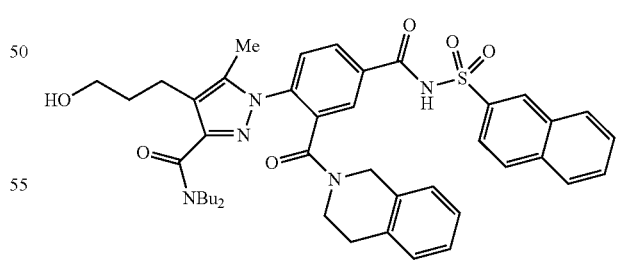

(Int-167A)

To a solution of (E)-tert-butyl 3-(3-(dibutylcarbamoyl)-5-methyl-1-(4-(naphthalen-2-ylsulfonylcarbamoyl)-2-(1,2,3,4-tetrahydroisoquinoline-2-carbonyl)phenyl)-1H-pyrazol-4-yl)acrylate (Intermediate 166C, 49 mg, 0.059 mmol) in CH$_2$Cl$_2$ (1.2 mL) was added TFA (340 μL, 4.39 mmol). The resulting reaction mixture was stirred at room temperature for 3.5 h and then concentrated in vacuo to provide a crude oil which was used in the subsequent step without purification.

The crude oil from above was dissolved in THF (2.3 mL) and CDI (15 mg, 0.094 mmol) was added. The resulting reaction mixture was stirred at room temperature for 2 h. Water (570 μL) was added followed by NaBH₄ (12 mg, 0.31 mmol), and the reaction mixture was stirred at room temperature for 1 h. The reaction mixture was quenched carefully with 1N aq. HCl solution (570 μL, 0.57 mmol) (exothermic) and extracted with EtOAc (3×). The combined organic extracts were dried over Na₂SO₄, filtered and concentrated in vacuo to give a crude oil which was subjected to a procedure analogous to that for the synthesis of Intermediate 91D to give the title compound (35 mg, 72%). MS(ESI$^+$) m/z 764.5 (M+H)$^+$.

Example 167

To N,N-dibutyl-4-(3-hydroxypropyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (35 mg, 0.045 mmol) in CH₂Cl₂ (1.0 mL) was added Et₃N (25 μL, 0.18 mmol) followed by MsCl (5 μL, 0.068 mmol). The resulting reaction mixture was stirred at room temperature for 1 h, then quenched with sat. aq. NH₄Cl and extracted with CH₂Cl₂ (3×). The combined organic extracts were dried over Na₂SO₄, filtered and concentrated in vacuo to give a pale yellow oil which was used in the subsequent step without purification.

The crude oil from above was dissolved in MeCN (1.0 mL) and Me₂NH (91 μL, 0.18 mmol, 2M solution in THF) was added. The resulting reaction mixture was stirred overnight at room temperature. i-Pr₂EtN (16 μL, 0.091 mmol) was then added, and the reaction mixture was stirred at 80° C. for 4 h and then at 80° C. for 3.5 h. Additional Me₂NH (91 μL, 0.18 mmol, 2M solution in THF) was added, and the reaction mixture was stirred at 80° C. for 2 h. The reaction mixture was then concentrated in vacuo and purified by preparative HPLC to give the title compound (4 mg, 10%) as a yellow solid after lyophilization. ¹H NMR (CD₃OD, 1:1 mixture of amide rotamers) δ 8.74 (br s, 1H), 8.17-7.97 (m, 6.5H), 7.79-7.61 (m, 2.5H), 7.31-7.07 (m, 3.5H), 6.94 (d, J=6.8 Hz, 0.5H), 4.74-4.44 (m, 1.5H), 4.29-3.39 (m, 6H), 3.22-2.36 (m, 10.5H), 2.29 (s, 1.5H), 2.26 (s, 1.5H), 2.03 (br s, 2H), 1.59-1.16 (m, 6H), 1.13-0.80 (m, 7H), 0.77-0.70 (m, 1.5H), 0.63-0.57 (m, 1.5H); MS(ESI$^+$) m/z 791.6 (M+H)$^+$.

Example 168

N,N-Dibutyl-1-(4-(naphthalen-2-ylsulfonylcarbamoyl)-2-(1,2,3,4-tetrahydroisoquinoline-2-carbonyl)phenyl)-1H-pyrazole-3-carboxamide Intermediate 168A N,N-Dibutyl-1H-pyrazole-3-carboxamide

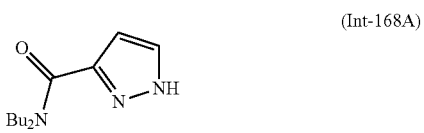

(Int-168A)

To 1H-pyrazole-3-carboxylic acid (Matrix, 350 mg, 3.12 mmol) in DMF (8.7 mL) were added EDC (658 mg, 3.43 mmol), HOBT (622 mg, 4.06 mmol), i-Pr₂EtN (1.6 mL, 9.37 mmol) and n-butylamine (550 μL, 3.28 mmol). The resulting solution was stirred at room temperature overnight. The reaction mixture was then quenched with sat. aq. NH₄Cl solution, washed with 1N aq. HCl solution and extracted with EtOAc (3×). The combined organic extracts were dried over Na₂SO₄, filtered and concentrated in vacuo. The crude oil was purified using flash column chromatography (gradient from 0% to 5% (MeOH/CH₂Cl₂) to give the title compound (530 mg, 76%) as a colorless crystalline solid. ¹H NMR (CD₃OD, 1.5:1 mixture of amide rotamers) δ 7.74 (br s, 1H), 6.67 (br s, 1H), 6.38 (br s, 1H), 3.70-3.39 (m, 4H), 1.64 (quin, J=7.6 Hz, 4H), 1.36 (dt, J=14.4, 7.0 Hz, 4H), 1.04-0.88 (m, 6H); MS(ESI$^+$) m/z 224.3 (M+H)$^+$.

Example 168

Following a procedure analogous to that for the synthesis of Intermediate 1E, N,N-dibutyl-1H-pyrazole-3-carboxamide (150 mg, 0.67 mmol) and ethyl 4-fluoro-3-(1,2,3,4-tetrahydroisoquinoline-2-carbonyl)benzoate (Intermediate 1D, 242 mg, 0.74 mmol) provided a crude oil which was used in the subsequent step without purification.

Following a procedure analogous to that for the synthesis of Intermediate 163C, the crude oil from above was converted to the title compound (212 mg, 48%). ¹H NMR (CDCl₃, mixture of amide rotamers) δ 8.76 (s, 1H), 8.13-7.82 (m, 7H), 7.72-7.57 (m, 3H), 7.24-6.98 (m, 3.5H), 6.82-6.66 (m, 1.5H), 4.97-4.66 (m, 1H), 4.17 (d, J=16.1 Hz, 0.5H), 4.05-3.65 (m, 2H), 3.61-3.19 (m, 4H), 3.14-3.08 (m, 0.5H), 2.94-2.78 (m, 1H), 2.72-2.59 (m, 0.5H), 2.54-2.37 (m, 0.5H), 1.67-1.08 (m, 7.5H), 0.93 (td, J=18.0, 7.3 Hz, 3.5H), 0.80 (t, J=7.3 Hz, 3H); MS(ESI$^+$) m/z 692.4 (M+H)$^+$.

Example 169

N,N-Dibutyl-4-chloro-1-(4-(naphthalen-2-ylsulfonylcarbamoyl)-2-(1,2,3,4-tetrahydroisoquinoline-2-carbonyl)phenyl)-1H-pyrazole-3-carboxamide

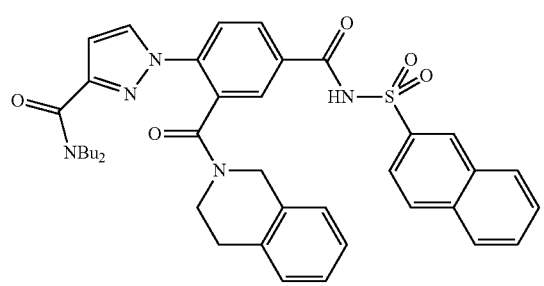

(168)

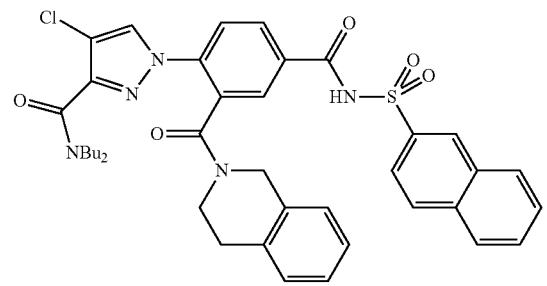

(169)

Intermediate 169A

N,N-Dibutyl-4-chloro-1H-pyrazole-3-carboxamide

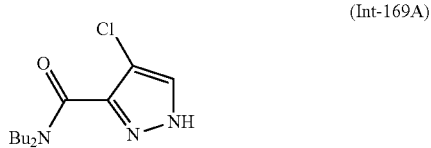
(Int-169A)

Following a procedure analogous to that for the synthesis of Intermediate 168A, 4-chloro-1H-pyrazole-3-carboxylic acid (Oakwood, 250 mg, 1.71 mmol) was converted to the title compound (433 mg, 91%). $^1$H NMR (CD$_3$OD) δ 8.00 (s, 1H), 7.80 (s, 1H), 3.61-3.47 (m, 2H), 3.37 (t, J=7.7 Hz, 2H), 1.74-1.63 (m, 2H), 1.56 (t, J=7.6 Hz, 2H), 1.50-1.38 (m, 2H), 1.29-1.12 (m, 2H), 1.01 (t, J=7.4 Hz, 3H), 0.82 (t, J=7.4 Hz, 3H); MS(ESI$^+$) m/z 258.2 (M+H)$^+$.

Intermediate 169B

Ethyl 4-(4-chloro-3-(dibutylcarbamoyl)-1H-pyrazol-1-yl)-3-(1,2,3,4-tetrahydroisoquinoline-2-carbonyl)benzoate

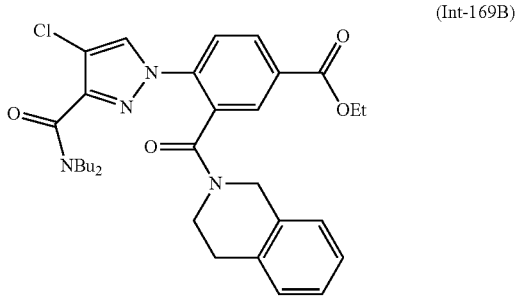
(Int-169B)

Following a procedure analogous to that for the synthesis of Intermediate 1E, N,N-dibutyl-4-chloro-1H-pyrazole-3-carboxamide (100 mg, 0.39 mmol) and ethyl 4-fluoro-3-(1,2,3,4-tetrahydroisoquinoline-2-carbonyl)benzoate (Intermediate 1D, 140 mg, 0.43 mmol) were converted to the title compound (156 mg, 71%). $^1$H NMR (CDCl$_3$, mixture of amide rotamers) δ 8.23-8.16 (m, 1H), 8.12-8.06 (m, 1H), 7.98-7.85 (m, 1H), 7.71-7.58 (m, 1H), 7.26-7.04 (m, 3.5H), 6.78 (d, J=7.5 Hz, 0.5H), 4.99-4.70 (m, 1H), 4.45-4.24 (m, 2.5H), 4.17-4.01 (m, 1H), 3.79-3.73 (m, 0.5H), 3.57-3.15 (m, 5H), 3.11-2.87 (m, 1H), 2.74 (t, J=5.8 Hz, 1H), 1.67-1.06 (m, 10.5H), 1.00-0.86 (m, 3.5H), 0.86-0.73 (m, 3H); MS(ESI$^+$) m/z 565.3 (M+H)$^+$.

Intermediate 169C 4-(4-Chloro-3-(dibutylcarbamoyl)-1H-pyrazol-1-yl)-3-(1,2,3,4-tetrahydroisoquinoline-2-carbonyl)benzoic acid

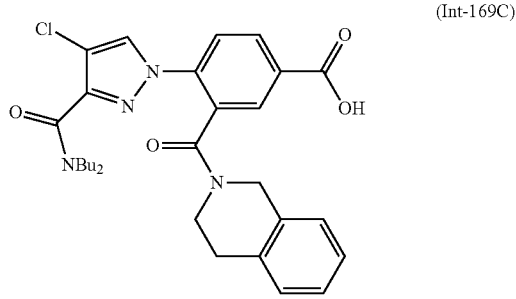
(Int-169C)

Following a procedure analogous to that for the synthesis of Intermediate 1F, ethyl 4-(4-chloro-3-(dibutylcarbamoyl)-1H-pyrazol-1-yl)-3-(1,2,3,4-tetrahydroisoquinoline-2-carbonyl)benzoate (155 mg, 0.27 mmol) was converted to the title compound (138 mg, 94%). MS(ESI$^+$) m/z 537.3 (M+H)$^+$.

Example 169

Following a procedure analogous to that for the synthesis of Example 1,4-(4-chloro-3-(dibutylcarbamoyl)-1H-pyrazol-1-yl)-3-(1,2,3,4-tetrahydroisoquinoline-2-carbonyl)benzoic acid (39 mg, 0.072 mmol) was converted to the title compound (29 mg, 54%). $^1$H NMR (DMSO-d$_6$, 2:1 mixture of amide rotamers) δ 8.79-8.58 (m, 2H), 8.29-7.92 (m, 6H), 7.88-7.63 (m, 3H), 7.28-7.03 (m, 3.5H), 6.97 (d, J=7.8 Hz, 0.5H), 4.79-4.61 (m, 1.5H), 4.51 (d, J=15.8 Hz, 0.5H), 4.26 (d, J=16.1 Hz, 0.5H), 3.89-3.84 (m, 0.5H), 3.67-3.61 (m, 0.5H), 3.21-2.60 (m, 6.5H), 1.51-1.36 (m, 0.5H), 1.30-0.89 (m, 7.5), 0.86 (t, J=7.4 Hz, 1H), 0.79 (t, J=7.2 Hz, 2H), 0.68 (t, J=7.4 Hz, 2H), 0.60 (t, J=7.4 Hz, 1H); MS(ESI$^+$) m/z 726.3 (M+H)$^+$.

Example 170

N,N-Dibutyl-4-chloro-5-(2-hydroxyethyl)-1-(4-(naphthalen-2-ylsulfonylcarbamoyl)-2-(1,2,3,4-tetrahydroisoquinoline-2-carbonyl)phenyl)-1H-pyrazole-3-carboxamide

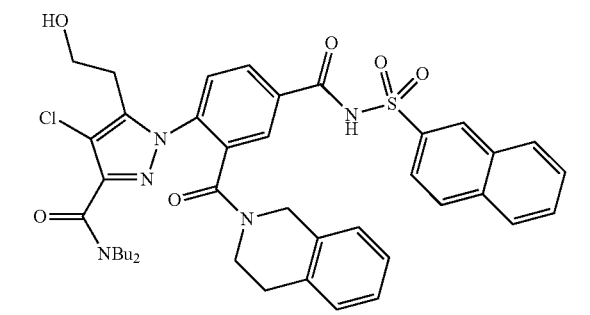
(170)

Intermediate 170A

Ethyl 5-(2-(tetrahydro-2H-pyran-2-yloxy)ethyl)-1H-pyrazole-3-carboxylate

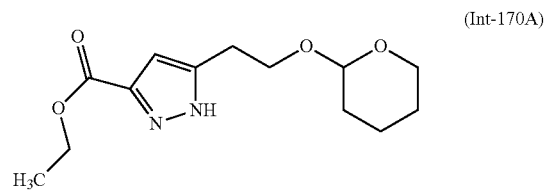 [SMILES: CCOC(=O)c1cc(CCOC2CCCCO2)[nH]n1]
(Int-170A)

CuCN (1.74 g, 19.4 mmol) and LiCl (4.95 g, 117.0 mmol) were dried under high vacuum with stirring at 160° C. overnight and then cooled to room temperature. To a solution of 2-(3-butynyloxy)tetrahydro-2H-pyran (3.1 mL, 19.5 mmol) in THF at −78° C. (40.0 mL) was added n-BuLi (12.2 mL, 19.4 mmol, 1.6M solution in hexane). The resulting solution was stirred at −78° C. for 1 h and then transferred to a −78° C. suspension of CuCN.6LiCl (6.70 g, 19.5 mmol, from above) in THF (60.0 mL). The resulting reaction mixture was warmed to −17° C. (dry ice/brine) and stirred for 1.5 h. A solution of ethyl diazoacetate (2.0 mL, 19.4 mmol) in THF (40.0 mL) was then added, and the reaction mixture was stirred at −17° C. for 30 min. The ice bath was removed and stirring was continued at room temperature for 4 h. The reaction mixture was quenched with sat. aq. $NH_4Cl$ solution and extracted with $Et_2O$ (3×). The combined organic extracts were washed with sat. aq. NaCl solution and then dried over $MgSO_4$, filtered and concentrated in vacuo. The crude oil was purified using flash column chromatography to give the title compound (2.76 g, 53%). $^1H$ NMR (DMSO-$d_6$) δ 6.55 (br s, 1H), 4.64-4.53 (m, 1H), 4.24 (q, J=7.0 Hz, 2H), 3.83 (td, J=9.7, 6.8 Hz, 1H), 3.72-3.53 (m, 2H), 3.47-3.34 (m, 1H), 2.88 (t, J=6.3 Hz, 2H), 1.76-1.52 (m, 2H), 1.51-1.35 (m, 4H), 1.27 (t, J=7.0 Hz, 3H); MS(ESI$^+$) m/z 269.2 (M+H)$^+$.

Intermediate 170B

N,N-Dibutyl-5-(2-(tetrahydro-2H-pyran-2-yloxy)ethyl)-1H-pyrazole-3-carboxamide

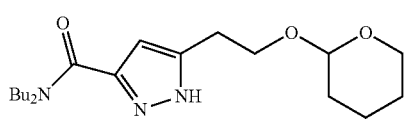
(Int-170B)

Following a procedure analogous to that for the synthesis of Intermediate 1B, ethyl 5-(2-(tetrahydro-2H-pyran-2-yloxy)ethyl)-1H-pyrazole-3-carboxylate (2.15 g, 8.01 mmol) was converted to the title compound (2.35 g, 83%). MS(ESI$^+$) m/z 352.4 (M+H)$^+$.

Intermediate 170C

N,N-Dibutyl-4-chloro-5-(2-(tetrahydro-2H-pyran-2-yloxy)ethyl)-1H-pyrazole-3-carboxamide

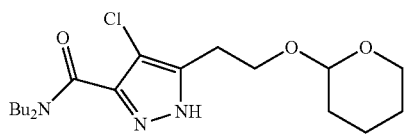
(Int-170C)

Following a procedure analogous to that for the synthesis of Intermediate 1A, N,N-dibutyl-5-(2-(tetrahydro-2H-pyran-2-yloxy)ethyl)-1H-pyrazole-3-carboxamide (355 mg, 1.01 mmol) was converted to the title compound (327 mg, 79%). $^1H$ NMR (CD$_3$OD) δ 4.60 (t, J=3.4 Hz, 1H), 3.94 (td, J=9.7, 6.5 Hz, 1H), 3.79-3.61 (m, 2H), 3.59-3.41 (m, 3H), 3.39-3.25 (m, 2H), 3.04-2.91 (m, 2H), 1.87-1.34 (m, 12H), 1.27-1.09 (m, 2H), 0.99 (t, J=7.3 Hz, 3H), 0.81 (t, J=7.4 Hz, 3H); MS(ESI$^+$) m/z 386.3 (M+H)$^+$.

Intermediate 170D

Ethyl 4-(4-chloro-3-(dibutylcarbamoyl)-5-(2-(tetrahydro-2H-pyran-2-yloxy)ethyl)-1H-pyrazol-1-yl)-3-(1,2,3,4-tetrahydroisoquinoline-2-carbonyl)benzoate

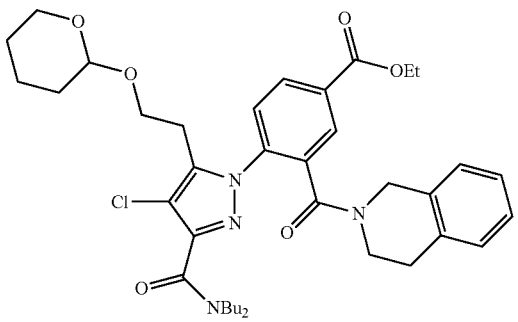
(Int-170D)

Following a procedure analogous to that for the synthesis of Intermediate 1E, N,N-dibutyl-4-chloro-5-(2-(tetrahydro-2H-pyran-2-yloxy)ethyl)-1H-pyrazole-3-carboxamide (407 mg, 1.06 mmol) and ethyl 4-fluoro-3-(1,2,3,4-tetrahydroisoquinoline-2-carbonyl)benzoate (380 mg, 1.16 mmol) were converted to the title compound (219 mg, 30%). $^1H$ NMR (CD$_3$OD, mixture of amide rotamers) δ 8.26 (td, J=8.4, 1.8 Hz, 1H), 8.19-8.10 (m, 1H), 7.98 (d, J=8.1 Hz, 1H), 7.29-7.07 (m, 3.5H), 6.94 (d, J=7.5 Hz, 0.5H), 4.71-4.48 (m, 2H), 4.47-4.39 (m, 2H), 4.16-3.86 (m, 1H), 3.80-3.37 (m, 5H), 3.26-2.58 (m, 5H), 1.87-0.74 (m, 22H), 0.72-0.66 (m, 1H); MS(ESI$^+$) m/z 609.3 (M+H−THP)$^+$.

Intermediate 170E

N,N-Dibutyl-4-chloro-1-(4-(naphthalen-2-ylsulfonylcarbamoyl)-2-(1,2,3,4-tetrahydroisoquinoline-2-carbonyl)phenyl)-5-(2-(tetrahydro-2H-pyran-2-yloxy)ethyl)-1H-pyrazole-3-carboxamide

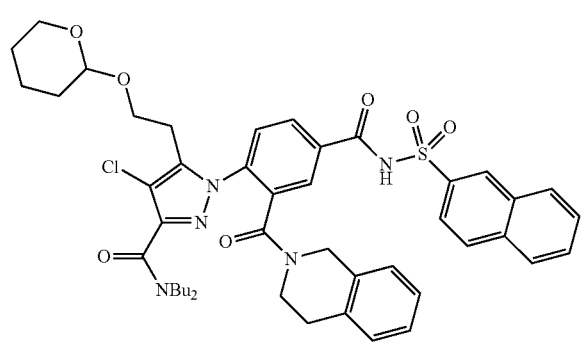
(Int-170E)

Following a procedure analogous to that for the synthesis of Intermediate 163C, ethyl 4-(4-chloro-3-(dibutylcarbamoyl)-5-(2-(tetrahydro-2H-pyran-2-yloxy)ethyl)-1H-pyrazol- 1-yl)-3-(1,2,3,4-tetrahydroisoquinoline-2-carbonyl)benzoate (141 mg, 0.20 mmol) was converted to the title compound (104 mg, 60%); MS(ESI⁺) m/z 770.3 (M+H-THP)⁺.

Example 170

To a solution of N,N-dibutyl-4-chloro-1-(4-(naphthalen-2-ylsulfonylcarbamoyl)-2-(1,2,3,4-tetrahydroisoquinoline-2-carbonyl)phenyl)-5-(2-(tetrahydro-2H-pyran-2-yloxy)ethyl)-1H-pyrazole-3-carboxamide (510 mg, 0.60 mmol) in MeOH (6.0 mL) was added conc. HCl (75 μL, 0.90 mmol). The resulting reaction mixture was stirred at room temperature for 45 min and then concentrated in vacuo. The residue was purified by flash column chromatography (gradient from 0% to 5% MeOH/CH₂Cl₂) to give the title compound (422 mg, 84%) as an off-white solid. ¹H NMR (CD₃OD, 2:1 mixture of amide rotamers) δ 8.74 (s, 1H), 8.14-8.04 (m, 4H), 8.03-7.96 (m, 2H), 7.87-7.80 (m, 1H), 7.75-7.65 (m, 2H), 7.25-7.06 (m, 3.5H), 6.92 (d, J=7.5 Hz, 0.5H), 5.00-4.92 (m, 1H), 4.65-4.44 (m, 1H), 4.12-3.95 (m, 0.5H), 3.85-2.69 (m, 1H), 2.54 (br s, 0.5H), 1.52-0.85 (m, 11H), 0.77 (t, J=7.4 Hz, 2H), 0.67 (t, J=7.4 Hz, 1H); MS(ESI⁺) m/z 770.4 (M+H)⁺.

Example 171

2-(4-Chloro-3-(dibutylcarbamoyl)-1-(4-(naphthalen-2-ylsulfonylcarbamoyl)-2-(1,2,3,4-tetrahydroisoquinoline-2-carbonyl)phenyl)-1H-pyrazol-5-yl)acetic acid (171)

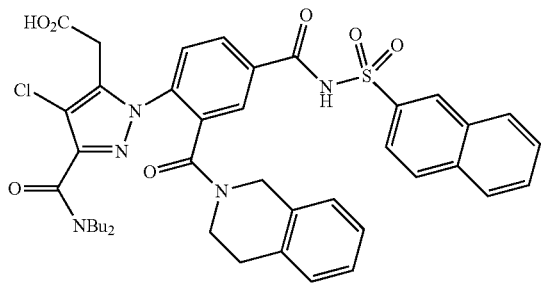

To N,N-dibutyl-4-chloro-5-(2-hydroxyethyl)-1-(4-(naphthalen-2-ylsulfonylcarbamoyl)-2-(1,2,3,4-tetrahydroisoquinoline-2-carbonyl)phenyl)-1H-pyrazole-3-carboxamide (Example 170, 27 mg, 0.035 mmol) in acetone (640 μL) was added Jones reagent (39 μL, 0.11 mmol). The resulting reaction mixture was stirred at room temperature for 25 min. Additional Jones reagent (39 μL, 0.11 mmol) was added and stirring was continued for 1.5 h. The reaction mixture was then quenched with i-PrOH followed by water. The aqueous layer was extracted with EtOAc (3×), and the combined organics were washed with sat. aq. NaCl solution and dried over Na₂SO₄. After filtering through a pipette containing a small plug of CELITE®, concentration in vacuo afforded a yellow oil. The crude oil was purified by preparative HPLC to give the title compound (6 mg, 22%) as a white solid after lyophilization. ¹H NMR (CD₃OD, 2:1 mixture of amide rotamers) δ 8.56 (s, 1H), 8.19 (ddd, J=8.4 Hz, 3.2, 1.9 1H), 8.12 (d, J=1.8 Hz, 1H), 8.04-7.99 (m, 2H), 7.96-7.90 (m, 2H), 7.85 (dd, J=12.8, 8.4 Hz, 1H), 7.63-7.54 (m, 2H), 7.25-7.06 (m, 3.5H), 6.94 (d, J=7.0 Hz, 0.5H), 4.77-4.41 (m, 1.5H), 4.09 (br s, 0.5H), 3.79-3.38 (m, 5H), 3.24-2.67 (m, 5H), 1.60-0.84 (m, 11H), 0.78 (t, J=7.3 Hz, 2H), 0.71-0.65 (m, 1H); MS(ESI⁺) m/z 784.3 (M+H)⁺.

Example 172

N,N-Dibutyl-4-chloro-5-(2-(cyclopropanesulfonamido)-2-oxoethyl)-1-(4-(naphthalen-2-ylsulfonylcarbamoyl)-2-(1,2,3,4-tetrahydroisoquinoline-2-carbonyl)phenyl)-1H-pyrazole-3-carboxamide (172)

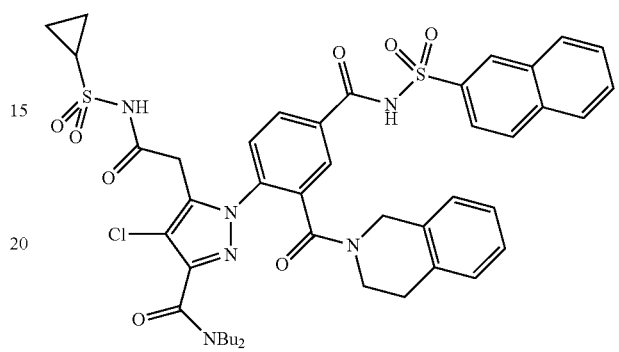

To a solution of 2-(4-chloro-3-(dibutylcarbamoyl)-1-(4-(naphthalen-2-ylsulfonylcarbamoyl)-2-(1,2,3,4-tetrahydroisoquinoline-2-carbonyl)phenyl)-1H-pyrazol-5-yl)acetic acid (Example 171, 24 mg, 0.031 mmol) in THF (625 μL) was added CDI (16 mg, 0.10 mmol). The resulting solution was heated at reflux for 30 min and then cooled to room temperature. Cyclopropanesulfonamide (14 mg, 0.12 mmol) was then added followed by DBU (24 μL, 0.16 mmol), and the resulting reaction mixture was stirred at room temperature overnight. The reaction mixture was then diluted with EtOAc, washed with 1N aq. HCl solution (2×) and extracted with EtOAc (3×). The combined organic extracts were washed with sat. aq. NaCl solution, dried over Na₂SO₄ and concentrated in vacuo. The residue was purified by preparative HPLC to give the title compound (5 mg, 16%) as a white solid after lyophilization. ¹H NMR (CD₃OD, 2:1 mixture of amide rotamers) δ 8.74 (s, 1H), 8.16-7.96 (m, 6H), 7.81-7.64 (m, 3H), 7.28-7.05 (m, 3.5H), 6.91 (d, J=7.5 Hz, 0.5H), 4.71-4.33 (m, 1.5H), 4.12-2.55 (m, 11.5H), 1.53-0.84 (m, 15H), 0.76 (t, J=7.4 Hz, 2H), 0.67 (t, J=7.4 Hz, 1H); MS(ESI⁺) m/z 887.5 (M+H)⁺.

Example 173

2-(4-Chloro-3-(dibutylcarbamoyl)-1-(4-(naphthalen-2-ylsulfonylcarbamoyl)-2-(1,2,3,4-tetrahydroisoquinoline-2-carbonyl)phenyl)-1H-pyrazol-5-yl)ethyl carbamate (173)

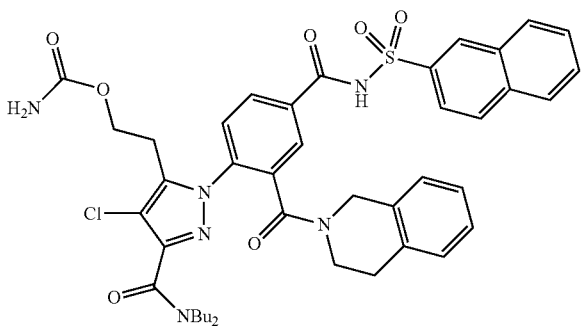

To a 0° C. solution of N,N-dibutyl-4-chloro-5-(2-hydroxyethyl)-1-(4-(naphthalen-2-ylsulfonylcarbamoyl)-2-(1,2,3,4-tetrahydroisoquinoline-2-carbonyl)phenyl)-1H-pyrazole-3-carboxamide (Example 170, 20 mg, 0.026 mmol) in $CH_2Cl_2$ (0.5 mL) was added trichloroacetyl isocyanate (4 μL, 0.031 mmol). After stirring at 0° C. for 30 min, $K_2CO_3$ (2 mg, 0.014 mmol) and MeOH (0.5 mL) were added. The ice bath was removed, and the reaction mixture was stirred at room temperature for 3 h. The reaction mixture was then diluted with water and EtOAc. The aqueous layer was extracted with EtOAc (2×), and the combined organic extracts were washed with sat. aq. NaCl solution, dried over $Na_2SO_4$, filtered and concentrated in vacuo to afford a colorless oil. The oil was dissolved in MeOH (3.0 mL) and water (3.0 mL) and $K_2CO_3$ (120 mg, 0.84 mmol) was added. The reaction mixture was stirred at room temperature for 30 minutes and then partitioned between EtOAc and $H_2O$. The layers were separated, and the aqueous layer was extracted with EtOAc (2×). The combined organic extracts were washed with sat. aq. NaCl solution, dried over $Na_2SO_4$, filtered and concentrated in vacuo to afford the title compound (10 mg, 44%) as a white solid. $^1H$ NMR ($CD_3OD$, 1.5:1 mixture of amide rotamers) δ 8.73 (br s, 1H), 8.13-8.04 (m, 4.5H), 8.02-7.95 (m, 2H), 7.78-7.64 (m, 3H), 7.23-7.08 (m, 4H), 7.02-6.88 (m, 0.5H), 4.94-4.89 (m, 1H), 4.67-4.41 (m, 1H), 4.25 (t, J=6.5 Hz, 2H), 4.18-4.05 (m, 1.5H), 4.01-3.71 (m, 1.5H), 3.65-3.46 (m, 4H), 3.37-3.34 (m, 2H), 3.02 (t, J=6.5 Hz, 1.5H), 2.92-2.77 (m, 1.5H), 1.68-1.53 (m, 2H), 1.31-1.25 (m, 3H), 1.20-1.17 (m, 1H), 0.99 (t, J=7.4 Hz, 2H), 0.94-0.86 (m, 3H), 0.78-0.73 (m, 2H), 0.68 (t, J=6.4 Hz, 1H); MS(ESI$^+$) m/z 813.5 (M+H)$^+$.

Example 174

2-(4-Chloro-3-(dibutylcarbamoyl)-1-(4-(naphthalen-2-ylsulfonylcarbamoyl)-2-(1,2,3,4-tetrahydroisoquinoline-2-carbonyl)phenyl)-1H-pyrazol-5-yl)ethyl 4-methylpiperazine-1-carboxylate (174)

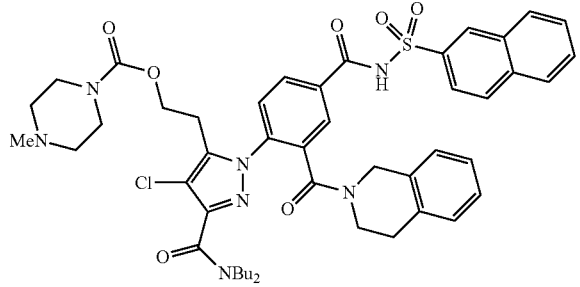

To a solution of N,N-dibutyl-4-chloro-5-(2-hydroxyethyl)-1-(4-(naphthalen-2-ylsulfonylcarbamoyl)-2-(1,2,3,4-tetrahydroisoquinoline-2-carbonyl)phenyl)-1H-pyrazole-3-carboxamide (Example 170, 110 mg, 0.14 mmol) in $CH_2Cl_2$ (3.0 mL) was added $Et_3N$ (22 μL, 0.16 mmol) followed by 4-nitrophenyl carbonochloridate (Aldrich, 32 mg, 0.16 mmol). After stirring at room temperature overnight, additional $Et_3N$ (22 μL, 0.16 mmol) was added. The reaction mixture was heated at reflux for 3 h and then at room temperature for 2 h. DMAP (20 mg, 0.16 mmol) was then added, and the reaction mixture was stirred at room temperature for 1 h. The reaction mixture was then diluted with $CHCl_3$ and sat. aq. NaCl solution. The aqueous layer was extracted with $CHCl_3$, and the combined organic extracts were dried over $Na_2SO_4$, filtered and concentrated in vacuo to give a crude oil which was used in the subsequent step without purification.

To a sealed tube containing the crude oil from above (44 mg, 0.047 mmol) in $CH_2Cl_2$ (1.5 mL) and THF (1.5 mL) was added 1-methylpiperazine (6 μL, 0.052 mmol) followed by $Et_3N$ (10 μL, 0.072 mmol). The sides of the tube were rinsed with 1:1 $CH_2Cl_2$/THF (1.0 mL) and the tube was sealed. The reaction mixture was stirred at room temperature for 3.5 h, then concentrated in vacuo and purified by preparative HPLC to give the title compound (9 mg, 21%). $^1H$ NMR (1:1 $CD_3OD:CDCl_3$, 1.5:1 mixture of amide rotamers) δ 8.59 (br s, 1H), 8.22-8.17 (m, 1H), 8.09-8.06 (m, 1H), 8.06-8.02 (m, 1H), 7.97 (d, J=7.8 Hz, 1H), 7.95-7.90 (m, 1.5H), 7.87 (d, J=7.5 Hz, 1H), 7.59-7.57 (m, 1H), 7.55-7.52 (m, 0.5H), 7.48 (dd, J=6.7, 8.3 Hz, 1H), 7.20-7.04 (m, 4.5H), 6.87 (d, J=7.5 Hz, 0.5H), 4.69-4.64 (m, 2H), 4.49 (s, 1H), 4.15-4.08 (m, 1H), 3.74-3.71 (m, 0.5H), 3.54-3.41 (m, 4H), 3.20-3.16 (m, 2H), 3.03-2.97 (m, 4.5H), 2.86-2.85 (m, 0.5H), 2.82-2.78 (m, 4.5H), 2.63 (s, 2H), 1.46-1.36 (m, 2.5H), 1.32-1.23 (m, 4H), 1.11-1.03 (m, 2H), 0.97-0.81 (m, 5H), 0.73 (t, J=7.4 Hz, 2H), 0.62 (t, J=7.4 Hz, 1.5H); MS(ESI$^+$) m/z 896.4 (M+H).

Example 175

2-(4-Chloro-3-(dibutylcarbamoyl)-1-(4-(naphthalen-2-ylsulfonylcarbamoyl)-2-(1,2,3,4-tetrahydroisoquinoline-2-carbonyl)phenyl)-1H-pyrazol-5-yl)ethyl 2-(4-methylpiperazin-1-yl)ethylcarbamate (175)

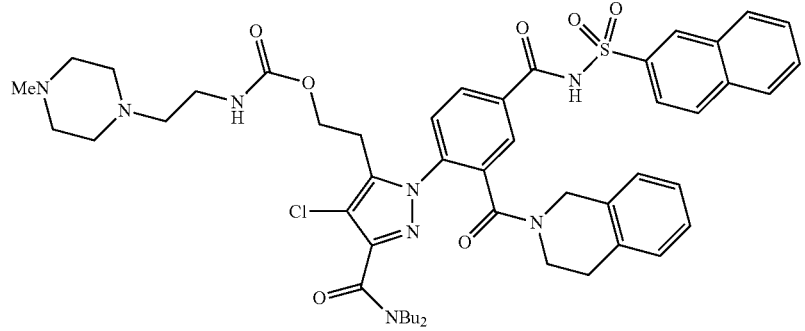

Following a procedure analogous to that for the synthesis of Example 174, N,N-dibutyl-4-chloro-5-(2-hydroxyethyl)-1-(4-(naphthalen-2-ylsulfonylcarbamoyl)-2-(1,2,3,4-tetrahydroisoquinoline-2-carbonyl)phenyl)-1H-pyrazole-3-carboxamide (Example 170, 110 mg, 0.14 mmol) and 2-(4-methylpiperazin-1-yl)ethanamine (7 mg, 0.052 mmol) were converted to the title compound (8 mg, 16%). $^1$H NMR (1:1 CD$_3$OD:CDCl$_3$, mixture of amide rotamers) δ 8.55 (s, 1H), 8.21 (d, J=8.3 Hz, 1H), 8.13-8.10 (m, 1H), 8.04-8.00 (m, 1H), 7.97-7.94 (m, 1.5H), 7.91 (d, J=8.6 Hz, 1H), 7.87 (d, J=7.5 Hz, 1H), 7.60-7.57 (m, 0.5H), 7.55-7.52 (m, 1H), 7.42-7.37 (m, 1H), 7.22-7.05 (m, 4.5H), 6.87 (d, J=7.5 Hz, 0.5H), 4.77-4.70 (m, 2H), 4.52-4.42 (m, 2H), 4.01-3.80 (m, 1H), 3.74-3.62 (m, 1H), 3.41-3.36 (m, 1H), 3.24-3.02 (m, 8H), 3.00-2.96 (m, 1.5H), 2.89-2.84 (m, 4.5H), 2.82-2.76 (m, 2H), 2.64-2.63 (m, 2H), 2.30 (br s, 2H), 1.46-1.02 (m, 9.5H), 0.95 (t, J=7.4 Hz, 1H), 0.90-0.81 (m, 3.5H), 0.72 (t, J=7.2 Hz, 2H), 0.62 (t, J=7.4 Hz, 1H); MS(ESI$^+$) m/z 939.5 (M+H).

Example 176 tert-Butyl 3-(N-butyl-4-chloro-1-(4-(7-iodonaphthalen-2-ylsulfonylcarbamoyl)-2-(1,2,3,4-tetrahydroisoquinoline-2-carbonyl)phenyl)-5-methyl-1H-pyrazole-3-carboxamido)propanoate

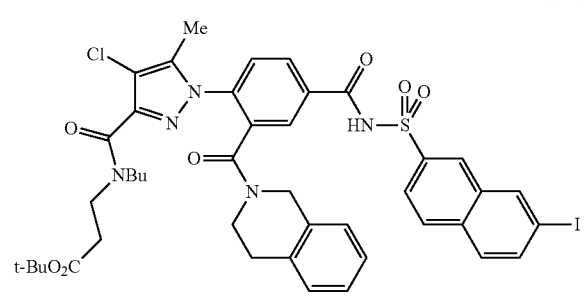

(176)

Intermediate 176A

Ethyl 4-chloro-1-(4-(7-iodonaphthalen-2-ylsulfonylcarbamoyl)-2-(1,2,3,4-tetrahydroisoquinoline-2-carbonyl)phenyl)-5-methyl-1H-pyrazole-3-carboxylate

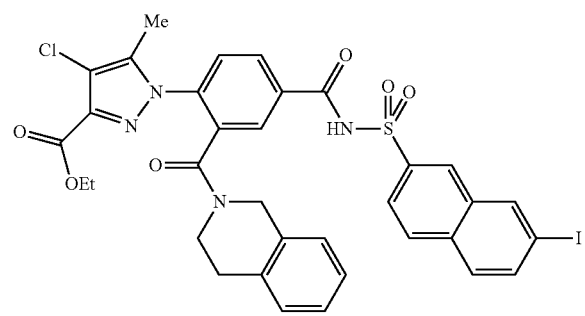

(Int-176A)

Following a procedure analogous to that for the synthesis of Example 1,4-(4-chloro-3-(ethoxycarbonyl)-5-methyl-1H-pyrazol-1-yl)-3-(1,2,3,4-tetrahydroisoquinoline-2-carbonyl)benzoic acid (Intermediate 122D, 60 mg, 0.13 mmol) and 7-iodonaphthalene-2-sulfonamide (Intermediate 11, 43 mg, 0.13 mmol) were converted to the title compound (27 mg, 25%) after purification by preparative HPLC. $^1$H NMR (CD$_3$OD, 2:1 mixture of amide rotamers) δ 8.62 (s, 1H), 8.53 (s, 1H), 8.15-7.99 (m, 4H), 7.98-7.91 (m, 1H), 7.79-7.63 (m, 2H), 7.23-7.05 (m, 3.5H), 6.97 (s, 0.5H), 6.89 (d, J=7.3 Hz, 1H), 4.75-4.53 (m, 1H), 4.47 (s, 1H), 4.43 (q, J=7.0 Hz, 1H), 4.17-4.05 (m, 1H), 3.83-3.45 (m, 2H), 3.19-2.73 (m, 2H), 2.32 (s, 2H), 2.24 (s, 1H), 1.18 (t, J=7.0 Hz, 1H), 1.10 (t, J=7.2 Hz, 2H); MS (ESI$^+$) m/z 783.0 (M+H)$^+$.

Intermediate 176B

4-Chloro-1-(4-(7-iodonaphthalen-2-ylsulfonylcarbamoyl)-2-(1,2,3,4-tetrahydroisoquinoline-2-carbonyl)phenyl)-5-methyl-1H-pyrazole-3-carboxylic acid

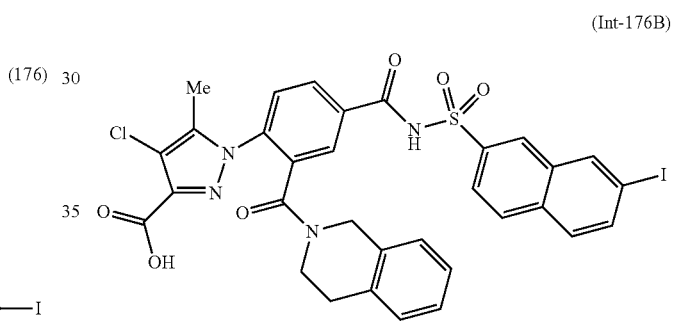

(Int-176B)

Following a procedure analogous to that for the synthesis of Example 45, ethyl 4-chloro-1-(4-(7-iodonaphthalen-2-ylsulfonylcarbamoyl)-2-(1,2,3,4-tetrahydroisoquinoline-2-carbonyl)phenyl)-5-methyl-1H-pyrazole-3-carboxylate (26 mg, 0.033 mmol) was converted to the title compound (25 mg, 95%). MS(ESI$^+$) m/z 755.0 (M+H)$^+$.

Example 176

Following a procedure analogous to that for the synthesis of Example 122, 4-chloro-1-(4-(7-iodonaphthalen-2-ylsulfonylcarbamoyl)-2-(1,2,3,4-tetrahydroisoquinoline-2-carbonyl)phenyl)-5-methyl-1H-pyrazole-3-carboxylic acid (25 mg, 0.033 mmol) and tert-butyl 3-(butylamino)propanoate (27 mg, 0.13 mmol) were converted to the title compound (18 mg, 57%). $^1$H NMR (CDCl$_3$, mixture of amide rotamers) δ 8.64 (s, 1H), 8.43 (s, 1H), 8.15-8.05 (m, 1H), 8.01-7.86 (m, 4H), 7.64 (d, J=8.6 Hz, 1H), 7.42-7.03 (m, 4.5H), 6.80 (d, J=7.9 Hz, 0.5H), 4.72 (d, J=11.0 Hz, 1H), 4.40-4.22 (m, 1H), 3.88-2.38 (m, 7.5), 2.33-2.13 (m, 3.5H), 1.63-1.22 (m, 13H), 1.07 (d, J=7.0 Hz, 1.5H), 0.98-0.84 (m, 1.5H), 0.81-0.63 (m, 2H); MS(ESI+) m/z 938.2 (M+H)+.

Example 177

N,N-Dibutyl-4-chloro-1-(4-(8-chloronaphthalen-2-ylsulfonylcarbamoyl)-2-((S)-3-(hydroxymethyl)-1,2,3,4-tetrahydroisoquinoline-2-carbonyl)phenyl)-5-methyl-1H-pyrazole-3-carboxamide (177)

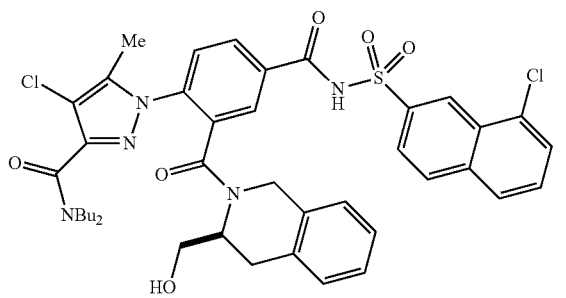

Following a procedure analogous to that for the synthesis of Example 1,4-(4-chloro-3-(dibutylcarbamoyl)-5-methyl-1H-pyrazol-1-yl)-3-(ethoxycarbonyl)benzoic acid (Intermediate 91D, 35 mg, 0.075 mmol) and 8-chloronaphthalene-2-sulfonamide (Intermediate 5, 27 mg, 0.11 mmol) provided a crude oil which was used in the subsequent step without purification.

The crude oil from above was subjected to a procedure analogous to that for the synthesis of Intermediate 164B. The resulting crude product was then subjected to a procedure analogous to that for the synthesis of Example 91 to give the title compound (14 mg, 44%). ¹H NMR (1:1 CD₃OD:CDCl₃, mixture of amide rotamers) δ 9.00 (s, 1H), 8.28-8.10 (m, 2.5H), 8.02-7.93 (m, 1.5H), 7.83 (d, J=8.1 Hz, 1H), 7.64 (d, J=7.5 Hz, 1H), 7.54-7.46 (m, 1H), 7.43-7.31 (m, 1H), 7.22-7.03 (m, 3.5H), 6.87 (br s, 0.5H), 5.22 (d, J=18.0 Hz, 0.5H), 4.36-4.06 (m, 2H), 3.64-2.71 (m, 8H), 2.35-2.17 (m, 3.5H), 1.63-0.54 (m, 14H); MS(ESI+) m/z 804.2 (M+H)+.

Example 178

N-Butyl-4-chloro-N-(3,4-dichlorobenzyl)-1-(4-(8-(ethylsulfonyl)naphthalen-2-ylsulfonylcarbamoyl)-2-(1,2,3,4-tetrahydroisoquinoline-2-carbonyl)phenyl)-5-methyl-1H-pyrazole-3-carboxamide (178)

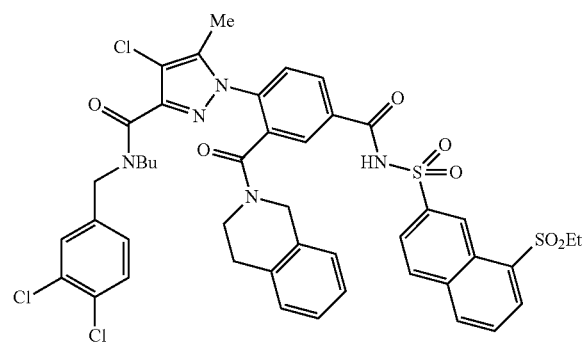

Following a procedure analogous to that for the synthesis of Example 1,4-(4-chloro-3-(ethoxycarbonyl)-5-methyl-1H-pyrazol-1-yl)-3-(1,2,3,4-tetrahydroisoquinoline-2-carbonyl)benzoic acid (Intermediate 122D, 17 mg, 0.037 mmol) and 8-(ethylsulfonyl)naphthalene-2-sulfonamide (Intermediate 14, 11 mg, 0.037 mmol) provided a crude oil which was used in the subsequent step without purification.

The crude oil from above was subjected to a procedure analogous to that for the synthesis of Intermediate 164B. The resulting crude oil was then subjected to procedure analogous to that used in the synthesis of Example 125 to give the title compound (1 mg, 3%). ¹H NMR (1:1 CD₃OD:CDCl₃, mixture of amide rotamers) δ 9.59 (s, 1H), 8.41-8.36 (m, 1H), 8.34-8.29 (m, 1H), 8.27-8.20 (m, 2H), 8.12-8.05 (m, 1H), 7.99-7.93 (m, 1H), 7.84 (t, J=7.8 Hz, 1H), 7.59-7.49 (m, 1H), 7.41-7.32 (m, 0.5H), 7.32-7.03 (m, 5.5H), 6.91-6.84 (m, 1H), 4.62-4.20 (m, 5H), 3.63 (d, J=6.4 Hz, 1H), 3.51-3.41 (m, 3H), 3.02 (t, J=7.9 Hz, 1H), 2.79 (br s, 2H), 2.31 (s, 1H), 2.27 (d, J=3.6 Hz, 1.5H), 2.19 (s, 0.5H), 1.49-0.79 (m, 8.5H), 0.71 (t, J=7.4 Hz, 1H), 0.65 (t, J=7.2 Hz, 0.5H); MS(ESI+) m/z 936.1 (M+H)+.

Example 179

N-Butyl-4-chloro-N-(3,4-dichlorobenzyl)-1-(4-(7-iodonaphthalen-2-ylsulfonylcarbamoyl)-2-(1,2,3,4-tetrahydroisoquinoline-2-carbonyl)phenyl)-5-methyl-1H-pyrazole-3-carboxamide (179)

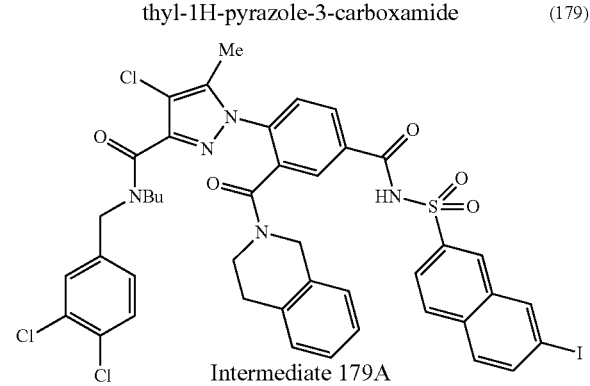

Intermediate 179A

4-Chloro-5-methyl-1H-pyrazole-3-carboxylic acid (Int-179A)

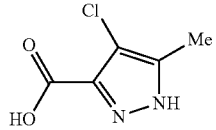

To a solution of ethyl 4-chloro-5-methyl-1H-pyrazole-3-carboxylate (Intermediate 1A, 2.01 g, 10.7 mmol) in MeOH (8.2 mL) and THF (8.2 mL) was added 2N aq. NaOH solution (27 mL, 53.3 mmol). The reaction mixture was stirred at room temperature overnight, then cooled to 0° C. and neutralized with 1N aq. HCl solution (pH=3-4). The resulting solid was collected by filtration and washed with water to give the title compound (1.50 g, 87%) as a white solid. ¹H NMR (DMSO-d₆) δ 2.19 (br s, 3H); MS (ESI+) m/z 160.9 (M+H)+.

Intermediate 179B

N-Butyl-4-chloro-N-(3,4-dichlorobenzyl)-5-methyl-1H-pyrazole-3-carboxamide (Int-179B)

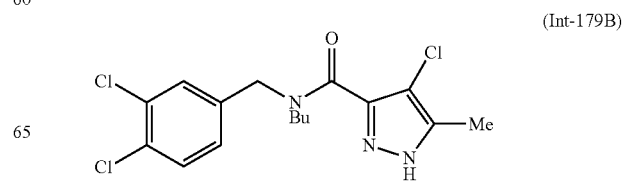

Following a procedure analogous to that for the synthesis of Intermediate 168A, 4-chloro-5-methyl-1H-pyrazole-3-carboxylic acid (1.50 g, 9.32 mmol) and N-(3,4-dichlorobenzyl)butan-1-amine (Intermediate 126, 2.16 g, 9.32 mmol) provided the title compound (1.67 g, 48%) as a colorless oil. $^1$H NMR (CDCl$_3$, 1:1 mixture of amide rotamers) δ 7.50-7.32 (m, 2H), 7.24-7.06 (m, 1H), 4.79-4.55 (m, 2H), 3.47-3.26 (m, 2H), 2.34-2.19 (m, 3H), 1.71-1.46 (m, 2H), 1.35 (br s, 1H), 1.18 (br s, 1H), 0.93 (d, J=6.4 Hz, 1.5H), 0.81 (d, J=6.8 Hz, 1.5H); MS(ESI$^+$) m/z 376.0 (M+H)$^+$.

Intermediate 179C

Benzyl 4-(3-(butyl(3,4-dichlorobenzyl)carbamoyl)-4-chloro-5-methyl-1H-pyrazol-1-yl)-3-(1,2,3,4-tetrahydroisoquinoline-2-carbonyl)benzoate

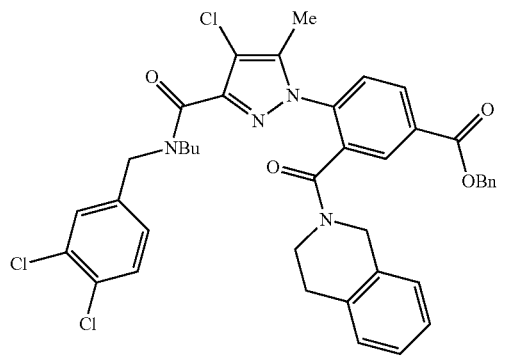

(Int-179C)

Following a procedure analogous to that for the synthesis of Intermediate 1E, N-butyl-4-chloro-N-(3,4-dichlorobenzyl)-5-methyl-1H-pyrazole-3-carboxamide (1.73 g, 4.62 mmol) and benzyl 4-fluoro-3-(1,2,3,4-tetrahydroisoquinoline-2-carbonyl)benzoate (Intermediate 122B, 1.80 g, 4.62 mmol) were converted to the title compound (2.20 g, 64%). $^1$H NMR (CDCl$_3$, mixture of amide rotamers) δ 8.24 (d, J=8.4 Hz, 1H), 8.16-8.09 (m, 1H), 7.53-7.03 (m, 12H), 6.98-6.76 (m, 1H), 5.41 (br s, 2H), 4.86-4.20 (m, 4H), 3.64-3.03 (m, 4H), 2.78 (br s, 2H), 2.37-2.17 (m, 3H), 1.61-1.38 (m, 1H), 1.36-1.21 (m, 2H), 1.18-1.01 (m, 1H), 0.97-0.83 (m, 2H), 0.80-0.67 (m, 1H); MS(ESI$^+$) m/z 745.2 (M+H)$^+$.

Intermediate 179D 4-(3-(Butyl(3,4-dichlorobenzyl)carbamoyl)-4-chloro-5-methyl-1H-pyrazol-1-yl)-3-(1,2,3,4-tetrahydroisoquinoline-2-carbonyl)benzoic acid

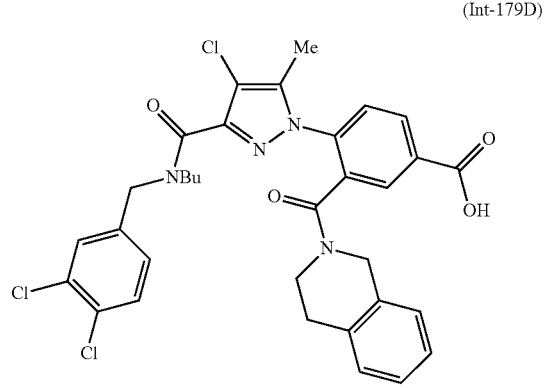

(Int-179D)

Following a procedure analogous to that for the synthesis of Intermediate 164B, benzyl 4-(3-(butyl(3,4-dichlorobenzyl)carbamoyl)-4-chloro-5-methyl-1H-pyrazol-1-yl)-3-(1,2,3,4-tetrahydroisoquinoline-2-carbonyl)benzoate (2.20 g, 2.96 mmol) was converted to the title compound (1.90 g, 98%). $^1$H NMR (DMSO-d$_6$, mixture of amide rotamers) δ 8.15 (d, J=8.4 Hz, 1H), 8.05 (d, J=2.2 Hz, 0.5H), 8.01-7.96 (m, 0.5H), 7.88-7.69 (m, 1H), 7.60-7.48 (m, 1.5H), 7.46-7.38 (m, 0.5H), 7.35-7.26 (m, 1H), 7.24-6.94 (m, 3H), 6.85 (d, J=7.5 Hz, 0.5H), 6.45-6.31 (m, 0.5H), 5.13 (br s, 0.5H), 4.85-4.15 (m, 4H), 3.74-3.36 (m, 2H), 3.23-2.92 (m, 1.5H), 2.82-2.60 (m, 2H), 2.31-2.11 (m, 3H), 1.45-1.08 (m, 3H), 1.05-0.90 (m, 1H), 0.82 (quin, J=7.2 Hz, 2H), 0.71-0.54 (m, 1H); MS (ESI$^+$) m/z 655.1 (M+H)$^+$.

Example 179

Following a procedure analogous to that for the synthesis of Example 1, 4-(3-(butyl(3,4-dichlorobenzyl)carbamoyl)-4-chloro-5-methyl-1H-pyrazol-1-yl)-3-(1,2,3,4-tetrahydroisoquinoline-2-carbonyl)benzoic acid (30 mg, 0.046 mmol) and 7-iodonaphthalene-2-sulfonamide (Intermediate 11, 18 mg, 0.055 mmol) were converted to the title compound (17 mg, 37%). $^1$H NMR (1:1 MeOD:CDCl$_3$, 2:1 mixture of amide rotamers) δ 8.59 (s, 1H), 8.44 (s, 1H), 8.07-8.03 (m, 2H), 7.97 (d, J=8.3 Hz, 1H), 7.92-7.88 (m, 2H), 7.68 (d, J=8.6 Hz, 1H), 7.53-7.47 (m, 1H), 7.30-7.03 (m, 5.5H), 6.88 (d, J=7.8 Hz, 0.5H), 6.84 (dd, J=6.0, 2.1 Hz, 1H), 4.79 (br s, 1H), 4.57-4.55 (m, 1H), 4.42 (d, J=9.2 Hz, 0.5H), 4.32-4.22 (m, 1.5H), 3.91 (br s, 1H), 3.58 (m, 1H), 3.47-3.44 (m, 1H), 3.00 (br s, 1.5H), 2.80-2.77 (m, 1.5H), 2.30-2.19 (m, 3H), 1.43-1.32 (m, 2H), 1.29-1.15 (m, 2H), 1.10-0.96 (m, 1H), 0.85 (dt, J=10.2, 7.3 Hz, 1.5H), 0.71 (t, J=7.4 Hz, 1H), 0.65 (t, J=7.4 Hz, 0.5H); MS(ESI$^+$) m/z 970.1 (M+H)$^+$.

Example 180

N-Butyl-4-chloro-N-(3,4-dichlorobenzyl)-5-methyl-1-(4-(7-(4-methylpiperazine-1-carbonyl)naphthalen-2-ylsulfonylcarbamoyl)-2-(1,2,3,4-tetrahydroisoquinoline-2-carbonyl)phenyl)-1H-pyrazole-3-carboxamide

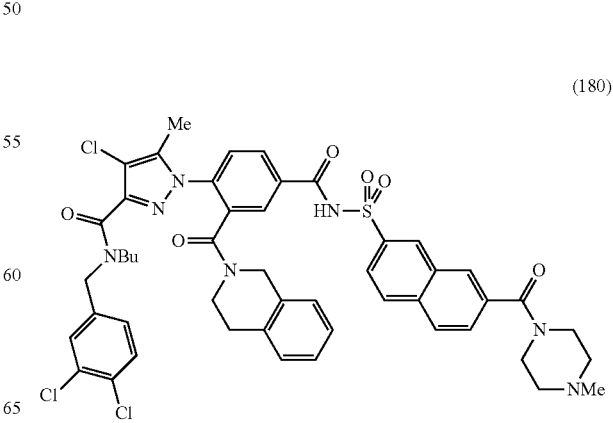

(180)

Intermediate 180A

Ethyl 7-(N-(4-(3-(butyl(3,4-dichlorobenzyl)carbamoyl)-4-chloro-5-methyl-1H-pyrazol-1-yl)-3-(1,2,3,4-tetrahydroisoquinoline-2-carbonyl)benzoyl)sulfamoyl)-2-naphthoate

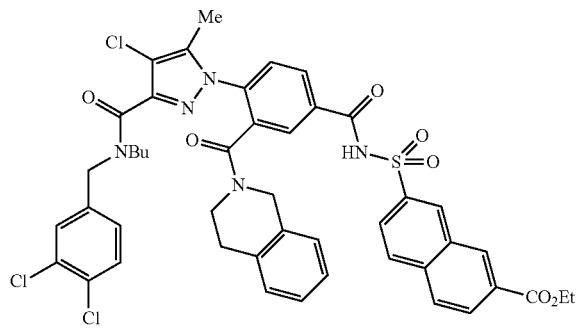

(Int-180A)

Following a procedure analogous to that for the synthesis of Example 1,4-(3-(butyl(3,4-dichlorobenzyl)carbamoyl)-4-chloro-5-methyl-1H-pyrazol-1-yl)-3-(1,2,3,4-tetrahydroisoquinoline-2-carbonyl)benzoic acid (Intermediate 179D, 100 mg, 0.18 mmol) and ethyl 7-sulfamoyl-2-naphthoate (Intermediate 16, 61 mg, 0.22 mmol) were converted to the title compound (84 mg, 57%). MS(ESI$^+$) m/z 812.2 (M+H)$^+$.

Intermediate 180B 7-(N-(4-(3-(Butyl(3,4-dichlorobenzyl)carbamoyl)-4-chloro-5-methyl-1H-pyrazol-1-yl)-3-(1,2,3,4-tetrahydroisoquinoline-2-carbonyl)benzoyl)sulfamoyl)-2-naphthoic acid

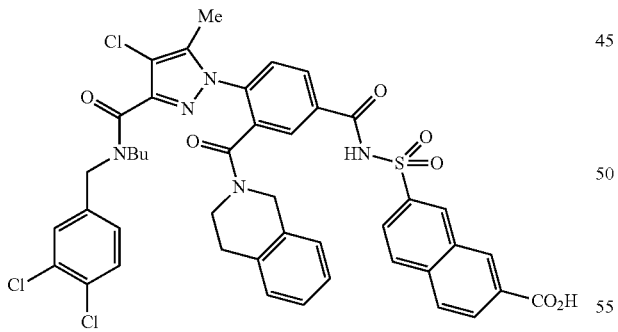

(Int-180B)

Following a procedure analogous to that for the synthesis of Intermediate 46A, ethyl 7-(N-(4-(3-(butyl(3,4-dichlorobenzyl)carbamoyl)-4-chloro-5-methyl-1H-pyrazol-1-yl)-3-(1,2,3,4-tetrahydroisoquinoline-2-carbonyl)benzoyl)sulfamoyl)-2-naphthoate (91 mg, 0.10 mmol) was converted to the title compound (73 mg, 83%). $^1$H NMR (DMSO-d$_6$, mixture of amide rotamers) δ 8.49 (s, 0.5H), 8.45 (s, 0.5H), 8.38 (s, 0.5H), 8.09 (dd, J=11.9, 8.4 Hz, 1.5H), 8.01-7.79 (m, 3H), 7.60-7.41 (m, 2H), 7.29-6.92 (m, 3.5H), 6.81 (d, J=8.4 Hz, 0.5H), 4.80-4.16 (m, 3H), 3.68-2.91 (m, 10.5H), 2.81-2.60 (m, 2H), 2.39-2.30 (m, 0.5H), 2.21-2.06 (m, 3H), 1.42-1.06 (m, 3H), 1.01-0.88 (m, 1.5H), 0.86-0.76 (m, 1H), 0.71-0.50 (m, 1.5H); MS(ESI$^+$) m/z 803.4 (M+H)$^+$.

Example 180

Following a procedure analogous to that for the synthesis of Intermediate 46A, 7-(N-(4-(3-(butyl(3,4-dichlorobenzyl)carbamoyl)-4-chloro-5-methyl-1H-pyrazol-1-yl)-3-(1,2,3,4-tetrahydroisoquinoline-2-carbonyl)benzoyl)sulfamoyl)-2-naphthoic acid (35 mg, 0.039 mmol) was converted to the title compound (8 mg, 21%). $^1$H NMR (1:1 CD$_3$OD:CDCl$_3$, 2:1 mixture of amide rotamers) δ 8.66 (s, 1H), 8.20-8.18 (m, 1H), 8.14-8.11 (m, 1H), 8.08-8.06 (m, 2H), 7.98 (d, J=8.9 Hz, 2H), 7.61 (d, J=8.6 Hz, 1H), 7.43-7.36 (m, 1.5H), 7.32-7.02 (m, 5H), 6.88-6.83 (m, 1.5H), 4.79 (br s, 1H), 4.65 (br s, 1H), 4.45 (s, 1H), 3.93-3.65 (m, 4H), 3.59 (br s, 1H), 3.48 (br s, 1H), 3.04-3.01 (m, 1.5H), 2.92 (br s, 3H), 2.78-2.76 (m, 1.5H), 2.64 (s, 3H), 2.28 (s, 1H), 2.24 (s, 1.5H), 2.17 (s, 0.5H), 1.44-1.34 (m, 1.5H), 1.29-1.18 (m, 3H), 1.07-0.95 (m, 1.5H), 0.85 (q, J=7.5 Hz, 1.5H), 0.71 (t, J=7.4 Hz, 1H), 0.65 (t, J=7.4 Hz, 0.5H); MS(ESI$^+$) m/z 970.4 (M+H)$^+$.

Example 181

N-Butyl-4-chloro-1-(4-(8-chloronaphthalen-2-ylsulfonylcarbamoyl)-2-((S)-3-(hydroxymethyl)-1,2,3,4-tetrahydroisoquinoline-2-carbonyl)phenyl)-N-(3,4-dichlorobenzyl)-5-methyl-1H-pyrazole-3-carboxamide

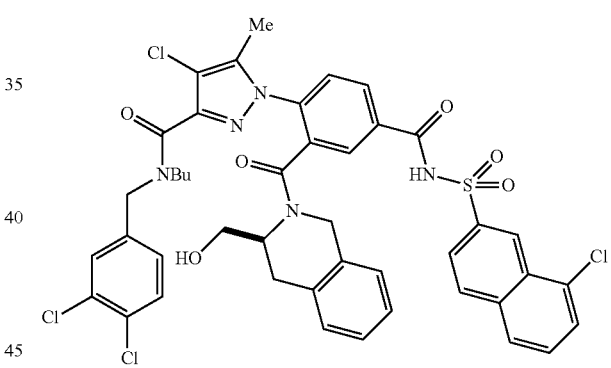

(181)

Intermediate 181A

1-Benzyl 3-ethyl 4-(3-(butyl(3,4-dichlorobenzyl)carbamoyl)-4-chloro-5-methyl-1H-pyrazol-1-yl)isophthalate

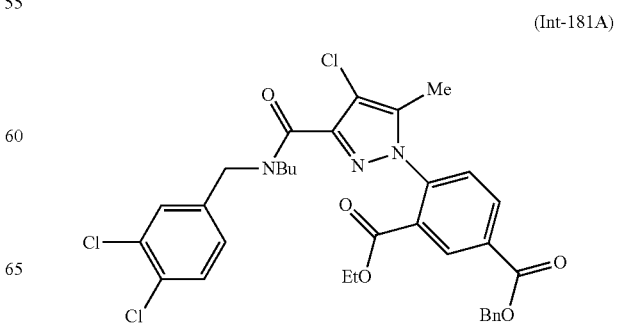

(Int-181A)

Following a procedure analogous to that for the synthesis of Intermediate 1E, 1-benzyl 3-ethyl 4-fluoroisophthalate (Intermediate 91B, 270 mg, 0.89 mmol) and N-butyl-4-chloro-N-(3,4-dichlorobenzyl)-5-methyl-1H-pyrazole-3-carboxamide (Intermediate 179B, 502 mg, 1.34 mmol) were converted to the title compound (458 g, 78%). ¹H NMR (CDCl₃, mixture of amide rotamers) δ 8.68 (dd, J=19.3, 1.9 Hz, 1H), 8.33 (dt, J=7.9, 2.0 Hz, 1H), 7.54-7.34 (m, 8H), 7.24-7.07 (m, 1H), 5.43 (d, J=3.1 Hz, 2H), 4.79-4.63 (m, 2H), 4.19 (q, J=7.3 Hz, 1H), 3.94 (q, J=7.2 Hz, 1H), 3.48-3.33 (m, 2H), 2.16 (d, J=6.6 Hz, 3H), 1.68-1.46 (m, 2H), 1.41-1.31 (m, 1H), 1.25-1.14 (m, 2.5H), 1.09 (t, J=7.2 Hz, 1.5H), 0.96-0.88 (m, 1.5H), 0.79 (t, J=7.4 Hz, 1.5H); MS(ESI⁺) m/z 656.0 (M+H)⁺.

Intermediate 181B 4-(3-(Butyl(3,4-dichlorobenzyl)carbamoyl)-4-chloro-5-methyl-1H-pyrazol-1-yl)-3-(ethoxycarbonyl)benzoic acid (Int-181B)

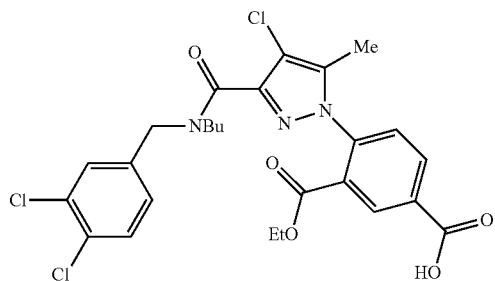

Following a procedure analogous to that for the synthesis of Intermediate 91D, 1-benzyl 3-ethyl 4-(3-(butyl(3,4-dichlorobenzyl)carbamoyl)-4-chloro-5-methyl-1H-pyrazol-1-yl)isophthalate (100 mg, 0.15 mmol) was converted to the title compound (86 mg, 100%). MS(ESI⁺) m/z 566.0 (M+H)⁺.

Example 181

Following a procedure analogous to that for the synthesis of Example 1,4-(3-(butyl(3,4-dichlorobenzyl)carbamoyl)-4-chloro-5-methyl-1H-pyrazol-1-yl)-3-(ethoxycarbonyl)benzoic acid (31 mg, 0.055 mmol) and 8-chloronaphthalene-2-sulfonamide (Intermediate 5, 16 mg, 0.066 mmol) were reacted to provide a crude oil which was used in the subsequent step without purification.

The crude oil from above was subjected to a procedure analogous to that for the synthesis of Intermediate 91F. The resulting crude oil was subjected to a procedure analogous to that for the synthesis of Example 91 to give the title compound (20 mg, 33%). ¹H NMR (1:1 CD₃OD:CDCl₃, mixture of amide rotamers) δ 9.01 (br s, 1H), 8.30-8.10 (m, 3H), 8.02-7.91 (m, 2H), 7.83 (d, J=8.0 Hz, 1H), 7.65 (d, J=7.5 Hz, 1H), 7.55-6.84 (m, 7.5H), 6.80-6.61 (m, 0.5H), 5.26-4.98 (m, 1H), 4.88-4.61 (m, 3H), 4.50-4.03 (m, 2H), 3.63-3.28 (m, 3H), 3.16-2.64 (m, 2H), 2.33-2.05 (m, 3H), 1.64-0.95 (m, 4H), 0.92-0.80 (m, 2H), 0.69-0.50 (m, 1H); MS(ESI⁺) m/z 908.1 (M+H)⁺.

Example 182

N-Butyl-4-chloro-1-(4-(8-chloronaphthalen-2-ylsulfonylcarbamoyl)-2-((S)-3-(2-hydroxyethyl)(methyl)amino)methyl)-1,2,3,4-tetrahydroisoquinoline-2-carbonyl)phenyl)-N-(3,4-dichlorobenzyl)-5-methyl-1H-pyrazole-3-carboxamide (182)

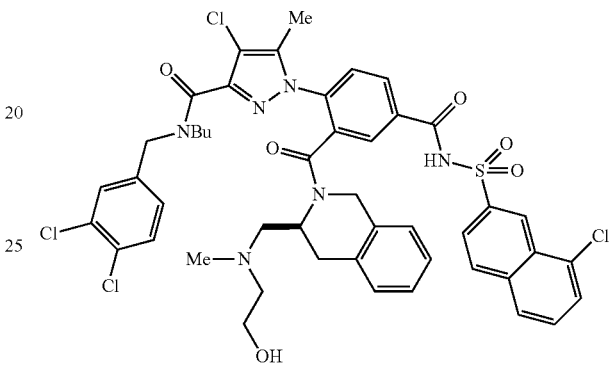

Following a procedure analogous to that for the synthesis of Example 91, 2-(3-(butyl-(3,4-dichlorobenzyl)carbamoyl)-4-chloro-5-methyl-1H-pyrazol-1-yl)-5-(8-chloronaphthalen-2-ylsulfonylcarbamoyl)benzoic acid (Example 181, 35 mg, 0.048 mmol) and (S)-2-(methyl((1,2,3,4-tetrahydroisoquinolin-3-yl)methyl)amino)ethanol (Intermediate 114, 11 mg, 0.048 mmol) were converted to the title compound (11 mg, 25%). ¹H NMR (1:1 CD₃OD:CDCl₃, mixture of amide rotamers) δ 8.63 (s, 1H), 8.30-8.19 (m, 1.5H), 8.11-7.82 (m, 4.5H), 7.65-7.54 (m, 2.5H), 7.51-6.87 (m, 6.5H), 5.17 (br s, 0.5H), 4.77 (br s, 2H), 4.46-4.05 (m, 0.5H), 3.88-3.45 (m, 2H), 3.40-2.78 (m, 7.5H), 2.71-2.62 (m, 6H), 2.35-2.12 (m, 2.5H), 1.54-1.02 (m, 4H), 0.98-0.48 (m, 3H); MS(ESI⁺) m/z 931.2 (M+H)⁺.

Example 183

N,N-Dibutyl-4-chloro-1-(2-((S)-3-(hydroxymethyl)-1,2,3,4-tetrahydroisoquinoline-2-carbonyl)-4-(8-(2-morpholinoethoxy)naphthalen-2-ylsulfonylcarbamoyl)phenyl)-5-methyl-1H-pyrazole-3-carboxamide (183)

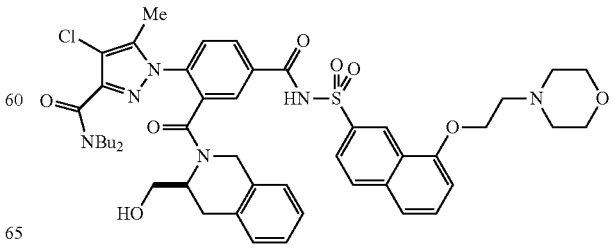

Intermediate 183A

Ethyl 2-(4-chloro-3-(dibutylcarbamoyl)-5-methyl-1H-pyrazol-1-yl)-5-(8-(2-morpholinoethoxy)naphthalen-2-ylsulfonylcarbamoyl)benzoate

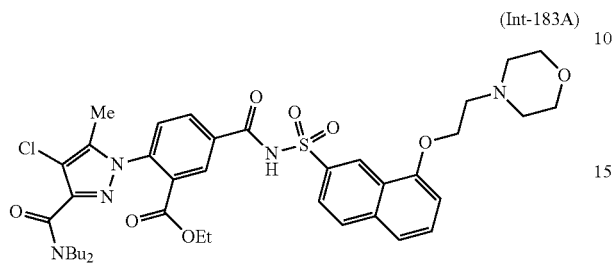
(Int-183A)

Following a procedure analogous to that for the synthesis of Example 1,4-(4-chloro-3-(dibutylcarbamoyl)-5-methyl-1H-pyrazol-1-yl)-3-(ethoxycarbonyl)benzoic acid (Intermediate 91D, 90 mg, 0.19 mmol) and 8-(2-morpholinoethoxy)naphthalene-2-sulfonamide (Intermediate 26, 65 mg, 0.19 mmol) were converted to the title compound (105 mg, 70%). MS(ESI$^+$) m/z 782.2 (M+H)$^+$.

Intermediate 183B 2-(4-Chloro-3-(dibutylcarbamoyl)-5-methyl-1H-pyrazol-1-yl)-5-(8-(2-morpholinoethoxy)naphthalen-2-ylsulfonylcarbamoyl)benzoic acid

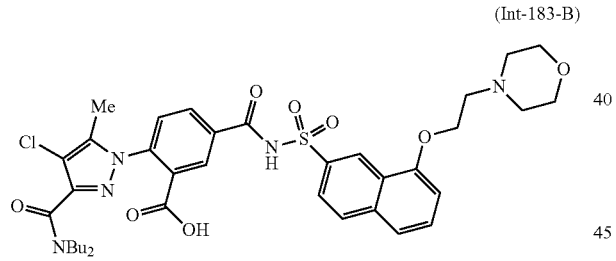
(Int-183-B)

Following a procedure analogous to that for the synthesis of Intermediate 91F, ethyl 2-(4-chloro-3-(dibutylcarbamoyl)-5-methyl-1H-pyrazol-1-yl)-5-(8-(2-morpholinoethoxy)naphthalen-2-ylsulfonylcarbamoyl)benzoate (105 mg, 0.13 mmol) was converted to the title compound (98 mg, 97%). MS(ESI$^+$) m/z 754.2 (M+H)$^+$.

Example 183

Following a procedure analogous to that for the synthesis of Example 91, 2-(4-chloro-3-(dibutylcarbamoyl)-5-methyl-1H-pyrazol-1-yl)-5-(8-(2-morpholinoethoxy) naphthalen-2-ylsulfonylcarbamoyl)benzoic acid (15 mg, 0.020 mmol) and (S)-(1,2,3,4-tetrahydroisoquinolin-3-yl)methanol (Aldrich, 10 mg, 0.060 mmol) were converted to the title compound (12 mg, 67%). $^1$H NMR (CD$_3$OD, 2:1 mixture of amide rotamers) δ 9.26-9.12 (m, 1H), 8.23 (d, J=1.5 Hz, 0.5H), 8.15-7.94 (m, 3.5H), 7.75-7.59 (m, 3H), 7.31-7.03 (m, 4.5H), 6.91 (s, 0.5H), 5.26 (d, J=17.8 Hz, 0.5H), 4.75-4.61 (m, 2H), 4.51 (br s, 0.5H), 4.37-2.51 (m, 19.5H), 2.44-2.34 (m, 0.5H), 2.33-2.24 (m, 3H), 1.63-0.0.63 (m, 1H), 0.74 (t, J=7.3 Hz, 2H), 0.64 (t, J=7.3 Hz, 1H); MS(ESI$^+$) m/z 899.3 (M+H)$^+$.

Example 184

N,N-Dibutyl-4-chloro-1-(2-((S)-3-((dimethylamino)methyl)-1,2,3,4-tetrahydroisoquinoline-2-carbonyl)-4-(8-(2-morpholinoethoxy)naphthalen-2-ylsulfonylcarbamoyl)phenyl)-5-methyl-1H-pyrazole-3-carboxamide

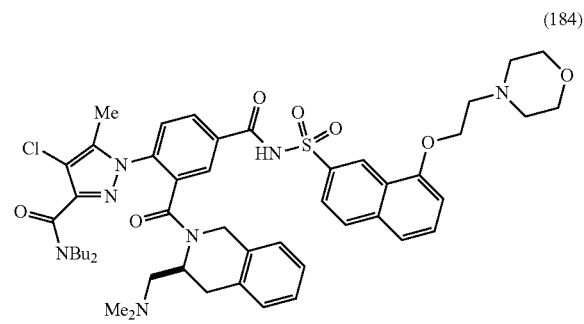
(184)

Intermediate 184A 1-(2-((S)-3-(Azidomethyl)-1,2,3,4-tetrahydroisoquinoline-2-carbonyl)-4-(8-(2-morpholinoethoxy)naphthalen-2-ylsulfonylcarbamoyl)phenyl)-N,N-dibutyl-4-chloro-5-methyl-1H-pyrazole-3-carboxamide

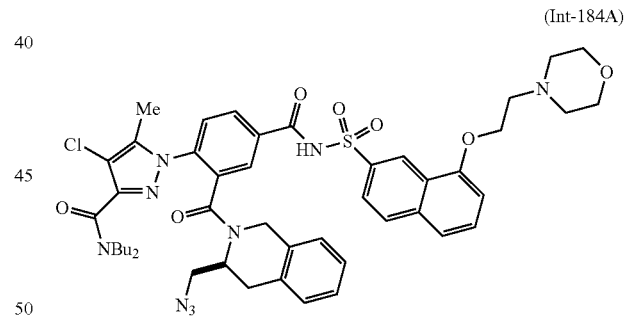
(Int-184A)

Following a procedure analogous to that for the synthesis of Example 91, 2-(4-chloro-3-(dibutylcarbamoyl)-5-methyl-1H-pyrazol-1-yl)-5-(8-(2-morpholinoethoxy) naphthalen-2-ylsulfonylcarbamoyl)benzoic acid (Intermediate 183B, 50 mg, 0.066 mmol) and (S)-3-(azidomethyl)-1,2,3,4-tetrahydroisoquinoline (Intermediate 92A, 37 mg, 0.20 mmol) were converted to the title compound (45 mg, 73%). $^1$H NMR (CD$_3$OD, 2:1 mixture of amide rotamers) δ 9.23-9.11 (m, 1H), 8.21 (d, J=1.9 Hz, 0.5H), 8.13-7.93 (m, 3.5H), 7.76-7.58 (m, 3H), 7.32-7.06 (m, 4.5H), 6.93 (d, J=7.2 Hz, 0.5H), 5.28 (d, J=18.3 Hz, 0.5H), 4.98 (br s, 0.5H), 4.73-4.62 (m, 2H), 4.59-3.21 (m, 15.5H), 3.18-2.69 (m, 3.5H), 2.58 (d, J=16.1 Hz, 0.5H), 2.48-2.40 (m, 0.5H), 2.34-2.21 (m, 3H), 1.55-0.82 (m, 1H), 0.78-0.70 (m, 2H), 0.69-0.55 (m, 1H); MS(ESI$^+$) m/z 924.3 (M+H)$^+$.

Intermediate 184B 1-(2-((S)-3-(Aminomethyl)-1,2,3,4-tetrahydroisoquinoline-2-carbonyl)-4-(8-(2-morpholinoethoxy)naphthalen-2-ylsulfonylcarbamoyl)phenyl)-N,N-dibutyl-4-chloro-5-methyl-1H-pyrazole-3-carboxamide (Int-184B)

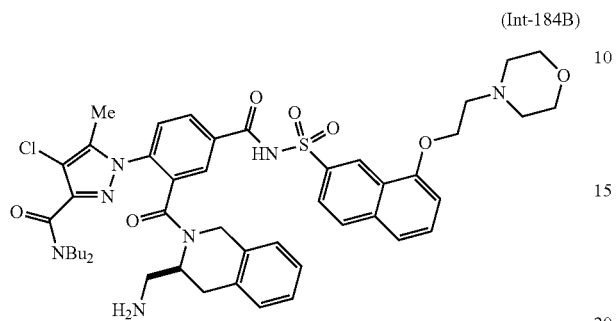

To a solution of (S)-1-(2-(3-(azidomethyl)-1,2,3,4-tetrahydroisoquinoline-2-carbonyl)-4-(8-(2-morpholinoethoxy)naphthalen-2-ylsulfonylcarbamoyl)phenyl)-N,N-dibutyl-4-chloro-5-methyl-1H-pyrazole-3-carboxamide (45 mg, 0.049 mmol) and PPh$_3$ (38 mg, 0.15 mmol) in THF (4.0 mL) and water (0.4 mL) was added 1N aq. NaOH solution (0.2 mL, 0.20 mmol). The resulting reaction mixture was heated at 50° C. for 3 h and then acidified (pH=1) with 1N aq. HCl solution. The solvent was removed in vacuo, and the residue was purified by preparative HPLC to give the title compound (33 mg, 72%) as a white solid. $^1$H NMR (CD$_3$OD, mixture of amide rotamers) δ 9.16 (s, 1H), 8.29-7.88 (m, 4H), 7.83-7.58 (m, 3H), 7.40-7.08 (m, 4H), 6.99 (br s, 1H), 5.04 (br s, 0.5H), 4.76-4.41 (m, 4H), 4.27-2.66 (m, 18.5H), 2.42-2.20 (m, 3H), 1.64-0.72 (m, 13H), 0.60 (br s, 1H); MS(ESI$^+$) m/z 898.1 (M+H)$^+$.

Example 184

To a solution of (S)-1-(2-(3-(aminomethyl)-1,2,3,4-tetrahydroisoquinoline-2-carbonyl)-4-(8-(2-morpholinoethoxy)naphthalen-2-ylsulfonylcarbamoyl)phenyl)-N,N-dibutyl-4-chloro-5-methyl-1H-pyrazole-3-carboxamide, TFA (20 mg, 0.022 mmol) in MeCN (2.0 mL) was added Et$_3$N (20 µL, 0.14 mmol). After stirring at room temperature for 10 min, 37% formalin (100 µL, 0.022 mmol) and AcOH (100 µL, 0.022 mmol) were added. The resulting reaction mixture was stirred at room temperature for 1 h. Na(CN)BH$_3$ (50 mg, 0.80 mmol) was then added, and the reaction mixture was stirred at room temperature for 1 h. The solvent was removed in vacuo, and the residue was purified by preparative HPLC to give the title compound (11 mg, 51%) as a white solid. $^1$H NMR (CD$_3$OD, 1:1 mixture of amide rotamers) δ 9.17 (br s, 1H), 8.23 (br s, 0.5H), 8.16-7.88 (m, 3.5H), 7.83-7.59 (m, 3H), 7.40-7.11 (m, 4H), 6.98 (d, J=7.7 Hz, 1H), 5.26 (br s, 1H), 4.70 (br s, 2H), 4.63-4.37 (m, 2H), 4.22-2.59 (m, 24H), 2.41-2.17 (m, 3H), 1.60-0.85 (m, 11H), 0.77 (t, J=6.8 Hz, 1.5H), 0.66-0.49 (m, 1.5H); MS(ESI$^+$) m/z 926.5 (M+H)$^+$.

Example 185

N,N-Dibutyl-4-chloro-5-methyl-1-(4-(8-(2-morpholinoethoxy)naphthalen-2-ylsulfonylcarbamoyl)-2-((S)-3-(morpholinomethyl)-1,2,3,4-tetrahydroisoquinoline-2-carbonyl)phenyl)-1H-pyrazole-3-carboxamide (185)

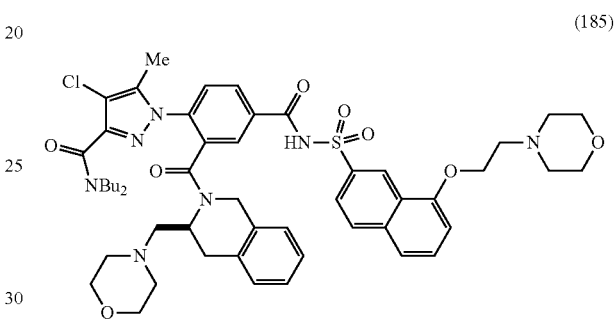

Following a procedure analogous to that for the synthesis of Example 91, 2-(4-chloro-3-(dibutylcarbamoyl)-5-methyl-1H-pyrazol-1-yl)-5-(8-(2-morpholinoethoxy) naphthalen-2-ylsulfonylcarbamoyl)benzoic acid (Intermediate 183B, 15 mg, 0.020 mmol) and (S)-4-((1,2,3,4-tetrahydroisoquinolin-3-yl)methyl)morpholine (Intermediate 109, 18 mg, 0.080 mmol) were converted to the title compound (14 mg, 62%). $^1$H NMR (CD$_3$OD, mixture of amide rotamers) δ 9.19-9.04 (m, 1H), 8.26-7.93 (m, 4H), 7.79-7.53 (m, 3H), 7.36-7.09 (m, 4H), 6.99 (d, J=7.7 Hz, 1H), 5.37-5.16 (m, 1H), 4.75-4.41 (m, 3.5H), 4.22-2.52 (m, 27.5H), 2.37-2.16 (m, 3H), 1.75-0.48 (m, 14H); MS(ESI$^+$) m/z 968.3 (M+H)$^+$.

Example 186

N-Butyl-4-chloro-N-(3,4-dichlorobenzyl)-5-methyl-1-(4-(8-(2-morpholinoethoxy)naphthalen-2-ylsulfonylcarbamoyl)-2-((S)-3-(morpholinomethyl)-1,2,3,4-tetrahydroisoquinoline-2-carbonyl)phenyl)-1H-pyrazole-3-carboxamide (186)

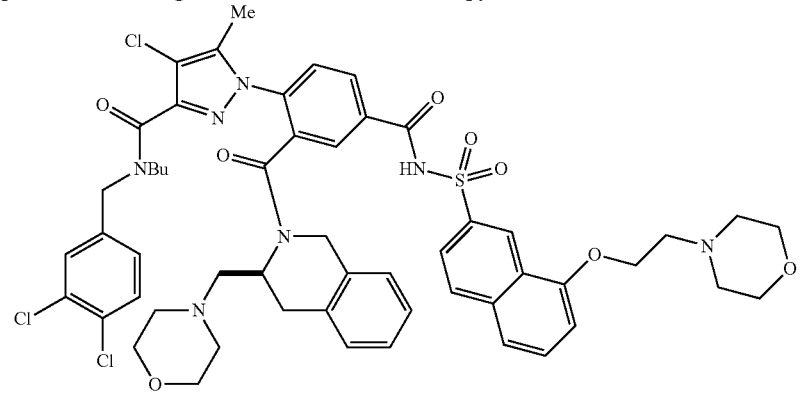

Intermediate 186A

Ethyl 2-(3-(butyl(3,4-dichlorobenzyl)carbamoyl)-4-chloro-5-methyl-1H-pyrazol-1-yl)-5-(8-(2-morpholinoethoxy)naphthalen-2-ylsulfonylcarbamoyl)benzoate

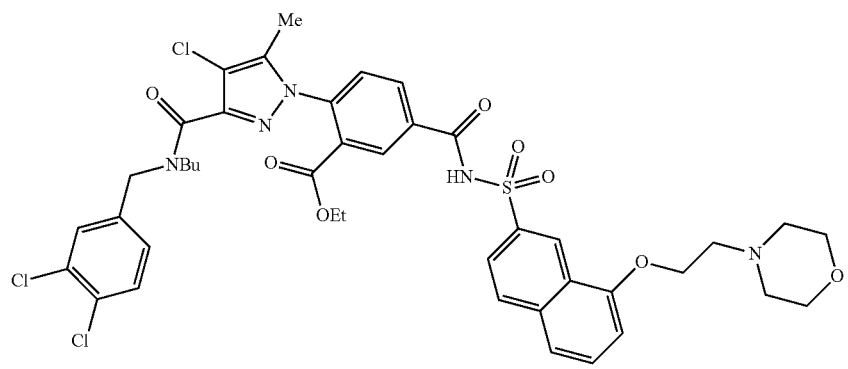

(Int-186A)

Following a procedure analogous to that for the synthesis of Example 1, 4-(3-(butyl(3,4-dichlorobenzyl)carbamoyl)-4-chloro-5-methyl-1H-pyrazol-1-yl)-3-(1,2,3,4-tetrahydroisoquinoline-2-carbonyl)benzoic acid (Intermediate 179D, 30 mg, 0.046 mmol) and 8-(2-morpholinoethoxy)naphthalene-2-sulfonamide (Intermediate 27, 10 mg, 0.030 mmol) were converted to the title compound (22 mg, 84%). MS(ESI$^+$) m/z 886.1 (M+H)$^+$.

Intermediate 186B 2-(3-(Butyl(3,4-dichlorobenzyl)carbamoyl)-4-chloro-5-methyl-1H-pyrazol-1-yl)-5-(8-(2-morpholinoethoxy)naphthalen-2-ylsulfonylcarbamoyl)benzoic acid

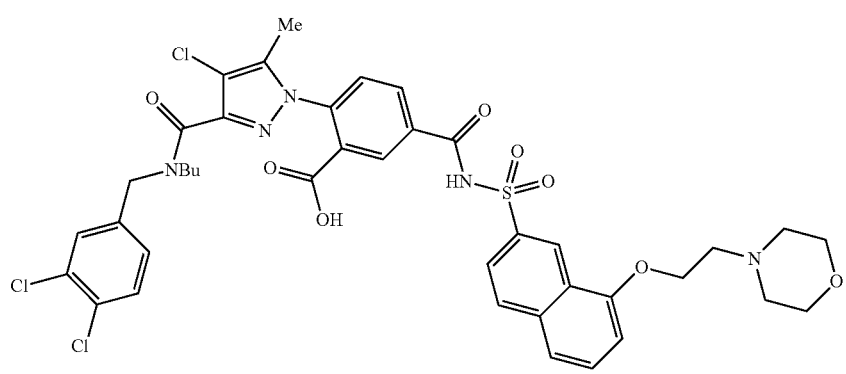

(Int-186B)

Following a procedure analogous to that for the synthesis of Intermediate 91F, ethyl 2-(3-(butyl(3,4-dichlorobenzyl)carbamoyl)-4-chloro-5-methyl-1H-pyrazol-1-yl)-5-(8-(2-morpholinoethoxy)naphthalen-2-ylsulfonylcarbamoyl)benzoate (75 mg, 0.085 mmol) was converted to the title compound (56 mg, 77%). MS(ESI+) m/z 858.5 (M+H)+.

Example 186

Following a procedure analogous to that for the synthesis of Example 91, 2-(3-(butyl(3,4-dichlorobenzyl)carbamoyl)-4-chloro-5-methyl-1H-pyrazol-1-yl)-5-(8-(2-morpholinoethoxy)naphthalen-2-ylsulfonylcarbamoyl)benzoic acid (12 mg, 0.014 mmol) and (S)-4-((1,2,3,4-tetrahydroisoquinolin-3-yl)methyl)morpholine (Intermediate 109, 13 mg, 0.056 mmol) were converted to the title compound (14 mg, 89%). ¹H NMR (CD₃OD, mixture of amide rotamers) δ 9.24-9.07 (m, 1H), 8.27-7.89 (m, 4H), 7.86-7.57 (m, 3H), 7.54-6.81 (m, 8H), 5.24 (br s, 1H), 5.05-2.54 (m, 28H), 2.41-2.05 (m, 4H), 1.63-0.68 (m, 6H), 0.65-0.49 (m, 1H); MS(ESI+) m/z 1070.2 (M+H)+.

Example 187

N-Butyl-4-chloro-N-(3,4-dichlorobenzyl)-1-(2-((S)-3-(hydroxymethyl)-1,2,3,4-tetrahydroisoquinoline-2-carbonyl)-4-(8-(2-morpholinoethoxy)naphthalen-2-ylsulfonylcarbamoyl)phenyl)-5-methyl-1H-pyrazole-3-carboxamide

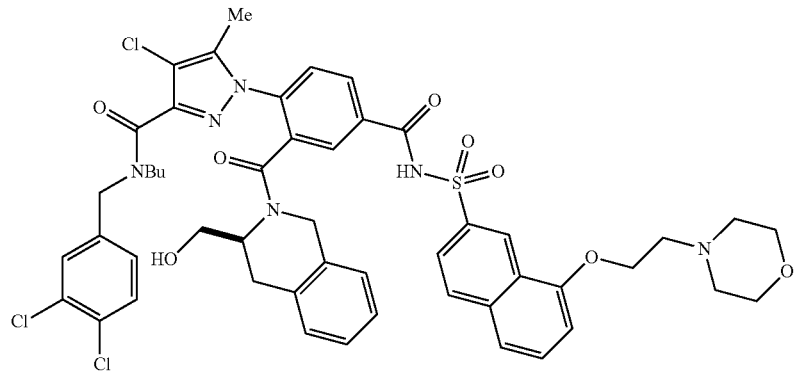

(187)

Following a procedure analogous to that for the synthesis of Example 91, 2-(3-(butyl(3,4-dichlorobenzyl)carbamoyl)-4-chloro-5-methyl-1H-pyrazol-1-yl)-5-(8-(2-morpholinoethoxy)naphthalen-2-ylsulfonylcarbamoyl)benzoic acid (Intermediate 186B, 12 mg, 0.014 mmol) and (S)-(1,2,3,4-tetrahydroisoquinolin-3-yl)methanol (Aldrich, 9 mg, 0.056 mmol) were converted to the title compound (10 mg, 70%). ¹H NMR (CD₃OD, mixture of amide rotamers) δ 9.23-9.09 (m, 1H), 8.24 (dd, J=1.7, 8.0 Hz, 0.5H), 8.10-7.94 (m, 3.5H), 7.76-7.59 (m, 3H), 7.53-7.29 (m, 1.5H), 7.27-6.80 (m, 6H), 6.68 (d, J=7.5 Hz, 0.5H), 5.27-5.04 (m, 1H), 4.75-4.59 (m, 3H), 4.54-2.44 (m, 18H), 2.39-2.26 (m, 3H), 2.25-2.06 (m, 1H), 1.65-0.81 (m, 5.5H), 0.75-0.65 (m, 1H), 0.61-0.51 (m, 0.5H); MS(ESI+) m/z 1005.3 (M+H)+.

Example 188

1-(2-((S)-3-(Aminomethyl)-1,2,3,4-tetrahydroiso-
quinoline-2-carbonyl)-4-(8-(2-morpholinoethoxy)
naphthalen-2-ylsulfonylcarbamoyl)phenyl)-N-butyl-
4-chloro-N-(3,4-dichlorobenzyl)-5-methyl-1H-
pyrazole-3-carboxamide

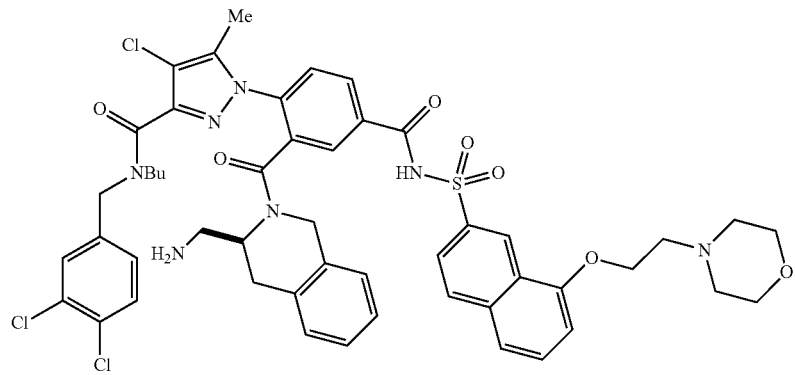

(188)

Intermediate 188A 1-(2-((S)-3-(Azidomethyl)-1,2,3,4-tetrahydroiso-
quinoline-2-carbonyl)-4-(8-(2-morpholinoethoxy)
naphthalen-2-ylsulfonylcarbamoyl)phenyl)-N-butyl-
4-chloro-N-(3,4-dichlorobenzyl)-5-methyl-1H-
pyrazole-3-carboxamide

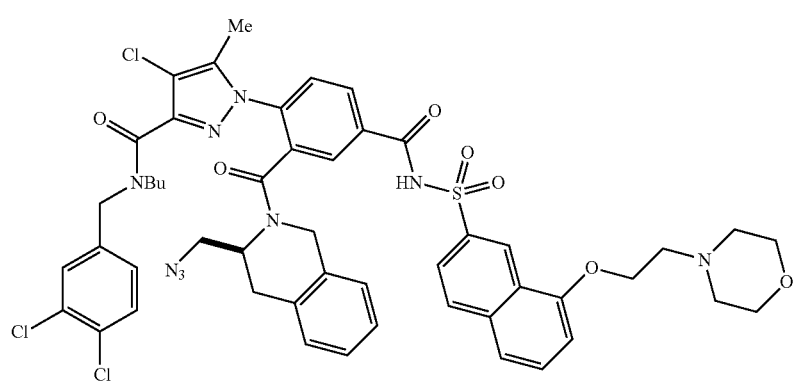

(Int-188A)

Following a procedure analogous to that for the synthesis of Example 91, 2-(3-(butyl(3,4-dichlorobenzyl)carbamoyl)-4-chloro-5-methyl-1H-pyrazol-1-yl)-5-(8-(2-morpholinoethoxy)naphthalen-2-ylsulfonylcarbamoyl)benzoic acid (Intermediate 186B, 17 mg, 0.020 mmol) and (S)-3-(azidomethyl)-1,2,3,4-tetrahydroisoquinoline (Intermediate 92A, 15 mg, 0.079 mmol) were converted to the title compound (16 mg, 79%). MS(ESI⁺) m/z 1028.1 (M+H)⁺.

Example 188

Following a procedure analogous to that for the synthesis of Example 182, (S)-1-(2-(3-(azidomethyl)-1,2,3,4-tetrahydroisoquinoline-2-carbonyl)-4-(8-(2-morpholinoethoxy)naphthalen-2-ylsulfonylcarbamoyl)phenyl)-N-butyl-4-chloro-N-(3,4-dichlorobenzyl)-5-methyl-1H-pyrazole-3-carboxamide (16 mg, 0.016 mmol) was converted to the title compound (7 mg, 43%). ¹H NMR (CD₃OD, mixture of amide rotamers) δ 9.14 (s, 1H), 8.36-7.88 (m, 4H), 7.83-6.76 (m, 11H), 5.16-2.62 (m, 23H), 2.46-2.15 (m, 3H), 1.61-0.82 (m, 5.5H), 0.80-0.65 (m, 1H), 0.56 (br s, 0.5H); MS(ESI⁺) m/z 1002.0 (M+H)⁺.

Example 189

N,N-Dibutyl-4-chloro-1-(4-(1-(3,4-dichlorobenzyl)indolin-5-ylsulfonylcarbamoyl)-2-((S)-3-(hydroxymethyl)-1,2,3,4-tetrahydroisoquinoline-2-carbonyl)phenyl)-5-methyl-1H-pyrazole-3-carboxamide (189)

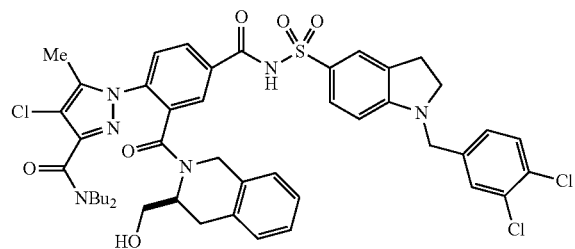

Intermediate 189A

Ethyl 2-(4-chloro-3-(dibutylcarbamoyl)-5-methyl-1H-pyrazol-1-yl)-5-(1-(3,4-dichlorobenzyl)indolin-5-ylsulfonylcarbamoyl)benzoate (Int-189A)

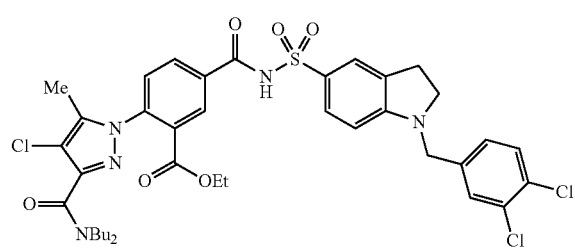

Following a procedure analogous to that for the synthesis of Example 1, 4-(4-chloro-3-(dibutylcarbamoyl)-5-methyl-1H-pyrazol-1-yl)-3-(ethoxycarbonyl)benzoic acid (Intermediate 91D, 727 mg, 1.57 mmol) and 1-(3,4-dichlorobenzyl)indoline-5-sulfonamide (Intermediate 59, 400 mg, 1.12 mmol) were converted to the title compound (360 mg, 40%). ¹H NMR (CD₃OD) δ 8.44 (d, J=2.0 Hz, 1H), 8.16 (dd, J=8.1, 2.2 Hz, 1H), 7.79 (dd, J=8.6, 2.0 Hz, 1H), 7.71 (d, J=1.54 Hz, 1H), 7.63 (d, J=8.4 Hz, 1H), 7.50-7.48 (m, 2H), 7.27 (dd, J=8.4, 2.0 Hz, 1H), 6.56 (d, J=8.6 Hz, 1H), 4.43 (s, 2H), 4.20 (q, J=7.0 Hz, 2H), 3.59-3.48 (m, 4H), 3.49-3.41 (m, 2H), 3.14-3.10 (m, 2H), 2.17 (s, 3H), 1.66-1.54 (m, 4H), 1.44-1.36 (m, 2H), 1.26-1.18 (m, 5H), 0.98 (t, J=7.4 Hz, 3H), 0.83 (t, J=7.4 Hz, 3H); MS(ESI⁺) m/z 804.3 (M+H)⁺.

Intermediate 189B 2-(4-Chloro-3-(dibutylcarbamoyl)-5-methyl-1H-pyrazol-1-yl)-5-(1-(3,4-dichlorobenzyl)indolin-5-ylsulfonylcarbamoyl)benzoic acid (Int-189B)

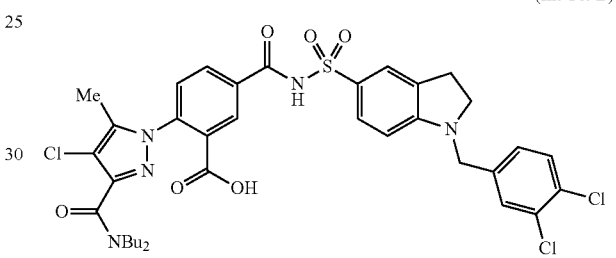

Following a procedure analogous to that for the synthesis of Intermediate 91F, ethyl 2-(4-chloro-3-(dibutylcarbamoyl)-5-methyl-1H-pyrazol-1-yl)-5-(1-(3,4-dichlorobenzyl)indolin-5-ylsulfonylcarbamoyl)benzoate (355 mg, 0.44 mmol) was converted to the title compound (290 mg, 85%). ¹H NMR (DMSO-d₆) δ 8.14 (d, J=2.0 Hz, 1H), 8.17 (dd, J=8.3, 2.1 Hz, 1H), 7.69-7.57 (m, 5H), 7.32-7.30 (m, 1H), 6.65 (d, J=8.6 Hz, 1H), 4.45 (s, 2H), 3.53 (t, J=8.7 Hz, 2H), 3.40-3.28 (m, 4H), 3.05 (t, J=8.4 Hz, 2H), 2.11 (s, 3H), 1.56-1.41 (m, 4H), 1.33-1.27 (m, 2H), 1.15-1.08 (m, 2H), 0.91 (t, J=7.3 Hz, 3H), 0.74 (t, J=7.4 Hz, 3H); MS(ESI⁺) m/z 776.2 (M+H)⁺.

Example 189

Following a procedure analogous to that for the synthesis of Example 91, 2-(4-chloro-3-(dibutylcarbamoyl)-5-methyl-1H-pyrazol-1-yl)-5-(1-(3,4-dichlorobenzyl) indolin-5-ylsulfonylcarbamoyl)benzoic acid (60 mg, 0.077 mmol) and (S)-(1,2,3,4-tetrahydroisoquinolin-3-yl)methanol (Aldrich, 38 mg, 0.23 mmol) were converted to the title compound (56 mg, 72%). ¹H NMR (DMSO-d₆, 2:1 mixture of amide rotamers) δ 8.23 (d, J=1.8 Hz, 0.5H), 8.08-8.04 (m, 1H), 7.72-7.58 (m, 5.5H) 7.32 (dd, J=8.3, 1.9 Hz, 1H), 7.19-7.06 (m, 4.5H), 6.66 (d, J=8.6 Hz, 0.5H), 5.08 (d, J=18.1 Hz, 1H), 4.45 (s, 2H), 4.40-4.19 (m, 1H), 3.95-3.90 (m, 1H), 3.54 (t, J=8.7 Hz, 2H), 3.41-3.16 (m, 3H), 3.07-2.88 (m, 4H), 2.76-2.54 (m, 1H), 2.35-2.22 (m, 2H), 2.21 (s, 2H), 2.18 (s, 1H), 1.25-0.90 (m, 5H), 0.93-0.79 (m, 6H), 0.66-0.58 (m, 3H); MS(ESI⁺) m/z 921.3 (M+H)⁺.

Example 190

N,N-Dibutyl-4-chloro-1-(4-(1-ethylindolin-5-ylsulfonylcarbamoyl)-2-((S)-3-(hydroxymethyl)-1,2,3,4-tetrahydroisoquinoline-2-carbonyl)phenyl)-5-methyl-1H-pyrazole-3-carboxamide (190)

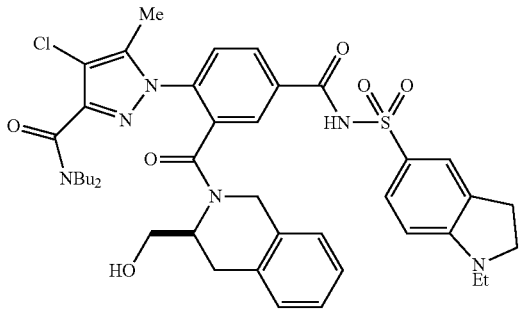

Intermediate 190A

Ethyl 2-(4-chloro-3-(dibutylcarbamoyl)-5-methyl-1H-pyrazol-1-yl)-5-(1-ethylindolin-5-ylsulfonylcarbamoyl)benzoate (Int-190A)

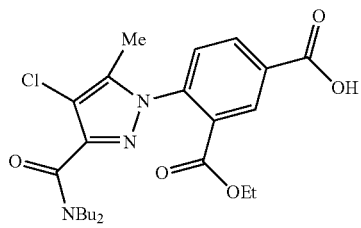

Following a procedure analogous to that for the synthesis of Example 1, 4-(4-chloro-3-(dibutylcarbamoyl)-5-methyl-1H-pyrazol-1-yl)-3-(ethoxycarbonyl)benzoic acid (Intermediate 91D, 400 mg, 0.69 mmol) and 1-ethylindoline-5-sulfonamide (Intermediate 53, 172 mg, 0.76 mmol) were converted to the title compound (180 mg, 27%) after purification by preparative HPLC. MS(ESI⁺) m/z 672.3 (M+H)⁺.

Intermediate 190B 2-(4-Chloro-3-(dibutylcarbamoyl)-5-methyl-1H-pyrazol-1-yl)-5-(1-ethylindolin-5-ylsulfonylcarbamoyl)benzoic acid (Int-190B)

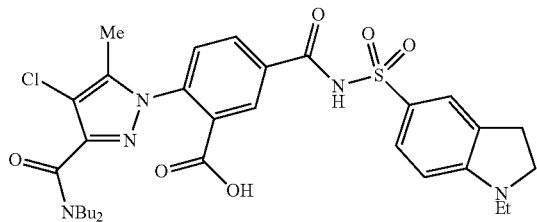

Following a procedure analogous to that for the synthesis of Intermediate 91F, ethyl 2-(4-chloro-3-(dibutylcarbamoyl)-5-methyl-1H-pyrazol-1-yl)-5-(1-ethylindolin-5-ylsulfonylcarbamoyl)benzoate (180 mg, 0.27 mmol) was converted to the title compound (58 mg, 32%) after purification by preparative HPLC. ¹H NMR (DMSO-d₆) δ 8.41 (d, J=2.0 Hz, 1H), 8.17 (dd, J=8.3, 2.1 Hz, 1H), 7.69-7.64 (m, 2H), 7.52 (d, J=1.8 Hz, 1H), 6.83 (d, J=8.6 Hz, 1H), 3.54 (t, J=8.6 Hz, 2H), 3.28-3.24 (m, 6H), 3.00 (t, J=8.6 Hz, 2H), 2.10 (s, 3H), 1.57-1.41 (m, 4H), 1.33-1.26 (m, 2H), 1.14-1.08 (m, 5H), 0.91 (t, J=7.4 Hz, 3H), 0.75 (t, J=7.3 Hz, 3H); MS(ESI⁺) m/z 644.3 (M+H)⁺.

Example 190

Following a procedure analogous to that for the synthesis of Example 91, 2-(4-chloro-3-(dibutylcarbamoyl)-5-methyl-1H-pyrazol-1-yl)-5-(1-ethylindolin-5-ylsulfonylcarbamoyl)benzoic acid (58 mg, 0.090 mmol) and (S)-(1,2,3,4-tetrahydroisoquinolin-3-yl)methanol (Aldrich, 24 mg, 0.14 mmol) were converted to the title compound (70 mg, 94%). ¹H NMR (CD₃OD, 2:1 mixture of amide rotamers) δ 8.24 (d, J=1.8 Hz, 0.5H), 8.07-8.01 (m, 1.5H), 7.77 (dd, J=8.6, 2.0 Hz, 1H), 7.71 (d, J=1.5 Hz, 1H), 7.66-7.62 (m, 2H), 7.25-7.10 (m, 3.5H), 6.95-6.93 (m, 0.5H), 6.48-6.46 (m, 1H), 5.30-5.25 (m, 1H), 4.54-4.10 (m, 2H), 3.62-3.56 (m, 4H), 3.45-3.41 (m, 3H), 3.14-3.01 (m, 6H), 2.61-2.40 (m, 2H), 2.32 (s, 2H), 2.29 (s, 1H), 1.46-1.22 (m, 4H), 1.20-1.16 (m, 4H), 1.07-0.90 (m, 5H), 0.77-0.66 (m, 3H); MS(ESI⁺) m/z 789.4 (M+H)⁺.

Example 191

4-(4-Chloro-3-(dibutylamino)-5-methyl-1H-pyrazol-1-yl)-N-(naphthalen-2-ylsulfonyl)-3-(1,2,3,4-tetrahydroisoquinoline-2-carbonyl)benzamide (191)

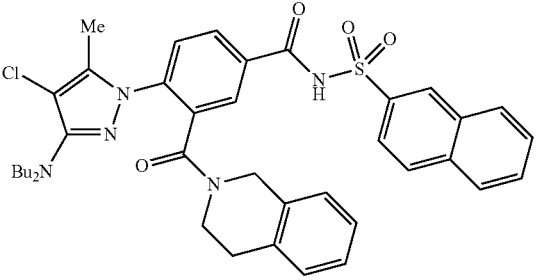

Intermediate 191A

N,N-Dibutyl-5-methyl-1H-pyrazol-3-amine (Int-191A)

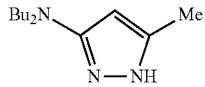

Following a procedure analogous to that for the synthesis Example 106, 5-methyl-1H-pyrazol-3-amine (Aldrich, 486 mg, 5.00 mmol) and butyraldehyde (541 mg, 7.50 mmol) were converted to the title compound (555 mg, 53%). ¹H NMR (CDCl₃) δ 5.34 (s, 1H), 3.17 (t, J=7.3 Hz, 4H), 2.21 (s, 3H), 1.55 (td, J=15.1, 7.5 Hz, 4H), 1.34 (qd, J=15.0, 7.3 Hz, 4H), 0.94 (t, J=7.4 Hz, 6H); MS(ESI⁺) m/z 210.1 (M+H)⁺.

Intermediate 191B

N,N-Dibutyl-4-chloro-5-methyl-1H-pyrazol-3-amine

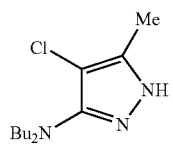
(Int-191B)

Following a procedure analogous to that for the synthesis of Intermediate 1A, N,N-dibutyl-5-methyl-1H-pyrazol-3-amine (419 mg, 2.00 mmol) was converted to the title compound (297 mg, 61%). $^1$H NMR (CDCl$_3$) δ 3.26-3.17 (m, 4H), 2.19 (s, 3H), 1.57-1.44 (m, 4H), 1.32 (qd, J=15.0, 7.3 Hz, 4H), 0.91 (t, J=7.4 Hz, 6H); MS(ESI$^+$) m/z 243.9 (M+H)$^+$.

Intermediate 191C

Ethyl 4-(4-chloro-3-(dibutylamino)-5-methyl-1H-pyrazol-1-yl)-3-(1,2,3,4-tetrahydroisoquinoline-2-carbonyl)benzoate

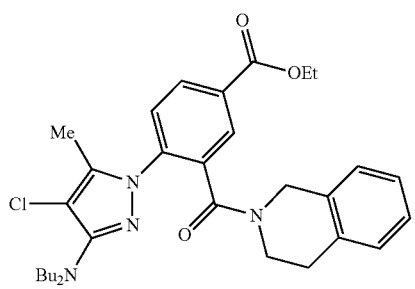
(Int-191C)

Following a procedure analogous to that for the synthesis of Intermediate 1E, N,N-dibutyl-4-chloro-5-methyl-1H-pyrazol-3-amine (160 mg, 0.66 mmol) and ethyl 4-fluoro-3-(1,2,3,4-tetrahydroisoquinoline-2-carbonyl)benzoate (Intermediate 1D, 258 mg, 0.79 mmol) were converted to the title compound (98 mg, 27%). $^1$H NMR (CDCl$_3$, 2:1 mixture of amide rotamers) δ 8.19 (d, J=8.1 Hz, 1H), 8.12 (d, J=1.7 Hz, 1H), 7.40 (d, J=8.33 Hz, 1H), 7.08-7.30 (m, 3.5H), 6.92 (d, J=7.5 Hz, 0.5H), 4.95 (d, J=17.1 Hz., 0.5H), 4.68 (d, J=17.10 Hz, 0.5H), 4.31-4.53 (m, 2.5H), 4.12 (d, J=4.1 Hz, 0.5H), 3.51-3.76 (m, 1.5H), 3.03-3.36 (m, 4.5H), 2.75-3.03 (m, 2H), 2.58 (s, 2H), 2.47 (s, 1H), 1.33-1.51 (m, 7H), 1.13-1.30 (m, 4H), 0.77-0.96 (m, 6H); MS(ESI$^+$) m/z 551.4 (M+H)$^+$.

Example 191

Following a procedure analogous to that for the synthesis of Example 163, ethyl 4-(4-chloro-3-(dibutylamino)-5-methyl-1H-pyrazol-1-yl)-3-(1,2,3,4-tetrahydroisoquinoline-2-carbonyl)benzoate (10 mg, 0.018 mmol) was converted to the title compound. $^1$H NMR (CD$_3$OD, 1:1 mixture of amide rotamers) δ 8.72 (s, 1H), 8.10-8.05 (m, 3H), 8.02-7.98 (m, 2H), 7.91-7.89 (m, 1H), 7.73-7.64 (m, 2H), 7.56-7.51 (m, 1H), 7.22-7.07 (m, 3.5H), 6.88 (d, J=7.5 Hz, 0.5H), 4.82-4.66 (m, 1H), 4.46-4.32 (m, 1H), 3.90-3.84 (m, 0.5H), 3.78-3.72 (m, 0.5H), 3.51-3.45 (m, 1H), 3.10-2.98 (m, 4H), 2.88 (t, J=5.9 Hz, 1H), 2.76-2.71 (m, 1H), 2.27 (s, 1.5H), 2.20 (s, 1.5H), 1.39-1.25 (m, 4H), 1.22-1.11 (m, 4H), 0.84 (t, J=6.8 Hz, 3H), 0.81 (t, J=7.3 Hz, 3H); MS(ESI$^+$) m/z 712.5 (M+H)$^+$.

Example 192

4-(4-Chloro-3-(dipropylamino)-5-methyl-1H-pyrazol-1-yl)-3-((S)-3-(hydroxymethyl)-1,2,3,4-tetrahydroisoquinoline-2-carbonyl)-N-(naphthalen-2-ylsulfonyl)benzamide

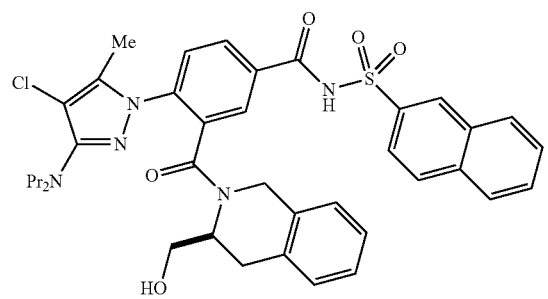
(192)

Intermediate 192A

5-Methyl-N,N-dipropyl-1H-pyrazol-3-amine

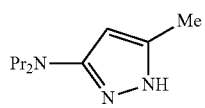
(Int-192A)

Following a procedure analogous to that for the synthesis Example 106, 5-methyl-1H-pyrazol-3-amine (Aldrich, 486 mg, 5.00 mmol) and propionaldehyde (436 mg, 7.50 mmol) were converted to the title compound (400 mg, 44%). $^1$H NMR (CDCl$_3$) δ 5.34 (s, 1H), 3.20-3.11 (m, 4H), 2.22 (s, 3H), 1.60 (sxt, J=7.4 Hz, 4H), 0.91 (t, J=7.4 Hz, 6H); MS(ESI$^+$) m/z 182.2 (M+H)$^+$.

Intermediate 192B

4-Chloro-5-methyl-N,N-dipropyl-1H-pyrazol-3-amine

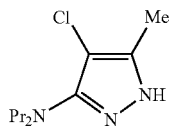
(Int-192B)

Following a procedure analogous to that for the synthesis of Intermediate 1A, 5-methyl-N,N-dipropyl-1H-pyrazol-3-amine (400 mg, 2.21 mmol) was converted to the title compound (290 mg, 61%). $^1$H NMR (CDCl$_3$) δ 3.20-3.16 (m, 4H), 2.18 (s, 3H), 1.55 (sxt, J=7.5 Hz, 4H), 0.88 (t, J=7.4 Hz, 6H); MS(ESI⁺) m/z 216.1 (M+H)⁺.

Intermediate 192C

1-Benzyl 3-ethyl 4-(4-chloro-3-(dipropylamino)-5-methyl-1H-pyrazol-1-yl)isophthalate

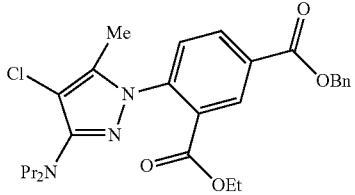
(Int-192C)

Following a procedure analogous to that for the synthesis of Intermediate 1E, 4-chloro-5-methyl-N,N-dipropyl-1H-pyrazol-3-amine (290 mg, 1.34 mmol) and 1-benzyl 3-ethyl 4-fluoroisophthalate (Intermediate 91B, 447 mg, 1.48 mmol) were converted to the title compound (315 mg, 47%). ¹H NMR (CDCl₃) δ 8.55 (d, J=2.0 Hz, 1H), 8.27 (dd, J=8.3, 2.1 Hz, 1H), 7.54-7.32 (m, 6H), 5.43 (s, 2H), 4.20 (q, J=7.0 Hz, 2H), 3.32-3.17 (m, 4H), 2.17 (s, 3H), 1.69-1.54 (m, 6H), 1.21 (t, J=7.2 Hz, 3H), 0.92 (t, J=7.4 Hz, 6H); MS(ESI⁺) m/z 498.2 (M+H)⁺.

Intermediate 192D 4-(4-Chloro-3-(dipropylamino)-5-methyl-1H-pyrazol-1-yl)-3-(ethoxycarbonyl)benzoic acid

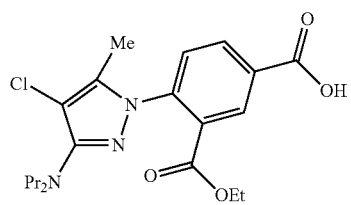
(Int-192D)

Following a procedure analogous to that for the synthesis of Intermediate 91D, 1-benzyl 3-ethyl 4-(4-chloro-3-(dipropylamino)-5-methyl-1H-pyrazol-1-yl)isophthalate (315 mg, 0.63 mmol) was converted to the title compound and used in the subsequent step without purification. ¹H NMR (CDCl₃) δ 10.06 (br s, 1H), 8.57 (d, J=1.8 Hz, 1H), 8.23 (dd, J=8.1, 2.0 Hz, 1H), 7.44 (d, J=8.1 Hz, 1H), 4.24 (q, J=7.3 Hz, 2H), 3.50-3.33 (m, 4H), 2.15 (s, 3H), 1.74-1.53 (m, 4H), 1.28 (s, 3H), 0.94 (t, J=7.4 Hz, 6H); MS (ESI⁺) m/z 408.2 (M+H)⁺.

Intermediate 192E

Ethyl 2-(4-chloro-3-(dipropylamino)-5-methyl-1H-pyrazol-1-yl)-5-(naphthalen-2-ylsulfonylcarbamoyl)benzoate

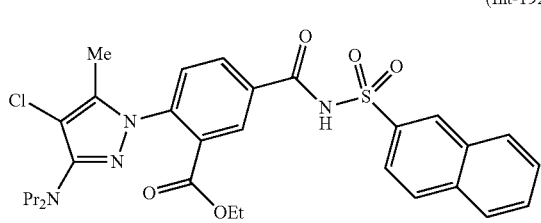
(Int-192E)

Following a procedure analogous to that for the synthesis of Example 1, 4-(4-chloro-3-(dipropylamino)-5-methyl-1H-pyrazol-1-yl)-3-(ethoxycarbonyl)benzoic acid (70 mg, 0.17 mmol) and naphthalene-2-sulfonamide (53 mg, 0.26 mmol) were converted to the title compound (50 mg, 49%). ¹H NMR (CDCl₃) δ 8.76 (s, 1H), 8.49 (d, J=2.0 Hz, 1H), 8.21-7.96 (m, 4H), 7.92 (d, J=8.1 Hz, 1H), 7.76-7.58 (m, 2H), 7.45 (d, J=8.1 Hz, 1H), 4.20 (q, J=7.0 Hz, 2H), 3.65-3.46 (m, 4H), 2.10 (s, 3H), 1.74-1.56 (m, 4H), 1.25 (t, J=7.0 Hz, 3H), 0.93 (t, J=7.3 Hz, 6H); MS(ESI⁺) m/z 597.2 (M+H)⁺.

Example 192

Following a procedure analogous to that for the synthesis of Intermediate 91F, ethyl 2-(4-chloro-3-(dipropylamino)-5-methyl-1H-pyrazol-1-yl)-5-(naphthalen-2-ylsulfonylcarbamoyl)benzoate (50 mg, 0.084 mmol) provided a crude oil which was used in the subsequent step without purification.

The crude oil from above was subject to a procedure analogous to that for the synthesis of Example 91 to give the title compound. ¹H NMR (CDCl₃, 1:1 mixture of amide rotamers) δ 8.84-8.66 (m, 1H), 8.18 (br s, 0.5H), 8.12-7.78 (m, 5.5H), 7.72-7.52 (m, 2H), 7.38-6.95 (m, 4.5H), 6.82 (d, J=7.3 Hz, 0.5H), 5.37-4.96 (m, 1H), 4.59-4.21 (m, 1.5H), 4.08 (br s, 0.5H), 3.84-2.55 (m, 7.5H), 2.39 (d, J=16.5 Hz, 0.5H), 2.24-2.02 (m, 3H), 1.65-1.19 (m, 4H), 0.94-0.55 (m, 6H); MS(ESI⁺) m/z 714.2 (M+H)⁺.

Example 193

4-(4-Chloro-3-(dipropylamino)-5-methyl-1H-pyrazol-1-yl)-N-(8-chloronaphthalen-2-ylsulfonyl)-3-((S)-3-(hydroxymethyl)-1,2,3,4-tetrahydroisoquinoline-2-carbonyl)benzamide

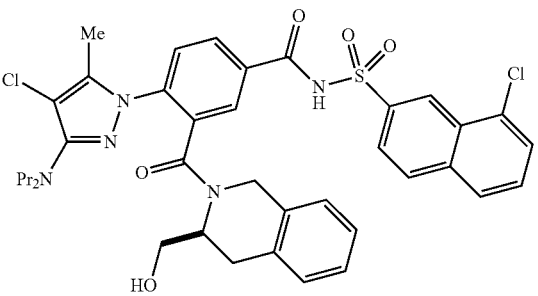
(193)

Intermediate 193A cl Ethyl 2-(4-chloro-3-(dipropylamino)-5-methyl-1H-pyrazol-1-yl)-5-(8-chloronaphthalen-2-ylsulfonylcarbamoyl)benzoate

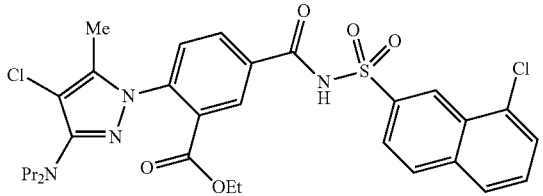
(Int-193A)

Following a procedure analogous to that for the synthesis of Example 1,4-(4-chloro-3-(dipropylamino)-5-methyl-1H-pyrazol-1-yl)-3-(ethoxycarbonyl)benzoic acid (70 mg, 0.17 mmol) and 8-chloronaphthalene-2-sulfonamide (Intermediate 5, 50 mg, 0.21 mmol) were converted to the title compound (78 mg, 72%). MS(ESI$^+$) m/z 631.1 (M+H)$^+$.

Intermediate 193B 2-(4-Chloro-3-(dipropylamino)-5-methyl-1H-pyrazol-1-yl)-5-(8-chloronaphthalen-2-ylsulfonylcarbamoyl)benzoic acid (Int-193B)

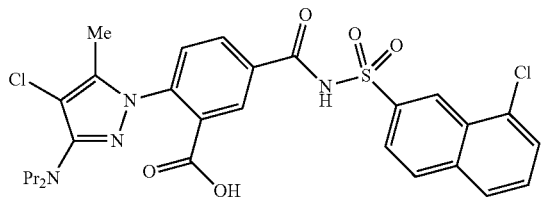

Following a procedure analogous to that for the synthesis of Intermediate 91F, ethyl 2-(4-chloro-3-(dipropylamino)-5-methyl-1H-pyrazol-1-yl)-5-(8-chloronaphthalen-2-ylsulfonylcarbamoyl)benzoate (76 mg, 0.12 mmol) was converted to the title compound and used in the subsequent step without purification. $^1$H NMR (CDCl$_3$) δ 9.14 (d, J=1.8 Hz, 1H), 8.67 (s, 1H), 8.19 (td, J=8.5, 2.2 Hz, 2H), 8.01 (d, J=8.8 Hz, 1H), 7.84 (d, J=8.4 Hz, 1H), 7.69 (dd, J=7.4, 1.0 Hz, 1H), 7.62-7.54 (m, 1H), 7.36 (d, J=8.4 Hz, 1H), 3.59-3.41 (m, 6H), 2.14 (s, 3H), 1.73-1.50 (m, 4H), 0.91 (t, J=7.3 Hz, 6H); MS(ESI$^+$) m/z 603.1 (M+H)$^+$.

Example 193

Following a procedure analogous to that for the synthesis of Example 91, 2-(4-chloro-3-(dipropylamino)-5-methyl-1H-pyrazol-1-yl)-5-(8-chloronaphthalen-2-ylsulfonylcarbamoyl)benzoic acid (25 mg, 0.041 mmol) was converted to the title compound. $^1$H NMR (CDCl$_3$, 1:1 mixture of amide rotamers) δ 9.01 (s, 1H), 8.15-8.05 (m, 3H), 8.01-7.94 (m, 1H), 7.84 (d, J=8.1 Hz, 1H), 7.66-7.63 (m, 1H), 7.54-7.50 (m, 1H), 7.35-7.28 (m, 1H), 7.19-7.06 (m, 3H), 6.99 (d, J=6.4 Hz, 0.5H), 6.86 (d, J=7.3 Hz, 0.5H), 5.17-5.12 (m, 1H), 4.87 (br s, 1H), 4.44-4.33 (m, 1H), 4.28-4.24 (m, 1H), 4.17 (br s, 1H), 3.92 (br s, 1H), 3.61-3.44 (m, 1H), 3.25-3.09 (m, 1H), 3.01 (br s, 1H), 2.94 (br s, 1H), 2.83-2.74 (m, 1.5H), 2.52-2.48 (m, 0.5H), 2.18-2.12 (m, 3H), 1.55-1.43 (m, 1H), 1.31-1.15 (m, 3H), 0.87-0.76 (m, 3H), 0.68-0.63 (m, 3H); MS(ESI$^+$) m/z 748.5 (M+H)$^+$.

Example 194

3-((S)-3-(Aminomethyl)-1,2,3,4-tetrahydroisoquinoline-2-carbonyl)-4-(4-chloro-3-(dipropylamino)-5-methyl-1H-pyrazol-1-yl)-N-(8-chloronaphthalen-2-ylsulfonyl)benzamide (194)

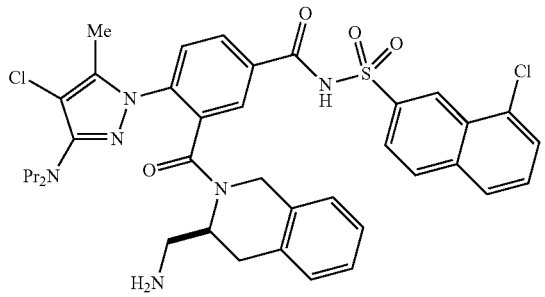

Intermediate 194A 3-((S)-3-(Azidomethyl)-1,2,3,4-tetrahydroisoquinoline-2-carbonyl)-4-(4-chloro-3-(dipropylamino)-5-methyl-1H-pyrazol-1-yl)-N-(8-chloronaphthalen-2-ylsulfonyl)benzamide (Int-194A)

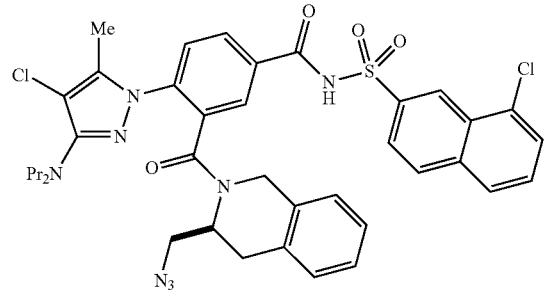

Following a procedure analogous to that for the synthesis of Example 91, 2-(4-chloro-3-(dipropylamino)-5-methyl-1H-pyrazol-1-yl)-5-(8-chloronaphthalen-2-ylsulfonylcarbamoyl)benzoic acid (Intermediate 193B, 50 mg, 0.083 mmol) and (S)-3-(azidomethyl)-1,2,3,4-tetrahydroisoquinoline (Intermediate 92A, 17 mg, 0.091 mmol) were converted to the title compound. $^1$H NMR (CDCl$_3$, 2:1 mixture of amide rotamers) δ 9.15 (s, 1H), 8.27-8.13 (m, 1.5H), 8.07-7.80 (m, 2H), 7.72 (d, J=7.5 Hz, 1.5H), 7.61-7.51 (m, 1H), 7.36 (d, J=8.4 Hz, 1H), 7.28-7.11 (m, 3.5H), 7.08-6.98 (m, 1H), 6.94-6.82 (m, 0.5H), 5.34 (d, J=18.5 Hz, 1H), 4.38-3.93 (m, 3H), 3.48-3.36 (m, 2H), 3.32-2.72 (m, 5H), 2.24 (s, 1H), 2.16 (s, 2H), 1.60-1.12 (m, 4H), 0.94-0.62 (m, 6H); MS(ESI$^+$) m/z 773.2 (M+H)$^+$.

Example 194

Following a procedure analogous to that for the synthesis of Intermediate 184B, (S)-3-(3-(azidomethyl)-1,2,3,4-tetrahydroisoquinoline-2-carbonyl)-4-(4-chloro-3-(dipropylamino)-5-methyl-1H-pyrazol-1-yl)-N-(8-chloronaphthalen-2-ylsulfonyl)benzamide (40 mg, 0.052 mmol) was converted to the title compound. $^1$H NMR (CDCl$_3$, 1:1 mixture of amide rotamers) δ 9.15 (s, 1H), 8.23-8.17 (m, 3H), 8.04 (d, J=8.8 Hz, 1H), 7.98 (dd, J=8.4, 2.0 Hz, 1H), 7.86 (d, J=8.1 Hz, 1H), 7.72 (d, J=7.5 Hz, 1H), 7.59 (t, J=7.9 Hz, 1H), 7.36 (d, J=8.4 Hz, 1H), 7.23-7.12 (m, 3.5H), 7.04 (d, J=7.4 Hz, 0.5H), 6.87 (br s, 1H), 5.36-5.31 (m, 1H), 4.95 (br s, 1H), 4.47-4.43 (m, 0.5H), 4.32-4.18 (m, 1.5H), 4.04-3.99 (m, 0.5H), 3.72-3.69 (m, 0.5H), 3.45-3.40 (m, 1H), 3.29-3.22 (m, 2H), 3.08 (br s, 2H), 2.94 (br s, 1H), 2.50-2.46 (m, 1H), 2.19 (s, 1.5H), 2.17 (s, 1.5H), 1.57-1.43 (m, 2H), 1.35-1.22 (m, 2H), 0.90-0.81 (m, 3H), 0.74-0.67 (m, 3H); MS(ESI$^+$) m/z 747.2 (M+H)$^+$.

Example 195

4-(4-Chloro-3-(dipropylamino)-5-(trifluoromethyl)-1H-pyrazol-1-yl)-N-(8-chloronaphthalen-2-ylsulfonyl)-3-((S)-3-(hydroxymethyl)-1,2,3,4-tetrahydroisoquinoline-2-carbonyl)benzamide (195)

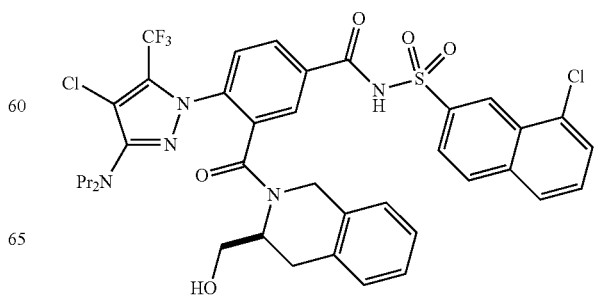

Intermediate 195A

1-Benzyl-5-(trifluoromethyl)-1H-pyrazol-3-amine

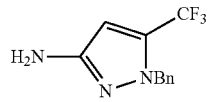
(Int-195A)

To a solution of (E)-4-amino-4-ethoxy-1,1,1-trifluorobut-3-en-2-one (Martins, M. A. P. et al., *Synthesis*, 9:1485-1493 (2006)) (1.84 g, 10.1 mmol) in EtOH (50.0 mL) was added Et₃N (3.0 mL, 21.2 mmol) followed by benzylhydrazine, 2HCl (1.97 g, 10.1 mmol). The resulting reaction mixture was stirred at 70° C. overnight and then concentrated in vacuo. The residue was redissolved in EtOAc and washed with sat. aq. NH₄Cl solution (2×). The aqueous layer was extracted with EtOAc (3×), and the combined organic extracts were dried over Na₂SO₄, filtered and concentrated in vacuo. The crude oil was purified using flash column chromatography (gradient from 0% to 40% EtOAc/hexanes) to give the title compound (1.25 g, 51%) as a 4:1 mixture of regioisomers by $^1$H NMR. $^1$H NMR (CDCl₃, major regioisomer) δ 7.41-7.29 (m, 3H), 7.22-7.14 (m, 2H), 5.83 (s, 1H), 5.26 (s, 2H), 3.47 (br s, 2H); MS(ESI$^+$) m/z 242.1 (M+H)$^+$.

Intermediate 195B

1-Benzyl-N,N-dipropyl-5-(trifluoromethyl)-1H-pyrazol-3-amine

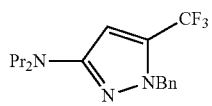
(Int-195B)

To a 0° C. solution of propionic acid (12.4 mL, 166.0 mmol) in PhMe (15.0 mL) was added NaBH₄ (1.96 g, 51.8 mmol) portionwise to control the bubbling. The mixture was stirred at 0° C. until the evolution of H₂ ceased. Next, 1-benzyl-5-(trifluoromethyl)-1H-pyrazol-3-amine (625 mg, 2.59 mmol) in PhMe (10.0 mL) was then added dropwise via syringe. The resulting reaction mixture was heated at 110° C. overnight. Additional propionic acid (5.0 mL, 66.9 mmol) and NaBH₄ (1.00 g, 25.9 mmol) were added, and the reaction mixture was stirred overnight at 110° C. The reaction mixture was then poured into EtOAc and 0.5N aq. NaOH solution (1:1). The layers were separated, and the organic layer was washed with 0.5N aq. NaOH solution. The aqueous layer was extracted with EtOAc (3×), and the combined organic extracts were washed with sat. aq. NaCl solution and dried over Na₂SO₄. Filtration and concentration in vacuo provided a crude residue which was purified by flash column chromatography (gradient from 0% to 20% EtOAc/hexanes) to give the title compound (597 mg, 64%) as a 4:1 mixture of regioisomers by $^1$H NMR. $^1$H NMR (CDCl₃, major regioisomer) δ 7.41-7.25 (m, 3H), 7.19 (d, J=7.0 Hz, 2H), 6.22 (s, 1H), 5.34 (s, 2H), 2.82-2.72 (m, 4H), 1.48-1.33 (m, 4H), 0.78 (t, J=7.4 Hz, 6H); MS(ESI$^+$) m/z 326.2 (M+H)$^+$.

Intermediate 195C

N,N-Dipropyl-5-(trifluoromethyl)-1H-pyrazol-3-amine

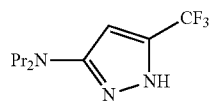
(Int-195C)

To a 1 dram pressure vial containing 1-benzyl-N,N-dipropyl-5-(trifluoromethyl)-1H-pyrazol-3-amine (597 mg, 1.83 mmol) in EtOH (9.2 mL) was added 10% Pd/C (585 mg, 5.50 mmol) followed by dropwise addition of formic acid (3.9 mL, 101.0 mmol). The vial was capped, and the resulting black reaction mixture was heated at 78° C. for 1 h. The reaction mixture was filtered through a pad of CELITE® and concentrated in vacuo to give the title compound (401 mg, 93%) as a white solid. $^1$H NMR (CDCl₃) δ 5.58 (s, 1H), 3.18-3.11 (m, 4H), 1.69-1.50 (m, 4H), 0.94 (t, J=7.4 Hz, 6H); MS(ESI$^+$) m/z 236.2 (M+H)$^+$.

Intermediate 195D

4-Chloro-N,N-dipropyl-5-(trifluoromethyl)-1H-pyrazol-3-amine

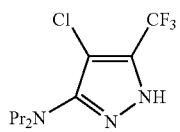
(Int-195D)

To N,N-dipropyl-5-(trifluoromethyl)-1H-pyrazol-3-amine (250 mg, 1.06 mmol) in DMF (5.3 mL) was added NCS (142 mg, 1.06 mmol). The resulting reaction mixture was stirred at 100° C. for 1 h and then poured into sat. aq. NH₄Cl solution and EtOAc (1:1). The organic layer was washed sat. aq. NH₄Cl solution (3×), and the combined aqueous layer was extracted with EtOAc (3×). The combined organic extracts were dried over Na₂SO₄, filtered and concentrated in vacuo to give the title compound (287 mg, 100%). $^1$H NMR (CDCl₃) δ 3.23-3.14 (m, 4H), 1.59-1.44 (m, 4H), 0.88 (t, J=7.4 Hz, 6H); MS(ESI$^+$) m/z 270.1 (M+H)$^+$.

Intermediate 195E

1-Benzyl 3-ethyl 4-(4-chloro-3-(dipropylamino)-5-(trifluoromethyl)-1H-pyrazol-1-yl)isophthalate

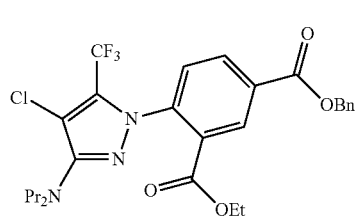
(Int-195E)

Following a procedure analogous to that for the synthesis of Intermediate 1E, 4-chloro-N,N-dipropyl-5-(trifluoromethyl)-1H-pyrazol-3-amine (287 mg, 1.06 mmol) and 1-benzyl 3-ethyl 4-fluoroisophthalate (Intermediate 91B, 268 mg, 0.89 mmol) were converted to the title compound (231 mg, 47%). MS(ESI⁺) m/z 552.3 (M+H)⁺.

Intermediate 195F 4-(4-Chloro-3-(dipropylamino)-5-(trifluoromethyl)-1H-pyrazol-1-yl)-3-(ethoxycarbonyl)benzoic acid

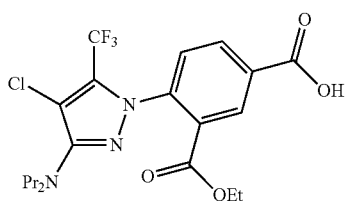

(Int-195F)

Following a procedure analogous to that for the synthesis of Intermediate 91D, 1-benzyl 3-ethyl 4-(4-chloro-3-(dipropylamino)-5-(trifluoromethyl)-1H-pyrazol-1-yl)isophthalate (131 mg, 0.24 mmol) was converted to the title compound (97 mg, 89%). ¹H NMR (CDCl₃) δ 8.62 (br s, 1H), 8.23 (d, J=7.9 Hz, 1H), 7.45 (d, J=8.1 Hz, 1H), 4.17-4.01 (m, 2H), 2.97-2.81 (m, 4H), 1.50-1.30 (m, 4H), 1.10 (t, J=7.0 Hz, 3H), 0.74 (t, J=7.3 Hz, 6H); MS(ESI⁺) m/z 462.2 (M+H)⁺.

Intermediate 195G

Ethyl 2-(4-chloro-3-(dipropylamino)-5-(trifluoromethyl)-1H-pyrazol-1-yl)-5-(8-chloronaphthalen-2-ylsulfonylcarbamoyl)benzoate

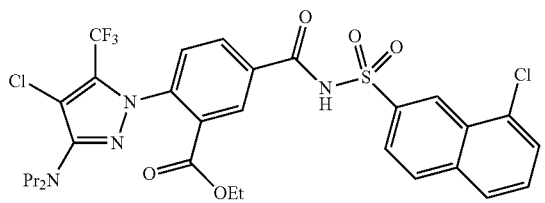

(Int-195G)

Following a procedure analogous to that for the synthesis of Example 1, 4-(4-chloro-3-(dipropylamino)-5-(trifluoromethyl)-1H-pyrazol-1-yl)-3-(ethoxycarbonyl)benzoic acid (64 mg, 0.14 mmol) and 8-chloronaphthalene-2-sulfonamide (Intermediate 5, 34 mg, 0.14 mmol) were converted to the title compound (56 mg, 58%). MS(ESI⁺) m/z 685.3 (M+H)⁺.

Example 195

Following a procedure analogous to that for the synthesis of Intermediate 91F, ethyl 2-(4-chloro-3-(dipropylamino)-5-(trifluoromethyl)-1H-pyrazol-1-yl)-5-(8-chloronaphthalen-2-ylsulfonylcarbamoyl)benzoate (56 mg, 0.081 mmol) was converted to the crude benzoic acid which was used in the subsequent step without purification. MS (ESI⁺) m/z 657.2 (M+H)⁺.

Following a procedure analogous to that for the synthesis of Example 91, the crude benzoic acid from above (25 mg, 0.038 mmol) and (S)-(1,2,3,4-tetrahydroisoquinolin-3-yl)methanol (Aldrich, 7 mg, 0.046 mmol) were converted to the title compound (13 mg, 40%). ¹H NMR (CD₃OD, mixture of amide rotamers) δ 9.00 (s, 1H), 8.26-7.96 (m, 4H), 7.92 (d, J=8.4 Hz, 1H), 7.77-7.52 (m, 3H), 7.28-7.05 (m, 3.5H), 6.93 (d, J=7.5 Hz, 0.5H), 5.10 (d, J=17.6 Hz, 0.5H), 4.70-4.42 (m, 1H), 4.35-3.91 (m, 1H), 3.69-3.34 (m, 2H), 3.21-2.76 (m, 6H), 2.63 (d, J=16.3 Hz, 0.5H), 1.57-1.33 (m, 4H), 0.88-0.72 (m, 6H); MS(ESI⁺) m/z 802.4 (M+H)⁺.

Example 196

4-(4-Chloro-3-(dipropylamino)-5-(trifluoromethyl)-1H-pyrazol-1-yl)-N-(8-chloronaphthalen-2-ylsulfonyl)-3-(1,2,3,4-tetrahydroisoquinoline-2-carbonyl)benzamide

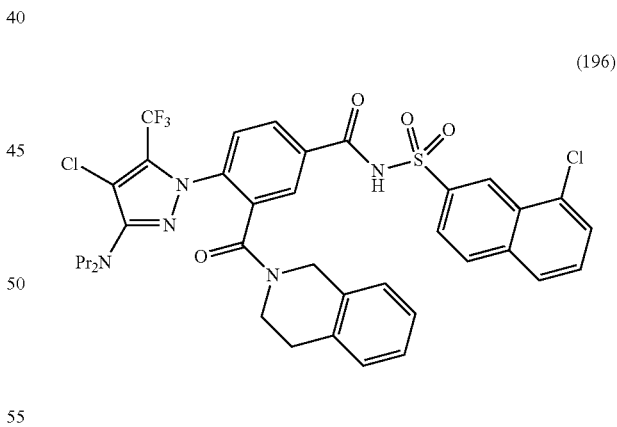

(196)

Following a procedure analogous to that for the synthesis of Example 91, the crude benzoic acid from above (see Example 195, 29 mg, 0.044 mmol) and 1,2,3,4-tetrahydroisoquinoline (7 mg, 0.053 mmol) were converted to the title compound (11 mg, 31%). ¹H NMR (CD₃OD, mixture of amide rotamers) δ 8.98 (s, 1H), 8.20-8.06 (m, 3H), 8.05-8.00 (m, 1H), 7.90 (d, J=8.1 Hz, 1H), 7.71-7.60 (m, 2H), 7.58-7.51 (m, 1H), 7.21-7.04 (m, 3.5H), 6.92 (d, J=7.3 Hz, 0.5H), 4.83-4.41 (m, 2H), 4.03-3.51 (m, 2H), 3.21-2.74 (m, 6H), 1.60-1.26 (m, 4H), 0.80 (dt, J=7.4, 4.6 Hz, 6H); MS(ESI⁺) m/z 772.4 (M+H)⁺.

Examples 197 to 222

The following Examples were prepared using the procedures described above.

| Ex. No. | Structure | Name | LCMS (M + H) |
|---|---|---|---|
| 197 | 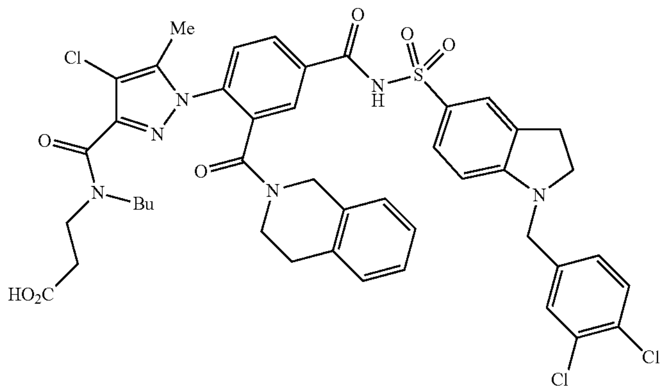 | 3-(N-butyl-4-chloro-1-(4-(1-(3,4-dichlorobenzyl)indolin-5-ylsulfonylcarbamoyl)-2-(1,2,3,4-tetrahydroisoquinoline-2-carbonyl)phenyl)-5-methyl-1H-pyrazole-3-carboxamido)propanoic acid | 905.5 |
| 198 | 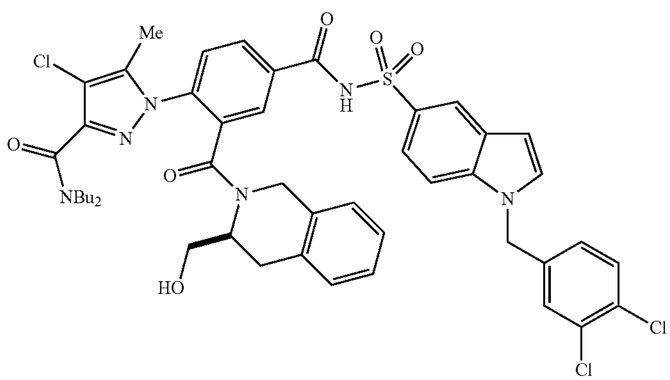 | N,N-dibutyl-4-chloro-1-(4-(1-(3,4-dichlorobenzyl)-1H-indol-5-ylsulfonylcarbamoyl)-2-((S)-3-(hydroxymethyl)-1,2,3,4-tetrahydroisoquinoline-2-carbonyl)phenyl)-5-methyl-1H-pyrazole-3-carboxamide | 919.3 |
| 199 | 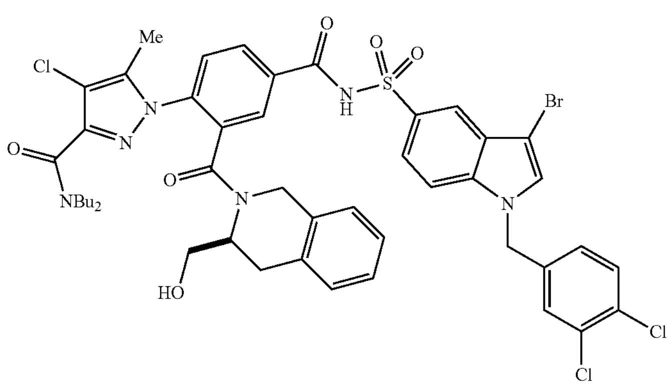 | 1-(4-(3-bromo-1-(3,4-dichlorobenzyl)-1H-indol-5-ylsulfonylcarbamoyl)-2-((S)-3-(hydroxymethyl)-1,2,3,4-tetrahydroisoquinoline-2-carbonyl)phenyl)-N,N-dibutyl-4-chloro-5-methyl-1H-pyrazole-3-carboxamide | 997.1 |

-continued

| Ex. No. | Structure | Name | LCMS (M + H) |
|---|---|---|---|
| 200 | 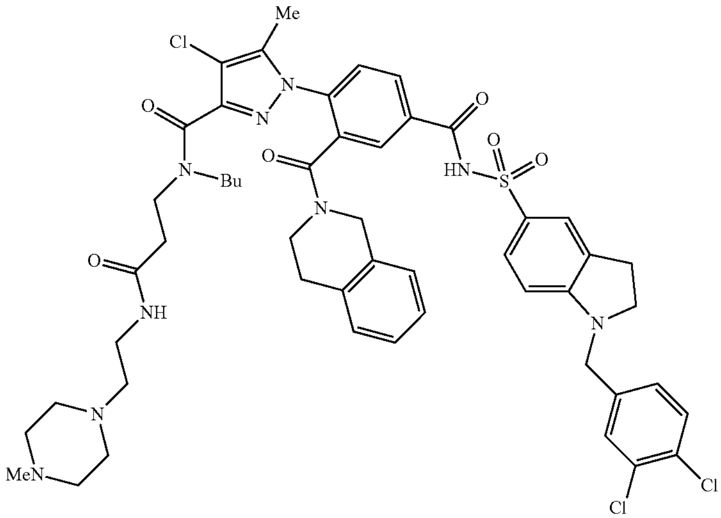 | N-butyl-4-chloro-1-(4-(1-(3,4-dichlorobenzyl)indolin-5-ylsulfonylcarbamoyl)-2-(1,2,3,4-tetrahydroisoquinoline-2-carbonyl)phenyl)-5-methyl-N-(3-(2-(4-methylpiperazin-1-yl)ethylamino)-3-oxopropyl)-1H-pyrazole-3-carboxamide | 1032.3 |
| 201 | 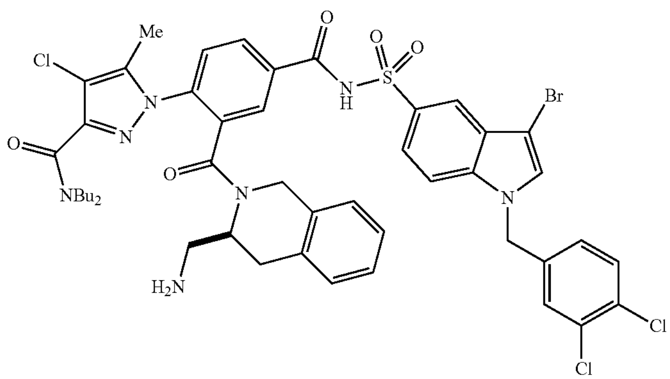 | 1-(2-((S)-3-(aminomethyl)-1,2,3,4-tetrahydroisoquinoline-2-carbonyl)-4-(3-bromo-1-(3,4-dichlorobenzyl)-1H-indol-5-ylsulfonylcarbamoyl)phenyl)-N,N-dibutyl-4-chloro-5-methyl-1H-pyrazole-3-carboxamide | 996.2 |
| 202 | 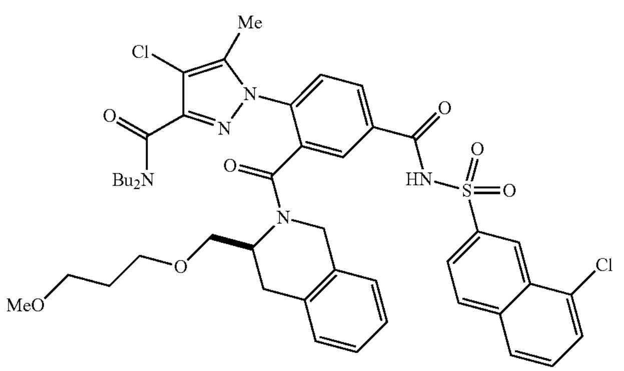 | N,N-dibutyl-4-chloro-1-(4-(8-chloronaphthalen-2-ylsulfonylcarbamoyl)-2-((S)-3-((3-methoxypropoxy)methyl)-1,2,3,4-tetrahydroisoquinoline-2-carbonyl)phenyl)-5-methyl-1H-pyrazole-3-carboxamide | 876.4 |
| 203 | 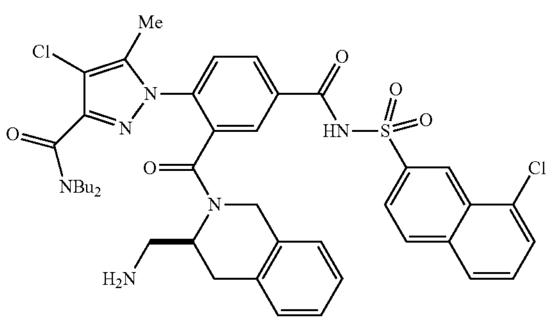 | 1-(2-((S)-3-(aminomethyl)-1,2,3,4-tetrahydroisoquinoline-2-carbonyl)-4-(8-chloronaphthalen-2-ylsulfonylcarbamoyl)phenyl)-N,N-dibutyl-4-chloro-5-methyl-1H-pyrazole-3-carboxamide | 803.1 |

-continued

| Ex. No. | Structure | Name | LCMS (M + H) |
|---|---|---|---|
| 204 | 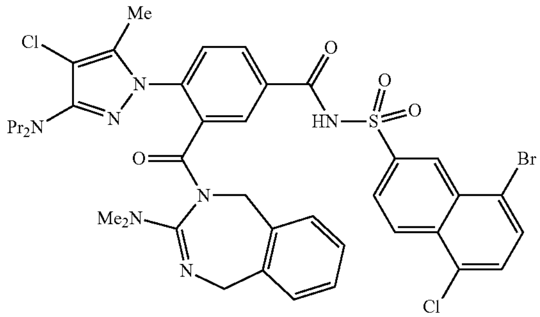 | (Z)-N-(8-bromo-5-chloronaphthalen-2-ylsulfonyl)-4-(4-chloro-3-(dipropylamino)-5-methyl-1H-pyrazol-1-yl)-3-(3-(dimethylamino)-2,5-dihydro-1H-benzo[e][1,3]diazepine-2-carbonyl)benzamide | 852.1 |
| 205 | 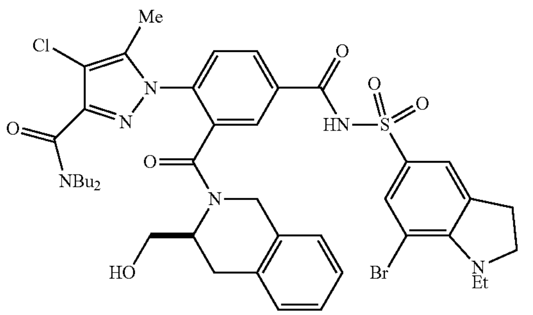 | 1-(4-(7-bromo-1-ethylindolin-5-ylsulfonylcarbamoyl)-2-((S)-3-(hydroxymethyl)-1,2,3,4-tetrahydroisoquinoline-2-carbonyl)phenyl)-N,N-dibutyl-4-chloro-5-methyl-1H-pyrazole-3-carboxamide | 869.2 |
| 206 | 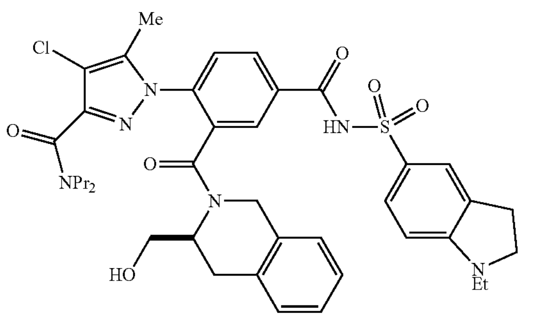 | 4-chloro-1-(4-(1-ethylindolin-5-ylsulfonylcarbamoyl)-2-((S)-3-(hydroxymethyl)-1,2,3,4-tetrahydroisoquinoline-2-carbonyl)phenyl)-5-methyl-N,N-dipropyl-1H-pyrazole-3-carboxamide | 761.3 |
| 207 | 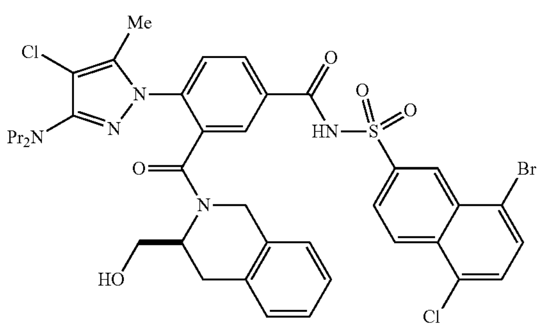 | N-(8-bromo-5-chloronaphthalen-2-ylsulfonyl)-4-(4-chloro-3-(dipropylamino)-5-methyl-1H-pyrazol-1-yl)-3-((S)-3-(hydroxymethyl)-1,2,3,4-tetrahydroisoquinoline-2-carbonyl)benzamide | 826.1 |
| 208 | 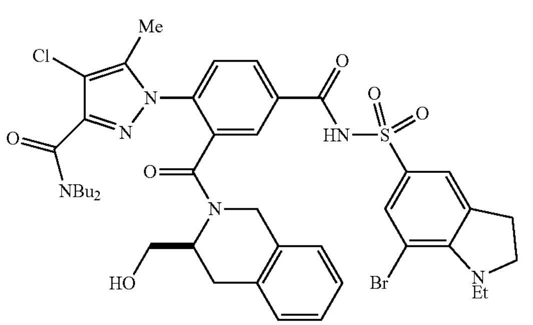 | 1-(4-(7-bromo-1-ethyl-1H-indol-5-ylsulfonylcarbamoyl)-2-((S)-3-(hydroxymethyl)-1,2,3,4-tetrahydroisoquinoline-2-carbonyl)phenyl)-N,N-dibutyl-4-chloro-5-methyl-1H-pyrazole-3-carboxamide | 867.3 |

-continued

| Ex. No. | Structure | Name | LCMS (M + H) |
|---|---|---|---|
| 209 | 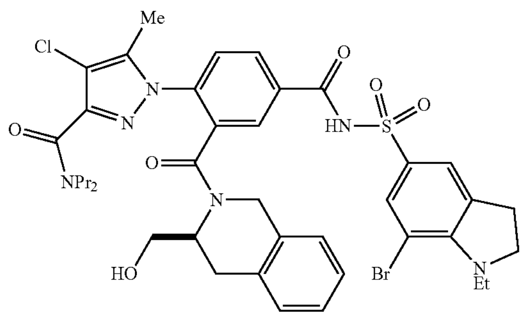 | 1-(4-(7-bromo-1-ethylindolin-5-ylsulfonylcarbamoyl)-2-((S)-3-(hydroxymethyl)-1,2,3,4-tetrahydroisoquinoline-2-carbonyl)phenyl)-4-chloro-5-methyl-N,N-dipropyl-1H-pyrazole-3-carboxamide | 841.2 |
| 210 | 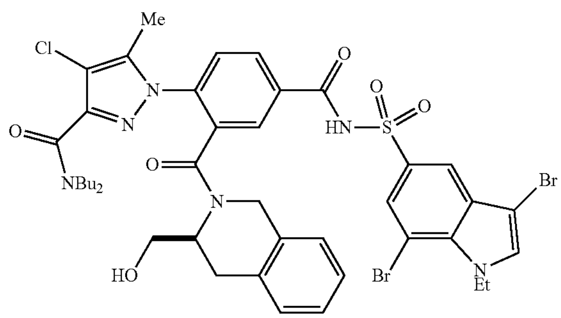 | N,N-dibutyl-4-chloro-1-(4-(3,7-dibromo-1-ethyl-1H-indol-5-ylsulfonylcarbamoyl)-2-((S)-3-(hydroxymethyl)-1,2,3,4-tetrahydroisoquinoline-2-carbonyl)phenyl)-5-methyl-1H-pyrazole-3-carboxamide | 945.3 |
| 211 | 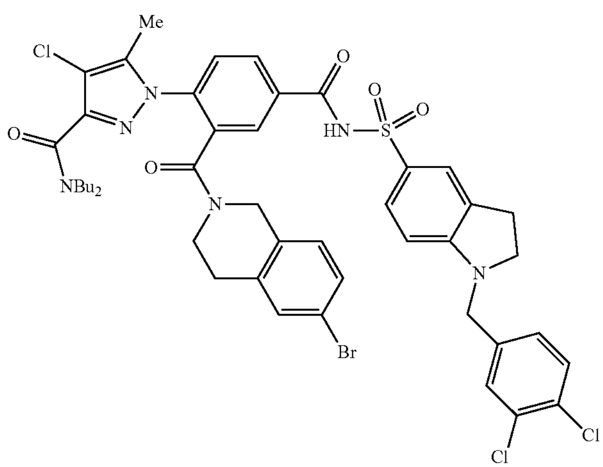 | 1-(2-(6-bromo-1,2,3,4-tetrahydroisoquinoline-2-carbonyl)-4-(1-(3,4-dichlorobenzyl)indolin-5-ylsulfonylcarbamoyl)phenyl)-N,N-dibutyl-4-chloro-5-methyl-1H-pyrazole-3-carboxamide | 969.2 |
| 212 | 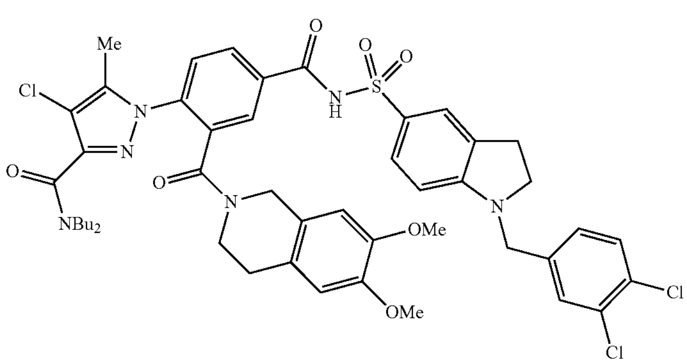 | N,N-dibutyl-4-chloro-1-(4-(1-(3,4-dichlorobenzyl)indolin-5-ylsulfonylcarbamoyl)-2-(6,7-dimethoxy-1,2,3,4-tetrahydroisoquinoline-2-carbonyl)phenyl)-5-methyl-1H-pyrazole-3-carboxamide | 951.3 |

| Ex. No. | Structure | Name | LCMS (M + H) |
|---|---|---|---|
| 213 | 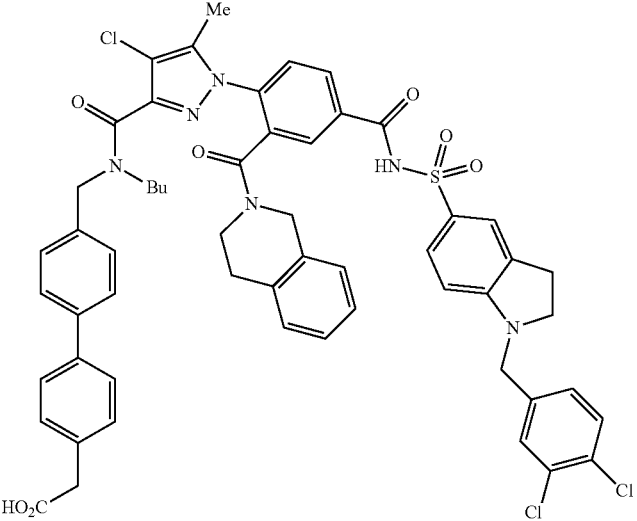 | 2-(4'-((N-butyl-4-chloro-1-(4-(1-(3,4-dichlorobenzyl)indolin-5-ylsulfonylcarbamoyl)-2-(1,2,3,4-tetrahydroisoquinoline-2-carbonyl)phenyl)-5-methyl-1H-pyrazole-3-carboxamido)methyl)biphenyl-4-yl)acetic acid | 1059.1 |
| 214 | 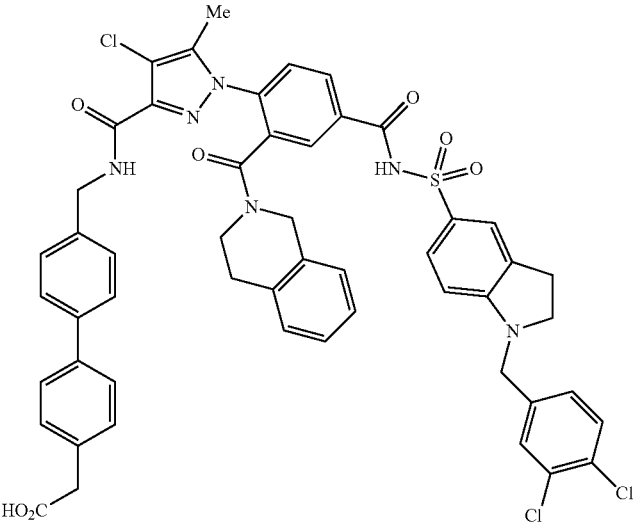 [SMILES: Cc1c(Cl)c(C(=O)NCc2ccc(-c3ccc(CC(=O)O)cc3)cc2)nn1-c1ccc(C(=O)NS(=O)(=O)c2ccc3c(c2)CCN3Cc2ccc(Cl)c(Cl)c2)cc1C(=O)N1CCc2ccccc2C1] | 2-(4'-((4-chloro-1-(4-(1-(3,4-dichlorobenzyl)indolin-5-ylsulfonylcarbamoyl)-2-(1,2,3,4-tetrahydroisoquinoline-2-carbonyl)phenyl)-5-methyl-1H-pyrazole-3-carboxamido)methyl)biphenyl-4-yl)acetic acid | 988.4 |
| 215 | 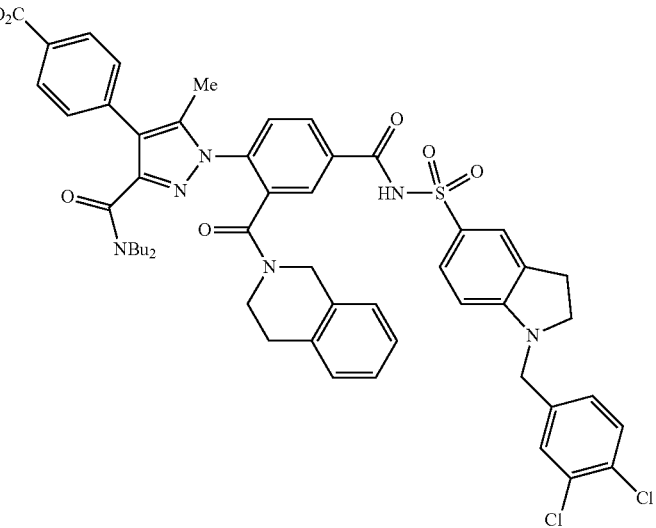 | 4-(3-(dibutylcarbamoyl)-1-(4-(1-(3,4-dichlorobenzyl)indolin-5-ylsulfonylcarbamoyl)-2-(1,2,3,4-tetrahydroisoquinoline-2-carbonyl)phenyl)-5-methyl-1H-pyrazol-4-yl)benzoic acid | 975.5 |

| Ex. No. | Structure | Name | LCMS (M + H) |
|---|---|---|---|
| 216 | 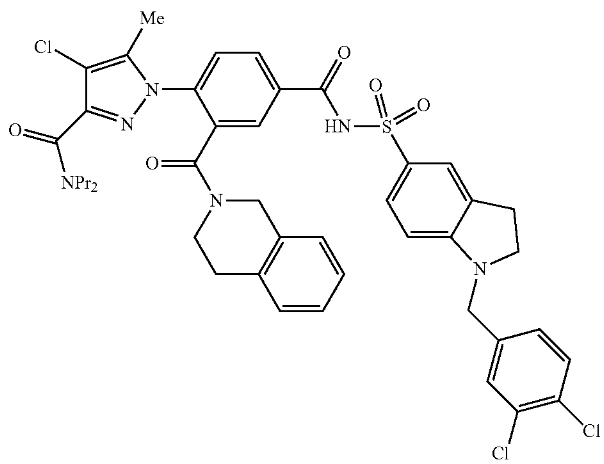 | 4-chloro-1-(4-(1-(3,4-dichlorobenzyl)indolin-5-ylsulfonylcarbamoyl)-2-(1,2,3,4-tetrahydroisoquinoline-2-carbonyl)phenyl)-5-methyl-N,N-dipropyl-1H-pyrazole-3-carboxamide | 863.3 |
| 217 | 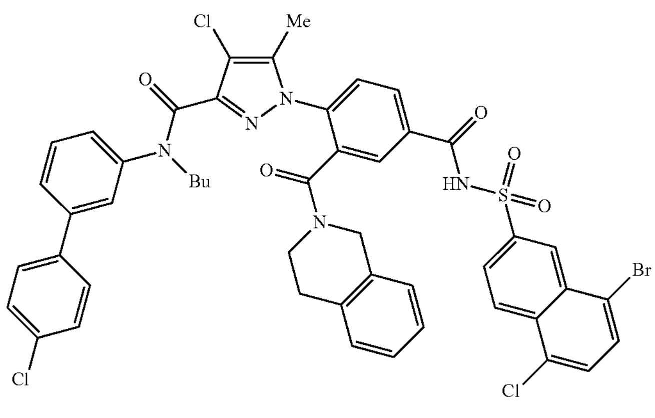 | 1-(4-(8-bromo-5-chloronaphthalen-2-ylsulfonylcarbamoyl)-2-(1,2,3,4-tetrahydroisoquinoline-2-carbonyl)phenyl)-N-butyl-4-chloro-N-(4'-chlorobiphenyl-3-yl)-5-methyl-1H-pyrazole-3-carboxamide | 982.1 |
| 218 | 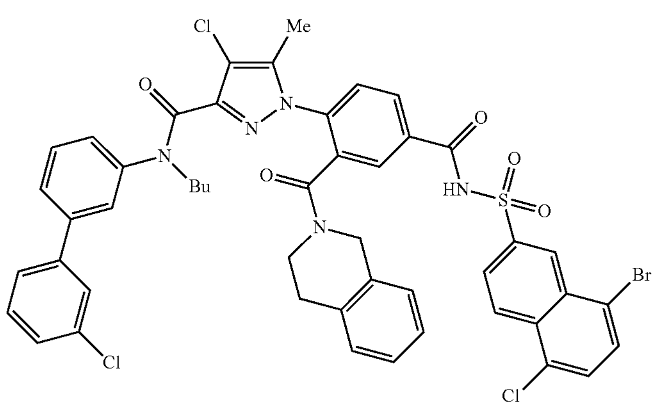 | 1-(4-(8-bromo-5-chloronaphthalen-2-ylsulfonylcarbamoyl)-2-(1,2,3,4-tetrahydroisoquinoline-2-carbonyl)phenyl)-N-butyl-4-chloro-N-(3'-chlorobiphenyl-3-yl)-5-methyl-1H-pyrazole-3-carboxamide | 982.1 |

| Ex. No. | Structure | Name | LCMS (M + H) |
|---|---|---|---|
| 219 | 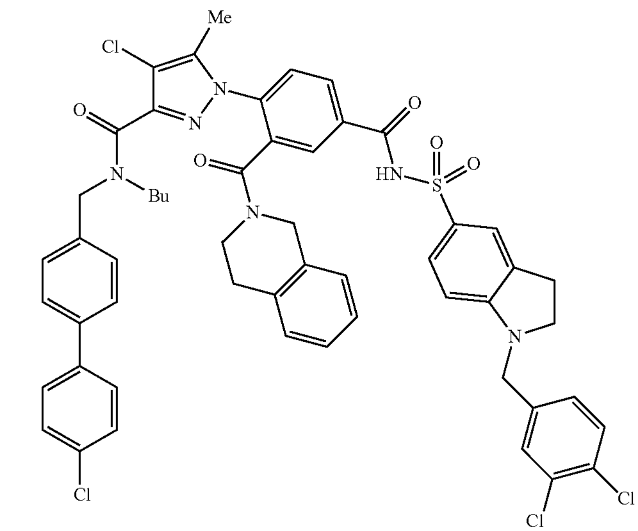 | N-butyl-4-chloro-N-((4'-chlorobiphenyl-4-yl)methyl)-1-(4-(1-(3,4-dichlorobenzyl)indolin-5-ylsulfonylcarbamoyl)-2-(1,2,3,4-tetrahydroisoquinoline-2-carbonyl)phenyl)-5-methyl-1H-pyrazole-3-carboxamide | 1035.2 |
| 220 | 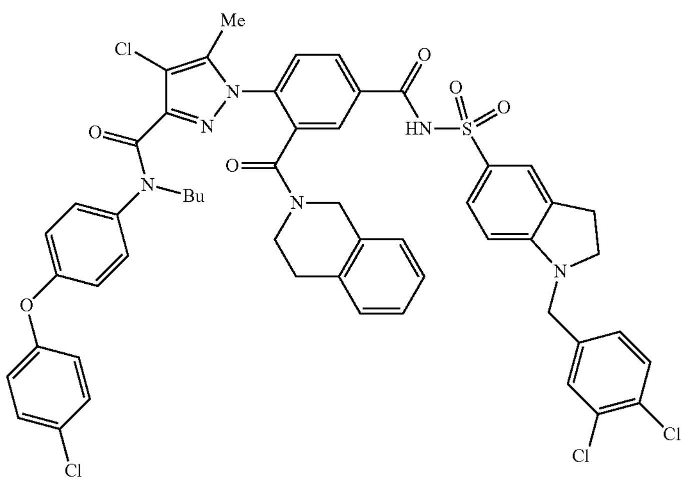 | N-butyl-4-chloro-N-(4-(4-chlorophenoxy)phenyl)-1-(4-(1-(3,4-dichlorobenzyl)indolin-5-ylsulfonylcarbamoyl)-2-(1,2,3,4-tetrahydroisoquinoline-2-carbonyl)phenyl)-5-methyl-1H-pyrazole-3-carboxamide | 1037.1 |
| 221 | 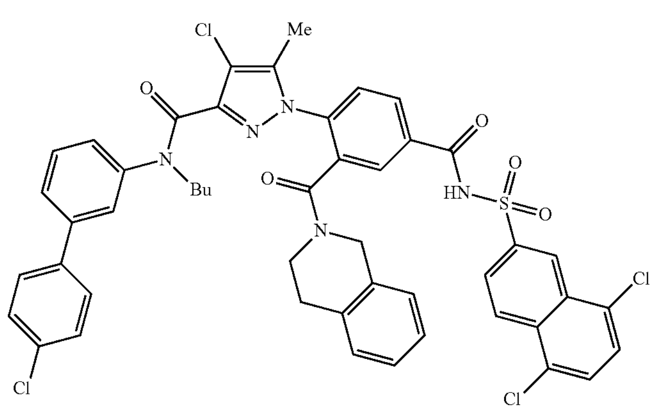 | N-butyl-4-chloro-N-(4'-chlorobiphenyl-3-yl)-1-(4-(5,8-dichloronaphthalen-2-ylsulfonylcarbamoyl)-2-(1,2,3,4-tetrahydroisoquinoline-2-carbonyl)phenyl)-5-methyl-1H-pyrazole-3-carboxamide | 938.1 |

| Ex. No. | Structure | Name | LCMS (M + H) |
|---|---|---|---|
| 222 | 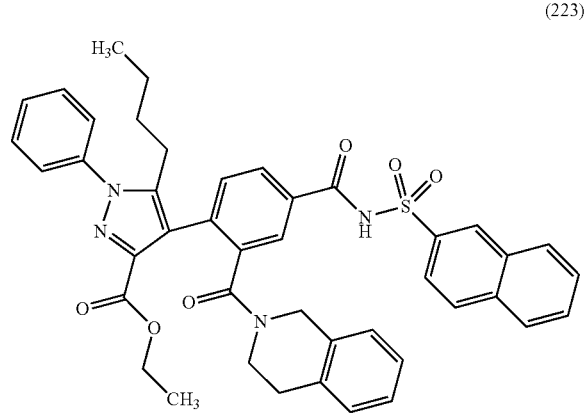 [SMILES: CCCCc1c(-c2ccc(C(=O)NS(=O)(=O)c3ccc4ccccc4c3)cc2C(=O)N2CCc3ccccc3C2)c(C(=O)OCC)nn1-c1ccccc1] | N-butyl-4-chloro-N-(3'-chlorobiphenyl-3-yl)-1-(4-(5,8-dichloronaphthalen-2-ylsulfonylcarbamoyl)-2-(1,2,3,4-tetrahydroisoquinoline-2-carbonyl)phenyl)-5-methyl-1H-pyrazole-3-carboxamide | 938.1 |

Example 223

Ethyl 5-butyl-4-(4-(naphthalen-2-ylsulfonylcarbamoyl)-2-(1,2,3,4-tetrahydroisoquinoline-2-carbonyl)phenyl)-1-phenyl-1H-pyrazole-3-carboxylate (223)

Intermediate 223A tert-Butyl 4-iodo-3-(1,2,3,4-tetrahydroisoquinoline-2-carbonyl)benzoate (Int-223A)

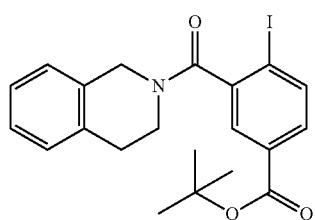

A 100 mL flask was charged with 3-(tert-butoxycarbonyl)benzoic acid (Matrix, 1.75 g, 7.87 mmol), palladium(II) acetate (0.177 g, 0.787 mmol), iodobenzene diacetate (2.54 g, 7.87 mmol), iodine (2.00 g, 7.87 mmol), and tetrabutylammonium iodide (2.91 g, 7.87 mmol). DCE (30 mL) was added and the dark reaction mixture was stirred at 80° C. for 6 h. The reaction mixture was concentrated in vacuo, diluted with 2M aq. sodium carbonate solution, and then extracted with ether (2×). The aqueous layer was made acidic with concentrated HCl and then extracted with EtOAc (2×). The pooled EtOAc extracts were dried over anhydrous magnesium sulfate and concentrated in vacuo to give crude 5-(tert-butoxycarbonyl)-2-iodobenzoic acid (1.7 g, 62%) which was used directly without further purification. A 200 mL round bottom flask was charged with crude 5-(tert-butoxycarbonyl)-2-iodobenzoic acid (1.7 g, 4.88 mmol) and HATU (2.23 g, 5.86 mmol). THF (30 mL), DMF (30.0 mL), and 2,6-lutidine (1.1 mL, 9.77 mmol) were added and the reaction mixture was stirred at room temperature for 1 h. Next, 1,2,3,4-tetrahydroisoquinoline (0.93 mL, 7.3 mmol) was then added. After stirring at room temperature 1 h, the reaction mixture was suspended in EtOAc, and then washed with sat. aq. sodium bicarbonate solution, 10% aq. LiCl solution, and then sat. aq. bicarbonate solution again. The organic layer was dried over anhydrous sodium sulfate and concentrated in vacuo. The residue was purified by flash chromatography (Isco 120 g column eluting with 0-40% EtOAc/hexanes) to give the title compound (1.46 g, 65%) as a white foam. $^1$H NMR (CDCl$_3$) δ 7.96-7.90 (m, 1H), 7.81-7.80 (m, 1H), 6.70-6.67 (m, 1H), 7.27-7.13 (m, 4H), 5.09-4.83 (m, 1H), 4.45-4.33 (m, 1H), 4.06-4.01 (m, 1H), 3.50-3.44 (m, 1H), 3.05-2.83 (m, 2H), 1.58 (s, 9H); MS(ESI$^+$) m/z 464.1 (M+H)$^+$.

Intermediate 223B tert-Butyl 4-formyl-3-(1,2,3,4-tetrahydroisoquinoline-2-carbonyl)benzoate (Int-223B)

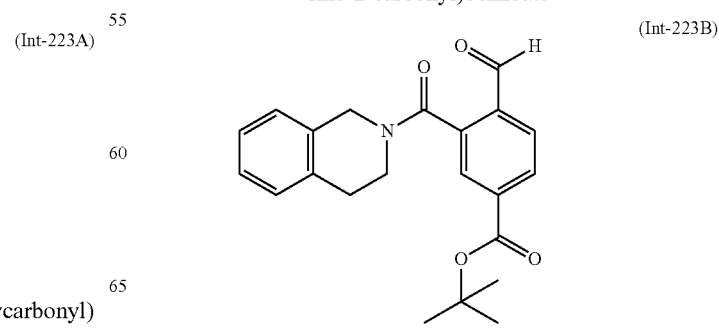

Carbon monoxide was bubbled through a solution of tert-butyl 4-iodo-3-(1,2,3,4-tetrahydroisoquinoline-2-carbonyl)benzoate (1.36 g, 2.94 mmol) and 1,1'-bis-(diphenylphosphino)-ferrocene) palladium dichloride (0.241 g, 0.294 mmol) in DMF (20 mL) at 70° C. for 10 min. DIPEA (1.28 mL, 7.34 mmol) and trioctylsilane (2.64 mL, 5.87 mmol) were added. The reaction mixture was stirred at 70° C. under CO (balloon) overnight. After cooling to room temperature, the reaction mixture was diluted with EtOAc and washed with sat. aq. sodium bicarbonate solution, 10% aq. LiCl solution, and then sat. aq. sodium bicarbonate solution again. The organic layer was dried over anhydrous sodium sulfate and concentrated in vacuo. The residue was purified by flash chromatography (Isco 40 g column eluting from 0-40% EtOAc/hexanes) to give the title compound (537 mg, 50%) as a yellow foam. $^1$H NMR (CDCl$_3$, 1.5:1 mixture of amide rotamers) δ 10.19 (s, 0.5H), 10.14 (s, 0.5H), 8.17-8.13 (m, 1H), 8.03-7.98 (m, 2H), 7.26-7.10 (m, 4H), 5.00 (s, 1H), 4.33 (m, 1H), 4.09 (t, J=6 Hz, 1H), 3.45 (t, J=6 Hz, 1H), 3.04 (t, J=6 Hz, 1H), 2.80 (t, J=6 Hz, 1H), 1.61 (s, 9H); MS(ESI$^+$) m/z 366.2 (M+H)$^+$.

Intermediate 223C tert-Butyl 4-(1-hydroxy-2-nitrohexyl)-3-(1,2,3,4-tetrahydroisoquinoline-2-carbonyl)benzoate (Int-223C)

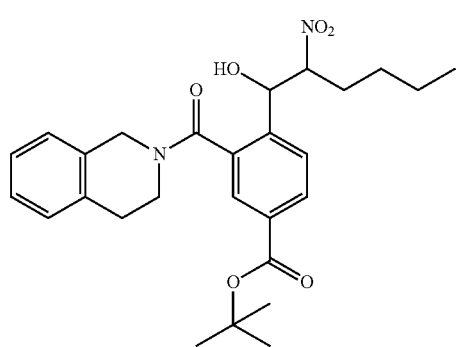

To a solution of tert-butyl 4-formyl-3-(1,2,3,4-tetrahydroisoquinoline-2-carbonyl)benzoate (480 mg, 1.31 mmol) in THF (3 mL) at 0° C. was added 1-nitropentane (0.323 mL, 2.63 mmol) followed by potassium tert-butoxide (0.131 mL, 0.131 mmol). The cooling bath was removed and the mixture was stirred at room temperature for 3 h. The reaction mixture was diluted with EtOAc and washed with sat. aq. sodium bicarbonate solution. The aqueous layer was back-extracted with EtOAc and the pooled organic extracts were dried over anhydrous sodium sulfate and concentrated in vacuo to give crude tert-butyl 4-(1-hydroxy-2-nitrohexyl)-3-(1,2,3,4-tetrahydroisoquinoline-2-carbonyl)benzoate as a brown oil (2:1 mixture of diastereomers by LC-MS) which was used directly without further purification. MS(ESI$^+$) m/z 483.3 (M+H)$^+$.

Intermediate 223D tert-Butyl 4-(2-nitrohex-1-enyl)-3-(1,2,3,4-tetrahydroisoquinoline-2-carbonyl)benzoate (Int-223D)

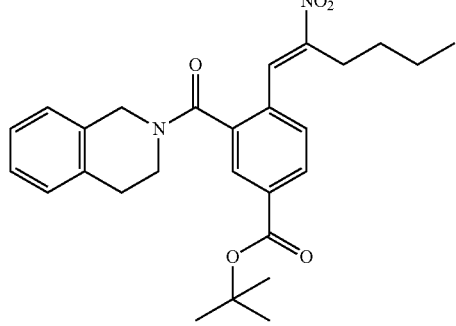

To a solution of tert-butyl 4-(1-hydroxy-2-nitrohexyl)-3-(1,2,3,4-tetrahydroisoquinoline-2-carbonyl)benzoate (632 mg, 1.31 mmol) in THF (3 mL) was added acetic anhydride (0.136 mL, 1.44 mmol) and a crystal of DMAP (~5 mg). After stirring at room temperature for 30 min, the reaction mixture was concentrated in vacuo. The residue was suspended in DCM (3.0 mL) and DMAP (192 mg, 1.57 mmol) was added. After stirring at room temperature overnight, the reaction mixture was diluted with DCM and washed with brine. The aqueous layer was back-extracted with DCM and the pooled organic layers were dried over anhydrous sodium sulfate and concentrated in vacuo. The residue was purified by flash chromatography (Isco 40 g column eluting with 0-25% EtOAc/hexanes) to give the title compound (485 mg, 80%) as a colorless oil. $^1$H NMR (CDCl$_3$, 1:1 mixture of amide rotamers) δ 8.12-8.09 (m, 1H), 8.01-8.00 (m, 1H), 7.97 (s, 0.5H), 7.81 (s, 0.5H), 7.46 (d, J=8 Hz, 0.5H), 7.39 (d, J=8 Hz, 0.5H), 7.24-6.79 (m, 4H), 4.94 (s, 1H), 4.31 (s, 1H), 3.47 (t, J=6 Hz, 1H), 3.00-2.47 (m, 5H), 1.65-1.31 (m, 4H), 1.63 (s, 9H), 0.95-0.86 (m, 3H); MS(ESI$^+$) m/z 465.3 (M+H)$^+$.

Intermediate 223E

Ethyl 4-(4-(tert-butoxycarbonyl)-2-(1,2,3,4-tetrahydroisoquinoline-2-carbonyl)phenyl)-5-butyl-1-phenyl-1H-pyrazole-3-carboxylate (Int-223E)

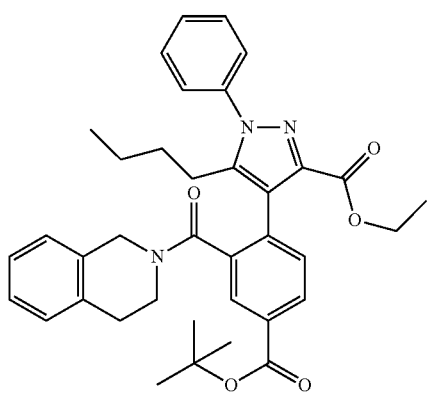

To a solution of (E)-ethyl 2-(2-phenylhydrazono)acetate (31 mg, 0.16 mmol) in THF (1 mL) at −78° C. was added potassium tert-butoxide (0.161 mL, 0.161 mmol). After stirring at −78° C. for 15 min, a solution of tert-butyl 4-(2-nitrohex-1-enyl)-3-(1,2,3,4-tetrahydroisoquinoline-2-carbonyl)benzoate (75 mg, 0.161 mmol) in THF (1.0 mL) was added. After stirring at −78° C. for 15 min, TFA (0.024 mL, 0.323 mmol) was added and the reaction mixture became colorless. The reaction mixture was stirred at −78° C. for 2 h and was then allowed to warm to room temperature and stirred at room temperature for 30 min. The reaction mixture was quenched with sat. aq. sodium bicarbonate solution and then extracted with EtOAc. The organic extracts were dried over anhydrous sodium sulfate and concentrated in vacuo. The residue was purified by flash chromatography (Isco 40 g column eluting with 0-40% EtOAc/hexanes) to give the title compound (33 mg, 34%) as a colorless oil. $^1$H NMR (CDCl$_3$, 1:1 mixture of amide rotamers) δ 8.09 (dd, J=8, 2 Hz, 1H), 8.05-8.03 (m, 1H), 7.49-7.37 (m, 6H), 7.26-6.81 (m, 4H), 5.02-4.98 (m, 1H), 4.47-4.38 (m, 1H), 4.32-4.27 (m, 2H), 4.16-3.98 (m, 1H), 3.58-3.40 (m, 1H), 2.82-2.51 (m, 4H), 1.61 (s, 9H), 1.28 (t, J=8 Hz, 1.5H), 1.20 (t, J=8 Hz, 1.5H), 1.47-0.91 (m, 4H), 0.60-0.56 (m, 3H); MS(ESI$^+$) m/z 608.3 (M+H)$^+$.

Intermediate 223F 4-(5-Butyl-3-(ethoxycarbonyl)-1-phenyl-1H-pyrazol-4-yl)-3-(1,2,3,4-tetrahydroisoquinoline-2-carbonyl)benzoic acid

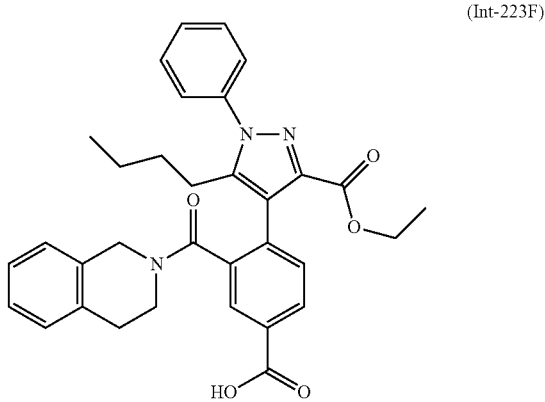 [SMILES: CCCCc1c(-c2ccc(C(=O)O)cc2C(=O)N2CCc3ccccc3C2)c(C(=O)OCC)nn1-c1ccccc1]
(Int-223F)

To a solution of ethyl 4-(4-(tert-butoxycarbonyl)-2-(1,2,3,4-tetrahydroisoquinoline-2-carbonyl)phenyl)-5-butyl-1-phenyl-1H-pyrazole-3-carboxylate (33 mg, 0.054 mmol) in DCM (2.0 mL) was added TFA (1.0 mL). After stirring at room temperature for 1 h, the reaction mixture was concentrated in vacuo. The residue was used directly in the next step without further purification. MS(ESI$^+$) m/z 552.3 (M+H)$^+$.

Example 223

Following a procedure analogous to that for the synthesis of Example 1,4-(5-butyl-3-(ethoxycarbonyl)-1-phenyl-1H-pyrazol-4-yl)-3-(1,2,3,4-tetrahydroisoquinoline-2-carbonyl)benzoic acid (15 mg, 0.027 mmol) and naphthalene-2-sulfonamide (11 mg, 0.054 mmol) were converted to the title compound (4.9 mg, 24%). $^1$H NMR (1:1 CD$_3$OD:CDCl$_3$, 1:1 mixture of amide rotamers) δ 8.76 (s, 1H), 8.19-8.03 (m, 3H), 8.00-7.97 (m, 2H), 7.90-7.89 (m, 1H), 7.73-7.64 (m, 2H), 7.52-7.33 (m, 6H), 7.22-7.06 (m, 3.5H), 6.79-6.78 (m, 0.5H), 4.90-4.85 (m, 0.5H), 4.58-4.50 (m, 0.5H), 4.28-4.21 (m, 2H), 4.06-4.02 (m, 0.5H), 3.92-3.88 (m, 0.5H), 3.50-3.42 (m, 2H), 2.78-2.48 (m, 4H), 1.34-0.94 (m, 7H), 0.56 (t, J=6 Hz, 3H); MS(ESI$^+$) m/z 741.4 (M+H).

Example 224

Ethyl 5-methyl-4-(4-(naphthalen-2-ylsulfonylcarbamoyl)-2-(1,2,3,4-tetrahydroisoquinoline-2-carbonyl)phenyl)-1-phenyl-1H-pyrazole-3-carboxylate

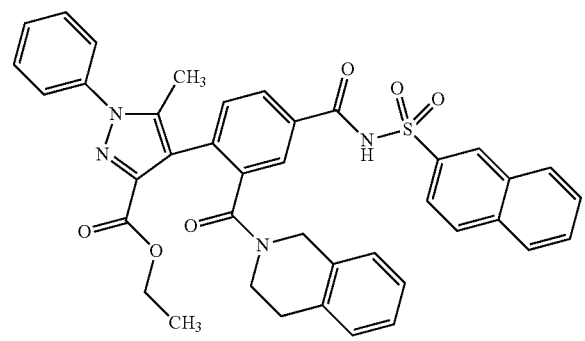
(224)

Intermediate 224A tert-Butyl 4-(1-hydroxy-2-nitropropyl)-3-(1,2,3,4-tetrahydroisoquinoline-2-carbonyl)benzoate

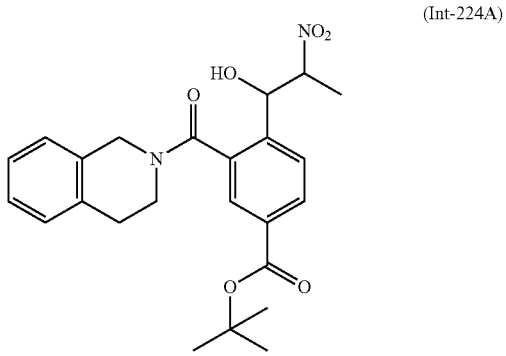 [SMILES: CC(C(O)c1ccc(C(=O)OC(C)(C)C)cc1C(=O)N1CCc2ccccc2C1)[N+](=O)[O-]]
(Int-224A)

Following a procedure analogous to that for the synthesis of Intermediate 223C, tert-butyl 4-formyl-3-(1,2,3,4-tetrahydroisoquinoline-2-carbonyl)benzoate (59 mg, 0.16 mmol) and nitroethane (0.023 mL, 0.32 mmol) were converted to the title compound as a crude brown oil (1:1 mixture of diastereomers by LC-MS) which was used directly without further purification. MS(ESI$^+$) m/z 441.3 (M+H)$^+$.

Intermediate 224B tert-Butyl 4-(2-nitroprop-1-enyl)-3-(1,2,3,4-tetrahydroisoquinoline-2-carbonyl)benzoate

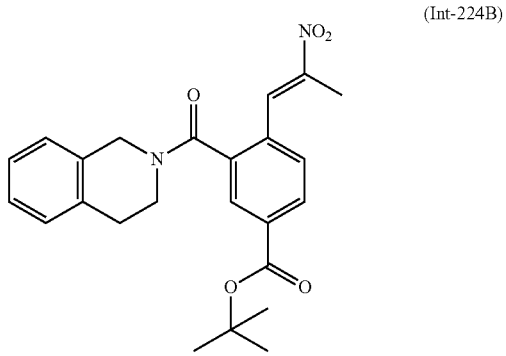 [SMILES: C/C(=C\c1ccc(C(=O)OC(C)(C)C)cc1C(=O)N1CCc2ccccc2C1)[N+](=O)[O-]]
(Int-224B)

Following a procedure analogous to that for the synthesis of Intermediate 223D, tert-butyl 4-(1-hydroxy-2-nitropropyl)-3-(1,2,3,4-tetrahydroisoquinoline-2-carbonyl)benzoate (70 mg, 0.16 mmol) was converted to the title compound (48 mg, 71%) as a colorless oil. $^1$H NMR (CDCl$_3$, 1:1 mixture of amide rotamers) δ 8.10 (dd, J=8, 4 Hz, 1H), 8.05 (s, 0.5H), 8.03-8.01 (m, 1H), 7.87 (s, 0.5H), 7.48 (d, J=8 Hz, 0.5H), 7.39 (d, J=8 Hz, 0.5H), 7.24-6.78 (m, 4H), 4.94 (s, 1H), 4.30 (s, 1H), 3.47 (t, J=6 Hz, 1H), 3.00 (t, J=4 Hz, 2H), 2.82 (t, J=6 Hz, 1H), 2.14 (s, 1.5H), 2.05 (s, 1.5H), 1.60 (s, 9H); MS(ESI$^+$) m/z 423.3 (M+H)$^+$.

Intermediate 224C

Ethyl 4-(4-(tert-butoxycarbonyl)-2-(1,2,3,4-tetrahydroisoquinoline-2-carbonyl)phenyl)-5-methyl-1-phenyl-1H-pyrazole-3-carboxylate

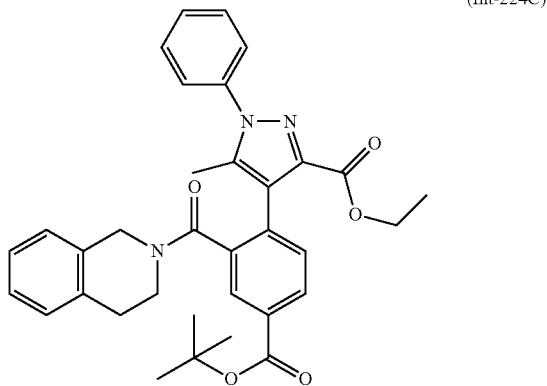
(Int-224C)

Following a procedure analogous to that for the synthesis of Intermediate 224E, (E)-ethyl 2-(2-phenylhydrazono)acetate (22 mg, 0.11 mmol) and tert-butyl 4-(2-nitroprop-1-enyl)-3-(1,2,3,4-tetrahydroisoquinoline-2-carbonyl)benzoate (48 mg, 0.11 mmol) were converted to the title compound (42 mg, 65%) as a colorless oil. $^1$H NMR (CDCl$_3$, 1:1 mixture of amide rotamers) δ 8.10 (dd, J=8, 2 Hz, 1H), 8.06-8.04 (m, 1H), 7.49-7.40 (m, 6H), 7.21-6.81 (m, 4H), 5.02-4.96 (m, 1H), 4.49-4.28 (m, 3H), 4.17-4.03 (m, 1H), 3.54-3.33 (m, 1H), 2.82-2.43 (m, 2H), 2.19 (s, 3H), 1.61 (s, 9H), 1.28 (t, J=8 Hz, 1.5H), 1.23 (t, J=8 Hz, 1.5H); MS(ESI$^+$) m/z 566.3 (M+H)$^+$.

Intermediate 224D 4-(3-(Ethoxycarbonyl)-5-methyl-1-phenyl-1H-pyrazol-4-yl)-3-(1,2,3,4-tetrahydroisoquinoline-2-carbonyl)benzoic acid

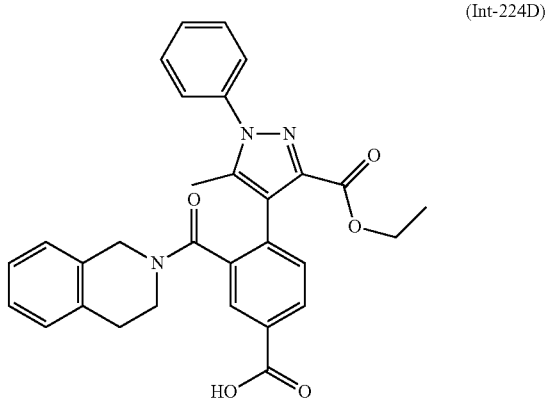 [SMILES: CCOC(=O)c1nn(-c2ccccc2)c(C)c1-c1ccc(C(=O)O)cc1C(=O)N1CCc2ccccc2C1]
(Int-224D)

Following a procedure analogous to that for the synthesis of Intermediate 223F, ethyl 4-(4-(tert-butoxycarbonyl)-2-(1,2,3,4-tetrahydroisoquinoline-2-carbonyl)phenyl)-5-methyl-1-phenyl-1H-pyrazole-3-carboxylate (42 mg, 0.074 mmol) was converted to the title compound which was used directly in the next step without purification. MS(ESI$^+$) m/z 510.2 (M+H)$^+$.

Example 224

Following a procedure analogous to that for the synthesis of Example 1, 4-(3-(ethoxycarbonyl)-5-methyl-1-phenyl-1H-pyrazol-4-yl)-3-(1,2,3,4-tetrahydroisoquinoline-2-carbonyl)benzoic acid (19 mg, 0.037 mmol) and naphthalene-2-sulfonamide (15 mg, 0.074 mmol) were converted to the title compound (13 mg, 50%). $^1$H NMR (1:1 CD$_3$OD:CDCl$_3$, 1:1 mixture of amide rotamers) δ 8.72-8.71 (m, 1H), 8.09-7.94 (m, 6H), 7.67-7.60 (m, 2H), 7.53-7.39 (m, 6H), 7.19-7.05 (m, 3.5H), 6.80-6.78 (m, 0.5H), 4.90-4.85 (m, 0.5H), 4.58-4.50 (m, 0.5H), 4.29-4.22 (m, 2H), 4.04-4.00 (m, 0.5H), 3.91-3.87 (m, 0.5H), 3.50-3.32 (m, 2H), 2.81-2.48 (m, 2H), 2.12 (s, 3H), 1.23-1.13 (m, 3H); MS (ESI$^+$) m/z 699.3 (M+H).

Example 225

Ethyl 5-butyl-1-(4-methoxyphenyl)-4-(4-(naphthalen-2-ylsulfonylcarbamoyl)-2-(1,2,3,4-tetrahydroisoquinoline-2-carbonyl)phenyl)-1H-pyrazole-3-carboxylate

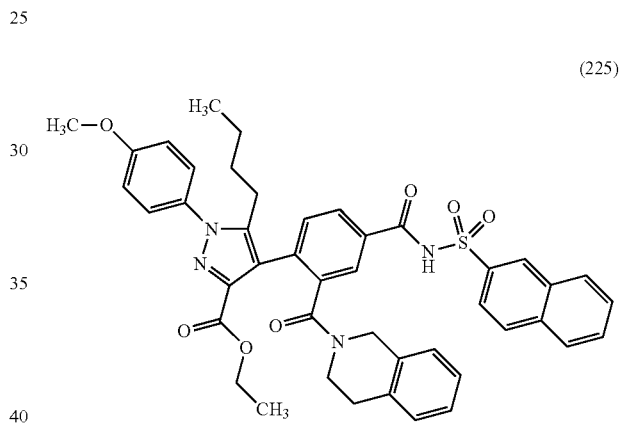
(225)

Intermediate 225A

Ethyl 4-(4-(tert-butoxycarbonyl)-2-(1,2,3,4-tetrahydroisoquinoline-2-carbonyl)phenyl)-5-butyl-1-(4-methoxyphenyl)-1H-pyrazole-3-carboxylate

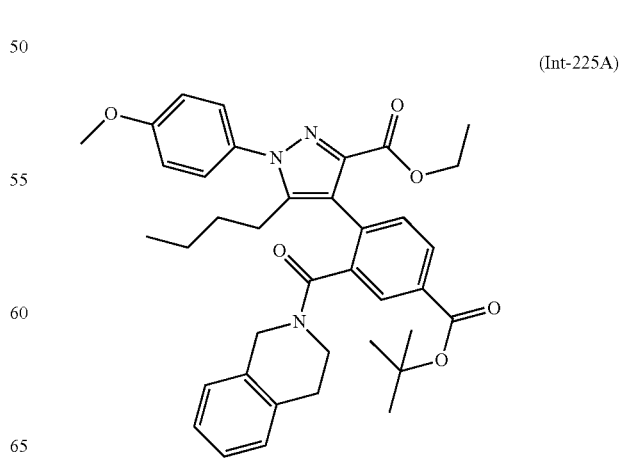
(Int-225A)

Following a procedure analogous to that for the synthesis of Intermediate 223E, (E)-ethyl 2-(2-(4-methoxyphenyl)hydrazono)acetate (24 mg, 0.108 mmol) and tert-butyl 4-(2-nitrohex-1-enyl)-3-(1,2,3,4-tetrahydroisoquinoline-2-carbonyl)benzoate (50 mg, 0.108 mmol) were converted to the title compound (31 mg, 45%) as a colorless oil. $^1$H NMR (CDCl$_3$, 1:1 mixture of amide rotamers) δ 8.08 (dd, J=8, 2 Hz, 1H), 8.03-8.02 (m, 1H), 7.42-6.81 (m, 9H), 5.02-4.98 (m, 1H), 4.46-4.38 (m, 1H), 4.32-4.26 (m, 2H), 4.15-3.98 (m, 1H), 3.86 (s, 1.5H), 3.85 (s, 1.5H), 3.54-3.33 (m, 1H), 2.81-2.45 (m, 4H), 1.61 (s, 9H), 1.28 (t, J=8 Hz, 1.5H), 1.22 (t, J=8 Hz, 1.5H), 1.30-0.95 (m, 4H), 0.61-0.57 (m, 3H); MS(ESI$^+$) m/z 638.3 (M+H)$^+$.

Intermediate 225B 4-(5-Butyl-3-(ethoxycarbonyl)-1-(4-methoxyphenyl)-1H-pyrazol-4-yl)-3-(1,2,3,4-tetrahydroisoquinoline-2-carbonyl)benzoic acid (Int-225B)

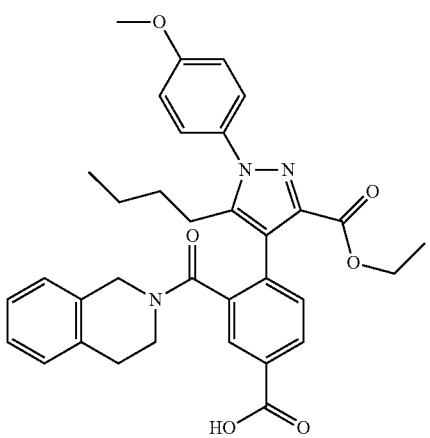

Following a procedure analogous to that for the synthesis of Intermediate 223F, ethyl 4-(4-(tert-butoxycarbonyl)-2-(1,2,3,4-tetrahydroisoquinoline-2-carbonyl)phenyl)-5-butyl-1-(4-methoxyphenyl)-1H-pyrazole-3-carboxylate (31 mg, 0.049 mmol) was converted to the title compound which was used directly in the next step without further purification. MS(ESI$^+$) m/z 582.3 (M+H)$^+$.

Example 225

Following a procedure analogous to that for the synthesis of Example 1,4-(5-butyl-3-(ethoxycarbonyl)-1-(4-methoxyphenyl)-1H-pyrazol-4-yl)-3-(1,2,3,4-tetrahydroisoquinoline-2-carbonyl)benzoic acid (14 mg, 0.024 mmol) and naphthalene-2-sulfonamide (10 mg, 0.048 mmol) were converted to the title compound (6.0 mg, 32%). $^1$H NMR (DMSO-d$_6$) δ 8.63 (s, 1H), 8.20 (d, J=8 Hz, 1H), 8.11-7.93 (m, 5H), 7.76-7.65 (m, 2H), 7.41-6.76 (m, 9H), 4.80-3.80 (m, 6H), 3.83 (s, 3H), 2.70-2.35 (m, 4H), 1.12-0.85 (m, 7H), 0.50 (t, J=6 Hz, 3H); MS(ESI$^+$) m/z 771.3 (M+H).

Example 226

Ethyl 5-butyl-1-(4-isopropylphenyl)-4-(4-(naphthalen-2-ylsulfonylcarbamoyl)-2-(1,2,3,4-tetrahydroisoquinoline-2-carbonyl)phenyl)-1H-pyrazole-3-carboxylate (226)

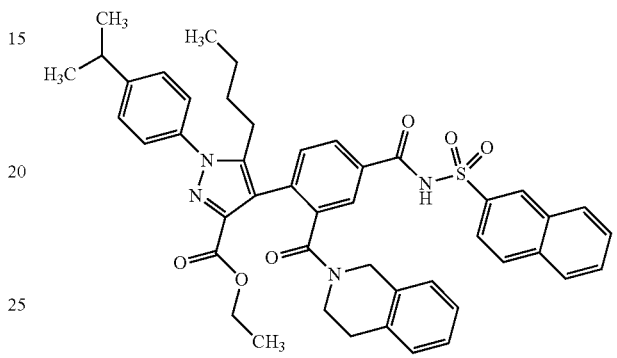

Intermediate 226A

Ethyl 4-(4-(tert-butoxycarbonyl)-2-(1,2,3,4-tetrahydroisoquinoline-2-carbonyl)phenyl)-5-butyl-1-(4-isopropylphenyl)-1H-pyrazole-3-carboxylate (Int-226A)

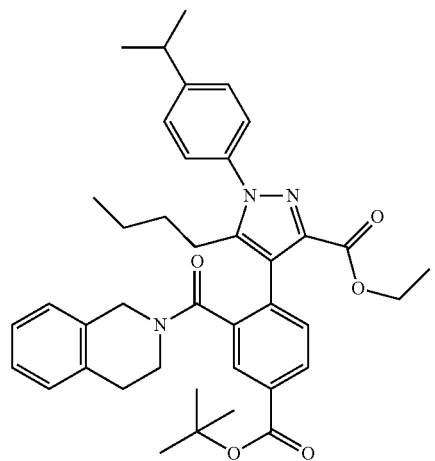

Following a procedure analogous to that for the synthesis of Intermediate 223E, (E)-ethyl 2-(2-(4-isopropylphenyl)hydrazono)acetate (25.2 mg, 0.108 mmol) and tert-butyl 4-(2-nitrohex-1-enyl)-3-(1,2,3,4-tetrahydroisoquinoline-2-carbonyl)benzoate (50 mg, 0.108 mmol) were converted to the title compound (36 mg, 52%) as a pale yellow oil. $^1$H NMR (CDCl$_3$, 1:1 mixture of amide rotamers) δ 8.08 (dd, J=8, 2 Hz, 1H), 8.04-8.03 (m, 1H), 7.43-6.81 (m, 9H), 5.02-4.98 (m, 1H), 4.46-4.38 (m, 1H), 4.30-4.27 (m, 2H), 4.15-3.98 (m, 1H), 3.54-3.33 (m, 1H), 2.98-2.50 (m, 5H), 1.61 (s, 9H), 1.29-1.24 (m, 7.5H), 1.22 (t, J=8 Hz, 1.5H), 1.18-0.95 (m, 4H), 0.60-0.56 (m, 3H); MS (ESI⁺) m/z 650.4 (M+H)⁺.

Intermediate 226B 4-(5-Butyl-3-(ethoxycarbonyl)-1-(4-isopropylphenyl)-1H-pyrazol-4-yl)-3-(1,2,3,4-tetrahydroisoquinoline-2-carbonyl)benzoic acid (Int-226B)

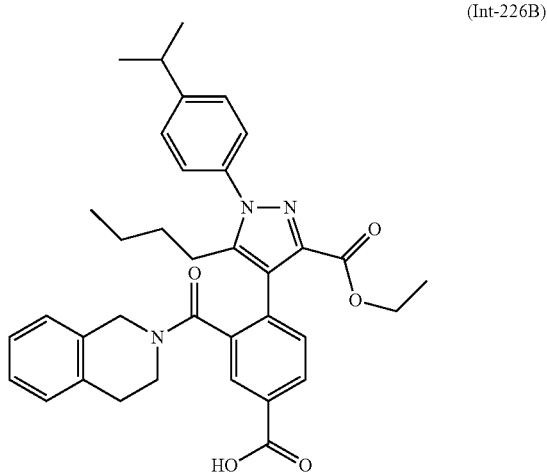 [SMILES: CCCCc1c(-c2ccc(C(=O)O)cc2C(=O)N2CCc3ccccc3C2)c(C(=O)OCC)nn1-c1ccc(C(C)C)cc1]

Following a procedure analogous to that for the synthesis of Intermediate 223F, ethyl 4-(4-(tert-butoxycarbonyl)-2-(1,2,3,4-tetrahydroisoquinoline-2-carbonyl)phenyl)-5-butyl-1-(4-isopropylphenyl)-1H-pyrazole-3-carboxylate (36 mg, 0.055 mmol) was converted to the title compound which was used directly in the next step without further purification. MS(ESI⁺) m/z 594.3 (M+H)⁺.

Example 226

Following a procedure analogous to that for the synthesis of Example 1, 4-(5-butyl-3-(ethoxycarbonyl)-1-(4-isopropylphenyl)-1H-pyrazol-4-yl)-3-(1,2,3,4-tetrahydroisoquinoline-2-carbonyl)benzoic acid (16 mg, 0.027 mmol) and naphthalene-2-sulfonamide (11 mg, 0.055 mmol) were converted to the title compound (8 mg, 37%). ¹H NMR (CD₃OD:CDCl₃, 1:1 mixture of amide rotamers) δ 8.70 (s, 1H), 8.10-8.04 (m, 3H), 8.01-7.98 (m, 2H), 7.95-7.93 (m, 1H), 7.67-7.59 (m, 2H), 7.44-7.04 (m, 8.5H), 6.80-6.78 (m, 0.5H), 4.90-4.85 (m, 0.5H), 4.58-4.50 (m, 0.5H), 4.28-4.21 (m, 2H), 4.06-4.02 (m, 0.5H), 3.92-3.88 (m, 0.5H), 3.50-3.42 (m, 2H), 2.80-2.48 (m, 5H), 1.43-0.96 (m, 13H), 0.58 (t, J=6 Hz, 3H); MS(ESI⁺) m/z 783.4 (M+H).

Example 227

Ethyl 5-butyl-4-(4-(naphthalen-2-ylsulfonylcarbamoyl)-2-(1,2,3,4-tetrahydroisoquinoline-2-carbonyl)phenyl)-1-(3-phenoxyphenyl)-1H-pyrazole-3-carboxylate (227)

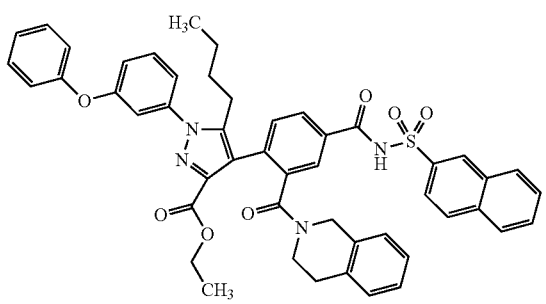

Intermediate 227A

Ethyl 4-(4-(tert-butoxycarbonyl)-2-(1,2,3,4-tetrahydroisoquinoline-2-carbonyl)phenyl)-5-butyl-1-(3-phenoxyphenyl)-1H-pyrazole-3-carboxylate (Int-227A)

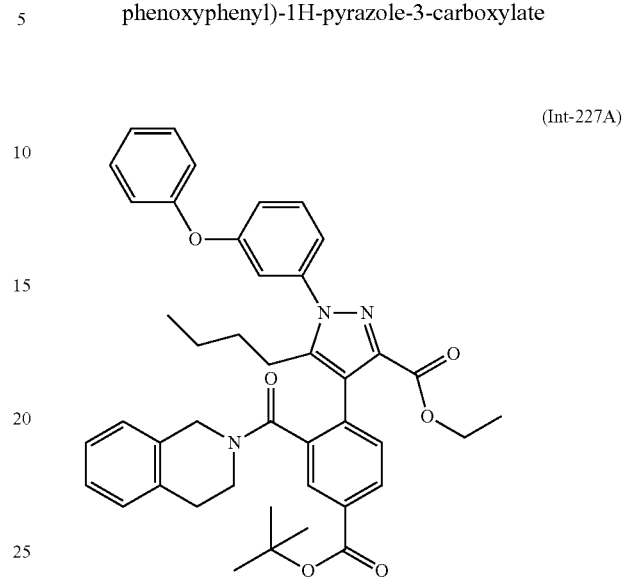

Following a procedure analogous to that for the synthesis of Intermediate 223E, (E)-ethyl 2-(2-(3-phenoxyphenyl)hydrazono)acetate (37 mg, 0.13 mmol) and tert-butyl 4-(2-nitrohex-1-enyl)-3-(1,2,3,4-tetrahydroisoquinoline-2-carbonyl)benzoate (60 mg, 0.13 mmol) were converted to the title compound (30 mg, 33%) as a pale yellow oil. ¹H NMR (CDCl₃, 1:1 mixture of amide rotamers) δ 8.08 (dd, J=8, 2 Hz, 1H), 8.04-8.02 (m, 1H), 7.44-6.78 (m, 14H), 5.02-4.98 (m, 1H), 4.41-4.35 (m, 1H), 4.31-4.26 (m, 2H), 4.16-3.98 (m, 1H), 3.58-3.28 (m, 1H), 2.81-2.50 (m, 4H), 1.61 (s, 9H), 1.28 (t, J=8 Hz, 1.5H), 1.22 (t, J=8 Hz, 1.5H), 1.13-0.88 (m, 4H), 0.63-0.59 (m, 3H); MS(ESI⁺) m/z 700.3 (M+H)⁺.

Intermediate 227B 4-(5-Butyl-3-(ethoxycarbonyl)-1-(3-phenoxyphenyl)-1H-pyrazol-4-yl)-3-(1,2,3,4-tetrahydroisoquinoline-2-carbonyl)benzoic acid (Int-227B)

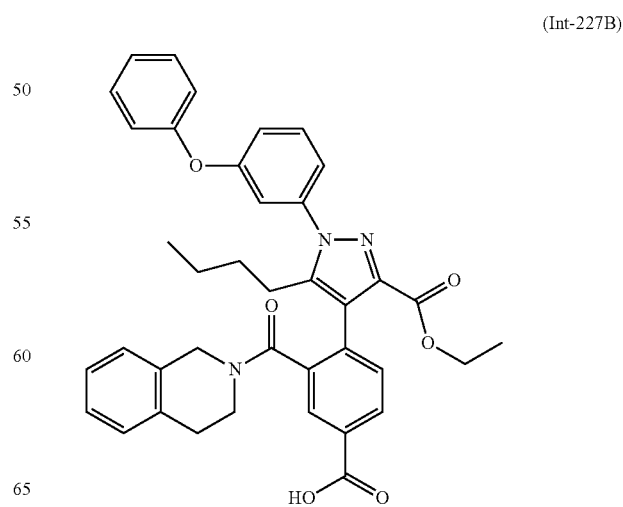

323

Following a procedure analogous to that for the synthesis of Intermediate 223F, ethyl 4-(4-(tert-butoxycarbonyl)-2-(1,2,3,4-tetrahydroisoquinoline-2-carbonyl)phenyl)-5-butyl-1-(3-phenoxyphenyl)-1H-pyrazole-3-carboxylate (30 mg, 0.043 mmol) was converted to the title compound which was used directly in the next step without further purification. MS(ESI+) m/z 644.3 (M+H)+.

Example 227

Following a procedure analogous to that for the synthesis of Example 1,4-(5-butyl-3-(ethoxycarbonyl)-1-(3-phenoxyphenyl)-1H-pyrazol-4-yl)-3-(1,2,3,4-tetrahydroisoquinoline-2-carbonyl)benzoic acid (28 mg, 0.043 mmol) and naphthalene-2-sulfonamide (18 mg, 0.086 mmol) were converted to the title compound (17 mg, 46%). $^1$H NMR (1:1 CD$_3$OD: CDCl$_3$, 1:1 mixture of amide rotamers) δ 8.75 (s, 1H), 8.22-7.86 (m, 6H), 7.73-7.62 (m, 2H), 7.49-7.35 (m, 4H), 7.18-6.95 (m, 9.5H), 6.79-6.76 (m, 0.5H), 4.84-4.79 (m, 0.5H), 4.47-4.43 (m, 0.5H), 4.25-4.21 (m, 2H), 4.05-4.01 (m, 0.5H), 3.91-3.87 (m, 0.5H), 3.52-3.46 (m, 2H), 2.77-2.71 (m, 2H), 2.52-2.47 (m, 2H), 1.44-0.97 (m, 7H), 0.60 (t, J=6 Hz, 3H); MS(ESI+) m/z 833.3 (M+H).

Example 228

Ethyl 5-butyl-4-(4-(naphthalen-2-ylsulfonylcarbamoyl)-2-(1,2,3,4-tetrahydroisoquinoline-2-carbonyl)phenyl)-1-(4-phenoxyphenyl)-1H-pyrazole-3-carboxylate (228)

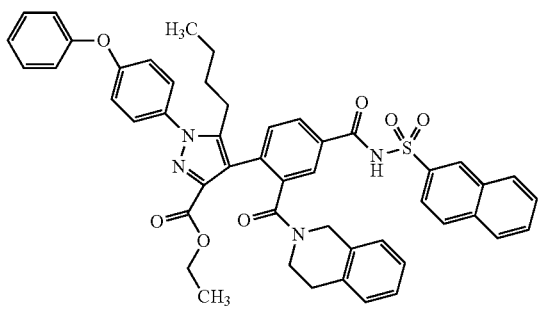

Intermediate 228A

Ethyl 4-(4-(tert-butoxycarbonyl)-2-(1,2,3,4-tetrahydroisoquinoline-2-carbonyl)phenyl)-5-butyl-1-(4-phenoxyphenyl)-1H-pyrazole-3-carboxylate (Int-228A)

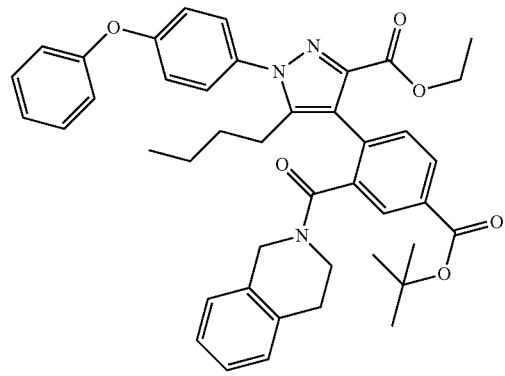

324

Following a procedure analogous to that for the synthesis of Intermediate 223E, (E)-ethyl 2-(2-(4-phenoxyphenyl)hydrazono)acetate (55 mg, 0.19 mmol) and tert-butyl 4-(2-nitrohex-1-enyl)-3-(1,2,3,4-tetrahydroisoquinoline-2-carbonyl)benzoate (90 mg, 0.19 mmol) were converted to the title compound (68 mg, 50%) as a pale yellow oil. $^1$H NMR (CDCl$_3$, 1:1 mixture of amide rotamers) δ 8.09 (dd, J=8, 2 Hz, 1H), 8.05-8.03 (m, 1H), 7.44-6.82 (m, 14H), 5.02-4.98 (m, 1H), 4.48-4.39 (m, 1H), 4.34-4.27 (m, 2H), 4.14-3.98 (m, 1H), 3.58-3.35 (m, 1H), 2.83-2.50 (m, 4H), 1.61 (s, 9H), 1.27 (t, J=8 Hz, 1.5H), 1.23 (t, J=8 Hz, 1.5H), 1.16-0.89 (m, 4H), 0.65-0.60 (m, 3H); MS(ESI+) m/z 700.3 (M+H)+.

Intermediate 228B 4-(5-Butyl-3-(ethoxycarbonyl)-1-(4-phenoxyphenyl)-1H-pyrazol-4-yl)-3-(1,2,3,4-tetrahydroisoquinoline-2-carbonyl)benzoic acid (Int-228B)

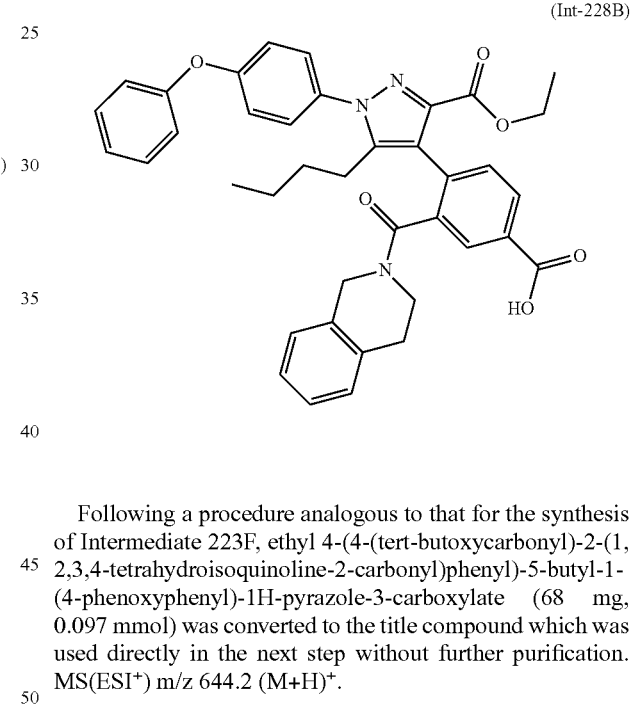

Following a procedure analogous to that for the synthesis of Intermediate 223F, ethyl 4-(4-(tert-butoxycarbonyl)-2-(1,2,3,4-tetrahydroisoquinoline-2-carbonyl)phenyl)-5-butyl-1-(4-phenoxyphenyl)-1H-pyrazole-3-carboxylate (68 mg, 0.097 mmol) was converted to the title compound which was used directly in the next step without further purification. MS(ESI+) m/z 644.2 (M+H)+.

Example 228C

Following a procedure analogous to that for the synthesis of Example 1,4-(5-butyl-3-(ethoxycarbonyl)-1-(4-phenoxyphenyl)-1H-pyrazol-4-yl)-3-(1,2,3,4-tetrahydroisoquinoline-2-carbonyl)benzoic acid (62 mg, 0.097 mmol) and naphthalene-2-sulfonamide (40 mg, 0.19 mmol) were converted to the title compound (73 mg, 90%). $^1$H NMR (1:1 CD$_3$OD: CDCl$_3$, 1:1 mixture of amide rotamers) δ 8.74 (s, 1H), 8.15-7.93 (m, 6H), 7.71-7.63 (m, 2H), 7.47-7.32 (m, 4H), 7.21-7.05 (m, 9.5H), 6.80-6.79 (m, 0.5H), 4.86-4.81 (m, 0.5H), 4.45-4.41 (m, 0.5H), 4.28-4.21 (m, 2H), 4.04-4.00 (m, 0.5H), 3.90-3.86 (m, 0.5H), 3.52-3.38 (m, 2H), 2.81-2.47 (m, 4H), 1.41-0.89 (m, 7H), 0.60 (t, J=6 Hz, 3H); MS(ESI+) m/z 833.2 (M+H).

Example 229

Ethyl 5-butyl-1-(4-(4-chlorophenoxy)phenyl)-4-(4-(naphthalen-2-ylsulfonylcarbamoyl)-2-(1,2,3,4-tetrahydroisoquinoline-2-carbonyl)phenyl)-1H-pyrazole-3-carboxylate

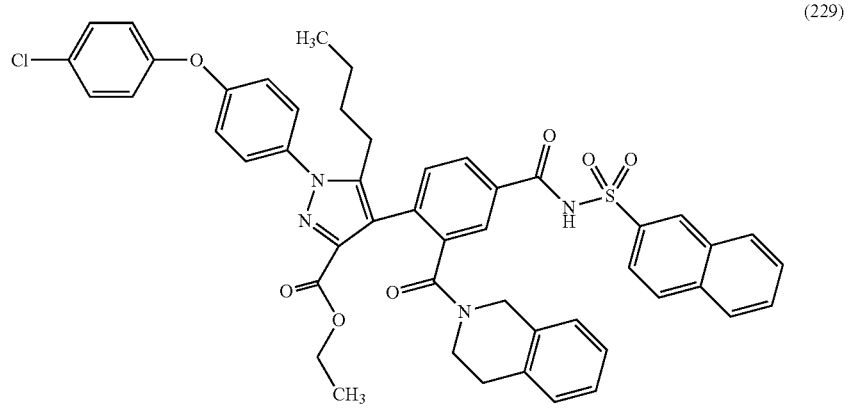 [SMILES: CCCCc1c(-c2ccc(C(=O)NS(=O)(=O)c3ccc4ccccc4c3)cc2C(=O)N2CCc3ccccc3C2)c(C(=O)OCC)nn1-c1ccc(Oc2ccc(Cl)cc2)cc1]

(229)

Intermediate 229A

Ethyl 4-(4-(tert-butoxycarbonyl)-2-(1,2,3,4-tetrahydroisoquinoline-2-carbonyl)phenyl)-5-butyl-1-(4-(4-chlorophenoxy)phenyl)-1H-pyrazole-3-carboxylate (Int-229A)

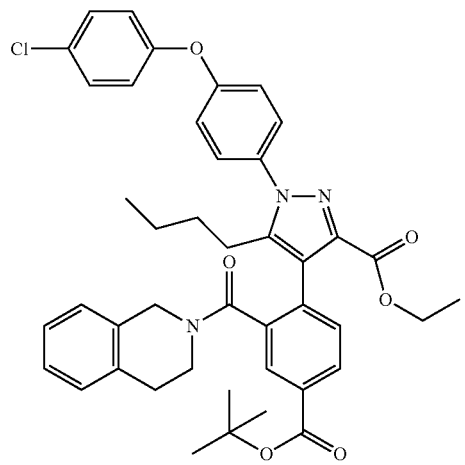

Following a procedure analogous to that for the synthesis of Intermediate 223E, (E)-ethyl 2-(2-(4-(4-chlorophenoxy)phenyl)hydrazono)acetate (41 mg, 0.13 mmol) and tert-butyl 4-(2-nitrohex-1-enyl)-3-(1,2,3,4-tetrahydroisoquinoline-2-carbonyl)benzoate (60 mg, 0.13 mmol) were converted to the title compound (44 mg, 46%) as a pale yellow oil. $^1$H NMR (CDCl$_3$, 1:1 mixture of amide rotamers) δ 8.09 (dd, J=8, 2 Hz, 1H), 8.04-8.03 (m, 1H), 7.43-6.81 (m, 13H), 5.02-4.98 (m, 1H), 4.48-4.38 (m, 1H), 4.33-4.27 (m, 2H), 4.18-3.98 (m, 1H), 3.58-3.32 (m, 1H), 2.85-2.48 (m, 4H), 1.61 (s, 9H), 1.28 (t, J=8 Hz, 1.5H), 1.20 (t, J=8 Hz, 1.5H), 1.15-0.91 (m, 4H), 0.63-0.59 (m, 3H); MS(ESI$^+$) m/z 734.2 (M+H)$^+$.

Intermediate 229B 4-(5-Butyl-1-(4-(4-chlorophenoxy)phenyl)-3-(ethoxycarbonyl)-1H-pyrazol-4-yl)-3-(1,2,3,4-tetrahydroisoquinoline-2-carbonyl)benzoic acid (Int-229B)

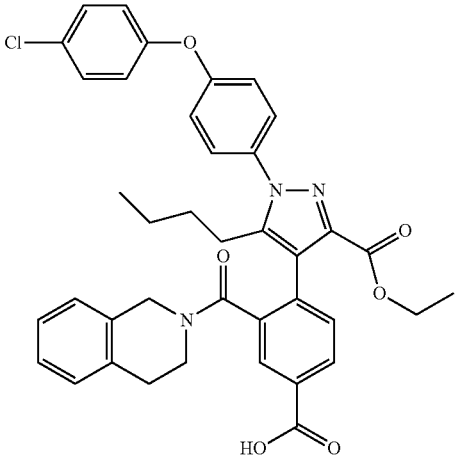

Following a procedure analogous to that for the synthesis of Intermediate 223F, ethyl 4-(4-(tert-butoxycarbonyl)-2-(1,2,3,4-tetrahydroisoquinoline-2-carbonyl)phenyl)-5-butyl-1-(4-(4-chlorophenoxy)phenyl)-1H-pyrazole-3-carboxylate (44 mg, 0.060 mmol) was converted to the title compound which was used directly in the next step without further purification. MS(ESI$^+$) m/z 678.2 (M+H)$^+$.

Example 229

Following a procedure analogous to that for the synthesis of Example 1,4-(5-butyl-1-(4-(4-chlorophenoxy)phenyl)-3-(ethoxycarbonyl)-1H-pyrazol-4-yl)-3-(1,2,3,4-tetrahydroisoquinoline-2-carbonyl)benzoic acid (41 mg, 0.06 mmol) and naphthalene-2-sulfonamide (25 mg, 0.12 mmol) were converted to the title compound (12 mg, 22%). $^1$H NMR (CD$_3$OD, 1:1 mixture of amide rotamers) δ 8.73 (s, 1H), 8.11-8.00 (m, 4H), 7.98-7.95 (m, 2H), 7.70-7.64 (m, 2H), 7.46-7.35 (m, 4H), 7.21-7.00 (m, 8.5H), 6.80-6.78 (m, 0.5H), 4.90-4.85 (m, 0.5H), 4.58-4.50 (m, 0.5H), 4.29-4.20 (m, 2H), 4.05-4.00 (m, 0.5H), 3.92-3.88 (m, 0.5H), 3.52-3.42 (m, 2H), 2.81-2.47 (m, 4H), 1.28-0.99 (m, 7H), 0.60 (t, J=6 Hz, 3H); MS(ESI$^+$) m/z 867.2 (M+H).

Example 230

Ethyl 5-butyl-1-(4-(3-chlorophenoxy)phenyl)-4-(4-(naphthalen-2-ylsulfonylcarbamoyl)-2(1,2,3,4-tetrahydroisoquinoline-2-carbonyl)phenyl)-1H-pyrazole-3-carboxylate

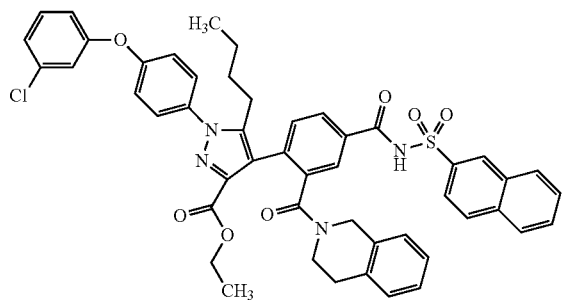

(230)

Intermediate 230A

Ethyl 4-(4-(tert-butoxycarbonyl)-2-(1,2,3,4-tetrahydroisoquinoline-2-carbonyl)phenyl)-5-butyl-1-(4-(3-chlorophenoxy)phenyl)-1H-pyrazole-3-carboxylate

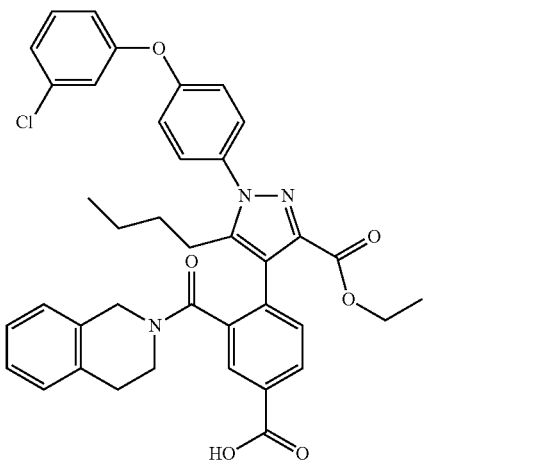

(Int-230A)

Following a procedure analogous to that for the synthesis of Intermediate 223E, (E)-ethyl 2-(2-(4-(3-chlorophenoxy)phenyl)hydrazono)acetate (60 mg, 0.19 mmol) and tert-butyl 4-(2-nitrohex-1-enyl)-3-(1,2,3,4-tetrahydroisoquinoline-2-carbonyl)benzoate (88 mg, 0.19 mmol) were converted to the title compound (62 mg, 45%) as a pale yellow oil. $^1$H NMR (CDCl$_3$, 1:1 mixture of amide rotamers) δ 8.10 (dd, J=8, 2 Hz, 1H), 8.05-8.04 (m, 1H), 7.44-6.83 (m, 13H), 5.02-4.98 (m, 1H), 4.48-4.38 (m, 1H), 4.33-4.28 (m, 2H), 4.18-3.98 (m, 1H), 3.58-3.32 (m, 1H), 2.85-2.50 (m, 4H), 1.61 (s, 9H), 1.29 (t, J=8 Hz, 1.5H), 1.19 (t, J=8 Hz, 1.5H), 1.15-0.81 (m, 4H), 0.65-0.61 (m, 3H); MS(ESI$^+$) m/z 734.3 (M+H)$^+$.

Intermediate 230B 4-(5-Butyl-1-(4-(3-chlorophenoxy)phenyl)-3-(ethoxycarbonyl)-1H-pyrazol-4-yl)-3-(1,2,3,4-tetrahydroisoquinoline-2-carbonyl)benzoic acid Following a procedure analogous to that for the synthesis of Intermediate 223F, ethyl 4-(4-(tert-butoxycarbonyl)-2-(1,2,3,4-tetrahydroisoquinoline-2-carbonyl)phenyl)-5-butyl-1-(4-(3-chlorophenoxy)phenyl)-1H-pyrazole-3-carboxylate (62 mg, 0.084 mmol) was converted to the title compound which was used directly in the next step without further purification. MS(ESI$^+$) m/z 678.2 (M+H)$^+$.

Example 230

Following a procedure analogous to that for the synthesis of Example 1,4-(5-butyl-1-(4-(3-chlorophenoxy)phenyl)-3-(ethoxycarbonyl)-1H-pyrazol-4-yl)-3-(1,2,3,4-tetrahydroisoquinoline-2-carbonyl)benzoic acid (57 mg, 0.084 mmol) and naphthalene-2-sulfonamide (35 mg, 0.17 mmol) were converted to the title compound (45 mg, 59%). $^1$H NMR (CDCl$_3$, 1:1 mixture of amide rotamers) δ 8.74 (s, 1H), 8.08 (d, J=8 Hz, 1H), 7.97-7.88 (m, 5H), 7.65-7.52 (m, 2H), 7.43-6.88 (m, 12.5H), 6.73-6.72 (m, 0.5H), 4.82-4.78 (m, 0.5H), 4.52-4.48 (m, 0.5H), 4.34-3.92 (m, 3H), 3.38-3.29 (m, 2H), 2.80-2.51 (m, 4H), 1.31-0.87 (m, 7H), 0.54 (t, J=6 Hz, 3H); MS(ESI$^+$) m/z 867.2 (M+H).

Example 231

Ethyl 1-(4-butoxyphenyl)-5-butyl-4-(4-(naphthalen-2-ylsulfonylcarbamoyl)-2-(1,2,3,4-tetrahydroisoquinoline-2-carbonyl)phenyl)-1H-pyrazole-3-carboxylate

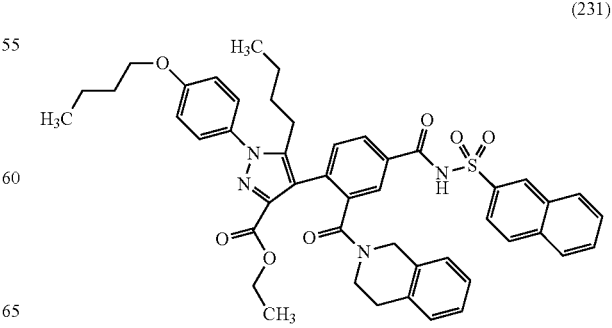

(231)

Intermediate 231A

Ethyl 4-(4-(tert-butoxycarbonyl)-2-(1,2,3,4-tetrahydroisoquinoline-2-carbonyl)phenyl)-1-(4-butoxyphenyl)-5-butyl-1H-pyrazole-3-carboxylate

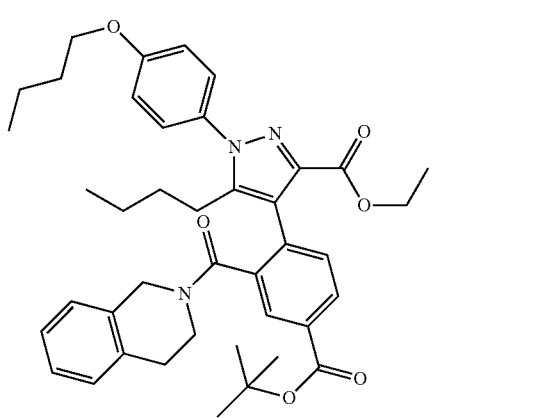
(Int-231A)

Following a procedure analogous to that for the synthesis of Intermediate 223E, (E)-ethyl 2-(2-(4-butoxyphenyl)hydrazono)acetate (51 mg, 0.19 mmol) and tert-butyl 4-(2-nitrohex-1-enyl)-3-(1,2,3,4-tetrahydroisoquinoline-2-carbonyl)benzoate (90 mg, 0.19 mmol) were converted to the title compound (90 mg, 68%) as a pale yellow oil. $^1$H NMR (CDCl$_3$, 1:1 mixture of amide rotamers) δ 8.11 (dd, J=8, 2 Hz, 1H), 8.07-8.05 (m, 1H), 7.46-6.88 (m, 9H), 5.02-4.98 (m, 1H), 4.48-4.38 (m, 1H), 4.33-4.28 (m, 2H), 4.18-3.98 (m, 3H), 3.58-3.32 (m, 1H), 2.85-2.50 (m, 4H), 1.85-1.79 (m, 2H), 1.61 (s, 9H), 1.59-1.51 (m, 2H), 1.31 (t, J=8 Hz, 1.5H), 1.23 (t, J=8 Hz, 1.5H), 1.13-0.95 (m, 7H), 0.65-0.60 (m, 3H); MS(ESI$^+$) m/z 680.3 (M+H)$^+$.

Intermediate 231B 4-(1-(4-Butoxyphenyl)-5-butyl-3-(ethoxycarbonyl)-1H-pyrazol-4-yl)-3-(1,2,3,4-tetrahydroisoquinoline-2-carbonyl)benzoic acid

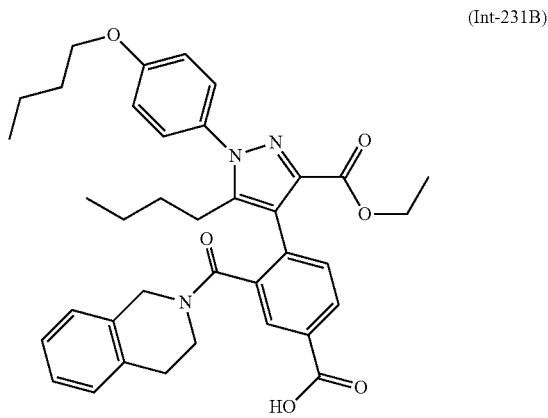 [SMILES: CCCCOc1ccc(-n2nc(C(=O)OCC)c(-c3ccc(C(=O)O)cc3C(=O)N3CCc4ccccc4C3)c2CCCC)cc1]
(Int-231B)

Following a procedure analogous to that for the synthesis of Intermediate 223F, ethyl 4-(4-(tert-butoxycarbonyl)-2-(1, 2,3,4-tetrahydroisoquinoline-2-carbonyl)phenyl)-1-(4-butoxyphenyl)-5-butyl-1H-pyrazole-3-carboxylate (68 mg, 0.10 mmol) was converted to the title compound which was used directly in the next step without further purification. MS(ESI$^+$) m/z 624.3 (M+H)$^+$.

Example 231

Following a procedure analogous to that for the synthesis of Example 1,4-(1-(4-butoxyphenyl)-5-butyl-3-(ethoxycarbonyl)-1H-pyrazol-4-yl)-3-(1,2,3,4-tetrahydroisoquinoline-2-carbonyl)benzoic acid (82 mg, 0.13 mmol) and naphthalene-2-sulfonamide (55 mg, 0.26 mmol) were converted to the title compound (76 mg, 69%). $^1$H NMR (CD$_3$OD, 1:1 mixture of amide rotamers) δ 8.68 (s, 1H), 8.23-7.97 (m, 6H), 7.69-7.62 (m, 2H), 7.47 (d, J=8 Hz, 0.5H), 7.41 (d, J=8 Hz, 0.5H), 7.32-7.30 (m, 1H), 7.29 (d, J=8 Hz, 1H), 7.21-7.04 (m, 5.5H), 6.79-6.78 (m, 0.5H), 4.61-3.80 (m, 6H), 3.50-3.35 (m, 2H), 2.77-2.45 (m, 4H), 1.84-1.78 (m, 2H), 1.61-1.53 (m, 2H), 1.16-1.01 (m, 10H), 0.59 (t, J=6 Hz, 3H); MS(ESI$^+$) m/z 813.3 (M+H).

Example 232

Ethyl 5-butyl-1-(4-(2-hydroxyethyl)phenyl)-4-(4-(naphthalen-2-ylsulfonylcarbamoyl)-2-(1,2,3,4-tetrahydroisoquinoline-2-carbonyl)phenyl)-1H-pyrazole-3-carboxylate

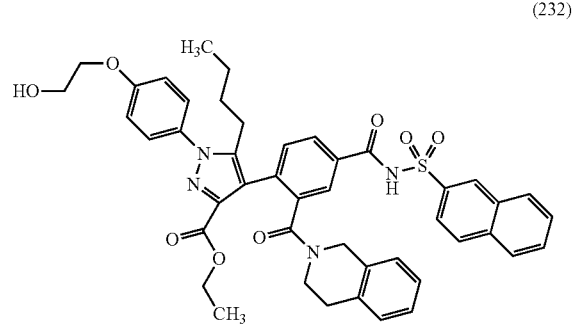 [SMILES: CCCCc1c(-c2ccc(C(=O)NS(=O)(=O)c3ccc4ccccc4c3)cc2C(=O)N2CCc3ccccc3C2)c(C(=O)OCC)nn1-c1ccc(OCCO)cc1]
(232)

Intermediate 232A

Ethyl 4-(4-(tert-butoxycarbonyl)-2-(1,2,3,4-tetrahydroisoquinoline-2-carbonyl)phenyl)-5-butyl-1-(4-(2-hydroxyethyl)phenyl)-1H-pyrazole-3-carboxylate

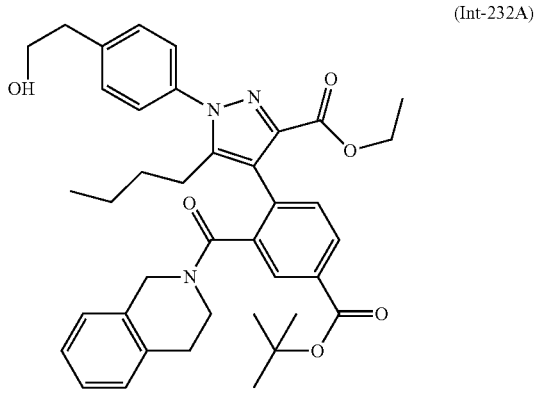 [SMILES: CCCCc1c(-c2ccc(C(=O)OC(C)(C)C)cc2C(=O)N2CCc3ccccc3C2)c(C(=O)OCC)nn1-c1ccc(CCO)cc1]
(Int-232A)

Following a procedure analogous to that for the synthesis of Intermediate 223E, (E)-ethyl 2-(2-(4-(2-hydroxyethyl)phenyl)hydrazono)acetate (61 mg, 0.26 mmol) and tert-butyl 4-(2-nitrohex-1-enyl)-3-(1,2,3,4-tetrahydroisoquinoline-2-carbonyl)benzoate (120 mg, 0.26 mmol) were converted to the title compound (29 mg, 17%) as a pale yellow oil. $^1$H NMR (CDCl$_3$, 1:1 mixture of amide rotamers) δ 8.10 (dd, J=8, 2 Hz, 1H), 8.05-8.03 (m, 1H), 7.44-6.82 (m, 9H), 5.02-4.98 (m, 1H), 4.48-4.38 (m, 1H), 4.32-4.26 (m, 2H), 4.15-3.98 (m, 1H), 3.89-3.88 (m, 2H), 3.58-3.38 (m, 1H), 2.96-2.92 (m, 2H), 2.88-2.50 (m, 4H), 1.61 (s, 9H), 1.29 (t, J=8 Hz, 1.5H), 1.21 (t, J=8 Hz, 1.5H), 1.13-0.95 (m, 4H), 0.62-0.57 (m, 3H); MS(ESI$^+$) m/z 652.3 (M+H)$^+$.

Intermediate 232B 4-(5-Butyl-3-(ethoxycarbonyl)-1-(4-(2-hydroxyethyl)phenyl)-1H-pyrazol-4-yl)-3-(1,2,3,4-tetrahydroisoquinoline-2-carbonyl)benzoic acid

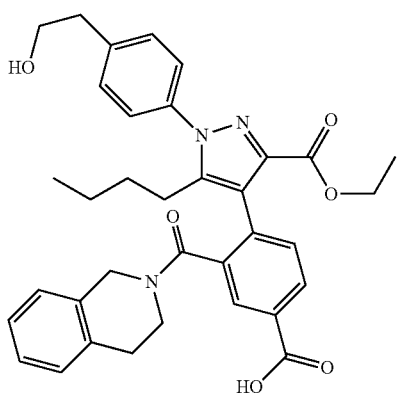

(Int-232B)

Following a procedure analogous to that for the synthesis of Intermediate 223F, ethyl 4-(4-(tert-butoxycarbonyl)-2-(1,2,3,4-tetrahydroisoquinoline-2-carbonyl)phenyl)-5-butyl-1-(4-(2-hydroxyethyl)phenyl)-1H-pyrazole-3-carboxylate (29 mg, 0.044 mmol) was converted to the title compound which was used directly in the next step without further purification. MS(ESI$^+$) m/z 596.3 (M+H)$^+$.

Example 232

Following a procedure analogous to that for the synthesis of Example 1,4-(5-butyl-3-(ethoxycarbonyl)-1-(4-(2-hydroxyethyl)phenyl)-1H-pyrazol-4-yl)-3-(1,2,3,4-tetrahydroisoquinoline-2-carbonyl)benzoic acid (26 mg, 0.044 mmol) and naphthalene-2-sulfonamide (27 mg, 0.13 mmol) were converted to the title compound (24 mg, 66%). $^1$H NMR (CD$_3$OD, 1:1 mixture of amide rotamers) δ 8.73 (s, 1H), 8.11-8.06 (m, 3H), 8.01-7.98 (m, 2H), 7.92-7.89 (m, 1H), 7.72-7.64 (m, 2H), 7.50-6.78 (m, 9H), 4.74-3.94 (m, 4H), 3.83-3.75 (m, 2H), 3.45-3.29 (m, 2H), 2.92-2.89 (m, 2H), 2.84-2.50 (m, 4H), 1.15-0.89 (m, 7H), 0.56 (t, J=6 Hz, 3H); MS(ESI$^+$) m/z 785.2 (M+H).

Example 233

Ethyl 1-(4-(allyloxy)phenyl)-5-butyl-4-(4-(naphthalen-2-ylsulfonylcarbamoyl)-2-(1,2,3,4-tetrahydroisoquinoline-2-carbonyl)phenyl)-1H-pyrazole-3-carboxylate

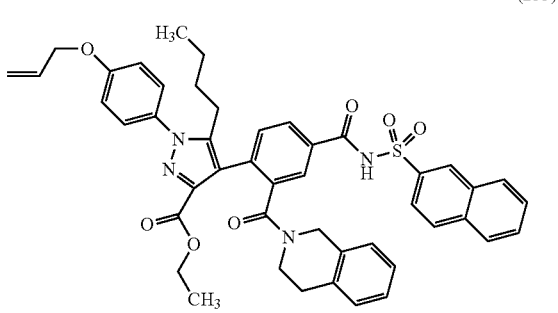

(233)

Intermediate 233A

Ethyl 1-(4-(allyloxy)phenyl)-4-(4-(tert-butoxycarbonyl)-2-(1,2,3,4-tetrahydroisoquinoline-2-carbonyl)phenyl)-5-butyl-1H-pyrazole-3-carboxylate

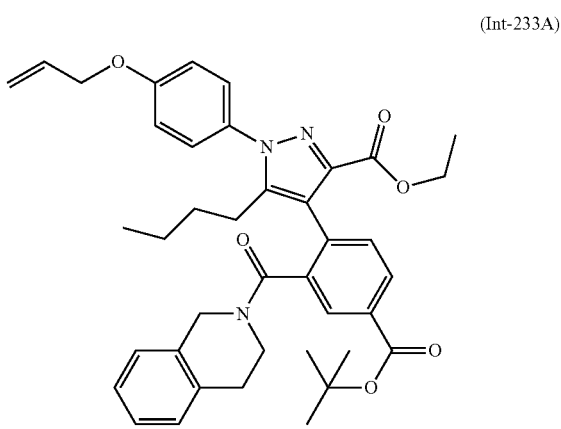 [SMILES: C=CCOc1ccc(-n2nc(C(=O)OCC)c(-c3ccc(C(=O)OC(C)(C)C)cc3C(=O)N3CCc4ccccc4C3)c2CCCC)cc1]

(Int-233A)

Following a procedure analogous to that for the synthesis of Intermediate 223E, (E)-ethyl 2-(2-(4-(allyloxy)phenyl)hydrazono)acetate (64 mg, 0.26 mmol) and tert-butyl 4-(2-nitrohex-1-enyl)-3-(1,2,3,4-tetrahydroisoquinoline-2-carbonyl)benzoate (120 mg, 0.26 mmol) were converted to the title compound (114 mg, 67%) as a pale yellow oil. $^1$H NMR (CDCl$_3$, 1:1 mixture of amide rotamers) δ 8.10 (dd, J=8, 2 Hz, 1H), 8.04-8.03 (m, 1H), 7.43-6.81 (m, 9H), 6.11-6.04 (m, 1H), 5.45-5.40 (m, 1H), 5.34-5.30 (m, 1H), 5.02-4.98 (m, 1H), 4.59-4.57 (m, 2H), 4.48-4.38 (m, 1H), 4.32-4.26 (m, 2H), 4.15-3.98 (m, 1H), 3.58-3.32 (m, 1H), 2.86-2.45 (m, 4H), 1.61 (s, 9H), 1.27 (t, J=8 Hz, 1.5H), 1.20 (t, J=8 Hz, 1.5H), 1.11-0.92 (m, 4H), 0.62-0.57 (m, 3H); MS(ESI⁺) m/z 664.4 (M+H)⁺.

Intermediate 233B 4-(1-(4-(Allyloxy)phenyl)-5-butyl-3-(ethoxycarbonyl)-1H-pyrazol-4-yl)-3-(1,2,3,4-tetrahydroisoquinoline-2-carbonyl)benzoic acid

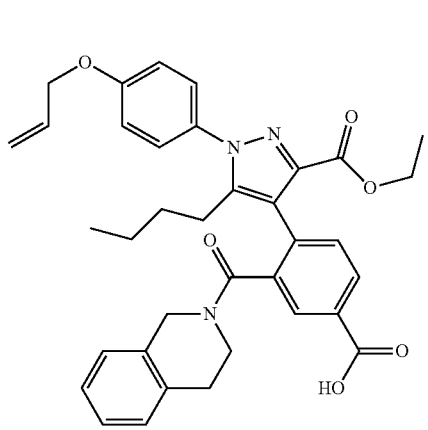

(Int-233B)

Following a procedure analogous to that for the synthesis of Intermediate 223F, ethyl 1-(4-(allyloxy)phenyl)-4-(4-(tert-butoxycarbonyl)-2-(1,2,3,4-tetrahydroisoquinoline-2-carbonyl)phenyl)-5-butyl-1H-pyrazole-3-carboxylate (114 mg, 0.172 mmol) was converted to the title compound which was used directly in the next step without further purification. MS(ESI⁺) m/z 608.3 (M+H)⁺.

Example 223

Following a procedure analogous to that for the synthesis of Example 1,4-(1-(4-(allyloxy)phenyl)-5-butyl-3-(ethoxycarbonyl)-1H-pyrazol-4-yl)-3-(1,2,3,4-tetrahydroisoquinoline-2-carbonyl)benzoic acid (105 mg, 0.172 mmol) and naphthalene-2-sulfonamide (107 mg, 0.516 mmol) were converted to the title compound (116 mg, 82%). ¹H NMR (CD₃OD, 1:1 mixture of amide rotamers) δ 8.68 (s, 1H), 8.13-7.93 (m, 6H), 7.66-7.59 (m, 2H), 7.45-6.76 (m, 9H), 6.15-6.05 (m, 1H), 5.47-5.43 (m, 1H), 5.32-5.29 (m, 1H), 4.64-4.63 (m, 2H), 4.56-4.15 (m, 4H), 3.91-3.26 (m, 2H), 2.79-2.45 (m, 4H), 1.15-0.92 (m, 7H), 0.60-0.56 (m, 3H); MS(ESI⁺) m/z 797.3 (M+H).

Example 234

Ethyl 1-(biphenyl-4-yl)-5-butyl-4-(4-(naphthalen-2-ylsulfonylcarbamoyl)-2-(1,2,3,4-tetrahydroisoquinoline-2-carbonyl)phenyl)-1H-pyrazole-3-carboxylate (234)

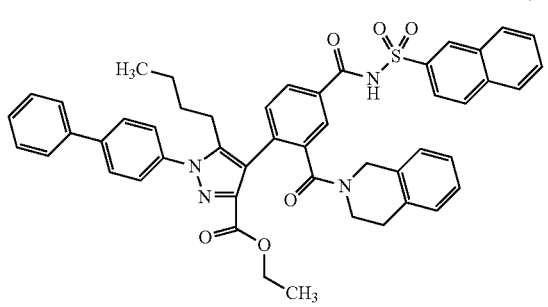

Intermediate 234A

Ethyl 1-(biphenyl-4-yl)-4-(4-(tert-butoxycarbonyl)-2-(1,2,3,4-tetrahydroisoquinoline-2-carbonyl)phenyl)-5-butyl-1H-pyrazole-3-carboxylate

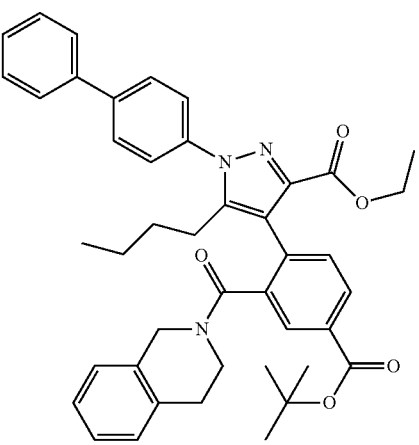

(Int-234A)

Following a procedure analogous to that for the synthesis of Intermediate 223E, (E)-ethyl 2-(2-(biphenyl-4-yl)hydrazono)acetate (35 mg, 0.13 mmol) and tert-butyl 4-(2-nitrohex-1-enyl)-3-(1,2,3,4-tetrahydroisoquinoline-2-carbonyl)benzoate (60 mg, 0.13 mmol) were converted to the title compound (55 mg, 62%) as a pale yellow solid. ¹H NMR (CDCl₃, 1:1 mixture of amide rotamers) δ 8.13 (dd, J=8, 2 Hz, 1H), 8.09-8.07 (m, 1H), 7.74-7.43 (m, 10H), 7.23-6.86 (m, 4H), 5.02-4.98 (m, 1H), 4.55-4.47 (m, 1H), 4.37-4.31 (m, 2H), 4.20-4.02 (m, 1H), 3.58-3.35 (m, 1H), 2.90-2.51 (m, 4H), 1.61 (s, 9H), 1.32 (t, J=8 Hz, 1.5H), 1.26 (t, J=8 Hz, 1.5H), 1.21-0.97 (m, 4H), 0.66-0.62 (m, 3H); MS (ESI⁺) m/z 684.4 (M+H)⁺.

Intermediate 234B 4-(1-(Biphenyl-4-yl)-5-butyl-3-(ethoxycarbonyl)-1H-pyrazol-4-yl)-3-(1,2,3,4-tetrahydroisoquinoline-2-carbonyl)benzoic acid (Int-234B)

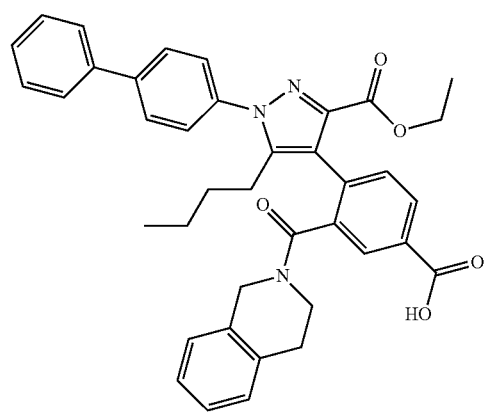

Following a procedure analogous to that for the synthesis of Intermediate 223F, ethyl 1-(biphenyl-4-yl)-4-(4-(tert-butoxycarbonyl)-2-(1,2,3,4-tetrahydroisoquinoline-2-carbonyl)phenyl)-5-butyl-1H-pyrazole-3-carboxylate (55 mg, 0.080 mmol) was converted to the title compound which was used directly in the next step without further purification. MS(ESI⁺) m/z 628.4 (M+H)⁺.

Example 234

Following a procedure analogous to that for the synthesis of Example 1,4-(1-(biphenyl-4-yl)-5-butyl-3-methyl-1H-pyrazol-4-yl)-3-(1,2,3,4-tetrahydroisoquinoline-2-carbonyl)benzoic acid (46 mg, 0.08 mmol) and naphthalene-2-sulfonamide (33 mg, 0.16 mmol) were converted to the title compound (40 mg, 81%). ¹H NMR (CDCl₃, 1:1 mixture of amide rotamers) δ 8.81 (s, 1H), 8.15-7.90 (m, 6H), 7.69-7.34 (m, 12H), 7.17-6.78 (m, 4H), 4.56-3.95 (m, 4H), 3.50-3.29 (m, 2H), 2.82-2.64 (m, 4H), 1.31-0.87 (m, 7H), 0.62-0.57 (m, 3H); MS(ESI⁺) m/z 817.4 (M+H).

Example 235

Ethyl 5-butyl-1-(3-(methoxycarbonyl)phenyl)-4-(4-(naphthalen-2-ylsulfonylcarbamoyl)-2-(1,2,3,4-tetrahydroisoquinoline-2-carbonyl)phenyl)-1H-pyrazole-3-carboxylate

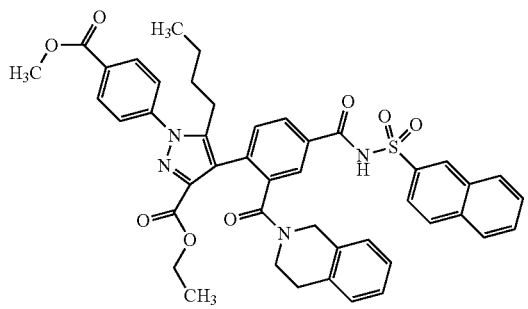

(235)

Intermediate 235A

Ethyl 4-(4-(tert-butoxycarbonyl)-2-(1,2,3,4-tetrahydroisoquinoline-2-carbonyl)phenyl)-5-butyl-1-(3-(methoxycarbonyl)phenyl)-1H-pyrazole-3-carboxylate

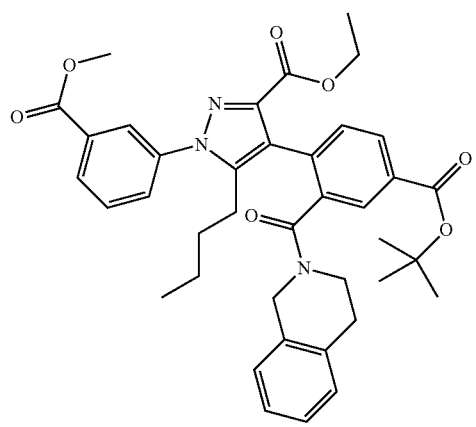

(Int-235A)

Following a procedure analogous to that for the synthesis of Intermediate 223E, (E)-methyl 3-(2-(2-ethoxy-2-oxoethylidene)hydrazinyl)benzoate (65 mg, 0.26 mmol) and tert-butyl 4-(2-nitrohex-1-enyl)-3-(1,2,3,4-tetrahydroisoquinoline-2-carbonyl)benzoate (120 mg, 0.26 mmol) were converted to the title compound (50 mg, 29%). MS(ESI⁺) m/z 666.3 (M+H)⁺.

Intermediate 235B 4-(5-Butyl-3-(ethoxycarbonyl)-1-(3-(methoxycarbonyl)phenyl)-1H-pyrazol-4-yl)-3-(1,2,3,4-tetrahydroisoquinoline-2-carbonyl)benzoic acid

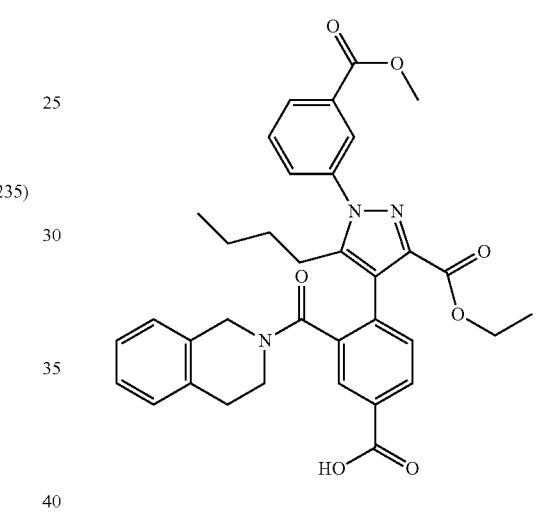

(Int-235B)

Following a procedure analogous to that for the synthesis of Intermediate 223F, ethyl 4-(4-(tert-butoxycarbonyl)-2-(1,2,3,4-tetrahydroisoquinoline-2-carbonyl)phenyl)-5-butyl-1-(3-(methoxycarbonyl)phenyl)-1H-pyrazole-3-carboxylate (70 mg, 0.11 mmol) was converted to the title compound which was used directly in the next step without further purification. MS(ESI⁺) m/z 610.2 (M+H)⁺.

Example 235

Following a procedure analogous to that for the synthesis of Example 1,4-(5-butyl-3-(ethoxycarbonyl)-1-(3-(methoxycarbonyl)phenyl)-1H-pyrazol-4-yl)-3-(1,2,3,4-tetrahydroisoquinoline-2-carbonyl)benzoic acid (64 mg, 0.11 mmol) and naphthalene-2-sulfonamide (44 mg, 0.21 mmol) were converted to the title compound (68 mg, 77%). ¹H NMR (CDCl₃, 1:1 mixture of amide rotamers) δ 8.51 (s, 1H), 8.09-7.79 (m, 8H), 7.69-7.57 (m, 4H), 7.37-7.28 (m, 1H), 7.13-7.00 (m, 3.5H), 6.70-6.69 (m, 0.5H), 4.66-3.95 (m, 4H), 3.85 (s, 1.5H), 3.82 (s, 1.5H), 3.30-3.19 (m, 2H), 2.73-2.42 (m, 4H), 1.12-0.84 (m, 7H), 0.44-0.42 (m, 3H); MS(ESI⁺) m/z 799.2 (M+H).

Example 236

4-(5-Butyl-3-(hydroxymethyl)-1-phenyl-1H-pyrazol-4-yl)-N-(naphthalen-2-ylsulfonyl)-3-(1,2,3,4-tetrahydroisoquinoline-2-carbonyl)benzamide (236)

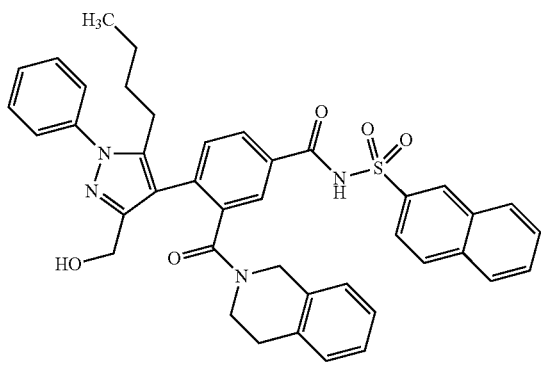

A 25 mL round bottom flask was charged with ethyl 5-butyl-4-(4-(naphthalen-2-ylsulfonylcarbamoyl)-2-(1,2,3,4-tetrahydroisoquinoline-2-carbonyl)phenyl)-1-phenyl-1H-pyrazole-3-carboxylate (Example 223, 23 mg, 0.031 mmol). THF (1.0 mL) and then 2M lithium borohydride solution in THF (0.078 mL, 0.16 mmol) were added. The reaction mixture was stirred at room temperature for 2 h. The reaction mixture was quenched with sat. aq. sodium bicarbonate solution and extracted with EtOAc. The combined organic extracts were dried over anhydrous sodium sulfate and concentrated in vacuo to give the crude product. The residue was purified by preparative HPLC to give the title compound (7.3 mg, 34%). $^1$H NMR (CDCl$_3$, 1:1 mixture of amide rotamers) δ 8.65 (s, 1H), 8.12-7.91 (m, 6H), 7.63-7.57 (m, 2H), 7.50-6.99 (m, 9.5H), 6.91-6.89 (m, 0.5H), 4.65-4.32 (m, 4H), 3.44-3.15 (m, 2H), 2.88-2.49 (m, 4H), 1.39-0.86 (m, 4H), 0.55-0.49 (m, 3H); MS(ESI$^+$) m/z 699.2 (M+H)$^+$.

Example 237

5-Butyl-4-(4-(naphthalen-2-ylsulfonylcarbamoyl)-2-(1,2,3,4-tetrahydroisoquinoline-2-carbonyl)phenyl)-1-phenyl-1H-pyrazole-3-carboxylic acid (237)

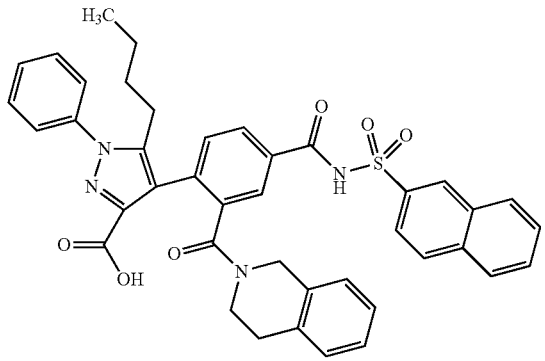

A 25 mL round bottom flask was charged with ethyl 5-butyl-4-(4-(naphthalen-2-ylsulfonylcarbamoyl)-2-(1,2,3,4-tetrahydroisoquinoline-2-carbonyl)phenyl)-1-phenyl-1H-pyrazole-3-carboxylate (Example 223, 52 mg, 0.070 mmol). THF (2.0 mL) and then 1N aq. NaOH solution (0.140 mL, 0.140 mmol) were added. The reaction mixture was stirred at room temperature overnight. After concentration in vacuo to remove the THF, the reaction mixture was made acidic (pH 3-4) with conc. HCl. The product was extracted with EtOAc and the organic layer was dried over anhydrous sodium sulfate and concentrated in vacuo to give the crude product (50 mg, 100%) as a yellow oil. A portion (approx. 10 mg) was purified by preparative HPLC to give the title compound (4 mg). $^1$H NMR (CDCl$_3$, 1:1 mixture of amide rotamers) δ 8.63 (s, 1H), 8.11-8.05 (m, 3H), 8.01-7.98 (m, 1H), 7.94 (d, J=4 Hz, 1H), 7.90 (d, J=4 Hz, 1H), 7.61-7.55 (m, 2H), 7.52-7.35 (m, 6H), 7.19-7.04 (m, 3.5H), 6.86-6.82 (m, 0.5H), 4.90-4.80 (m, 0.5H), 4.51-4.36 (m, 1.5H), 3.65-3.43 (m, 2H), 2.88-2.49 (m, 4H), 1.12-0.89 (m, 4H), 0.61-0.56 (m, 3H); MS (ESI$^+$) m/z 713.3 (M+H)$^+$.

Example 238

4-(5-Butyl-3-(hydroxymethyl)-1-(3-(hydroxymethyl)phenyl)-1H-pyrazol-4-yl)-N-(naphthalen-2-ylsulfonyl)-3-(1,2,3,4-tetrahydroisoquinoline-2-carbonyl)benzamide (238)

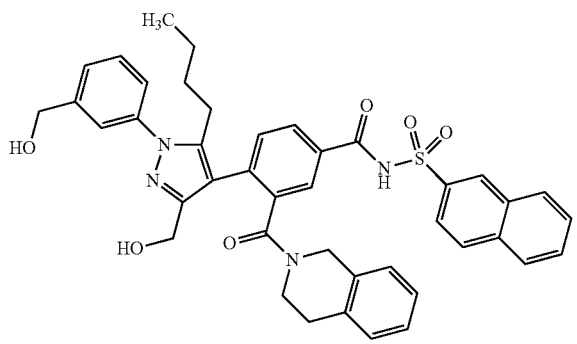

Following a procedure analogous to that for the synthesis of Example 236, ethyl 5-butyl-1-(3-(methoxycarbonyl)phenyl)-4-(4-(naphthalen-2-ylsulfonylcarbamoyl)-2-(1,2,3,4-tetrahydroisoquinoline-2-carbonyl)phenyl)-1H-pyrazole-3-carboxylate (25 mg, 0.031 mmol, Example 235) was converted to the title compound (9 mg, 39%). $^1$H NMR (CD$_3$OD) δ 8.69 (s, 1H), 8.11-7.98 (m, 7H), 7.70-7.63 (m, 3H), 7.47-7.33 (m, 3H), 7.22-7.00 (m, 3.5H), 6.95-6.85 (m, 0.5H), 4.80-4.20 (m, 6H), 3.44-3.16 (m, 2H), 2.88-2.45 (m, 4H), 1.10-0.82 (m, 4H), 0.59-0.48 (m, 3H); MS(ESI$^+$) m/z 729.2 (M+H)$^+$.

Example 239

Ethyl 5-butyl-1-phenyl-4-(2-(1,2,3,4-tetrahydroisoquinoline-2-carbonyl)-4-(2-(trimethylsilyl)ethylsulfonylcarbamoyl)phenyl)-1H-pyrazole-3-carboxylate (239)

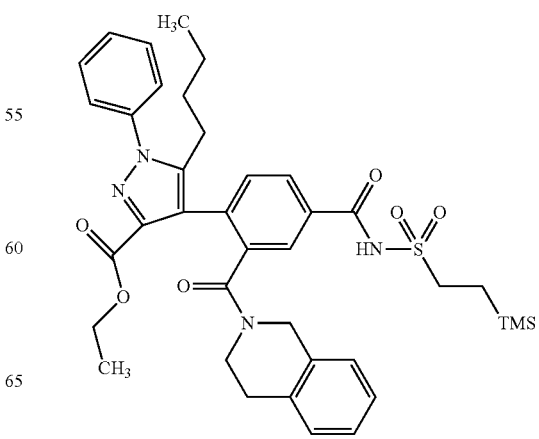

Following a procedure analogous to that for the synthesis of Example 1,4-(5-butyl-3-(ethoxycarbonyl)-1-phenyl-1H-pyrazol-4-yl)-3-(1,2,3,4-tetrahydroisoquinoline-2-carbonyl)benzoic acid (Intermediate 223F, 55 mg, 0.10 mmol) and 2-(trimethylsilyl)ethanesulfonamide (Aldrich, 36 mg, 0.20 mmol) were converted to the title compound (65 mg, 86%). $^1$H NMR (CD$_3$OD, 1:1 mixture of amide rotamers) δ 8.08 (dd, J=8, 2 Hz, 1H), 8.01 (s, 1H), 7.58-7.38 (m, 6H), 7.22-7.10 (m, 3.5H), 6.82-6.78 (m, 0.5H), 4.65-3.86 (m, 6H), 3.54-3.49 (m, 2H), 2.83-2.53 (m, 4H), 1.21-0.99 (m, 9H), 0.59 (t, J=6 Hz, 3H), 0.10 (s, 9H); MS(ESI$^+$) m/z 715.3 (M+H)$^+$.

Example 240

4-(5-Butyl-3-(hydroxymethyl)-1-phenyl-1H-pyrazol-4-yl)-3-(1,2,3,4-tetrahydroisoquinoline-2-carbonyl)-N-(2-(trimethylsilyl)ethylsulfonyl)benzamide

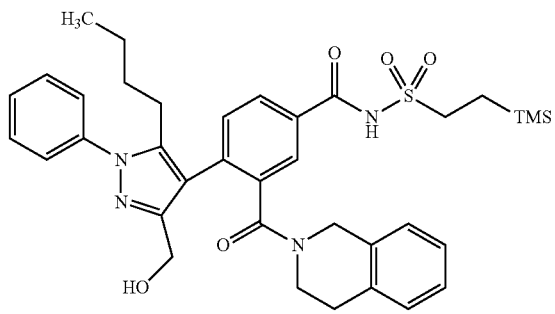

(240)

Following a procedure analogous to that for the synthesis of Example 236, ethyl 5-butyl-1-phenyl-4-(2-(1,2,3,4-tetrahydroisoquinoline-2-carbonyl)-4-(2-(trimethylsilyl)ethyl-sulfonylcarbamoyl)phenyl)-1H-pyrazole-3-carboxylate (Example 239, 45 mg, 0.063 mmol) was converted to the title compound (24 mg, 55%). $^1$H NMR (1:1 CD$_3$OD:CDCl$_3$) δ 8.02-8.00 (m, 1H), 7.96-7.95 (m, 1H), 7.56-7.23 (m, 5H), 7.13-6.77 (m, 5H), 4.45-4.10 (m, 6H), 3.41-3.37 (m, 2H), 2.90-2.42 (m, 4H), 1.02-0.80 (m, 6H), 0.548-0.44 (m, 3H), 0.01 (s, 9H); MS(ESI$^+$) m/z 673.3 (M+H)$^+$.

Examples 241 to 247

The following Examples were prepared from the corresponding ethyl esters (described above) according to the procedure for the synthesis of Example 236.

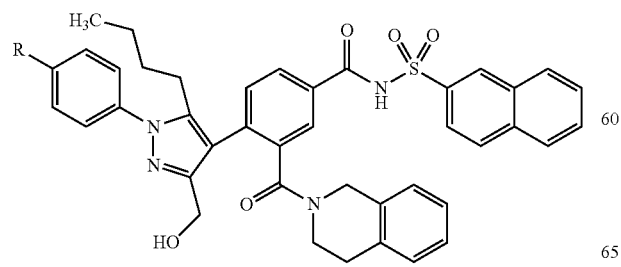

| Ex. No. | R | Name | LCMS (M + H) |
|---|---|---|---|
| 241 | phenoxy | 4-(5-butyl-3-(hydroxymethyl)-1-(4-phenoxyphenyl)-1H-pyrazol-4-yl)-N-(naphthalen-2-ylsulfonyl)-3-(1,2,3,4-tetrahydroisoquinoline-2-carbonyl)benzamide | 791.2 |
| 242 | 4-chlorophenoxy | 4-(5-butyl-1-(4-(4-chlorophenoxy)phenyl)-3-(hydroxymethyl)-1H-pyrazol-4-yl)-N-(naphthalen-2-ylsulfonyl)-3-(1,2,3,4-tetrahydroisoquinoline-2-carbonyl)benzamide | 825.2 |
| 243 | 3-chlorophenoxy | 4-(5-butyl-1-(4-(3-chlorophenoxy)phenyl)-3-(hydroxymethyl)-1H-pyrazol-4-yl)-N-(naphthalen-2-ylsulfonyl)-3-(1,2,3,4-tetrahydroisoquinoline-2-carbonyl)benzamide | 825.1 |
| 244 | butoxy | 4-(5-butyl-1-(4-butoxyphenyl)-3-(hydroxymethyl)-1H-pyrazol-4-yl)-N-(naphthalen-2-ylsulfonyl)-3-(1,2,3,4-tetrahydroisoquinoline-2-carbonyl)benzamide | 771.2 |
| 245 | 2-hydroxyethyl | 4-(5-butyl-1-(4-(2-hydroxyethyl)phenyl)-3-(hydroxymethyl)-1H-pyrazol-4-yl)-N-(naphthalen-2-ylsulfonyl)-3-(1,2,3,4-tetrahydroisoquinoline-2-carbonyl)benzamide | 743.3 |
| 246 | allyloxy | 4-(1-(4-(allyloxy)phenyl)-5-butyl-3-(hydroxymethyl)-1H-pyrazol-4-yl)-N-(naphthalen-2-ylsulfonyl)-3-(1,2,3,4-tetrahydroisoquinoline-2-carbonyl)benzamide | 755.2 |
| 247 | phenyl | 4-(1-(biphenyl-4-yl)-5-butyl-3-(hydroxymethyl)-1H-pyrazol-4-yl)-N-(naphthalen-2-ylsulfonyl)-3-(1,2,3,4-tetrahydroisoquinoline-2-carbonyl)benzamide | 775.5 |

Examples 248 to 251

The following Examples were prepared using 4-(5-butyl-1-(4-(3-chlorophenoxy)phenyl)-3-(ethoxycarbonyl)-1H-pyrazol-4-yl)-3-(1,2,3,4-tetrahydroisoquinoline-2-carbonyl)benzoic acid (Intermediate 230B) and the corresponding sulfonamide intermediates (described above or commercially available) according to the procedure for the synthesis of Example 1.

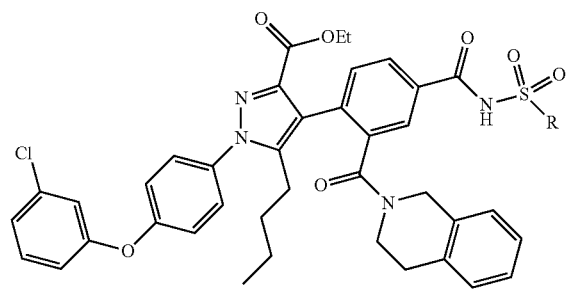

| Ex. No. | R | Name | LCMS (M + H) |
|---|---|---|---|
| 248 | ![naphthyl-Cl] | ethyl 5-butyl-4-(4-(8-chloronaphthalen-2-ylsulfonylcarbamoyl)-2-(1,2,3,4-tetrahydroisoquinoline-2-carbonyl)phenyl)-1-(4-(3-chlorophenoxy)phenyl)-1H-pyrazole-3-carboxylate | 901.5 |
| 249 | —CH₂CH₃ | ethyl 5-butyl-1-(4-(3-chlorophenoxy)phenyl)-4-(4-(ethylsulfonylcarbamoyl)-2-(1,2,3,4-tetrahydroisoquinoline-2-carbonyl)phenyl)-1H-pyrazole-3-carboxylate | 769.5 |
| 250 | —CH₂CH₂CH₂CH₂CH₃ | ethyl 5-butyl-1-(4-(3-chlorophenoxy)phenyl)-4-(4-(pentylsulfonylcarbamoyl)-2-(1,2,3,4-tetrahydroisoquinoline-2-carbonyl)phenyl)-1H-pyrazole-3-carboxylate | 811.5 |
| 251 | ![naphthyl-Cl-Br] | ethyl 4-(4-(8-bromo-5-chloronaphthalen-2-ylsulfonylcarbamoyl)-2-(1,2,3,4-tetrahydroisoquinoline-2-carbonyl)phenyl)-5-butyl-1-(4-(3-chlorophenoxy)phenyl)-1H-pyrazole-3-carboxylate | 981.4 |

Examples 252 to 255

The following Examples were prepared from the corresponding ethyl esters (described above) according to the procedure for the synthesis of Example 236.

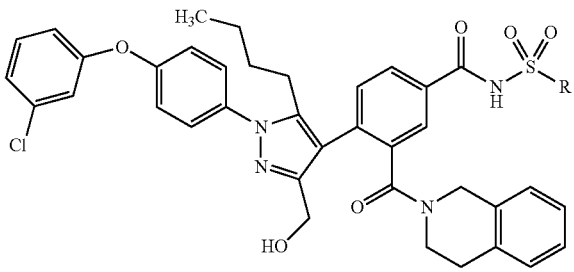

| Ex. No. | R | Name | LCMS (M + H) |
|---|---|---|---|
| 252 | ![naphthyl-Cl] | 4-(5-butyl-1-(4-(3-chlorophenoxy)phenyl)-3-(hydroxymethyl)-1H-pyrazol-4-yl)-N-(8-chloronaphthalen-2-ylsulfonyl)-3-(1,2,3,4-tetrahydroisoquinoline-2-carbonyl)benzamide | 859.4 |
| 253 | ![ethyl] | 4-(5-butyl-1-(4-(3-chlorophenoxy)phenyl)-3-(hydroxymethyl)-1H-pyrazol-4-yl)-N-(ethylsulfonyl)-3-(1,2,3,4-tetrahydroisoquinoline-2-carbonyl)benzamide | 727.5 |
| 254 | ![pentyl] | 4-(5-butyl-1-(4-(3-chlorophenoxy)phenyl)-3-(hydroxymethyl)-1H-pyrazol-4-yl)-N-(pentylsulfonyl)-3-(1,2,3,4-tetrahydroisoquinoline-2-carbonyl)benzamide | 769.5 |
| 255 | ![naphthyl-Cl-Br] | N-(8-bromo-5-chloronaphthalen-2-ylsulfonyl)-4-(5-butyl-1-(4-(3-chlorophenoxy)phenyl)-3-(hydroxymethyl)-1H-pyrazol-4-yl)-3-(1,2,3,4-tetrahydroisoquinoline-2-carbonyl)benzamide | 939.4 |

Example 256

4-(5-Butyl-3-(hydroxymethyl)-1-(4-hydroxyphenyl)-1H-pyrazol-4-yl)-N-(naphthalen-2-ylsulfonyl)-3-(1,2,3,4-tetrahydroisoquinoline-2-carbonyl)benzamide (256)

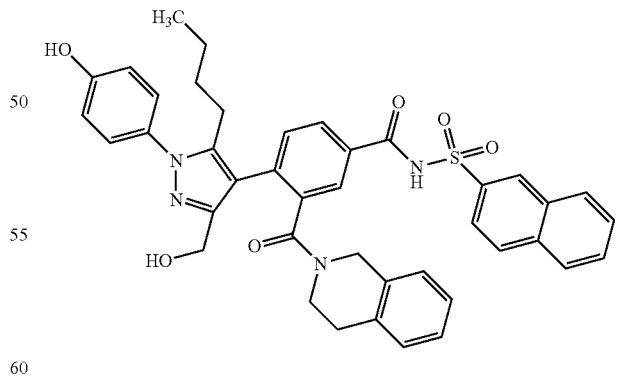

Isolation of a by-product from Example 246 gave the title compound (16 mg, 16%). $^1$H NMR (1:1 CD$_3$OD:CDCl$_3$, 1:1 mixture of amide rotamers) δ 8.65-8.64 (m, 1H), 8.29-7.90 (m, 6H), 7.61-7.56 (m, 2H), 7.32-6.80 (m, 9H), 4.78-4.19 (m, 6H), 2.89-2.41 (m, 4H), 1.05-0.83 (m, 4H), 0.65-0.51 (m, 3H); MS(ESI$^+$) m/z 715.2 (M+H).

Example 257

4-(5-Butyl-3-(hydroxymethyl)-1-(4-(3-hydroxypropoxy)phenyl)-1H-pyrazol-4-yl)-N-(naphthalen-2-ylsulfonyl)-3-(1,2,3,4-tetrahydroisoquinoline-2-carbonyl)benzamide

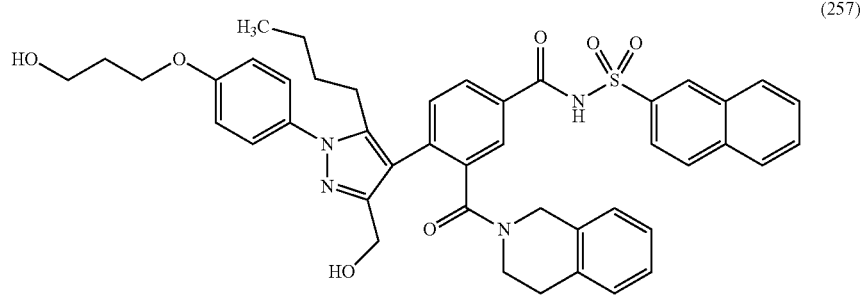 [SMILES: CCCCc1c(-c2ccc(C(=O)NS(=O)(=O)c3ccc4ccccc4c3)cc2C(=O)N2CCc3ccccc3C2)c(CO)nn1-c1ccc(OCCCO)cc1]

(257)

Isolation of a by-product from Example 246 to give the title compound (8.5 mg, 8%). $^1$H NMR (1:1 CD$_3$OD:CDCl$_3$, 1:1 mixture of amide rotamers) δ 8.74 (s, 1H), 8.11-7.94 (m, 6H), 7.71-7.63 (m, 2H), 7.34-6.82 (m, 9H), 4.55-4.21 (m, 6H), 4.13 (t, J=8 Hz, 2H), 3.80-3.76 (m, 2H), 2.89-2.41 (m, 4H), 2.04 (t, J=8 Hz, 2H), 1.02-0.86 (m, 4H), 0.55-0.54 (m, 3H); MS(ESI$^+$) m/z 773.2 (M+H).

Example 258

(±)-4-(5-Butyl-1-(4-(2,3-dihydroxypropoxy)phenyl)-3-(hydroxymethyl)-1H-pyrazol-4-yl)-N-(naphthalen-2-ylsulfonyl)-3-(1,2,3,4-tetrahydroisoquinoline-2-carbonyl)benzamide

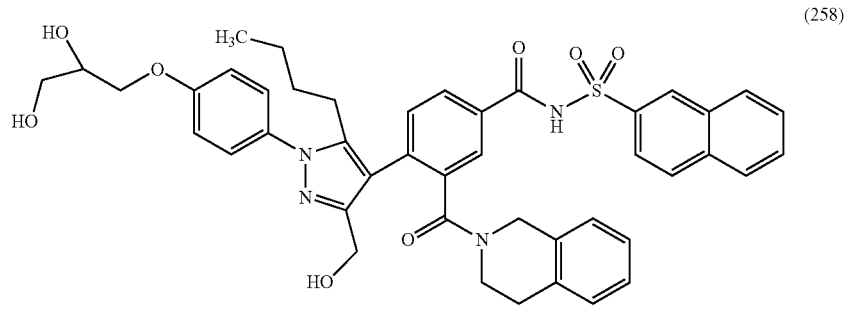 [SMILES: CCCCc1c(-c2ccc(C(=O)NS(=O)(=O)c3ccc4ccccc4c3)cc2C(=O)N2CCc3ccccc3C2)c(CO)nn1-c1ccc(OCC(O)CO)cc1]

(258)

To a solution of 4-(1-(4-(allyloxy)phenyl)-5-butyl-3-(hydroxymethyl)-1H-pyrazol-4-yl)-N-(naphthalen-2-ylsulfonyl)-3-(1,2,3,4-tetrahydroisoquinoline-2-carbonyl)benzamide (Example 246, 30 mg, 0.040 mmol) in tert-BuOH (1 mL), THF (0.3 mL), and water (0.1 mL) at 0° C. was added NMO (5.6 mg, 0.048 mmol) followed by osmium tetroxide (0.062 mL, 7.9 mmol, 4 wt %). After stirring at room temperature overnight, the reaction mixture was diluted with EtOAc, washed with brine, dried over anhydrous sodium sulfate, and concentrated in vacuo. The residue was purified by flash chromatography (Isco 40 g column eluting with 0-15% methanol/DCM). The resulting solid was lyophilized from acetonitrile/water to give the title compound (22 mg, 70%) as a white solid. $^1$H NMR (CD$_3$OD, 1:1 mixture of amide rotamers) δ 8.62 (s, 1H), 8.14-7.93 (m, 6H), 7.64-7.57 (m, 2H), 7.40-6.87 (m, 9H), 4.87-4.00 (m, 9H), 3.70-3.67 (m, 2H), 3.12-2.35 (m, 4H), 1.07-0.88 (m, 4H), 0.56-0.52 (m, 3H); MS(ESI⁺) m/z 789.5 (M+H).

Example 259

Ethyl 5-butyl-4-(2-((S)-3-(hydroxymethyl)-1,2,3,4-tetrahydroisoquinoline-2-carbonyl)-4-(naphthalen-2-ylsulfonylcarbamoyl)phenyl)-1-phenyl-1H-pyrazole-3-carboxylate (259)

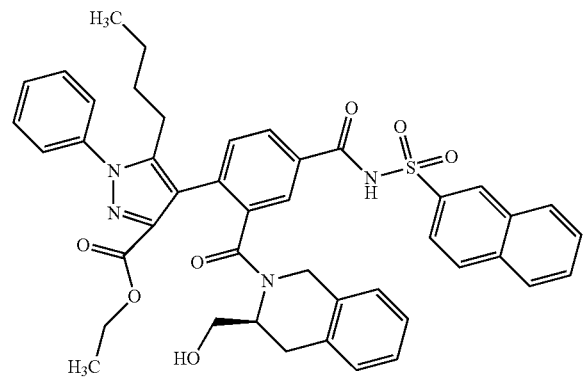

Intermediate 259A (S)-tert-Butyl 3-(3-((tert-butyldimethylsilyloxy)methyl)-1,2,3,4-tetrahydroisoquinoline-2-carbonyl)-4-iodobenzoate (Int-259A)

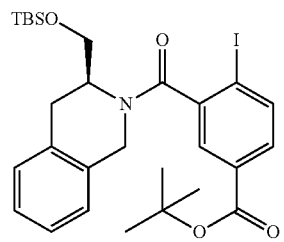

Following a procedure analogous to that for the synthesis of Intermediate 223A, 5-(tert-butoxycarbonyl)-2-iodobenzoic acid (1.67 g, 4.81 mmol) and (S)-3-((tert-butyldimethylsilyloxy)methyl)-1,2,3,4-tetrahydroisoquinoline (1.6 g, 5.8 mmol) were converted to the title compound (1.57 g, 54%). MS(ESI⁺) m/z 608.1 (M+H)⁺.

Intermediate 259B (S)-tert-Butyl 3-(3-((tert-butyldimethylsilyloxy)methyl)-1,2,3,4-tetrahydroisoquinoline-2-carbonyl)-4-formylbenzoate

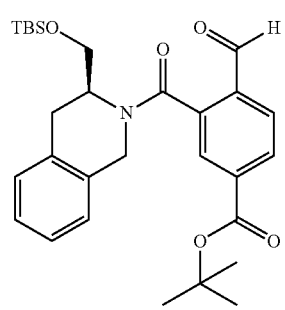

(Int-259B)

Following a procedure analogous to that for the synthesis of Intermediate 223B, (S)-tert-butyl 3-(3-((tert-butyldimethylsilyloxy)methyl)-1,2,3,4-tetrahydroisoquinoline-2-carbonyl)-4-iodobenzoate (1.57 g, 2.58 mmol) was converted to the title compound (0.58 g, 44%). ¹H NMR (CDCl₃, 1.5:1 mixture of amide rotamers) δ 10.16 (s, 0.6H), 10.09 (s, 0.4H), 8.19-8.15 (m, 1H), 8.05-7.97 (m, 2H), 7.53-7.11 (m, 4H), 5.48-5.09 (m, 1H), 4.45-3.82 (m, 2H), 3.55-3.42 (m, 3H), 3.20-2.95 (m, 1H), 1.61 (s, 9H), 0.94 (s, 9H), 0.01 (s, 6H); MS(ESI⁺) m/z 510.3 (M+H)⁺.

Intermediate 259C tert-Butyl 3-((S)-3-((tert-butyldimethylsilyloxy)methyl)-1,2,3,4-tetrahydroisoquinoline-2-carbonyl)-4-(1-hydroxy-2-nitrohexyl)benzoate (Int-259C)

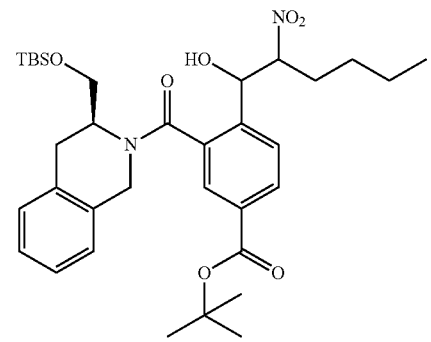

Following a procedure analogous to that for the synthesis of Intermediate 223C, (S)-tert-butyl 3-(3-((tert-butyldimethylsilyloxy)methyl)-1,2,3,4-tetrahydroisoquinoline-2-carbonyl)-4-formylbenzoate (0.53 g, 1.0 mmol) was converted to the title compound as a crude 1:1 mixture of diastereomers which was used directly without purification. MS(ESI⁺) m/z 627.3 (M+H)⁺.

Intermediate 259D (S)-tert-Butyl 3-(3-((tert-butyldimethylsilyloxy)methyl)-1,2,3,4-tetrahydroisoquinoline-2-carbonyl)-4-(2-nitrohex-1-enyl)benzoate (Int-259D)

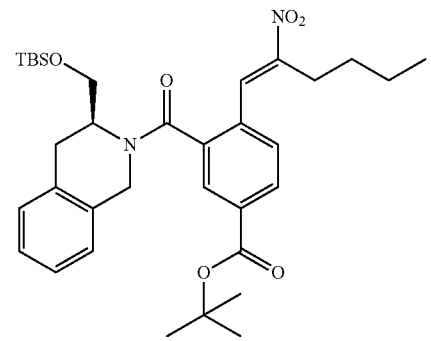

Following a procedure analogous to that for the synthesis of Intermediate 223D, tert-butyl 3-((S)-3-((tert-butyldimethylsilyloxy)methyl)-1,2,3,4-tetrahydroisoquinoline-2-carbonyl)-4-(1-hydroxy-2-nitrohexyl)benzoate (652 mg, 1.04 mmol) was converted to the title compound (0.42 g, 66%). $^1$H NMR (CDCl$_3$, 1:1 mixture of amide rotamers) δ 8.13-8.10 (m, 1H), 8.05 (s, 0.5H), 7.96 (d, J=8 Hz, 1H), 7.82 (s, 0.5H), 7.45 (t, J=8 Hz, 1H), 7.25-7.10 (m, 3.5H), 6.79 (d, J=4 Hz, 0.5H), 5.33-5.10 (m, 1H), 4.43-4.19 (m, 1H), 3.81-3.73 (m, 1H), 3.50-3.40 (m, 1H), 3.09-2.98 (m, 1.5H), 2.83-2.60 (m, 3.5H), 1.65-1.32 (m, 4H), 1.61 (s, 9H), 0.96-0.86 (m, 3H), 0.81 (s, 4.5H), 0.77 (s, 4.5H), 0.05 (s, 6H); MS(ESI$^+$) m/z 609.3 (M+H)$^+$.

Intermediate 259E

Ethyl 4-(4-(tert-butoxycarbonyl)-2-((S)-3-((tert-butyldimethylsilyloxy)methyl)-1,2,3,4-tetrahydroisoquinoline-2-carbonyl)phenyl)-5-butyl-1-phenyl-1H-pyrazole-3-carboxylate (Int-259E)

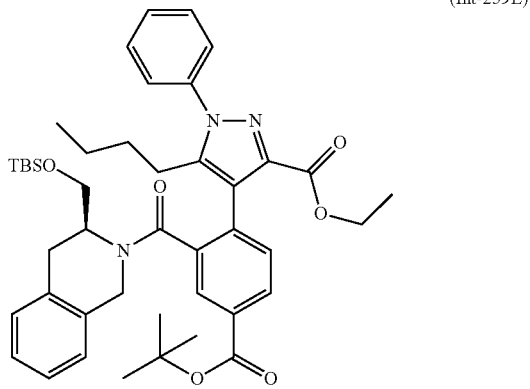

Following a procedure analogous to that for the synthesis of Intermediate 223E, (E)-ethyl 2-(2-phenylhydrazono)acetate (133 mg, 0.690 mmol) and of (S)-tert-butyl 3-(3-((tert-butyldimethylsilyloxy)methyl)-1,2,3,4-tetrahydroisoquinoline-2-carbonyl)-4-(2-nitrohex-1-enyl)benzoate (420 mg, 0.690 mmol) were converted to the title compound (335 mg, 65%). $^1$H NMR (CDCl$_3$, 1:1 mixture of amide rotamers) δ 8.15-8.06 (m, 2H), 7.51-7.39 (m, 5H), 7.22-6.80 (m, 5H), 5.02-4.98 (m, 1H), 4.39-4.04 (m, 3H), 3.82-3.28 (m, 2H), 3.04-3.00 (m, 1H), 2.90-2.78 (m, 1H), 2.61-2.24 (m, 2H), 1.61 (s, 9H), 1.32-0.90 (m, 7H), 0.77 (s, 9H), 0.59 (t, J=8 Hz, 1.5H), 0.55 (t, J=8 Hz, 1.5H), 0.00 (s, 9H); MS(ESI$^+$) m/z 752.4 (M+H)$^+$.

Intermediate 259F 4-(5-Butyl-3-(ethoxycarbonyl)-1-phenyl-1H-pyrazol-4-yl)-3-((S)-3-((tert-butyldimethylsilyloxy)methyl)-1,2,3,4-tetrahydroisoquinoline-2-carbonyl)benzoic acid (Int-259F)

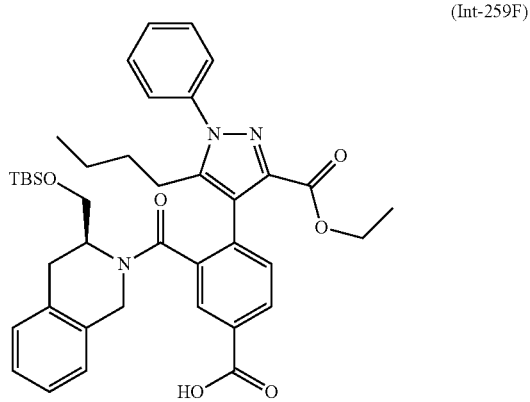 [SMILES: CCCCc1c(-c2ccc(C(=O)O)cc2C(=O)N2Cc3ccccc3C[C@H]2CO[Si](C)(C)C(C)(C)C)c(C(=O)OCC)nn1-c1ccccc1]

To a solution of ethyl 4-(4-(tert-butoxycarbonyl)-2-((S)-3-((tert-butyldimethylsilyloxy)methyl)-1,2,3,4-tetrahydroisoquinoline-2-carbonyl)phenyl)-5-butyl-1-phenyl-1H-pyrazole-3-carboxylate (335 mg, 0.445 mmol) in THF (5.0 mL) was added 2,6-lutidine (0.10 mL, 0.89 mmol) followed by TMS-OTf (0.121 mL, 0.668 mmol). After stirring at room temperature for 1 h, the reaction mixture was heated at 50° C. for 1 h. Additional equivalents of both 2,6-lutidine and TMS-OTf were added hourly until consumption of the starting material (6 additions). After cooling to room temperature, the reaction mixture was quenched with sat. aq. sodium bicarbonate solution. The mixture was extracted with EtOAc concentrated in vacuo. The residue was purified by flash chromatography (Isco 40 g column eluting with 0-80% EtOAc/hexanes) to give the title compound (115 mg, 37%). MS(ESI$^+$) m/z 696.3 (M+H)$^+$.

Example 259

Following a procedure analogous to that for the synthesis of Example 1,4-(5-butyl-3-(ethoxycarbonyl)-1-phenyl-1H-pyrazol-4-yl)-3-((S)-3-((tert-butyldimethylsilyloxy)methyl)-1,2,3,4-tetrahydroisoquinoline-2-carbonyl)benzoic acid (55 mg, 0.079 mmol) and naphthalene-2-sulfonamide (82 mg, 0.40 mmol) were converted to give ethyl 5-butyl-4-(2-((S)-3-((tert-butyldimethylsilyloxy)methyl)-1,2,3,4-tetrahydroisoquinoline-2-carbonyl)-4-(naphthalen-2-ylsulfonylcarbamoyl)phenyl)-1-phenyl-1H-pyrazole-3-carboxylate (40 mg, 57%). To a solution of ethyl 5-butyl-4-(2-((S)-3-((tert-butyldimethylsilyloxy)methyl)-1,2,3,4-tetrahydroisoquinoline-2-carbonyl)-4-(naphthalen-2-ylsulfonylcarbamoyl)phenyl)-1-phenyl-1H-pyrazole-3-carboxylate (30 mg, 0.034 mmol) in THF (2 mL) at room temperature was added TBAF (0.051 mL, 0.051 mmol). After stirring at room temperature for 1 h, the reaction mixture was diluted with EtOAc, washed with sat. aq. sodium bicarbonate solution, dried over anhydrous sodium sulfate, and concentrated in vacuo. The residue was purified by flash chromatography (Isco 40 g column eluting with 0-5% methanol/DCM). The residue was lyophilized from acetonitrile/water to give the title compound (23 mg, 88%) as a white solid. $^1$H NMR (CD$_3$OD, 1:1 mixture of amide rotamers) δ 8.73-8.70 (m, 1H), 8.12-7.82 (m, 6H), 7.72-7.65 (m, 2H), 7.57-7.41 (m, 6H), 7.19-6.92 (m, 3.5H), 6.82-6.79 (m, 0.5H), 5.09-4.56 (m, 1H), 4.35-4.03 (m, 3H), 3.63-3.26 (m, 3H), 2.86-2.15 (m, 4H), 1.24-0.89 (m, 7H), 0.59-0.52 (m, 3H); MS(ESI$^+$) m/z 771.2 (M+H).

Example 260

4-(5-Butyl-3-(hydroxymethyl)-1-phenyl-1H-pyrazol-4-yl)-3-((S)-3-(hydroxymethyl)-1,2,3,4-tetrahydroisoquinoline-2-carbonyl)-N-(naphthalen-2-ylsulfonyl)benzamide (260)

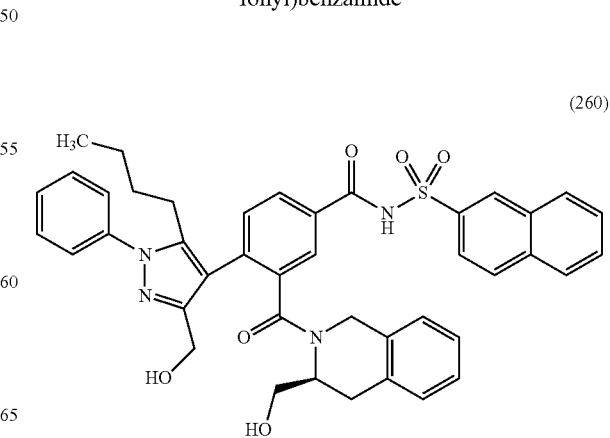

Following a procedure analogous to that for the synthesis of Example 236, ethyl 5-butyl-4-(2-((S)-3-(hydroxymethyl)-1,2,3,4-tetrahydroisoquinoline-2-carbonyl)-4-(naphthalen-2-ylsulfonylcarbamoyl)phenyl)-1-phenyl-1H-pyrazole-3-carboxylate (Example 259, 38 mg, 0.049 mmol) was converted to the title compound (24 mg, 62%). $^1$H NMR (CD$_3$OD) δ 8.67 (s, 1H), 8.17-7.96 (m, 6H), 7.70-6.82 (m, 12H), 5.18-4.73 (m, 1H), 4.54-3.85 (m, 4H), 3.58-3.25 (m, 2H), 2.88-2.39 (m, 4H), 1.16-0.89 (m, 4H), 0.61-0.48 (m, 3H); MS(ESI$^+$) m/z 729.2 (M+H)$^+$.

Example 261

Ethyl 4-(2-((S)-3-(azidomethyl)-1,2,3,4-tetrahydroisoquinoline-2-carbonyl)-4-(naphthalen-2-ylsulfonylcarbamoyl)phenyl)-5-butyl-1-phenyl-1H-pyrazole-3-carboxylate

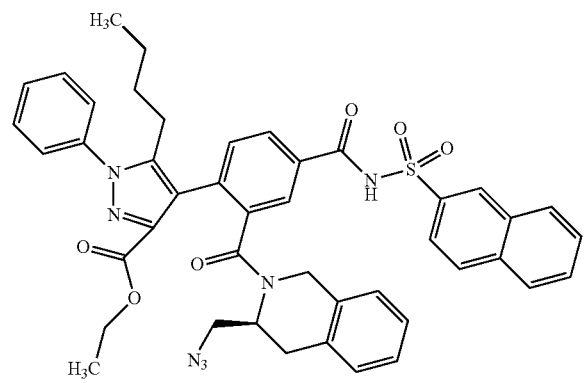

(261)

Intermediate 261A

Ethyl 4-(2-((S)-3-(azidomethyl)-1,2,3,4-tetrahydroisoquinoline-2-carbonyl)-4-(tert-butoxycarbonyl)phenyl)-5-butyl-1-phenyl-1H-pyrazole-3-carboxylate

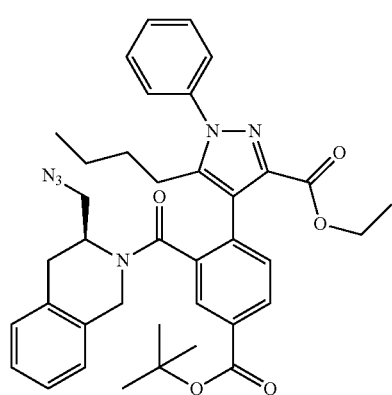

(Int-261A)

To a solution of ethyl 4-(4-(tert-butoxycarbonyl)-2-((S)-3-((tert-butyldimethylsilyloxy)methyl)-1,2,3,4-tetrahydroisoquinoline-2-carbonyl)phenyl)-5-butyl-1-phenyl-1H-pyrazole-3-carboxylate (Intermediate 259E, 207 mg, 0.275 mmol) in THF (2.0 mL) at room temperature was added TBAF (0.413 mL, 0.413 mmol). After stirring at room temperature for 1 h, the reaction mixture was diluted with EtOAc, washed with sat. aq. sodium bicarbonate solution, dried over anhydrous sodium sulfate and concentrated in vacuo. The residue was purified by flash chromatography (Isco 40 g column eluting with 0-70% EtOAc/hexanes) to give ethyl 4-(4-(tert-butoxycarbonyl)-2-((S)-3-(hydroxymethyl)-1,2,3,4-tetrahydroisoquinoline-2-carbonyl)phenyl)-5-butyl-1-phenyl-1H-pyrazole-3-carboxylate (113 mg, 0.177 mmol, 64%) as a colorless oil.

To a solution of ethyl 4-(4-(tert-butoxycarbonyl)-2-((S)-3-(hydroxymethyl)-1,2,3,4-tetrahydroisoquinoline-2-carbonyl)phenyl)-5-butyl-1-phenyl-1H-pyrazole-3-carboxylate (113 mg, 0.177 mmol) in THF (2 mL) was added triphenylphosphine (55.8 mg, 0.213 mmol) followed by DIAD (0.041 mL, 0.213 mmol) and diphenyl phosphorazidate (58 mg, 0.21 mmol). After stirring at room temperature overnight, a second addition of all three reagents was added (1.2 eq each) and stirring was continued for 3 h. The reaction mixture was diluted with EtOAc, washed with sat. aq. sodium bicarbonate, dried over anhydrous sodium sulfate and concentrated in vacuo. The crude material was purified by flash chromatography (Isco 40 g column eluting with 0-50% EtOAc/hexanes) to give the title compound (86 mg, 73%). $^1$H NMR (CDCl$_3$, 1:1 mixture of amide rotamers) δ 8.25 (s, 0.5H), 8.15-8.10 (m, 1H), 7.97 (s, 0.5H), 7.51-7.34 (m, 5H), 7.25-6.90 (m, 5H), 5.04-4.97 (m, 1.5H), 4.41-3.97 (m, 3.5H), 3.50-3.01 (m, 3.5H), 2.88-2.46 (m, 3.5H), 1.66-1.62 (m, 3H), 1.61 (s, 4.5H), 1.60 (s, 4.5H), 1.18-0.94 (m, 4H), 0.64-0.56 (m, 3H); MS(ESI) m/z 663.5 (M+H)$^+$.

Intermediate 261B 3-((S)-3-(Azidomethyl)-1,2,3,4-tetrahydroisoquinoline-2-carbonyl)-4-(5-butyl-3-(ethoxycarbonyl)-1-phenyl-1H-pyrazol-4-yl)benzoic acid

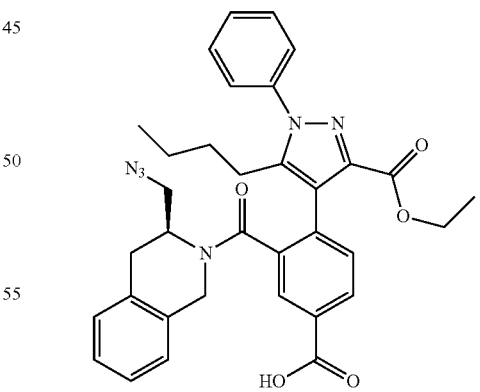

(Int-261B)

Following a procedure analogous to that for the synthesis of Intermediate 223F, ethyl 4-(2-((S)-3-(azidomethyl)-1,2,3,4-tetrahydroisoquinoline-2-carbonyl)-4-(tert-butoxycarbonyl)phenyl)-5-butyl-1-phenyl-1H-pyrazole-3-carboxylate (86 mg, 0.13 mmol) was converted to the title compound which was used directly in the next step without further purification. MS(ESI$^+$) m/z 607.3 (M+H)$^+$.

Example 261

Following a procedure analogous to that for the synthesis of Example 1, 3-((S)-3-(azidomethyl)-1,2,3,4-tetrahydroisoquinoline-2-carbonyl)-4-(5-butyl-3-(ethoxycarbonyl)-1-phenyl-1H-pyrazol-4-yl)benzoic acid (79 mg, 0.13 mmol) and naphthalene-2-sulfonamide (54 mg, 0.26 mmol) were converted to the title compound (64 mg, 60%). $^1$H NMR (CD$_3$OD, 1:1 mixture of amide rotamers) δ 8.69-8.64 (m, 1H), 8.17-7.91 (m, 6H), 7.64-7.41 (m, 8H), 7.20-6.98 (m, 3.5H), 6.79-6.78 (m, 0.5H), 5.09-4.63 (m, 1H), 4.39-4.05 (m, 3H), 3.63-3.08 (m, 3H), 2.82-2.49 (m, 4H), 1.21-0.92 (m, 4H), 1.02 (t, J=8 Hz, 3H), 0.56-0.51 (m, 3H); MS(ESI$^+$) m/z 796.5 (M+H).

Example 262

Ethyl 4-(2-((S)-3-(aminomethyl)-1,2,3,4-tetrahydroisoquinoline-2-carbonyl)-4-(naphthalen-2-ylsulfonylcarbamoyl)phenyl)-5-butyl-1-phenyl-1H-pyrazole-3-carboxylate (262)

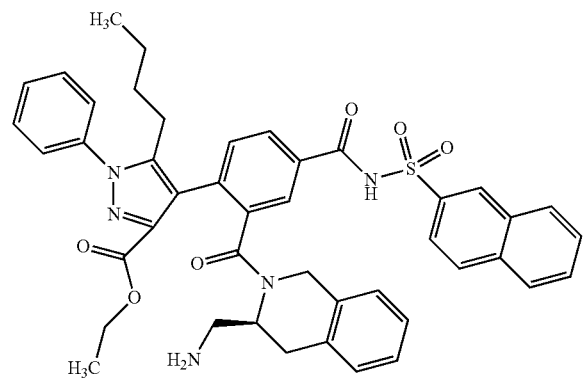

To the solution of ethyl 4-(2-((S)-3-(azidomethyl)-1,2,3,4-tetrahydroisoquinoline-2-carbonyl)-4-(naphthalen-2-ylsulfonylcarbamoyl)phenyl)-5-butyl-1-phenyl-1H-pyrazole-3-carboxylate (60 mg, 0.075 mmol, Example 261) in THF (2.0 mL) was added triphenylphosphine (59 mg, 0.226 mmol) followed by 0.2 ml of 1N NaOH. The reaction mixture was stirred at 50° C. for 2 h. The reaction mixture was quenched with sat. aq. sodium bicarbonate solution and then extracted with EtOAc. The organic extracts were dried over anhydrous sodium sulfate and concentrated in vacuo. The residue was purified by flash chromatography (Isco 40 g column eluting with 0-15% methanol/DCM). The residue was lyophilized from acetonitrile/water to give the title compound (29 mg, 50%). $^1$H NMR (CD$_3$OD, 1:1 mixture of amide rotamers) δ 8.60 (s, 1H), 8.32 (s, 1H), 8.19-7.91 (m, 5H), 7.58-7.34 (m, 8H), 7.21-7.00 (m, 3.5H), 6.79-6.78 (m, 0.5H), 5.21-5.20 (m, 0.5H), 4.74-4.70 (m, 0.5H), 4.43-4.10 (m, 3H), 3.75-3.74 (m, 0.5H), 3.62-3.60 (m, 0.5H), 3.01-3.00 (m, 2H), 2.75-2.48 (m, 4H), 1.13-0.92 (m, 4H), 0.99 (t, J=8 Hz, 3H), 0.57-0.54 (m, 3H); MS(ESI$^+$) m/z 770.5 (M+H)$^+$.

Example 263

3-((S)-3-(Aminomethyl)-1,2,3,4-tetrahydroisoquinoline-2-carbonyl)-4-(5-butyl-3-(hydroxymethyl)-1-phenyl-1H-pyrazol-4-yl)-N-(naphthalen-2-ylsulfonyl)benzamide (263)

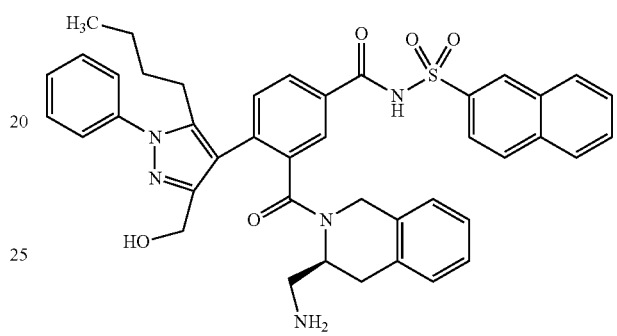

Following a procedure analogous to that for the synthesis of Example 236, ethyl 4-(2-((S)-3-(aminomethyl)-1,2,3,4-tetrahydroisoquinoline-2-carbonyl)-4-(naphthalen-2-ylsulfonylcarbamoyl)phenyl)-5-butyl-1-phenyl-1H-pyrazole-3-carboxylate (Example 262, 25 mg, 0.032 mmol) was converted to the title compound (18 mg, 73%). $^1$H NMR (CD$_3$OD) δ 8.72-8.67 (m, 1H), 8.23-7.93 (m, 6H), 7.73-7.65 (m, 2H), 7.61-6.85 (m, 10H), 5.19-5.15 (m, 1H), 4.62-4.10 (m, 4H), 2.82-2.49 (m, 6H), 1.31-0.87 (m, 4H), 0.61-0.52 (m, 3H); MS(ESI$^+$) m/z 728.5 (M+H)$^+$.

Example 264

N,N-Dibutyl-1-methyl-2-(4-(naphthalen-2-ylsulfonylcarbamoyl)-2-(1,2,3,4-tetrahydroisoquinoline-2-carbonyl)phenyl)-1H-imidazole-4-carboxamide (264)

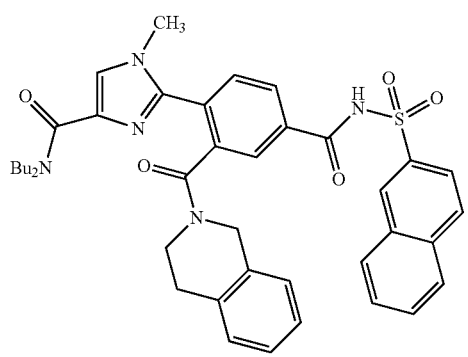

Intermediate 264A

Methyl 1-((2-(trimethylsilyl)ethoxy)methyl)-1H-imidazole-4-carboxylate

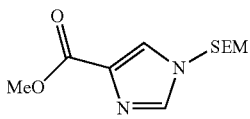
(Int-264A)

To a stirred suspension of sodium hydride (572 mg, 23.8 mmol, 94%) in dry DMF (50 mL) at 0° C. was added methyl 1H-imidazole-4-carboxylate (3.0 g, 23.8 mmol) in DMF (90 mL) and was allowed to warm up to room temperature over 30 min. The reaction mixture was cooled to 0° C. and was treated dropwise with (2-(chloromethoxy)ethyl)trimethylsilane (Aldrich, 4.77 g, 28.6 mmol). The cold bath was removed and the mixture was stirred for 16 h. The reaction mixture was quenched by the addition of ice-flakes and then by water, and extracted with EtOAc (3×). The combined organic layers were washed with brine, dried over $Na_2SO_4$ and concentrated in vacuo to give crude product. The crude material was purified by flash chromatography (gradient from 2 to 5% MeOH/$CH_2Cl_2$) to provide the title compound (4.46 g, 73%). $^1$H NMR ($CDCl_3$) δ 7.72 (s, 1H), 7.61 (s, 1H), 5.29 (s, 2H), 3.90 (s, 3H), 3.49 (t, J=8.0 Hz, 2H), 0.90 (t, J=8.0 Hz, 2H), 0.01 (s, 9H); MS(ESI$^+$) m/z 257.2 (M+H)$^+$.

Intermediate 264B

Methyl 2-bromo-1-((2-(trimethylsilyl)ethoxy)methyl)-1H-imidazole-4-carboxylate

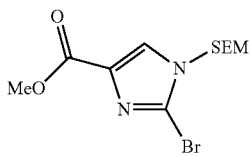
(Int-264B)

To a stirred solution of methyl 1-((2-(trimethylsilyl)ethoxy)methyl)-1H-imidazole-4-carboxylate (5.0 g, 19.5 mmol) in carbon tetrachloride (50 mL) was added N-bromosuccinimide (3.47 g, 19.5 mmol) and AIBN (160 mg, 5 mol %) at room temperature. The reaction mixture was heated at 60° C. for 3 h, cooled to room temperature, and filtered through a small pad of CELITE®. The filtrate was concentrated in vacuo to give light yellow colored residue which was dissolved in EtOAc and washed with 10% $NaHCO_3$ solution. The organic layer was dried over $Na_2SO_4$ and concentrated to give crude compound. The crude material was purified by flash chromatography (gradient from 20 to 30% EtOAc/hexanes), to provide the title compound (2.85 g, 43%). $^1$H NMR ($CDCl_3$) δ 7.76 (s, 1H), 5.30 (s, 2H), 3.90 (s, 3H), 3.55 (t, J=8.0 Hz, 2H), 0.92 (t, J=8.0 Hz, 2H), 0.01 (s, 9H); MS(ESI$^+$) m/z 335.0 (M+H)$^+$.

Intermediate 264C

2-Bromo-1-((2-(trimethylsilyl)ethoxy)methyl)-1H-imidazole-4-carboxylic acid

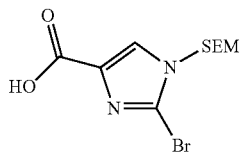
(Int-264C)

To a stirred solution of methyl 2-bromo-1-((2-(trimethylsilyl)ethoxy)methyl)-1H-imidazole-4-carboxylate (2.85 g, 8.50 mmol) in mixed solvents (THF/MeOH/water; 2:2:1; 50 mL) was added LiOH $H_2O$ (1.07 g, 25.5 mmol) at 0° C. The cold bath was removed and stirring was continued for 2 h. The reaction mixture was concentrated in vacuo, diluted with water and washed with MTBE. The aqueous layer was neutralized with 1.5N HCl and extracted with EtOAc (2×). The combined organic layers were dried over $Na_2SO_4$ and concentrated in vacuo to provide the title compound (2.4 g, 88%) as a white solid. $^1$H NMR ($CDCl_3$) δ 12.54 (br s, 1H), 8.14 (s, 1H), 5.33 (s, 2H), 3.54 (t, J=8.0 Hz, 2H), 0.85 (t, J=8.0 Hz, 2H), 0.01 (s, 9H); MS(ESI$^+$) m/z 323.0 (M+H)$^+$.

Intermediate 264D

2-Bromo-N,N-dibutyl-1-((2-(trimethylsilyl)ethoxy)methyl)-1H-imidazole-4-carboxamide

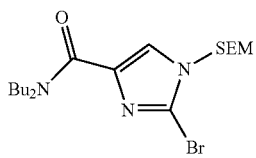
(Int-264D)

To a stirred solution of 2-bromo-1-((2-(trimethylsilyl)ethoxy)methyl)-1H-imidazole-4-carboxylic acid (2.4 g, 7.47 mmol) in dry DMF (40 mL) was added HATU (4.26 g, 11.2 mmol), dibutylamine (1.15 g, 8.9 mmol) and diisopropyl ethylamine (2.84 g, 22.4 mmol) successively at 0° C. The reaction mixture was allowed to warm to room temperature over 30 minutes and stirring was continued for 16 h. The reaction mixture was concentrated in vacuo, diluted with EtOAc and washed with water. The organic layer was dried over $Na_2SO_4$ and concentrated in vacuo to give crude compound. The crude material was purified by flash chromatography (gradient from 20 to 30% EtOAc/hexanes) to provide the title compound (2.81 g, 87%). $^1$H NMR ($CDCl_3$) δ 7.68 (s, 1H), 5.28 (s, 2H), 3.89 (t, J=8.0 Hz, 2H), 3.56 (t, J=8.0 Hz, 2H), 3.44 (t, J=8.0 Hz, 2H), 1.57-1.65 (m, 4H), 1.25-1.45 (m, 4H), 0.91-0.95 (m, 8H), 0.01 (s, 9H); MS(ESI⁺) m/z 434.2 (M+H)⁺.

Intermediate 264E

2-Hydroxy-5-(methoxycarbonyl)benzoic acid

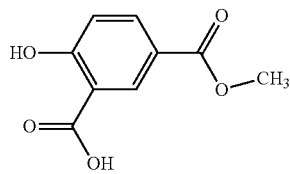
(Int-264E)

A solution of dimethyl-4-hydroxyisophthalate (10.0 g, 47.6 mmol) in pyridine (70 mL) was heated to reflux for 15 h. The reaction mixture was concentrated in vacuo and acidified with 1N HCl at 0° C. The resulting solid was collected by filtration, washed with water and dried in vacuo to provide the title compound (9.3 g, 100%) as a white solid. ¹H NMR (DMSO-d₆) δ 8.40 (d, J=2.0 Hz, 1H), 8.06 (dd, J=8.4, 2.0 Hz, 1H), 7.07 (d, J=8.4 Hz, 1H), 3.84 (s, 3H); MS(ESI⁻) m/z 195.2 (M−H)⁻.

Intermediate 264F

Methyl 4-hydroxy-3-(1,2,3,4-tetrahydroisoquinoline-2-carbonyl)benzoate

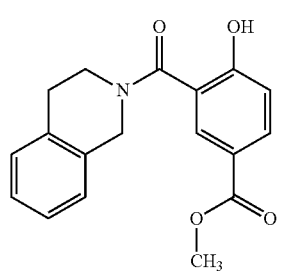
(Int-264F)

To a solution of 1H-benzotriazole (9.11 g, 76.5 mmol) in mixed solvents (CH₂Cl₂/THF; 50 mL/50 mL) at room temperature was added thionylchloride (3.03 g, 25.5 mmol). After stirring for 30 min at room temperature, the mixture was treated with a solution of 2-hydroxy-5-(methoxycarbonyl)benzoic acid (5.0 g, 25.48 mmol) in THF (20 mL THF). The formation of a white precipitate was observed and the mixture was stirred for additional 1 h. The precipitate was allowed to settle and the supernatant was added to a mixture of 1,2,3,4-tetahydroisoquinoline (5.1 g, 38.3 mmol) and triethylamine (5.5 mL, 38.2 mmol) in THF (10 mL) and stirred at room temperature for 1 h. The reaction mixture was concentrate in vacuo, and the resulting crude compound was dissolved in EtOAc, washed with water, followed by 1N HCl and then brine. The organic layer was dried over Na₂SO₄ and concentrated in vacuo to give crude product. The crude material was purified by flash chromatography (gradient from 0% to 30% EtOAc/hexanes) to provide the title compound (5.0 g, 63%). ¹H NMR (DMSO-d₆, 3:1 mixture of amide rotamers) δ 10.84 (s, 1H), 7.88 (dd, J=8.8, 2.4 Hz, 1H), 7.75 (br s, 1H), 7.30-7.15 (m, 3.5H), 7.01 (d, J=8.4 Hz, 1.5H), 4.78 (br s, 1.5H), 4.41 (br s, 0.5H), 3.85-3.84 (m, 0.5H), 3.80 (s, 3H), 3.44 (br s, 1.5H), 2.86-2.80 (m, 2H); MS(ESI⁺) m/z 312.2 (M+H)⁺.

Intermediate 264G

Methyl 3-(1,2,3,4-tetrahydroisoquinoline-2-carbonyl)-4-(trifluoromethylsulfonyloxy)benzoate

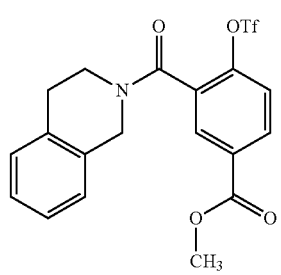
(Int-264G)

To a solution of methyl 4-hydroxy-3-(1,2,3,4-tetrahydroisoquinoline-2-carbonyl)benzoate (3.0 g, 9.63 mmol) and 2,6-dimethylpyridine (3.37 mL, 28.9 mmol), in DCM (40 mL) was added trifluoromethanesulfonic anhydride (2.0 mL, 11.6 mmol) at −78° C. The cold bath was removed and the reaction mixture was stirred at room temperature for an additional 2 h. The reaction mixture was diluted with DCM, washed with 5% aq. citric acid solution and then with brine. The organic layer was dried over Na₂SO₄ and concentrated in vacuo to give the crude product. Purification using flash chromatography (gradient from 0 to 25%, EtOAc/hexanes) provided the title compound (3.07 g, 72%). ¹H NMR (DMSO-d₆, 1:1 mixture of amide rotamers) δ 8.22 (dd, J=8.8, 2.4 Hz, 1H), 8.13 (dd, J=18.0, 2.0 Hz, 1H) 7.76-7.72 (m, 1H), 7.31-7.10 (m, 3.5H), 7.02 (d, J=7.6 Hz, 0.5H), 4.79 (br s, 1H), 4.45 (br s, 1H), 3.90 (s, 3H), 3.48 (t, J=6.0 Hz, 1H), 3.36-3.34 (m, 1H) 2.90-2.80 (m, 2H); MS(ESI⁺) m/z 444.0 (M+H)⁺.

Intermediate 264H

Methyl 4-(5,5-dimethyl-1,3,2-dioxaborinan-2-yl)-3-(1,2,3,4-tetrahydroisoquinoline-2-carbonyl)benzoate

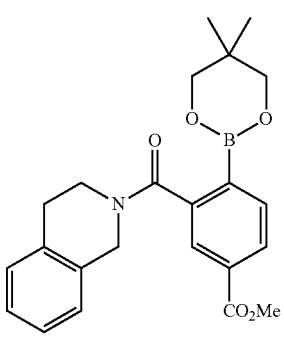
(Int-264H)

To a stirred solution of methyl 3-(1,2,3,4-tetrahydroisoquinoline-2-carbonyl)-4-(trifluoromethylsulfonyloxy)benzoate (2.0 g, 4.51 mmol) in PhMe in a pressure tube was added bis(neopentyl glycolato)diboron (1.53 g, 6.76 mmol), Pd(PPh$_3$)$_4$ (520 mg, 0.45 mmol) and potassium acetate (1.33 g, 13.5 mmol). The reaction mixture was degassed (bubbled) with argon for 20 min, sealed and heated at 85° C. for 4 h. The reaction mixture was allowed to warm up to room temperature, diluted with EtOAc, washed with water, dried over Na$_2$SO$_4$ and concentrated in vacuo to give the title compound (2.3 g), which was used without further purification.

Intermediate 264I

Methyl 4-(4-(dibutylcarbamoyl)-1-((2-(trimethylsilyl)ethoxy)methyl)-1H-imidazol-2-yl)-3-(1,2,3,4-tetrahydroisoquinoline-2-carbonyl)benzoate (Int-264I)

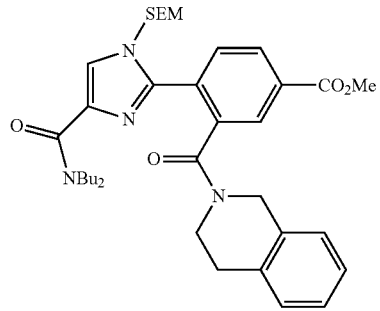

To a solution of methyl 4-(5,5-dimethyl-1,3,2-dioxaborinan-2-yl)-3-(1,2,3,4-tetrahydroisoquinoline-2-carbonyl)benzoate (2.0 g, 5.05 mmol) in dioxane (40 mL) was added Pd(dppf)$_2$Cl$_2$ (77 mg, 0.10 mmol), 2-bromo-N,N-dibutyl-1-((2-(trimethylsilyl)ethoxy)methyl)-1H-imidazole-4-carboxamide (910 mg, 2.10 mmol) and K$_3$PO$_4$ (1.34 g, 6.31 mmol). The reaction mixture was degassed for 30 min, heated at 100° C. for 16 h and concentrated in vacuo. The resulting residue was dissolved in EtOAc and washed with water, dried over Na$_2$SO$_4$, and concentrated to give the crude product. The crude material was purified by flash chromatography (gradient from 0% to 80%, EtOAc/hexanes) to provide the title compound (800 mg, 57%). $^1$H NMR (CD$_3$OD, 1:1 mixture of amide rotamers) δ 8.23 (dd, J=6.4, 1.6 Hz, 1H), 8.13-8.12 (m, 1H), 7.98 (dd, J=14.4, 8.0 Hz, 1H), 7.78 (s, 0.5H), 7.67 (s, 0.5H), 7.24-7.12 (m, 3.5H), 6.93 (d, J=7.2 Hz, 0.5H), 5.39 (s, 1H), 5.30 (s, 1H), 4.85-4.75 (m, 2H), 4.58-4.35 (m, 1H), 3.99 (s, 3H), 3.71-3.62 (m, 3H), 3.56 (t, J=6.0 Hz, 2H), 3.45-3.36 (m, 2H), 2.90-2.80 (m, 2H), 1.65-1.31 (m, 8H), 1.00-0.91 (m, 5H), 0.80-0.73 (m, 3H), 0.04 (s, 4.5H), 0.02 (s, 4.5H); MS (ESI$^-$) m/z 646.2 (M−H)$^-$.

Intermediate 264J

Methyl 4-(4-(dibutylcarbamoyl)-1H-imidazol-2-yl)-3-(1,2,3,4-tetrahydroisoquinoline-2-carbonyl)benzoate (Int-264J)

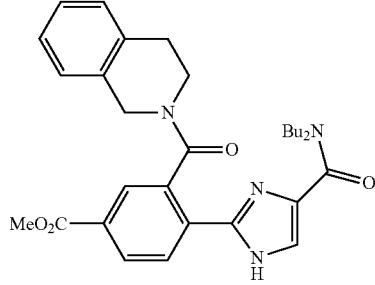

To a solution methyl 4-(4-(dibutylcarbamoyl)-1-((2-(trimethylsilyl)ethoxy)methyl)-1H-imidazol-2-yl)-3-(1,2,3,4-tetrahydroisoquinoline-2-carbonyl)benzoate (180 mg, 0.28 mmol) in DCM (4 mL) was added trifluoroacetic acid (4 mL) at 0° C. The reaction mixture was allowed to warm to room temperature and stirring was continued for 4 h. The reaction mixture was concentrated in vacuo. The resulting residue was dissolved in DCM and washed with sat. NaHCO$_3$ solution. The organic layer was dried over Na$_2$SO$_4$ and concentrated to give crude product. The crude material was purified by flash chromatography (gradient from 0 to 5% methanol/CHCl$_3$) to provide the title compound (130 mg, 91%). $^1$H NMR (CD$_3$OD) δ 8.25-8.06 (m, 2H), 8.00-7.50 (m, 2H), 7.28-6.83 (m, 4H), 4.36 (br s, 1H), 4.01 (br s, 4H), 3.60-3.24 (m, 6H), 2.88-2.69 (m, 2H), 1.60-1.52 (m, 4H), 1.36-1.30 (m, 4H), 1.05-0.90 (m, 6H); MS(ESI$^-$) m/z 515.2 (M−H)$^-$.

Intermediate 264K

Methyl 4-(4-(dibutylcarbamoyl)-1-methyl-1H-imidazol-2-yl)-3-(1,2,3,4-tetrahydroisoquinoline-2-carbonyl)benzoate (Int-264K)

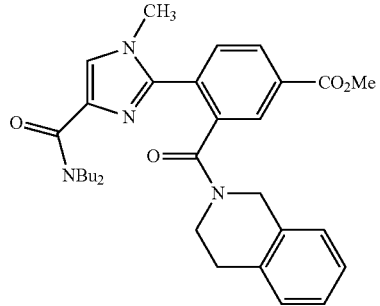

To a stirred solution of methyl 4-(4-(dibutylcarbamoyl)-1H-imidazol-2-yl)-3-(1,2,3,4-tetrahydroisoquinoline-2-carbonyl)benzoate (80 mg, 0.15 mmol) in dry DMF (3 mL) was added K$_2$CO$_3$ (42 mg, 0.30 mmol) and methyl iodide (22 mg, 0.15 mmol, a solution in 100 µL of DMF) at 0° C. The reaction mixture was allowed to warm to room temperature and stirring was continued for 4 h. The reaction mixture was diluted with MTBE and washed with water. The organic layer was dried over Na$_2$SO$_4$ and concentrated in vacuo to give crude product. The crude material was purified by flash chromatography (gradient from 0% to 2% MeOH/CHCl$_3$) to provide the title compound (65 mg, 79%). $^1$H NMR (CD$_3$OD) δ 8.25-8.00 (m, 2H), 7.92-7.00 (m, 6H), 4.80-4.60 (m, 2H), 4.02 (s, 3H), 3.70-3.40 (m, 6H), 3.01 (s, 3H), 2.90-2.80 (m, 2H), 1.60-1.50 (m, 4H), 1.50-1.30 (m, 4H), 1.05-0.90 (m, 6H); MS(ESI$^+$) m/z 531.4 (M+H)$^+$.

Intermediate 264L 4-(4-(Dibutylcarbamoyl)-1-methyl-1H-imidazol-2-yl)-3-(1,2,3,4-tetrahydroisoquinoline-2-carbonyl)benzoic acid (Int-264L)

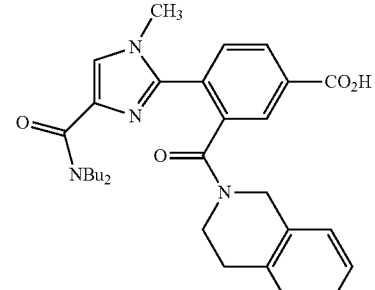

To a solution of methyl 4-(4-(dibutylcarbamoyl)-1-methyl-1H-imidazol-2-yl)-3-(1,2,3,4-tetrahydroisoquinoline-2-carbonyl)benzoate (65 mg, 0.12 mmol) in mixed solvents (THF/MeOH/H₂O; 2:2:1; 5 mL) was added LiOH H₂O (15 mg, 0.36 mmol) at 0° C. The reaction mixture was allowed to room temperature over 30 min. and stirring was continued for 1 h. The reaction mixture was concentrated to give crude product, which was diluted with water and extracted with MTBE. The aqueous layer was neutralized with 0.5N HCl and extracted with DCM (3×). The combined organic layer was dried over Na₂SO₄ and concentrated in vacuo to give the title compound (55 mg, 87%). $^1$H NMR (CD₃OD, 1:1 mixture of amide rotamers) δ 8.28 (dd, J=8.0, 1.6 Hz, 1H), 8.14 (s, 1H), 7.77 (dd, J=13.6, 8.4 Hz, 1H), 7.63 (s, 0.5H), 7.51 (s, 0.5H), 7.23-7.13 (m, 3.5H), 6.95 (d, J=9.2 Hz, 0.5H), 4.79 (s, 1H), 4.48 (s, 1H), 3.77 (s, 1.5H), 3.68 (s, 1.5H), 3.58-3.01 (m, 6H), 2.88-2.80 (m, 2H), 1.60-1.40 (m, 2H), 1.39-1.20 (m, 4H), 1.19-1.00 (m, 2H), 0.99-0.90 (m, 3H), 0.85-0.75 (m, 3H); MS(ESI⁺) m/z 517.4 (M+H)⁺.

Example 264

To a solution of 4-(4-(dibutylcarbamoyl)-1-methyl-1H-imidazol-2-yl)-3-(1,2,3,4-tetrahydroisoquinoline-2-carbonyl)benzoic acid (40 mg, 0.077) in dry DMF (2 mL) were added HATU (147 mg, 0.387 mmol), naphthalene-2-sulfonamide (48 mg, 0.23 mmol) and diisopropylethyl amine (134 μL, 0.77 mmol) at 0° C. The reaction mixture was allowed to warm to room temperature and stirred for 16 h. The reaction mixture was concentrated in vacuo to dryness, dissolved in water and extracted with EtOAc (3×). The combined organic layer was dried over Na₂SO₄ and concentrated in vacuo to afford crude product. The crude material was purified by preparative TLC to provide the title compound (12 mg, 16%) $^1$H NMR (CD₃OD, 1:1 mixture of amide rotamers) δ 8.61 (br s, 1H), 8.20-8.14 (m, 1H), 8.08-7.94 (m, 5.5H), 7.63-7.54 (m, 3.5H), 7.20-7.02 (m, 3.5H), 6.86 (d, J=9.2 Hz, 0.5H), 4.75 (br s, 1H), 4.60 (br s, 1H), 4.40 (br s, 1H), 3.74-3.72 (m, 2H), 3.55-3.50 (m, 4H), 3.07 (s, 1.5H), 2.93 (s, 1.5H), 2.80-2.65 (m, 2H), 1.60-1.50 (m, 4H), 1.50-1.30 (m, 2H), 1.20-1.05 (m, 2H), 1.00-0.90 (m, 3H), 0.85-0.75 (m, 3H); MS (ESI⁺) m/z 706.2 (M+H)⁺.

Example 265

N,N-Dibutyl-1-(2-(methylamino)-2-oxoethyl)-2-(4-(naphthalen-2-ylsulfonylcarbamoyl)-2-(1,2,3,4-tetrahydroisoquinoline-2-carbonyl)phenyl)-1H-imidazole-4-carboxamide (265)

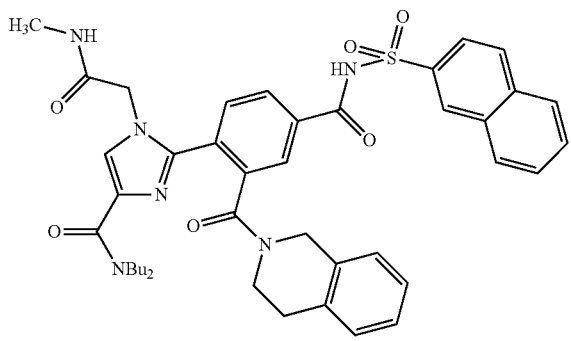

Intermediate 265A

Methyl 4-(1-(2-tert-butoxy-2-oxoethyl)-4-(dibutylcarbamoyl)-1H-imidazol-2-yl)-3-(1,2,3,4-tetrahydroisoquinoline-2-carbonyl)benzoate (Int-265A)

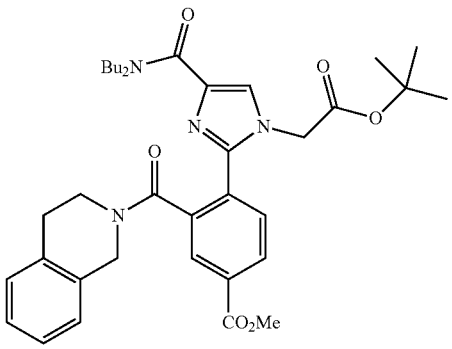

Following a procedure analogous to that for the synthesis of Intermediate 264K, methyl 4-(4-(dibutylcarbamoyl)-1H-imidazol-2-yl)-3-(1,2,3,4-tetrahydroisoquinoline-2-carbonyl)benzoate (310 mg, 0.6 mmol) and t-butylbromoacetate (117 mg, 0.6 mmol) were converted to the title compound (300 mg, 90%). MS(ESI⁺) m/z 631.4 (M+H)⁺.

Intermediate 265B 2-(4-(Dibutylcarbamoyl)-2-(4-(methoxycarbonyl)-2-(1,2,3,4-tetrahydroisoquinoline-2-carbonyl)phenyl)-1H-imidazol-1-yl)acetic acid (Int-265B)

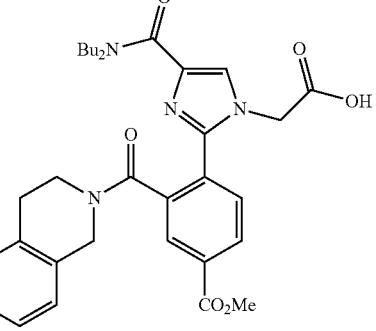

To a solution of methyl 4-(1-(2-tert-butoxy-2-oxoethyl)-4-(dibutylcarbamoyl)-1H-imidazol-2-yl)-3-(1,2,3,4-tetrahydroisoquinoline-2-carbonyl)benzoate (300 mg, 0.44 mmol) in DCM (3.0 mL) was added trifluoroacetic acid (3.0 mL) at 0° C. The reaction mixture was allowed to room temperature and stirring was continued for 1 h. The reaction mixture was concentrated in vacuo and the resulting residue was dissolved in DCM and washed with sat. NaHCO₃ solution. The organic layer was dried over Na₂SO₄ and concentrated to give the title compound (200 mg, 80%). MS(ESI) m/z 575.4 (M+H)⁺.

Intermediate 265C

Methyl 4-(4-(dibutylcarbamoyl)-1-(2-(methylamino)-2-oxoethyl)-1H-imidazol-2-yl)-3-(1,2,3,4-tetrahydroisoquinoline-2-carbonyl)benzoate

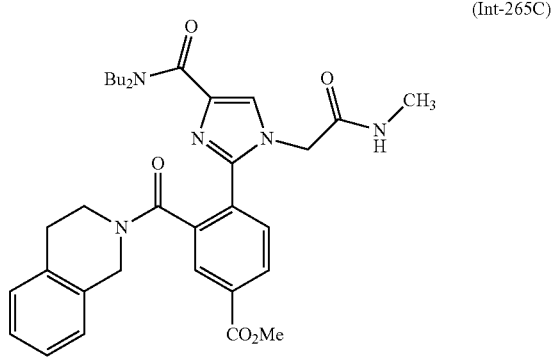
(Int-265C)

To a solution of 2-(4-(dibutylcarbamoyl)-2-(4-(methoxycarbonyl)-2-(1,2,3,4-tetrahydroisoquinoline-2-carbonyl)phenyl)-1H-imidazol-1-yl)acetic acid (180 mg, 0.31 mmol) in dry DMF (5 mL) was added HATU (595 mg, 1.56 mmol), methylamine (Aldrich, 78 μL, 1.56 mmol, 2.0 M in THF) and diisopropylethyl amine (544 μL, 3.13 mmol) at 0° C. The reaction mixture was allowed to warm to room temperature over 30 min and stirring was continued for 16 h. The reaction mixture was diluted with water, and extracted with EtOAc (3×). The combined organic layers were dried over Na$_2$SO$_4$ and concentrated in vacuo to give crude product. The crude material was purified by flash chromatography (gradient from 20 to 50% EtOAc/hexanes) to provide (85 mg, 46%). $^1$H NMR (CDCl$_3$, 1:1 mixture of amide rotamers) δ 8.22-8.19 (m, 1H), 8.10 (dd, J=6.0, 1.6 Hz, 1H), 7.58 (s, 0.5H), 7.56-7.52 (m, 1H), 7.50 (s, 0.5H), 7.36-7.10 (m, 3.5H), 6.94 (d, J=7.6 Hz, 0.5H), 4.76 (br s, 1H), 4.65 (br s, 3H), 3.98 (s, 3H), 3.97-3.95 (m, 1.5H), 3.73 (t, J=5.6 Hz, 1.5H), 3.60-3.30 (m, 3H), 3.00-2.85 (m, 2H), 2.65 (s, 1.5H), 2.64 (s, 1.5H), 1.47-1.24 (m, 6H), 0.96-0.84 (m, 5H), 0.80 (t, J=7.4 Hz, 1.5H), 0.60 (t, J=7.4 Hz, 1.5H); MS(ESI$^+$) m/z 588.4 (M+H)$^+$.

Intermediate 265D 4-(4-(Dibutylcarbamoyl)-1-(2-(methylamino)-2-oxoethyl)-1H-imidazol-2-yl)-3-(1,2,3,4-tetrahydroisoquinoline-2-carbonyl)benzoic acid

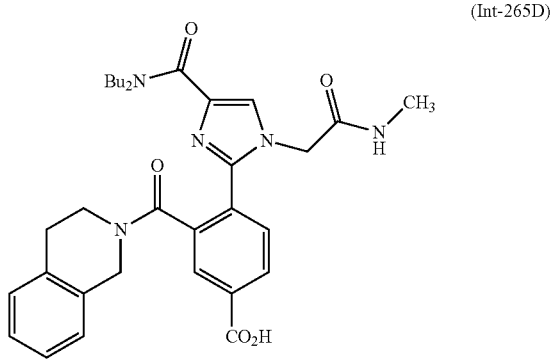
(Int-265D)

Following a procedure analogous to that for the synthesis of Intermediate 264L, methyl 4-(4-(dibutylcarbamoyl)-1-(2-(methylamino)-2-oxoethyl)-1H-imidazol-2-yl)-3-(1,2,3,4-tetrahydroisoquinoline-2-carbonyl)benzoate (80 mg, 0.13 mmol) was converted to the title compound (60 mg, 77%). MS(ESI$^+$) m/z 574.4 (M+H)$^+$.

Example 265

To a solution of 4-(4-(dibutylcarbamoyl)-1-(2-(methylamino)-2-oxoethyl)-1H-imidazol-2-yl)-3-(1,2,3,4-tetrahydroisoquinoline-2-carbonyl)benzoic acid (60 mg, 0.1 mmol) in dry DMF (8 mL) was added EDC (60 mg, 0.3 mmol), naphthalene-2-sulfonamide (43 mg, 0.2 mmol) and 4-dimethylamino pyridine (19 mg, 0.15 mmol) at 0° C. The reaction mixture was allowed to warm to room temperature and stirring was continued for 16 h. The reaction mixture was concentrated in vacuo, dissolved in water and extracted with EtOAc (3×). The combined organic layer was dried over Na$_2$SO$_4$ and concentrated in vacuo to afford crude product. The crude material was purified by preparative HPLC to provide the title compound (8 mg, 10%). $^1$H NMR (CD$_3$OD, 1:1 mixture of amide rotamers) δ 8.58 (s, 1H), 8.17 (t, J=6.4 Hz, 1H), 8.11 (s, 1H), 8.04-8.02 (m, 2H), 7.96-7.92 (m, 2H), 7.62-7.54 (m, 4H), 7.23-7.11 (m, 3.5H), 6.95 (d, J=7.2 Hz, 0.5H), 4.74 (s, 1H), 4.69 (s, 1H), 4.64-4.61 (m, 1H), 4.55 (br s, 1H), 4.18-3.70 (m, 2H), 3.61 (t, J=6.0 Hz, 2H), 3.55-3.45 (m, 1.5H), 3.30-3.15 (m, 0.5H), 2.88-2.78 (m, 2H), 2.70 (s, 3H), 1.54-1.40 (m, 2H), 1.40-1.20 (m, 4H), 1.20-1.10 (m, 2H), 0.99-0.90 (m, 3H), 0.78 (t, J=8.4 Hz, 1.5H), 0.69 (t, J=8.4 Hz, 1.5H); MS(ESI$^-$) m/z 761.4 (M−H)$^-$.

Example 266

N,N-Dibutyl-1-(3-hydroxypropyl)-2-(4-(naphthalen-2-ylsulfonylcarbamoyl)-2-(1,2,3,4-tetrahydroisoquinoline-2-carbonyl)phenyl)-1H-imidazole-4-carboxamide

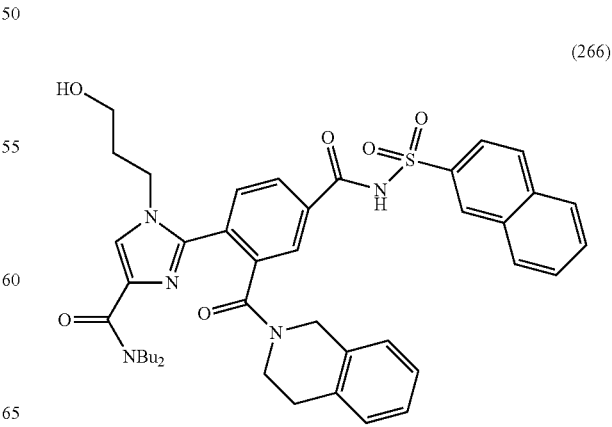
(266)

Intermediate 266A

Methyl 4-(4-(dibutylcarbamoyl)-1-(3-hydroxypropyl)-1H-imidazol-2-yl)-3-(1,2,3,4-tetrahydroisoquinoline-2-carbonyl)benzoate

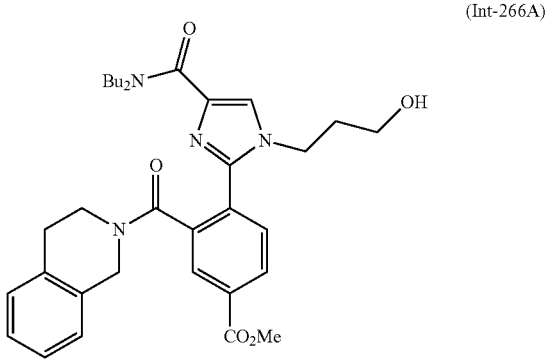
(Int-266A)

To a stirred solution of methyl 4-(4-(dibutylcarbamoyl)-1H-imidazol-2-yl)-3-(1,2,3,4-tetrahydroisoquinoline-2-carbonyl)benzoate (200 mg, 0.38 mmol) in DMF (8 mL) was added $K_2CO_3$ (107 mg, 0.77 mmol) and 3-bromopropanol (54 mg, 0.38 mmol). The reaction mixture was heated at 40° C. for 4 h, cooled to room temperature, diluted with MTBE, and quenched with water. The organic layer was separated and the aqueous layer was extracted with MTBE (3×). The combined organic layer was dried over $Na_2SO_4$ and concentrated in vacuo to provide crude product. The crude material was purified by flash chromatography (gradient from 10 to 50% EtOAc/hexanes) to provide the title compound (67 mg, 32%). $^1H$ NMR (CDCl$_3$, 1:1 mixture of amide rotamers) δ 8.19-8.15 (m, 1H), 8.04 (dd, J=11.2, 1.6 Hz, 1H), 7.62 (s, 0.5H), 7.55 (s, 0.5H), 7.50-7.46 (m, 1H), 7.25-7.14 (m, 3.5H), 6.94 (d, J=7.2 Hz, 0.5H), 4.84-4.59 (m, 2H), 4.29-4.13 (m, 2H), 3.96 (s, 3H), 3.82-3.70 (m, 2H), 3.50-3.35 (m, 4H), 3.31-2.88 (m, 4H), 1.89-1.87 (m, 2H), 1.55-1.49 (m, 2H), 1.40-1.05 (m, 6H), 0.93-0.88 (m, 3H), 0.74 (t, J=7.2 Hz, 1.5H), 0.65 (t, J=7.2 Hz, 1.5H); MS(ESI$^+$) m/z 575.6 (M+H)$^+$.

Intermediate 266B 4-(4-(Dibutylcarbamoyl)-1-(3-hydroxypropyl)-1H-imidazol-2-yl)-3-(1,2,3,4-tetrahydroisoquinoline-2-carbonyl)benzoic acid

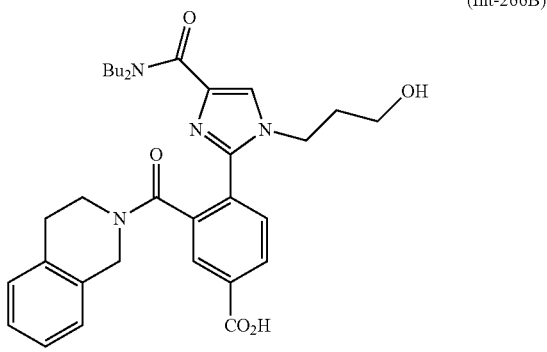
(Int-266B)

Following a procedure analogous to that for synthesis of Intermediate 264L, methyl 4-(4-(dibutylcarbamoyl)-1-(3-hydroxypropyl)-1H-imidazol-2-yl)-3-(1,2,3,4-tetrahydroisoquinoline-2-carbonyl)benzoate (70 mg, 0.12 mmol) was converted to the title compound (60 mg, 88%). MS(ESI$^-$) m/z 559.4 (M–H)$^-$.

Example 266

Following a procedure analogous to that for the synthesis of Example 265, 4-(4-(dibutylcarbamoyl)-1-(3-hydroxypropyl)-1H-imidazol-2-yl)-3-(1,2,3,4-tetrahydroisoquinoline-2-carbonyl)benzoic acid (60 mg, 0.11 mmol) was converted to the title compound (24 mg, 30%). $^1H$ NMR (CD$_3$OD, 1:1 mixture of amide rotamers) δ 8.60 (s, 1H), 8.21-8.17 (m, 1H), 8.10-8.09 (m, 1H), 8.05-8.03 (m, 2H), 7.98-7.93 (m, 2H), 7.63-7.58 (m, 4H), 7.23-7.11 (m, 3.5H), 6.95 (d, J=6.8 Hz, 0.5H), 4.75 (s, 1H), 4.60 (br s, 1H), 4.12 (t, J=8.0 Hz, 1H), 4.05 (br s, 1H), 3.61 (t, J=5.6 Hz, 2H), 3.46-3.42 (m, 2H), 3.40-3.35 (m, 2H), 3.30-3.25 (m, 2H), 2.89-2.82 (m, 2H), 1.92-1.88 (m, 2H), 1.53-1.47 (m, 2H), 1.40-1.31 (m, 4H), 1.20-1.10 (m, 1H), 0.99-0.90 (m, 4H), 0.76 (t, J=6.8 Hz, 1.5H), 0.72 (t, J=6.8 Hz, 1.5H); MS(ESI$^-$) m/z 748.4 (M–H)$^-$.

Example 267

N,N-Dibutyl-1-(3-(dimethylamino)propyl)-2-(4-(naphthalen-2-ylsulfonylcarbamoyl)-2-(1,2,3,4-tetrahydroisoquinoline-2-carbonyl)phenyl)-1H-imidazole-4-carboxamide

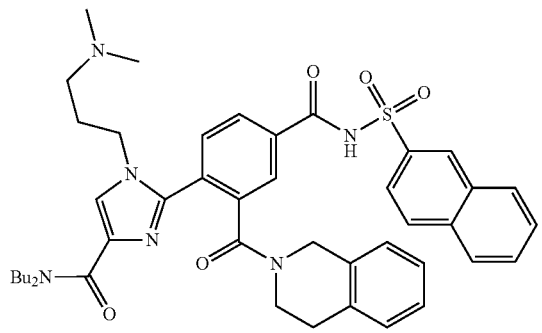
(267)

Intermediate 267A

Methyl 4-(4-(dibutylcarbamoyl)-1-(3-(dimethylamino)propyl)-1H-imidazol-2-yl)-3-(1,2,3,4-tetrahydroisoquinoline-2-carbonyl)benzoate

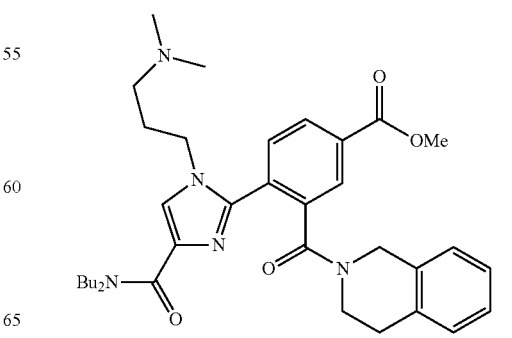
(Int-267A)

Following a procedure analogous to that for the synthesis of Intermediate 266A, methyl 4-(4-(dibutylcarbamoyl)-1H-imidazol-2-yl)-3-(1,2,3,4-tetrahydroisoquinoline-2-carbonyl)benzoate (200 mg, 0.38 mmol) and 3-bromo-N,N-dimethylpropan-1-amine (77 mg, 0.46 mmol) were converted to the title compound (180 mg, 78%). MS(ESI⁺) m/z 602.6 (M+H)⁺.

Intermediate 267B 4-(4-(Dibutylcarbamoyl)-1-(3-(dimethylamino)propyl)-1H-imidazol-2-yl)-3-(1,2,3,4-tetrahydroisoquinoline-2-carbonyl)benzoic acid (Int-267B)

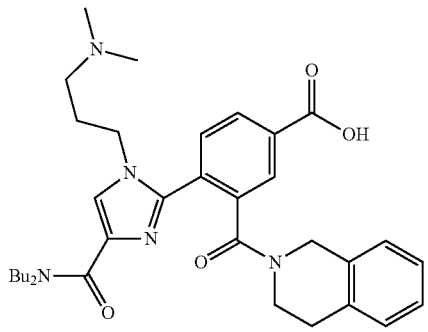

Following a procedure analogous to that for the synthesis of Intermediate 264L, methyl 4-(4-(dibutylcarbamoyl)-1-(3-(dimethylamino)propyl)-1H-imidazol-2-yl)-3-(1,2,3,4-tetrahydroisoquinoline-2-carbonyl)benzoate (180 mg, 0.3 mmol) was converted to the title product (160 mg, 86%). MS(ESI) m/z 588.4 (M+H)⁺.

Example 267

Following a procedure analogous to that for the synthesis of Example 265, 4-(4-(dibutylcarbamoyl)-1-(3-(dimethylamino) propyl)-1H-imidazol-2-yl)-3-(1,2,3,4-tetrahydroisoquinoline-2-carbonyl)benzoic acid (160 mg, 0.27 mmol) was converted to the title compound (30 mg, 14%). ¹H NMR (CD₃OD, 1:1 mixture of amide rotamers) δ 8.58 (s, 1H), 8.22-8.19 (m, 1H), 8.12-8.10 (m, 1H), 8.05-8.01 (m, 2H), 7.96-7.92 (m, 2H), 7.64-7.56 (m, 4H), 7.25-7.12 (m, 3.5H), 6.98 (d, J=7.2 Hz, 0.5H), 4.73 (s, 1H), 4.65 (s, 1H), 4.15 (br s, 3H), 3.68-3.64 (m, 2H), 3.49-3.39 (m, 3H), 2.90-2.80 (m, 4H), 2.66 (br s, 6H), 2.00-1.90 (m, 2H), 1.60-1.40 (m, 2H), 1.39-1.25 (m, 3H), 1.22-1.05 (m, 2H), 1.00-0.85 (m, 4H), 0.75 (t, J=7.2 Hz, 1.5H), 0.63 (t, J=7.2 Hz, 1.5H); MS(ESI⁺) m/z 779.1 (M+H)⁺.

Example 268

N,N-Dibutyl-2-(4-(naphthalen-2-ylsulfonylcarbamoyl)-2-(1,2,3,4-tetrahydroisoquinoline-2-carbonyl)phenyl)-1-((2-(trimethylsilyl)ethoxy)methyl)-1H-imidazole-4-carboxamide (268)

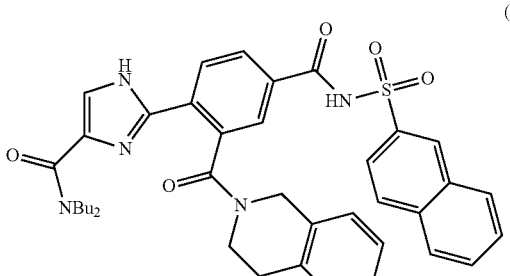

Intermediate 268A 4-(4-(Dibutylcarbamoyl)-1-((2-(trimethylsilyl)ethoxy)methyl)-1H-imidazol-2-yl)-3-(1,2,3,4-tetrahydroisoquinoline-2-carbonyl)benzoic acid (Int-268A)

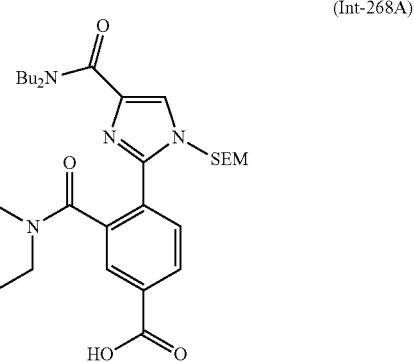

Following a procedure analogous to that for the synthesis of Intermediate 264L, methyl 4-(4-(dibutylcarbamoyl)-1-((2-(trimethylsilyl)ethoxy)methyl)-1H-imidazol-2-yl)-3-(1,2,3,4-tetrahydroisoquinoline-2-carbonyl)benzoate (350 mg, 0.54 mmol) was converted to the title compound (320 mg, 93%), which was used without further purification. MS(ESI⁻) m/z 631.4 (M−H)⁻.

Intermediate 268B

N,N-Dibutyl-2-(4-(naphthalen-2-ylsulfonylcarbamoyl)-2-(1,2,3,4-tetrahydroisoquinoline-2-carbonyl)phenyl)-1-((2-(trimethylsilyl)ethoxy)methyl)-1H-imidazole-4-carboxamide (Int-268B)

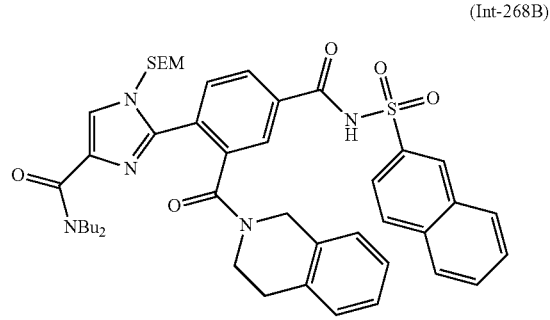

Following a procedure analogous to that for the synthesis of Example 265, 4-(4-(dibutylcarbamoyl)-1-((2-(trimethylsilyl)ethoxy)methyl)-1H-imidazol-2-yl)-3-(1,2,3,4-tetrahydroisoquinoline-2-carbonyl)benzoic acid (40 mg, 0.063 mmol) was converted to the title compound (20 mg, 38%). ¹H NMR (CD₃OD, 1:1 mixture of amide rotamers) δ 8.59 (d, J=2.8 Hz, 1H), 8.20 (t, J=7.6 Hz, 1H), 8.11 (br s, 1H), 8.06-8.00 (m, 2H), 7.97-7.91 (m, 2H), 7.82 (d, J=7.6 Hz, 0.5H), 7.76 (d, J=7.6 Hz, 0.5H), 7.72 (s, 0.5H), 7.63-7.58 (m, 2.5H), 7.25-7.05 (m, 3.5H), 6.87 (d, J=6.8 Hz, 0.5H), 5.34 (s, 1H), 5.14 (s, 1H), 4.78 (s, 1H), 4.63 (s, 1H), 4.40 (br s, 2H), 3.68-3.54 (m, 6H), 2.88-2.80 (m, 2H), 1.65-1.40 (m, 2H), 1.39-1.26 (m, 4H), 1.25-1.05 (m, 4H), 0.99-0.78 (m, 6H), 0.02 (s, 9H); MS (ESI⁺) m/z 821.2 (M−H)⁻.

Example 268

Following a procedure analogous to that for the synthesis of Intermediate 264J, N,N-dibutyl-2-(4-(naphthalen-2-ylsulfonylcarbamoyl)-2-(1,2,3,4-tetrahydroisoquinoline-2-carbonyl)phenyl)-1-((2-(trimethylsilyl)ethoxy)methyl)-1H-imidazole-4-carboxamide (100 mg, 0.12 mmol) was converted to the title compound (16 mg, 19%). $^1$H NMR (DMSO-$d_6$, 1:1 mixture of amide rotamers) δ 12.8 (br s, 1H), 8.52 (br s, 0.5H), 8.13 (br s, 0.5H), 8.00-7.90 (m, 4H), 7.84-7.80 (m, 2H), 7.70-7.58 (m, 3H), 7.25-6.97 (m, 4.5H), 6.87 (d, J=6.0 Hz, 0.5H), 4.86 (d, J=17.2 Hz, 0.5H), 4.71 (d, J=17.2 Hz, 0.5H), 4.31-4.15 (m, 1H), 3.90 (br s, 0.5H), 3.72 (br s, 0.5H), 3.50-3.43 (m, 1H), 3.10-2.87 (m, 4H), 2.62-2.51 (m, 2H), 1.52-1.40 (m, 2H), 1.42-1.00 (m, 6H), 0.86-0.81 (m, 3H), 0.70-0.64 (m, 3H); MS(ESI$^-$) m/z 691.2 (M–H)$^-$.

Example 269

2-(4-(Dibutylcarbamoyl)-2-(4-(naphthalen-1-ylsulfonylcarbamoyl)-2-(1,2,3,4-tetrahydroisoquinoline-2-carbonyl)phenyl)-1H-imidazol-1-yl)acetic acid

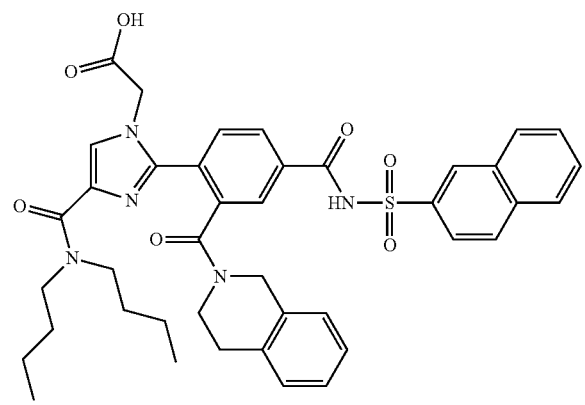

(269)

Intermediate 269A

Benzyl 4-(4-(dibutylcarbamoyl)-1-((2-(trimethylsilyl)ethoxy)methyl)-1H-imidazol-2-yl)-3-(1,2,3,4-tetrahydroisoquinoline-2-carbonyl)benzoate

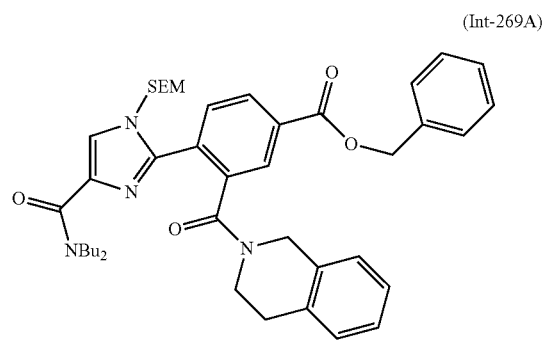

(Int-269A)

To a stirred solution of 4-(4-(dibutylcarbamoyl)-1-((2-(trimethylsilyl)ethoxy)methyl)-1H-imidazol-2-yl)-3-(1,2,3,4-tetrahydroisoquinoline-2-carbonyl)benzoic acid (320 mg, 0.96 mmol) in dry DCM (5.0 mL) was added EDC (932 mg, 4.81 mmol), benzyl alcohol (208 mg, 1.92 mmol) and DMAP (235 mg, 1.92 mmol) at 0° C. The reaction mixture was allowed to warm to room temperature and stirring was continued for 16 h. The reaction mixture was diluted with water and extracted with DCM (2×). The combined organic layer was dried over Na$_2$SO$_4$ and concentrated in vacuo to give crude product. The crude material was purified by flash chromatography (gradient 10 to 30% EtOAc/hexanes) to provide the title compound (400 mg, 92%). MS(ESI$^+$) m/z 723.6 (M+H)$^+$.

Intermediate 269B

Benzyl 4-(4-(dibutylcarbamoyl)-1H-imidazol-2-yl)-3-(1,2,3,4-tetrahydroisoquinoline-2-carbonyl)benzoate

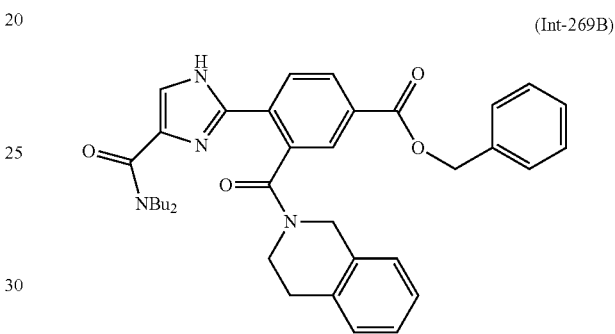

(Int-269B)

Following a procedure analogous to that for the synthesis of Intermediate 264J, benzyl 4-(4-(dibutylcarbamoyl)-1-((2-(trimethylsilyl)ethoxy)methyl)-1H-imidazol-2-yl)-3-(1,2,3,4-tetrahydroisoquinoline-2-carbonyl)benzoate (400 mg, 0.55 mmol) was converted to the title compound (300 mg, 91%). $^1$H NMR (CDCl$_3$) δ 8.23-8.19 (m, 1H), 8.03 (d, J=10.0 Hz, 1H), 7.45-7.34 (m, 7H), 7.23-7.05 (m, 3.5H), 6.76 (d, J=6.4 Hz, 0.5H), 5.39-5.36 (m, 2H), 5.14 (d, J=16.0 Hz, 1H), 4.81 (d, J=16.8 Hz, 1H), 4.40-4.14 (m, 2H), 3.83-3.31 (m, 4H), 3.01-2.79 (m, 2H), 1.55-1.1.50 (m, 4H), 1.39-1.33 (m, 4H), 0.99-0.92 (m, 6H); MS(ESI$^-$) m/z 591.4 (M–H)$^-$.

Intermediate 269C

Benzyl 4-(4-(dibutylcarbamoyl)-1-(2-ethoxy-2-oxoethyl)-1H-imidazol-2-yl)-3-(1,2,3,4-tetrahydroisoquinoline-2-carbonyl)benzoate

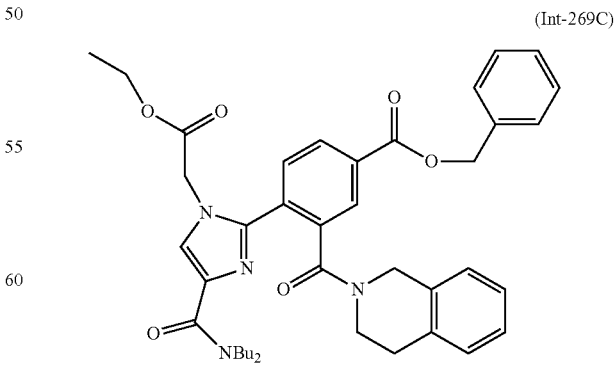

(Int-269C)

Following a procedure analogous to that for the synthesis of Intermediate 264K, benzyl 4-(4-(dibutylcarbamoyl)-1H-imidazol-2-yl)-3-(1,2,3,4-tetrahydroisoquinoline-2-carbonyl)benzoate (300 mg, 0.5 mmol) and ethylbromo acetate (84 mg, 0.5 mmol) were converted to the title compound (255 mg, 73%). MS(ESI⁺) m/z 679.6 (M+H)⁺.

Intermediate 269D 4-(4-(Dibutylcarbamoyl)-1-(2-ethoxy-2-oxoethyl)-1H-imidazol-2-yl)-3-(1,2,3,4-tetrahydroisoquinoline-2-carbonyl)benzoic acid (Int-269D)

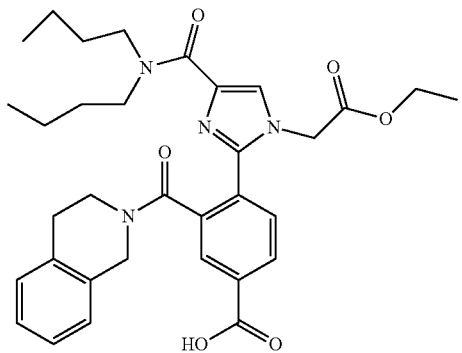

To a solution of benzyl 4-(4-(dibutylcarbamoyl)-1-(2-ethoxy-2-oxoethyl)-1H-imidazol-2-yl)-3-(1,2,3,4-tetrahydroisoquinoline-2-carbonyl)benzoate (250 mg, 0.36 mmol) in MeOH (5.0 mL) was added Pd/C (10%). The resulting reaction mixture was stirred under H₂ atmosphere for 2 h. The reaction mixture was filtered through a small pad of CELITE®, washed thoroughly with MeOH and concentrated in vacuo to provide the title compound (190 mg, 88%). ¹H NMR (DMSO-d₆, 1:1 mixture of amide rotamers) δ 13.4 (br s, 1H), 8.07 (d, J=8.0 Hz, 1H), 7.94 (d, J=9.6 Hz, 1H), 7.71 (s, 0.5H), 7.65 (s, 0.5H), 7.50 (t, J=8.6 Hz, 1H), 7.19-7.08 (m, 3.5H), 6.95 (d, J=7.6 Hz, 0.5H), 4.93 (br s, 2H), 4.63 (br s, 1H), 4.40-4.30 (br s, 1H), 4.15 (q, J=14.0, 6.8 Hz, 2H), 3.68 (br s, 2H), 3.46-3.42 (m, 2H), 3.30-3.20 (m, 2H), 2.74-2.62 (m, 2H), 1.44-1.27 (m, 4H), 1.22-1.20 (m, 3H), 1.19-1.16 (m, 4H), 0.95-0.72 (m, 6H); MS(ESI⁺) m/z 589.6 (M+H)⁺.

Intermediate 269E

Ethyl 2-(4-(dibutylcarbamoyl)-2-(4-(naphthalen-1-ylsulfonylcarbamoyl)-2-(1,2,3,4-tetrahydroisoquinoline-2-carbonyl)phenyl)-1H-imidazol-1-yl)acetate (Int-269E)

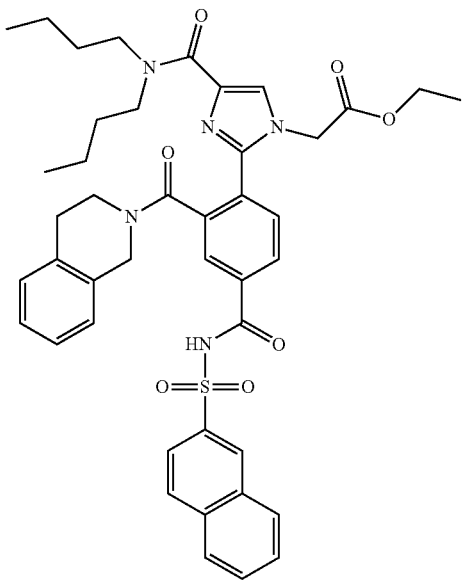

Following a procedure analogous to that for the synthesis of Example 265, 4-(4-(dibutylcarbamoyl)-1-(2-ethoxy-2-oxoethyl)-1H-imidazol-2-yl)-3-(1,2,3,4-tetrahydroisoquinoline-2-carbonyl)benzoic acid (190 mg, 0.32 mmol) was converted to the title compound (100 mg, 40%). MS(ESI⁺) m/z 778.2.6 (M+H)⁺.

Example 269

To a solution of ethyl 2-(4-(dibutylcarbamoyl)-2-(4-(naphthalen-1-ylsulfonylcarbamoyl)-2-(1,2,3,4-tetrahydroisoquinoline-2-carbonyl)phenyl)-1H-imidazol-1-yl)acetate (100 mg, 0.12 mmol) in mixed solvents (2:2:1 EtOH/THF/water, 15 mL) was added LiOH H₂O (17 mg, 0.36 mmol) at 0° C. The reaction mixture was allowed to warm to room temperature and stirring was continued for 2 h. The reaction mixture was quenched with 0.5N HCl, and then extracted with EtOAc (4×). The combined organic extracts were dried over Na₂SO₄, filtered and concentrated in vacuo to afford the title compound (60 mg, 62%). ¹H NMR (CD₃OD, 1:1 mixture of amide rotamers) δ 8.61 (s, 1H), 8.14 (t, J=7.2 Hz, 1H), 8.07-8.03 (m, 3H), 7.98-7.93 (m, 2H), 7.65-7.58 (m, 3.5H), 7.39 (br s, 0.5H), 7.19-7.06 (m, 3.5H), 6.90 (d, J=6.8 Hz, 0.5H), 4.72 (s, 1H), 4.66 (s, 1H), 4.49 (br s, 1H), 4.39 (br s, 1H), 3.66 (br s, 2H), 3.49 (t, J=5.6 Hz, 2H), 3.34 (br s, 2H), 2.76-2.69 (m, 2H), 1.57-1.31 (m, 6H), 1.17-1.13 (m, 2H), 0.97-0.79 (m, 6H); MS (ESI⁻) m/z 748.6 (M−H)⁻.

Example 270

N,N-Dibutyl-2-(4-(8-iodonaphthalen-2-ylsulfonylcarbamoyl)-2-(1,2,3,4-tetrahydroisoquinoline-2-carbonyl)phenyl)-1-methyl-1H-imidazole-4-carboxamide (270)

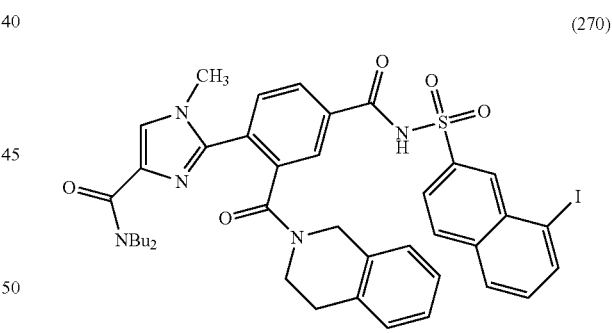

Following a procedure analogous to that for the synthesis of Example 265, 4-(4-(dibutylcarbamoyl)-1-methyl-1H-imidazol-2-yl)-3-(1,2,3,4-tetrahydroisoquinoline-2-carbonyl)benzoic acid (Intermediate 264L, 45 mg, 0.09 mmol) and 8-iodonaphthalene-2-sulfonamide (Intermediate 6, 72 mg, 0.21 mmol) were converted to the title compound (11 mg, 15%). ¹H NMR (CD₃OD, 1:1 mixture of amide rotamers) δ 8.93 (s, 1H), 8.26 (d, J=7.2 Hz, 1H), 8.15 (dd, J=8.8, 1.6 Hz, 2H), 8.05-8.02 (m, 3H), 7.69 (dd, J=15.6, 8.0 Hz, 1H), 7.58 (s, 0.5H), 7.46 (br s, 0.5H), 7.40 (t, J=7.2 Hz, 1H), 7.23-7.11 (m, 3.5H), 6.91 (d, J=7.2 Hz, 0.5H), 4.76 (s, 1H), 4.45 (s, 1H), 3.73 (s, 3H), 3.63-3.52 (m, 6H), 2.82-2.78 (m, 2H), 1.56-1.46 (m, 2H), 1.45-1.27 (m, 4H), 1.20-1.00 (m, 2H), 1.00-0.92 (m, 3H), 0.85-0.75 (m, 3H); MS(ESI⁺) m/z 832.2 (M+H)⁺.

Example 271

N,N-Dibutyl-2-(4-(8-chloronaphthalen-2-ylsulfonyl-carbamoyl)-2-((S)-3-(hydroxymethyl)-1,2,3,4-tetrahydroisoquinoline-2-carbonyl)phenyl)-1-phenethyl-1H-imidazole-4-carboxamide

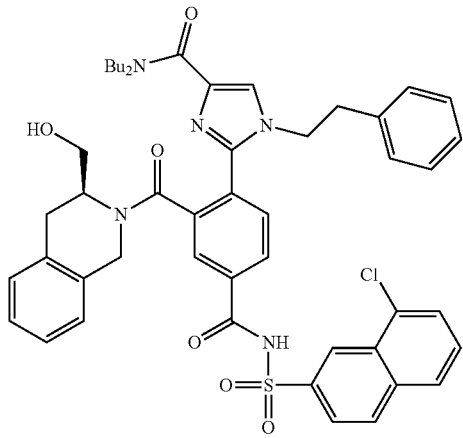

(271)

Intermediate 271A

3-Benzyl 1-methyl 4-hydroxyisophthalate

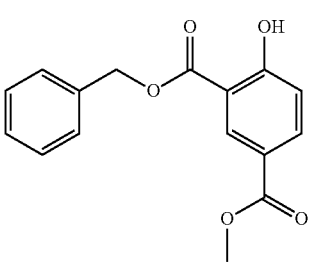

(Int-271A)

To a solution of 2-hydroxy-5-(methoxycarbonyl)benzoic acid (4.0 g, 20.4 mmol) in DMF (40 mL) was added KHCO$_3$ (2.04 g, 20.4 mmol) and benzyl bromide (3.49 g, 20.4 mmol) at 0° C. The reaction mixture was allowed to warm to room temperature and stirring was continued for 20 h. The reaction mixture was diluted with water, extracted with EtOAc (2×) and the combined organic layer was washed with brine, dried over Na$_2$SO$_4$, filtered and concentrated in vacuo to give a crude oil. The crude material was purified by flash chromatography (gradient from 0% to 30% EtOAc/hexanes) to provide the title compound (5.3 g, 92%) as an off-white solid. $^1$H NMR (CDCl$_3$) δ 11.21 (s, 1H), 8.58 (d, J=2.0 Hz, 1H), 8.11 (dd, J=8.8, 2.4 Hz, 1H), 7.47-7.37 (m, 5H), 7.01 (d, J=8.8 Hz, 1H), 5.42 (s, 2H), 3.89 (s, 3H); MS(ESI$^-$) m/z 285.2 (M–H)$^-$.

Intermediate 271B

3-Benzyl 1-methyl 4-(trifluoromethylsulfonyloxy)isophthalate

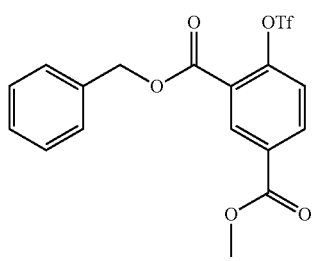

(Int-271B)

Following a procedure analogous to that for the synthesis of Intermediate 271G, 3-benzyl 1-methyl 4-hydroxyisophthalate (3.0 g, 10 mmol) was converted to the title compound (3.3 g, 77%). $^1$H NMR (CDCl$_3$) δ 8.71 (d, J=2.4 Hz, 1H), 8.27 (dd, J=8.4, 2.4 Hz, 1H), 7.58-7.47 (d, J=6.4 Hz, 1H), 7.48-7.46 (m, 2H), 7.41-7.35 (m, 3H), 5.43 (s, 2H), 3.95 (s, 3H); MS(ESI$^+$) m/z 436.0 (M+H$_2$O)$^+$.

Intermediate 271C

3-Benzyl 1-methyl 4-(5,5-dimethyl-1,3,2-dioxaborinan-2-yl)isophthalate

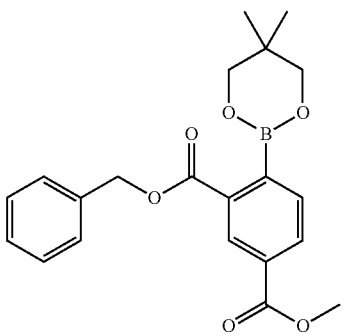

(Int-271C)

In a resealable pressure tube, a solution of 3-benzyl 1-methyl 4-(trifluoromethylsulfonyloxy)isophthalate (3.3 g, 7.9 mmol) in PhMe under argon was treated with bis(neopentylglycolato)diboron (2.50 g, 11.1 mmol), Pd(Ph$_3$)$_4$ (912 mg, 0.789 mmol) and KOAc (2.32 g, 23.68 mmol). The reaction vessel was purged with argon for 10 min, sealed with a Teflon lid and heated at 85° C. for 16 h. The reaction mixture was cooled to room temperature and diluted with EtOAc. The organic layer was washed with water, dried over Na$_2$SO$_4$, filtered and concentrated in vacuo to give a crude oil. The crude material was purified by flash chromatography (gradient from 0% to 10% EtOAc/hexane) to provide the title compound (2.2 g, 73%) as an off-white solid. $^1$H NMR (CDCl$_3$) δ 8.61 (d, J=1.6 Hz, 1H), 8.16 (dd, J=7.6, 1.6 Hz, 1H), 7.58 (d, J=7.6 Hz, 1H), 7.47-7.36 (m, 5H), 5.37 (s, 2H), 3.92 (s, 3H), 3.62 (s, 4H), 1.05 (s, 6H); MS (ESI⁺) m/z 592.0 (3-benzyl 1-dimethyl 4,4'-(1,3,2,4-dioxadiboretane-2,4-diyl)diisophthalate).

Intermediate 271D

3-Benzyl 1-methyl 4-(4-(dibutylcarbamoyl)-1-((2-(trimethylsilyl) ethoxy)methyl)-1H-imidazol-2-yl) isophthalate

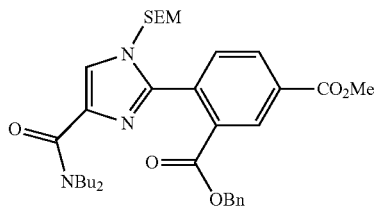

(Int-271D)

Following a procedure analogous to that for the synthesis of Intermediate 264I, 3-benzyl 1-methyl 4-(5,5-dimethyl-1,3,2-dioxaborinan-2-yl)isophthalate (1.76 g, 4.62 mmol) and 2-bromo-N,N-dibutyl-1-((2-(trimethylsilyl)ethoxy)methyl)-1H-imidazole-4-carboxamide (1.0 g, 2.31 mmol) were converted to the title compound (900 mg, 62%). ¹H NMR (CDCl₃) δ 8.66 (d, J=1.6 Hz, 1H), 8.23 (dd, J=8.0, 1.6 Hz, 1H), 7.62 (s, 1H), 7.58 (d, J=7.6 Hz, 1H), 7.36-7.32 (m, 3H), 7.25-7.23 (m, 2H), 5.14 (s, 2H), 4.87 (s, 2H), 3.97 (s, 3H), 3.89 (br s, 2H), 3.45 (br s, 2H), 3.34 (t, J=8.0 Hz, 2H), 1.60-1.54 (m, 2H), 1.39-1.21 (m, 6H), 0.95-0.78 (m, 6H), 0.76 (t, J=8.0 Hz, 2H), −0.06 (s, 9H); MS(ESI⁺) m/z 622.2 (M+H)⁺.

Intermediate 271E

3-Benzyl 1-methyl 4-(4-(dibutylcarbamoyl)-1H-imidazol-2-yl)isophthalate

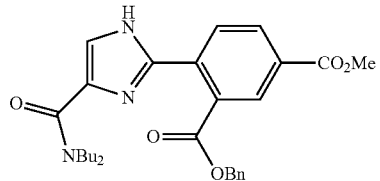

(Int-271E)

Following a procedure analogous to that for the synthesis of Intermediate 264J, 3-benzyl 1-methyl 4-(4-(dibutylcarbamoyl)-1-((2-(trimethylsilyl)ethoxy)methyl)-1H-imidazol-2-yl)isophthalate (900 mg, 1.44 mmol) was converted to the title compound (586 mg, 82%, light yellow oil). ¹H NMR (CD₃OD) δ 8.55 (s, 1H), 8.30 (dd, J=8.0, 1.6 Hz, 1H), 7.84 (d, J=8.0 Hz, 1H), 7.63 (s, 1H), 7.35-7.29 (m, 5H), 5.27 (s, 2H), 3.98 (s, 3H), 3.78 (br s, 2H), 3.50 (br s, 2H), 1.67-1.62 (m, 4H), 1.40-1.30 (m, 4H), 0.97-0.93 (m, 6H); MS(ESI⁺) m/z 492.2 (M+H)⁺.

Intermediate 271F

3-Benzyl 1-methyl 4-(4-(dibutylcarbamoyl)-1-phenethyl-1H-imidazol-2-yl)isophthalate

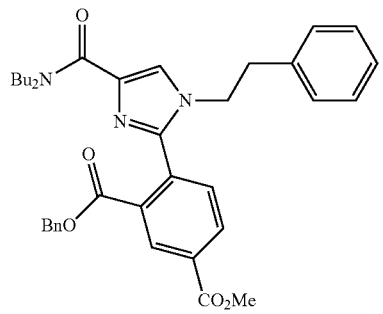

(Int-271F)

To a stirred solution of 3-benzyl 1-methyl 4-(4-(dibutylcarbamoyl)-1H-imidazol-2-yl)isophthalate (200 mg, 0.4 mmol) in dry DMF (5 mL) was added K₂CO₃ (168 mg, 1.22 mmol) and 2-phenethyl bromide (90 mg, 0.48 mmol) at 0° C. The mixture was allowed to warm to room temperature and stirred for 48 h. The reaction mixture was then cooled to 0° C., diluted with MTBE and quenched with water. The layers were separated and the aqueous layer was extracted with MTBE (3×). The combined organic layers were dried over Na₂SO₄, filtered and concentrated in vacuo to give a crude oil. The crude material was purified by flash chromatography (gradient from 10% to 50% EtOAc/hexanes) to provide the title compound (175 mg, 72%). ¹H NMR (CDCl₃) 8.65 (d, J=2.0 Hz, 1H), 8.06 (dd, J=8.0, 2.0 Hz, 1H), 7.53 (s, 1H), 7.36-7.34 (m, 3H), 7.25-7.17 (m, 5H), 6.90 (d, J=8.0 Hz, 1H), 6.81-6.79 (m, 2H), 5.14 (s, 2H), 3.99 (s, 3H), 3.97-3.95 (m, 2H), 3.67 (t, J=7.2 Hz, 2H), 3.50 (br s, 2H), 2.76 (t, J=7.2 Hz, 2H), 1.70-1.60 (m, 4H), 1.40-1.20 (m, 4H), 0.98-0.84 (m, 6H); MS(ESI⁺) m/z 596.2 (M+H)⁺.

Intermediate 271G 2-(4-(Dibutylcarbamoyl)-1-phenethyl-1H-imidazol-2-yl)-5-(methoxycarbonyl)benzoic acid

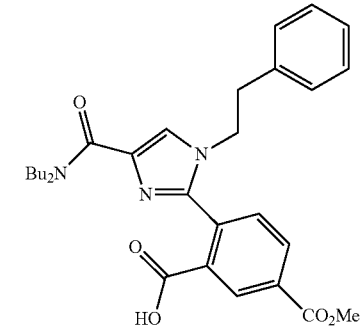

(Int-271G)

To a solution of 3-benzyl 1-methyl 4-(4-(dibutylcarbamoyl)-1-phenethyl-1H-imidazol-2-yl)isophthalate (170 mg, 0.28 mmol) in MeOH (5.0 mL) was added Pd/C (10%). The reaction mixture was stirred under H₂ atmosphere for 2 h. The reaction mixture was then filtered through a small pad of CELITE®, washing thoroughly with MeOH. The filtrate was concentrated in vacuo to provide the title compound (133 mg, 92%), which was used without further purification. MS(ESI⁺) m/z 506.2 (M+H)⁺.

Intermediate 271H

Methyl 4-(4-(dibutylcarbamoyl)-1-phenethyl-1H-imidazol-2-yl)-3-((S)-3-(hydroxymethyl)-1,2,3,4-tetrahydroisoquinoline-2-carbonyl)benzoate (Int-271H)

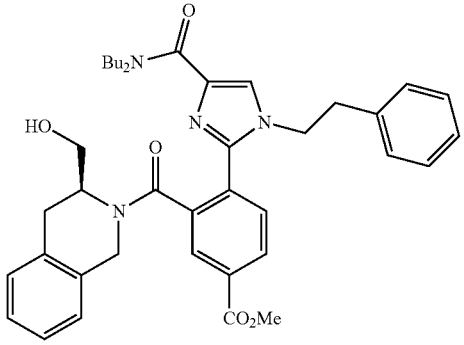

To a solution of 2-(4-(dibutylcarbamoyl)-1-phenethyl-1H-imidazol-2-yl)-5-(methoxycarbonyl)benzoic acid (130 mg, 0.25 mmol) in DMF (5 mL) was added HATU (293 mg, 0.77 mmol), (S)-1,2,3,4-tetrahydroisoquinoline-3-yl-methanol (84 mg, 0.51 mmol) and diisopropylethylamine (269 μL, 1.54 mmol) at 0° C. The reaction mixture was allowed to warm to room temperature and stirred for 16 h. The reaction mixture was diluted with water and extracted with MTBE (3×). The combined organic layer was dried over Na₂SO₄ and concentrated to give crude product. The crude material was purified by flash chromatography (gradient from 0% to 50% EtOAc/hexanes) to provide the title compound (113 mg, 61%) as a light yellow oil. ¹H NMR (DMSO-d₆, 1:1 mixture amide rotamers) δ 8.14-8.01 (m, 2H), 7.64 (s, 1H), 7.34 (d, J=7.2 Hz, 1H), 7.26-7.21 (m, 3H), 7.17-7.03 (m, 5.5H), 6.98 (d, J=6.8 Hz, 0.5H), 5.03 (d, J=18.4 Hz, 0.5H), 4.91 (br s, 1H), 4.39 (br s, 0.5H), 4.24 (d, J=18.4 Hz, 0.5H), 4.16-4.07 (m, 2.5H), 3.91 (s, 3H), 3.88-3.85 (m, 0.5H), 3.76-3.73 (m, 0.5H), 3.65-3.55 (m, 1H), 3.39-3.34 (m, 2H), 3.24-3.00 (m, 2H), 2.96-2.85 (m, 3H), 2.70-2.65 (m, 2H), 1.50-1.11 (m, 8H), 0.88-0.76 (m, 6H); MS(ESI⁺) m/z 651.4 (M+H)⁺.

Intermediate 271I 4-(4-(Dibutylcarbamoyl)-1-phenethyl-1H-imidazol-2-yl)-3-((S)-3-(hydroxymethyl)-1,2,3,4-tetrahydroisoquinoline-2-carbonyl)benzoic acid (Int-271I)

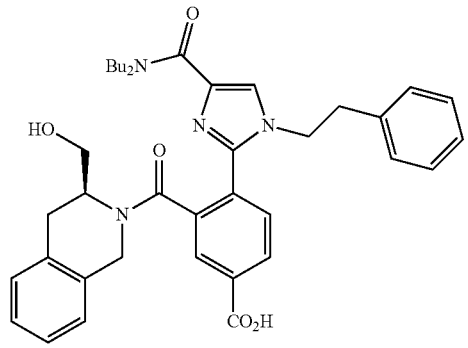

To a solution of methyl 4-(4-(dibutylcarbamoyl)-1-phenethyl-1H-imidazol-2-yl)-3-((S)-3-(hydroxymethyl)-1,2,3,4-tetrahydroisoquinoline-2-carbonyl)benzoate (110 mg, 0.169 mmol) in mixed solvents (2:2:1 THF/MeOH/H₂O, 5.0 mL) was treated with LiOH H₂O (21 mg, 0.507 mmol) at 0° C. The reaction mixture was allowed to warm to room temperature over 30 min and stirring was continued for 1 h. The reaction mixture was concentrated to give crude product, which was diluted with water and extracted with MTBE. The aqueous layer was neutralized with 0.5N HCl and extracted with DCM (3×). The combined organic layers were dried over Na₂SO₄ and concentrated in vacuo to give the title product (100 mg, 91%), which was used without purification. MS(ESI⁺) m/z 637.2 (M+H)⁺.

Example 271

To a solution of 4-(4-(dibutylcarbamoyl)-1-phenethyl-1H-imidazol-2-yl)-3-((S)-3-(hydroxymethyl)-1,2,3,4-tetrahydroisoquinoline-2-carbonyl)benzoic acid (100 mg, 0.16 mmol) in dry DMF (8 mL) was added EDC (90 mg, 0.48 mmol), 8-chloronaphthalene-2-sulfonamide (Intermediate 5, 76 mg, 0.32 mmol) and DMAP (28 mg, 0.24 mmol) at 0° C. The reaction mixture was allowed to warm to room temperature and stirred for 16 h. The reaction mixture was concentrated in vacuo, dissolved in water and extracted with EtOAc (3×). The combined organic layers were dried over Na₂SO₄ and concentrated in vacuo to afford crude product. The crude material was purified by preparative HPLC to provide the title compound (27 mg, 20%). ¹H NMR (CD₃OD, 1:1 mixture of amide rotamers) δ 9.02 (s, 1H), 8.17-8.00 (m, 4H), 7.95 (d, J=8.0 Hz, 1H), 7.78 (d, J=8.0 Hz, 1H), 7.61-7.57 (m, 1H), 7.50 (s, 1H), 7.23-6.89 (m, 10H), 5.11 (d, J=18.0 Hz, 0.5H), 4.70-4.38 (m, 1H), 4.30 (d, J=18.0 Hz, 0.5H), 4.20-3.95 (m, 3H), 3.63-3.51 (m, 1H), 3.48-3.39 (m, 2H), 3.28-3.21 (m, 1H), 3.18-3.11 (m, 1H), 3.02-2.97 (m, 2.5H), 2.88-2.78 (m, 2.5H), 1.60-1.10 (m, 8H), 1.00-0.80 (m, 6H); MS(ESI⁺) m/z 861.2 (M+H)⁺.

Example 272

N,N-Dibutyl-2-(4-(8-chloronaphthalen-2-ylsulfonylcarbamoyl)-2-((S)-3-(hydroxymethyl)-1,2,3,4-tetrahydroisoquinoline-2-carbonyl)phenyl)-1-(3-phenylpropyl)-1H-imidazole-4-carboxamide (272)

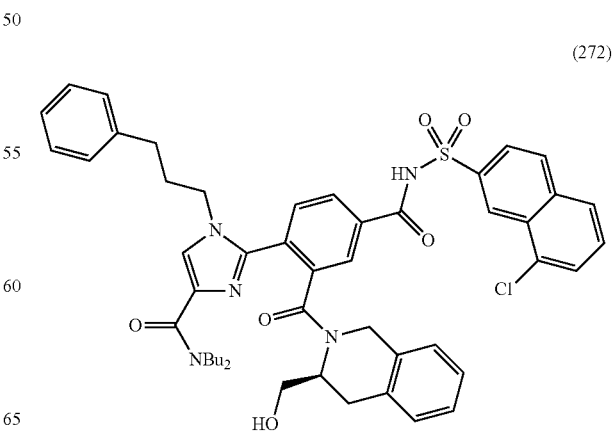

Intermediate 272A

3-Benzyl 1-methyl 4-(4-(dibutylcarbamoyl)-1-(3-phenylpropyl)-1H-imidazol-2-yl)isophthalate

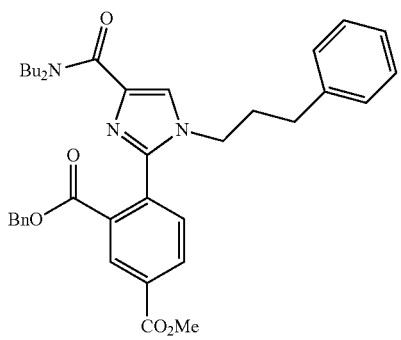
(Int-272A)

Following a procedure analogous to that for the synthesis of Intermediate 271F, 3-benzyl 1-methyl 4-(4-(dibutylcarbamoyl)-1H-imidazol-2-yl)isophthalate (200 mg, 0.4 mmol) and (3-bromopropyl)benzene (97 mg, 0.48 mmol) were converted the title compound (187 mg, 74%). $^1$H NMR (CDCl$_3$) 8.65 (d, J=1.6 Hz, 1H), 8.20 (dd, J=8.0, 1.6 Hz, 1H), 7.53 (s, 1H), 7.43 (d, J=8.0 Hz, 1H), 7.33-7.30 (m, 4H), 7.24-7.14 (m, 4H), 6.94 (d, J=8.0 Hz, 2H), 5.13 (s, 2H), 4.00 (s, 3H), 3.99 (br s, 2H), 3.52 (t, J=7.6 Hz, 2H), 3.46 (br s, 2H), 2.39 (t, J=7.6 Hz, 2H), 1.82-1.78 (m, 2H), 1.55-1.50 (m, 4H), 1.26-1.22 (m, 4H), 0.96-0.83 (m, 6H); MS(ESI$^+$) m/z 610.2 (M+H)$^+$.

Intermediate 272B 2-(4-(Dibutylcarbamoyl)-1-(3-phenylpropyl)-1H-imidazol-2-yl)-5-(methoxycarbonyl)benzoic acid

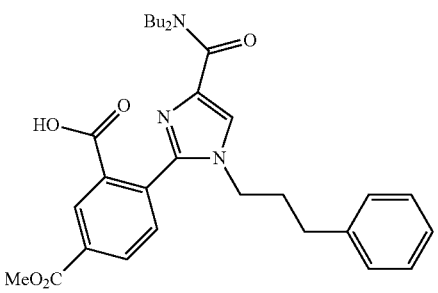
(Int-272B)

Following a procedure analogous to that for the synthesis of Intermediate 271G, 3-benzyl 1-methyl 4-(4-(dibutylcarbamoyl)-1-(3-phenylpropyl)-1H-imidazol-2-yl)isophthalate (180 mg, 0.29 mmol) was converted to the title product (143 mg, 93%). MS (ESI$^+$) m/z 520.2 (M+H)$^+$.

Intermediate 272C

Methyl 4-(4-(dibutylcarbamoyl)-1-(3-phenylpropyl)-1H-imidazol-2-yl)-3-((S)-3-(hydroxymethyl)-1,2,3,4-tetrahydroisoquinoline-2-carbonyl)benzoate

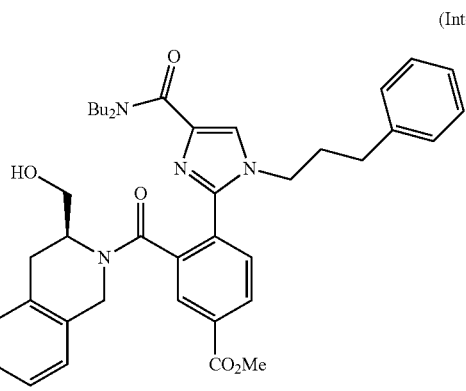
(Int-272C)

Following a procedure analogous to that for the synthesis of Intermediate 271H, 2-(4-(dibutylcarbamoyl)-1-(3-phenylpropyl)-1H-imidazol-2-yl)-5-(methoxycarbonyl)benzoic acid (140 mg, 0.27 mmol) was converted to the title compound (160 mg, 89%). MS(ESI$^+$) m/z 665.4 (M+H)$^+$.

Intermediate 272D 4-(4-(Dibutylcarbamoyl)-1-(3-phenylpropyl)-1H-imidazol-2-yl)-3-((S)-3-(hydroxymethyl)-1,2,3,4-tetrahydroisoquinoline-2-carbonyl)benzoic acid

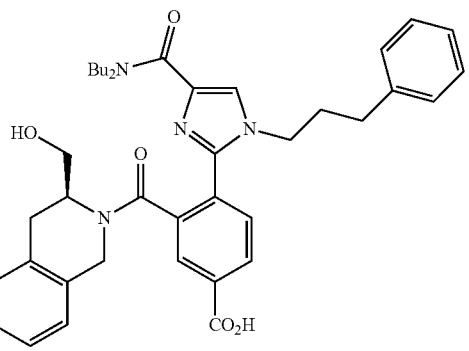
(Int-272D)

Following a procedure analogous to that for the synthesis of Intermediate 271I, methyl 4-(4-(dibutylcarbamoyl)-1-(3-phenylpropyl)-1H-imidazol-2-yl)-3-((S)-3-(hydroxymethyl)-1,2,3,4-tetrahydroisoquinoline-2-carbonyl)benzoate (180 mg, 0.27 mmol) was converted to the title compound (130 mg, 7.3%). MS(ESI$^+$) m/z 651.4 (M+H)$^+$.

Example 272

Following a procedure analogous to that for the synthesis of Example 271, 4-(4-(dibutylcarbamoyl)-1-(3-phenylpropyl)-1H-imidazol-2-yl)-3-((S)-3-(hydroxymethyl)-1,2,3,4-tetrahydroisoquinoline-2-carbonyl)benzoic acid (125 mg, 0.19 mmol) was converted to the title compound (32 mg, 20%). $^1$H NMR (CD$_3$OD, 1:1 mixture of amide rotamers) δ 9.09 (s, 1H), 8.22-7.96 (m, 5H), 7.79 (d, J=7.2 Hz, 1H), 7.66-7.59 (m, 2H), 7.51-7.48 (m, 1H), 7.22-7.02 (m, 8.5H), 6.89 (d, J=7.6 Hz, 0.5H), 5.17 (d, J=18.0 Hz, 0.5H), 4.50 (br s, 1H), 4.33 (d, J=18.0 Hz, 0.5H), 3.99-3.94 (m, 3H), 3.70-3.40 (m, 4H), 3.25-2.85 (m, 3H), 2.57-2.52 (m, 3H), 2.06-2.01 (m, 2H), 1.51-1.10 (m, 8H), 1.02-0.91 (m, 3H), 0.85-0.62 (m, 3H); MS(ESI$^+$) m/z 875.2 (M+H)$^+$.

Example 273

1-Benzyl-N,N-dibutyl-2-(4-(8-chloronaphthalen-2-ylsulfonylcarbamoyl)-2-((S)-3-(hydroxymethyl)-1,2,3,4-tetrahydroisoquinoline-2-carbonyl)phenyl)-1H-imidazole-4-carboxamide

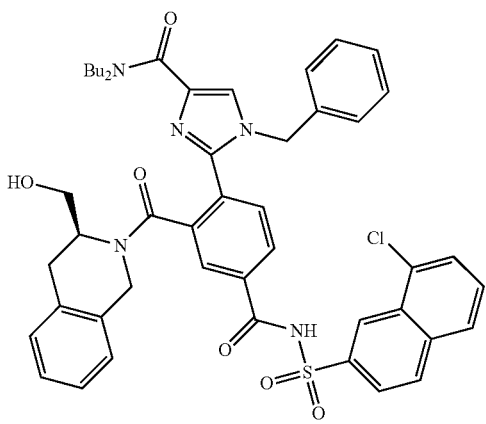

(273)

Intermediate 273A

3-Benzyl 1-methyl 4-(1-benzyl-4-(dibutylcarbamoyl)-1H-imidazol-2-yl)isophthalate

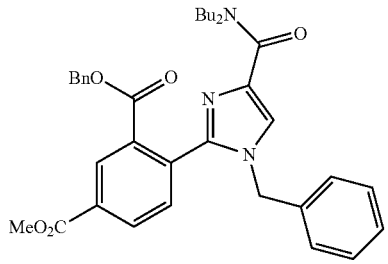

(Int-273A)

Following a procedure analogous to that for the synthesis of Intermediate 271F, 3-benzyl 1-methyl 4-(4-(dibutylcarbamoyl)-1H-imidazol-2-yl)isophthalate (200 mg, 0.40 mmol) and benzylbromide (83 mg, 0.48 mmol) were converted to the title compound (180 mg, 76%). $^1$H NMR (CDCl$_3$) 8.68 (d, J=1.6 Hz, 1H), 8.15 (dd, J=8.0, 2.0 Hz, 1H), 7.43 (s, 1H), 7.39-7.34 (m, 4H), 7.28-7.26 (m, 2H), 7.21-7.17 (m, 3H), 6.90-6.88 (m, 2H), 5.15 (s, 2H), 4.64 (s, 2H), 3.96 (s, 3H), 3.90 (br s, 2H), 3.43 (br s, 2H), 1.70-1.59 (m, 4H), 1.37-1.23 (m, 4H), 0.93-0.82 (m, 6H); MS(ESI$^+$) m/z 582.2 (M+H)$^+$.

Intermediate 273B 2-(1-Benzyl-4-(dibutylcarbamoyl)-1H-imidazol-2-yl)-5-(methoxycarbonyl)benzoic acid

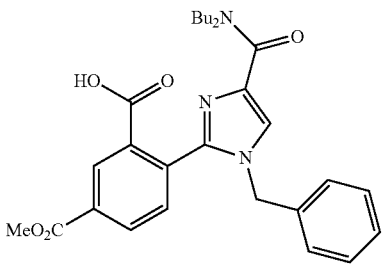

(Int-273B)

To a solution of 3-benzyl 1-methyl 4-(4-(dibutylcarbamoyl)-1-phenethyl-1H-imidazol-2-yl)isophthalate (100 mg, 0.17 mmol) in EtOAc (5 mL) was added Pd/C (10%). The reaction mixture was stirred under H$_2$ atmosphere for 6 h, filtered through a small pad of CELITE® and washed thoroughly with MeOH. The solvents were removed in vacuo to provide the title compound (75 mg, 89%), which was used without further purification. MS(ESI$^+$) m/z 506.2 (M+H)$^+$.

Intermediate 273C

Methyl 4-(1-benzyl-4-(dibutylcarbamoyl)-1H-imidazol-2-yl)-3-((S)-3-(hydroxymethyl)-1,2,3,4-tetrahydroisoquinoline-2-carbonyl)benzoate

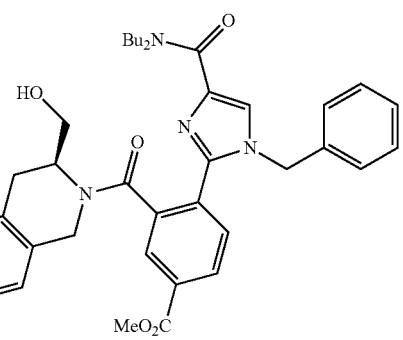

(Int-273C)

Following a procedure analogous to that for the synthesis of Intermediate 271H, 2-(4-(dibutylcarbamoyl)-1-(3-phenylpropyl)-1H-imidazol-2-yl)-5-(methoxycarbonyl)benzoic

Intermediate 273D 4-(1-Benzyl-4-(dibutylcarbamoyl)-1H-imidazol-2-yl)-3-((S)-3-(hydroxymethyl)-1,2,3,4-tetrahydroisoquinoline-2-carbonyl)benzoic acid

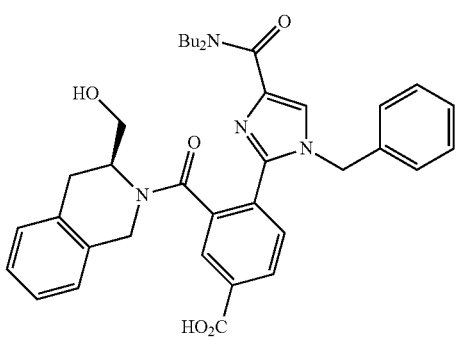
(Int-273D)

Following a procedure analogous to that for the synthesis of Intermediate 271I, methyl 4-(1-benzyl-4-(dibutylcarbamoyl)-1H-imidazol-2-yl)-3-((S)-3-(hydroxymethyl)-1,2,3,4-tetrahydroisoquinoline-2-carbonyl)benzoate (120 mg, 0.27 mmol) was converted to the title compound (130 mg). MS(ESI$^+$) m/z 623.2 (M+H)$^+$.

Example 273

Following a procedure analogous to that for the synthesis of Example 271, 4-(1-benzyl-4-(dibutylcarbamoyl)-1H-imidazol-2-yl)-3-((S)-3-(hydroxymethyl)-1,2,3,4-tetrahydroisoquinoline-2-carbonyl)benzoic acid (125 mg, 0.19 mmol) was converted to the title compound (4 mg, 2%). $^1$H NMR (CD$_3$OD δ 9.06 s, 1H), 8.19-7.97 (m, 5H), 7.78 (d, J=7.2 Hz, 1H), 7.64 (t, J=7.2 Hz, 1H), 7.50-7.44 (m, 2H), 7.32-7.30 (m, 3H), 7.23-6.90 (m, 6H), 5.22-5.19 (m, 2H), 4.47 (br s, 1H), 4.33 (d, J=17.6 Hz, 1H), 4.00-3.95 (m, 1H), 3.70-3.60 (m, 1H), 3.45-3.40 (m, 2H), 3.35-3.25 (m, 3H), 2.95-2.80 (m, 2H), 1.70-1.49 (m, 2H), 1.48-1.10 (m, 6H), 1.00-0.60 (m, 6H); MS(ESI$^-$) m/z 845.1 (M–H)$^-$.

Example 274

N,N-Dibutyl-1-(2-hydroxyethyl)-2-(2-((S)-3-(hydroxymethyl)-1,2,3,4-tetrahydroisoquinoline-2-carbonyl)-4-(naphthalen-2-ylsulfonylcarbamoyl)phenyl)-1H-imidazole-4-carboxamide

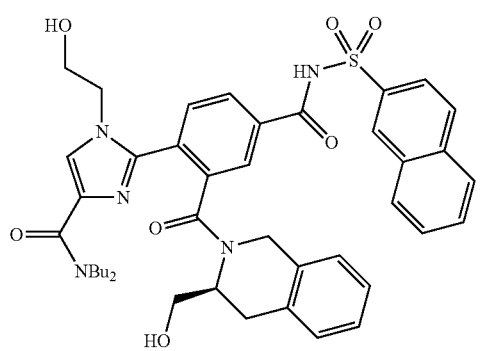
(274)

Intermediate 274A

3-Benzyl 1-methyl 4-(1-(2-(tert-butyldimethylsilyloxy)ethyl)-4-(dibutylcarbamoyl)-1H-imidazol-2-yl)isophthalate

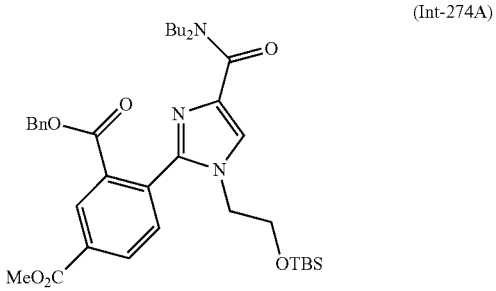
(Int-274A)

To a stirred solution of 3-benzyl 1-methyl 4-(4-(dibutylcarbamoyl)-1H-imidazol-2-yl)isophthalate (190 mg, 0.40 mmol) in dry DMF (5 mL) was added K$_2$CO$_3$ (160 mg, 1.16 mmol) and (2-bromoethoxy)(tert-butyl)dimethylsilane (92 mg, 0.38 mmol) at 0° C. The mixture was allowed to warm to room temperature and heated at 50° C. for 24 h. The reaction mixture was cooled to 0° C., diluted with MTBE and quenched with water. The organic layer was separated and the aqueous layer was extracted with MTBE (3×). The combined organic layer was dried over Na$_2$SO$_4$ and concentrated in vacuo to provide crude product. The crude material was purified by flash chromatography (gradient 10 to 30% ethylacetate/hexane) to provide the title compound (144 mg, 54%). $^1$H NMR (CD$_3$OD) 8.66 (d, J=1.6 Hz, 1H), 8.30 (dd, J=8.0, 2.0 Hz, 1H), 7.70 (d, J=8.0 Hz, 1H), 7.65 (s, 1H), 7.38-7.29 (m, 5H), 5.20 (s, 2H), 3.99 (s, 3H), 3.83-3.82 (m, 2H), 3.77 (t, J=5.0 Hz, 2H), 3.70 (t, J=5.0 Hz, 2H), 3.49 (br s, 2H), 1.70-1.55 (m, 4H), 1.45-1.26 (m, 4H), 1.05-0.85 (m, 6H), 0.83 (s, 9H), 0.03 (s, 6H); MS(ESI$^+$) m/z 650.2 (M+H)$^+$.

Intermediate 274B 2-(1-(2-(tert-Butyldimethylsilyloxy)ethyl)-4-(dibutylcarbamoyl)-1H-imidazol-2-yl)-5-(methoxycarbonyl)benzoic acid

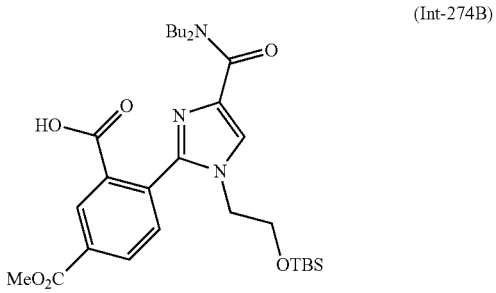
(Int-274B)

Following a procedure analogous to that for the synthesis of Intermediate 273B, 3-benzyl 1-methyl 4-(1-(2-(tert-butyldimethylsilyloxy)ethyl)-4-(dibutylcarbamoyl)-1H-imidazol-2-yl)isophthalate (140 mg, 0.21 mmol) was converted to the title compound (105 mg, 87%). MS(ESI$^+$) m/z 560.2 (M+H)$^+$.

Intermediate 274C

Methyl 4-(1-(2-(tert-butyldimethylsilyloxy)ethyl)-4-(dibutylcarbamoyl)-1H-imidazol-2-yl)-3-((S)-3-((tert-butyldimethylsilyloxy)methyl)-1,2,3,4-tetrahydroisoquinoline-2-carbonyl)benzoate

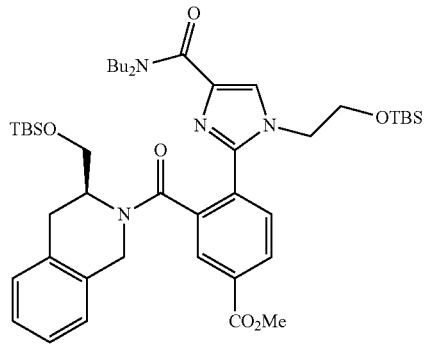
(Int-274C)

Following a procedure analogous to that for the synthesis of Intermediate 271H, 2-(1-(2-(tert-butyldimethylsilyloxy)ethyl)-4-(dibutylcarbamoyl)-1H-imidazol-2-yl)-5-(methoxycarbonyl)benzoic acid (105 mg, 0.19 mmol) and (S)-3-((tert-butyldimethylsilyloxy)methyl)-1,2,3,4-tetrahydroisoquinoline (62 mg, 0.22 mmol) were converted to the title compound (133 mg, 87%). MS(ESI$^+$) m/z 820.2 (M+H)$^+$.

Intermediate 274D 4-(1-(2-(tert-Butyldimethylsilyloxy)ethyl)-4-(dibutylcarbamoyl)-1H-imidazol-2-yl)-3-((S)-3-((tert-butyldimethylsilyloxy)methyl)-1,2,3,4-tetrahydroisoquinoline-2-carbonyl)benzoic acid

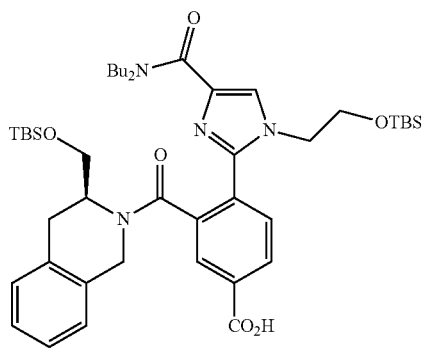
(Int-274D)

Following a procedure analogous to that for the synthesis of Intermediate 271I, methyl 4-(1-(2-(tert-butyldimethylsilyloxy)ethyl)-4-(dibutylcarbamoyl)-1H-imidazol-2-yl)-3-((S)-3-((tert-butyldimethylsilyloxy)methyl)-1,2,3,4-tetrahydroisoquinoline-2-carbonyl)benzoate (130 mg, 0.16 mmol) was converted to the title compound (110 mg, 86%). MS(ESI$^+$) m/z 806.2 (M+H)$^+$.

Intermediate 274E

N,N-Dibutyl-1-(2-(tert-butyldimethylsilyloxy)ethyl)-2-(2-((S)-3-((tert-butyldimethylsilyloxy)methyl)-1,2,3,4-tetrahydroisoquinoline-2-carbonyl)-4-(naphthalen-2-ylsulfonylcarbamoyl)phenyl)-1H-imidazole-4-carboxamide

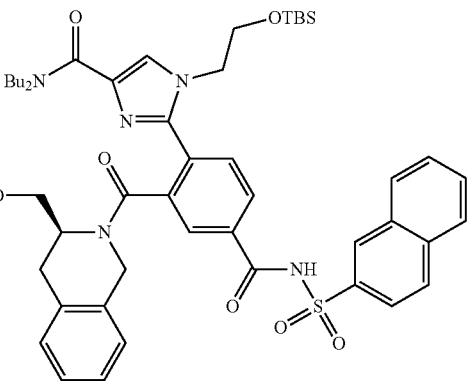
(Int-274E)

Following a procedure analogous to that for the synthesis of Example 271, 4-(1-(2-(tert-butyldimethylsilyloxy)ethyl)-4-(dibutylcarbamoyl)-1H-imidazol-2-yl)-3-((S)-3-((tert-butyldimethylsilyloxy)methyl)-1,2,3,4-tetrahydroisoquinoline-2-carbonyl)benzoic acid (100 mg, 0.12 mmol) was converted to the title compound (50 mg, 41%). MS(ESI$^+$) m/z 995.2 (M+H)$^+$.

Example 274

To a solution of N,N-dibutyl-1-(2-(tert-butyldimethylsilyloxy)ethyl)-2-(2-((S)-3-((tert-butyldimethylsilyloxy)methyl)-1,2,3,4-tetrahydroisoquinoline-2-carbonyl)-4-(naphthalen-2-ylsulfonylcarbamoyl)phenyl)-1H-imidazole-4-carboxamide (50 mg, 0.05 mmol) in THF was added 3 drops of conc. HCl at 0° C. The mixture was allowed to warm to room temperature over 1 h. The reaction mixture was then cooled to 0° C., quenched with MeOH/NH$_3$ and concentrated in vacuo to provide a precipitate. The solid was dissolved in water and extracted with EtOAc (4×). The combined organic layers were dried over Na$_2$SO$_4$ and concentrated in vacuo to give the crude product. The crude material was purified by flash chromatography (gradient from 0% to 15% MeOH (saturated with NH$_3$/CHCl$_3$) to provide the title compound (25 mg, 66%). $^1$H NMR (CD$_3$OD, 1:1 mixture of amide rotamers) δ 8.63 (s, 1H), 8.16-8.14 (m, 1.5H), 8.06-7.94 (m, 4.5H), 7.69-7.59 (m, 4H), 7.20-7.13 (m, 3.5H), 6.95 (d, J=6.8 Hz, 0.5H), 5.15 (d, J=18.0 Hz, 0.5H), 4.60-4.50 (br s, 1H), 4.30 (d, J=18.0 Hz, 0.5H), 4.09-3.71 (m, 7.5H), 3.47-3.38 (m, 2.5H), 3.25-3.17 (m, 1H), 2.93-2.64 (m, 2H), 1.51-1.45 (m, 2H), 1.40-1.10 (m, 6H), 0.97-0.68 (m, 6H); MS(ESI$^+$) m/z 767.0 (M+H)$^+$.

Example 275

N,N-Dibutyl-2-(2-((S)-3-(hydroxymethyl)-1,2,3,4-tetrahydroisoquinoline-2-carbonyl)-4-(naphthalen-2-ylsulfonylcarbamoyl)phenyl)-1-(2-methoxyethyl)-1H-imidazole-4-carboxamide

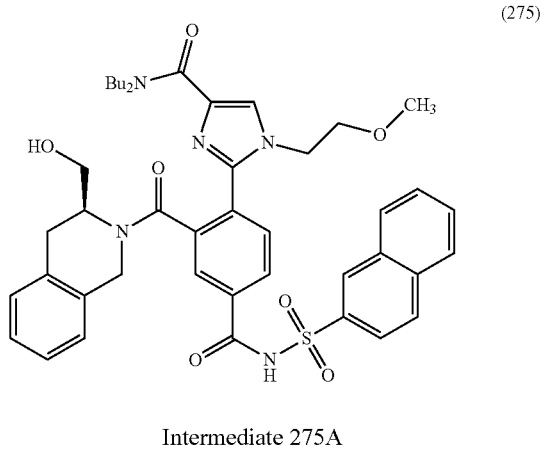

(275)

Intermediate 275A

3-Benzyl 1-methyl 4-(4-(dibutylcarbamoyl)-1-(2-methoxyethyl)-1H-imidazol-2-yl)isophthalate

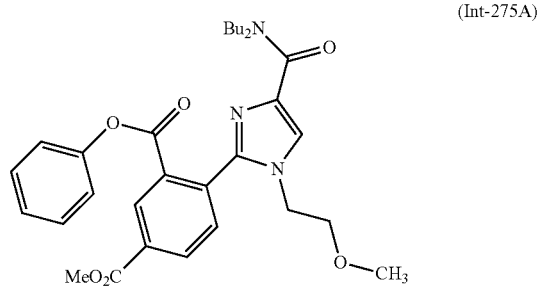

(Int-275A)

Following a procedure analogous to that for the synthesis of Intermediate 274A, 3-benzyl 1-methyl 4-(4-(dibutylcarbamoyl)-1H-imidazol-2-yl)isophthalate (200 mg, 0.40 mmol) and bromoethylmethylether (68 mg, 0.38 mmol) were converted to the title compound (165 mg, 74%). $^1$H NMR (CDCl$_3$) δ 8.67 (d, J=1.6 Hz, 1H), 8.23 (dd, J=8.0, 2.0 Hz, 1H), 7.61 (s, 1H), 7.53 (d, J=8.0 Hz, 1H), 7.35-7.32 (m, 3H), 7.25-7.23 (m, 2H), 5.14 (s, 2H), 3.97 (s, 3H), 3.92-3.85 (m, 2H), 3.67 (t, J=5.4 Hz, 2H), 3.45-3.41 (m, 2H), 3.60 (t, J=5.4 Hz, 2H), 3.17 (s, 3H), 1.70-1.55 (m, 4H), 1.40-1.20 (m, 4H), 0.98-0.82 (m, 6H); MS(ESI$^+$) m/z 550.2 (M+H)$^+$.

Intermediate 275B 2-(4-(Dibutylcarbamoyl)-1-(2-methoxyethyl)-1H-imidazol-2-yl)-5-(methoxycarbonyl)benzoic acid

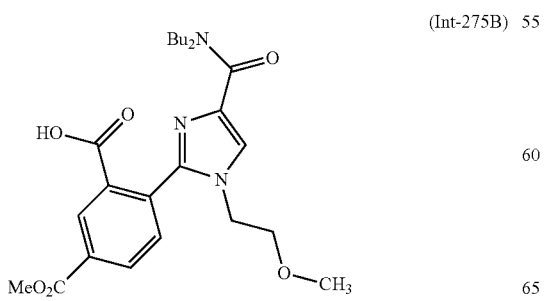

(Int-275B)

Following a procedure analogous to that for the synthesis of Intermediate 271G, 3-benzyl 1-methyl 4-(4-(dibutylcarbamoyl)-1-(2-methoxyethyl)-1H-imidazol-2-yl)isophthalate (165 mg, 0.30 mmol) was converted to the title compound (125 mg, 91%). MS (ESI$^+$) m/z 460.2 (M+H)$^+$.

Intermediate 275C

Methyl 4-(4-(dibutylcarbamoyl)-1-(2-methoxyethyl)-1H-imidazol-2-yl)-3-((S)-3-(hydroxymethyl)-1,2,3,4-tetrahydroisoquinoline-2-carbonyl)benzoate

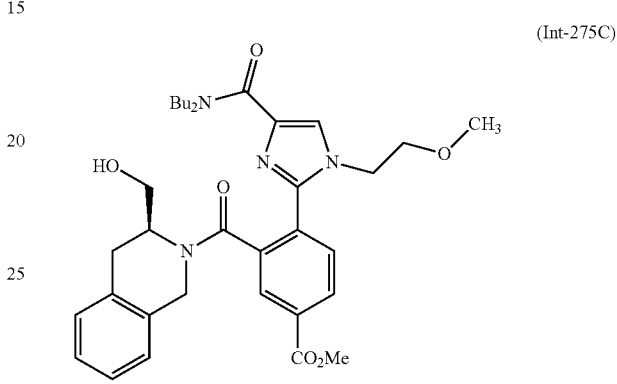

(Int-275C)

Following a procedure analogous to that for the synthesis of Intermediate 271H, 2-(4-(dibutylcarbamoyl)-1-(2-methoxyethyl)-1H-imidazol-2-yl)-5-(methoxycarbonyl)benzoic acid (120 mg, 0.26 mmol) was converted to the title compound (110 mg, 62%). MS(ESI$^+$) m/z 605.2 (M+H)$^+$.

Intermediate 275D 4-(4-(Dibutylcarbamoyl)-1-(2-methoxyethyl)-1H-imidazol-2-yl)-3-((S)-3-(hydroxymethyl)-1,2,3,4-tetrahydroisoquinoline-2-carbonyl)benzoic acid

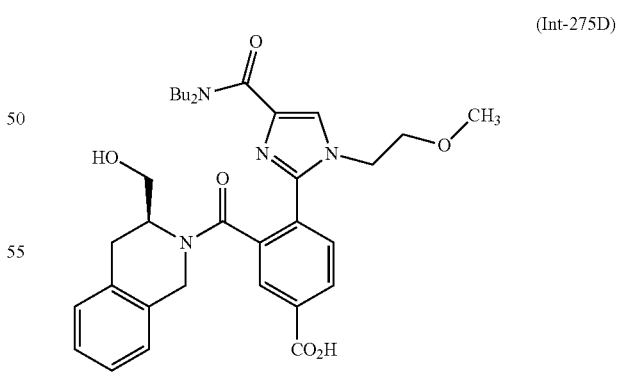

(Int-275D)

Following a procedure analogous to that for the synthesis of Intermediate 271I, methyl 4-(4-(dibutylcarbamoyl)-1-(2-methoxyethyl)-1H-imidazol-2-yl)-3-((S)-3-(hydroxymethyl)-1,2,3,4-tetrahydroisoquinoline-2-carbonyl)benzoate (110 mg, 0.18 mmol) was converted to the title product (90 mg, 84%). MS(ESI$^+$) m/z 591.4 (M+H)$^+$.

Example 275

Following a procedure analogous to that for the synthesis of Example 271, 4-(4-(dibutylcarbamoyl)-1-(2-methoxyethyl)-1H-imidazol-2-yl)-3-((S)-3-(hydroxymethyl)-1,2,3,4-tetrahydroisoquinoline-2-carbonyl)benzoic acid (90 mg, 0.152 mmol) was converted to the title product (6 mg, 5%). $^1$H NMR (CD$_3$OD, 1:1 mixture of amide rotamers) δ 8.59 (s, 1H), 8.21-8.17 (m, 2H), 8.06-8.02 (m, 2H), 7.97-7.92 (m, 2H), 7.63-7.57 (m, 4H), 7.20-7.13 (m, 3.5H), 6.94 (d, J=6.8 Hz, 0.5H), 5.15 (d, J=18.4 Hz, 0.5H), 4.58 (s, 0.5H), 4.50 (br s, 1H), 4.31 (d, J=18.4 Hz, 1H), 4.18-4.09 (m, 3H), 3.65-3.43 (m, 6H), 3.30 (s, 3H), 3.16-2.51 (m, 3H); 1.53-1.14 (m, 8H), 0.97-0.73 (m, 6H); MS (ESI$^+$) m/z 781.2 (M+H)$^+$.

Example 276

N,N-Dibutyl-1-(2-(2-hydroxyethoxy)ethyl)-2-(2-((S)-3-(hydroxymethyl)-1,2,3,4-tetrahydroisoquinoline-2-carbonyl)-4-(naphthalen-2-ylsulfonylcarbamoyl)phenyl)-1H-imidazole-4-carboxamide (276)

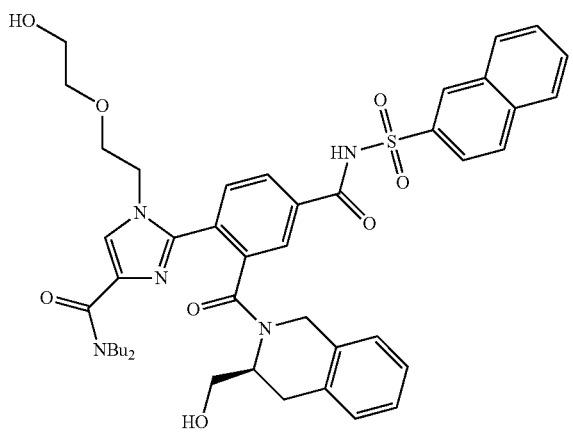

Intermediate 276A

3-Benzyl 1-methyl 4-(1-(2-(2-(tert-butyldiphenylsilyloxy)ethoxy)ethyl)-4-(dibutylcarbamoyl)-1H-imidazol-2-yl)isophthalate (Int-276A)

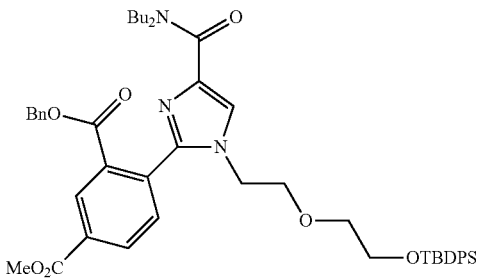

Following a procedure analogous to that for the synthesis of Intermediate 274A, 3-benzyl 1-methyl 4-(4-(dibutylcarbamoyl)-1H-imidazol-2-yl)isophthalate (200 mg, 0.40 mmol) and (2-(2-bromoethoxy)ethoxy)(tert-butyl)diphenylsilane (165 mg, 0.40 mmol) were converted to the title compound (280 mg, 84%). $^1$H NMR (CDCl$_3$) δ 8.66 (d, J=2.0 Hz, 1H), 8.16 (dd, J=8.0, 2.0 Hz, 1H), 7.62-7.57 (m, 4H), 7.57 (s, 1H), 7.52 (d, J=8.0 Hz, 1H), 7.42-7.32 (m, 9H), 7.24-7.22 (m, 2H), 5.12 (s, 2H), 3.96 (s, 3H), 3.94-3.85 (m, 2H), 3.69-3.63 (m, 4H), 3.46-3.43 (m, 4H), 3.67 (t, J=5.2 Hz, 2H), 1.65-1.55 (m, 4H), 1.40-1.15 (m, 4H), 1.01 (s, 9H), 1.00-0.85 (m, 6H); MS(ESI$^+$) m/z 819.4 (M+H)$^+$.

Intermediate 276B 2-(1-(2-(2-(tert-Butyldiphenylsilyloxy)ethoxy)ethyl)-4-(dibutylcarbamoyl)-1H-imidazol-2-yl)-5-(methoxycarbonyl)benzoic acid (Int-276B)

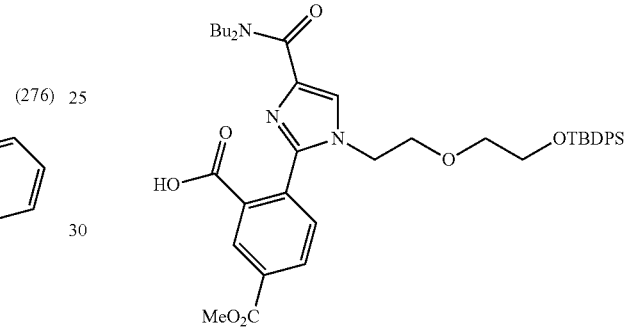

Following a procedure analogous to that for the synthesis of Intermediate 271G, 3-benzyl 1-methyl 4-(1-(2-(2-(tert-butyldiphenylsilyloxy)ethoxy)ethyl)-4-(dibutylcarbamoyl)-1H-imidazol-2-yl)isophthalate (280 mg, 0.34 mmol) was converted to the title compound. (126 mg, 51%). MS(ESI$^+$) m/z 728 (M+H)$^+$.

Intermediate 276C

Methyl 3-((S)-3-((tert-butyldimethylsilyloxy)methyl)-1,2,3,4-tetrahydroisoquinoline-2-carbonyl)-4-(1-(2-(2-(tert-butyldiphenylsilyloxy)ethoxy)ethyl)-4-(dibutylcarbamoyl)-1H-imidazol-2-yl)benzoate (Int-276C)

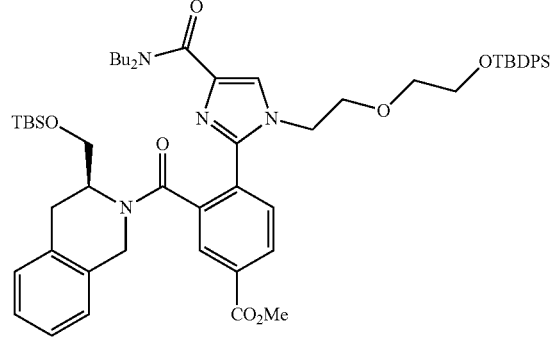

Following a procedure analogous to that for the synthesis of Intermediate 271H, 2-(1-(2-(2-(tert-butyldiphenylsilyloxy)ethoxy)ethyl)-4-(dibutylcarbamoyl)-1H-imidazol-2-yl)-5-(methoxycarbonyl)benzoic acid (126 mg, 0.17 mmol) was converted to the title compound (140 mg, 81%). MS(ESI+) m/z 988.4 (M+H)+.

Intermediate 276D 3-((S)-3-((tert-Butyldimethylsilyloxy)methyl)-1,2,3,4-tetrahydroisoquinoline-2-carbonyl)-4-(1-(2-(2-(tert-butyldiphenylsilyloxy)ethoxy)ethyl)-4-(dibutylcarbamoyl)-1H-imidazol-2-yl)benzoic acid

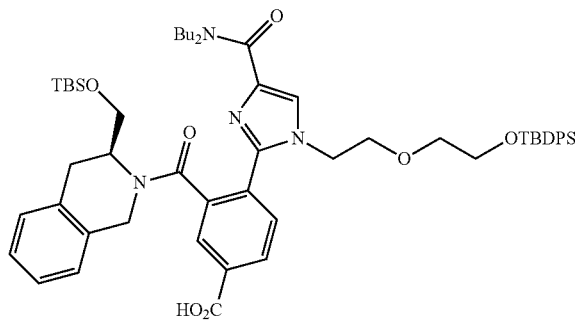

(Int-276D)

Following a procedure analogous to that for the synthesis of Intermediate 271I, methyl 3-((S)-3-((tert-butyldimethylsilyloxy)methyl)-1,2,3,4-tetrahydroisoquinoline-2-carbonyl)-4-(1-(2-(2-(tert-butyldiphenylsilyloxy)ethoxy)ethyl)-4-(dibutylcarbamoyl)-1H-imidazol-2-yl)benzoate (140 mg, 0.14 mmol) was converted to the title compound (120 mg, 87%). MS(ESI+) m/z 974.4 (M+H)+.

Intermediate 276E

N,N-Dibutyl-2-(2-((S)-3-((tert-butyldimethylsilyloxy)methyl)-1,2,3,4-tetrahydroisoquinoline-2-carbonyl)-4-(naphthalen-2-ylsulfonylcarbamoyl)phenyl)-1-(2-(2-(tert-butyldiphenylsilyloxy)ethoxy)ethyl)-1H-imidazole-4-carboxamide

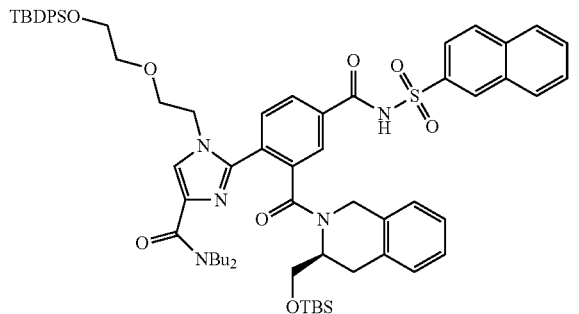

(Int-276E)

Following a procedure analogous to that for the synthesis of Example 271, 3-((S)-3-((tert-butyldimethylsilyloxy)methyl)-1,2,3,4-tetrahydroisoquinoline-2-carbonyl)-4-(1-(2-(2-(tert-butyldiphenylsilyloxy)ethoxy)ethyl)-4-(dibutylcarbamoyl)-1H-imidazol-2-yl)benzoic acid (120 mg, 0.12 mmol) was converted to the title compound (60 mg, 42%). MS (ESI+) m/z 1163.2 (M+H)+.

Example 276

To a solution of N,N-dibutyl-2-(2-((S)-3-((tert-butyldimethylsilyloxy)methyl)-1,2,3,4-tetrahydroisoquinoline-2-carbonyl)-4-(naphthalen-2-ylsulfonylcarbamoyl)phenyl)-1-(2-(2-(tert-butyldiphenylsilyloxy)ethoxy)ethyl)-1H-imidazole-4-carboxamide (60 mg, 0.05 mmol) in THF (3.0 mL) was added tetrabutylammonium fluoride (153 µL, 0.15 mmol, 1.0M in THF) at 0° C. The reaction mixture was allowed to warm to room temperature over 30 min and then stirred for 30 min. The reaction mixture was then quenched with sat. NH4Cl solution and extracted with DCM (5×). The combined organic layers were dried over Na2SO4 and concentrated in vacuo to give the crude compound, which was dissolved in MeOH and treated with DOWEX® (H+) resin. The mixture was filtered, concentrated in vacuo and purified using preparative TLC (15% MeOH (saturated with NH3)/CHCl3 to provide the title compound (13 mg, 31%). 1H NMR (CD3OD, 1:1 mixture of amide rotamers) δ 8.58 (s, 1H), 8.21-8.17 (m, 2H), 8.05-8.01 (m, 2H), 7.96-7.91 (m, 2H), 7.74-7.56 (m, 4H), 7.20-7.13 (m, 3.5H), 6.95 (d, J=8.0 Hz, 0.5H), 5.15 (d, J=18.0 Hz, 0.5H), 4.68-4.45 (m, 8H), 4.30 (d, J=18.0 Hz, 0.5H), 4.15-4.10 (m, 2H), 3.72-3.71 (m, 2.5H), 3.63-3.61 (m, 2.5H), 3.50-3.47 (m, 1H) 2.98-2.85 (m, 2H), 1.51-1.42 (m, 2H), 1.35-1.10 (m, 6H), 0.96-0.65 (m, 6H); MS(ESI+) m/z 811.0 (M+H)+.

Example 277

N,N-Dibutyl-2-(2-((S)-3-(hydroxymethyl)-1,2,3,4-tetrahydroisoquinoline-2-carbonyl)-4-(naphthalen-2-ylsulfonylcarbamoyl)phenyl)-1-(2-morpholinoethyl)-1H-imidazole-4-carboxamide (277)

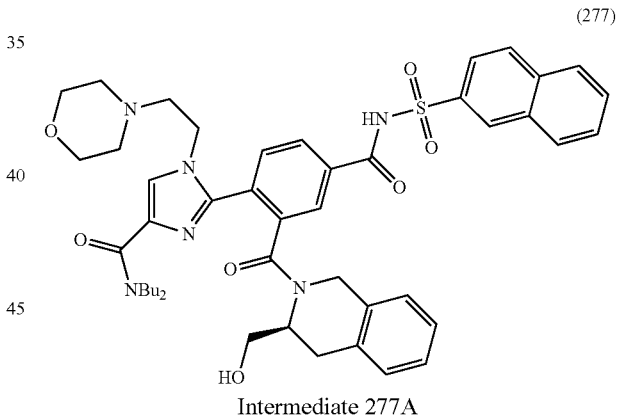

Intermediate 277A

3-Benzyl 1-methyl 4-(4-(dibutylcarbamoyl)-1-(2-morpholinoethyl)-1H-imidazol-2-yl)isophthalate (Int-277A)

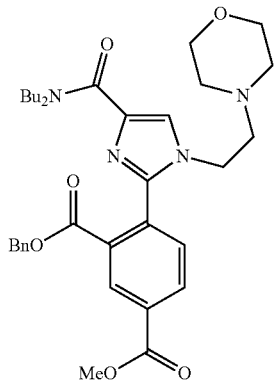

Following a procedure analogous to that for the synthesis of Intermediate 274A, 3-benzyl 1-methyl 4-(4-(dibutylcarbamoyl)-1H-imidazol-2-yl)isophthalate (280 mg, 0.57 mmol) and 4-(2-chloroethyl)morpholine hydrochloride (106 mg, 0.57 mmol) were converted to the title compound (240 mg, 70%). ¹H NMR (CDCl₃) δ 8.68 (d, J=1.6 Hz, 1H), 8.23 (dd, J=8.0, 1.6 Hz, 1H), 7.62 (s, 1H), 7.53 (d, J=8.0 Hz, 1H), 7.36-7.32 (m, 3H), 7.25-7.23 (m, 2H), 5.14 (s, 2H), 3.97 (s, 3H), 3.92 (br s, 2H), 3.60-3.54 (m, 6H), 3.45 (br s, 2H), 2.37 (t, J=6.4 Hz, 2H), 2.20-2.18 (m, 4H), 1.63-1.56 (m, 4H), 1.38-1.22 (m, 4H), 0.95-0.82 (m, 6H); MS(ESI⁺) m/z 605.4 (M+H)⁺.

Intermediate 277B 2-(4-(Dibutylcarbamoyl)-1-(2-morpholinoethyl)-1H-imidazol-2-yl)-5-(methoxycarbonyl)benzoic acid

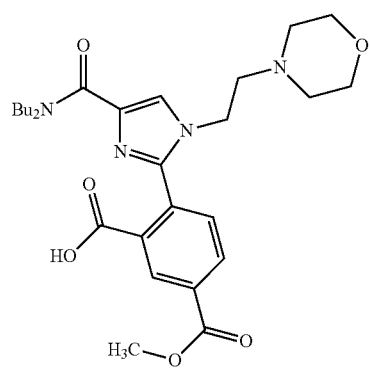

(Int-277B)

Following a procedure analogous to that for the synthesis of Intermediate 271G, 3-benzyl 1-methyl 4-(4-(dibutylcarbamoyl)-1-(2-morpholinoethyl)-1H-imidazol-2-yl)isophthalate (230 mg, 0.38 mmol) was converted to the title compound (186 mg, 95%). ¹H NMR (CD₃OD) δ 8.60 (d, J=1.6 Hz, 1H), 8.23 (dd, J=8.0, 2.0 Hz, 1H), 7.77 (s, 1H), 7.63 (d, J=8.0 Hz, 1H), 4.10 (t, J=6.0 Hz, 2H), 3.99 (s, 3H), 3.86 (br s, 2H), 3.64-3.62 (m, 4H), 3.50-3.48 (m, 2H), 2.89-2.86 (m, 2H), 2.51-2.49 (m, 4H), 1.66-1.62 (m, 4H), 1.40-1.27 (m, 4H), 0.99-0.89 (m, 6H); MS(ESI⁺) m/z 515.2 (M+H)⁺.

Intermediate 277C

Methyl 4-(4-(dibutylcarbamoyl)-1-(2-morpholinoethyl)-1H-imidazol-2-yl)-3-((S)-3-(hydroxymethyl)-1,2,3,4-tetrahydroisoquinoline-2-carbonyl)benzoate

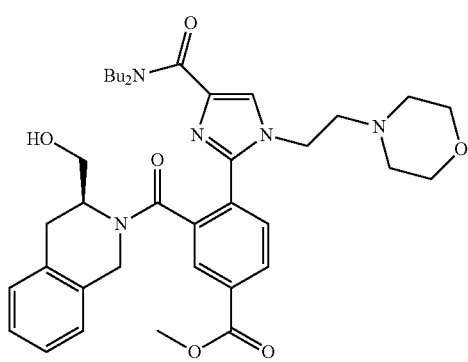

(Int-277C)

Following a procedure analogous to that for the synthesis of Intermediate 271H, 2-(4-(dibutylcarbamoyl)-1-(2-morpholinoethyl)-1H-imidazol-2-yl)-5-(methoxycarbonyl)benzoic acid (186 mg, 0.36 mmol) was converted to the title compound (225 mg, 94%). ¹H NMR (CDCl₃, 1:1 mixture of amide rotamers) δ 8.21-8.16 (m, 1H), 8.04 (d, J=6.4 Hz, 1H), 7.64-7.53 (m, 2H), 7.21-7.10 (m, 3.5H), 6.86 (d, J=7.2 Hz, 0.5H), 5.81 (br s, 0.5H), 5.34 (d, J=16.0 Hz, 0.5H), 4.90-4.86 (m, 0.5H), 4.42-4.24 (m, 2H), 4.04-3.95 (m, 5.5H), 3.68-3.62 (m, 6H), 3.38-3.30 (m, 2H), 3.24-3.19 (m, 1H), 2.74-2.67 (m, 3H), 2.44-2.43 (m, 5H), 1.60-1.56 (m, 4H), 1.31-1.26 (m, 4H), 0.91-0.87 (m, 6H); MS(ESI⁺) m/z 661.4 (M+H)⁺.

Intermediate 277D 4-(4-(Dibutylcarbamoyl)-1-(2-morpholinoethyl)-1H-imidazol-2-yl)-3-((S)-3-(hydroxymethyl)-1,2,3,4-tetrahydroisoquinoline-2-carbonyl)benzoic acid

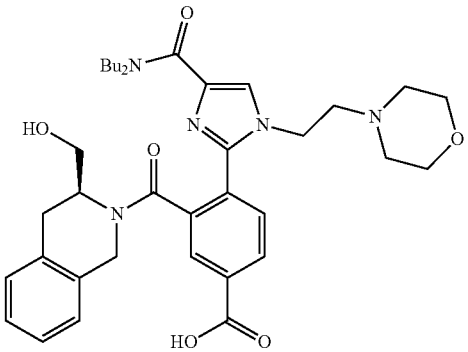

(Int-277D)

Following a procedure analogous to that for the synthesis of Intermediate 271I, methyl 4-(4-(dibutylcarbamoyl)-1-(2-morpholinoethyl)-1H-imidazol-2-yl)-3-((S)-3-(hydroxymethyl)-1,2,3,4-tetrahydroisoquinoline-2-carbonyl)benzoate (225 mg, 0.34 mmol) was converted to the title compound (210 mg, 95%). MS(ESI⁺) m/z 646.4 (M+H)⁺.

Example 277

Following a procedure analogous to that for the synthesis of Example 271, 4-(4-(dibutylcarbamoyl)-1-(2-morpholinoethyl)-1H-imidazol-2-yl)-3-((S)-3-(hydroxymethyl)-1,2,3,4-tetrahydroisoquinoline-2-carbonyl)benzoic acid (200 mg, 0.31 mmol) was converted to the title compound (34 mg, 13%). ¹H NMR (CD₃OD, 1:1 mixture of amide rotamers) δ 8.59 (s, 1H), 8.22-8.10 (m, 2H), 8.06-8.01 (m, 2H), 7.96-7.92 (m, 2H), 7.73-7.56 (m, 4H), 7.20-7.10 (m, 3.5H), 6.94 (d, J=7.6 Hz, 0.5H), 5.14 (d, J=19.2 Hz, 0.5H), 4.75-4.50 (m, 2H), 4.31 (d, J=18.4 Hz, 0.5H), 4.08-4.02 (m, 3H), 3.63-3.61 (m, 5.5H), 3.55-3.40 (m, 2.5H), 2.95-2.60 (m, 5H), 2.49-2.38 (m, 4H), 1.52-1.11 (m, 8H), 0.96-0.71 (m, 6H); MS(ESI⁺) m/z 836.4 (M+H)⁺.

Example 278

N,N-Dibutyl-2-(2-((S)-3-(hydroxymethyl)-1,2,3,4-tetrahydroisoquinoline-2-carbonyl)-4-(naphthalen-2-ylsulfonylcarbamoyl)phenyl)-1-(3-morpholinopropyl)-1H-imidazole-4-carboxamide

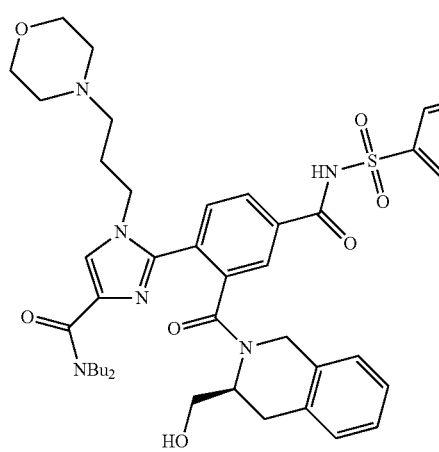

(278)

Intermediate 278A

3-Benzyl 1-methyl 4-(4-(dibutylcarbamoyl)-1-(3-morpholinopropyl)-1H-imidazol-2-yl)isophthalate

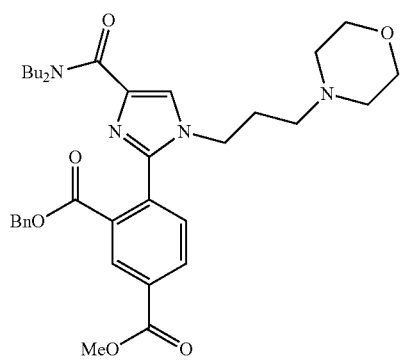

(Int-278A)

Following a procedure analogous to that for the synthesis of Intermediate 274A, 3-benzyl 1-methyl 4-(4-(dibutylcarbamoyl)-1H-imidazol-2-yl)isophthalate (130 mg, 0.26 mmol) and 4-(3-chloropropyl)morpholine (53 mg, 0.27 mmol) were converted to the title compound. (65 mg, 40%). $^1$H NMR (CD$_3$OD) δ 8.67 (d, J=2.0 Hz, 1H), 8.33 (dd, J=8.0, 1.6 Hz, 1H), 7.70 (d, J=8.0 Hz, 1H), 7.62 (s, 1H), 7.38-7.32 (m, 5H), 5.21 (s, 2H), 4.01 (s, 3H), 3.84-3.80 (m, 4H), 3.59-3.50 (m, 6H), 2.20-2.11 (m, 6H), 1.70-1.60 (m, 6H), 1.45-1.25 (m, 4H), 1.05-0.82 (m, 6H); MS(ESI$^+$) m/z 619 (M+H)$^+$.

Intermediate 278B 2-(4-(Dibutylcarbamoyl)-1-(3-morpholinopropyl)-1H-imidazol-2-yl)-5-(methoxycarbonyl)benzoic acid

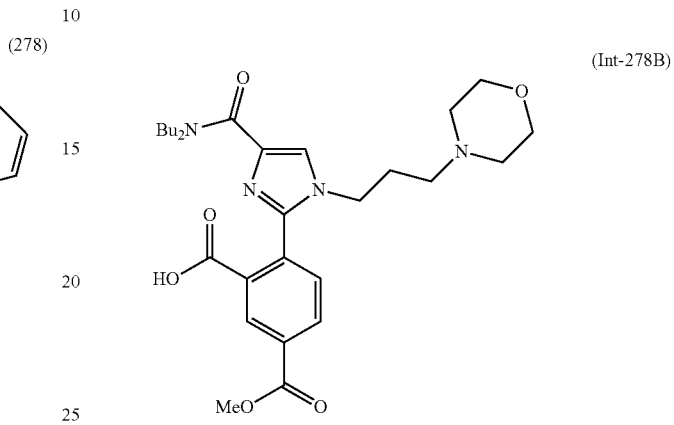

(Int-278B)

Following a procedure analogous to that for the synthesis of Intermediate 271G, 3-benzyl 1-methyl 4-(4-(dibutylcarbamoyl)-1-(3-morpholinopropyl)-1H-imidazol-2-yl)isophthalate (80 mg, 0.13 mmol) was converted to the title compound (70 mg, 97%). MS (ESI$^+$) m/z 529 (M+H)$^+$.

Intermediate 278C

Methyl 4-(4-(dibutylcarbamoyl)-1-(3-morpholinopropyl)-1H-imidazol-2-yl)-3-((S)-3-(hydroxymethyl)-1,2,3,4-tetrahydroisoquinoline-2-carbonyl)benzoate

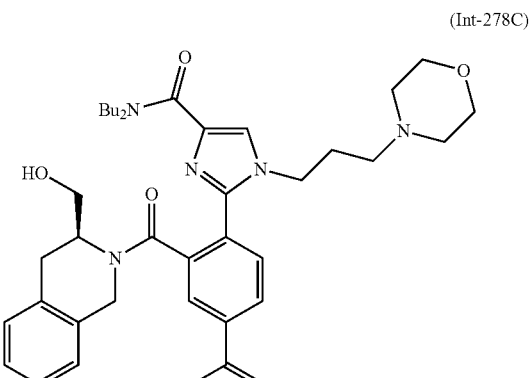

(Int-278C)

Following a procedure analogous to that for the synthesis of Intermediate 271H, 2-(4-(dibutylcarbamoyl)-1-(3-morpholinopropyl)-1H-imidazol-2-yl)-5-(methoxycarbonyl)benzoic acid (70 mg, 0.132 mmol), was converted to the title compound (80 mg, 91%). MS(ESI$^+$) m/z 674.4 (M+H)$^+$.

Intermediate 278D 4-(4-(Dibutylcarbamoyl)-1-(3-morpholinopropyl)-1H-imidazol-2-yl)-3-((S)-3-(hydroxymethyl)-1,2,3,4-tetrahydroisoquinoline-2-carbonyl)benzoic acid (Int-278D)

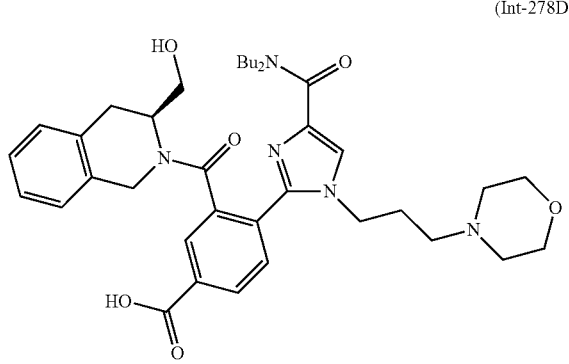

Following a procedure analogous to that for the synthesis of Intermediate 271I, methyl 4-(4-(dibutylcarbamoyl)-1-(3-morpholinopropyl)-1H-imidazol-2-yl)-3-((S)-3-(hydroxymethyl)-1,2,3,4-tetrahydroisoquinoline-2-carbonyl)benzoate (90 mg, 0.13 mmol) was converted to title compound (85 mg, 96%). MS(ESI$^+$) m/z 660.4 (M+H)$^+$.

Example 278

Following a procedure analogous to that for the synthesis of Example 271, 4-(4-(dibutylcarbamoyl)-1-(3-morpholinopropyl)-1H-imidazol-2-yl)-3-((S)-3-(hydroxymethyl)-1,2,3,4-tetrahydroisoquinoline-2-carbonyl)benzoic acid (85 mg, 0.13 mmol) was converted to the title compound (5 mg, 5%). $^1$H NMR (CD$_3$OD) δ 8.59 (s, 1H), 8.21 (br s, 1H), 8.03-7.93 (m, 4H), 7.61-7.59 (m, 4H), 7.19-7.13 (m, 4.5H), 6.94 (d, J=6.8 Hz, 0.5H), 5.15 (m, 1H), 4.58-4.40 (m, 2H), 4.35-4.15 (m, 4H), 3.64 (m, 5H), 2.75 (br s, 2H), 2.46-2.35 (m, 7H), 2.10-1.96 (m, 4H), 1.65-1.55 (m, 3H), 1.20-1.10 (m, 2H), 1.00-0.85 (m, 9H); MS(ESI$^-$) m/z 848.2 (M−H)$^-$.

Example 279

N,N-Dibutyl-2-(2-((S)-3-(hydroxymethyl)-1,2,3,4-tetrahydroisoquinoline-2-carbonyl)-4-(naphthalen-2-ylsulfonylcarbamoyl)phenyl)-1-(3-(4-methylpiperazin-1-yl)propyl)-1H-imidazole-4-carboxamide (279)

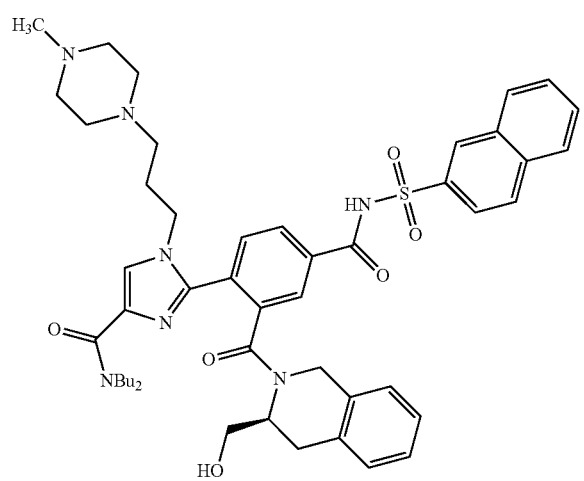

Intermediate 279A

3-Benzyl 1-methyl 4-(4-(dibutylcarbamoyl)-1-(3-(4-methylpiperazin-1-yl)propyl)-1H-imidazol-2-yl) isophthalate (Int-279A)

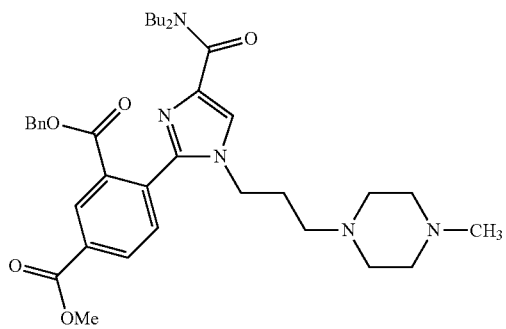

Following a procedure analogous to that for the synthesis of Intermediate 271F, 3-benzyl 1-methyl 4-(4-(dibutylcarbamoyl)-1H-imidazol-2-yl)isophthalate (200 mg, 0.40 mmol) and 1-(3-bromopropyl)-4-methylpiperazine (112 mg, 0.81 mmol) were converted to the title compound (180 mg, 70%). $^1$H NMR (CD$_3$OD) δ 8.67 (d, J=2.0 Hz, 1H), 8.33 (dd, J=8.0, 1.6 Hz, 1H), 7.69 (d, J=8.0 Hz, 1H), 7.62 (s, 1H), 7.38-7.30 (m, 5H), 5.21 (s, 2H), 4.00 (s, 3H), 3.82-3.78 (m, 4H), 3.50 (br s, 2H), 2.35-2.12 (m, 13H), 1.71-1.64 (m, 6H), 1.41-1.27 (m, 4H), 1.00-0.87 (m, 6H); MS(ESI$^+$) m/z 632.4 (M+H)$^+$.

Intermediate 279B 2-(4-(Dibutylcarbamoyl)-1-(3-(4-methylpiperazin-1-yl)propyl)-1H-imidazol-2-yl)-5-(methoxycarbonyl)benzoic acid (Int-279B)

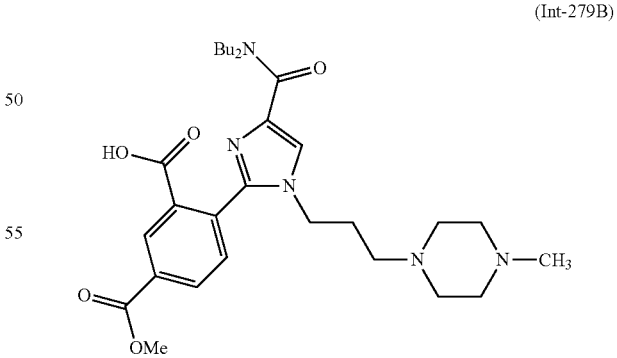

Following a procedure analogous to that for the synthesis of Intermediate 271G, 3-benzyl 1-methyl 4-(4-(dibutylcarbamoyl)-1-(3-(4-methylpiperazin-1-yl)propyl)-1H-imidazol-2-yl) isophthalate (180 mg, 0.28 mmol) was converted to the title compound (110 mg, 71%). MS(ESI$^-$) m/z 540.2 (M−H)$^-$.

Intermediate 279C

Methyl 3-((S)-3-((tert-butyldimethylsilyloxy)methyl)-1,2,3,4-tetrahydroisoquinoline-2-carbonyl)-4-(4-(dibutylcarbamoyl)-1-(3-(4-methylpiperazin-1-yl)propyl)-1H-imidazol-2-yl)benzoate

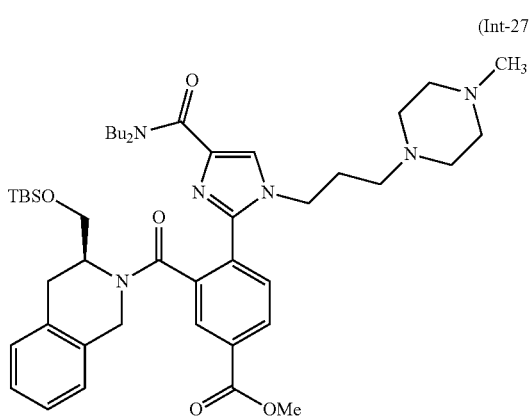

(Int-279C)

Following a procedure analogous to that for the synthesis of Intermediate 271H, 2-(4-(dibutylcarbamoyl)-1-(3-(4-methylpiperazin-1-yl)propyl)-1H-imidazol-2-yl)-5-(methoxycarbonyl)benzoic acid (110 mg, 0.2 mmol) and (S)-3-((tert-butyldimethylsilyloxy)methyl)-1,2,3,4-tetrahydroisoquinoline (73 mg, 0.26 mmol) were converted to the title compound (150 mg, 93%). MS(ESI⁺) m/z 802.4 (M+H)⁺.

Intermediate 279D 3-((S)-3-((tert-Butyldimethylsilyloxy)methyl)-1,2,3,4-tetrahydroisoquinoline-2-carbonyl)-4-(4-(dibutylcarbamoyl)-1-(3-(4-methylpiperazin-1-yl)propyl)-1H-imidazol-2-yl)benzoic acid

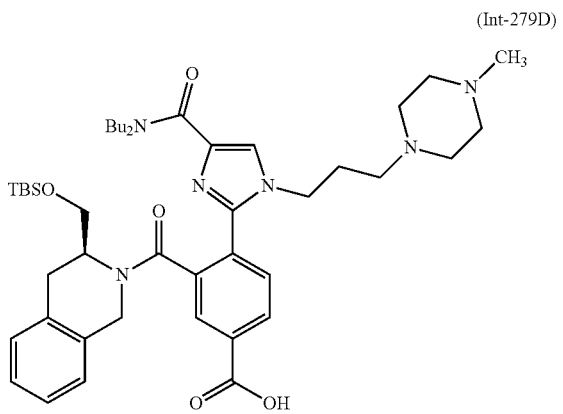

(Int-279D)

Following a procedure analogous to that for the synthesis of Intermediate 271I, methyl 3-((S)-3-((tert-butyldimethylsilyloxy)methyl)-1,2,3,4-tetrahydroisoquinoline-2-carbonyl)-4-(4-(dibutylcarbamoyl)-1-(3-(4-methylpiperazin-1-yl)propyl)-1H-imidazol-2-yl)benzoate (150 mg, 0.18 mmol) was converted to the title compound (110 mg, 68%). MS(ESI⁺) m/z 788.4 (M+H)⁺.

Intermediate 279E

N,N-Dibutyl-2-(2-((S)-3-((tert-butyldimethylsilyloxy)methyl)-1,2,3,4-tetrahydroisoquinoline-2-carbonyl)-4-(naphthalen-2-ylsulfonylcarbamoyl)phenyl)-1-(3-(4-methylpiperazin-1-yl)propyl)-1H-imidazole-4-carboxamide

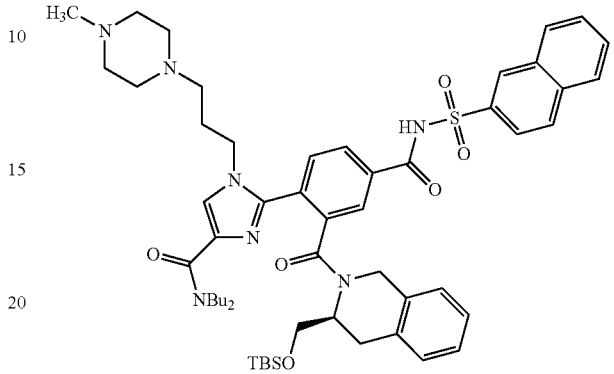

(Int-279E)

Following a procedure analogous to that for the synthesis of Example 271, 3-((S)-3-((tert-butyldimethylsilyloxy)methyl)-1,2,3,4-tetrahydroisoquinoline-2-carbonyl)-4-(4-(dibutylcarbamoyl)-1-(3-(4-methylpiperazin-1-yl)propyl)-1H-imidazol-2-yl)benzoic acid (110 mg, 0.14 mmol) was converted to the title compound (33 mg, 24%). MS(ESI⁻) m/z 975.2 (M–H)⁻.

Example 279

Following a procedure analogous to that for the synthesis of Example 274, N,N-dibutyl-2-(2-((S)-3-((tert-butyldimethylsilyloxy)methyl)-1,2,3,4-tetrahydroisoquinoline-2-carbonyl)-4-(naphthalen-2-ylsulfonylcarbamoyl)phenyl)-1-(3-(4-methylpiperazin-1-yl)propyl)-1H-imidazole-4-carboxamide (28 mg, 0.028 mmol) was converted to the title compound (25 mg, 86%). ¹H NMR (CD₃OD, 1:1 mixture of amide rotamers) δ 8.61 (s, 1H), 8.25-8.20 (m, 2H), 8.09-8.03 (m, 2H), 7.99-7.94 (m, 2H), 7.67-7.57 (m, 4H), 7.22-6.94 (m, 4H), 5.16 (d, J=17.6 Hz, 0.5H), 4.58 (br s, 1.5H), 4.30 (d, J=17.6 Hz, 1H), 4.10 (br s, 3H), 3.58-3.39 (m, 5H), 3.25-3.15 (m, 1H), 2.91-2.55 (m, 15H), 1.92-1.84 (m, 2H), 1.52-1.11 (m, 8H), 0.98-0.79 (m, 6H); MS(ESI⁺) m/z 863.4 (M+H)⁺.

Example 280

N,N-Dibutyl-2-(2-((S)-3-(hydroxymethyl)-1,2,3,4-tetrahydroisoquinoline-2-carbonyl)-4-(naphthalen-2-ylsulfonylcarbamoyl)phenyl)-1-(2-(4-methylpiperazin-1-yl)ethyl)-1H-imidazole-4-carboxamide

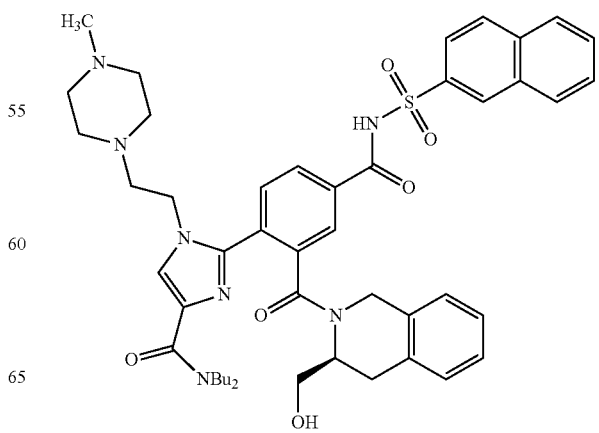

(280)

Intermediate 280A

3-Benzyl 1-methyl 4-(1-(2-chloroethyl)-4-(dibutylcarbamoyl)-1H-imidazol-2-yl)isophthalate

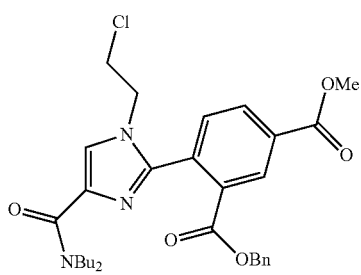
(Int-280A)

To a solution of 3-benzyl 1-methyl 4-(4-(dibutylcarbamoyl)-1H-imidazol-2-yl)isophthalate (275 mg, 0.56 mmol) in dry MeCN (8.0 mL) was added cesium carbonate (182 mg, 0.56 mmol) and 1-bromo-2-chloroethane (80 mg, 0.56 mmol). The reaction mixture was heated at 50° C. for 10 h, diluted with water and extracted with EtOAc (3×). The combined organic layers were dried over $Na_2SO_4$ and concentrated in vacuo to give the crude product. The crude material was purified by flash chromatography (gradient from 0% to 2% MeOH/$CH_2Cl_2$) to provide the title compound (170 mg, 54%). $^1$H NMR (DMSO-$d_6$) δ 8.46 (d, J=1.6 Hz, 1H), 8.26 (dd, J=8.0, 1.6 Hz, 1H), 7.85 (s, 1H), 7.75 (d, J=8.0 Hz, 1H), 7.36-7.33 (m, 3H), 7.27-7.25 (m, 2H), 5.16 (s, 2H), 4.08-4.03 (m, 4H), 3.93 (s, 1.5H), 3.77-3.73 (m, 3.5H), 3.50-3.40 (m, 2H), 1.50-1.45 (m, 4H), 1.35-1.10 (m, 4H), 0.92-0.75 (m, 6H); MS(ESI$^+$) m/z 555.0 (M+H)$^+$.

Intermediate 280B

3-Benzyl 1-methyl 4-(4-(dibutylcarbamoyl)-1-(2-(4-methylpiperazin-1-yl)ethyl)-1H-imidazol-2-yl)isophthalate

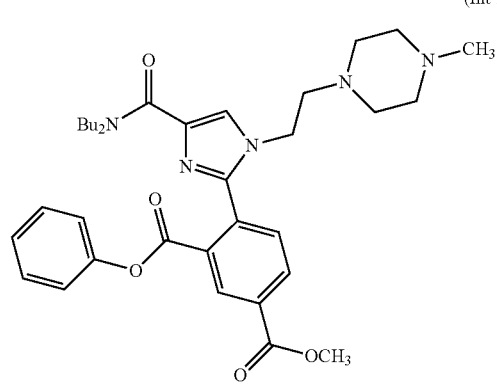
(Int-280B)

To a solution of 3-benzyl 1-methyl 4-(1-(2-chloroethyl)-4-(dibutylcarbamoyl)-1H-imidazol-2-yl)isophthalate (120 mg, 0.21 mmol) in dry DMF (2 mL) was added diisopropylethyl amine (26.5 mg, 0.21 mmol) and 1-methylpiperazine (21 mg, 0.21 mmol at room temperature. The reaction mixture was heated at 90° C. for 16 h, diluted with water and extracted with MTBE (3×). The combined organic layer was dried over $Na_2SO_4$ and concentrated in vacuo to give the crude product. The crude material was purified by flash chromatography (gradient from 0 to 5% MeOH/$CH_2Cl_2$) to provide the title compound (60 mg, 45%). MS(ESI$^+$) m/z 619.2 (M+H)$^+$

Intermediate 280C 2-(4-(Dibutylcarbamoyl)-1-(2-(4-methylpiperazin-1-yl)ethyl)-1H-imidazol-2-yl)-5-(methoxycarbonyl)benzoic acid

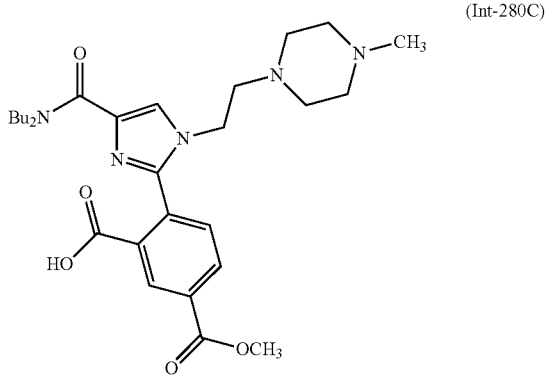
(Int-280C)

Following a procedure analogous to that for the synthesis of Intermediate 271G, 3-benzyl 1-methyl 4-(4-(dibutylcarbamoyl)-1-(2-(4-methylpiperazin-1-yl)ethyl)-1H-imidazol-2-yl)isophthalate (70 mg, 0.11 mmol) was converted to the title compound (55 mg, 93%). MS(ESI$^+$) m/z 528.2 (M+H)$^+$.

Intermediate 280D

Methyl 3-((S)-3-((tert-butyldimethylsilyloxy)methyl)-1,2,3,4-tetrahydroisoquinoline-2-carbonyl)-4-(4-(dibutylcarbamoyl)-1-(2-(4-methylpiperazin-1-yl)ethyl)-1H-imidazol-2-yl)benzoate

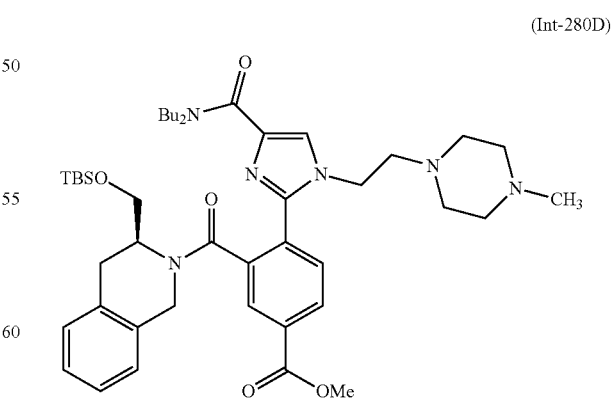
(Int-280D)

Following a procedure analogous to that for the synthesis of Intermediate 271H, 2-(4-(dibutylcarbamoyl)-1-(2-(4-methylpiperazin-1-yl)ethyl)-1H-imidazol-2-yl)-5-(methoxycarbonyl)benzoic acid (55 mg, 0.10 mmol) was converted to the title compound (45 mg, 56%). MS(ESI⁺) m/z 788.4 (M+H)⁺.

Intermediate 280E 3-((S)-3-((tert-Butyldimethylsilyloxy)methyl)-1,2,3,4-tetrahydroisoquinoline-2-carbonyl)-4-(4-(dibutylcarbamoyl)-1-(2-(4-methylpiperazin-1-yl)ethyl)-1H-imidazol-2-yl)benzoic acid

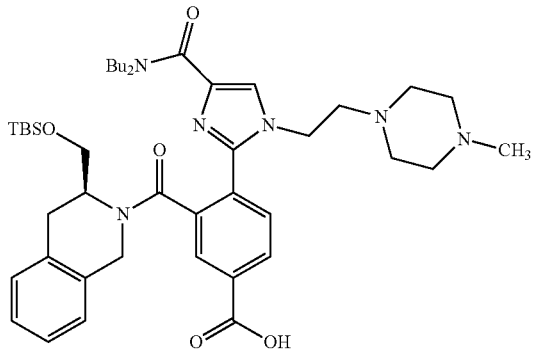

(Int-280E)

Following a procedure analogous to that for the synthesis of Intermediate 271I, methyl 3-((S)-3-((tert-butyldimethylsilyloxy)methyl)-1,2,3,4-tetrahydroisoquinoline-2-carbonyl)-4-(4-(dibutylcarbamoyl)-1-(2-(4-methylpiperazin-1-yl)ethyl)-1H-imidazol-2-yl)benzoate (45 mg, 0.057 mmol) was converted to title compound (35 mg, 79%). MS(ESI⁻) m/z 772.0 (M−H)⁻.

Intermediate 280F

N,N-Dibutyl-2-(2-((S)-3-((tert-butyldimethylsilyloxy)methyl)-1,2,3,4-tetrahydroisoquinoline-2-carbonyl)-4-(naphthalen-2-ylsulfonylcarbamoyl)phenyl)-1-(2-(4-methylpiperazin-1-yl)ethyl)-1H-imidazole-4-carboxamide (Int-280F)

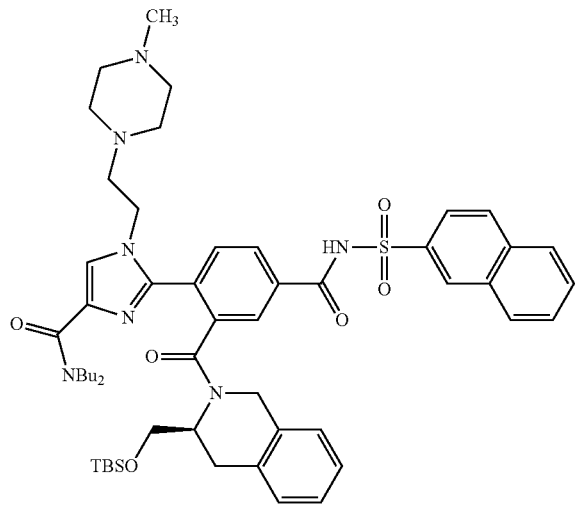

Following a procedure analogous to that for the synthesis of Example 271, 3-((S)-3-((tert-butyldimethylsilyloxy)methyl)-1,2,3,4-tetrahydroisoquinoline-2-carbonyl)-4-(4-(dibutylcarbamoyl)-1-(2-(4-methylpiperazin-1-yl)ethyl)-1H-imidazol-2-yl)benzoic acid (35 mg, 0.045 mmol) was converted to the title compound (12 mg, 28%); MS(ESI⁻) m/z 961.2 (M−H)⁻.

Example 280

Following a procedure analogous to that for the synthesis of Example 274, N,N-dibutyl-2-(2-((S)-3-((tert-butyldimethylsilyloxy)methyl)-1,2,3,4-tetrahydroisoquinoline-2-carbonyl)-4-(4-(naphthalen-2-ylsulfonylcarbamoyl)phenyl)-1-(2-(4-methylpiperazin-1-yl)ethyl)-1H-imidazole-4-carboxamide (12 mg, 0.012 mmol) was converted to the title compound (7 mg, 86%). ¹H NMR (CD₃OD, 1:1 mixture of amide rotamers) δ 8.59 (s, 1H), 8.22-8.18 (m, 2H), 8.06-8.01 (m, 2H), 7.97-7.92 (m, 2H), 7.71-7.57 (m, 4H), 7.21-7.13 (m, 3.5H), 6.94 (d, J=6.8 Hz, 0.5H), 5.15 (d, J=18.0 Hz, 0.5H), 4.57 (br s, 1.5H), 4.30 (d, J=18.0 Hz, 1H), 4.10-4.08 (m, 3H), 3.70-3.40 (m, 3H), 3.02-2.68 (m, 9H), 2.54-2.34 (m, 8H), 1.64-1.32 (m, 4H), 1.30-1.11 (m, 4H), 0.97-0.67 (m, 6H); MS(ESI⁺) m/z 848.0 (M+H)⁺.

Example 281

2-(2-((S)-3-(Aminomethyl)-1,2,3,4-tetrahydroisoquinoline-2-carbonyl)-4-(naphthalen-2-ylsulfonylcarbamoyl)phenyl)-N,N-dibutyl-1-methyl-1H-imidazole-4-carboxamide (281)

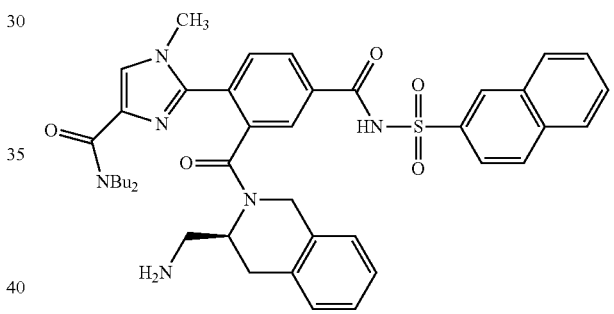

Intermediate 281A

3-Benzyl 1-methyl 4-(4-(dibutylcarbamoyl)-1-methyl-1H-imidazol-2-yl)isophthalate (Int-281A)

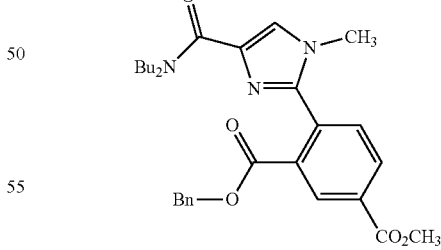

Following a procedure analogous to that for the synthesis of Intermediate 271F, 3-benzyl 1-methyl 4-(4-(dibutylcarbamoyl)-1H-imidazol-2-yl)isophthalate (370 mg, 0.75 mmol) and methyl iodide (106 mg, 0.75 mmol) were converted to the title compound (260 mg, 68%). ¹H NMR (CDCl₃) δ 8.70 (d, J=1.2 Hz, 1H), 8.24 (dd, J=8.0, 1.6 Hz, 1H), 7.52 (d, J=7.6 Hz, 1H), 7.43 (s, 1H), 7.37-7.33 (m, 3H), 7.28-7.27 (m, 2H), 5.17 (s, 2H), 3.98 (s, 3H), 3.92 (br s, 2H), 3.45 (br s, 2H), 3.24 (s, 3H), 1.68-1.52 (m, 4H), 1.37-1.24 (m, 4H), 0.94-0.90 (m, 6H); MS(ESI⁺) m/z 507.0 (M+H)⁺

Intermediate 281B 2-(4-(Dibutylcarbamoyl)-1-methyl-1H-imidazol-2-yl)-5-(methoxycarbonyl)benzoic acid

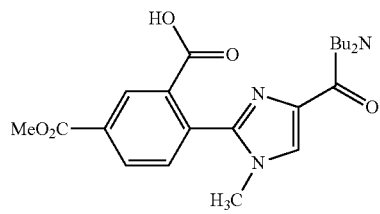
(Int-281B)

Following a procedure analogous to that for the synthesis of Intermediate 271G, 3-benzyl 1-methyl 4-(4-(dibutylcarbamoyl)-1-methyl-1H-imidazol-2-yl)isophthalate (260 mg, 0.51 mmol) was converted to the title compound (210 mg, 98%). MS (ESI$^+$) m/z 416.0 (M+H)$^+$.

Intermediate 281C

Methyl 3-((S)-3-(azidomethyl)-1,2,3,4-tetrahydroisoquinoline-2-carbonyl)-4-(4-(dibutylcarbamoyl)-1-methyl-1H-imidazol-2-yl)benzoate

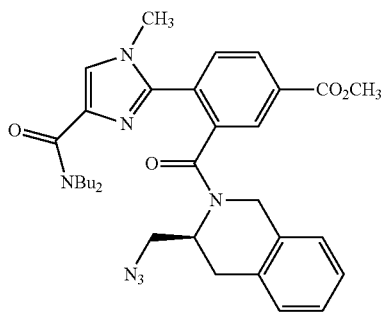
(Int-281C)

Following a procedure analogous to that for the synthesis of Intermediate 271H, 2-(4-(dibutylcarbamoyl)-1-methyl-1H-imidazol-2-yl)-5-(methoxycarbonyl)benzoic acid (230 mg, 0.55 mmol) and (S)-3-(azidomethyl)-1,2,3,4-tetrahydroisoquinoline (135 mg, 0.72 mmol) were converted to the title compound (280 mg, 91%). MS(ESI$^+$) m/z 586.2 (M+H)$^+$.

Intermediate 281D 3-((S)-3-(Azidomethyl)-1,2,3,4-tetrahydroisoquinoline-2-carbonyl)-4-(4-(dibutylcarbamoyl)-1-methyl-1H-imidazol-2-yl)benzoic acid

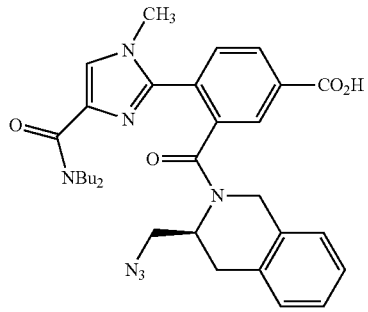
(Int-281D)

Following a procedure analogous to that for the synthesis of Intermediate 271I, methyl 3-((S)-3-(azidomethyl)-1,2,3,4-tetrahydroisoquinoline-2-carbonyl)-4-(4-(dibutylcarbamoyl)-1-methyl-1H-imidazol-2-yl)benzoate (280 mg, 0.48 mmol) was converted to the title compound (240 mg, 88%). MS(ESI$^+$) m/z 572.2 (M+H)$^+$.

Intermediate 281E 2-(2-((S)-3-(Azidomethyl)-1,2,3,4-tetrahydroisoquinoline-2-carbonyl)-4-(naphthalen-2-ylsulfonylcarbamoyl)phenyl)-N,N-dibutyl-1-methyl-1H-imidazole-4-carboxamide

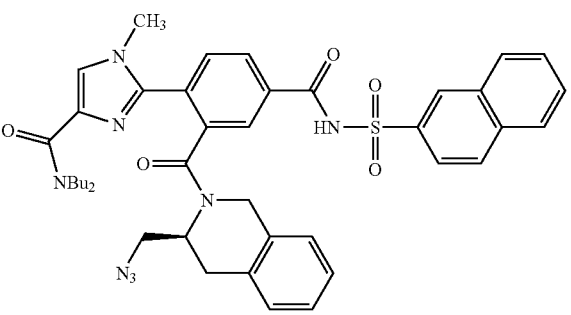
(Int-281E)

Following a procedure analogous to that for the synthesis of Example 271, 3-((S)-3-(azidomethyl)-1,2,3,4-tetrahydroisoquinoline-2-carbonyl)-4-(4-(dibutylcarbamoyl)-1-methyl-1H-imidazol-2-yl)benzoic acid (120 mg, 0.21 mmol) was converted to the title compound (98 mg, 62%). MS(ESI$^+$) m/z 762.0 (M+H)$^+$.

Example 281

To a solution of 2-(2-((S)-3-(azidomethyl)-1,2,3,4-tetrahydroisoquinoline-2-carbonyl)-4-(naphthalen-2-ylsulfonylcarbamoyl)phenyl)-N,N-dibutyl-1-methyl-1H-imidazole-4-carboxamide (60 mg, 0.08 mmol) in THF (5 mL) and water (0.5 mL) at 0° C. was added 1M aq. NaOH solution (50 µL) and PPh$_3$ (29 mg, 0.11 mmol). The reaction mixture was stirred at 0° C. for 2 h, then warmed to room temperature and stirred for 3 h. The reaction mixture was concentrated in vacuo and the residue was diluted with water and extracted with EtOAc (3×). The combined organic layers were dried over Na$_2$SO$_4$ and concentrated in vacuo to give the crude compound. The crude material was purified by preparative HPLC to provide the title compound (17 mg, 30%). $^1$H NMR (CD$_3$OD, 1:1 mixture of amide rotamers) δ 8.76 (s, 1H), 8.18-8.03 (m, 6H), 7.92 (d, J=8.0 Hz, 0.5H), 7.84 (d, J=8.0 Hz, 0.5H), 7.76-7.65 (m, 2.5H), 7.55 (br s, 0.5H), 7.30-7.15 (m, 3.5H), 6.96 (d, J=8.0 Hz, 0.5H), 5.38 (d, J=18.4 Hz, 0.5H), 5.09 (br s, 0.5H), 4.85-4.42 (m, 2H), 3.82 (s, 3.5H), 3.70-3.40 (m, 4.5H), 3.01-2.90 (m, 1H), 2.86-2.83 (m, 2H), 1.67-1.54 (m, 3.5H), 1.40-1.31 (m, 4.5H), 1.00-0.75 (m, 6H); MS(ESI$^-$) m/z 732.8 (M−H)$^-$.

Example 282

2-(2-((S)-3-(Aminomethyl)-1,2,3,4-tetrahydroisoquinoline-2-carbonyl)-4-(8-iodonaphthalen-2-ylsulfonylcarbamoyl)phenyl)-N,N-dibutyl-1-methyl-1H-imidazole-4-carboxamide

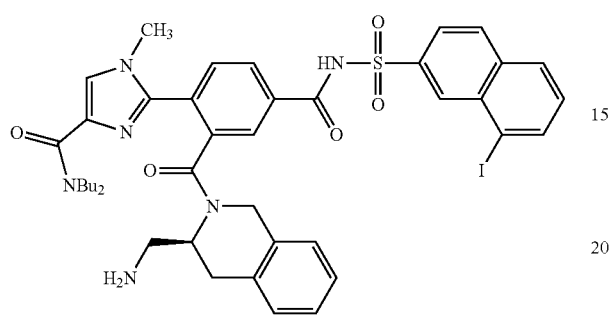

(282)

Intermediate 282A 2-(2-((S)-3-(Azidomethyl)-1,2,3,4-tetrahydroisoquinoline-2-carbonyl)-4-(8-iodonaphthalen-2-ylsulfonylcarbamoyl)phenyl)-N,N-dibutyl-1-methyl-1H-imidazole-4-carboxamide

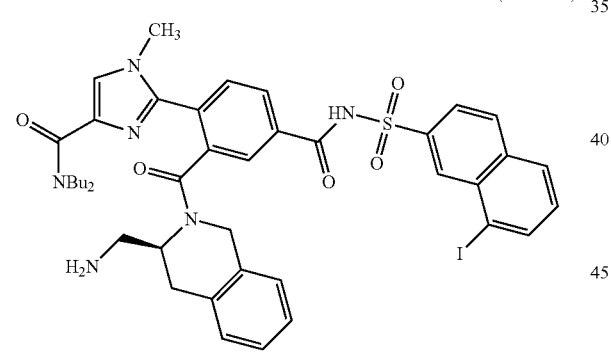

(Int-282A)

Following a procedure analogous to that for the synthesis of Example 271, 3-((S)-3-(azidomethyl)-1,2,3,4-tetrahydroisoquinoline-2-carbonyl)-4-(4-(dibutylcarbamoyl)-1-methyl-1H-imidazol-2-yl)benzoic acid (Intermediate 281D, 120 mg, 0.21 mmol) and 8-iodonaphthalene-2-sulfonamide (Intermediate 8, 139 mg, 0.42 mmol) were converted to the title compound (76 mg, 41%). MS(ESI⁻) m/z 885.8 (M−H)⁻.

Example 282

Following a procedure analogous to that for the synthesis of Example 281, 2-(2-((S)-3-(azidomethyl)-1,2,3,4-tetrahydroisoquinoline-2-carbonyl)-4-(8-iodonaphthalen-2-ylsulfonylcarbamoyl)phenyl)-N,N-dibutyl-1-methyl-1H-imidazole-4-carboxamide (75 mg, 0.08 mmol) was converted to the title compound (35 mg, 48%). $^1$H NMR (CD$_3$OD, 1:1 mixture of amide rotamers) δ 8.85 (s, 1H), 8.28-8.13 (m, 4H), 7.99-7.94 (m, 2H), 7.75-7.52 (m, 2H), 7.34 (t, J=8.0 Hz, 1H), 7.27-7.17 (m, 3.5H), 7.00 (d, J=7.2 Hz, 0.5H), 5.37 (d, J=18.4 Hz, 0.5H), 5.09 (br s, 0.5H), 4.64-4.50 (m, 1.5H), 4.37 (d, J=18.4 Hz, 0.5H), 3.81-3.69 (m, 4.5H), 3.65-3.40 (m, 2.5H), 3.15-2.90 (m, 1H), 2.87-2.77 (m, 3H), 1.66-1.54 (m, 3H), 1.36-1.31 (m, 5H), 0.98-0.70 (m, 6H); MS(ESI⁺) m/z 862.0 (M+H)⁺.

Example 283

N,N-Dibutyl-2-(4-(8-chloronaphthalen-2-ylsulfonylcarbamoyl)-2-((S)-3-(hydroxymethyl)-1,2,3,4-tetrahydroisoquinoline-2-carbonyl)phenyl)-1-methyl-1H-imidazole-4-carboxamide

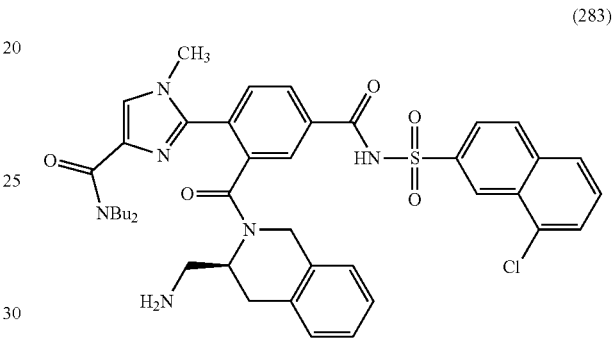

(283)

Intermediate 283A

Methyl 3-((S)-3-((tert-butyldimethylsilyloxy)methyl)-1,2,3,4-tetrahydroisoquinoline-2-carbonyl)-4-(4-(dibutylcarbamoyl)-1-methyl-1H-imidazol-2-yl)benzoate

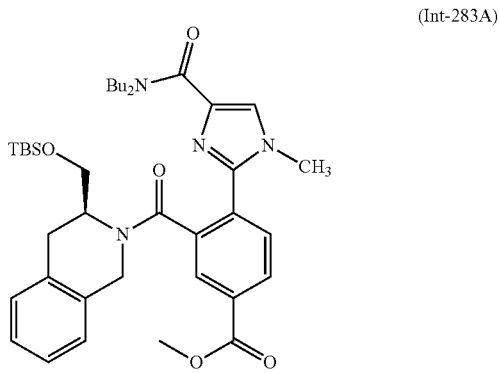

(Int-283A)

Following a procedure analogous to that for the synthesis of Intermediate 271H, 2-(4-(dibutylcarbamoyl)-1-methyl-1H-imidazol-2-yl)-5-(methoxycarbonyl)benzoic acid (Intermediate 281B, 170 mg, 0.42 mmol) and (S)-3-((tert-butyldimethylsilyloxy)methyl)-1,2,3,4-tetrahydroisoquinoline (237 mg, 0.85 mmol) were converted to the title compound (248 mg, 87%). MS(ESI⁺) m/z 675 (M+H)⁺.

Intermediate 283B 3-((S)-3-((tert-Butyldimethylsilyloxy)methyl)-1,2,3,4-tetrahydroisoquinoline-2-carbonyl)-4-(4-(dibutylcarbamoyl)-1-methyl-1H-imidazol-2-yl)benzoic acid

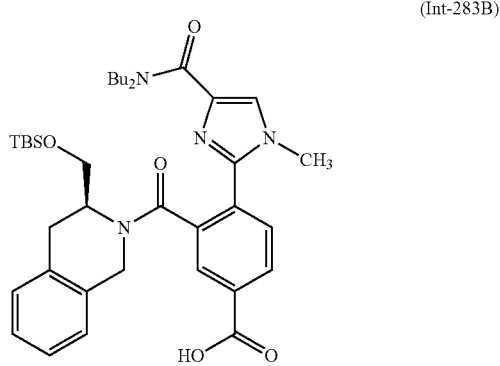

(Int-283B)

Following a procedure analogous to that for synthesis of Intermediate 271I, methyl 3-((S)-3-((tert-butyldimethylsilyloxy)methyl)-1,2,3,4-tetrahydroisoquinoline-2-carbonyl)-4-(4-(dibutylcarbamoyl)-1-methyl-1H-imidazol-2-yl)benzoate (240 mg, 0.35 mmol) was converted to the title compound (230 mg, 98%). MS(ESI⁺) m/z 662.2 (M+H)⁺.

Intermediate 283C

N,N-Dibutyl-2-(2-((S)-3-((tert-butyldimethylsilyloxy)methyl)-1,2,3,4-tetrahydroisoquinoline-2-carbonyl)-4-(8-chloronaphthalen-2-ylsulfonylcarbamoyl)phenyl)-1-methyl-1H-imidazole-4-carboxamide

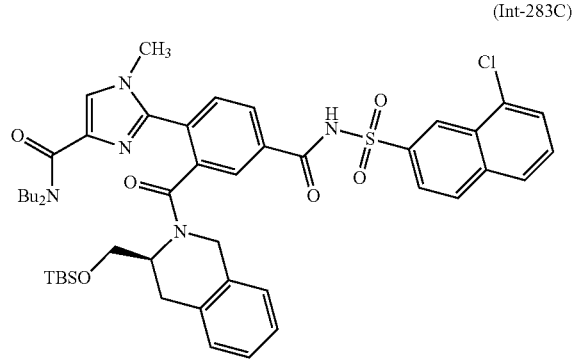

(Int-283C)

Following a procedure analogous to that for the synthesis of Example 271, 3-((S)-3-((tert-butyldimethylsilyloxy)methyl)-1,2,3,4-tetrahydroisoquinoline-2-carbonyl)-4-(4-(dibutylcarbamoyl)-1-methyl-1H-imidazol-2-yl)benzoic acid (230 mg, 0.35 mmol) was converted to the title compound (130 mg, 42%). MS(ESI⁺) m/z 886.0 (M+H)⁺.

Example 283

Following a procedure analogous to that for the synthesis of Example 274, N,N-dibutyl-2-(2-((S)-3-((tert-butyldimethylsilyloxy)methyl)-1,2,3,4-tetrahydroisoquinoline-2-carbonyl)-4-(8-chloronaphthalen-2-ylsulfonylcarbamoyl)phenyl)-1-methyl-1H-imidazole-4-carboxamide (130 mg, 0.15 mmol) was converted to the title compound (80 mg, 71%). ¹H NMR (CD₃OD, 1:1 mixture of amide rotamers) δ 8.96 (s, 1H), 8.21-8.02 (m, 4H), 7.94-7.91 (m, 1H), 7.73-7.70 (m, 1H), 7.59-7.54 (m, 3H), 7.10-6.86 (m, 4H), 5.20 (d, J=17.2 Hz, 0.5H), 4.40-3.85 (m, 2.5H), 3.72 (s, 2H), 3.51-3.40 (m, 5H), 3.31-3.00 (m, 1.5H), 2.82-2.59 (m, 2.5H), 1.65-1.15 (m, 8H), 0.94-0.82 (m, 6H); MS(ESI⁺) m/z 771.0 (M+H)⁺.

Example 284

N,N-Dibutyl-5-(4-(8-iodonaphthalen-2-ylsulfonylcarbamoyl)-2-(1,2,3,4-tetrahydroisoquinoline-2-carbonyl)phenyl)-1-methyl-1H-imidazole-4-carboxamide

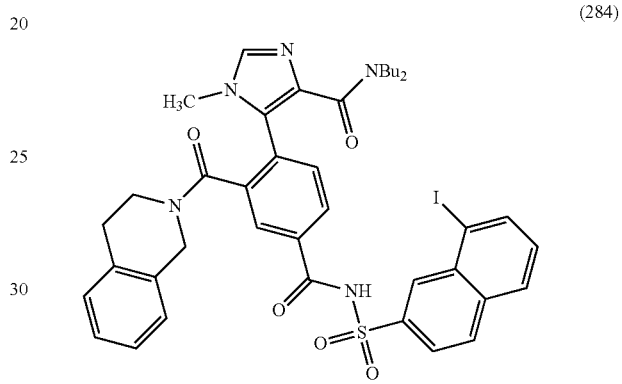

(284)

Intermediate 284A

N,N-Dibutyl-1-methyl-1H-imidazole-4-carboxamide

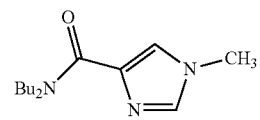

(Int-284A)

Following a procedure analogous to that for the synthesis of Intermediate 264D, 1-methyl-1H-imidazole-4-carboxylic acid (1.0 g, 7.93 mmol) was converted to the title compound (1.3 g, 72%). ¹H NMR (DMSO-d₆) δ 7.61 (s, 1H), 7.55 (s, 1H), 3.88 (br s, 2H), 3.67 (s, 3H), 3.32 (br s, 2H), 1.52 (br s, 4H), 1.25 (s, 4H), 0.88 (br s, 6H); MS(ESI⁺) m/z 238.4 (M+H)⁺.

Intermediate 284B

5-Bromo-N,N-dibutyl-1-methyl-1H-imidazole-4-carboxamide

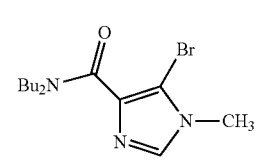

(Int-284B)

Following a procedure analogous to that for the synthesis of Compound B Example 264, N,N-dibutyl-1-methyl-1H-imidazole-4-carboxamide (1.3 g, 5.5 mmol) was converted to the title compound (700 mg, 41%). ¹H NMR (CD₃OD) δ 7.85 (s, 1H), 3.71 (s, 3H), 3.51-3.46 (m, 4H), 1.70-1.62 (m, 2H), 1.58-1.51 (m, 2H), 1.46-1.40 (m, 2H), 1.23-1.17 (m, 2H), 0.99 (t, J=7.6 Hz, 3H) 0.80 (t, J=7.6 Hz, 3H); MS(ESI⁺) m/z 317.2 (M+H)⁺.

Intermediate 284C

Methyl 4-(4-(dibutylcarbamoyl)-1-methyl-1H-imidazol-5-yl)-3-(1,2,3,4-tetrahydroisoquinoline-2-carbonyl)benzoate

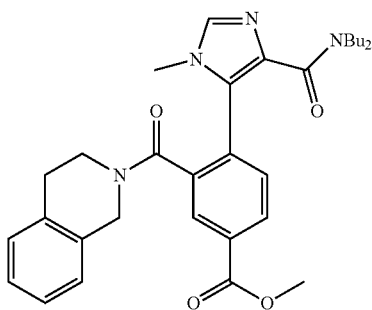
(Int-284C)

Following a procedure analogous to that for the synthesis of Intermediate 264I, 5-bromo-N,N-dibutyl-1-methyl-1H-imidazole-4-carboxamide (600 mg, 1.9 mmol) and methyl 4-(5,5-dimethyl-1,3,2-dioxaborinan-2-yl)-3-(1,2,3,4-tetrahydroisoquinoline-2-carbonyl)benzoate (Intermediate 264H, 1.55 g, 3.8 mmol) were converted to the title compound (400 mg, 40%). MS(ESI⁺) m/z 531.6 (M+H)⁺.

Intermediate 284D 4-(4-(Dibutylcarbamoyl)-1-methyl-1H-imidazol-5-yl)-3-(1,2,3,4-tetrahydroisoquinoline-2-carbonyl)benzoic acid

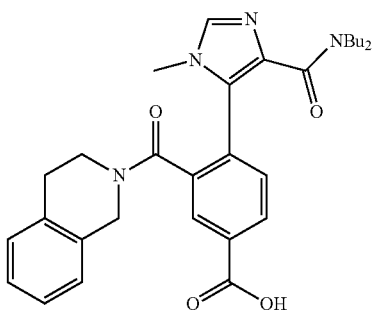
(Int-284D)

Following a procedure analogous to that for the synthesis of Intermediate 264L, methyl 4-(4-(dibutylcarbamoyl)-1-methyl-1H-imidazol-5-yl)-3-(1,2,3,4-tetrahydroisoquinoline-2-carbonyl)benzoate (400 mg, 0.75 mmol) was converted to the title compound (300 mg, 77%). MS(ESI⁺) m/z 517.6 (M+H)⁺.

Example 284

Following a procedure analogous to that for the synthesis of Example 265, 4-(4-(dibutylcarbamoyl)-1-methyl-1H-imidazol-5-yl)-3-(1,2,3,4-tetrahydroisoquinoline-2-carbonyl)benzoic acid (160 mg, 0.31 mmol) and 8-iodonaphthalene-2-sulfonamide (Intermediate 6, 258 mg, 0.78 mmol) were converted to the title compound (53 mg, 21%). ¹H NMR (CD₃OD, 1:1 mixture of amide rotamers) δ 8.87 (s, 1H), 8.21 (dd, J=7.2, 3.2 Hz, 1H), 8.17-8.14 (m, 1H), 8.12-8.07 (m, 2H), 8.01-7.96 (m, 2H), 7.69 (s, 0.5H), 7.62 (s, 0.5H), 7.44 (dd, J=8.0, 4.4 Hz, 1H), 7.36 (ddd, J=10.8, 8.0, 3.2 Hz, 1H), 7.21-7.06 (m, 3.5H), 6.95 (d, J=8.0 Hz, 0.5H), 4.77 (d, J=17.2 Hz, 0.5H), 4.56-4.50 (m, 1.5H), 3.90 (br s, 1H), 3.70-3.60 (br s, 1H), 3.51 (s, 3H), 3.49-3.35 (m, 3H), 3.30-3.10 (m, 1H), 2.90-2.67 (m, 3H), 1.51-1.09 (m, 8H), 0.90-0.79 (m, 6H); MS(ESI⁺) m/z 832.4 (M+H)⁺.

Example 285

N,N-Dibutyl-5-(4-(8-chloronaphthalen-2-ylsulfonylcarbamoyl)-2-(1,2,3,4-tetrahydroisoquinoline-2-carbonyl)phenyl)-1-methyl-1H-imidazole-4-carboxamide

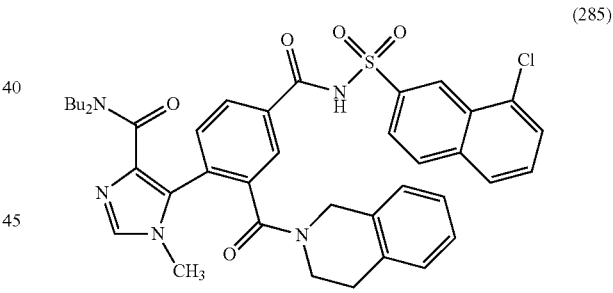
(285)

Following a procedure analogous to that for the synthesis of Example 265, 4-(4-(dibutylcarbamoyl)-1-methyl-1H-imidazol-5-yl)-3-(1,2,3,4-tetrahydroisoquinoline-2-carbonyl)benzoic acid (150 mg, 0.29 mmol) and 8-chloronaphthalene-2-sulfonamide (Intermediate 5, 140 mg, 0.58 mmol) were converted to the title compound (26 mg, 12%). ¹H NMR (CD₃OD, 1:1 mixture of amide rotamers) δ 8.99 (s, 1H), 8.18-8.09 (m, 3H), 8.05 (dd, J=8.4, 2.0 Hz, 1H), 7.94-7.91 (m, 1H), 7.72 (dd, J=7.2, 1.2 Hz, 1H), 7.69 (s, 0.5H), 7.62-7.55 (m, 1.5H), 7.42 (dd, J=8.0, 4.8 Hz, 1H), 7.21-7.13 (m, 3.5H), 6.93 (d, J=8.0 Hz, 0.5H), 4.78 (br s, 0.5H), 4.62-4.49 (m, 1.5H), 3.90 (br s, 0.5H), 3.60 (br s, 0.5H), 3.50 (s, 3H), 3.49-3.39 (m, 2H), 3.24 (t, J=6.4 Hz, 0.5H), 3.18-3.13 (m, 1.5H), 2.90 (br s, 1.5H), 2.85-2.65 (m, 2.5H), 1.50-1.09 (m, 8H), 0.89-0.79 (m, 6H); MS(ESI⁺) m/z 742.2 (M+H)⁺.

Example 286

N,N-Dibutyl-6-(4-(naphthalen-2-ylsulfonylcarbamoyl)-2-(1,2,3,4-tetrahydroisoquinoline-2-carbonyl)phenyl)picolinamide

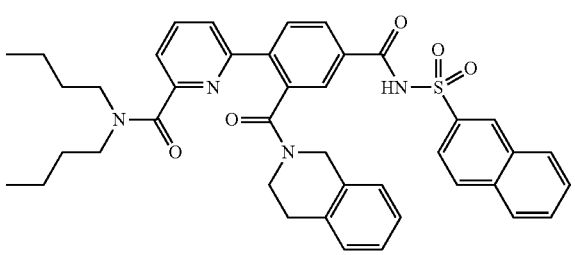

(286)

Intermediate 286A

6-Bromo-N,N-dibutylpicolinamide

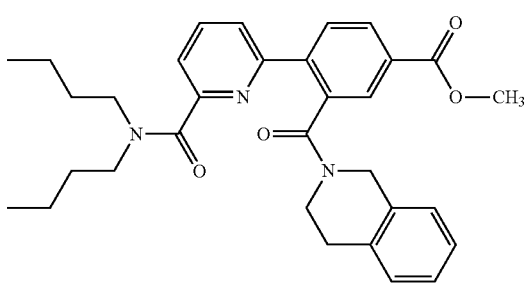

(Int-286A)

To a solution of 6-bromopicolinic acid (Aldrich, 404 mg, 2.00 mmol) in DMF (3.0 mL) were added dibutylamine (Aldrich, 258 mg, 2.00 mmol), HATU (760 mg, 2.00 mmol) and DIEA (1.1 mL, 6.00 mmol). The reaction mixture was stirred at room temperature for 3 h and then quenched by adding sat. aq. NH₄Cl solution. The mixture was extracted with EtOAc (3×). The combined organic extracts were dried over Na₂SO₄, filtered and concentrated in vacuo. The residue was purified by flash column chromatography, gradient from 0 to 20% EtOAc/DCM to give a light brown oil (450 mg, 72%). ¹H NMR (CDCl₃) δ 7.67-7.57 (m, 2H), 7.51 (dd, J=7.5, 1.3 Hz, 1H), 3.53-3.42 (m, 2H), 3.36-3.27 (m, 2H), 1.72-1.56 (m, 4H), 1.46-1.33 (m, 2H), 1.27-1.15 (m, 2H), 0.97 (t, J=7.4 Hz, 3H), 0.85 (t, J=7.4 Hz, 3H); MS(ESI⁺) m/z 313.2 (M+H)⁺.

Intermediate 286B

Methyl 4-(6-(dibutylcarbamoyl)pyridin-2-yl)-3-(1,2,3,4-tetrahydroisoquinoline-2-carbonyl)benzoate

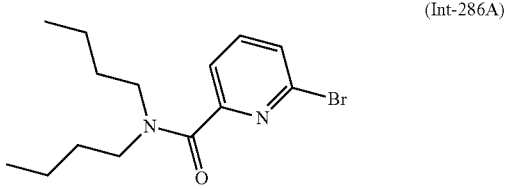 [SMILES: CCCCN(CCCC)C(=O)c1cccc(Br)n1]

(Int-286B)

A heterogeneous solution containing methyl 3-(1,2,3,4-tetrahydroisoquinoline-2-carbonyl)-4-(trifluoromethylsulfonyloxy)benzoate (Intermediate 271G, 1.03 g, 2.50 mmol), bis(pinacolato)diboron (762 mg, 3.00 mmol), potassium acetate (368 mg, 3.75 mmol), tetrakis(triphenylphosphine)palladium(0) (289 mg, 0.25 mmol) and 1,4-dioxane (15.0 mL) was purged with argon for 5 min and stirred in a sealed tube at 90° C. for 16 h. The resulting solution was stored in the freezer as a 0.17M solution.

To a solution of 6-bromo-N,N-dibutylpicolinamide (211 mg, 0.675 mmol) in 1,4-dioxane (4.0 mL) were added aq. 2N potassium phosphate (0.68 mL, 1.35 mmol), Pd(dppf)₂Cl₂ (66 mg, 0.09 mmol) and the above boronic ester solution (4.0 mL, 0.68 mmol, 0.17M in 1,4-dioxane). The flask was evacuated and purged with argon (3×) and then heated at 90° C. for 9 h. The reaction mixture was then diluted with EtOAc and filtered through CELITE®. The filtrate was concentrated in vacuo and the residue was purified by flash column chromatography (gradient from 0 to 40% EtOAc/DCM) to afford the title compound (167 mg, 47%) as a light yellow semi-solid. ¹H NMR (CD₃OD, 2:1 mixture of amide rotamers) δ 8.24 (dd, J=8.3, 1.7 Hz, 1H), 8.08-7.89 (m, 3.5H), 7.83 (dd, J=8.0, 0.8 Hz, 0.5H), 7.48-7.41 (m, 1H), 7.27-7.10 (m, 3.5H), 6.87 (d, J=7.5 Hz, 0.5H), 4.50-4.36 (m, 0.5H), 3.97 (s, 2H), 3.96 (s, 1H), 3.93-3.83 (m, 1.5H), 3.62-3.42 (m, 2H), 3.33 (dt, J=3.2, 1.7 Hz, 1H), 3.27-3.03 (m, 3H), 2.92 (t, J=5.9 Hz, 1H), 2.79 (d, J=5.5 Hz, 1H), 1.58-1.23 (m, 5H), 1.13-1.04 (m, 3H), 0.93 (t, J=7.4 Hz, 1H), 0.85 (t, J=7.3 Hz, 2H), 0.72 (t, J=7.4 Hz, 2H), 0.64 (t, J=7.4 Hz, 1H); MS(ESI⁺) m/z 528.4 (M+H)⁺.

Intermediate 286C 4-(6-(Dibutylcarbamoyl)pyridin-2-yl)-3-(1,2,3,4-tetrahydroisoquinoline-2-carbonyl)benzoic acid

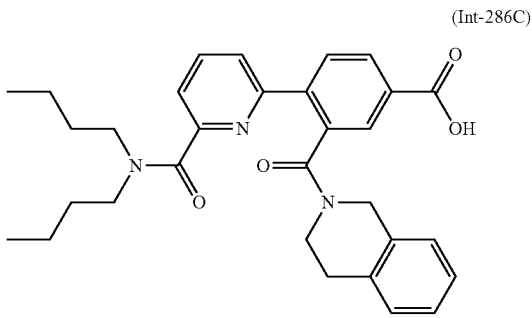 [SMILES: CCCCN(CCCC)C(=O)c1cccc(-c2ccc(C(=O)O)cc2C(=O)N2CCc3ccccc3C2)n1]

(Int-286C)

To a solution of methyl 4-(6-(dibutylcarbamoyl)pyridin-2-yl)-3-(1,2,3,4-tetrahydroisoquinoline-2-carbonyl)benzoate (158 mg, 0.30 mmol) in THF (2.0 mL) and MeOH (2.0 mL) was added 2N NaOH (1.5 mL, 3.00 mmol). The resulting reaction mixture was stirred at room temperature for 2 h. At 0° C., the reaction mixture was neutralized to pH 4-5 with 1N HCl. The solution was extracted with EtOAc (3×) and the combined organic extracts were dried over MgSO₄, filtered and concentrated in vacuo to afford the title compound (146 mg, 95%). MS(ESI⁺) m/z 514.4 (M+H)⁺.

Example 286

To a solution of 4-(6-(dibutylcarbamoyl)pyridin-2-yl)-3-(1,2,3,4-tetrahydroisoquinoline-2-carbonyl)benzoic acid (41 mg, 0.080 mmol) in DMF (1.0 mL) were added EDC (31 mg, 0.16 mmol) and DMAP (29 mg, 0.24 mmol). The resulting reaction mixture was stirred at room temperature for 16 h. The solvent was removed in vacuo and the residue was purified by preparative HPLC to give the title compound (11 mg, 20%). $^1$H NMR (CD$_3$OD, 2:1 mixture of amide rotamers) δ 8.72 (s, 1H), 8.12-7.83 (m, 7H), 7.77 (dd, J=7.9, 0.7 Hz, 1H), 7.73-7.63 (m, 3.5H), 7.43-7.36 (m, 1.5H), 7.23-7.09 (m, 3H), 7.08-7.04 (m, 0.5H), 6.81 (d, J=7.8 Hz, 0.5H), 4.48-4.40 (br s, 1H), 4.33-4.27 (m, 1H), 3.52-3.37 (m, 2.5H), 3.23-3.10 (m, 1.5H), 3.05 (br s., 1H), 2.90-2.85 (m, 1H), 2.80-2.67 (m, 2H), 1.54-1.39 (m, 4H), 1.35-1.29 (m, 2H), 1.28-1.22 (m, 1H), 1.06-1.01 (m, 1H), 0.90 (t, J=7.4 Hz, 1H), 0.82 (t, J=7.4 Hz, 2H), 0.68 (t, J=7.5 Hz, 2H), 0.60 (t, J=7.5 Hz, 1H); MS(ESI$^+$) m/z 703.2 (M+H)$^+$.

Example 287

4-(6-(Dibutylamino)pyridin-2-yl)-N-(naphthalen-2-ylsulfonyl)-3-(1,2,3,4-tetrahydroisoquinoline-2-carbonyl)benzamide

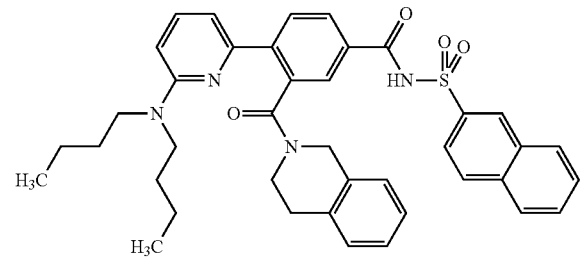

(287)

Intermediate 287A

6-Bromo-N,N-dibutylpyridin-2-amine

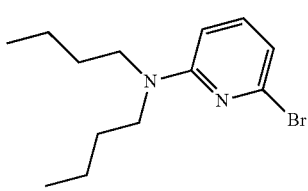

(Int-287A)

To a solution of 2,6-dibromopyridine (Aldrich, 1.42 g, 6.00 mmol) in DMF (2.0 mL) were added dibutylamine (Aldrich, 388 g, 3.00 mmol) and potassium carbonate (829 mg, 6.00 mmol). The reaction mixture was heated at 90° C. for 20 h. After cooling to room temperature, the reaction mixture was quenched by adding cold water. The mixture was extracted with DCM (3×), and the combined organic extracts were dried over Na$_2$SO$_4$, filtered and concentrated in vacuo to give a crude oil. Purification using flash column chromatography (eluting with DCM) provided the title compound (368 mg, 43%) as a light brown oil. $^1$H NMR (CDCl$_3$) δ 0.22 (dd, J=8.4, 7.4 Hz, 1H), 6.62 (d, J=7.0 Hz, 1H), 6.33 (d, J=8.3 Hz, 1H), 3.49-3.37 (m, 4H), 1.65-1.52 (m, 4H), 1.44-1.30 (m, 4H), 0.98 (t, J=7.3 Hz, 6H); MS(ESI$^+$) m/z 272.1 (M+H)$^+$.

Intermediate 287B

Methyl 4-(6-(dibutylamino)pyridin-2-yl)-3-(1,2,3,4-tetrahydroisoquinoline-2-carbonyl)benzoate

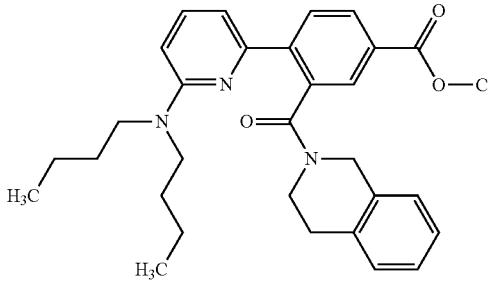

(Int-287B)

To a solution of 6-bromo-N,N-dibutylpyridin-2-amine (143 mg, 0.50 mmol) in 1,4-dioxane (5.0 mL) were added aq. 2N potassium phosphate (0.750 mL, 1.50 mmol), Pd(dppf)$_2$Cl$_2$ (75 mg, 0.050 mmol) and the boronic ester stock solution prepared in the synthesis of Intermediate 286B (3.0 mL, 0.50 mmol, 0.17M in 1,4-dioxane). The flask was evacuated and purged with argon (3×) and then heated at 90° C. for 8 h. After cooling to room temperature, the reaction mixture was diluted with EtOAc and filtered through CELITE®. The filtrate was concentrated in vacuo and the residue was purified by flash chromatography (gradient from 0 to 40% EtOAc/DCM) to afford the title compound (127 mg, 51%) as a light yellow solid. $^1$H NMR (CD$_3$OD, 2:1 mixture of amide rotamers) δ 8.28 (dd, J=8.3, 1.7 Hz, 1H), 8.08-7.89 (m, 3.5H), 7.83 (dd, J=8.0, 0.8 Hz, 0.5H), 7.48-7.41 (m, 1H), 7.27-7.10 (m, 3.5H), 6.86 (d, J=7.5 Hz, 0.5H), 4.50-4.36 (m, 0.5H), 3.97 (s, 2H), 3.96 (s, 1H), 3.93-3.83 (m, 1.5H), 3.62-3.42 (m, 2H), 3.33 (dt, J=3.2, 1.7 Hz, 1H), 3.27-3.03 (m, 3H), 2.92 (t, J=5.9 Hz, 1H), 2.79 (d, J=5.5 Hz, 1H), 1.58-1.23 (m, 5H), 1.13-1.04 (m, 3H), 0.93 (t, J=7.4 Hz, 1H), 0.85 (t, J=7.3 Hz, 2H), 0.72 (t, J=7.4 Hz, 2H), 0.64 (t, J=7.4 Hz, 1H); MS(ESI$^+$) m/z 500.5 (M+H)$^+$.

Intermediate 287C 4-(6-(Dibutylamino)pyridin-2-yl)-3-(1,2,3,4-tetrahydroisoquinoline-2-carbonyl)benzoic acid

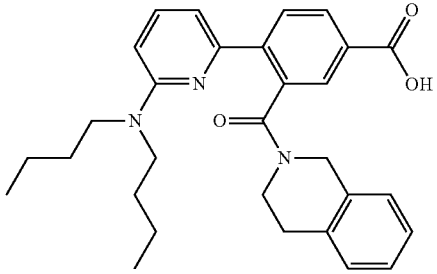

(Int-287C)

To a solution of methyl 4-(6-(dibutylamino)pyridin-2-yl)-3-(1,2,3,4-tetrahydroisoquinoline-2-carbonyl)benzoate (75 mg, 0.15 mmol) in THF (1.0 mL) and MeOH (1.0 mL) was added 2N NaOH (0.75 mL, 1.50 mmol). The resulting reaction mixture was stirred at room temperature for 1 h. At 0° C., the reaction mixture was neutralized to pH 4-5 with 1N HCl. The solution was extracted with EtOAc (3×) and the combined organic extracts were dried over MgSO$_4$, filtered and concentrated in vacuo to give the title compound (69 mg, 95%). MS(ESI$^+$) m/z 486.4 (M+H)$^+$.

Example 287

To a solution of 4-(6-(dibutylamino)pyridin-2-yl)-3-(1,2,3,4-tetrahydroisoquinoline-2-carbonyl)benzoic acid (20 mg, 0.041 mmol) in DMF (0.5 mL) and DCM (0.5 mL) were added naphthalene-2-sulfonamide (Aldrich, 17 mg, 0.082 mmol), EDC (Aldrich, 16 mg, 0.082 mmol) and DMAP (Aldrich, 15 mg, 0.12 mmol). The resulting reaction mixture was stirred at room temperature for 16 h. The solvents were removed in vacuo and the residue was purified by preparative HPLC to give the title compound (17 mg, 60%) as a white solid. $^1$H NMR (CD$_3$OD, 1:1 mixture of amide rotamers) δ 8.63 (s, 1H), 8.05-7.87 (m, 4H), 7.78 (dd, J=5.5, 1.8 Hz, 0.5H), 7.74 (d, J=8.3 Hz, 0.5H), 7.69-7.54 (m, 3H), 7.48 (dd, J=8.5, 7.5 Hz, 1H), 7.22 (dd, J=8.5, 7.5 Hz, 1H), 7.09-6.88 (m, 3H), 6.85 (d, J=7.3 Hz, 1H), 6.79 (d, J=7.3 Hz, 1H), 6.60 (d, J=7.3 Hz, 0.5H), 6.56-6.48 (m, 1H), 6.39 (d, J=8.5 Hz, 0.5H), 4.48-4.40 (br s, 1H), 4.33-4.27 (m, 1H), 3.52-3.37 (m, 2.5H), 3.23-3.10 (m, 1.5H), 3.05 (br s., 1H), 2.90-2.85 (m, 1H), 2.80-2.67 (m, J=19.7 Hz, 2H), 1.54-1.39 (m, 4H), 1.35-1.29 (m, 2H), 1.28-1.22 (m, 1H), 1.06-1.01 (m, 1H), 0.90 (t, J=7.4 Hz, 1H), 0.82 (t, J=7.4 Hz, 2H), 0.68 (t, J=7.5 Hz, 2H), 0.60 (t, J=7.5 Hz, 1H); MS(ESI$^+$) m/z 675.5 (M+H)$^+$.

Example 288

4-(3-Bromo-6-(dibutylamino)pyridin-2-yl)-N-(7-chloronaphthalen-2-ylsulfonyl)-3-(1,2,3,4-tetrahydroisoquinoline-2-carbonyl)benzamide

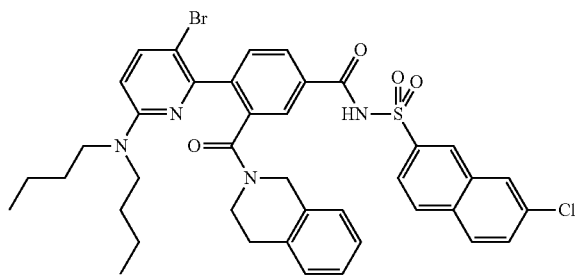

(288)

The title compound was prepared following a procedure analogous to that for the synthesis of Example 287, where 2,3,6-tribromopyridine was used to replace 2,6-dibromopyridine (Intermediate 287A) and 7-chloronaphthalene-2-sulfonamide (Intermediate 9) was used to replace naphthalene-2-sulfonamide (Example 287). MS (ESI$^+$) m/z 789.2 (M+H)$^+$.

Example 289

4-(3-Bromo-6-(dibutylamino)pyridin-2-yl)-N-(8-chloronaphthalen-2-ylsulfonyl)-3-(1,2,3,4-tetrahydroisoquinoline-2-carbonyl)benzamide

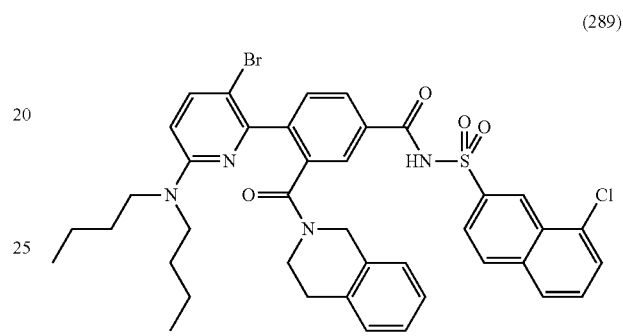

(289)

The title compound was prepared following a procedure analogous to that for the synthesis of Example 287, where 2,3,6-tribromopyridine (Matrix Scientific) was used to replace 2,6-dibromopyridine (Intermediate 287A) and 8-chloronaphthalene-2-sulfonamide (Intermediate 5) was used to replace naphthalene-2-sulfonamide (Example 287). MS(ESI$^+$) m/z 789.2 (M+H)$^+$.

Example 290

4-(3-Bromo-6-(dibutylamino)pyridin-2-yl)-N-(1-(3,4-dichlorobenzyl)indolin-5-ylsulfonyl)-3-(1,2,3,4-tetrahydroisoquinoline-2-carbonyl)benzamide

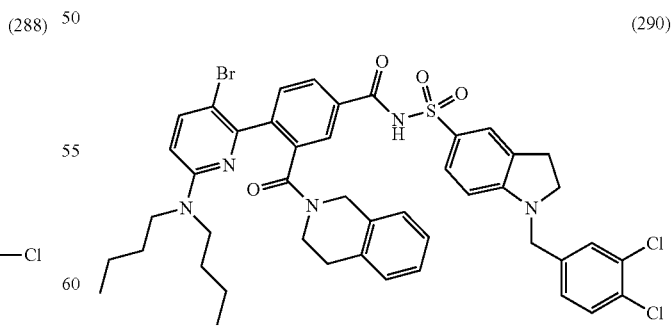

(290)

The title compound was prepared following a procedure analogous to that for the synthesis of Example 287, where 2,3,6-tribromopyridine was used to replace 2,6-dibromopyridine (Intermediate 287A) and 1-(3,4-dichlorobenzyl)indoline-5-sulfonamide (Intermediate 51) was used to replace naphthalene-2-sulfonamide (Example 287). MS (ESI⁺) m/z 904.2 (M+H)⁺.

Example 291

4-(2-(Dibutylamino)pyrimidin-4-yl)-N-(naphthalen-2-ylsulfonyl)-3-(1,2,3,4-tetrahydroisoquinoline-2-carbonyl)benzamide

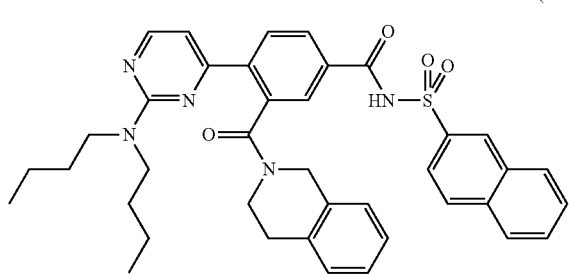

(291)

Intermediate 291A

Methyl 4-(2-chloropyrimidin-4-yl)-3-(1,2,3,4-tetrahydroisoquinoline-2-carbonyl)benzoate

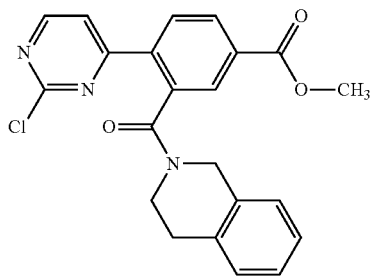

(Int-291A)

To a solution of 2,4-dichloropyrimidine (67 mg, 0.45 mmol) in 1,4-dioxane (0.02 mL) were added aq. 2N potassium phosphate (0.34 mL, 0.68 mmol), Pd(dppf)₂Cl₂ (33 mg, 0.045 mmol) and the boronic ester stock solution prepared in the synthesis of Intermediate 286B (1.4 mL, 0.50 mmol, 0.17 M in 1,4-dioxane). The flask was evacuated and purged with argon (3×) and then heated at 90° C. for 9 h. After cooling to room temperature, the reaction mixture was then diluted with EtOAc and filtered through CELITE®. The filtrate was concentrated in vacuo and the residue was purified by flash column chromatography (gradient from 0 to 40% EtOAc/DCM) to afford the title compound (700 mg, 76%) as a light yellow solid. ¹H NMR (CD₃OD, 1:1 mixture of amide rotamers) δ 8.78 (d, J=5.3 Hz, 0.5H), 8.62 (d, J=5.3 Hz, 0.5H), 8.27 (d, J=1.8 Hz, 0.5H), 8.25 (d, J=1.8 Hz, 0.5H), 8.11 (d, J=5.1 Hz, 0.5H), 8.09 (t, J=1.5 Hz, 1H), 8.02 (d, J=8.1 Hz, 0.5H), 7.92 (d, J=5.3 Hz, 0.5H), 7.79 (d, J=5.1 Hz, 0.5H), 7.27-7.15 (m, 3H), 7.12-7.07 (m, 0.5H), 6.83 (d, J=7.5 Hz, 0.5H), 4.44 (br s, 1H), 4.26 (s, 0.5H), 3.98 (s, 3H), 3.74 (br s., 0.5H), 3.61 (t, J=5.7 Hz, 1H), 3.33 (dt, J=3.3, 1.7 Hz, 1H), 3.13 (br s, 0.5H), 2.97 (br s, 0.5H), 2.92 (d, J=5.3 Hz, 1H); MS(ESI⁺) m/z 408.2 (M+H)⁺.

Intermediate 291B 4-(2-(Dibutylamino)pyrimidin-4-yl)-3-(1,2,3,4-tetrahydroisoquinoline-2-carbonyl)benzoic acid

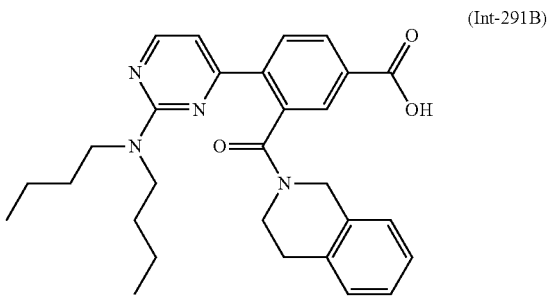 [SMILES: CCCCN(CCCC)c1nccc(-c2ccc(C(=O)O)cc2C(=O)N2CCc3ccccc3C2)n1]

(Int-291B)

To a solution of methyl 4-(2-chloropyrimidin-4-yl)-3-(1,2,3,4-tetrahydroisoquinoline-2-carbonyl)benzoate (82 mg, 0.20 mmol) in DMF (1.0 mL) were added dibutylamine (Aldrich, 52 mg, 0.40 mmol) and potassium carbonate (83 mg, 0.60 mmol). The reaction mixture was heated at 60° C. for 5 h and 80° C. for 3 h. After cooling to room temperature, the reaction mixture was quenched with cold water. The mixture was extracted with EtOAc (3×). The combined organic extracts were dried over MgSO₄, filtered and concentrated in vacuo to give the title compound (69 mg, 95%). MS (ESI⁺) m/z 501.2 (M+H)⁺.

The above residue was dissolved in THF (1.0 ml) and MeOH (1.0 ml). To the solution was added 2M NaOH (1.0 mL, 2.0 mmol). The resulting reaction mixture was stirred at room temperature for 1 h. At 0° C., the reaction mixture was neutralized to pH 3-4 with 1N HCl. The solution was extracted with EtOAc (3×) and the combined organic extracts were dried over MgSO₄, filtered and concentrated in vacuo. The residue was purified by preparative HPLC to give the title compound (64 mg, 66% for two steps). ¹H NMR (CD₃OD, 1:1 mixture of amide rotamers) δ 8.21 (d, J=5.7 Hz, 1H), 8.16-8.08 (m, 1H), 8.00 (dd, J=7.8, 1.4 Hz, 1H), 7.96-7.87 (m, 1.5H), 7.79 (d, J=8.1 Hz, 1H), 7.12-6.89 (m, 3H), 6.87 (d, J=5.9 Hz, 0.5H), 6.66 (d, J=7.5 Hz, 0.5H), 4.72 (m, 0.5H), 4.16 (m, 0.5H), 3.48-3.27 (m, 5H), 3.18 (dt, J=3.2, 1.6 Hz, 2H), 2.79-2.71 (m, 2H), 1.45-1.23 (m, 4H), 1.17-1.04 (m, 4H), 0.88-0.81 (m, 3H), 0.80-0.72 (m, 3H); MS(ESI⁺) m/z 487.3 (M+H)⁺.

Example 291

To a solution of 4-(2-(dibutylamino)pyrimidin-4-yl)-3-(1,2,3,4-tetrahydroisoquinoline-2-carbonyl)benzoic acid (25 mg, 0.051 mmol) in DMF (0.5 mL) and DCM (0.5 mL) were added naphthalene-2-sulfonamide (16 mg, 0.077 mmol), EDC (16 mg, 0.082 mmol) and DMAP (15 mg, 0.12 mmol). The resulting reaction mixture was stirred at room temperature for 16 h. The solvents were removed in vacuo and the residue was purified by preparative HPLC to give the title compound (20 mg, 59%). ¹H NMR (CD₃OD, 1:1 mixture of amide rotamers) δ 8.64 (s, 1H), 8.27 (d, J=5.0 Hz, 0.5H), 8.16-7.92 (m, 5.5H), 7.91-7.82 (m, 1H), 7.76 (d, J=8.3 Hz, 0.5H), 7.69-7.55 (m, 3.5H), 7.22-6.93 (m, 2.5H), 6.84 (d, J=5.0 Hz, 0.5H), 6.71 (d, J=7.5 Hz, 0.5H), 6.65 (d, J=5.0 Hz, 0.5H), 4.72-4.61 (m, 0.5H), 4.37-4.24 (m, 0.5H), 3.69-3.45 (m, 3H), 3.42-3.33 (m, 2H), 3.22 (d, J=10.5 Hz, 2.5H), 2.81 (t, J=6.1 Hz, 0.5H), 2.57 (br. s., 0.5H), 2.14 (br. s., 0.5H), 1.50-1.32 (m, 4H), 1.31-1.17 (m, 4H), 0.94-0.81 (m, 6H); MS(ESI⁺) m/z 676.7 (M+H)⁺.

Examples 292 to 295

The following Examples were prepared using 4-(2-(dibutylamino)pyrimidin-4-yl)-3-(1,2,3,4-tetrahydroisoquinoline-2-carbonyl)benzoic acid (Intermediate 291B) and the sulfonamide intermediates described previously, according to the procedure for the synthesis of Example 291.

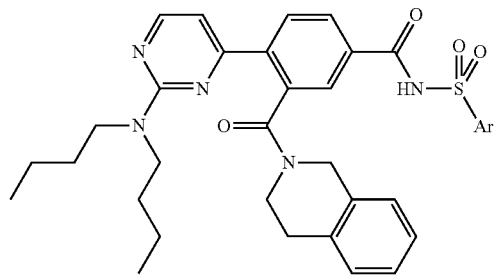

| Ex. No. | Ar | Name | LCMS (M + H) |
|---|---|---|---|
| 292 | (8-chloronaphthalen-2-yl) | N-(8-chloronaphthalen-2-ylsulfonyl)-4-(2-(dibutylamino)pyrimidin-4-yl)-3-(1,2,3,4-tetrahydroisoquinoline-2-carbonyl)benzamide | 710.2 |
| 293 | (7-iodonaphthalen-2-yl) | 4-(2-(dibutylamino)pyrimidin-4-yl)-N-(7-iodonaphthalen-2-ylsulfonyl)-3-(1,2,3,4-tetrahydroisoquinoline-2-carbonyl)benzamide | 802.1 |
| 294 | (1-ethyl-1H-indol-5-yl) | 4-(2-(dibutylamino)pyrimidin-4-yl)-N-(1-ethyl-1H-indol-5-ylsulfonyl)-3-(1,2,3,4-tetrahydroisoquinoline-2-carbonyl)benzamide | 695.3 |
| 295 | (1-(3,4-dichlorobenzyl)-1H-indol-5-yl) | 4-(2-(dibutylamino)pyrimidin-4-yl)-N-(1-(3,4-dichlorobenzyl)-1H-indol-5-ylsulfonyl)-3-(1,2,3,4-tetrahydroisoquinoline-2-carbonyl)benzamide | 825.5 |

Examples 296 to 302

The following Examples were prepared following a procedure analogous to that for the synthesis of Example 291. Dibutylamine in the synthesis of Intermediate 291B was replaced with corresponding alkyl amines

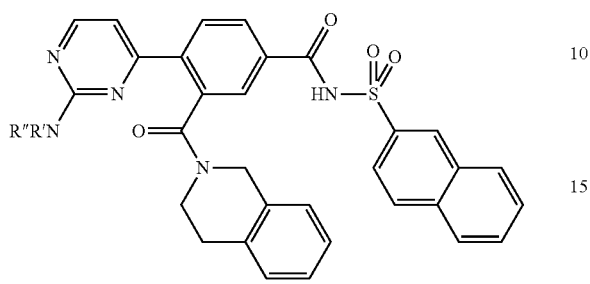

| Ex. No. | —NR'R" | Name | LCMS (M + H) |
|---|---|---|---|
| 296 | —N(CH₂CH₂CH₂CH₂CH₃)₂ | 4-(2-(dipentylamino)pyrimidin-4-yl)-N-(naphthalen-2-ylsulfonyl)-3-(1,2,3,4-tetrahydroisoquinoline-2-carbonyl)benzamide | 704.4 |
| 297 | (3-propylpyrrolidin-1-yl) | N-(naphthalen-2-ylsulfonyl)-4-(2-(3-propylpyrrolidin-1-yl)pyrimidin-4-yl)-3-(1,2,3,4-tetrahydroisoquinoline-2-carbonyl)benzamide | 660.5 |
| 298 | butyl(3,4-dichlorobenzyl)amino | 4-(2-(butyl(3,4-dichlorobenzyl)amino)pyrimidin-4-yl)-N-(naphthalen-2-ylsulfonyl)-3-(1,2,3,4-tetrahydroisoquinoline-2-carbonyl)benzamide | 778.1 |
| 299 | —N(CH₂CH₂CH₃)₂ | 4-(2-(dipropylamino)pyrimidin-4-yl)-N-(naphthalen-2-ylsulfonyl)-3-(1,2,3,4-tetrahydroisoquinoline-2-carbonyl)benzamide | 648.3 |
| 300 | (cyclopropylmethyl)(propyl)amino | 4-(2-((cyclopropylmethyl)(propyl)amino)pyrimidin-4-yl)-N-(naphthalen-2-ylsulfonyl)-3-(1,2,3,4-tetrahydroisoquinoline-2-carbonyl)benzamide | 660.2 |
| 301 | —N(CH₂CH₃)₂ | 4-(2-(diethylamino)pyrimidin-4-yl)-N-(naphthalen-2-ylsulfonyl)-3-(1,2,3,4-tetrahydroisoquinoline-2-carbonyl)benzamide | 620.2 |
| 302 | (3-phenethylpyrrolidin-1-yl) | N-(naphthalen-2-ylsulfonyl)-4-(2-(3-phenethylpyrrolidin-1-yl)pyrimidin-4-yl)-3-(1,2,3,4-tetrahydroisoquinoline-2-carbonyl)benzamide | 722.4 |

Example 303

(S)-4-(2-(Dibutylamino)pyrimidin-4-yl)-3-(3-(hydroxymethyl)-1,2,3,4-tetrahydroisoquinoline-2-carbonyl)-N-(naphthalen-2-ylsulfonyl)benzamide

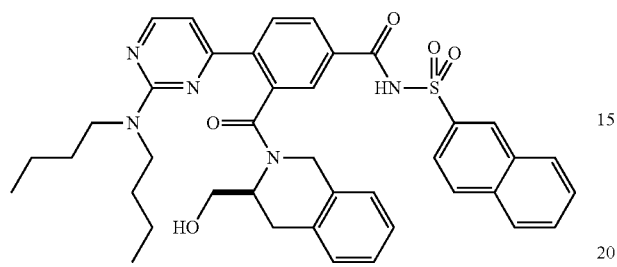

(303)

Intermediate 303A 3-tert-Butyl 1-methyl 4-(4,4,5,5-tetramethyl-1,3,2-dioxaborolan-2-yl)isophthalate

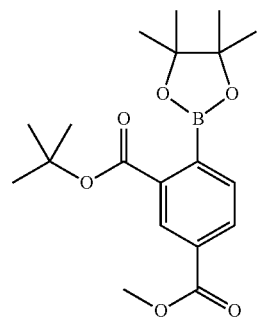

(Int-303A)

A solution of 3-tert-butyl 1-methyl 4-(trifluoromethylsulfonyloxy)isophthalate (Miura, M. et al., *Synth. Commun.*, 36:3809-3820 (2006)) (3.00 g, 7.81 mmol) in 1,4-dioxane (30.0 mL) was degassed with argon for 5 minutes while stirring. Potassium acetate (2.68 g, 27.3 mmol), 4,4,4',4',5,5,5',5'-octamethyl-2,2'-bi(1,3,2-dioxaborolane) (2.38 g, 9.37 mmol) and Pd(dppf)$_2$Cl$_2$-CH$_2$Cl$_2$ (637 mg, 0.78 mmol) were then added sequentially while bubbling argon through the mixture. After 5 min at room temperature, the argon stream was removed and the reaction mixture was stirred at 70° C. for 16 h in a sealed tube. The reaction mixture was then cooled to room temperature, diluted with DCM, and washed with water and brine solution. The organic layer was dried over MgSO$_4$, filtered, concentrated in vacuo. The residue was purified by flash column chromatography (eluting with DCM) to afford the title compound (2.30 g, 81%) as a white solid. $^1$H NMR (CDCl$_3$) δ 8.43 (d, J=1.1 Hz, 1H), 8.13 (dd, J=8.1, 1.1 Hz, 1H), 7.55 (d, J=8.1 Hz, 1H), 3.94 (s, 3H), 1.61 (s, 9H), 1.43 (s, 12H); MS(ESI$^+$) m/z 307.2 (M+H-C(CH$_3$)$_3$)$^+$.

Intermediate 303B 3-tert-Butyl 1-methyl 4-(2-chloropyrimidin-4-yl)isophthalate

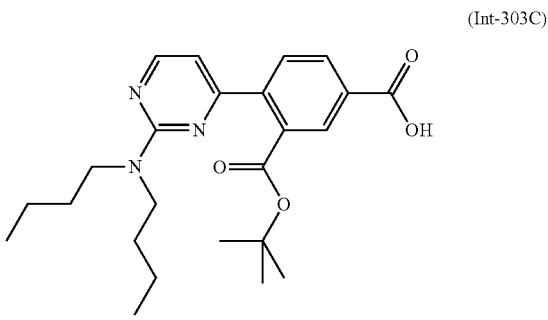 [SMILES: CCCCN(CCCC)c1nccc(-c2ccc(C(=O)O)cc2C(=O)OC(C)(C)C)n1]

(Int-303B)

To a solution of 2,4-dichloropyrimidine (1.61 g, 8.78 mmol) in 1,4-dioxane (20.0 mL) were added aq. 2N potassium phosphate (12.8 mL, 25.6 mmol), Pd(dppf)$_2$Cl$_2$ (268 mg, 0.37 mmol) 3-tert-butyl 1-methyl 4-(4,4,5,5-tetramethyl-1,3,2-dioxaborolan-2-yl)isophthalate (2.65 g, 7.32 mmol). The flask was evacuated and purged with argon (3 x) and then heated at 80° C. for 10 h. After cooling to room temperature, the reaction mixture was diluted with EtOAc and filtered through CELITE®. The filtrate was concentrated in vacuo and the residue was purified by flash chromatography (gradient from 0 to 40% EtOAc/DCM) to afford the title compound (1.87 g, 67%) as a white solid. $^1$H NMR (CDCl$_3$) δ 8.70 (d, J=5.1 Hz, 1H), 8.51 (d, J=1.5 Hz, 1H), 8.29-8.19 (m, 1H), 7.56-7.50 (m, 1H), 7.42 (d, J=5.1 Hz, 1H), 3.98 (s, 3H), 1.43 (s, 9H); MS(ESI$^+$) m/z 349.0 (M+H)$^+$.

Intermediate 303C 3-(tert-Butoxycarbonyl)-4-(2-(dibutylamino)pyrimidin-4-yl)benzoic acid (Int-303C)

Following a procedure analogous to that for the synthesis of Intermediate 291B, 3-tert-butyl 1-methyl 4-(2-chloropyrimidin-4-yl)isophthalate (244 mg, 0.70 mmol) was converted to the title compound (210 mg, 70% for two steps). MS(ESI⁺) m/z 428.2 (M+H)⁺.

Intermediate 303D tert-Butyl 2-(2-(dibutylamino)pyrimidin-4-yl)-5-(naphthalen-2-ylsulfonylcarbamoyl)benzoate

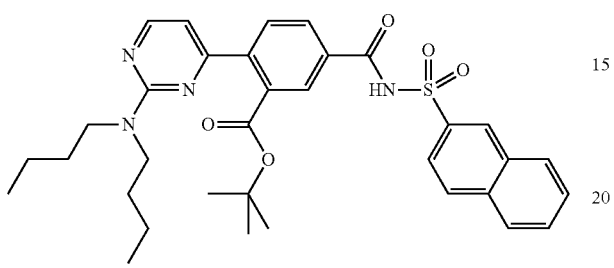

(Int-303D)

Following a procedure analogous to that for the synthesis of Example 291, 3-(tert-butoxycarbonyl)-4-(2-(dibutylamino)pyrimidin-4-yl)benzoic acid (244 mg, 0.70 mmol) was converted to the title compound (111 mg, 61%). MS(ESI⁺) m/z 617.2 (M+H)⁺.

Intermediate 303E 2-(2-(Dibutylamino)pyrimidin-4-yl)-5-(naphthalen-2-ylsulfonylcarbamoyl)benzoic acid

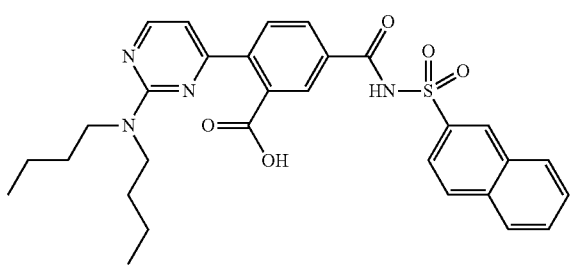

(Int-303E)

To a solution of tert-butyl 2-(2-(dibutylamino)pyrimidin-4-yl)-5-(naphthalen-2-ylsulfonylcarbamoyl)benzoate (110 mg, 0.18 mmol) in DCM (2.0 mL) was added TFA (2.0 mL). The reaction mixture was stirred at room temperature for 3 h and concentrated in vacuo to give the title compound (95 mg, 95%), which was used in subsequent reaction without purification. MS(ESI⁺) m/z 561.2 (M+H)⁺.

Example 303

To a solution of crude 2-(2-(dibutylamino)pyrimidin-4-yl)-5-(naphthalen-2-ylsulfonylcarbamoyl)benzoic acid (17 mg, 0.03 mmol) in DMF (0.8 mL) were added (S)-(1,2,3,4-tetrahydroisoquinolin-3-yl)methanol (Aldrich, 6 mg, 0.036 mmol), HATU (23 mg, 0.06 mmol) and DIEA (19 mg, 0.15 mmol). The reaction mixture was stirred at room temperature for 1 h. The solution was purified by preparative HPLC to give the title compound (8 mg, 37%). ¹H NMR (CD₃OD:CDCl₃, 1:1 mixture of amide rotamers) δ 9.62 (s, 1H), 8.41 (d, J=7.5 Hz, 1H), 8.35 (d, J=8.3 Hz, 1H), 8.26 (br s, 2H), 8.12 (d, J=8.3 Hz, 1H), 8.01-7.95 (m, 1H), 7.87 (t, J=7.8 Hz, 1H), 7.63-7.51 (m, 1H), 7.38-7.27 (m, 2H), 7.21-7.05 (m, 4.5H), 6.95-6.86 (m, 0.5H), 4.60 (br s, 0.5H), 4.33 (br s, 1.5H), 3.66 (br s, 1H), 3.55-3.44 (m, 4H), 3.04 (d, J=7.8 Hz, 1H), 2.82 (br s, 2H), 2.34 (s, 1H), 2.22 (s, 1H), 1.32-1.18 (m, 4H), 1.13-0.97 (m, 2H), 0.88 (dt, J=10.8, 7.2 Hz, 5H), 0.74 (t, J=7.4 Hz, 2H), 0.68 (t, J=7.4 Hz, 1H); MS(ESI⁺) m/z 706.3 (M+H)⁺.

Example 304

(S)-3-(3-(Aminomethyl)-1,2,3,4-tetrahydroisoquinoline-2-carbonyl)-4-(2-(dibutylamino)pyrimidin-4-yl)-N-(naphthalen-2-ylsulfonyl)benzamide

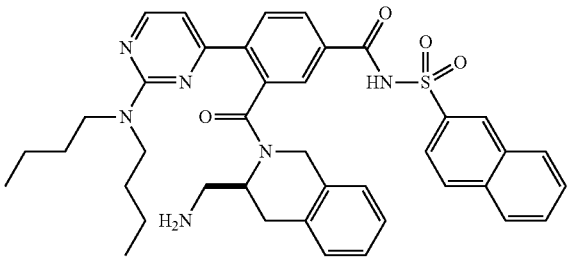

(304)

Following a procedure analogous to that for the synthesis of Example 303, 2-(2-(dibutylamino)pyrimidin-4-yl)-5-(naphthalen-2-ylsulfonylcarbamoyl)benzoic acid (Intermediate 303E, 25 mg, 0.05 mmol) was reacted with ((S)-3-(azidomethyl)-1,2,3,4-tetrahydroisoquinoline (Intermediate 92A, 11 mg, 0.06 mmol) and provided a crude oil which was dissolved in THF (1.1 mL). PPh₃ (10 mg, 0.014 mmol) was added followed by aq. 0.5N NaOH (100 µL). The resulting reaction mixture was stirred at 50° C. for 1.5 h and then neutralized with 1N HCl solution (100 µL). The volatiles were removed in vacuo, and the residue was purified by preparative HPLC to give the title compound (5 mg, 52%). MS(ESI⁺) m/z 705.2 (M+H)⁺.

Examples 305 to 307

The following Examples were prepared using 2-(2-(dibutylamino)pyrimidin-4-yl)-5-(naphthalen-2-ylsulfonylcarbamoyl)benzoic acid (Intermediate 303E) and the corresponding commercially available amines according to the procedure for the synthesis of Example 303.

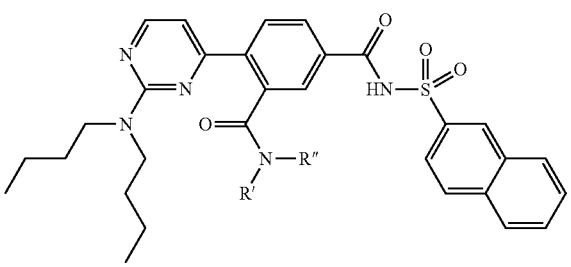

| Ex. No. | —NR'R" | Name | LCMS (M + H) |
|---|---|---|---|
| 305 | isoindoline | 4-(2-(dibutylamino)-pyrimidin-4-yl)-3-(isoindoline-2-carbonyl)-N-(naphthalen-2-ylsulfonyl)benzamide | 662.2 |
| 306 | 7-CF₃-tetrahydroisoquinoline | 4-(2-(dibutylamino)-pyrimidin-4-yl)-N-(naphthalen-2-ylsulfonyl)-3-(7-(trifluoromethyl)-1,2,3,4-tetrahydro-isoquinoline-2-carbonyl)benzamide | 744.2 |
| 307 | —N(CH₃)₂ | 4-(2-(dibutylamino)-pyrimidin-4-yl)-N3,N3-dimethyl-N1-(naphthalen-2-ylsulfonyl) isophthalamide | 588.2 |

Example 308

(S)—N-(8-Chloronaphthalen-2-ylsulfonyl)-4-(2-(dibutylamino)pyrimidin-4-yl)-3-(3-(hydroxymethyl)-1,2,3,4-tetrahydroisoquinoline-2-carbonyl)benzamide (308)

The title compound was prepared by following a procedure analogous to that for the synthesis of Example 303, where 8-chloronaphthalene-2-sulfonamide (Intermediate 5) was used to replace naphthalene-2-sulfonamide (Intermediate 303D). MS (ESI⁺) m/z 740.2 (M+H)⁺.

Example 309

(S)-4-(2-(Dibutylamino)pyrimidin-4-yl)-3-(3-(hydroxymethyl)-1,2,3,4-tetrahydroisoquinoline-2-carbonyl)-N-(7-iodonaphthalen-2-ylsulfonyl)benzamide (309)

The title compound was prepared following a procedure analogous to that for the synthesis of Example 303, where 7-iodonaphthalene-2-sulfonamide (Intermediate 10) was used to replace naphthalene-2-sulfonamide (Intermediate 303D). MS(ESI⁺) m/z 832.1 (M+H)⁺.

Example 310

(S)-4-(2-(Dibutylamino)pyrimidin-4-yl)-N-(1-ethylindolin-5-ylsulfonyl)-3-(3-(hydroxymethyl)-1,2,3,4-tetrahydroisoquinoline-2-carbonyl)benzamide (310)

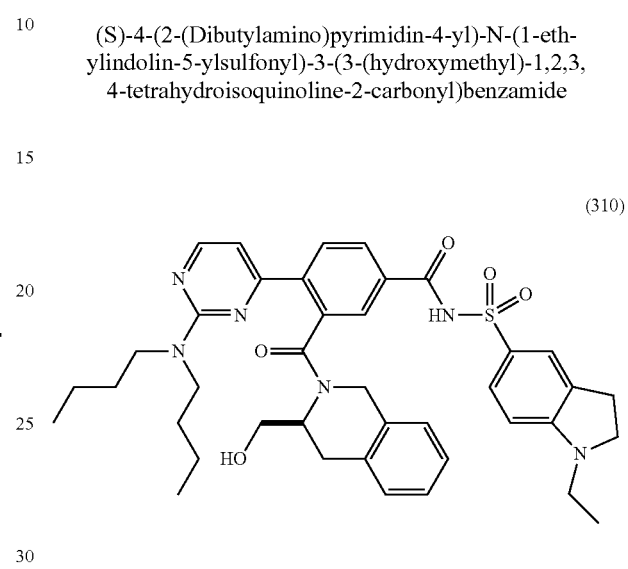

The title compound was prepared following a procedure analogous to that for the synthesis of Example 303, where 1-ethylindoline-5-sulfonamide (Intermediate 45) was used to replace naphthalene-2-sulfonamide (Intermediate 303D). MS(ESI⁺) m/z 725.3 (M+H)⁺.

Example 311

4-(5-Chloro-2-(dibutylamino)pyrimidin-4-yl)-N-(naphthalen-2-ylsulfonyl)-3-(1,2,3,4-tetrahydroisoquinoline-2-carbonyl)benzamide (311)

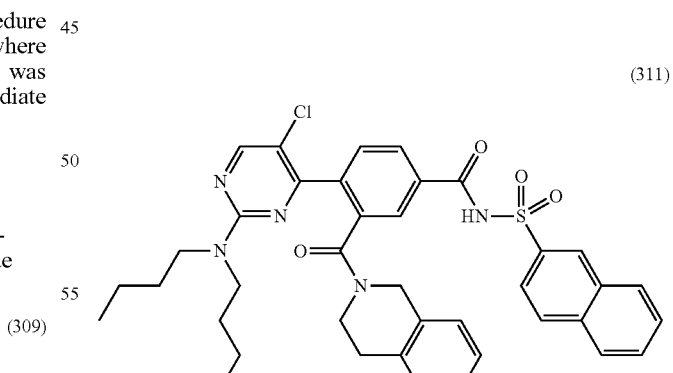

The title compound was prepared following a procedure analogous to that for the synthesis of Example 291, where 2,4,5-trichloropyrimidine (Aldrich) was used to replace 2,4-dichloropyrimidine (Intermediate 291A). MS(ESI⁺) m/z 710.2 (M+H)⁺.

Example 312

4-(2-(Dibutylamino)-5-methylpyrimidin-4-yl)-N-(naphthalen-2-ylsulfonyl)-3-(1,2,3,4-tetrahydroisoquinoline-2-carbonyl)benzamide (312)

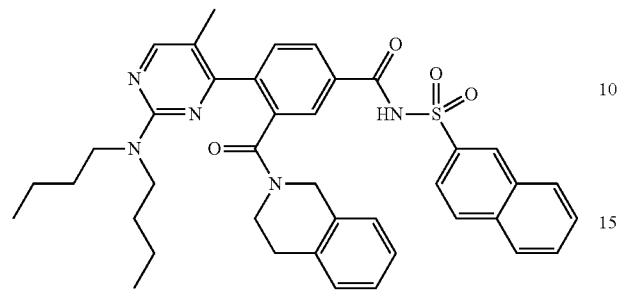

The title compound was prepared following a procedure analogous to that for the synthesis of Example 291, where 2,4-dichloro-5-methylpyrimidine was used to replace 2,4-dichloropyrimidine (Intermediate 291A). MS(ESI⁺) m/z 690.3 (M+H)⁺.

Example 313

4-(5-Chloro-2-(dibutylamino)pyrimidin-4-yl)-N-(8-chloronaphthalen-2-ylsulfonyl)-3-(1,2,3,4-tetrahydroisoquinoline-2-carbonyl)benzamide (313)

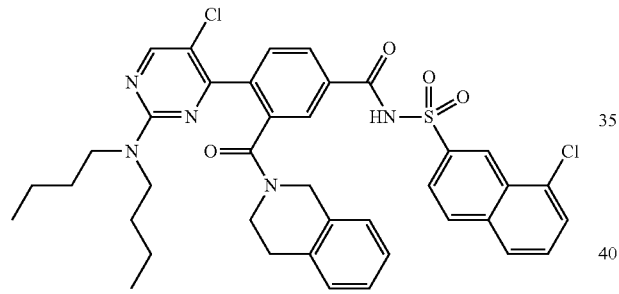

The title compound was prepared following a procedure analogous to that for the synthesis of Example 291, where 2,4,5-trichloropyrimidine was used to replace 2,4-dichloropyrimidine (Intermediate 291A) and 8-chloronaphthalene-2-sulfonamide (Intermediate 5) was used to replace naphthalene-2-sulfonamide (Example 291). MS (ESI⁺) m/z 744.1 (M+H)⁺.

Example 314

N-(8-Chloronaphthalen-2-ylsulfonyl)-4-(2-(dibutylamino)-5-methylpyrimidin-4-yl)-3-(1,2,3,4-tetrahydroisoquinoline-2-carbonyl)benzamide (314)

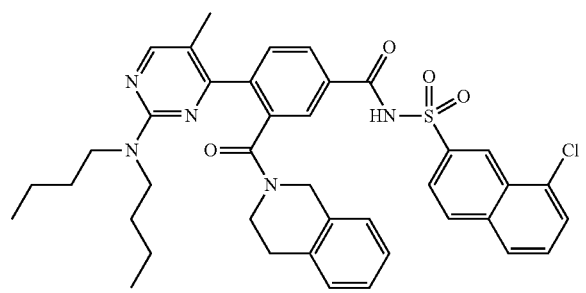

The title compound was prepared following a procedure analogous to that for the synthesis of Example 291, where 2,4-dichloro-5-methylpyrimidine (TCI) was used to replace 2,4-dichloropyrimidine (Intermediate 291A) and 8-chloronaphthalene-2-sulfonamide (Intermediate 5) was used to replace naphthalene-2-sulfonamide (Example 291). MS(ESI⁺) m/z 724.3 (M+H)⁺.

Example 315

4-(5-Chloro-2-(dibutylamino)pyrimidin-4-yl)-3-((S)-3-(hydroxymethyl)-1,2,3,4-tetrahydroisoquinoline-2-carbonyl)-N-(naphthalen-2-ylsulfonyl)benzamide (315)

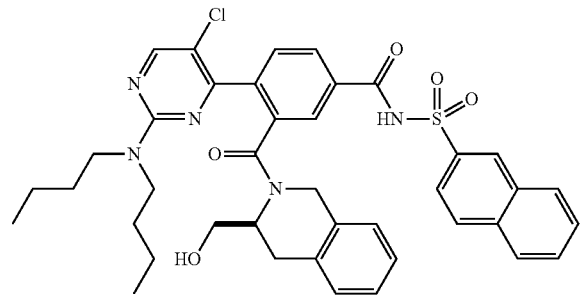

The title compound was prepared following a procedure analogous to that for the synthesis of Example 303, where 2,4,5-trichloropyrimidine (Aldrich) was used to replace 2,4-dichloropyrimidine (Intermediate 303B). MS(ESI⁺) m/z 740.4 (M+H)⁺.

Example 316

4-(5-Bromo-2-(dibutylamino)pyrimidin-4-yl)-3-((S)-3-(hydroxymethyl)-1,2,3,4-tetrahydroisoquinoline-2-carbonyl)-N-(naphthalen-2-ylsulfonyl)benzamide (316)

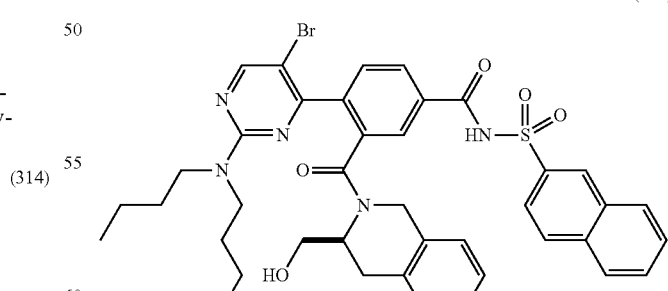

The title compound was prepared following a procedure analogous to that for the synthesis of Example 303, where 5-bromo-2,4-dichloropyrimidine (Aldrich) was used to replace 2,4-dichloropyrimidine (Intermediate 303B). MS(ESI⁺) m/z 786.2 (M+H)⁺.

Example 317

4-(5-Bromo-2-(dibutylamino)pyrimidin-4-yl)-N-(8-chloronaphthalen-2-ylsulfonyl)-3-(1,2,3,4-tetrahydroisoquinoline-2-carbonyl)benzamide (317)

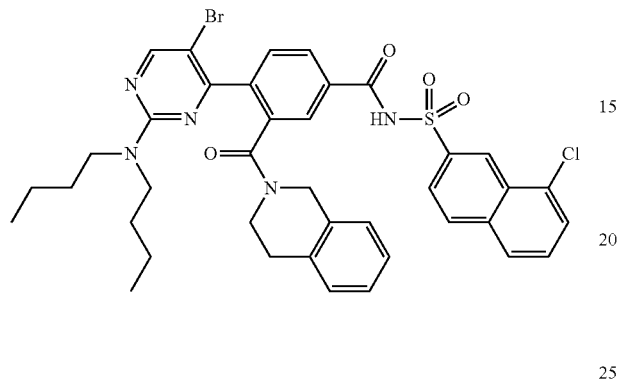

The title compound was prepared following a procedure analogous to that for the synthesis of Example 291, where 5-bromo-2,4-dichloropyrimidine (Aldrich) was used to replace 2,4-dichloropyrimidine (Intermediate 291A) and 8-chloronaphthalene-2-sulfonamide (Intermediate 5) was used to replace naphthalene-2-sulfonamide (Example 291). MS(ESI+) m/z 790.3 (M+H)+.

Example 318

4-(5-Chloro-2-(dibutylamino)pyrimidin-4-yl)-N-(7-chloronaphthalen-2-ylsulfonyl)-3-(1,2,3,4-tetrahydroisoquinoline-2-carbonyl)benzamide (318)

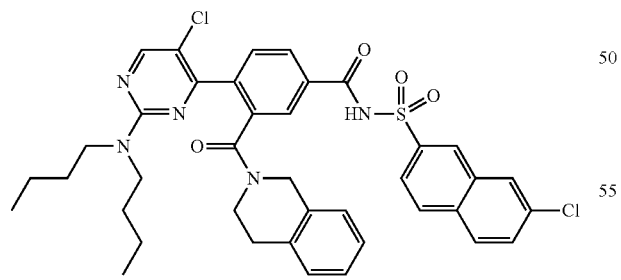

The title compound was prepared following a procedure analogous to that for the synthesis of Example 291, where 2,4,5-trichloropyrimidine was used to replace 2,4-dichloropyrimidine (Intermediate 291A) and 7-chloronaphthalene-2-sulfonamide (Intermediate 9) was used to replace naphthalene-2-sulfonamide (Example 291). MS (ESI+) m/z 744.3 (M+H)+.

Example 319

Ethyl 4-(4-(7-chloronaphthalen-2-ylsulfonylcarbamoyl)-2-(1,2,3,4-tetrahydroisoquinoline-2-carbonyl)phenyl)-2-(dibutylamino)pyrimidine-5-carboxylate (319)

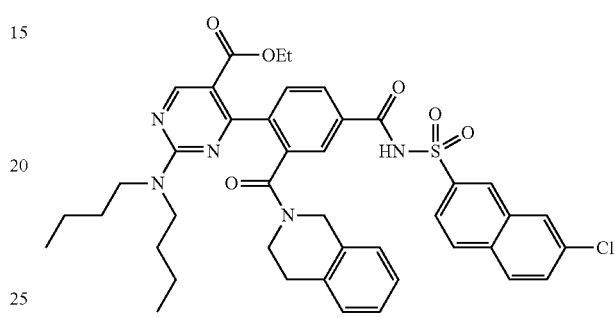

The title compound was prepared following a procedure analogous to that for the synthesis of Example 291, where ethyl 2,4-dichloropyrimidine-5-carboxylate (Aldrich) was used to replace 2,4-dichloropyrimidine (Intermediate 291A) and 7-chloronaphthalene-2-sulfonamide (Intermediate 9) was used to replace naphthalene-2-sulfonamide (Example 291). $^1$H NMR (CDCl$_3$, 1:1 mixture of amide rotamers) δ 8.89 (s, 1H), 8.69 (s, 0.5H), 8.49 (s, 0.5H), 8.13-8.06 (m, 1.5H), 8.03 (d, J=1.3 Hz, 0.5H), 7.99-7.82 (m, 5H), 7.62 (dd, J=8.7, 2.1 Hz, 1H), 7.45-7.45 (m, 1H), 7.23-6.93 (m, 3.5H), 6.69 (d, J=7.3 Hz, 0.5H), 4.70 (s, 0.5H), 4.39-4.31 (m, 1.5H), 4.20-4.13 (m, 1H), 4.10 (q, J=7.0 Hz, 2H), 3.62-3.47 (m, 4H), 3.41 (br s, 1H), 2.65 (br s, 1.5H), 2.52 (br s, 0.5H), 1.60-1.41 (m, 4H), 1.30-1.13 (m, 4H), 0.99 (t, J=7.3 Hz, 3H), 0.94-0.79 (m, 6H); MS(ESI+) m/z 782.3 (M+H)+.

Example 320

4-(4-(7-Chloronaphthalen-2-ylsulfonylcarbamoyl)-2-(1,2,3,4-tetrahydroisoquinoline-2-carbonyl)phenyl)-2-(dibutylamino)pyrimidine-5-carboxylic acid (320)

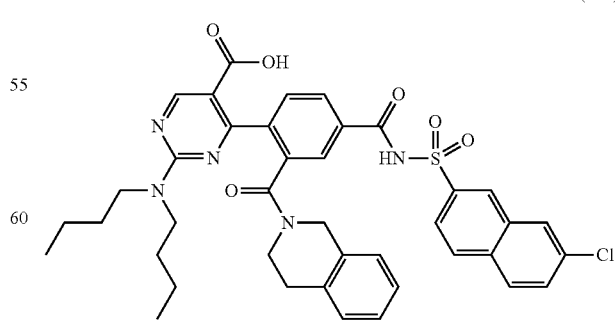

To a solution of ethyl 4-(4-(7-chloronaphthalen-2-ylsulfonylcarbamoyl)-2-(1,2,3,4-tetrahydroisoquinoline-2-carbonyl)phenyl)-2-(dibutylamino)pyrimidine-5-carboxylate (Example 319, 23 mg, 0.03 mmol) in THF (1.0 mL) and MeOH (1.0 mL) was added 2N NaOH (0.15 mL, 0.30 mmol). The resulting reaction mixture was stirred at 55° C. for 3 h. At 0° C., the reaction mixture was neutralized to pH 3-4 with aq. 1N HCl. The solution was extracted with EtOAc (3×) and the combined organic extracts were dried over MgSO$_4$, filtered and concentrated in vacuo. The residue was purified by preparative HPLC to give the title compound (14 mg, 63%). MS(ESI$^+$) m/z 754.3 (M+H)$^+$.

Example 321

4-(5-Chloro-2-(dibutylamino)pyrimidin-4-yl)-N-(1-(3,4-dichlorobenzyl)indolin-5-ylsulfonyl)-3-(1,2,3,4-tetrahydroisoquinoline-2-carbonyl)benzamide (321)

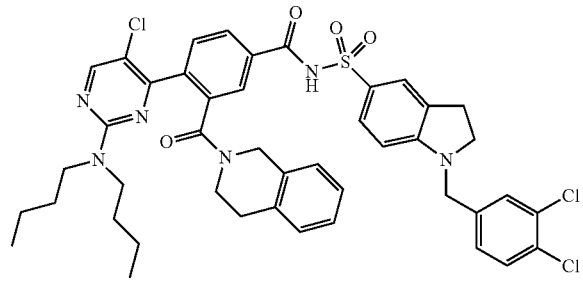

The title compound was prepared following a procedure analogous to that for the synthesis of Example 291, where 2,4,5-trichloropyrimidine (Aldrich) was used to replace 2,4-dichloropyrimidine (Intermediate 291A) and 1-(3,4-dichlorobenzyl)indoline-5-sulfonamide (Intermediate 51) was used to replace naphthalene-2-sulfonamide (Example 291). $^1$H NMR (DMSO-d$_6$, 1:1 mixture of amide rotamers) δ 8.45 (s, 1H), 8.08 (s, 1H), 8.05-7.97 (m, 2H), 7.73 (d, J=8.6 Hz, 0.5H), 7.69-7.50 (m, 4.5H), 7.32 (d, J=8.4 Hz, 1H), 7.24-7.03 (m, 4H), 6.96 (d, J=7.0 Hz, 0.5H), 6.67 (d, J=7.0 Hz, 0.5H), 4.60 (br. s., 0.5H), 4.47 (s, 2H), 4.37-4.28 (m, 0.5H), 3.55 (t, J=8.5 Hz, 2H), 3.45-3.30 (m, 4H), 3.19 (br s, 3H), 3.07 (t, J=8.5 Hz, 2H), 2.76-2.60 (m, 1.5H), 2.39-2.29 (m, 0.5H), 1.47-1.35 (m, 4H), 1.28-1.15 (m, 4H), 0.87-0.71 (m, 6H); MS(ESI$^+$) m/z 861.3 (M+H)$^+$.

Example 322

4-(2-(Butyl(3,4-dichlorobenzyl)amino)-5-chloropyrimidin-4-yl)-N-(8-chloronaphthalen-2-ylsulfonyl)-3-(1,2,3,4-tetrahydroisoquinoline-2-carbonyl)benzamide (322)

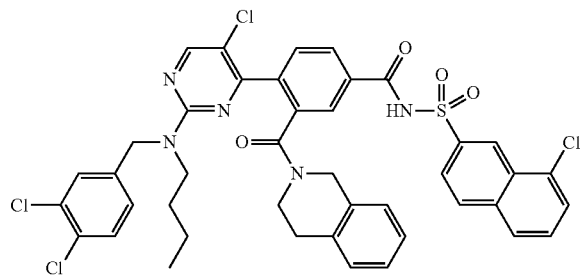

The title compound was prepared following a procedure analogous to that for the synthesis of Example 291, where 2,4,5-trichloropyrimidine (Aldrich) was used to replace 2,4-dichloropyrimidine (Intermediate 291A), N-(3,4-dichlorophenethyl)butan-1-amine (Intermediate 89) was used to replace dibutylamine (Intermediate 291B), and 8-chloronaphthalene-2-sulfonamide (Intermediate 5) was used to replace naphthalene-2-sulfonamide (Example 291). $^1$H NMR (CDCl$_3$, 1:1 mixture of amide rotamers) δ 9.14 (s, 1H), 8.34 (s, 1H), 8.20 (d, J=8.8 Hz, 1H), 8.02 (d, J=8.8 Hz, 1H), 7.95 (s, 0.5H), 7.90-7.82 (m, 3.5H), 7.73 (d, J=6.8 Hz, 1H), 7.65-7.52 (m, 3H), 7.26-7.02 (m, 5H), 6.95 (d, J=6.8 Hz, 0.5H), 6.82 (d, J=6.8 Hz, 0.5H), 4.72 (br s, 2H), 4.26 (d, J=5.7 Hz, 2H), 3.56-3.19 (m, 4H), 2.74 (br s, 1.5H), 2.58 (br s, 0.5H), 1.53-1.41 (m, 2H), 1.34-1.17 (m, 2H), 1.01-0.81 (m, 3H); MS(ESI$^+$) m/z 848.3 (M+H)$^+$.

Example 323

4-(5-Chloro-2-(dipropylamino)pyrimidin-4-yl)-N-(naphthalen-2-ylsulfonyl)-3-(1,2,3,4-tetrahydroisoquinoline-2-carbonyl)benzamide (323)

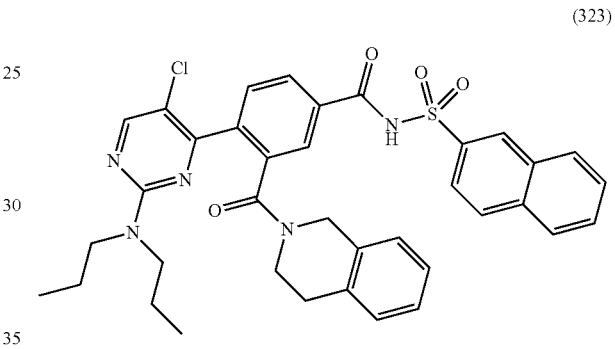

The title compound was prepared following a procedure analogous to that for the synthesis of Example 291, where 2,4,5-trichloropyrimidine (Aldrich) was used to replace 2,4-dichloropyrimidine (Intermediate 291A) and dipropylamine was used to replace dibutylamine (Intermediate 291B). $^1$H NMR (CD$_3$OD, 1:1 mixture of amide rotamers) δ 8.70 (s, 1H), 8.13-7.89 (m, 5.5H), 7.82 (s, 0.5H), 7.74-7.58 (m, 3H), 7.53 (s, 1H), 7.23-7.05 (m, 3H), 7.02 (d, J=6.8 Hz, 0.5H), 6.84 (d, J=6.8 Hz, 0.5H), 4.67 (br s, 0.5H), 4.28 (br s, 1H), 4.07 (br s, 0.5H), 3.45-3.37 (m, 2H), 3.01 (br s, 2H), 2.89 (br s, 2H), 2.71 (br s, 2H), 1.58-1.43 (m, 4H), 0.87-0.79 (m, 6H); MS(ESI$^+$) m/z 682.2 (M+H)$^+$.

Example 324

4-(5-Chloro-2-(dipropylamino)pyrimidin-4-yl)-3-((S)-3-(hydroxymethyl)-1,2,3,4-tetrahydroisoquinoline-2-carbonyl)-N-(naphthalen-2-ylsulfonyl)benzamide (324)

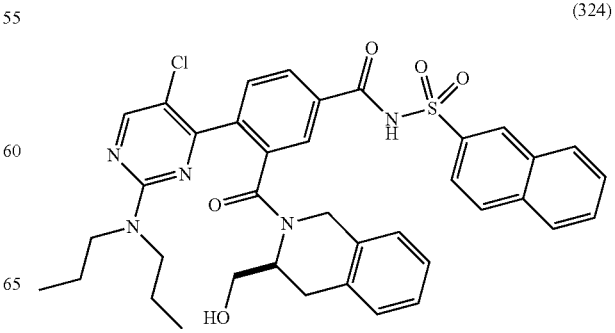

The title compound was prepared following a procedure analogous to that for the synthesis of Example 303, where 2,4,5-trichloropyrimidine (Aldrich) was used to replace 2,4-dichloropyrimidine (Intermediate 303B) and dipropylamine was used to replace dibutylamine (Intermediate 303C). $^1$H NMR (CDCl$_3$, 1:1 mixture of amide rotamers) δ 8.72 (s, 1H), 8.27 (s, 0.5H), 8.11-7.79 (m, 6.5H), 7.77-7.54 (m, 4H), 7.18-7.05 (m, 3H), 6.95 (d, J=7.0 Hz, 0.5H), 6.84 (d, J=7.0 Hz, 0.5H), 5.15 (d, J=18.3 Hz, 0.5H), 4.50 (d, J=18.3 Hz, 0.5H), 4.32-4.19 (m, 1.5H), 4.04-3.90 (m, 0.5H), 3.70 (br s, 1H), 3.43-3.19 (m, 3H), 2.80-2.45 (m, 5H), 1.61-1.31 (m, 4H), 0.98-0.63 (m, 6H); MS (ESI$^+$) m/z 712.3 (M+H)$^+$.

Example 325

4-(5-Bromo-2-(dipropylamino)pyrimidin-4-yl)-3-((S)-3-(hydroxymethyl)-1,2,3,4-tetrahydroisoquinoline-2-carbonyl)-N-(naphthalen-2-ylsulfonyl)benzamide (325)

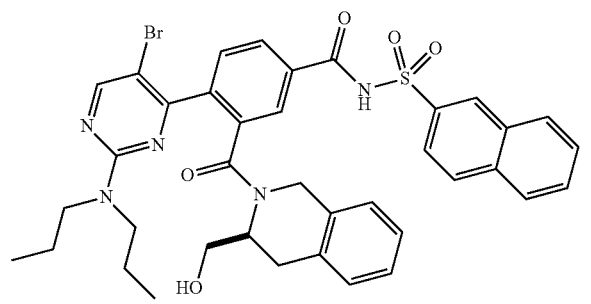

The title compound was prepared following a procedure analogous to that for the synthesis of Example 303, where 5-bromo-2,4-dichloropyrimidine (Aldrich) was used to replace 2,4-dichloropyrimidine (Intermediate 303B) and dipropylamine was used to replace dibutylamine (Intermediate 303C). $^1$H NMR (CD$_3$OD, 1:1 mixture of amide rotamers) δ 8.69 (s, 1H), 8.33 (s, 0.5H), 8.12-7.88 (m, 5.5H), 7.74-7.55 (m, 4H), 7.19-7.05 (m, 3H), 6.97 (d, J=6.6 Hz, 1H), 6.90 (d, J=6.6 Hz, 1H), 5.05 (br s, 0.5H), 5.00 (br s, 0.5H), 4.35 (m, 1.5H), 3.83 (br s, 0.5H), 3.52-3.41 (m., 3H), 3.31-3.14 (m, 3H), 2.73 (m, 1.5H), 2.57-2.42 (m, 0.5H), 1.55-1.33 (m, 4H), 1.01-0.62 (m, 6H); MS(ESI$^+$) m/z 758.1 (M+H)$^+$.

Example 326

4-(5-Chloro-2-((cyclopropylmethyl)(propyl)amino)pyrimidin-4-yl)-3-((S)-3-(hydroxymethyl)-1,2,3,4-tetrahydroisoquinoline-2-carbonyl)-N-(naphthalen-2-ylsulfonyl)benzamide (326)

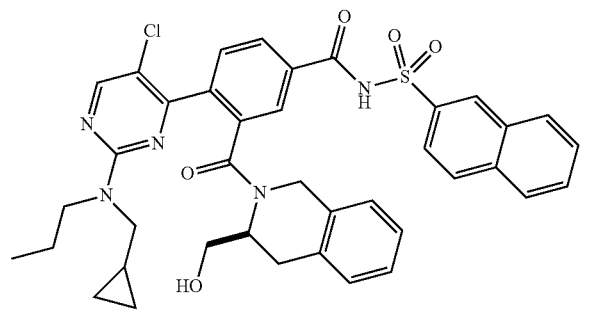

The title compound was prepared following a procedure analogous to that for the synthesis of Example 303, where 5-bromo-2,4-dichloropyrimidine (Aldrich) was used to replace 2,4-dichloropyrimidine (Intermediate 303B) and N-(cyclopropylmethyl)propan-1-amine (Aldrich) was used to replace dibutylamine (Intermediate 303C). $^1$H NMR (CD$_3$OD, 1:1 mixture of amide rotamers) δ 8.73 (s, 1H), 8.24 (s, 0.5H), 8.11-8.01 (m, 3.5H), 7.96 (d, J=7.9 Hz, 2H), 7.73-7.63 (m, 3H), 7.18-7.06 (m, 3H), 7.01-6.93 (m, 1H), 6.87 (s, 0.5H), 6.85 (s, 0.5H), 5.04 (br s, 0.5H), 4.99 (br s, 0.5H), 4.37-4.28 (m, 1.5H), 3.82 (br s, 0.5H), 3.61-3.49 (m, 2H), 3.30-3.24 (m, 2H), 3.19 (q, J=7.4 Hz, 2H), 2.82-2.74 (m, 1H), 2.51-2.43 (m, 1H), 1.59-1.47 (m, 2H), 1.40 (m, 2H), 1.34 (t, J=7.4 Hz, 3H), 0.88-0.71 (m, 2H), 0.42 (br s, 1H); MS(ESI$^+$) m/z 724.1 (M+H)$^+$.

Example 327

3-((S)-3-(Aminomethyl)-1,2,3,4-tetrahydroisoquinoline-2-carbonyl)-4-(5-chloro-2-(dipropylamino)pyrimidin-4-yl)-N-(naphthalen-2-ylsulfonyl)benzamide (327)

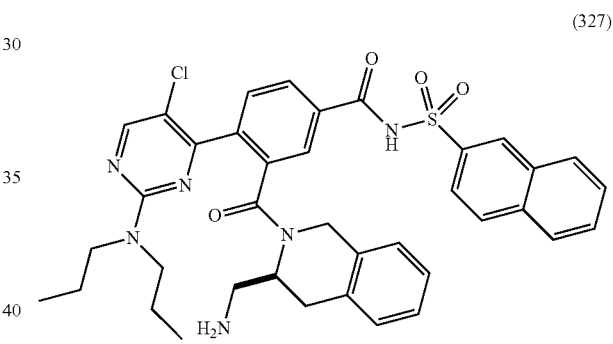

Following a procedure analogous to that for the synthesis of Example 303, 2-(2-(dipropylamino)pyrimidin-4-yl)-5-(naphthalen-2-ylsulfonylcarbamoyl)benzoic acid (30 mg, 0.053 mmol) was reacted with ((S)-3-(azidomethyl)-1,2,3,4-tetrahydroisoquinoline (Intermediate 92A, 15 mg, 0.079 mmol) to give a crude oil, which was used in the subsequent step without purification.

The crude oil from above was dissolved in THF (1.0 mL), and PPh$_3$ (21 mg, 0.081 mmol) was added followed by 0.5N NaOH (100 µL). The resulting reaction mixture was stirred at 50° C. for 3 h and then neutralized with 1N HCl solution (100 µL). The volatiles were removed in vacuo, and the residue was purified by preparative HPLC to give the title compound (14 mg, 37% for two steps). $^1$H NMR (CD$_3$OD, 1:1 mixture of amide rotamers) δ 8.78 (s, 1H), 8.19-8.09 (m, 4H), 8.05 (dd, J=8.1, 1.8 Hz, 1H), 7.83-7.67 (m, 5H), 7.25-7.12 (m, 2H), 7.06 (d, J=6.5 Hz, 1H), 6.95 (d, J=6.5 Hz, 1H), 5.22 (br s, 1H), 4.35 (s, 2H), 3.54-3.14 (m, 4H), 3.04 (d, J=6.4 Hz, 2H), 2.84-2.65 (m, 2H), 1.55-1.33 (m, 4H), 1.01-0.62 (m, 6H); MS(ESI$^+$) m/z 711.3 (M+H)$^+$.

Example 328

4-(5-Chloro-2-(dipropylamino)pyrimidin-4-yl)-N-(8-chloronaphthalen-2-ylsulfonyl)-3-((S)-3-(hydroxymethyl)-1,2,3,4-tetrahydroisoquinoline-2-carbonyl)benzamide

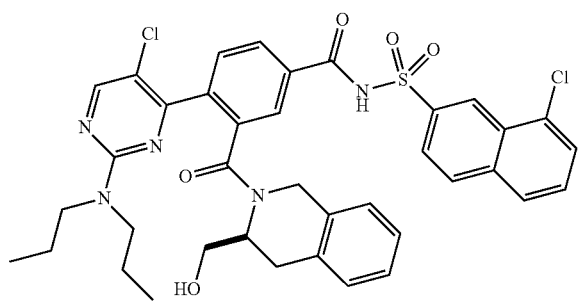

(328)

The title compound was prepared following a procedure analogous to that for the synthesis of Example 303, where 2,4,5-trichloropyrimidine was used to replace 2,4-dichloropyrimidine (Intermediate 303B), dipropylamine was used to replace dibutylamine (Intermediate 303C) and 8-chloronaphthalene-2-sulfonamide (Intermediate 5) was used to replace naphthalene-2-sulfonamide (Intermediate 303C). $^1$H NMR (CD$_3$OD, 1:1 mixture of amide rotamers) δ 9.05 (s, 1H), 8.96 (br s, 1H), 8.24 (br s, 1H), 8.14-8.04 (m, 2H), 7.85-7.49 (m, 5H), 7.16-6.89 (m, 3H), 6.82 (br s, 1H), 5.22-5.05 (m, 1H), 4.53 (br. s, 1H), 4.24 (br. s, 1H), 3.45-3.05 (m, 5H), 2.80-2.34 (m, 3H), 1.65-1.50 (m, 4H), 0.99-0.52 (m, 6H); MS(ESI$^+$) m/z 746.1 (M+H)$^+$.

Example 329

3-((S)-3-(Aminomethyl)-1,2,3,4-tetrahydroisoquinoline-2-carbonyl)-4-(5-chloro-2-(dipropylamino)pyrimidin-4-yl)-N-(8-chloronaphthalen-2-ylsulfonyl)benzamide

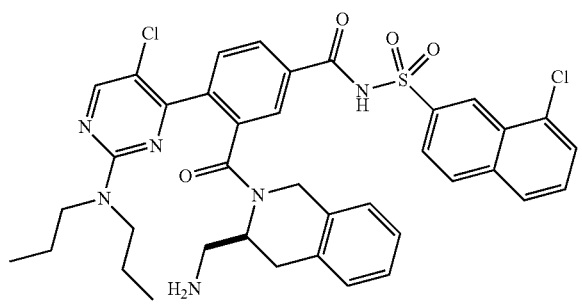

(329)

Following a procedure analogous to that for the synthesis of Example 303, 2-(5-chloro-2-(dipropylamino)pyrimidin-4-yl)-5-(8-chloronaphthalen-2-ylsulfonylcarbamoyl)benzoic acid (32 mg, 0.053 mmol) was reacted with ((S)-3-(azidomethyl)-1,2,3,4-tetrahydroisoquinoline (Intermediate 92A, 20 mg, 0.106 mmol) to give a crude oil which was used in the subsequent step without purification.

The crude oil from above was dissolved in THF (1.0 mL). PPh$_3$ (39 mg, 0.15 mmol) was added followed by 0.5N NaOH (100 μL). The resulting reaction mixture was stirred at 50° C. for 3 h and then neutralized with 1N HCl solution (100 μL). The volatiles were removed in vacuo, and the residue was purified by preparative HPLC to give the title compound (19 mg, 49% for two steps). $^1$H NMR (CDCl$_3$, 1:1 mixture of amide rotamers) δ 9.16 (s, 1H), 8.42-8.14 (m, 4 H), 8.02 (d, J=8.1 Hz, 1H), 7.82 (d, J=8.6 Hz, 1H), 7.76-7.47 (m, 5H), 7.15-7.04 (m, 2 H), 6.94 (d, J=6.0 Hz, 0.5H), 6.85 (d, J=6.0 Hz, 0.5H), 5.43 (br s, 1H), 4.48 (d, J=17.6 Hz, 1H), 4.28 (d, J=17.6 Hz, 1H), 3.45-2.98 (m, 5H), 2.88-2.48 (m, 5H), 1.65-1.23 (m, 4H), 1.01-0.51 (m, 6H); MS(ESI$^+$) m/z 745.1 (M+H)$^+$.

Example 330

1-(4-(((1-((2-Aminoethyl)thio)isoquinolin-6-yl)sulfonyl)carbamoyl)-2-(1,2,3,4-tetrahydroisoquinoline-2-carbonyl)phenyl)-N,N-dibutyl-4-chloro-5-methyl-1H-pyrazole-3-carboxamide

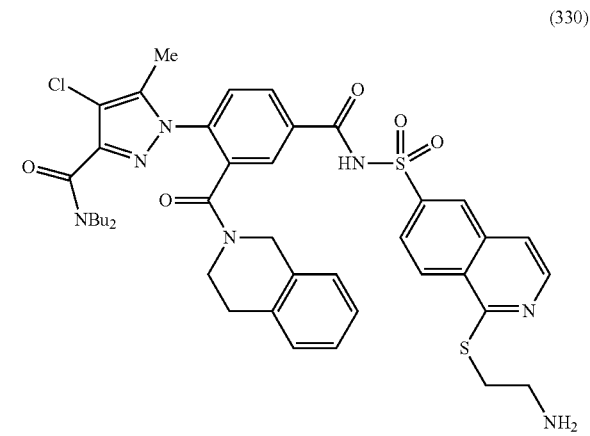

(330)

The title compound was prepared following procedures outlined above. MS (ESI$^+$) m/z 816.2 (M+H)$^+$.

Example 331

2-((6-(N-(4-(4-Chloro-3-(dibutylcarbamoyl)-5-methyl-1H-pyrazol-1-yl)-3-(1,2,3,4-tetrahydroisoquinoline-2-carbonyl)benzoyl)sulfamoyl)isoquinolin-1-yl)thio)acetic acid

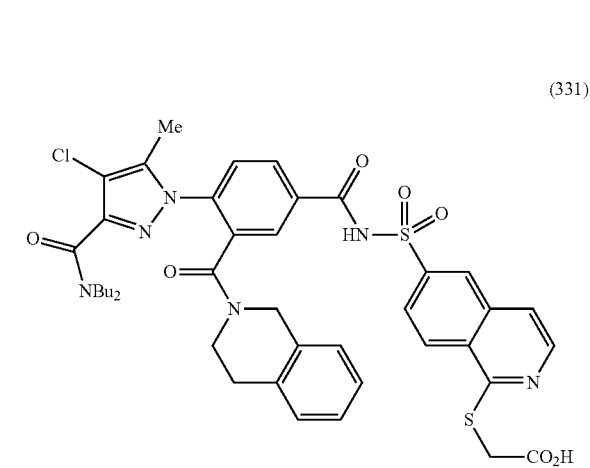

(331)

The title compound was prepared following procedures outlined above. MS (ESI+) m/z 831.2 (M+H)+.

| Ex. No. | ¹H NMR (2:1 mixture of amide rotamers) |
|---|---|
| 2 | (DMSO-d₆) δ 8.60-8.47 (m, 1H), 8.26-7.93 (m, 5H), 7.79 (d, J = 6.8 Hz, 1H), 7.67-7.48 (m, 2H), 7.33-7.10 (m, 3.5H), 7.06-6.96 (m, 0.5H), 4.57 (br s, 1H), 4.39-4.06 (m, 1H), 3.62-3.38 (m, 4H), 3.24-3.07 (m, 1H), 3.04-2.91 (m, 1H), 2.85-2.65 (m, 2H), 2.24 (s, 2H), 2.13 (s, 1H), 1.34-1.09 (m, 6H), 1.02-0.91 (m, 2H), 0.89-0.80 (m, 4H), 0.74-0.54 (m, 2H) |
| 3 | (DMSO-d₆) δ 8.23-8.15 (m, 1H), 8.12-8.02 (m, 1H), 8.02-7.92 (m, 1H), 7.88-7.79 (m, 1H), 7.79-7.69 (m, 1H), 7.64-7.45 (m, 2H), 7.30-7.03 (m, 5H), 7.00-6.89 (m, 1H), 4.62-4.27 (m, 2H), 3.62-3.37 (m, 4H), 3.20-3.08 (m, 1H), 3.03 (s, 6H), 3.00-2.92 (m, 1H), 2.80-2.64 (m, 2H), 2.19 (s, 2H), 2.14 (s, 1H), 1.41-1.06 (m, 6H), 1.02-0.91 (m, 2H), 0.89-0.77 (m, 3H), 0.73-0.60 (m, 3H) |
| 4 | (DMSO-d₆) δ 8.50 (br s, 1H), 8.45-8.32 (m, 2H), 8.10-7.98 (m, 2H), 7.81-7.66 (m, 2H), 7.59 (br s, 1H), 7.30-7.13 (m, 4.5H), 6.98-6.96 (m, 0.5H), 4.74-4.46 (m, 2H), 3.62-3.42 (m, 4H), 3.23-3.07 (m, 1H), 3.03-2.98 (m, 1H), 2.82 (s, 6H), 2.76 (br s, 2H), 2.21 (s, 2H), 2.17 (s, 1H), 1.40-1.10 (m, 6H), 1.02-0.89 (m, 2H), 0.88-0.75 (m, 3H), 0.73-0.55 (m, 3H) |
| 5 | (DMSO-d₆) δ 8.88 (s, 1H), 8.33-8.23 (m, 1H), 8.18-8.01 (m, 5H), 7.91 (d, J = 7.5 Hz, 1H), 7.81-7.67 (m, 2H), 7.29-7.13 (m, 3.5H), 6.99-6.97 (m, 0.5H) 4.73 (br s, 1H), 4.56 (br s, 1H), 3.76-3.53 (m, 4H), 3.22-3.07 (m, 1H), 3.03-2.90 (m, 1H), 2.82-2.71 (m, 2H), 2.22 (s, 2H), 2.18 (s, 1H), 1.41-1.06 (m, 6H), 1.03-0.89 (m, 2H), 0.88-0.75 (m, 3H), 0.73-0.54 (m, 3H) |
| 6 | (DMSO-d₆) δ 8.72 (s, 1H), 8.33-8.24 (m, 1H), 8.24-8.18 (m, 1H), 8.18-7.97 (m, 4H), 7.79-7.65 (m, 3H), 7.24-7.03 (m, 3.5H), 6.99-6.97 (m, 0.5H), 4.80-4.66 (m, 1H), 4.57 (br s, 1H), 3.62-3.41 (m, 4H), 3.15-3.04 (m, 1H), 3.00-2.88 (m, 1H), 2.82-2.73 (m, 2H), 2.22 (s, 2H), 2.18 (s, 1H), 1.38-1.07 (m, 6H), 1.04-0.89 (m, 2H), 0.87-0.76 (m, 3H), 0.73-0.55 (m, 3H) |
| 7 | (DMSO-d₆) δ 8.78-8.64 (m, 1H), 8.34-8.24 (m, 1H), 8.21-7.97 (m, 5H), 7.80-7.61 (m, 2H), 7.51-7.35 (m, 1H), 7.31-7.12 (m, 3.5H), 7.09-6.98 (m, 0.5H), 4.84-4.66 (m, 1H), 4.62-4.44 (m, 1H), 3.60-3.28 (m, 4H), 3.21-3.08 (m, 1H), 3.07-2.88 (m, 1H), 2.86-2.69 (m, 2H), 2.22 (s, 2H), 2.18 (s, 1H), 1.45-1.08 (m, 6H), 1.05-0.91 (m, 2H), 0.89-0.78 (m, 3H), 0.74-0.57 (m, 3H) |
| 8 | (CD₃OD) δ 9.00-8.96 (m, 1H), 8.38-8.33 (m, 1H), 8.27 (d, J = 1.1 Hz, 2H), 8.22-8.18 (m, 1H), 8.13-8.08 (m, 1H), 8.02-7.99 (m, 1H), 7.86-7.80 (m, 1H), 7.71-7.65 (m, 1H), 7.25-7.06 (m, 3.5H), 6.91-6.90 (m, 0.5H), 4.66-4.42 (m, 2H), 3.59-3.37 (m, 4H), 3.14-2.96 (m, 2H), 2.91-2.67 (m, 2H), 2.34 (s, 2H), 2.29 (s, 1H), 1.50-1.21 (m, 6H), 1.13-0.97 (m, 2H), 0.96-0.86 (m, 3H), 0.80-0.65 (m, 3H) |
| 9 | (CD₃OD) δ 9.80 (s, 1H), 8.35 (dd, J = 7.3, 1.3 Hz, 1H), 8.26-8.21 (m, 1H), 8.17 (d, J = 1.1 Hz, 2H), 8.09 (dd, J = 8.4, 2.0 Hz, 1H), 7.99 (t, J = 2.3 Hz, 1H), 7.80-7.74 (m, 1H), 7.67 (t, J = 7.9 Hz, 1H), 7.25-7.05 (m, 3.5H), 6.91-6.89 (m, 0.5H), 4.64-4.54 (m, 2H), 4.50 (dq, J = 7.1, 1.8 Hz, 2H), 3.57-3.35 (m, 4H), 3.18-2.96 (m, 2H), 2.92-2.62 (m, 2H), 2.33 (s, 2H), 2.28 (s, 1H), 1.51-1.45 (m, 3H), 1.40-1.04 (m, 8H), 0.96-0.86 (m, 3H), 0.80-0.65 (m, 3H) |
| 10 | (DMSO-d₆) δ 8.38 (s, 1H), 8.18 (s, 1H), 7.99 (dd, J = 8.3, 1.7 Hz, 1H), 7.97-7.86 (m, 4H), 7.54-7.47 (m, 2H), 7.15-7.00 (m, 3.5H), 6.91 (d, J = 7.0 Hz, 0.5H), 4.67 (br s, 1H), 4.50-4.26 (m, 3H), 3.04 (br s, 1.5H), 2.90 (br s, 1.5H), 2.68 (br s, 3H), 2.13 (s, 2H), 2.08 (s, 1H), 1.36-1.28 (m, 1H), 1.21-1.06 (m, 6H), 0.94-0.85 (m, 1H), 0.78 (q, J = 7.4 Hz, 3H), 0.62-0.54 (m, 3H) |
| 11 | (DMSO-d₆) δ 8.51 (s, 1H), 8.34 (s, 1H), 7.98 (dd, J = 8.4, 1.8 Hz, 1H), 7.93 (d, J = 1.5 Hz, 1H), 7.88 (s, 2H), 7.79 (dd, J = 8.6, 1.3 Hz, 1H), 7.71-7.69 (m, 1H), 7.53-7.49 (m, 1H), 7.13-7.01 (m, 3.5H), 6.91 (d, J = 7.5 Hz, 0.5H), 4.67 (br s, 1H), 4.50-4.27 (m, 3H), 3.05 (br s, 1.5H), 2.92-2.88 (m, 1.5H), 2.68 (br s, 3H), 2.13 (s, 2H), 2.08 (s, 1H), 1.36-1.28 (m, 1H), 1.21-1.08 (m, 6H), 0.91-0.86 (m, 1H), 0.78 (q, J = 7.4 Hz, 3H), 0.62-0.54 (m, 3H) |
| 12 | (1:1 CD₃OD:CDCl₃) δ 9.39-9.19 (m, 1H), 8.57 (d, J = 8.4 Hz, 2H), 8.18-8.10 (m, 2H), 8.07 (s, 1H), 7.89-7.74 (m, 1H), 7.68-7.59 (m, 1H), 7.43-7.33 (m, 1H), 7.21-6.99 (m, 3.5H), 6.85-6.83 (m, 0.5H), 4.78-4.61 (m, 2H), 3.49 (br s, 2H), 3.31-3.12 (m, 2H), 2.98 (s, 1H), 2.91-2.63 (m, 3H), 2.26 (s, 2H), 2.22 (s, 1H), 1.48-1.17 (m, 6H), 1.12-0.96 (m, 2H), 0.94-0.81 (m, 3H), 0.77-0.59 (m, 3H) |
| 13 | (DMSO-d₆) δ 8.88 (s, 1H), 8.68 (d, J = 8.4 Hz, 1H), 8.64-8.44 (m, 2H), 8.31-8.19 (m, 1H), 8.10-8.00 (m, 2H), 7.95 (s, 1H), 7.87 (t, J = 7.9 Hz, 1H), 7.79-7.66 (m, 1H), 7.24-7.04 (m, 2.5H), 6.97-6.94 (m, 0.5H), 4.71 (br s, 1H), 4.58 (br s, 1H), 3.45 (br s, 4H), 2.94 (br s, 2H), 2.82-2.69 (m, 2H), 2.25 (s, 2H), 2.12 (s, 1H), 1.42-1.08 (m, 6H), 1.02-0.91 (m, 2H), 0.88-0.76 (m, 3H), 0.73-0.56 (m, 3H) |
| 14 | (CD₃OD) δ 9.61 (s, 1H), 8.42-8.33 (m, 2H), 8.31-8.20 (m, 2H), 8.08 (dd, J = 8.4, 2.0 Hz, 1H), 8.02-7.96 (m, 1H), 7.87 (t, J = 7.9 Hz, 1H), 7.69-7.61 (m, 1H), 7.25-7.03 (m, 3.5H), 6.89-6.88 (m, 0.5H), 4.67-4.39 (m, 2H), 3.72-3.61 (m, 1H), 3.60-3.52 (m, 1H), 3.47 (dq, J = 7.4, 3.9 Hz, 2H), 3.31 (td, J = 3.3, 1.7 Hz, 1H), 3.27-3.09 (m, 1H), 3.05-2.96 (m, 1H), 2.89-2.59 (m, 2H), 2.32 (s, 2H), 2.27 (s, 1H), 1.42-1.42 (m, 1H), 1.52-1.15 (m, 9H), 1.13-0.97 (m, 2H), 0.90 (td, J = 16.3, 7.4 Hz, 3H), 0.80-0.64 (m, 3H) |
| 15 | (DMSO-d₆) δ 8.83 (s, 1H), 8.66 (s, 1H), 8.18 (d, J = 8.6 Hz, 1H), 8.14 (s, 2H), 8.07-8.04 (m, 1H), 8.02 (d, J = 1.7 Hz, 0.5H), 7.98 (d, J = 1.3 Hz, 0.5H), 7.90 (dd, J = 8.5, 1.0 Hz, 1H), 7.62 (t, J = 8.8 Hz, 1H), 7.21-7.10 (m, 3.5H), 6.98 (d, J = 7.5 Hz, 0.5H), 4.73 (br s, 1H), 4.58-4.33 (m, 3H), 3.12 (br s, 1.5H), 2.98-2.95 (m, 1.5H), 2.75 (br s, 3H), 2.21 (s, 2H), 2.16 (s, 1H), 1.42-1.35 (m, 1H), 1.30-1.12 (m, 6H), 1.00-0.92 (m, 1H), 0.87-0.82 (m, 3H), 0.69-0.61 (m, 3H) |
| 16 | (DMSO-d₆) δ 8.77 (s, 1H), 8.64 (s, 1H), 8.08-8.05 (m, 4H), 8.01 (d, J = 1.8 Hz, 1H), 7.97 (d, J = 1.8 Hz, 1H), 7.60-7.56 (m, 1H), 7.20-7.07 (m, 3.5H), 6.98 (d, J = 7.7 Hz, 0.5H), 4.75 (br s, 1H), 4.57 (br s, 1H), 4.39 (q, J = 7.0 Hz, 2H), 3.74 (br s, 1H), 3.51 (br s, 1H), 3.13 (br s, 1.5H), 2.99-2.95 (m, 1.5H), 2.75 (br s, 3H), 2.20 (s, 2H), 2.15 (s, 1H), 1.38 (t, J = 7.2 Hz, 4H), 1.29-1.12 (m, 6H), 1.00-0.93 (m, 1H), 0.88-0.82 (m, 3H), 0.69-0.61 (m, 3H) |
| 17 | (DMSO-d₆) δ 8.65 (s, 1H), 8.61 (s, 1H), 8.17 (d, J = 8.4 Hz, 1H), 8.07 (s, 2H), 8.01 (d, J = 8.2 Hz, 1H), 7.95 (s, 1H), 7.91-7.88 (m, 1H), 7.53-7.48 (m, 1H), 7.15-7.03 (m, 3.5H), 6.93 (d, J = 9.0 Hz, 0.5H), 4.75 (br s, 1H), 4.58-4.33 (m, 3H), 3.34 (q, J = 7.6 Hz, 2H), 3.13 (br s, 1.5H), 2.99-2.95 (m, 1.5H), 2.75 (br s, 3H), 2.14 (s, 2H), 2.09 (s, 1H), 1.40-1.32 (m, 1H), 1.18-1.05 (m, 9H), 0.94-0.86 (m, 1H), 0.82-0.77 (m, 3H), 0.63-0.57 (m, 3H) |
| 18 | (DMSO-d₆) δ 8.57 (s, 1H), 8.08-8.05 (m, 3H), 7.99 (d, J = 9.0 Hz, 1H), 7.82 (dd,, J = 8.7, 1.9 Hz, 1H), 7.78 (s, 1H), 7.76-7.73 (m, 1H), 7.53 (d, J = 7.0 Hz, 2H), 7.47 (d, J = 2.6 Hz, 1H), 7.44-7.40 (m, 2H), 7.37-7.34 (m, 1H), 7.21-7.08 (m, 3.5H), 6.96 (d, J = 9.1 Hz, 0.5H), 5.28 (s, 2H), 4.71 (br s, 1H), 4.57-4.32 (m, 3H), 3.13 (br s, 1.5H), 2.97-2.93 (m, 1.5H), 2.75 (br s, 3H), 2.23 (s, 2H), 2.18 (s, 1H), 1.44-1.33 (m, 1H), 1.27-1.16 (m, 6H), 1.02-0.93 (m, 1H), 0.87-0.81 (m, 3H), 0.68 (t, J = 7.3 Hz, 2H), 0.62 (t, J = 7.4 Hz, 3H) |
| 19 | (1:1 CD₃OD:CDCl₃) δ 8.84 (s, 1H), 8.22 (d, J = 1.9 Hz, 1H), 8.11-8.03 (m, 3H), 8.01-7.91 (m, 2H), 7.88 (d, J = 8.3 Hz, 1H), 7.81 (d, J = 7.5 Hz, 1H), 7.70 (t, J = 7.9 Hz, 1H), 7.67-7.60 (m, 1H), 7.56 (s, 1H), 7.53-7.43 (m, 1H), 7.25-7.00 (m, 2.5H), 6.84-6.83 (m, 0.5H), 4.41 (br s, 2H), 3.51-3.35 (m, 2H), 3.27-3.08 (m, 2H), 2.98 (s, 1H), 2.87-2.79 (m, 1H), 2.78-2.57 (m, 2H), 2.30 (s, 2H), 2.16 (s, 1H), 1.51-1.16 (m, 6H), 1.10-0.98 (m, 2H), 0.95-0.81 (m, 3H), 0.77-0.62 (m, 3H) |
| 20 | (DMSO-d₆) δ 8.26 (s, 1H), 8.00-7.97 (m, 1H), 7.93 (s, 1H), 7.90 (d, J = 8.4 Hz, 3H), 7.86-7.78 (m, 2H), 7.73-7.67 (m, 2H), 7.62-7.47 (m, 3H), 7.29-7.26 (m, 1H), 7.14-7.03 (m, 3.5H), 6.97 (d, J = 9.0 Hz, 0.5H), 5.33 (s, 2H), 4.67 (br s, 1H), 4.54-4.34 (m, 3H), 3.14 (s, 3H), 2.91 (br s, 2H), 2.69 (br s, 2H), 2.61-2.59 (m, 1H), 2.13 (s, 2H), 2.08 (s, 1H), 1.36-1.28 (m, 1H), 1.27-1.16 (m, 6H), 0.92-0.86 (m, 2H), 0.81-0.76 (m, 3H), 0.62-0.54 (m, 3H) |
| 21 | (1:1 CD₃OD:CDCl₃) δ 9.11 (s, 1H), 8.11-8.03 (m, 2H), 7.98-7.91 (m, 2H), 7.64 (d, J = 1.9 Hz, 1H), 7.58-7.47 (m, 5H), 7.45-7.40 (m, 1H), 7.22-7.05 (m, 4H), 7.02 (d, J = 7.5 Hz, 1H), 5.27 (s, 2H), 4.41 (br s, 2H), 3.25-3.07 (m, 4H), 3.04-2.96 (m, 2H), 2.87-2.72 (m, 2H), 2.30 (s, 2H), 2.22 (s, 1H), 1.51-1.16 (m, 6H), 1.12-0.97 (m, 2H), 0.92-0.83 (m, 3H), 0.77-0.66 (m, 3H) |
| 23 | (1:1 CD₃OD:CDCl₃) δ 8.60 (s, 1H), 8.06 (d, J = 8.1 Hz, 1H), 7.93 (d, J = 1.6 Hz, 1H), 7.88 (s, 1H), 7.79 (d, J = 9.4 Hz, 1H), 7.50 (br s, 1H), 7.32-7.31 (m, 2H), 7.20-7.06 (m, 3.5H), 6.83 (d, J = 7.5 Hz, 0.5H), 4.65 (br s, 1H), 4.13-4.11 (m, 1H), 4.08-4.05 (m, 1H), 3.96-3.92 (m, 1H), 3.87-3.82 (m, 1H), 3.77 (br s, 1H), 3.63-3.35 (m, 3H), 3.22-3.08 (m, 2H), 3.03-3.00 (m, 1H), 2.97 (s, 1H), 2.83-2.80 (m, 1H), 2.73 (br s, 1H), 2.26 (s, 2H), 2.22 (s, |

| Ex. No. | ¹H NMR (2:1 mixture of amide rotamers) |
|---|---|
|  | 1H), 2.16-2.09 (m, 1H), 2.04-1.93 (m, 2H), 1.85-1.78 (m, 1H), 1.49-1.43 (m, 1H), 1.39-1.34 (m, 2H), 1.31-1.18 (m, 4H), 1.09-0.99 (m, 2H), 0.90-0.84 (m, 3H), 0.73 (t, J = 7.2 Hz, 2H), 0.68 (t, J = 7.4 Hz, 1H) |
| 24 | (1:1 CD₃OD:CDCl₃) δ 8.56 (s, 1H), 8.07-8.04 (m, 1H), 7.94-7.91 (m, 1H), 7.88-7.86 (m, 2H), 7.81 (d, J = 9.0 Hz, 2H), 7.51-7.48 (m, 1H), 7.32 (d, J = 2.3 Hz, 1H), 7.26 (dd, J = 8.9, 2.4 Hz, 1H), 7.21-7.07 (m, 2.5H), 6.64 (d, J = 7.5 Hz, 0.5H), 4.74 (dt, J = 12.1, 6.1 Hz, 2H), 4.41 (s, 1H), 3.81 (br s, 1H), 3.64 (br s, 1H), 3.45 (br s, 1H), 3.13 (m, 1H), 3.03-2.99 (m, 1.5H), 2.83 (br s, 1.5H), 2.28 (s, 2H), 2.24 (s, 1H), 1.48-1.43 (m, 1H), 1.40-1.35 (m, 7H), 1.29-1.17 (m, 6H), 1.10-0.98 (m, 1H), 0.91-0.84 (m, 3H), 0.74 (t, J = 7.3 Hz, 2H), 0.68 (t, J = 7.4 Hz, 1H) |
| 25 | (1:1 CD₃OD:CDCl₃) δ 8.51 (s, 1H), 8.17 (dd, J = 8.3, 2.0 Hz, 1H), 8.08 (d, J = 1.8 Hz, 1H), 7.91-7.88 (m, 1H), 7.85-7.82 (m, 1H), 7.78 (d, J = 9.0 Hz, 1H), 7.40 (dd, J = 8.3, 2.3, 1H), 7.36 (d, J = 2.3 Hz, 1H), 7.29-7.34 (m, 3H), 7.20-7.07 (m, 3.5H), 6.97-6.92 (m, 3H), 6.86 (d, J = 7.5 Hz, 0.5H), 4.78 (br s, 1H), 4.45 (dd, J = 6.0, 3.3 Hz, 2H), 4.39-4.37 (m, 2H), 3.63 (br s, 1H), 3.53-3.42 (m, 2H), 3.22-3.10 (m, 2H), 3.01 (br s, 1.5H), 2.83 (br s, 1.5H), 2.27 (s, 2H), 2.23 (s, 1H), 1.48-1.43 (m, 1H), 1.40-1.34 (m, 2H), 1.31-1.17 (m, 4H), 1.12-0.99 (m, 2H), 0.91-0.85 (m, 3H), 0.74 (t, J = 7.3 Hz, 2H), 0.67 (t, J = 7.3 Hz, 1H) |
| 26 | (CD₃OD) δ 9.14 (s, 1H), 8.22-7.94 (m, 6H), 7.77-7.51 (m, 5H), 7.31-7.02 (m, 4.5H), 6.89-6.87 (m, 0.5H), 5.45 (s, 2H), 4.53 (br s, 2H), 4.01-3.83 (m, 3H), 3.73-3.39 (m, 4H), 3.23-3.08 (m, 1H), 3.03 (br s, 1H), 2.92-2.62 (m, 2H), 2.33 (s, 2H), 2.27 (s, 1H), 1.57-1.19 (m, 6H), 1.16-1.01 (m, 2H), 0.93 (td, J = 16.2, 7.3 Hz, 3H), 0.83-0.58 (m, 3H) |
| 27 | (CD₃OD) δ 9.20 (s, 1H), 8.22-7.95 (m, 4H), 7.77-7.59 (m, 3H), 7.29-7.07 (m, 4.5H), 6.90-6.88 (m, 0.5H), 4.77-4.65 (m, 2H), 4.56 (d, J = 2.0 Hz, 2H), 4.05 (br s, 4H), 3.96-3.85 (m, 2H), 3.75-3.48 (m, 4H), 3.39-3.33 (m, 4H), 3.23-2.99 (m, 2H), 3.00-2.72 (m, 2H), 2.32 (s, 2H), 2.27 (s, 1H), 1.59-1.21 (m, 6H), 1.19-1.02 (m, 2H), 0.96 (ddd, J = 14.6, 7.3, 7.2 Hz, 3H), 0.86-0.67 (m, 3H) |
| 28 | (1:1 CD₃OD:CDCl₃) δ 8.58 (s, 1H), 8.07 (dt, J = 8.4, 2.0 Hz, 1H), 7.94-7.93 (m, 1H), 7.89 (s, 2H), 7.82 (d, J = 8.9 Hz, 1H), 7.50-7.47 (m, 1H), 7.36-7.32 (m, 2H), 7.21-7.07 (m, 3.5H), 6.65 (d, J = 7.5 Hz, 0.5H), 4.77 (br s, 1H), 4.42 (s, 1H), 4.27-4.25 (m, 2H), 3.84-3.82 (m, 2H), 3.60 (br s, 1H), 3.53-3.38 (m, 5H), 3.25-3.10 (m, 2H), 3.02 (br s, 1.5H), 2.84 (br s, 1.5H), 2.29 (s, 2H), 2.24 (s, 1H), 1.50-1.44 (m, 1H), 1.40-1.34 (m, 1H), 1.32-1.20 (m, 5H), 1.12-0.99 (m, 2H), 0.91-0.85 (m, 3H), 0.74 (t, J = 7.4 Hz, 2H), 0.68 (t, J = 7.4 Hz, 1H) |
| 29 | (1:1 CD₃OD:CDCl₃) δ 8.55 (s, 1H), 8.08-8.05 (m, 1H), 7.95 (t, J = 4.8 Hz, 2H), 7.81 (dd, J = 8.7, 1.6 Hz, 1H), 7.72 (d, J = 9.0 Hz, 1H), 7.65 (s, 1H), 7.35 (dd, J = 8.8, 2.3 Hz, 1H), 7.20-7.07 (m, 3.5H), 6.99 (d, J = 7.5 Hz, 0.5H), 4.71 (br s, 1H), 4.58 (br s, 1H), 4.33 (br s, 1H), 3.91 (s, 3H), 3.49 (br s, 2H), 3.12 (br s, 1H), 2.97-2.94 (m, 1.5H), 2.77-2.74 (m, 1.5H), 2.22 (s, 2H), 2.18 (s, 1H), 1.42-1.34 (m, 1H), 1.30-1.12 (m, 6H), 1.04-0.92 (m, 2H), 0.87-0.81 (m, 3H), 0.68 (t, J = 7.3 Hz, 2H), 0.61 (t, J = 7.3 Hz, 1H) |
| 30 | (1:1 CD₃OD:CDCl₃) δ 8.58 (s, 1H), 8.08-8.05 (m, 1H), 7.93-7.92 (m, 1H), 7.90-7.88 (m, 2H), 7.82 (d, J = 8.9 Hz, 1H), 7.50-7.48 (m, 1H), 7.36-7.33 (m, 2H), 7.21-7.08 (m, 3.5H), 6.85 (d, J = 7.5 Hz, 0.5H), 4.78 (br s, 1H), 4.66 (br s, 1H), 4.42 (s, 1H), 4.27-4.25 (m, 2H), 3.88-3.86 (m, 2H), 3.63 (q, J = 7.1 Hz, 2H), 3.45 (br s, 2H), 3.16 (br s, 2H), 3.02 (br s, 1.5H), 2.84 (br s, 1.5H), 2.29 (s, 2H), 2.24 (s, 1H), 1.50-1.44 (m, 1H), 1.40-1.34 (m, 2H), 1.32-1.20 (m, 7H), 1.12-0.99 (m, 2H), 0.91-0.85 (m, 3H), 0.74 (t, J = 7.4 Hz, 2H), 0.68 (t, J = 7.2 Hz, 1H) |
| 31 | (CD₃OD) δ 9.08 (d, J = 1.8 Hz, 1H), 8.53 (d, J = 9.0 Hz, 1H), 8.31-8.10 (m, 2H), 8.09-7.98 (m, 1H), 7.98-7.84 (m, 1H), 7.73 (t, J = 7.8 Hz, 1H), 7.39-7.05 (m, 4.5H), 6.91-6.89 (m, 0.5H), 4.58 (br s, 2H), 3.80-3.43 (m, 4H), 3.21-3.00 (m, 2H), 2.95 (s, 6H), 2.84-2.60 (m, 2H), 2.33 (s, 2H), 2.28 (s, 1H), 1.61-1.22 (m, 6H), 1.21-1.02 (m, 2H), 0.96 (td, J = 16.7, 7.3 Hz, 3H), 0.86-0.62 (m, 3H) |
| 32 | (CD₃OD) δ 9.07 (d, J = 1.5 Hz, 1H), 8.22 (dd, J = 8.4, 1.8 Hz, 1H), 8.17-7.92 (m, 4H), 7.66-7.55 (m, 3H), 7.32-7.06 (m, 4.5H), 6.91-6.89 (m, 0.5H), 4.74-4.51 (m, 2H), 4.42 (t, J = 5.3 Hz, 2H), 4.11-3.87 (m, 4H), 3.80-3.38 (m, 10H), 3.29-3.01 (m, 2H), 3.01-2.71 (m, 2H), 2.57-2.44 (m, 2H), 2.32 (s, 2H), 2.26 (s, 1H), 1.61-1.23 (m, 6H), 1.08 (br s, 2H), 1.01-0.88 (m, 3H), 0.87-0.68 (m, 3H) |
| 33 | (1:1 CD₃OD:CDCl₃) δ 8.44 (s, 1H), 8.18-8.15 (m, 1H), 8.05 (d, J = 1.8 Hz, 1H), 7.94 (s, 1H), 7.90-7.87 (m, 2H), 7.73 (d, J = 8.8 Hz, 1H), 7.41 (d, J = 8.4 Hz, 1H), 7.24-7.06 (m, 4.5H), 6.84 (d, J = 7.7 Hz, 0.5H), 4.75 (br s, 1H), 4.43 (s, 1H), 4.32 (t, J = 4.1 Hz, 2H), 3.86-3.84 (m, 4H), 3.65-3.40 (m, 3H), 3.26 (br s, 2H), 3.04 (br s, 4H), 2.82 (br s, 2H), 2.74 (br s, 2H), 2.27 (s, 2H), 2.22 (s, 1H), 1.51-1.43 (m, 1H), 1.40-1.34 (m, 2H), 1.32-1.20 (m, 6H), 1.10-0.99 (m, 2H), 0.91-0.85 (m, 3H), 0.74 (t, J = 7.3 Hz, 2H), 0.68 (t, J = 7.4 Hz, 1H) |
| 34 | (1:1 CD₃OD:CDCl₃) δ 8.46 (s, 1H), 8.28-8.24 (m, 1H), 8.16-8.14 (m, 1H), 7.95 (s, 1H), 7.86-7.80 (m, 2H), 7.72 (d, J = 8.8 Hz, 1H), 7.41 (d, J = 8.4 Hz, 1H), 7.19-7.06 (m, 4.5H), 6.86 (d, J = 7.7 Hz, 0.5H), 4.76 (br s, 1H), 4.46 (s, 1H), 4.19 (br s, 2H), 3.89-3.83 (m, 4H), 3.63-3.43 (m, 3H), 3.13 (br s, 6H), 2.83 (br s, 2H), 2.75 (br s, 2H), 2.28 (s, 2H), 2.24 (s, 1H), 2.09-2.02 (m, 2H), 1.52-1.45 (m, 1H), 1.42-1.35 (m, 2H), 1.33-1.22 (m, 4H), 1.11-1.00 (m, 2H), 0.92-0.85 (m, 3H), 0.75 (t, J = 7.4 Hz, 2H), 0.69 (t, J = 7.4 Hz, 1H) |
| 35 | (1:1 CD₃OD:CDCl₃) δ 8.49 (s, 1H), 8.13-8.10 (m, 1H), 7.98 (t, J = 2.1 Hz, 1H), 7.88 (s, 2H), 7.80 (d, J = 9.0 Hz, 1H), 7.46 (dd, J = 8.4, 2.6 Hz, 1H), 7.32 (d, J = 2.4 Hz, 1H), 7.24 (dd, J = 9.0, 2.4 Hz, 1H), 7.19-7.07 (m, 3.5H), 6.85 (d, J = 7.5 Hz, 0.5H), 4.75 (br s, 1H), 4.43 (s, 1H), 4.15 (t, J = 6.0 Hz, 2H), 3.81 (br s, 1H), 3.62-3.40 (m, 4H), 3.24-3.13 (m, 4H), 3.04-3.02 (m, 2H), 2.92 (br s, 2H), 2.86-2.74 (m, 7H), 2.28 (s, 2H), 2.23 (s, 1H), 2.06 (ddd, J = 13.4, 6.6, 6.4 Hz, 2H), 1.51-1.43 (m, 1H), 1.40-1.34 (m, 2H), 1.32-1.20 (m, 4H), 1.11-0.99 (m, 2H), 0.91-0.85 (m, 3H), 0.74 (t, J = 7.3 Hz, 2H), 0.68 (t, J = 7.3 Hz, 1H) |
| 36 | (DMSO-d₆) δ 8.62, (s, 1H), 8.10-8.07 (m, 1H), 7.96-7.93 (m, 3H), 7.86 (d, J = 9.0 Hz, 1H), 7.49-7.46 (m, 1H), 7.35 (dd, J = 9.0, 2.6 Hz, 1H), 7.26 (d, J = 1.3 Hz, 1H), 7.21-7.06 (m, 5.5H), 6.85 (d, J = 7.5 Hz, 0.5H), 5.39 (s, 2H), 4.77 (br s, 1H), 4.43 (s, 1H), 3.87 (s, 3H), 3.62 (br s, 1H), 3.15 (br s, 1H), 3.04-3.00 (m, 1.5H), 2.82 (br s, 1.5H), 2.63 (s, 3H), 2.28 (s, 2H), 2.24 (s, 1H), 1.51-1.43 (m, 1H), 1.40-1.34 (m, 2H), 1.32-1.17 (m, 4H), 1.11-0.99 (m, 2H), 0.91-0.84 (m, 3H), 0.74 (t, J = 7.4 Hz, 2H), 0.68 (t, J = 7.3 Hz, 1H) |
| 37 | (1:1 CD₃OD:CDCl₃) δ 8.54 (s, 1H), 8.15 (dd, J = 8.4, 2.0 Hz, 1H), 8.05 (s, 1H), 7.94-7.91 (m, 1H), 7.88-7.80 (m, 2H), 7.46 (br s, 1H), 7.42 (d, J = 8.4 Hz, 1H), 7.31-7.26 (m, 1H), 7.21-7.07 (m, 3.5H), 6.86 (d, J = 7.5 Hz, 0.5H), 5.05 (br s, 1H), 4.78 (br s, 1H), 4.45 (s, 1H), 4.40 (dd, J = 11.4, 3.7 Hz, 1H), 4.30-4.25 (m, 1H), 3.90-3.86 (m, 1H), 3.81 (br s, 1H), 3.64 (br s, 2H), 3.51-3.39 (m, 3H), 3.24-3.10 (m, 2H), 3.03 (br s, 1.5H), 2.94 (d, J = 7.3 Hz, 4H), 2.82 (br s, 1.5H), 2.27 (s, 2H), 2.23 (s, 1H), 1.50 (d, J = 6.8 Hz, 1H), 1.47-1.43 (m, 1H), 1.40 (d, J = 5.9 Hz, 2H), 1.38-1.34 (m, 2H), 1.33-1.18 (m, 4H), 1.11-0.99 (m, 2H), 0.92-0.85 (m, 3H), 0.74 (t, J = 7.4 Hz, 2H), 0.68 (t, J = 7.3 Hz, 1H) |
| 38 | (1:1 CD₃OD:CDCl₃) δ 8.60 (s, 1H), 8.07 (dt, J = 8.4, 2.2 Hz, 1H), 7.94-7.84 (m, 4H), 7.52-7.49 (m, 1H), 7.39 (d, J = 2.2 Hz, 1H), 7.21-7.07 (m, 3.5H), 6.85 (d, J = 7.5 Hz, 0.5H), 4.93 (br s, 1H), 4.77 (br s, 1H), 4.42 (s, 1H), 4.26 (br s, 1H), 3.72 (br s, 2H), 3.56 (br s, 3H), 3.41 (br s, 1H), 3.17 (br s, 3H), 3.04-3.00 (m, 1.5H), 2.92 (s, 3H), 2.84 (br s, 1.5H), 2.29 (s, 2H), 2.24 (s, 1H), 2.14 (br s, 3H), 1.94 (br s, 2H), 1.51-1.43 (m, 1H), 1.37 (br s, 2H), 1.33-1.19 (m, 4H), 1.12-0.99 (m, 2H), 0.91-0.85 (m, 3H), 0.74 (t, J = 7.4 Hz, 2H), 0.68 (t, J = 7.4 Hz, 1H) |
| 39 | (1:1 CD₃OD:CDCl₃) δ 8.44 (s, 1H), 8.26-8.22 (m, 1H), 8.14-8.12 (m, 1H), 7.87-7.84 (m, 1H), 7.80-7.79 (m, 1H), 7.71 (d, J = 8.6 Hz, 1H), 7.39 (d, J = 8.3 Hz, 1H), 7.19-7.06 (m, 5.5H), 6.85 (d, J = 7.5 Hz, 0.5H), 4.76 (br s, 1H), 4.46 (s, 1H), 4.19 (br s, 2H), 3.96-3.93 (m, 2H), 3.81 (br s, 1H), 3.65 (br s, 2H), 3.53 (br s, 1H), 3.42 (br s, 1H), 3.29-3.26 (m, 2H), 3.05-3.03 (m, 1.5H), 2.91 (s, 3H), 2.82 (br s, 1.5H), 2.27 (s, 2H), 2.23 (s, 1H), 2.14-2.08 (m, 2H), 1.50-1.44 (m, 1H), 1.38 (br s, 2H), 1.32-1.19 (m, 4H), 1.10-1.00 (m, 2H), 0.91-0.85 (m, 3H), 0.74 (t, J = 7.4 Hz, 2H), 0.69 (t, J = 7.4 Hz, 1H) |
| 40 | (1:1 CD₃OD:CDCl₃) δ 8.49 (s, 1H), 8.21 (d, J = 7.5 Hz, 1H), 8.10 (br s, 1H), 7.87-7.82 (m, 2H), 7.75 (d, J = 9.3 Hz, 1H), 7.42 (d, J = 8.3 Hz, 1H), 7.20-7.07 (m, 5.5H), 6.85 (d, J = 7.8 Hz, 0.5H), 4.77 (br s, 1H), 4.45 (s, 1H), 4.00 (s, 3H), 3.81-3.60 (m, 3H), 3.52 (br s, 1H), 3.37-3.34 (m, 2H), 3.25-3.13 (m, 3H), 3.05-3.03 (m, 1.5H), 2.90 (br s, 1H), 2.83 (br s, 1.5H), 2.28 (s, 2H), 2.23 (s, 1H), 2.19-2.05 (m, 6H), 1.50-1.44 (m, 1H), 1.40-1.36 (m, 3H), 1.32-1.19 (m, 5H), 1.11-1.00 (m, 2H), 0.91-0.85 (m, 3H), 0.74 (t, J = 7.4 Hz, 2H), 0.69 (t, J = 7.4 Hz, 1H) |

| Ex. No. | ¹H NMR (2:1 mixture of amide rotamers) |
|---|---|
| 41 | (1:1 CD₃OD:CDCl₃) δ 8.48 (s, 1H), 8.22 (t, J = 7.1 Hz, 1H), 8.12 (d, J = 5.5 Hz, 1H), 7.88-7.81 (m, 2H), 7.74 (d, J = 9.4 Hz, 1H), 7.43-7.39 (m, 2H), 7.22-7.07 (m, 5.5H), 6.85 (d, J = 7.5 Hz, 0.5H), 4.79 (br s, 1H), 4.45 (s, 1H), 3.96 (s, 2H), 3.72-3.50 (m, 4H), 3.26-3.23 (m, 2H), 3.17-3.13 (m, 2H), 3.07-3.03 (m, 1H), 3.01-2.97 (m, 1H), 2.94-2.81 (m, 3H), 2.27 (s, 2H), 2.23 (s, 1H), 2.16 (br s, 2H), 1.92-1.83 (m, 4H), 1.53-1.44 (m, 2H), 1.39-1.36 (m, 3H), 1.33-1.21 (m, 5H), 1.11-1.00 (m, 2H), 0.94-0.85 (m, 3H), 0.74 (t, J = 7.4 Hz, 2H), 0.69 (t, J = 7.4 Hz, 1H) |
| 42 | (CDCl₃) δ 8.60 (s, 1H), 8.51 (d, J = 5.0 Hz, 2H), 8.03-7.97 (m, 2H), 7.92 (d, J = 8.1 Hz, 1H), 7.81-7.78 (m, 1H), 7.75-7.71 (m, 1H), 7.24-7.02 (m, 8.5H), 6.76 (br s, 0.5H), 4.66 (s, 1H), 4.28 (s, 1H), 4.03 (br s, 2H), 3.71 (br s, 1H), 3.42 (br s, 2H), 3.08 (br s, 1H), 2.96 (s, 1H), 2.89 (s, 1H), 2.84-2.73 (m, 3.5H), 2.62 (br s, 0.5H), 2.17 (s, 3H), 2.16-2.08 (m, 2H), 1.55-1.49 (m, 0.5H), 1.47-1.41 (m, 1.5H), 1.35-1.24, (m, 5H), 1.10-1.02 (m, 2H), 0.94-0.88 (m, 3H), 0.75 (t, J = 7.4 Hz, 1.5H), 0.71 (t, J = 7.4 Hz, 1.5H) |
| 43 | (CD₃OD) δ 9.11 (d, J = 1.8 Hz, 1H), 8.51 (d, J = 9.0 Hz, 1H), 8.30 (d, J = 9.0, 1.8 Hz, 1H), 8.11 (dd, J = 8.4, 1.8 Hz, 1H), 8.02-8.01 (m, 1H), 7.96 (d, J = 8.1 Hz, 1H), 7.73 (d, J = 8.1 Hz, 1H), 7.66 (t, J = 8.0 Hz, 1H), 7.24-7.07 (m, 3.5H), 6.91 (d, J = 7.5 Hz, 0.5H), 4.91 (br s, 1H), 4.54 (br s, 1H), 3.96 (br s, 1H), 3.69 (br s, 1H), 3.01 (br s, 1H), 2.89-2.77 (m, 2H), 2.66 (br s, 1H), 2.33 (s, 2H), 2.28 (s, 1H), 1.53-1.45 (m, 2H), 1.39-1.17 (m, 5H), 1.12-0.99 (m, 3H), 0.94 (t, J = 7.3 Hz, 1H), 0.89 (t, J = 7.3 Hz, 2H), 0.76 (t, J = 7.4 Hz, 2H), 0.68 (t, J = 7.4 Hz, 1H) |
| 44 | (CDCl₃) δ 9.16-9.15 (m, 1H), 8.47 (d, J = 8.8 Hz, 1H), 8.35 (dd, J = 9.0, 1.8 Hz, 1H), 8.02 (d, J = 7.9 Hz, 1H), 7.92-7.88 (m, 1H), 7.69-7.62 (m, 2H), 7.24-7.08 (m, 4.5H), 6.82 (d, J = 7.7 Hz, 0.5H), 4.76 (br s, 1H), 4.33 (s, 1H), 3.97 (br s, 1H), 3.50 (br s, 2H), 3.20 (br s, 2H), 2.87 (br s, 1H), 2.64 (br s, 1H), 2.17 (s, 2H), 2.16 (s, 1H), 1.61-1.53 (m, 1H), 1.50-1.41 (m, 2H), 1.39-1.24 (m, 4H), 1.14-1.01 (m, 2H), 0.95-0.90 (m, 3H), 0.79-0.74 (m, 3H) |
| 53 | (CD₃OD) δ 8.12 (dd, J = 8.3, 1.8 Hz, 1H), 8.03-8.02 (m, 1H), 7.74 (dd, J = 8.3, 1.8 Hz, 1H), 7.64-7.59 (m, 1H), 7.24-7.10 (m, 3.5H), 6.94 (d, J = 7.3 Hz, 0.5H), 6.46 (d, J = 8.3 Hz, 1H), 4.75-4.55 (m, 2H), 4.16-3.65 (m, 2H), 3.53 (t, J = 8.5 Hz, 2H), 3.29-3.23 (m, 2H), 3.20-2.65 (m, 6H), 2.34 (s, 2H), 2.29 (s, 1H), 1.50-0.99 (m, 13H), 0.95-0.87 (m, 3H), 0.79-0.75 (m, 2H), 0.70-0.66 (m, 1H) |
| 54 | (CD₃OD) δ 8.38 (d, J = 1.7 Hz, 1H), 8.12-8.10 (m, 1H), 8.02-8.01 (m, 1H), 7.81 (dd, J = 8.6 Hz, 1.7 Hz, 1H), 7.62-7.58 (m, 1H), 7.51 (d, J = 8.9 Hz, 1H), 7.39 (d, J = 3.1 Hz, 1H), 7.22-7.09 (m, 3.5H), 6.91 (d, J = 7.5 Hz, 0.5H), 6.63 (d, J = 2.2 Hz, 1H), 4.75-4.45 (m, 2H), 3.90-3.40 (m, 2H), 3.12-2.55 (m, 4H), 2.32 (s, 2H), 2.27 (s, 1H), 1.53-0.99 (m, 10H), 0.94-0.87 (m, 3H), 0.76 (t, J = 7.4 Hz, 2H), 0.68 (t, J = 7.4 Hz, 1H) |
| 55 | (CD₃OD) δ 8.25 (br s, 1H), 8.14-8.11 (m, 1H), 8.02-8.01 (m, 1H), 7.91 (s, 1H), 7.88 (d, J = 8.9 Hz, 1H), 7.64-7.61 (m, 1H), 7.24-7.10 (m, 3.5H), 6.92 (d, J = 7.5 Hz, 0.5H), 4.75-4.40 (m, 2H), 4.27 (t, J = 8.3 Hz, 2H), 3.95-3.40 (m, 3H), 3.27 (t, J = 8.3 Hz, 2H), 3.20-2.55 (m, 6H), 2.33 (s, 2H), 2.28 (s, 1H), 1.89-1.70 (m, 5H), 1.55-0.99 (m, 13H), 0.94-0.88 (m, 3H), 0.77 (t, J = 7.4 Hz, 2H), 0.69 (t, J = 7.4 Hz, 1H) |
| 56 | (CD₃OD) δ 8.34 (d, J = 1.4 Hz, 1H), 8.16-8.13 (m, 1H), 8.05-8.04 (m, 1H), 7.84 (dd, J = 8.7, 1.8 Hz, 1H), 7.58-7.55 (m, 1H), 7.52 (d, J = 8.9 Hz, 1H), 7.37 (d, J = 3.3 Hz, 1H), 7.23-7.09 (m, 3.5H), 6.92 (d, J = 7.5 Hz, 0.5H), 6.61 (d, J = 2.8 Hz, 1H), 4.75-4.48 (m, 2H), 4.27 (q, J = 7.2 Hz, 2H), 3.80-3.40 (m, 2H), 3.12-2.55 (m, 4H), 2.32 (s, 2H), 2.27 (s, 1H), 1.51-0.98 (m, 13H), 0.94-0.88 (m, 3H), 0.76 (t, J = 7.4 Hz, 2H), 0.71-0.67 (m, 1H) |
| 57 | (CD₃OD) δ 8.06 (dd, J = 8.4, 2.0 Hz, 1H), 7.97-7.95 (m, 1H), 7.74 (dd, J = 8.5, 1.9 Hz, 1H), 7.69-7.65 (m, 1H), 7.61-7.59 (m, 1H), 7.35-7.0 (m, 3.5H), 6.93 (d, J = 7.5 Hz, 0.5H), 6.42 (d, J = 8.6 Hz, 1H), 4.85-4.40 (m, 2H), 3.61 (t, J = 8.7 Hz, 2H), 3.07-2.97 (m, 4H), 3.16-2.55 (m, 4H), 2.34 (s, 2H), 2.29 (s, 1H), 1.79-1.67 (m, 7H), 1.53-1.00 (m, 16H), 0.95-0.87 (m, 3H), 0.77 (t, J = 7.3 Hz, 2H), 0.69 (t, J = 7.3 Hz, 1H) |
| 58 | (1:1 CD₃OD:CDCl₃) δ 8.18-8.15 (m, 1H), 8.06 (d, J = 1.5 Hz, 1H), 7.94 (s, 1H), 7.67-7.66 (m, 1H), 7.58 (d, J = 8.1 Hz, 1H), 7.43-7.40 (m, 3H), 7.19-7.09 (m, 4.5H), 6.89-6.87 (m, 0.5H), 4.85-4.50 (m, 2H), 4.11 (t, J = 8.3 Hz, 2H), 3.70-3.50 (m, 2H), 3.24-3.19 (m, 2H), 3.15-2.70 (m, 4H), 2.28 (s, 2H), 2.23 (s, 1H), 1.50-0.99 (m, 10H), 0.92-0.85 (m, 3H), 0.75 (t, J = 7.3 Hz, 2H), 0.69 (t, J = 7.4 Hz, 1H) |
| 59 | (CD₃OD) δ 8.06 (dd, J = 8.4, 2.0 Hz, 1H), 7.97-7.95 (m, 1H), 7.78 (d, J = 8.6 Hz, 1H), 7.71-7.66 (m, 2H), 7.49-7.47 (m, 2H), 7.27-7.09 (m, 4.5H), 6.93 (d, J = 7.5 Hz, 0.5H), 6.55 (d, J = 8.4 Hz, 1H), 4.85-4.40 (m, 2H), 4.42 (s, 2H), 4.10-3.50 (m, 2H), 3.57 (t, J = 8.6 Hz, 2H), 3.09 (t, J = 8.6 Hz, 2H), 3.16-2.55 (m, 4H), 2.34 (s, 2H), 2.29 (s, 1H), 1.52-0.99 (m, 10H), 0.95-0.87 (m, 3H), 0.79-0.75 (m, 2H), 0.71-0.68 (m, 1H) |
| 60 | (CD₃OD) δ 8.79 (d, J = 1.3 Hz, 1H), 8.07 (dd, J = 8.4, 2.0 Hz, 1H), 7.97-7.96 (m, 1H), 7.82 (dd, J = 7.8, 1.7 Hz, 1H), 7.70-7.66 (m, 1H), 7.44 (d, J = 7.9 Hz, 1H), 7.25-7.0.9 (m, 3.5H), 6.93 (d, J = 7.7 Hz, 0.5H), 4.90-4.80 (m, 1H), 4.65-4.50 (m, 2H), 4.21 (t, J = 8.5 Hz, 2H), 4.10-3.40 (m, 3H), 3.28-2.50 (m, 4H), 2.34 (s, 2H), 2.29 (s, 1H), 2.24 (s, 3H), 1.51-0.99 (m, 10H), 0.95-0.87 (m, 3H), 0.79-0.75 (m, 2H), 0.71-0.67 (m, 1H) |
| 61 | (CD₃OD) δ 8.07 (dd, J = 8.4, 2.2 Hz, 1H), 7.97-7.95 (m, 1H), 7.77 (dd, J = 8.5, 1.9 Hz, 1H), 7.70-7.66 (m, 2H), 7.35-7.09 (m, 8.5H), 6.93 (d, J = 7.3 Hz, 0.5H), 6.56 (d, J = 8.6 Hz, 1H), 4.85-4.40 (m, 2H), 4.43 (s, 2H), 4.10-3.50 (m, 2H), 3.56 (t, J = 8.7 Hz, 2H), 3.07 (t, J = 8.7 Hz, 2H), 3.15-2.55 (m, 4H), 2.34 (s, 2H), 2.29 (s, 1H), 1.52-1.00 (m, 10H), 0.95-0.88 (m, 3H), 0.79-0.75 (m, 2H), 0.71-0.68 (m, 1H) |
| 62 | (CD₃OD) δ 8.07 (dd, J = 8.4, 2.2 Hz, 1H), 7.97-7.96 (m, 1H), 7.78 (dd, J = 8.5, 1.9 Hz, 1H), 7.70-7.66 (m, 2H), 7.26-7.09 (m, 6.5H), 6.93 (d, J = 7.5 Hz, 0.5H), 6.55 (d, J = 8.6 Hz, 1H), 4.85-4.40 (m, 2H), 4.41 (s, 2H), 4.10-3.50 (m, 2H), 3.57 (t, J = 8.7 Hz, 2H), 3.09 (t, J = 8.7 Hz, 2H), 3.15-2.55 (m, 4H), 2.34 (s, 2H), 2.30 (s, 1H), 1.52-0.99 (m, 10H), 0.95-0.88 (m, 3H), 0.79-0.75 (m, 2H), 0.71-0.68 (m, 1H) |
| 63 | (CD₃OD) δ 8.08 (dd, J = 8.4, 2.2 Hz, 1H), 7.98-7.96 (m, 1H), 7.71-7.67 (m, 1H), 7.32 (d, J = 7.6, 1.7 Hz, 1H), 7.25-7.23-7.09 (m, 4.5H), 7.08 (d, J = 1.8 Hz, 1H), 6.93 (d, J = 7.3 Hz, 0.5H), 4.85-4.40 (m, 2H), 4.16-3.50 (m, 2H), 3.48-3.44 (m, 2H), 3.23 (q, J = 7.3 Hz, 2H), 3.12-2.55 (m, 4H), 3.01 (t, J = 8.5 Hz, 2H), 2.34 (s, 2H), 2.29 (s, 1H), 1.52-0.99 (m, 13H), 0.95-0.87 (m, 3H), 0.79-0.75 (m, 2H), 0.71-0.67 (m, 1H) |
| 64 | (CD₃OD) δ 8.26 (d, J = 7.5 Hz, 1H), 8.07 (dd, J = 8.4, 2.2 Hz, 1H), 7.97-7.95 (m, 2H), 7.92 (d, J = 8.8 Hz, 1H), 7.70-7.67 (m, 1H), 7.49-7.47 (m, 4.5H), 6.92 (d, J = 7.5 Hz, 0.5H), 4.80-4.40 (m, 2H), 4.33-4.27 (m, 4H), 3.92 (s, 2H), 3.60-3.35 (m, 2H), 3.15-2.60 (m, 4H), 2.34 (s, 2H), 2.29 (s, 1H), 1.52-0.99 (m, 10H), 0.95-0.87 (m, 3H), 0.79-0.75 (m, 2H), 0.71-0.67 (m, 1H) |
| 65 | (CD₃OD) δ 8.07 (d, J = 8.4, 2.0 Hz, 1H), 7.97-7.95 (m, 1H), 7.74-7.66 (m, 2H), 7.63 (br s, 1H), 7.44 (d, J = 2.0 Hz, 1H), 7.40-7.38 (m, 1H), 7.23-7.10 (m, 4.5H), 6.93 (d, J = 7.3 Hz, 0.5H), 6.40-6.37 (m, 1H), 4.80-4.40 (m, 2H), 4.10-3.55 (m, 2H), 3.59 (t, J = 8.7 Hz, 2H), 3.51-3.47 (m, 2H), 3.50-3.40 (m, 2H), 3.03 (t, J = 8.8 Hz, 2H), 2.89 (t, J = 7.2 Hz, 2H), 3.10-2.60 (m, 2H), 2.34 (s, 2H), 2.29 (s, 1H), 1.52-0.98 (m, 10H), 0.95-0.87 (m, 3H), 0.79-0.75 (m, 2H), 0.71-0.67 (m, 1H) |
| 66 | (CD₃OD) δ 8.23-8.21 (m, 1H), 8.08 (dd, J = 8.4, 2.0 Hz, 1H), 7.98-7.96 (m, 2H), 7.92 (d, J = 8.6 Hz, 1H), 7.68 (t, J = 7.7 Hz, 1H), 7.44 (d, J = 7.3 Hz, 2H), 7.32-7.10 (m, 6.5H), 6.93-6.91 (m, 0.5H), 4.70-4.50 (m, 2H), 4.28 (t, J = 8.6 Hz,, 2H), 3.97 (s, 2H), 3.70-3.40 (m, 4H), 3.10-2.65 (m, 4H), 2.34 (s, 2H), 2.29 (s, 1H), 1.52-1.00 (m, 10H), 0.95-0.87 (m, 3H), 0.79-0.75 (m, 2H), 0.71-0.67 (m, 1H) |
| 67 | (CD₃OD) δ 8.07 (dd, J = 8.4, 2.0 Hz, 1H), 7.97-7.96 (m, 1H), 7.73-7.66 (m, 2H), 7.59 (br s, 1H), 7.37-7.34 (m, 2H), 7.26-7.09 (m, 6.5H), 6.90 (d, J = 7.5 Hz, 0.5H), 6.31 (d, J = 8.6 Hz, 1H), 4.60-4.40 (m, 2H), 4.00-3.55 (m, 2H), 3.60 (t, J = 8.7 Hz, 2H), 3.49-3.45 (m, 2H), 3.18 (t, J = 6.8 Hz, 2H), 2.95 (t, J = 8.7 Hz, 2H), 3.00-2.60 (m, 4H), 2.34 (s, 2H), 2.29 (s, 1H), 1.51-0.99 (m, 10H), 0.95-0.87 (m, 3H), 0.79-0.75 (m, 2H), 0.71-0.67 (m, 1H) |
| 68 | (CD₃OD) δ 8.45 (d, J = 1.8 Hz, 1H), 8.05 (dd, J = 8.4, 2.0 Hz, 1H), 7.95-7.93 (m, 1H), 7.87 (dd, J = 8.8, 1.8 Hz, 1H), 7.68-7.64 (m, 1H), 7.4-7.52 (m, 2H), 7.43 (d, |

| Ex. No. | $^1$H NMR (2:1 mixture of amide rotamers) |
|---|---|
| | J = 8.4 Hz, 1H), 7.32 (d, J = 2.0 Hz, 1H), 7.33-7.02 (m, 4.5H), 6.90 (d, J = 7.3 Hz, 0.5H), 6.77 (d, J = 3.1 Hz, 1H), 5.47 (s, 2H), 4.65-4.50 (m, 2H), 4.10-3.50 (m, 2H), 3.45-2.60 (m, 4H), 2.33 (s, 2H), 2.28 (s, 1H), 1.50-0.99 (m, 10H), 0.95-0.87 (m, 3H), 0.78-0.74 (m, 2H), 0.70-0.66 (m, 1H) |
| 69 | (CD$_3$OD) δ 8.35 (d, J = 1.8 Hz, 1H), 8.07 (dd, J = 8.4, 2.0 Hz, 1H), 7.97-7.96 (m, 1H), 7.81-7.78 (m, 2H), 7.71-7.66 (m, 2H), 7.44 (d, J = 8.4 Hz, 1H), 7.23-7.09 (m, 3.5H), 6.93 (d, J = 7.3 Hz, 0.5H), 6.61 (d, J = 8.4 Hz, 1H), 4.70-4.55 (m, 2H), 4.02-3.40 (m, 2H), 3.57 (t, J = 8.6 Hz, 2H), 3.15-2.95 (m, 4H), 2.90-2.55 (m, 2H), 2.34 (s, 2H), 2.29 (s, 1H), 1.51-1.00 (m, 10H), 0.95-0.88 (m, 3H), 0.79-0.75 (m, 2H), 0.71-0.68 (m, 1H) |
| 70 | (CD$_3$OD) δ 8.07 (dd, J = 8.4, 2.0 Hz, 1H), 7.97-7.95 (m, 1H), 7.79-7.77 (m, 1H), 7.69-7.66 (m, 2H), 7.49 (d, J = 8.1 Hz, 1H), 7.31 (s, 1H), 7.21-7.10 (m, 4.5H), 7.00 (d, J = 8.1 Hz, 1H), 6.94-6.93 (m, 0.5H), 6.63 (d, J = 8.6 Hz, 1H), 6.39-6.38 (m, 1H), 4.60-4.50 (m, 2H), 4.54 (s, 2H), 3.75 (s, 3H), 3.78-3.60 (m, 3H), 3.56 (t, J = 8.7 Hz, 2H), 3.05 (t, J = 8.5 Hz, 2H), 3.08-2.70 (m, 3H), 2.34 (s, 2H), 2.29 (s, 1H), 1.55-1.00 (m, 10H), 0.95-0.88 (m, 3H) 0.79-0.75 (m, 2H), 0.70 (t, J = 7.4 Hz) |
| 71 | (CD$_3$OD) δ 8.15-8.12 (m, 1H), 8.04-8.03 (m, 1H), 7.71 (d, J = 7.9 Hz, 1H), 7.34-7.33 (m, 1H), 7.28 (s, 1H), 7.25-7.10 (m, 3.5H), 6.95 (d, J = 7.5 Hz, 0.5H), 4.95-4.50 (m, 2H), 3.95-3.55 (m, 3H), 3.50 (t, J = 8.5 Hz, 2H), 3.26 (q, J = 7.2 Hz, 2H), 3.25-3.20 (m, 2H), 3.02 (t, J = 8.5 Hz, 2H), 2.95-2.70 (m, 2H), 2.36 (s, 2H), 2.31 (s, 1H), 1.52-1.01 (m, 13H), 0.95-0.87 (m, 3H), 0.79-0.76 (m, 2H), 0.70 (t, J = 7.4 Hz, 1H) |
| 72 | (DMSO-d$_6$) δ 8.10-8.06 (m, 2H), 7.62-7.60 (m, 2H), 7.36 (dd, J = 8.3, 1.9 Hz, 1H), 7.24-7.23 (m, 1H), 7.20-7.08 (m, 4.5H), 6.99 (d, J = 7.3 Hz, 0.5H), 6.95 (s, 1H), 4.36 (s, 2H), 3.55-3.24 (m, 8H), 3.01-2.97 (m, 2H), 2.70 (br s, 2H), 2.24 (s, 2H), 2.19 (s, 1H), 1.42-0.90 (m, 10H), 0.88-0.82 (m, 3H), 0.70-0.62 (m, 3H) |
| 73 | (CD$_3$OD) δ 8.06 (dd, J = 8.4, 2.2 Hz, 1H), 7.96-7.95 (m, 1H), 7.80 (d, J = 8.4 Hz, 1H), 7.73 (s, 1H), 7.70-7.60 (m, 1H), 7.51 (s, 1H), 7.48 (d, J = 8.1 Hz, 1H), 7.28-7.09 (m, 4.5H), 6.93 (d, J = 7.5 Hz, 0.5H), 6.48 (d, J = 8.6 Hz, 1H), 4.70-4.40 (m, 4H), 3.69 (s, 3H), 3.59-3.48 (m, 2H), 3.30-3.22 (m, 2H), 3.20-2.65 (m, 5H), 2.34 (s, 2H), 2.29 (s, 1H), 1.61-1.00 (m, 10H), 0.95-0.88 (m, 3H), 0.79-0.75 (m, 2H) 0.69 (t, J = 7.4 Hz, 1H) |
| 74 | (CD$_3$OD) δ 8.07 (dd, J = 8.4, 2.0 Hz, 1H), 7.98-7.96 (m, 1H), 7.94-7.92 (m, 2H), 7.71-7.67 (m, 1H), 7.25-7.10 (m, 4.5H), 6.93 (d, J = 7.5 Hz, 0.5H), 4.88-4.48 (m, 4H), 4.02 (t, J = 8.4 Hz, 2H), 3.74-3.72 (m, 4H), 3.45-3.43 (m, 4H), 3.16 (t, J = 8.4 Hz, 2H), 3.10-2.60 (m, 4H), 2.34 (s, 2H), 2.29 (s, 1H), 1.55-0.98 (m, 10H), 0.95-0.87 (m, 3H), 0.77 (t, J = 7.3 Hz, 2H), 0.69 (t, J = 7.3 Hz, 1H) |
| 75 | (CD$_3$OD) δ 8.31 (d, J = 8.6 Hz, 1H), 8.08 (dd, J = 8.5, 2.1 Hz, 1H), 8.01-7.96 (m, 3H), 7.70 (d, J = 8.4 Hz, 1H), 7.24-7.10 (m, 3.5H), 6.93 (d, J = 7.5 Hz, 0.5H), 4.90-4.50 (m, 2H), 4.38 (s, 2H), 4.18 (t, J = 8.6 Hz, 2H), 4.00-3.95 (m, 6H), 3.70-3.36 (m, 8H), 3.38 (t, J = 8.5 Hz, 2H), 3.25-2.60 (m, 2H), 2.34 (s, 2H), 2.29 (s, 1H), 1.49-1.00 (m, 8H), 0.96-0.87 (m, 3H), 0.79-0.75 (m, 2H), 0.71-0.68 (m, 1H) |
| 76 | (CD$_3$OD) δ 8.08 (dd, J = 8.4, 2.0 Hz, 1H), 7.99-7.97 (m, 1H), 7.88 (d, J = 1.8 Hz, 1H), 7.71-7.67 (m, 1H), 7.58 (d, J = 1.3 Hz, 1H), 7.25-7.09 (m, 3.5H), 6.94 (d, J = 7.3 Hz, 0.5H), 4.60-4.50 (m, 2H), 3.85-3.68 (m, 1H), 3.76 (q, J = 7.0 Hz, 2H), 3.69 (t, J = 9.0 Hz, 2H), 3.65-3.43 (m, 2H), 3.15-3.00 (m, 2H), 3.07-2.80 (m, 2H), 2.66 (s, 2H), 2.35 (s, 2H), 2.30 (s, 1H), 1.55-1.00 (m, 12H), 0.95-0.88 (m, 3H), 0.79-0.75 (m, 2H), 0.71-0.67 (m, 1H) |
| 77 | (CD$_3$OD) δ 8.06 (dd, J = 8.4, 2.0 Hz, 1H), 7.96-7.94 (m, 1H), 7.87-7.85 (m, 1H), 7.75 (br s, 1H), 7.69 (d, J = 8.4 Hz, 1H), 7.24-7.05 (m, 3.5H), 6.93 (d, J = 7.7 Hz, 0.5H), 6.73 (d, J = 8.6 Hz, 1H), 5.00-4.60 (m, 2H), 4.10-3.80 (m, 2H), 3.65-3.60 (m, 6H), 3.52-3.45 (m, 8H), 3.15-2.87 (m, 6H), 2.34 (s, 2H), 2.29 (s, 1H), 1.49-0.96 (m, 10H), 0.96-0.88 (m, 3H), 0.79-0.75 (m, 2H), 0.69 (t, J = 7.3 Hz, 1H) |
| 78 | (1:1 CD$_3$OD:CDCl$_3$) δ 8.39 (d, J = 2.2 Hz, 1H), 8.13-8.11 (m, 1H), 8.02-7.94 (m, 2H), 7.84 (dd, J = 8.6, 2.5 Hz, 2H), 7.47-7.45 (m, 1H), 7.20-7.08 (m, 4.5H), 6.88-6.86 (m, 1.5H), 4.60-4.40 (m, 2H), 4.18 (t, J = 8.3 Hz, 2H), 3.80 (t, J = 4.7 Hz, 6H), 3.22 (t, J = 8.2 Hz, 2H), 3.20-2.98 (m, 4H), 2.87-2.84 (m, 6H), 2.64 (s, 3H), 2.29 (s, 2H), 2.24 (s, 1H), 1.49-1.03 (m, 9H), 0.91-0.85 (m, 3H) 0.75 (t, J = 7.4 Hz, 2H), 0.69 (t, J = 7.4 Hz, 1H) |
| 79 | (CD$_3$OD) δ 8.53-8.50 (m, 1H), 8.15 (d, J = 1.8 Hz, 1H), 8.08-8.05 (m, 1H), 8.02-8.00 (m, 2H), 7.87 (s, 1H), 7.84-7.80 (m, 1H), 7.24-7.10 (m, 3.5H), 7.03 (d, J = 6.6 Hz, 0.5H), 4.71-4.60 (m, 1H), 4.10-3.50 (m, 3H), 3.20-2.80 (m, 4H), 2.43 (s, 2H), 2.38 (s, 1H), 1.55-1.05 (m, 10H), 0.97-0.88 (m, 3H), 0.82-0.78 (m, 2H), 0.75-0.72 (m, 1H) |
| 80 | (CD$_3$OD) δ 8.31 (d, J = 1.8 Hz, 1H), 8.08-8.05 (m, 1H), 7.97-7.94 (m, 2H), 7.69-7.65 (m, 2H), 7.59 (s, 1H), 7.24-7.07 (m, 3.5H), 6.91 (d, J = 7.5 Hz, 0.5H), 4.70-4.45 (m, 2H), 4.31 (q, J = 7.3 Hz, 2H), 4.10-3.40 (m, 2H), 3.20-3.00 (m, 2H), 2.90-2.60 (m, 2H), 2.33 (s, 2H), 2.28 (s, 1H), 1.60-0.98 (m, 13H), 0.95-0.87 (m, 3H), 0.78-0.74 (m, 2H), 0.68 (t, J = 7.3 Hz, 1H) |
| 81 | (1:1 CD$_3$OD:CDCl$_3$) δ 8.23 (d, J = 8.4 Hz, 1H), 8.09-8.06 (m, 1H), 7.95-7.89 (m, 3H), 7.52-7.49 (m, 1H), 7.20-7.10 (m, 3.5H), 6.87 (d, J = 7.5 Hz, 0.5H), 4.20-4.10 (m, 4H), 4.00-3.85 (m, 6H), 3.55-3.43 (m, 2H), 3.30-3.28 (m, 6H), 3.10-2.95 (m, 4H), 2.91-2.89 (m, 2H), 2.30 (s, 2H), 2.25 (s, 1H), 1.46-0.92 (m, 10H), 0.92-0.85 (m, 3H), 0.75 (t, J = 7.4 Hz, 2H), 0.69 (t, J = 7.3 Hz, 1H) |
| 82 | (CD$_3$OD) δ 8.43 (d, J = 1.8 Hz, 1H), 8.06 (dd, J = 8.4, 2.0 Hz, 1H), 7.95-7.92 (m, 2H), 7.70-7.66 (m, 2H), 7.49 (d, J = 3.3 Hz, 1H), 7.25-7.08 (m, 3.5H), 6.91 (d, J = 7.5 Hz, 0.5H), 6.75 (d, J = 3.3 Hz, 1H), 4.93 (br s, 1H), 4.64-4.47 (m, 2H), 4.41 (t, J = 6.6 Hz, 2H), 4.00 (br s, 2H), 3.68 (br s, 2H), 3.42 (br s, 2H), 3.16-3.12 (m, 4H), 3.01 (br s, 2H), 2.78 (br s, 1H), 2.33-2.28 (m, 5H), 1.53-1.45 (m, 4H), 1.39-1.19 (m, 6H), 1.12-0.98 (m, 3H), 0.93 (t, J = 7.4 Hz, 1.5H), 0.89 (t, J = 7.3 Hz, 1.5H), 0.76 (t, J = 7.3 Hz, 1.5H), 0.69 (t, J = 7.4 Hz, 1.5H) |
| 83 | (CD$_3$OD) δ 8.37 (d, J = 1.8 Hz, 1H), 8.06 (dd, J = 8.4, 2.0 Hz, 1H), 7.97-7.94 (m, 2H), 7.69-7.65 (m, 2H), 7.55 (s, 1H), 7.24-7.08 (m, 3.5H), 6.91 (d, J = 7.7 Hz, 0.5H), 4.92 (br s, 1H), 4.63-4.46 (m, 2H), 4.28 (q, J = 7.3 Hz, 2H), 4.02 (br s, 2H), 3.68 (br s, 1H), 3.58-3.41 (m, 2H), 3.01 (br s, 1H), 2.65 (br s, 1H), 2.33 (s, 2H), 2.28 (s, 1H), 1.52-1.43 (m, 4H), 1.39-1.18 (m, 6H), 1.12-0.98 (m, 2H), 0.93 (t, J = 7.4 Hz, 1H), 0.89 (t, J = 7.2 Hz, 2H), 0.76 (t, J = 7.3 Hz, 2H), 0.68 (t, J = 7.3 Hz, 1H) |
| 84 | (CD$_3$OD) δ 8.18 (d, J = 1.8 Hz, 1H), 8.07 (d, J = 2.2 Hz, 0.5H), 8.05 (d, J = 2.2 Hz, 0.5H), 7.97-7.94 (m, 2H), 7.68 (d, J = 8.4 Hz, 1H), 7.65-7.62 (m, 2H), 7.24-7.07 (m, 3.5H), 6.90 (d, J = 7.3 Hz, 0.5H), 4.93 (br s, 1H), 4.62-4.45 (m, 2H), 4.32 (q, J = 7.3 Hz, 2H), 4.01 (br s, 1H), 3.69 (br s, 1H), 3.59-3.42 (m, 2H), 3.00 (br s, 1H), 2.66 (br s, 1H), 2.33 (s, 2H), 2.28 (s, 1H), 1.52-1.43 (m, 4H), 1.39-1.16 (m, 6H), 1.13-0.98 (m, 2H), 0.93 (t, J = 7.4 Hz, 1H), 0.89 (t, J = 7.3 Hz, 2H), 0.76 (t, J = 7.4 Hz, 2H), 0.68 (t, J = 7.4 Hz, 1H) |
| 85 | (CD$_3$OD) δ 8.27 (d, J = 1.8 Hz, 1H), 8.12 (d, J = 1.8 Hz, 1H), 8.10 (d, J = 2.2 Hz, 0.5H), 8.08 (d, J = 2.2 Hz, 0.5H), 7.99-7.98 (m, 1H), 7.68 (t, J = 8.4 Hz, 1H), 7.64 (s, 1H), 7.24-7.07 (m, 3.5H), 6.92 (d, J = 7.3 Hz, 0.5H), 4.95 (br s, 1H), 4.69 (q, J = 7.3 Hz, 2H), 4.61-4.48 (m, 2H), 4.03 (br s, 1H), 3.69 (br s, 1H), 3.55 (br s, 1H), 3.43 (br s, 1H), 3.00 (br s, 1H), 2.66 (br s, 1H), 2.34 (s, 2H), 2.29 (s, 1H), 1.52-1.45 (m, 4H), 1.39-1.17 (m, 6H), 1.12-0.99 (m, 2H), 0.93 (t, J = 7.4 Hz, 1H), 0.89 (t, J = 7.3 Hz, 2H), 0.76 (t, J = 7.3 Hz, 2H), 0.68 (t, J = 7.3 Hz, 1H) |

| Ex. No. | $^1$H NMR (mixture of amide rotamers) |
|---|---|
| 108 | (CD$_3$OD) δ 8.63-8.53 (m, 1H), 8.35-7.86 (m, 6H), 7.63-7.50 (m, 3H), 7.32-7.11 (m, 3H), 7.05-6.92 (m, 1H), 5.42-5.19 (m, 0.5H), 4.69-4.24 (m, 2H), 3.54-3.33 (m, 3.5H), 3.18-2.65 (m, 10H), |

| Ex. No. | ¹H NMR (mixture of amide rotamers) |
|---|---|
| | 2.56-2.51 (m, 0.5H), 2.49-2.40 (m, 0.5H), 2.26 (br s, 3H), 1.65-0.74 (m, 12.5H), 0.63-0.51 (m, 1.5H) |
| 109 | (CD₃OD) δ 8.65-8.54 (m, 1H), 8.33-8.15 (m, 2H), 8.10-7.88 (m, 4H), 7.59 (br s, 3H), 7.30-7.07 (m, 3.5H), 7.01-6.84 (m, 0.5H), 5.29-5.11 (m, 1H), 4.66-4.49 (m, 1H), 4.32-4.07 (m, 1H), 3.92-3.68 (m, 3H), 3.57-3.34 (m, 3H), 3.27-2.57 (m, 8.5H), 2.50-2.38 (m, 0.5H), 2.34-2.20 (m, 4H), 1.66-0.61 (m, 14H) |
| 110 | (DMSO-d₆) δ 8.54-8.41 (m, 1H), 8.32-8.24 (m, 0.5H), 8.16-8.03 (m, 1.5H), 7.96 (d, J = 4.8 Hz, 3.5H), 7.68-7.50 (m, 2.5H), 7.3-7.00 (m, 4.5H), 6.98-6.92 (m, 0.5H), 5.27-4.91 (m, 1.5H), 4.65-4.50 (m, 0.5H), 4.45-4.32 (m, 1H), 3.98-2.64 (m, 13H), 2.27-2.16 (m, 1H), 2.09 (s, 2H), 2.02-0.61 (m, 16H), 0.57-0.45 (m, 2H) |
| 111 | (1:1 CD₃OD:CDCl₃) δ 8.64-8.56 (m, 1H), 8.38-8.00 (m, 3H), 7.98-7.92 (m, 1H), 7.91-7.82 (m, 2H), 7.58-7.51 (m, 3.5H), 7.30-7.07 (m, 3H), 6.98-6.87 (m, 0.5H), 5.43-5.12 (m, 0.5H), 4.91-4.74 (m, 0.5H), 4.37-4.19 (m, 0.5H), 3.73-2.57 (m, 13.5H), 2.35-2.18 (m, 3H), 2.15-1.79 (m, 4H), 1.67-0.70 (m, 13H), 0.62-0.49 (m, 1H). |
| 112 | (1:1 CD₃OD:CDCl₃) δ 8.55 (d, J = 7.7 Hz, 1H), 8.41-8.30 (m, 1H), 8.26-8.18 (m, 1H), 8.02 (td, J = 2.0, 8.6 Hz, 1H), 7.95 (d, J = 7.0 Hz, 1H), 7.92-7.82 (m, 2H), 7.56-7.48 (m, 2H), 7.38 (dd, J = 8.4, 15.0 Hz, 1H), 7.24-7.03 (m, 3.5H), 6.94 (d, J = 6.2 Hz, 0.5H), 5.26 (d, J = 18.5 Hz, 0.5H), 5.21-5.12 (m, 0.5H), 4.56-4.45 (m, 1.5H), 4.27-4.09 (m, 1.5H), 3.49-2.93 (m, 4.5H), 2.90-2.77 (m, 4H), 2.74-2.52 (m, 4H), 2.46-2.31 (m, 2H), 2.27 (s, 1.5H), 2.24 (s, 1.5H), 1.39-0.92 (m, 8H), 0.92-0.84 (m, 3H), 0.76-0.70 (m, 1.5H), 0.66 (t, J = 7.3 Hz, 1.5H) |
| 113 | (1:1 CD₃OD:CDCl₃) δ 8.67-8.58 (m, 1H), 8.33-7.82 (m, 6.5H), 7.64-7.38 (m, 3.5H), 7.31-7.07 (m, 3.5H), 7.03-6.90 (m, 1H), 5.32-5.12 (m, 0.5H), 4.81-4.66 (m, 1H), 4.50-4.35 (m, 1H), 3.68-2.82 (m, 17H), 2.78-2.54 (m, 1H), 2.40-2.34 (m, 0.5H), 2.33-2.22 (m, 3H), 1.64-0.69 (m, 13H), 0.66-0.54 (m, 1H) |
| 114 | (1:1 CD₃OD:CDCl₃) δ 8.64-8.53 (m, 1H), 8.36-8.13 (m, 2H), 8.08-8.00 (m, 1H), 8.00-7.81 (m, 3H), 7.56-7.39 (m, 3.5H), 7.30-7.08 (m, 3H), 6.98 (d, J = 7.3 Hz, 0.5H), 5.29-5.10 (m, 0.5H), 4.80-4.66 (m, 0.5H), 4.48-4.35 (m, 0.5H), 4.34-4.09 (m, 0.5H), 3.84-3.58 (m, 1.5H), 3.76-2.64 (s, 14.5H), 2.33-2.20 (m, 3H), 1.68-0.54 (m, 14H) |
| 115 | (1:1 CD₃OD:CDCl₃) δ 8.58 (d, J = 8.6 Hz, 1H), 8.44-8.35 (m, 1H), 8.23 (ddd, J = 2.0, 8.4, 14.3 Hz, 1H), 8.08-8.03 (m, 1H), 8.02-7.96 (m, 1H), 7.95-7.87 (m, 2H), 7.63-7.53 (m, 1.55H), 7.43 (d, J = 8.4 Hz, 0.5H), 7.39 (d, J = 8.4 Hz, 0.5H), 7.29-7.07 (m, 4H), 6.98 (d, J = 6.4 Hz, 0.5H), 5.32-5.18 (m, 0.5H), 4.55-4.51 (m, 1H), 4.28-4.13 (m, 1.5H), 3.95-3.72 (m, 2H), 3.42-2.97 (m, 14.5H), 2.95-2.82 (m, 0.5H), 2.79-2.56 (m, 2.5H), 2.52-2.32 (m, 1.5H), 2.30 (s, 2H), 2.27 (s, 1H), 1.36-0.86 (m, 10.5H), 0.79-0.74 (m, 1.5H), 0.72-0.67 (m, 2H) |
| 116 | (1:1 CD₃OD:CDCl₃) δ 8.60-8.48 (m, 1H), 8.37-8.32 (m, 1.5H), 8.20 (br s, 0.5H), 8.07-7.81 (m, 4H), 7.59-7.53 (m, 2H), 7.39 (d, J = 8.6 Hz, 1H), 7.25-7.01 (m, 3.5H), 6.94 (d, J = 7.7 Hz, 0.5H), 5.42 (d, J = 18.0 Hz, 1H), 5.26-5.12 (m, 0.5H), 4.55-4.42 (m, 1H), 4.18 (d, J = 18.0 Hz, 1H), 3.75-3.56 (m, 3H), 3.51-3.20 (m, 4.5H), 3.16-3.04 (m, 1.5H), 3.01-2.85 (m, 2.5H), 2.80 (s, 4.5H), 2.50 (d, J = 16.3 Hz, 0.5H), 2.34-2.24 (m, 3H), 2.21-2.10 (m, 1H), 1.44-0.71 (m, 13H), 0.67-0.59 (m, 0.5H) |
| 117 | (1:1 CD₃OD:CDCl₃) δ 8.65 (br s, 1H), 8.34 (s, 0.5H), 8.16 (br s, 0.5H), 8.11-7.80 (m, 4.5H), 7.65-7.52 (m, 3H), 7.46-7.34 (m, 1H), 7.32-6.96 (m, 8H), 6.83 (d, J = 6.9 Hz, 0.5H), 5.23 (d, J = 17.8 Hz, 0.5H), 4.41-4.29 (m, 1.5H), 4.23 (d, J = 17.8 Hz, 2H), 3.68-3.14 (m, 8.5H), 3.12-2.88 (m, 2.5H), 2.63 (d, J = 0.8 Hz, 0.5H), 2.53 (d, J = 16.1 Hz, 0.5H), 2.26 (s, 2H), 2.23 (s, 1H), 1.57-0.82 (m, 11.5H), 0.72 (t, J = 7.4 Hz, 2H), 0.64 (br s, 0.5H) |
| 118 | (1:1 CD₃OD:CDCl₃) δ 8.55 (d, J = 7.7 Hz, 1H), 8.41-8.30 (m, 1H), 8.26-8.18 (m, 1H), 8.02 (td, J = 2.0, 8.6 Hz, 1H), 7.95 (d, J = 7.0 Hz, 1H), 7.92-7.82 (m, 2H), 7.56-7.48 (m, 2H), 7.38 (dd, J = 8.4, 15.0 Hz, 1H), 7.24-7.03 (m, 3.5H), 6.94 (d, J = 6.2 Hz, 0.5H), 5.26 (d, J = 18.5 Hz, 0.5H), 5.21-5.12 (m, 0.5H), 4.56-4.45 (m, 1.5H), 4.27-4.09 (m, 1.5H), 3.49-2.93 (m, 4.5H), 2.90-2.77 |
| | (m, 4H), 2.74-2.52 (m, 4H), 2.46-2.31 (m, 2H), 2.27 (s, 1.5H), 2.24 (s, 1.5H), 1.39-0.92 (m, 8H), 0.92-0.84 (m, 3H), 0.76-0.70 (m, 1.5H), 0.66 (t, J = 7.3 Hz, 1.5H) |
| 126 | (1:1 CD₃OD:CDCl₃) δ 8.70 (s, 1H), 8.12-7.98 (m, 4H), 7.96-7.89 (m, 2H), 7.71-7.59 (m, 2H), 7.55-7.45 (m, 1H), 7.39-6.98 (m, 6H), 6.94-6.76 (m, 1H), 4.80-4.67 (m, 1H), 4.45-4.18 (m, 2H), 3.77-3.35 (m, 3H), 3.26-2.97 (m, 2H), 2.84-2.66 (m, 2H), 2.30 (s, 3H), 2.25 (d, J = 3.3 Hz, 1.5H), 2.18 (s, 0.5H), 1.46-0.93 (m, 4H), 0.89-0.80 (m, 1.5H), 0.71 (t, J = 7.4 Hz, 1H), 0.65 (t, J = 7.4 Hz, 0.5H) |
| 127 | (DMSO-d₆) δ 8.69 (s, 1H), 8.24 (d, J = 8.0 Hz, 1H), 8.15 (d, J = 8.6 Hz, 1H), 8.12-8.02 (m, 2.5H), 8.01-7.92 (m, 2H), 7.80-7.65 (m, 2.5H), 7.51-7.44 (m, 0.5H), 7.38 (d, J = 8.0 Hz, 0.5H), 7.32 (d, J = 8.3 Hz, 0.5H), 7.24-6.91 (m, 5H), 6.87-6.79 (m, 0.5H), 4.69-4.48 (m, 1.5H), 4.30 (br s, 0.5H), 3.64-3.43 (m, 3.5H), 3.22-2.97 (m, 2H), 2.95-2.53 (m, 4H), 2.45-2.31 (m, 0.5H), 2.21 (s, 2H), 2.18-2.13 (m, 1H), 1.43-0.80 (m, 6H), 0.66 (t, J = 7.4 Hz, 0.5H), 0.59 (t, J = 7.4 Hz, 0.5H) |
| 128 | (1:1 CD₃OD:CDCl₃) δ 8.71 (s, 1H), 8.08-8.03 (m, 3H), 8.01-7.99 (m, 1H), 7.94-7.92 (m, 2H), 7.68-7.61 (m, 2H), 7.53-7.48 (m, 1H), 7.21-7.06 (m, 3.5H), 6.84 (t, J = 7.6 Hz, 0.5H), 4.83 (br s, 1H), 4.42 (br s, 1H), 4.04-3.88 (br s, 1H), 3.61 (br s, 1H), 3.49 (br s, 2H), 3.22 (br s, 1H), 3.10-3.07 (m, 0.5H), 3.00 (br s, 0.5H), 2.82-2.69 (m, 2H), 2.29-2.22 (m, 3H), 2.14-2.05 (m, 1H), 1.88 (br s, 1H), 1.78-1.72 (m, 1H), 1.69-1.63 (m, 1H), 1.58-1.52 (m, 1H), 1.44-1.34 (m, 1H), 1.31-1.16 (m, 2H), 1.09-0.98 (m, 1H), 0.92-0.66 (m, 3H) |
| 129 | (1:1 CD₃OD:CDCl₃) δ 8.70 (s, 1H), 8.09 (dd, J = 8.3, 1.9 Hz, 1H), 8.06-8.03 (m, 2H), 8.02-7.99 (m, 1H), 7.97-7.92 (m, 1H), 7.68-7.61 (m, 2H), 7.53-7.48 (m, 1H), 7.22-7.06 (m, 3.5H), 6.84 (t, J = 7.8 Hz, 0.5H), 4.43 (br s, 1H), 4.24 (br s, 0.5H), 4.12 (br s, 0.5H), 3.67-3.58 (m, 1H), 3.53 (br s, 1H), 3.25 (br s, 1H), 3.14-3.11 (m, 1H), 2.77-2.72 (m, 2H), 2.37 (br s, 1H), 2.29 (s, 1.5H), 2.21 (s, 1.5H), 2.19-2.05 (m, 2H), 1.95-1.85 (m, 1.5H), 1.81-1.68 (m, 1.5H), 1.60-1.54 (m, 1H), 1.40 (br s, 1H) |
| 130 | (1:1 CD₃OD:CDCl₃) δ 8.71 (d, J = 2.9 Hz, 1H), 8.10-8.07 (m, 1H), 8.05-7.98 (m, 3H), 7.97-7.92 (m, 2H), 7.68-7.60 (m, 2H), 7.51-7.47 (m, 1H), 7.21-7.07 (m, 3.5H), 6.84 (t, J = 7.5 Hz, 0.5H), 4.70 (br s, 1H), 4.45-4.39 (m, 2H), 4.23 (br s, 1H), 3.59 (br s, 1H), 3.53-3.50 (m, 1H), 3.27 (br s, 2H), 2.82 (br s, 1H), 2.73-2.70 (m, 1H), 2.39 (br s, 2H), 2.25 (s, 1.5H), 2.20 (s, 1.5H), 1.91 (br s, 2H) |
| 131 | (1:1 CD₃OD:CDCl₃) δ 8.57 (br s, 1H), 8.26-8.18 (m, 1H), 8.14-8.07 (m, 1H), 8.06-7.99 (m, 1H), 7.98-7.93 (m, 1H), 7.91-7.79 (m, 2H), 7.66-7.47 (m, 3.5H), 7.43-7.33 (m, 1H), 7.22-6.98 (m, 4H), 6.91-6.84 (m, 0.5H), 6.82-6.70 (m, 1.5H), 6.65 (d, J = 5.8 Hz, 0.5H), 6.56-6.49 (m, 1H), 4.54-4.13 (m, 6.5H), 3.69-3.39 (m, 2H), 3.26-3.04 (m, 1H), 2.83-2.72 (m, 1.5H), 2.31-2.15 (m, 3H), 1.49-1.12 (m, 8.5H), 0.99-0.78 (m, 3H), 0.69 (t, J = 7.3 Hz, 1H), 0.62 (t, J = 7.3 Hz, 0.5H) |
| 132 | (1:1 CD₃OD:CDCl₃) δ 8.60 (s, 1H), 8.19 (d, J = 8.3 Hz, 1H), 8.10-7.84 (m, 5H), 7.65-7.50 (m, 3H), 7.46-6.68 (m, 11.5H), 4.55-4.14 (m, 4.5H), 3.74-3.44 (m, 2H), 3.04-2.92 (m, 1H), 2.83-2.67 (m, 2.5H), 2.31-2.15 (m, 3H), 1.44-0.79 (m, 5.5H), 0.70 (t, J = 7.3 Hz, 1H), 0.63 (t, J = 7.3 Hz, 0.5H) |
| 133 | (1:1 CD₃OD:CDCl₃) δ 8.62 (br s, 1H), 8.15 (d, J = 8.1 Hz, 1H), 8.08-7.79 (m, 4.5H), 7.66-7.51 (m, 3H), 7.42 (d, J = 7.9 Hz, 1H), 7.21-6.96 (m, 4H), 6.93-6.78 (m, 2H), 6.74-6.59 (m, 1.5H), 4.50-4.13 (m, 3H), 3.97-3.46 (m, 3.5H), 3.23-3.03 (m, 1H), 2.79-2.61 (m, 1.5H), 2.33-2.08 (m, 3H), 1.81-1.61 (m, 1H), 1.54-1.13 (m, 6H), 1.04-0.79 (m, 5H), 0.74-0.60 (m, 1H) |
| 134 | (1:1 CD₃OD:CDCl₃) δ 8.71 (s, 1H), 8.11-7.92 (m, 5H), 7.72-7.65 (m, 2H), 7.46 (br s, 1H), 7.35 (br s, 1H), 7.21-6.93 (m, 6H), 6.62 (br s, 1H), 4.72 (br s, 0.5H), 4.46 (br s, 0.5H), 4.33 (br s, 0.5H), 4.13 (br s, 0.5H), 3.92 (br s, 1H), 3.64 (br s, 1H), 3.48 (br s, 2H), 3.08 (br s, 0.5H), 2.95 (br s, 0.5H), 2.81 (br s, 1H), 2.12 (s, 3H), 1.45-1.21 (m, 4H), 0.92-0.82 (m, 3H) |
| 135 | (1:1 CD₃OD:CDCl₃) δ 8.70 (s, 1H), 8.08-7.97 (m, 4H), 7.96-7.87 (m, 2H), 7.69-7.58 (m, 2H), 7.52-7.45 (m, 1H), 7.26-7.01 (m, 6.5H), 6.95 (s, 0.5H), 6.90-6.81 (m, 1H), 4.72-4.19 (m, 3.5H), 3.97 (br s, 0.5H), 3.73-3.66 (m, 1H), |

| Ex. No. | ¹H NMR (mixture of amide rotamers) |
|---|---|
|  | 3.45 (d, J = 1.4 Hz, 2H), 3.25-3.00 (m, 1H), 2.78 (d, J = 5.5 Hz, 2H), 2.32-2.15 (m, 3H), 1.44-0.93 (m, 4H), 0.88-0.80 (m, 1.5H), 0.70 (t, J = 7.4 Hz, 1H), 0.64 (t, J = 7.4 Hz, 0.5H) |
| 136 | (1:1 CD₃OD:CDCl₃) δ 8.70 (s, 1H), 8.10-7.97 (m, 4H), 7.96-7.88 (m, 2H), 7.69-7.58 (m, 2H), 7.54-7.44 (m, 1H), 7.25-6.99 (m, 6.5H), 6.92 (dd, J = 3.6, 8.3 Hz, 1H), 6.84 (t, J = 6.7 Hz, 0.5H), 4.80 (br s, 1H), 4.50-4.17 (m, 2.5H), 3.99 (br s, 0.5H), 3.76-3.36 (m, 2.5H), 3.17 (br s, 1H), 2.81-2.65 (m, 2.5H), 2.33-2.16 (m, 3H), 1.47-0.93 (m, 3.5H), 0.84 (q, J = 7.5 Hz, 2H), 0.70 (t, J = 7.4 Hz, 1H), 0.65 (t, J = 7.4 Hz, 0.5H) |
| 137 | (1:1 CD₃OD:CDCl₃) δ 8.71 (s, 1H), 8.10-7.97 (m, 4H), 7.98-7.85 (m, 2H), 7.73-7.59 (m, 2H), 7.45-7.23 (m, 1H), 7.21-7.11 (m, 3.5H), 7.11-6.96 (m, 2.5H), 6.91-6.77 (m, 3H), 6.71 (d, J = 8.0 Hz, 1H), 6.59 (s, 2H), 4.23 (br s, 1H), 3.88 (br s, 2H), 3.60 (br s, 1H), 3.45 (dd, J = 3.3, 1.7 Hz, 1H), 3.08-2.97 (m, 1H), 2.91-2.73 (m, 2H), 2.17 (s, 2H), 2.07 (s, 1H), 1.50-1.17 (m, 4H), 0.96-0.78 (m, 3H) |
| 138 | (1:1 CD₃OD:CDCl₃) δ 8.62 (s, 1H), 8.17-7.85 (m, 6H), 7.63-7.50 (m, 2H), 7.35-7.21 (m, 2H), 7.17-7.09 (m, 4H), 6.94-6.81 (m, 3.5H), 6.78-6.70 (m, 2H), 6.63-6.51 (m, 1.5H), 4.28 (br s, 1H), 3.89 (br s, 2H), 3.65-3.40 (m, 2H), 3.08-2.95 (m, 1H), 2.92-2.76 (m, 2H), 2.20 (s, 2H), 2.05 (s, 1H), 1.50-1.19 (m, 4H), 0.91-0.79 (m, 3H) |
| 139 | (1:1 CD₃OD:CDCl₃) δ 8.70 (s, 1H), 8.14-7.87 (m, 6H), 7.77-7.34 (m, 5.5H), 7.22-6.95 (m, 4.5H), 6.89-6.72 (m, 1H), 6.42-6.29 (m, 1H), 4.53-4.35 (m, 2H), 3.72 (s, 2H), 3.63-3.56 (m, 3H), 3.50-3.35 (m, 2H), 3.19-3.03 (m, 2H), 2.77-2.62 (m, 2H), 2.31 (s, 2H), 2.14 (s, 1H), 1.40-1.06 (m, 3H), 1.04-0.90 (m, 1H), 0.82-0.60 (m, 3H) |
| 140 | (1:1 CD₃OD:CDCl₃) δ 8.64 (br s, 1H), 8.13-7.84 (m, 6H), 7.68-7.48 (m, 5H), 7.28-7.06 (m, 4.5H), 6.51-6.40 (m, 0.5H), 4.52-4.40 (m, 2H), 3.83-3.71 (m, 3H), 3.66 (br s, 3H), 3.63-3.50 (m, 2H), 3.17-3.13 (m, 2H), 2.89-2.75 (m, 2H), 2.08 (s, 1H), 2.06 (s, 1H), 1.48-1.38 (m, 2H), 1.35-1.27 (m, 2H), 0.95-0.74 (m, 3H) |
| 141 | (1:1 CD₃OD:CDCl₃) δ 8.70 (br s, 1H), 8.12-7.82 (m, 6H), 7.79-7.57 (m, 2H), 7.26 (dd, J = 19.0, 8.3 Hz, 1H), 7.20-7.08 (m, 5H), 6.95-6.76 (m, 1H), 6.66-6.57 (m, 1H), 6.50 (d, J = 8.8 Hz, 1H), 4.71 (br s, 1H), 4.41 (br s, 1H), 4.25 (br s, 1H), 3.82 (br s, 2H), 3.73-3.61 (m, 1H), 3.50-3.39 (m, 1H), 2.08 (s, 2H), 2.06 (s, 1H), 2.81-2.69 (m, 2H), 1.50-1.25 (m, 4H), 1.28-1.13 (m, 6H), 0.92-0.79 (m, 3H) |
| 142 | (1:1 CD₃OD:CDCl₃) δ 8.65 (s, 1H), 8.16-7.84 (m, 8H), 7.70-7.48 (m, 4H), 7.26-6.85 (m, 4H), 4.78-4.51 (m, 2H), 4.34-3.90 (m, 2H), 3.76-3.41 (m, 2H), 2.94-2.75 (m, 2H), 2.21 (br. s, 2H), 2.11 (br s, 4H), 1.45-1.33 (m, 2H), 1.29-1.19 (m, 2H), 0.95-0.68 (m, 3H) |
| 143 | (1:1 CD₃OD:CDCl₃) δ 8.69 (s, 1H), 8.09-7.77 (m, 7H), 7.75-7.56 (m, 2H), 7.51-7.21 (m, 8H), 7.20-6.74 (m, 5H), 4.72 (br s, 1H), 4.22 (br s, 1H), 4.03 (br s, 1H), 3.89 (br s, 1H), 3.66-3.42 (m, 2H), 2.75 (br s, 2H), 2.10 (s, 1H), 2.07 (s, 2H), 1.55-1.39 (m, 2H), 1.35-1.17 (m, 2H), 0.95-0.76 (m, 3H) |
| 144 | (1:1 CD₃OD:CDCl₃) δ 8.66 (br s, 1H), 8.13-7.84 (m, 6H), 7.68-7.48 (m, 4H), 7.30-7.12 (m, 4H), 6.95-6.80 (m, 1H), 6.66 (d, J = 8.6 Hz, 1H), 6.53 (d, J = 8.6 Hz, 1H), 4.25 (br s, 1H), 4.07 (br s, 1H), 3.88-3.68 (m, 3H), 3.65-3.50 (m, 3H), 3.35 (br s, 2H), 3.01-2.70 (m, 2H), 2.10 (s, 1H), 2.07 (s, 2H), 1.52-1.16 (m, 4H), 0.95-0.74 (m, 3H) |
| 145 | (1:1 CD₃OD:CDCl₃) δ 8.65 (s, 1H), 8.15-7.85 (m, 6H), 7.69-7.49 (m, 4H), 7.32-7.06 (m, 4H), 7.04-6.79 (m, 1H), 6.65-6.25 (m, 2H), 4.34-4.05 (m, 2H), 3.84-3.67 (m, 4H), 3.68-3.57 (m, 3H), 2.93-2.72 (m, 2H), 2.09 (s, 1H), 2.08 (s., 2H), 1.51-1.14 (m, 4H), 0.96-0.72 (m, 3H) |
| 146 | (1:1 CD₃OD:CDCl₃) δ 8.63 (s, 1H), 8.10-7.85 (m, 5H), 7.68-7.47 (m, 5H), 7.34-6.88 (m, 6H), 6.70 (br s, 0.5H), 6.44 (br s., 0.5H), 4.50-4.16 (m, 2H), 3.98-3.75 (m, 2H), 3.43-3.23 (m, 2H), 2.83-2.75 (m, 2H), 2.05 (s, 1H), 2.04 (s, 2H), 1.55-1.25 (m, 4H), 1.23-1.05 (m, 9H), 0.90-0.75 (m, 3H) |
| 147 | (1:1 CD₃OD:CDCl₃) δ 8.62 (s, 1H), 8.16-7.82 (m, 6H), 7.66-7.51 (m, 5H), 7.44-7.20 (m, 6H), 7.17-6.65 (m, 5H), 4.19 (br s, 2H), 3.83 (br s, 2H), 3.55 (br s, 2H), 2.91-2.67 (m, 2H), 2.09 (s, 1H), 2.07 (s, 2H), 1.57-1.22 (m, 4H), 0.90-0.78 (m, 3H) |
| 148 | (1:1 CD₃OD:CDCl₃) δ 8.71-8.57 (m, 1H), 8.17-7.79 (m, 6H), 7.68-7.44 (m, 5H), 7.26-6.99 (m, 5H), 6.93-6.80 (m, 1H), 4.36-4.12 (m, 2H), 3.94-3.79 (m, 2H), 3.68-3.60 (m, 1H), 3.53-3.38 (m, 1H), 2.88-2.76 (m, 2H), 2.16-1.91 (m, 3H), 1.54-1.06 (m, 13H), 0.96-0.74 (m, 3H) |
| 149 | (DMSO-d₆) δ 8.69 (s, 1H), 8.39-7.89 (m, 6H), 7.86-7.62 (m, 3H), 7.51 (br s, 1H), 7.28-7.09 (m, 4H), 6.75-6.13 (m, 1H), 4.44 (br s, 1H), 4.32-4.00 (m, 5H), 3.84-3.27 (m, 4H), 2.92-2.71 (m, 2H), 2.24-1.97 (br s, 3H), 1.38-1.02 (m, 4H), 0.96-0.56 (m, 3H) |
| 150 | (1:1 CD₃OD:CDCl₃) δ 8.69 (s, 1H), 8.13-7.80 (m, 6H), 7.74-7.53 (m, 3H), 7.35-7.06 (m, 4H), 7.01-6.76 (m, 2H), 6.66-6.21 (m, 2H), 4.79 (br s, 1H), 4.38 (br s, 2H), 3.88-3.61 (m, 2H), 3.53 (br s, 1 H), 3.28-3.14 (m, 1H), 2.95-2.74 (m, 2H), 2.08 (br s, 3H), 1.54-1.10 (m, 10H), 0.95-0.76 (m, 3H) |
| 151 | (1:1 CD₃OD:CDCl₃) δ 8.61 (d, J = 4.2 Hz, 1H), 8.22-8.10 (m, 1H), 8.08-7.82 (m, 5H), 7.82-7.51 (m, 5H), 7.50-7.27 (m, 5H), 7.19-6.72 (m, 4H), 4.57-4.42 (m, 2H), 4.29 (br s, 2H), 3.65-3.35 (m, 4H), 2.78-2.65 (m, 2H), 2.24 (s, 2H), 2.16 (s, 1H), 1.50-0.94 (m, 4H), 0.93-0.58 (m, 3H) |
| 152 | (CDCl₃) δ 9.25-9.05 (m, 2H), 8.50-8.40 (m, 1H), 8.36-8.20 (m, 1H), 7.96-7.74 (m, 3H), 7.65-7.55 (m, 1H), 7.40-6.81 (m, 14H), 4.30 (br s, 1H), 4.10 (br s, 1H), 3.97-3.76 (m, 2H), 3.53-3.35 (m, 2H), 3.28-3.16 (m, 1H), 2.83 (br s, 1H), 2.70-2.55 (m, 1H), 2.07 (s, 1H), 2.05 (br s, 2H), 1.55-1.22 (m, 4H), 0.95-0.77 (m, 3H) |
| 153 | (CDCl₃) δ 9.40-9.11 (m, 1H), 8.76 (d, J = 3.1 Hz, 1H), 8.11-7.76 (m, 5H), 7.74-7.54 (m, 2H), 7.44-6.80 (m, 13H), 4.28 (br s, 1H), 4.10 (br s, 1H), 3.87 (br s, 2H), 3.47 (br s, 1H), 3.26 (br s, 1H), 2.85-2.67 (m, 1H), 2.61 (br s, 1H), 2.06 (br s, 1H), 2.04 (br s, 2H), 1.76-1.43 (m, 3H), 1.42-1.16 (m, 1H), 0.93-0.70 (m, 3H) |
| 154 | (1:1 CD₃OD:CDCl₃) δ 8.61 (s, 1H), 8.20-7.80 (m, 6H), 7.72 (d, J = 8.1 Hz, 1H), 7.61-7.48 (m, 3H), 7.22-7.08 (m, 5H), 6.98 (d, J = 8.6 Hz, 1H), 6.74 (br s, 1H), 4.39-4.09 (m, 2H), 3.98-3.77 (m, 5H), 3.50 (br s, 2H), 2.86-2.76 (m, 2H), 2.11 (s, 1H), 2.09 (s, 2H), 1.46-1.10 (m, 4H), 0.91-0.70 (m, 3H) |
| 155 | (1:1 CD₃OD:CDCl₃) δ 8.61 (s, 1H), 8.20-7.80 (m, 6H), 7.72 (d, J = 8.1 Hz, 1H), 7.61-7.48 (m, 3H), 7.22-7.08 (m, 5H), 6.98 (d, J = 8.6 Hz, 1H), 6.74 (br s, 1H), 4.39-4.09 (m, 2H), 3.98-3.77 (m, 5H), 3.50 (br s, 2H), 2.86-2.76 (m, 2H), 2.11 (s, 1H), 2.09 (s, 2H), 1.46-1.10 (m, 4H), 0.91-0.70 (m, 3H) |

| Ex. No. | ¹H NMR (mixture of amide rotamers) |
|---|---|
| 241 | (DMSO-d₆) δ 8.74 (s, 1H), 8.31 (d, J = 8 Hz, 1H), 8.21 (d, J = 8 Hz, 1H), 8.15 (d, J = 8 Hz, 1H), 8.10-8.03 (m, 3H), 7.86-7.74 (m, 2H), 7.69-6.97 (m, 14H), 4.89-4.10 (m, 4H), 3.28-3.22 (m, 2H), 2.78-2.44 (m, 4H), 1.18-0.98 (m, 4H), 0.65-0.60 (m, 3H) |
| 242 | (1:1 CD₃OD:CDCl₃) δ 8.68 (s, 1H), 8.09-7.97 (m, 5H), 7.92 (d, J = 8 Hz, 1H), 7.65-7.58 (m, 2H), 7.37-6.96 (m, 12.5H), 6.89-6.88 (m, 0.5H), 4.53-4.23 (m, 4H), 3.38-3.15 (m, 2H), 2.81-2.47 (m, 4H), 1.06-0.87 (m, 4H), 0.56-0.54 (m, 3H) |
| 243 | (CD₃OD) δ 8.73 (s, 1H), 8.12-7.98 (m, 6H), 7.73-7.66 (m, 2H), 7.63-6.94 (m, 13H), 4.62-4.18 (m, 4H), 3.65-3.17 (m, 2H), 2.79-2.45 (m, 4H), 1.31-0.91 (m, 4H), 0.65-0.58 (m, 3H) |
| 244 | (1:1 CD₃OD:CDCl₃) δ 8.73 (s, 1H), 8.23-8.03 (m, 4H), 7.96-7.91 (m, 2H), 7.70-7.62 (m, 2H), 7.45-6.80 (m, 9H), 4.50-4.22 (m, 4H), 4.03-4.00 (m, 2H), 3.28-3.17 (m, 2H), 2.83-2.40 (m, 4H), 1.83-1.76 (m, 2H), 1.56-1.49 (m, 2H), 1.02-0.87 (m, 7H), 0.55-0.52 (m, 3H) |
| 245 | (CD₃OD) δ 8.66 (s, 1H), 8.17-7.95 (m, 6H), 7.69-7.59 (m, 2H), 7.47-6.82 (m, 9H), 4.74-4.20 (m, 6H), 3.82-3.79 (m, 2H), 2.92-2.90 (m, 2H), 2.82-2.54 (m, 4H), 1.04-0.88 (m, 4H), 0.65-0.52 (m, 3H) |
| 246 | (CD₃OD) δ 8.69 (s, 1H), 8.12-7.96 (m, 6H), 7.69-7.61 (m, 2H), 7.43-6.84 (m, 9H), 6.11-6.02 (m, 1H), 5.44-5.39 (m, 1H), 5.29-5.25 |

| Ex. No. | $^1$H NMR (mixture of amide rotamers) |
|---|---|
| | (m, 1H), 4.72-4.16 (m, 8H), 2.90-2.41 (m, 4H), 1.10-0.96 (m, 4H), 0.54-0.52 (m, 3H) |
| 247 | (CD$_3$OD) δ 8.67 (s, 1H), 8.12-7.97 (m, 6H), 7.81-7.61 (m, 7H), 7.48-7.37 (m, 4H), 7.25-7.04 (m, 4.5H), 6.94-6.93 (m, 0.5H), 4.75-4.22 (m, 6H), 2.90-2.42 (m, 4H), 1.21-0.89 (m, 4H), 0.58-0.54 (m, 3H) |
| 248 | (CD$_3$OD) δ 9.10 (s, 1H), 8.21-8.14 (m, 2H), 8.05-7.97 (m, 3H), 7.81-7.78 (m, 1H), 7.68-7.64 (m, 1H), 7.51-7.38 (m, 3H), 7.22-7.01 (m, 9.5H), 6.82-6.81 (m, 0.5H), 4.51-3.47 (m, 6H), 2.81-2.48 (m, 4H), 1.17-0.89 (m, 7H), 0.62 (t, J = 6 Hz, 3H) |
| 249 | (CD$_3$OD) δ 8.18-8.17 (m, 1H), 8.13 (s, 1H), 7.57-7.39 (m, 4H), 7.22-7.02 (m, 8.5H), 6.86-6.85 (m, 0.5H), 4.56-3.58 (m, 6H), 3.42-3.40 (m, 2H), 2.81-2.48 (m, 4H), 1.42-1.38 (m, 3H), 1.19-1.04 (m, 7H), 0.64 (t, J = 6 Hz, 3H) |
| 250 | (CD$_3$OD) δ 8.18-8.17 (m, 1H), 8.13 (s, 1H), 7.50-7.49 (m, 4H), 7.22-7.02 (m, 8.5H), 6.85-6.84 (m, 0.5H), 4.56-3.80 (m, 6H), 3.41-3.40 (m, 2H), 2.79-2.53 (m, 4H), 1.90-1.85 (m, 2H), 1.51-1.36 (m, 4H), 1.19-1.03 (m, 7H), 0.94 (t, J = 8 Hz, 3H), 0.65 (t, J = 6 Hz, 3H) |
| 251 | (CDCl$_3$) δ 9.15 (s, 1H), 8.48-8.35 (m, 2H), 7.92-7.84 (m, 2H), 7.49-6.77 (m, 16H), 4.90-4.80 (m, 0.5H), 4.55-4.45 (m, 0.5H), 4.36-3.95 (m, 3H), 3.52-3.32 (m, 2H), 2.80-2.49 (m, 4H), 1.33-0.87 (m, 7H), 0.60-0.56 (m, 3H) |
| 252 | (CD$_3$OD) δ 8.19-7.98 (m, 6H), 7.80 (d, J = 8 Hz, 1H), 7.66 (t, J = 8 Hz, 1H), 7.57-7.37 (m, 2H), 7.23-6.87 (m, 11H), 4.61-4.21 (m, 4H), 3.62-3.19 (m, 2H), 2.84-2.55 (m, 4H), 1.20-0.91 (m, 4H), 0.62-0.57 (m, 3H) |
| 253 | (CD$_3$OD) δ 8.14-8.02 (m, 2H), 7.43-7.39 (m, 2H), 7.24-7.00 (m, 10.5H), 6.92-6.91 (m, 0.5H), 4.78-4.10 (m, 6H), 3.57 (q, J = 4 Hz, 2H), 2.87-2.50 (m, 4H), 1.40 (t, J = 4 Hz, 3H), 1.14-0.92 (m, 4H), 0.65-0.60 (m, 3H) |
| 254 | (CD$_3$OD) δ 8.13-8.07 (m, 2H), 7.45-7.38 (m, 2H), 7.24-7.01 (m, 10.5H), 6.92-6.91 (m, 0.5H), 4.78-4.10 (m, 6H), 3.56 (q, J = 4 Hz, 2H), 2.90-2.50 (m, 4H), 1.91-1.84 (m, 2H), 1.51-1.46 (m, 2H), 1.43-1.38 (m, 2H), 1.13-1.02 (m, 4H), 0.94 (t, J = 4 Hz, 3H), 0.68-0.62 (m, 3H) |
| 255 | (1:1 CD$_3$OD:CDCl$_3$) δ 9.09 (s, 1H), 8.44 (d, J = 8 Hz, 1H), 8.31 (t, J = 8 Hz, 1H), 8.13-7.98 (m, 2H), 7.85 (d, J = 8 Hz, 1H), 7.61-7.56 (m, 2H), 7.41-7.31 (m, 2H), 7.20-6.82 (m, 10H), 4.61-4.16 (m, 4H), 3.38-3.15 (m, 2H), 2.86-2.49 (m, 4H), 1.07-0.85 (m, 4H), 0.60-0.53 (m, 3H) |

Biological Assays

The pharmacological properties of the compounds of this invention may be confirmed by a number of biological assays. The exemplified biological assays, which follow, have been carried out with compounds of the invention and/or salts thereof.

In general, compounds of the present invention inhibit at least one of the following pro-survival proteins: Bcl-x$_L$ and/or Bcl-2.

Bcl-x$_L$/Bim Fluorescence Resonance Energy Transfer Assay (FRET)

The assays were performed in black flat-bottom 384-well plates. The final assay volume was 55 μl prepared from additions of Biotin-Bcl-x$_L$ (Bcl-x$_L$: GENBANK® Accession No. Q07817), fluoresceinated 18-mer BIM peptide (NH$_2$-YYAN-FEDGIRRLEQAIWI-[FAM]) (SEQ ID NO: 1), Streptavidin-Terbium FRET detection reagent, and test compounds in assay buffer consisting of 20 mM Sodium Phosphate, 1 mM EDTA, 50 mM NaCl, and 0.05% Pluronic Acid. The reaction was incubated at room temperature for 60 minutes. After 60 minutes, 5 μL of Streptavidin-Terbium FRET detection reagent (Perkin Elmer) was added to the reaction mixture and incubated at room temperature in the dark for 30 mins. The FRET signal generated by the reaction was detected on the Envision Plate Reader Inhibition data were calculated from FRET values generated by the no protein control reactions for 100% inhibition and vehicle-only reactions for 0% inhibition.

The final concentration of reagents in the assay was 10 nM Bcl-x$_L$, 5 nM fluoresceinated 18-mer BIM peptide, 5 nM Streptavidin-Terbium FRET detection reagent, and 1% DMSO. Dose response curves were generated to determine the concentration required inhibiting 50% of kinase activity (IC$_{50}$). Compounds were dissolved at 10 mM in dimethylsulfoxide (DMSO) and evaluated at eleven concentrations. IC$_{50}$ values were derived by non-linear regression analysis.

Bcl-2/Bim Fluorescence Polarization Assay (FPA)

The assays were performed in black flat-bottom 384-well plates. The final assay volume was 50 μl prepared from additions of Gst-Bcl-2 (Bcl-2: GENBANK® Accession No. P10415), fluoresceinated 18-mer BIM peptide (NH$_2$-YYAN-FEDGIRRLEQAIWI-[FAM]) (SEQ ID NO: 1), and test compounds in assay buffer consisting of 20 mM Sodium Phosphate, 1 mM EDTA, 50 mM NaCl, and 0.05% Pluronic Acid. The reaction was incubated at room temperature for 60 minutes and fluorescence polarization of the reaction was detected on the LJL Plate Reader. Inhibition data were calculated from mP values generated by the no protein control reactions for 100% inhibition and vehicle-only reactions for 0% inhibition. The final concentrations of reagents in the assay were 4.9 nM BCL-2, 5 nM fluoresceinated 18-mer BIM peptide and 1% DMSO. Dose response curves were generated to determine the concentration required inhibiting 50% of kinase activity (IC$_{50}$). Compounds were dissolved at 10 mM in dimethylsulfoxide (DMSO) and evaluated at eleven concentrations. IC$_{50}$ values were derived by non-linear regression analysis.

Table 3 below lists the Bcl-2 IC$_{50}$ and Bcl-x$_L$ values for the following examples of this invention measured in the assays described hereinabove. The compounds of the present invention, as exemplified by the following examples, showed Bcl-2 IC$_{50}$ and Bcl-x$_L$ values of less than 5 μM and 10 μM, respectively.

TABLE 3

Bcl IC$_{50}$ Inhibition Values

| Example No. | Bcl-2 IC$_{50}$ Value (μM) | Bcl-x$_L$ IC$_{50}$ Value (μM) |
|---|---|---|
| 1 | 0.03 | 0.02 |
| 2 | 0.20 | 0.03 |
| 5 | 0.03 | 0.07 |
| 7 | 0.04 | 0.04 |
| 8 | 0.92 | 0.02 |
| 10 | 0.09 | 0.09 |
| 11 | 0.04 | 0.05 |
| 18 | 0.01 | 0.03 |
| 24 | 0.05 | 0.02 |
| 27 | 0.11 | 0.04 |
| 31 | 0.03 | 0.07 |
| 32 | 0.29 | 0.05 |
| 34 | 0.29 | 0.04 |
| 35 | 0.51 | 0.04 |
| 37 | 0.49 | 0.01 |
| 38 | 0.86 | 0.02 |
| 39 | 1.46 | 0.02 |
| 40 | 3.78 | 0.03 |
| 43 | 3.93E-03 | 0.02 |
| 44 | 7.25E-03 | 0.03 |
| 46 | 0.09 | 0.04 |
| 48 | 0.15 | 0.08 |
| 53 | 0.06 | 0.01 |
| 55 | 0.25 | 0.23 |
| 59 | 0.02 | 0.04 |
| 64 | 0.20 | 2.45 |
| 67 | 0.05 | 0.06 |
| 68 | 0.05 | 0.11 |
| 74 | 0.34 | 0.06 |

TABLE 3-continued

Bcl IC$_{50}$ Inhibition Values

| Example No. | Bcl-2 IC$_{50}$ Value (μM) | Bcl-x$_L$ IC$_{50}$ Value (μM) |
|---|---|---|
| 82 | 0.39 | 0.03 |
| 83 | 0.02 | 0.04 |
| 84 | 7.69E−03 | 0.08 |
| 85 | 4.19E−03 | 0.02 |
| 91 | 0.05 | 6.27E−03 |
| 92 | 8.41E−03 | 0.01 |
| 93 | 1.65 | 0.20 |
| 96 | 0.12 | 0.06 |
| 100 | 4.71 | 3.51 |
| 104 | 0.44 | 0.13 |
| 105 | 0.02 | 0.03 |
| 106 | 0.02 | 7.06E−03 |
| 115 | 0.09 | 0.02 |
| 106 | 0.01 | 9.01E−03 |
| 119 | 0.05 | 0.01 |
| 127 | 0.03 | 0.22 |
| 128 | 0.11 | 0.08 |
| 130 | 0.08 | 0.03 |
| 149 | 0.07 | 0.03 |
| 152 | 0.05 | 0.16 |
| 154 | 0.09 | 0.08 |
| 158 | 0.07 | 0.02 |
| 164 | 0.23 | 0.03 |
| 179 | 0.02 | 0.08 |
| 181 | 8.49E−03 | 0.05 |
| 189 | 0.01 | 0.04 |
| 191 | 0.26 | 0.69 |
| 192 | 0.06 | 0.03 |
| 195 | 0.03 | 0.29 |
| 196 | 0.04 | 0.51 |
| 198 | 8.85E−03 | 0.05 |
| 200 | 1.01 | 0.13 |
| 203 | 0.01 | 0.01 |
| 205 | 9.15E−03 | 8.85E−03 |
| 207 | 7.84E−03 | 0.04 |
| 208 | 3.59E−03 | 7.88E−03 |
| 213 | 0.01 | 0.08 |
| 214 | 0.05 | 8.07 |
| 217 | 0.01 | 0.07 |
| 221 | 0.04 | 0.04 |
| 222 | 0.07 | 0.04 |
| 228 | 0.10 | 0.06 |
| 230 | 0.02 | 0.06 |
| 239 | 0.58 | 0.03 |
| 241 | 0.13 | 0.03 |
| 242 | 0.02 | 0.04 |
| 243 | 7.83E−03 | 0.02 |
| 245 | 0.02 | 6.14E−03 |
| 251 | 0.02 | 0.05 |
| 252 | 6.37E−03 | 0.01 |
| 258 | 8.13E−03 | 4.96E−03 |
| 260 | 0.01 | 8.01E−03 |
| 264 | 0.11 | 0.04 |
| 265 | 0.43 | 0.07 |
| 267 | 0.20 | 0.03 |
| 269 | 0.14 | 0.03 |
| 277 | 0.12 | 0.06 |
| 282 | 6.97E−03 | 0.01 |
| 286 | 0.60 | 0.07 |
| 289 | 0.01 | 0.06 |
| 315 | 0.06 | 0.08 |
| 322 | 0.01 | 0.16 |
| 328 | 8.78E−03 | 0.01 |
| 329 | 5.09E−03 | 0.02 |

What is claimed is:

1. A compound of Formula (I)

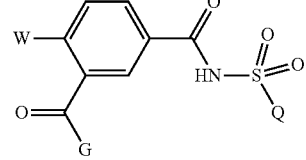

or a pharmaceutically acceptable salt thereof, wherein:

W is:

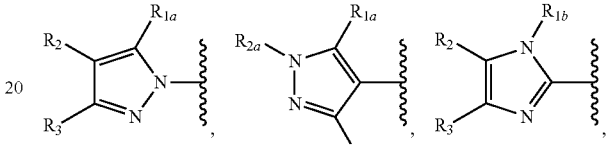

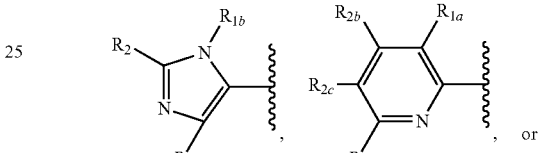

Q is:
(a) naphthalenyl or isoquinolinyl, each substituted with zero to 3 substituents independently selected from —OH, —CN, halo, —NO$_2$, —C(O)OH, —C(O)O (C$_{1-4}$ alkyl), —S(O)$_2$(C$_{1-4}$ alkyl), —S(CH$_2$)$_{1-3}$C(O) OH, —S(CH$_2$)$_{1-3}$NH$_2$, C$_{1-4}$ alkoxy, —OCH(CH$_3$) CH$_2$N(C$_{1-4}$ alkyl)$_2$, —O(CH$_2$)$_{1-3}$R$_x$, —O(CH$_2$)$_3$N (CH$_3$)$_2$, —O(CH$_2$)$_{1-4}$OH, —O(CH$_2$)$_{1-4}$O(C$_{1-4}$ alkyl), —O(CH$_2$)$_{1-4}$O(phenyl), —N(C$_{1-4}$ alkyl)$_2$, —C(O)N (C$_{1-4}$ alkyl)$_2$, —C(O)R$_x$, and/or —NHC(O)R$_x$;

(b)

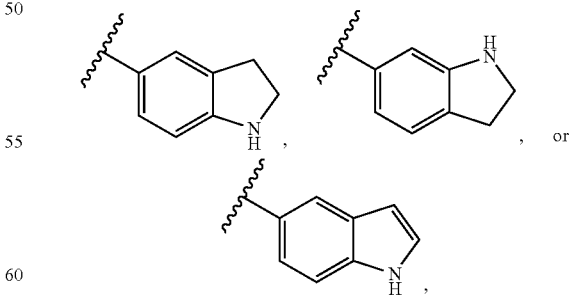

each substituted with zero to 3 substituents independently selected from halo, C$_{1-4}$ alkyl, C(O)(C$_{1-4}$ alkyl), —C(O)R$_x$, —C(O)(CH$_2$)$_{1-3}$R$_x$, —C(O)O(C$_{1-4}$ alkyl), —(CH$_2$)$_{1-3}$R$_x$, —C(O)(CH$_2$)$_{1-3}$S(phenyl), —(CH$_2$)$_{1-3}$S (phenyl), C$_{2-4}$ alkenyl, and/or morpholinyl; or (c) $C_{1-6}$ alkyl or —$(CH_2)_{1-3}$(trimethylsilyl), provided that W is

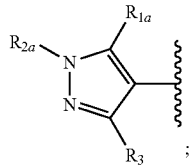
;

each $R_x$ is independently $C_{3-6}$ cycloalkyl, phenyl, chlorophenyl, difluorophenyl, dichlorophenyl, benzoic acid, methyl benzoate, methylsulfonylphenyl, pyridinyl, chloropyridinyl, furanyl, pyrrolidinyl, piperidinyl, morpholinyl, (morpholinoethoxy)pyridinyl, N-methylpyrrolidinyl, N-methylpiperazinyl, N-methyl-1H-imidazolyl, 1-methyl-1H-indolyl, or N-(2-hydroxyethyl) piperazinyl;

G is:
(a) —$N(C_{1-4}$ alkyl$)_2$; or
(b) a bicyclic heterocyclyl selected from:

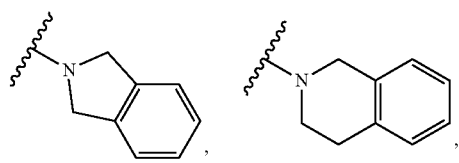,

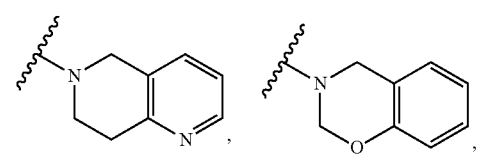,

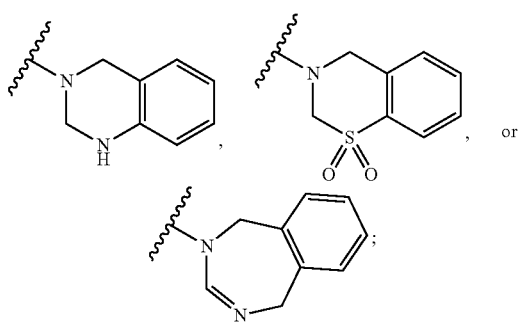 ;

wherein said bicyclic heterocyclyl is substituted with zero to 3 substituents independently selected from: halo, $C_{1-4}$ alkyl, $C_{1-4}$ fluoroalkyl, $C_{1-4}$ hydroxyalkyl, $C_{1-4}$ alkoxy, —$(CH_2)_{0-3}C(O)OH$, —$(CH_2)_{1-3}NH_2$, —$(CH_2)_{1-3}N_3$, —$(CH_2)_{1-3}N(CH_3)(C_{1-4}$ hydroxyalkyl), —$(CH_2)_{1-3}$ $N(CH_3)((CH_2)_{1-3}OCH_3)$, —$(CH_2)_{1-3}O$ $(CH_2)_{1-3}N(C_{1-4}$ alkyl$)_2$, —$(CH_2)_{1-3}O(CH_2)_{1-3}OH$, —$(CH_2)_{1-3}O(CH_2)_{1-3}(C_{1-4}$ alkyl), —$(CH_2)_{1-3}$ $O(CH_2)_{1-3}$ O(phenyl), —$(CH_2)_{1-3}O(CH_2)_{1-3}CH_3$, —$(CH_2)_{1-3}R_x$, —$(CH_2)_{0-3}N(CH_3)_2$, —$N(CH_3)$ $((CH_2)_{1-3}$ $O(C_{1-4}$ alkyl),

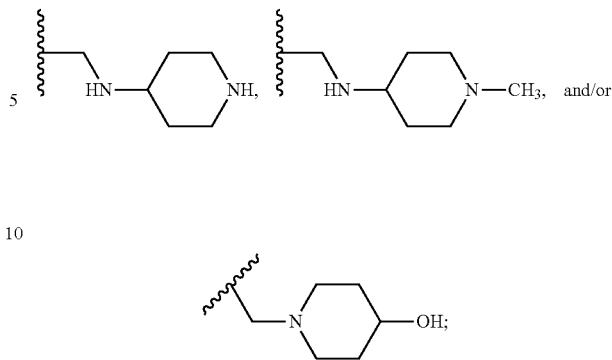

$R_{1a}$ is H, halo, $C_{1-6}$ alkyl, —$CF_3$, $C_{1-4}$ hydroxyalkyl, —$(CH_2)_{1-3}O(C_{1-4}$ alkyl), —$(CH_2)_{1-3}O(C_{1-4}$ hydroxyalkyl), —$(CH_2)_{0-3}C(O)OH$, —$(CH_2)_{0-3}N(C_{1-4}$ alkyl$)_2$, —$(CH_2)_{0-3}C(O)NH(C_{1-4}$ alkyl), —$(CH_2)_{1-3}R_x$, —$(CH_2)_{0-3}OC(O)NH_2$, —$(CH_2)_{0-3}C(O)NHS(O)_2(C_{3-6}$ cycloalkyl), —$(CH_2)_{1-3}OC(O)R_x$, or —$(CH_2)_{0-3}OC(O)$ $NH(CH_2)_{1-3}R_x$;

$R_{1b}$ is H, $C_{1-6}$ alkyl, —$CF_3$, $C_{1-4}$ hydroxyalkyl, —$(CH_2)_{1-3}$ $O(C_{1-4}$ alkyl), —$(CH_2)_{1-3}O(C_{1-4}$ hydroxyalkyl), —$(CH_2)_{0-3}C(O)OH$, —$(CH_2)_{0-3}N(C_{1-4}$ alkyl$)_2$, —$(CH_2)_{0-3}C(O)NH(C_{1-4}$ alkyl), —$(CH_2)_{1-3}R_x$, —$(CH_2)_{0-3}OC(O)NH_2$, —$(CH_2)_{0-3}C(O)NHS(O)_2(C_{3-6}$ cycloalkyl), —$(CH_2)_{1-3}OC(O)R_x$, or —$(CH_2)_{0-3}$ $OC(O)$ $NH(CH_2)_{1-3}R_x$;

$R_2$ is:
(a) H, Cl, Br, $C_{1-3}$ hydroxyalkyl, —$(CH_2)_{0-3}C(O)OH$, or —$(CH_2)_{0-3}N(CH_3)_2$; or
(b) phenyl substituted with zero to 2 substituents independently selected from $C_{1-4}$ alkyl, —$(CH_2)_{0-3}OH$, —$O(CH_3)_{0-3}CH_3$, —$O(CH_2)_{1-3}OH$, —$O(CH_2)_{1-2}CH(OH)(CH_2)_{1-2}OH$, —$O(C_{2-4}$ alkenyl), —$OR_x$, —$C(O)O(C_{1-4}$ alkyl), and/or phenyl;

$R_{2a}$ is:
(a) H, $C_{1-3}$ hydroxyalkyl, —$(CH_2)_{0-3}C(O)OH$, or —$(CH_2)_{0-3}N(CH_3)_2$; or
(b) phenyl substituted with zero to 2 substituents independently selected from $C_{1-4}$ alkyl, —$(CH_2)_{0-3}OH$, —$O(CH_3)_{0-3}CH_3$, —$O(CH_2)_{1-3}OH$, —$O(CH_2)_{1-2}CH(OH)(CH_2)_{1-2}OH$, —$O(C_{2-4}$ alkenyl), —$OR_x$, —$C(O)O(C_{1-4}$ alkyl), and/or phenyl;

one of $R_{2b}$ and $R_{2c}$ is H and the other of $R_{2b}$ and $R_{2c}$ is $R_2$;

$R_3$ is —$(CH_2)_{1-3}OH$, —$C(O)OH$, —$C(O)O(C_{1-4}$ alkyl), —$C(O)NR_aR_b$, or —$NR_aR_b$;

$R_a$ is H, $C_{1-6}$ alkyl, or $C_{1-4}$ fluoroalkyl; and $R_b$ is
(a) $C_{1-6}$ alkyl, $C_{1-4}$ fluoroalkyl, —$(CH_2)_{1-3}C(O)OH$, —$(CH_2)_{1-3}C(O)O(C_{1-4}$ alkyl), —$(CH_2)_{1-3}(C_{3-6}$ cycloalkyl), —$CH_2$(naphthalenyl), —$(CH_2)_{1-3}C(O)$ $NHCH(C_{1-4}$ hydroxyalkyl$)_2$, —$(CH_2)_{1-3}C(O)NHCH$ $(C_{1-4}$ hydroxyalkyl$)_3$, or —$(CH_2)_{1-3}C(O)NH$ $(CH_2)_{1-3}R_x$;
(b) —$(CH_2)_{0-2}$(phenyl) wherein said phenyl is substituted with zero to 2 substituents independently selected from Cl, I, $C_{1-4}$ alkyl, $C_{1-4}$ alkoxy, —$(CH_2)_{0-3}$ $C(O)OH$, —$C(O)O(C_{1-4}$alkyl), —(CH$_2$)$_{1-3}$C(O)O(C$_{1-4}$alkyl), phenyl, halophenyl, halophenoxy, phenyl acetic acid, and/or —(CH$_2$)$_{1-3}$C(O)R$_x$; or (c)

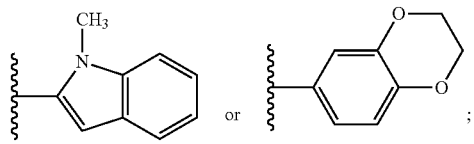 [SMILES: *c1cc2ccccc2n1C ; *c1ccc2c(c1)OCCO2]

or R$_a$ and R$_b$, together with the nitrogen atom to which they are attached, form a pyrrolidinyl ring substituted with zero to 1 substituent selected from C$_{1-4}$alkyl or —(CH$_2$)$_{1-3}$(phenyl).

2. The compound according to claim 1 or a pharmaceutically acceptable salt thereof, wherein:

Q is:
(a) naphthalenyl substituted with zero to 3 substituents independently selected from —OH, —CN, Cl, Br, I, —NO$_2$, —N(CH$_3$)$_2$, —C(O)OH, —C(O)OCH$_2$CH$_3$, —S(O)$_2$CH$_2$CH$_3$, C$_{1-3}$ alkoxy, —OCH(CH$_3$)CH$_2$N(CH$_3$)$_2$, —O(CH$_2$)$_3$N(CH$_3$)$_2$, —OCH$_2$(phenyl), —OCH$_2$(dichlorophenyl), —OCH$_2$(benzoic acid), —OCH$_2$(methyl benzoate), —OCH$_2$(methylsulfonylphenyl), —OCH$_2$(furanyl), —OCH$_2$(N-methyl-1H-imidazolyl), —O(CH$_2$)$_2$(N-methylpyrrolidinyl), —O(CH$_2$)$_{2-3}$(morpholinyl), —O(CH$_2$)$_3$(pyrrolidinyl), —O(CH$_2$)$_3$(piperidinyl), O(CH$_2$)$_3$(N-methylpiperazinyl), —O(CH$_2$)$_3$(pyridinyl), —OCH$_2$CH$_2$OH, —OCH$_2$CH$_2$O(C$_{1-2}$ alkyl), —OCH$_2$CH$_2$O(phenyl), —C(O)N(CH$_3$)$_2$, —C(O)(N-methylpiperazinyl), —C(O)(morpholinyl), and/or —NHC(O)(dichlorophenyl);

(b) isoquinolinyl substituted with —OCH$_2$CH$_2$(morpholinyl), —SCH$_2$CH$_2$NH$_2$, or —SCH$_2$C(O)OH;

(c)

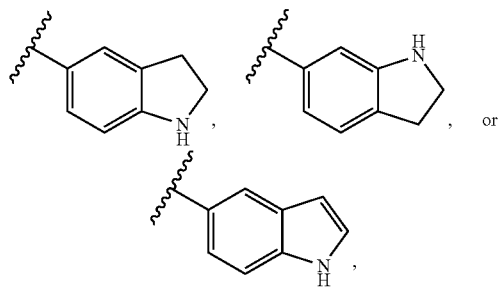

each substituted with zero to 3 substituents independently selected from Cl, Br, I, —CH$_2$CH$_3$, —CH$_2$(cyclohexyl), —CH$_2$(phenyl), —CH$_2$(difluorophenyl), —(CH$_2$)$_{1-2}$(dichlorophenyl), —CH$_2$(chloropyridinyl), —CH$_2$(1-methyl-1H-indolyl), —(CH$_2$)$_{1-3}$(morpholinyl), —C(O)(cyclohexyl), —C(O)(dichlorophenyl), —C(O)(morpholinyl), —C(O)((morpholinoethoxy)pyridinyl), —C(O)OCH$_3$, —C(O)CH$_2$(dichlorophenyl), —C(O)(CH$_2$)$_{1-3}$(morpholinyl), —C(O)CH$_2$S(phenyl), —CH$_2$CH$_2$S(phenyl), —CH=CHCH$_3$, —CH=CHCH$_2$CH$_3$, and/or morpholinyl; or (d) ethyl, pentyl, or —CH$_2$CH$_2$(trimethylsilyl)), provided that W is

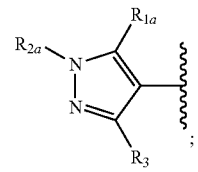

G is:
(a) —N(CH$_3$)$_2$; or
(b) a bicyclic heterocyclyl selected from:

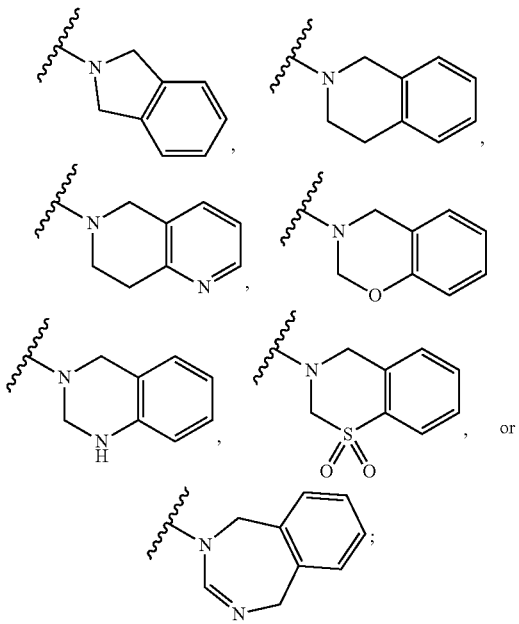

wherein said bicyclic heterocyclyl is substituted with zero to 2 substituents independently selected from: Br, —CH$_3$, —CF$_3$, —CH$_2$OH, —CH$_2$NH$_2$, —CH$_2$N$_3$, —CH$_2$N(CH$_3$)(CH$_2$CH$_2$OH), —CH$_2$N(CH$_3$)(CH$_2$CH$_2$OCH$_3$), —CH$_2$OCH$_2$CH$_2$N(CH$_3$)$_2$, —CH$_2$OCH$_2$CH$_2$OH, —CH$_2$OCH$_2$CH$_2$O(phenyl), —CH$_2$OCH$_2$CH$_2$CH$_2$OCH$_3$, —CH$_2$(pyrrolidinyl), —CH$_2$(N-methyl piperazinyl), —CH$_2$(N-(2-hydroxyethyl)piperazinyl), —CH$_2$(morpholinyl), —OCH$_3$, —C(O)OH, —(CH$_2$)$_{0-1}$N(CH$_3$)$_2$, —N(CH$_3$)(CH$_2$CH$_2$OCH$_3$),

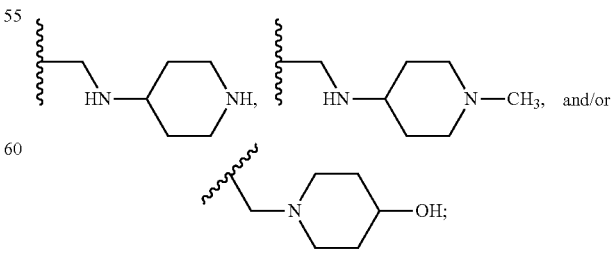

R$_{1a}$ is H, Cl, Br, —CH$_3$, butyl, —CF$_3$, —(CH$_2$)$_{2-3}$OH, —CH$_2$CH$_2$OCH$_3$, —CH$_2$CH$_2$OCH$_2$CH$_2$OH, —CH$_2$C (O)OH, —(CH$_2$)$_3$N(CH$_3$)$_2$, —CH$_2$C(O)NHCH$_3$, —(CH$_2$)$_{1-3}$(phenyl), —(CH$_2$)$_{2-3}$(morpholinyl), —(CH$_2$)$_{2-3}$(N-methyl piperazinyl), —(CH$_2$)$_2$OC(O)NH$_2$, —CH$_2$C(O)NHS(O)$_2$(cyclopropyl), —(CH$_2$)$_2$OC(O)(N-methyl piperazinyl), or —(CH$_2$)$_2$OC(O)NH(CH$_2$)$_2$(N-methyl piperazinyl);

R$_{1b}$ is H, —CH$_3$, butyl, —CF$_3$, —(CH$_2$)$_{2-3}$OH, —CH$_2$CH$_2$OCH$_3$, —CH$_2$CH$_2$OCH$_2$CH$_2$OH, —CH$_2$C(O)OH, —(CH$_2$)$_3$N(CH$_3$)$_2$, —CH$_2$C(O)NHCH$_3$, —(CH$_2$)$_{1-3}$(phenyl), —(CH$_2$)$_{2-3}$(morpholinyl), —(CH$_2$)$_{2-3}$(N-methyl piperazinyl), —(CH$_2$)$_2$OC(O)NH$_2$, —CH$_2$C(O)NHS(O)$_2$(cyclopropyl), —(CH$_2$)$_2$OC(O)(N-methyl piperazinyl), or —(CH$_2$)$_2$OC(O)NH(CH$_2$)$_2$(N-methyl piperazinyl);

R$_2$ is:
(a) H, Cl, Br, C$_{1-3}$ hydroxyalkyl, —(CH$_2$)$_2$C(O)OH, or —(CH$_2$)$_3$N(CH$_3$)$_2$; or
(b) phenyl substituted with zero to 1 substituent selected from propyl, —(CH$_2$)$_{0-2}$OH, —O(CH$_3$)$_{0-3}$CH$_3$, —O(CH$_2$)$_3$OH, —OCH$_2$CH(OH)CH$_2$OH, —C(O)OH, —OCH$_2$CH=CH$_2$, —O(phenyl), —O(chlorophenyl), —C(O)OCH$_3$, or phenyl;

R$_{2a}$ is:
(a) H, C$_{1-3}$ hydroxyalkyl, —(CH$_2$)$_2$C(O)OH, or —(CH$_2$)$_3$N(CH$_3$)$_2$; or
(b) phenyl substituted with zero to 1 substituent selected from propyl, —(CH$_2$)$_{0-2}$OH, —O(CH$_3$)$_{0-3}$CH$_3$, —O(CH$_2$)$_3$OH, —OCH$_2$CH(OH)CH$_2$OH, —C(O)OH, —OCH$_2$CH=CH$_2$, —O(phenyl), —O(chlorophenyl), —C(O)OCH$_3$, or phenyl;

R$_3$ is —CH$_2$OH, —C(O)OH, —C(O)OCH$_2$CH$_3$, —C(O)NR$_a$R$_b$, or —NR$_a$R$_b$;

R$_a$ is H, C$_{1-5}$ alkyl, or C$_{1-4}$ fluoroalkyl; and

R$_b$ is
(a) C$_{1-5}$ alkyl, C$_{3-4}$ fluoroalkyl, —(CH$_2$)$_2$C(O)OH, —(CH$_2$)$_2$C(O)O(butyl), —CH$_2$(cyclopropyl), —CH$_2$(naphthalenyl), —(CH$_2$)$_2$C(O)NHCH(C$_{1-2}$ hydroxyalkyl)$_2$, —(CH$_2$)$_2$C(O)NHC(CH$_2$OH)$_3$, or —(CH$_2$)$_2$C(O)NHCH$_2$CH$_2$(N-methyl piperazinyl);

(b) —(CH$_2$)$_{0-2}$(phenyl) wherein said phenyl is substituted with zero to 2 substituents independently selected from Cl, I, C$_{1-4}$ alkyl, C$_{1-4}$ alkoxy, —(CH$_2$)$_{0-2}$C(O)OH, —C(O)OCH$_3$, —CH$_2$C(O)OCH$_2$CH$_3$, phenyl, chlorophenyl, fluorophenoxy, chlorophenoxy, phenyl acetic acid, and/or —(CH$_2$)$_2$C(O)(piperidinyl carboxylic acid); or (c)

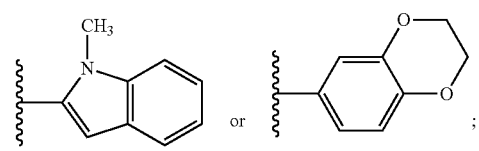 [SMILES: *c1cc2ccccc2n1C ; *c1ccc2c(c1)OCCO2]

or R$_a$ and R$_b$ together with the nitrogen atom to which they are attached, form a pyrrolidinyl ring substituted with zero to 1 substituent selected from propyl or —CH$_2$CH$_2$(phenyl).

3. The compound according to claim 1 or a pharmaceutically acceptable salt thereof, wherein W is:

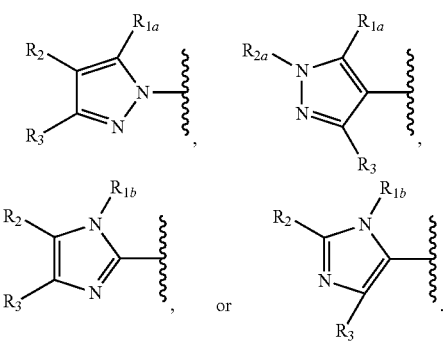

4. The compound according to claim 1 or a pharmaceutically acceptable salt thereof, wherein:
W is

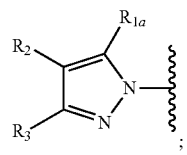

Q is
(a) naphthalenyl substituted with zero to 3 substituents independently selected from —OH, —CN, Cl, Br, I, —NO$_2$, —N(CH$_3$)$_2$, —C(O)OH, —C(O)OCH$_2$CH$_3$, —S(O)$_2$CH$_2$CH$_3$, C$_{1-3}$ alkoxy, —OCH(CH$_3$)CH$_2$N(CH$_3$)$_2$, —O(CH$_2$)$_3$N(CH$_3$)$_2$, —OCH$_2$(phenyl), —OCH$_2$(dichlorophenyl), —OCH$_2$(benzoic acid), —OCH$_2$(methyl benzoate), —OCH$_2$(methylsulfonylphenyl), —OCH$_2$(furanyl), —OCH$_2$(N-methyl-1H-imidazolyl), —O(CH$_2$)$_2$(N-methylpyrrolidinyl), —O(CH$_2$)$_{2-3}$(morpholinyl), —O(CH$_2$)$_3$(pyrrolidinyl), —O(CH$_2$)$_3$(piperidinyl), O(CH$_2$)$_3$(N-methyl piperazinyl), —O(CH$_2$)$_3$(pyridinyl), —O(CH$_2$)$_2$OH, —O(CH$_2$)$_2$O(C$_{1-2}$ alkyl), —O(CH$_2$)$_2$O(phenyl), —C(O)N(CH$_3$)$_2$, —C(O)(N-methylpiperazinyl), —C(O)(morpholinyl), and/or —NHC(O)(dichlorophenyl);

(b) isoquinolinyl substituted with —OCH$_2$CH$_2$(morpholinyl), —SCH$_2$CH$_2$NH$_2$, or —SCH$_2$C(O)OH; or (c)

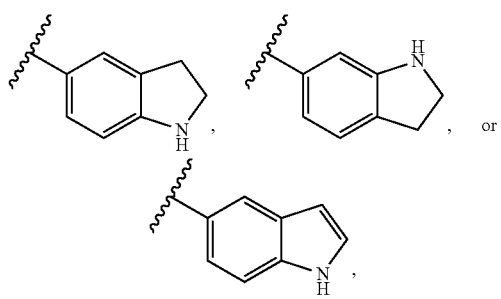

each substituted with zero to 3 substituents independently selected from Cl, Br, I, —CH$_2$CH$_3$, —CH$_2$(cyclohexyl), —CH₂(phenyl), —CH₂(difluorophenyl), —(CH₂)₁₋₂(dichlorophenyl), —CH₂(chloropyridinyl), —CH₂(1-methyl-1H-indolyl), —(CH₂)₁₋₃(morpholinyl), —C(O)(cyclohexyl), —C(O)(dichlorophenyl), —C(O)(morpholinyl), —C(O)((morpholinoethoxy)pyridinyl), —C(O)OCH₃, —C(O)CH₂(dichlorophenyl), —C(O)(CH₂)₁₋₃(morpholinyl), —C(O)CH₂S(phenyl), —CH₂CH₂S(phenyl), —CH=CHCH₃, —CH=CHCH₂CH₃, and/or morpholinyl;

G is a bicyclic heterocyclyl selected from:

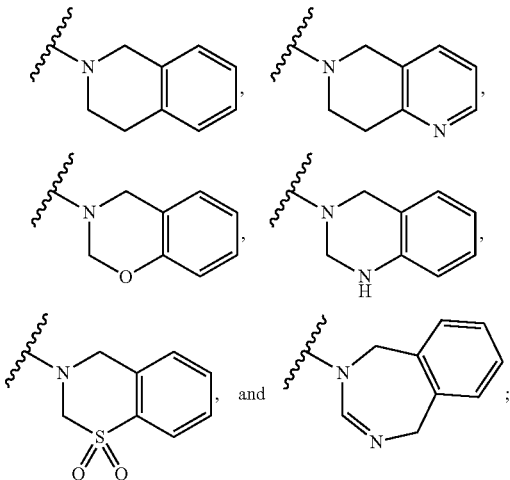

wherein said bicyclic heterocyclyl is substituted with zero to 2 substituents independently selected from: Br, —CH₃, —CF₃, —CH₂OH, —CH₂NH₂, —CH₂N(CH₃)(CH₂CH₂OH), —CH₂N(CH₃)(CH₂CH₂OCH₃), —CH₂OCH₂CH₂N(CH₃)₂, —CH₂O(CH₂)₂OH, —CH₂O(CH₂)₂O(phenyl), —CH₂O(CH₂)₃OCH₃, —CH₂(pyrrolidinyl), —CH₂(N-methyl piperazinyl), —CH₂(N-(2-hydroxyethyl)piperazinyl), —CH₂(morpholinyl), —OCH₃, —C(O)OH, —(CH₂)₀₋₁N(CH₃)₂, —N(CH₃)(CH₂CH₂OCH₃),

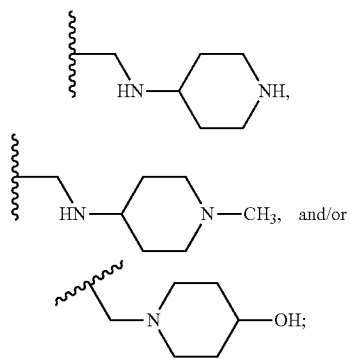

$R_{1a}$ is H, —CH₃, —CF₃, —(CH₂)₂OH, —CH₂C(O)OH, —(CH₂)₂OC(O)NH₂, —CH₂C(O)NHS(O)₂(cyclopropyl), —(CH₂)₂OC(O)(N-methyl piperazinyl), or —(CH₂)₂OC(O)NHCH₂CH₂(N-methyl piperazinyl);

$R_2$ is H, Cl, Br, $C_{1-3}$ hydroxyalkyl, —(CH₂)₂C(O)OH, —(CH₂)₃N(CH₃)₂, or benzoic acid;

$R_3$ is —N(C₃₋₄alkyl)₂ or —C(O)NR$_a$R$_b$;

$R_a$ is H, $C_{1-4}$ alkyl, or $C_{3-4}$ fluoroalkyl; and $R_b$ is:

(a) $C_{1-4}$ alkyl, $C_{3-4}$ fluoroalkyl, —(CH₂)₂C(O)OH, —(CH₂)₂C(O)O(butyl), —CH₂(naphthalenyl), —(CH₂)₂C(O)NHCH(CH₂OH)₂, —(CH₂)₂C(O)NHC(CH₂OH)₃, or —(CH₂)₂C(O)NHCH₂CH₂(N-methyl piperazinyl);

(b) —(CH₂)₀₋₂(phenyl) wherein said phenyl is substituted with zero to 2 substituents independently selected from Cl, I, $C_{1-4}$ alkyl, $C_{1-4}$ alkoxy, —C(O)OH, —(CH₂)₀₋₂C(O)OH, —C(O)OCH₃, —CH₂C(O)OCH₂CH₃, phenyl, chlorophenyl, fluorophenoxy, chlorophenoxy, phenyl acetic acid, and/or —(CH₂)₂C(O)(piperidinyl carboxylic acid); or (c)

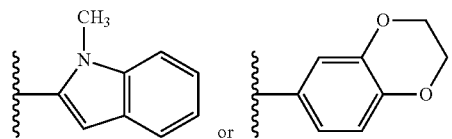

5. The compound according to claim 1 or a pharmaceutically acceptable salt thereof, wherein:

W is

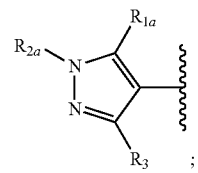

Q is ethyl, pentyl, —(CH₂)₂(trimethylsilyl), or naphthalenyl substituted zero to 2 substituents independently selected from Cl and/or Br;

G is

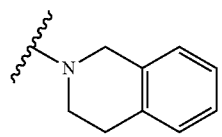

substituted with zero to 1 substituent selected from —CH₂OH, —CH₂N₃, or —CH₂NH₂;

$R_{1a}$ is —CH₃ or butyl;

$R_{2a}$ is phenyl substituted with zero to 1 substituent selected from propyl, —OH, —(CH₂)₂OH, —OCH₃, —O(CH₂)₃CH₃, —O(CH₂)₃OH, —OCH₂CH(OH)CH₂OH, —OCH₂CH=CH₂, —O(phenyl), —O(chlorophenyl), C(O)OCH₃, and phenyl; and $R_3$ is —CH₂OH, —C(O)OH, or —C(O)OCH₂CH₃.

6. The compound according to claim 1 or a pharmaceutically acceptable salt thereof, wherein:

W is

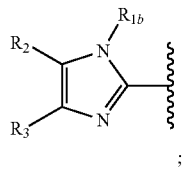

;

Q is naphthalenyl substituted with zero to 1 substituent selected from Cl or I;

G is

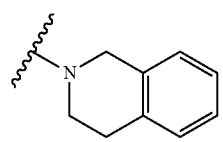 [SMILES: *N1CCc2ccccc2C1]

substituted with zero to 1 substituent selected from —CH$_2$OH or —CH$_2$NH$_2$;

R$_{1b}$ is H, —CH$_3$, —(CH$_2$)$_{2-3}$OH, —(CH$_2$)$_{1-3}$(phenyl), —(CH$_2$)$_{2-3}$(morpholinyl), —(CH$_2$)$_{2-3}$(N-methyl piperazinyl), —(CH$_2$)$_2$OCH$_3$, —(CH$_2$)$_2$O(CH$_2$)$_2$OH, —(CH$_2$)$_3$N(CH$_3$)$_2$, —CH$_2$C(O)OH, or —CH$_2$C(O)NHCH$_3$;

R$_2$ is H; and

R$_3$ is —C(O)N(n-butyl)$_2$.

7. The compound according to claim 1 or a pharmaceutically acceptable salt thereof, wherein:

W is

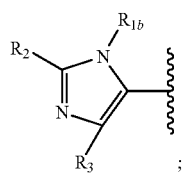

;

Q is naphthalenyl substituted Cl or I;

G is

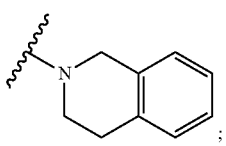

;

R$_{1b}$ is —CH$_3$,

R$_2$ is H; and

R$_3$ is —C(O)N(n-butyl)$_2$.

8. The compound according to claim 1 or a pharmaceutically acceptable salt thereof, wherein:

W is

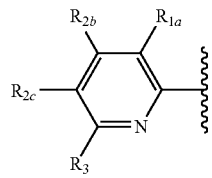

,

Q is:
(a) naphthalenyl substituted with zero to 1 substituent selected from Cl; or
(b)

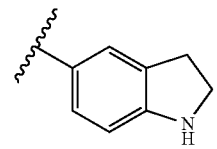 [SMILES: *c1ccc2c(c1)CCN2]

substituted with zero to 1 substituent selected from —CH$_2$(dichlorophenyl);

G is

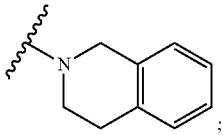

;

R$_{1a}$ is H or Br;
R$_{2b}$ is H;
R$_2$ is H; and
R$_3$ is —N(n-butyl)$_2$ or —C(O)N(n-butyl)$_2$.

9. The compound according to claim 1 or a pharmaceutically acceptable salt thereof, wherein:

W is

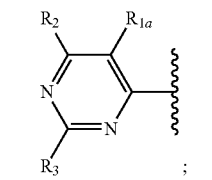

;

Q is:
(a) naphthalenyl substituted with zero to 1 substituent selected from Cl or I; or
(b)

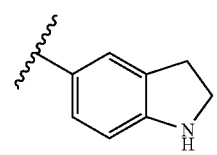 [SMILES: *c1ccc2c(c1)CCN2]

substituted with zero to 1 substituent selected from —CH$_2$CH$_3$ or —CH$_2$(dichlorophenyl);

G is:

(a) —N(CH$_3$)$_2$;

(b)

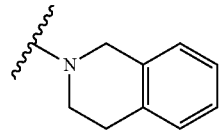 [SMILES: *N1CCc2ccccc2C1]

substituted with zero to 1 substituent selected from —CF$_3$, —CH$_2$OH, or —CH$_2$NH$_2$; or (c)

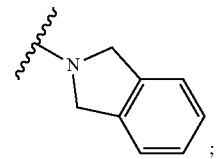 [SMILES: *N1Cc2ccccc2C1]

;

R$_{1a}$ is H, Cl, Br, —CH$_3$, or —C(O)OCH$_2$CH$_3$;

R$_2$ is H;

R$_3$ is —NR$_a$R$_b$;

R$_a$ is C$_{2-5}$ alkyl; and

R$_b$ is C$_{2-5}$ alkyl, —CH$_2$(cyclopropyl), or —CH$_2$(dichlorophenyl);

or R$_a$ and R$_b$ together with the nitrogen atom to which they are attached, form a pyrrolidinyl ring substituted with zero to 1 substituent selected from propyl or —CH$_2$CH$_2$(phenyl).

10. A pharmaceutical composition, comprising; a pharmaceutically acceptable carrier and a compound according to claim 1 or pharmaceutically acceptable salts thereof.

11. A method for treating cancer in a patient in need of such treatment, comprising administering to the patient a compound according to claim 1 or a pharmaceutically acceptable salt thereof wherein said cancer is selected from breast cancer, ovarian cancer, and prostate cancer.

12. The compound according to claim 1 or a pharmaceutically acceptable salt thereof, wherein said compound is selected from: N,N-Dibutyl-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (1); N,N-dibutyl-4-chloro-1-(4-(5-chloronaphthalen-2-ylsulfonylcarbamoyl)-2-(1,2,3,4-tetrahydroisoquinoline-2-carbonyl)phenyl)-5-methyl-1H-pyrazole-3-carboxamide (2); N,N-dibutyl-4-chloro-1-(4-(6-(dimethylamino)naphthalen-2-ylsulfonylcarbamoyl)-2-(1,2,3,4-tetrahydroisoquinoline-2-carbonyl)phenyl)-5-methyl-1H-pyrazole-3-carboxamide (3); N,N-dibutyl-4-chloro-1-(4-(5-(dimethylamino)naphthalen-1-ylsulfonylcarbamoyl)-2-(1,2,3,4-tetrahydroisoquinoline-2-carbonyl)phenyl)-5-methyl-1H-pyrazole-3-carboxamide (4); N,N-dibutyl-4-chloro-1-(4-(8-chloronaphthalen-2-ylsulfonylcarbamoyl)-2-(1,2,3,4-tetrahydroisoquinoline-2-carbonyl)phenyl)-5-methyl-1H-pyrazole-3-carboxamide (5); N,N-dibutyl-4-chloro-1-(4-(6-chloronaphthalen-2-ylsulfonylcarbamoyl)-2-(1,2,3,4-tetrahydroisoquinoline-2-carbonyl)phenyl)-5-methyl-1H-pyrazole-3-carboxamide (6); N,N-dibutyl-4-chloro-1-(4-(8-iodonaphthalen-2-ylsulfonylcarbamoyl)-2-(1,2,3,4-tetrahydroisoquinoline-2-carbonyl)phenyl)-5-methyl-1H-pyrazole-3-carboxamide (7); N,N-dibutyl-4-chloro-1-(4-(8-cyanonaphthalen-2-ylsulfonylcarbamoyl)-2-(1,2,3,4-tetrahydroisoquinoline-2-carbonyl)phenyl)-5-methyl-1H-pyrazole-3-carboxamide (8); ethyl 7-(N-(4-(4-chloro-3-(dibutylcarbamoyl)-5-methyl-1H-pyrazol-1-yl)-3-(1,2,3,4-tetrahydroisoquinoline-2-carbonyl)benzoyl)sulfamoyl)-1-naphthoate (9); N,N-dibutyl-4-chloro-1-(4-(7-chloronaphthalen-2-ylsulfonylcarbamoyl)-2-(1,2,3,4-tetrahydroisoquinoline-2-carbonyl)phenyl)-5-methyl-1H-pyrazole-3-carboxamide (10); N,N-dibutyl-4-chloro-1-(4-(7-iodonaphthalen-2-ylsulfonylcarbamoyl)-2-(1,2,3,4-tetrahydroisoquinoline-2-carbonyl)phenyl)-5-methyl-1H-pyrazole-3-carboxamide (11); N,N-dibutyl-4-chloro-5-methyl-1-(4-(5-nitronaphthalen-1-ylsulfonylcarbamoyl)-2-(1,2,3,4-tetrahydroisoquinoline-2-carbonyl)phenyl)-1H-pyrazole-3-carboxamide (12); N,N-dibutyl-4-chloro-5-methyl-1-(4-(4-(5-nitronaphthalen-2-ylsulfonylcarbamoyl)-2-(1,2,3,4-tetrahydroisoquinoline-2-carbonyl)phenyl)-1H-pyrazole-3-carboxamide (13); N,N-dibutyl-4-chloro-1-(4-(6-chloronaphthalen-2-ylsulfonylcarbamoyl)-2-(1,2,3,4-tetrahydroisoquinoline-2-carbonyl)phenyl)-5-methyl-1H-pyrazole-3-carboxamide (14); N,N-dibutyl-4-chloro-1-(4-(7-cyanonaphthalen-2-ylsulfonylcarbamoyl)-2-(1,2,3,4-tetrahydroisoquinoline-2-carbonyl)phenyl)-5-methyl-1H-pyrazole-3-carboxamide (15); ethyl 7-(N-(4-(4-chloro-3-(dibutylcarbamoyl)-5-methyl-1H-pyrazol-1-yl)-3-(1,2,3,4-tetrahydroisoquinoline-2-carbonyl)benzoyl)sulfamoyl)-2-naphthoate (16); ethyl 7-(N-(4-(4-chloro-3-(dibutylcarbamoyl)-5-methyl-1H-pyrazol-1-yl)-3-(1,2,3,4-tetrahydroisoquinoline-2-carbonyl)benzoyl)sulfamoyl)-2-naphthoate (17); 1-(4-(7-(benzyloxy)naphthalen-2-ylsulfonylcarbamoyl)-2-(1,2,3,4-tetrahydroisoquinoline-2-carbonyl)phenyl)-N,N-dibutyl-4-chloro-5-methyl-1H-pyrazole-3-carboxamide (18); N,N-dibutyl-4-chloro-1-(4-(8-(3,4-dichlorobenzamido) naphthalen-2-ylsulfonylcarbamoyl)-2-(1,2,3,4-tetrahydroisoquinoline-2-carbonyl)phenyl)-5-methyl-1H-pyrazole-3-carboxamide (19); N,N-dibutyl-4-chloro-5-methyl-1-(4-(7-(4-(methylsulfonyl)benzyloxy)-naphthalen-2-ylsulfonylcarbamoyl)-2-(1,2,3,4-tetrahydroisoquinoline-2-carbonyl)phenyl)-1H-pyrazole-3-carboxamide (20); N,N-dibutyl-4-chloro-1-(4-(8-(3,4-dichlorobenzyloxy)naphthalen-2-ylsulfonylcarbamoyl)-2-(1,2,3,4-tetrahydroisoquinoline-2-carbonyl)phenyl)-5-methyl-1H-pyrazole-3-carboxamide (21); N,N-dibutyl-4-chloro-1-(4-(7-(3,4-dichlorobenzyloxy) naphthalen-2-ylsulfonylcarbamoyl)-2-(1,2,3,4-tetrahydroisoquinoline-2-carbonyl)phenyl)-5-methyl-1H-pyrazole-3-carboxamide (22); N,N-dibutyl-4-chloro-5-methyl-1-(4-(7-((tetrahydrofuran-2-yl)methoxy) naphthalen-2-ylsulfonylcarbamoyl)-2-(1,2,3,4-tetrahydroisoquinoline-2-carbonyl)phenyl)-1H-pyrazole-3-carboxamide (23); N,N-dibutyl-4-chloro-1-(4-(7-isopropoxynaphthalen-2-ylsulfonylcarbamoyl)-2-(1,2,3,4-tetrahydroisoquinoline-2-carbonyl)phenyl)-5-methyl-1H-pyrazole-3-carboxamide (24); N,N-dibutyl-4-chloro-5-methyl-1-(4-(7-(2-phenoxyethoxy)naphthalen-2-ylsulfonylcarbamoyl)-2-(1,2,3,4-tetrahydroisoquinoline-2-carbonyl)phenyl)-1H-pyrazole-3-carboxamide (25); methyl 4-((7-(N-(4-(4-chloro-3-(dibutylcarbamoyl)-5-methyl-1H-pyrazol-1-yl)-3-(1,2,3,4-tetrahydroisoquinoline-2-carbonyl)benzoyl)sulfamoyl)naphthalen-1-yloxy)methyl)benzoate (26); N,N-dibutyl-4-chloro-5-methyl-1-(4-(8-(2-morpholinoethoxy)naphthalen-2-ylsulfonylcarbamoyl)-2-(1,2,3,4-tetrahydroisoquinoline-2-carbonyl)phenyl)-1H-pyrazole-3-carboxamide (27); N,N-dibutyl-4-chloro-1-(4-(7-(2-methoxyethoxy)naphthalen-2-ylsulfonylcarbamoyl)-2-(1,2,3,4-tetrahydroisoquinoline-2-carbonyl)phenyl)-5-methyl-1H-pyrazole-3-carboxamide (28); N,N-dibutyl-4-chloro-1-(4-(7-methoxynaphthalen-2-ylsulfonylcarbamoyl)-2-(1,2,3, 4-tetrahydroisoquinoline-2-carbonyl)phenyl)-5-methyl-1H-pyrazole-3-carboxamide (29); N,N-dibutyl-4-chloro-1-(4-(7-(2-ethoxyethoxy) naphthalen-2-ylsulfonylcarbamoyl)-2-(1,2,3,4-tetrahydroisoquinoline-2-carbonyl)phenyl)-5-methyl-1H-pyrazole-3-carboxamide (30); 1-(4-(8-bromo-5-(dimethylamino)naphthalen-2-ylsulfonylcarbamoyl)-2-(1,2,3,4-tetrahydroisoquinoline-2-carbonyl)phenyl)-N,N-dibutyl-4-chloro-5-methyl-1H-pyrazole-3-carboxamide (31); N,N-dibutyl-4-chloro-5-methyl-1-(4-(8-(3-morpholinopropoxy)naphthalen-2-ylsulfonylcarbamoyl)-2-(1,2,3,4-tetrahydroisoquinoline-2-carbonyl)phenyl)-1H-pyrazole-3-carboxamide (32); N,N-dibutyl-4-chloro-5-methyl-1-(4-(7-(2-morpholinoethoxy)naphthalen-2-ylsulfonylcarbamoyl)-2-(1,2,3,4-tetrahydroisoquinoline-2-carbonyl)phenyl)-1H-pyrazole-3-carboxamide (33); N,N-dibutyl-4-chloro-5-methyl-1-(4-(7-(3-morpholinopropoxy)naphthalen-2-ylsulfonylcarbamoyl)-2-(1,2,3,4-tetrahydroisoquinoline-2-carbonyl)phenyl)-1H-pyrazole-3-carboxamide (34); N,N-dibutyl-4-chloro-5-methyl-1-(4-(7-(3-(4-methylpiperazin-1-yl)propoxy)naphthalen-2-ylsulfonylcarbamoyl)-2-(1,2,3,4-tetrahydroisoquinoline-2-carbonyl)phenyl)-1H-pyrazole-3-carboxamide (35); N,N-dibutyl-4-chloro-5-methyl-1-(4-(7-((1-methyl-1H-imidazol-2-yl)methoxy)naphthalen-2-ylsulfonylcarbamoyl)-2-(1,2,3,4-tetrahydroisoquinoline-2-carbonyl)phenyl)-1H-pyrazole-3-carboxamide (36); N,N-dibutyl-4-chloro-1-(4-(7-(1-(dimethylamino)propan-2-yloxy)naphthalen-2-ylsulfonylcarbamoyl)-2-(1,2,3,4-tetrahydroisoquinoline-2-carbonyl)phenyl)-5-methyl-1H-pyrazole-3-carboxamide (37); N,N-dibutyl-4-chloro-5-methyl-1-(4-((7-(2-(1-methylpyrrolidin-2-yl)ethoxy) naphthalene-2-sulfonamido)methyl)-2-(1,2,3,4-tetrahydroisoquinoline-2-carbonyl)phenyl)-1H-pyrazole-3-carboxamide (38); N,N-dibutyl-4-chloro-1-(4-(7-(3-(dimethylamino) propoxy)-naphthalen-2-ylsulfonylcarbamoyl)-2-(1,2,3,4-tetrahydroisoquinoline-2-carbonyl)phenyl)-5-methyl-1H-pyrazole-3-carboxamide (39); N,N-dibutyl-4-chloro-5-methyl-1-(4-(7-(3-(pyrrolidin-1-yl)propoxy)naphthalen-2-ylsulfonylcarbamoyl)-2-(1,2,3,4-tetrahydroisoquinoline-2-carbonyl)phenyl)-1H-pyrazole-3-carboxamide (40); N,N-dibutyl-4-chloro-5-methyl-1-(4-(7-(3-(piperidin-1-yl)propoxy)naphthalen-2-ylsulfonylcarbamoyl)-2-(1,2,3,4-tetrahydroisoquinoline-2-carbonyl)phenyl)-1H-pyrazole-3-carboxamide (41); N,N-Dibutyl-4-chloro-5-methyl-1-(4-(7-(3-(pyridin-4-yl)propoxy)naphthalen-2-ylsulfonylcarbamoyl)-2-(1,2,3,4-tetrahydroisoquinoline-2-carbonyl)phenyl)-1H-pyrazole-3-carboxamide (42); 1-(4-(8-bromo-5-chloronaphthalen-2-ylsulfonylcarbamoyl)-2-(1,2,3,4-tetrahydroisoquinoline-2-carbonyl)phenyl)-N,N-dibutyl-4-chloro-5-methyl-1H-pyrazole-3-carboxamide (43); N,N-dibutyl-4-chloro-1-(4-(5,8-dichloronaphthalen-2-ylsulfonylcarbamoyl)-2-(1,2,3,4-tetrahydroisoquinoline-2-carbonyl)phenyl)-5-methyl-1H-pyrazole-3-carboxamide (44); 7-(N-(4-(4-Chloro-3-(dibutylcarbamoyl)-5-methyl-1H-pyrazol-1-yl)-3-(1,2,3,4-tetrahydroisoquinoline-2-carbonyl)benzoyl)sulfamoyl)-1-naphthoic acid (45); N,N-Dibutyl-4-chloro-5-methyl-1-(4-(7-(4-methylpiperazine-1-carbonyl)naphthalen-2-ylsulfonylcarbamoyl)-2-(1,2,3,4-tetrahydroisoquinoline-2-carbonyl)phenyl)-1H-pyrazole-3-carboxamide (46); N,N-Dibutyl-4-chloro-5-methyl-1-(4-(7-(morpholine-4-carbonyl)naphthalen-2-ylsulfonylcarbamoyl)-2-(1,2,3,4-tetrahydroisoquinoline-2-carbonyl)phenyl)-1H-pyrazole-3-carboxamide (47); N,N-Dibutyl-4-chloro-1-(4-(7-(dimethylcarbamoyl)naphthalen-2-ylsulfonylcarbamoyl)-2-(1,2,3,4-tetrahydroisoquinoline-2-carbonyl)phenyl)-5-methyl-1H-pyrazole-3-carboxamide (48); 4-((7-(N-(4-(4-Chloro-3-(dibutylcarbamoyl)-5-methyl-1H-pyrazol-1-yl)-3-(1,2,3,4-tetrahydroisoquinoline-2-carbonyl)benzoyl)sulfamoyl)naphthalen-1-yloxy)methyl)benzoic acid (48); N,N-Dibutyl-4-chloro-1-(4-(7-(2-hydroxyethoxy)naphthalen-2-ylsulfonylcarbamoyl)-2-(1,2,3,4-tetrahydroisoquinoline-2-carbonyl)phenyl)-5-methyl-1H-pyrazole-3-carboxamide (50); N,N-Dibutyl-4-chloro-1-(4-(7-hydroxynaphthalen-2-ylsulfonylcarbamoyl)-2-(1,2,3,4-tetrahydroisoquinoline-2-carbonyl)phenyl)-5-methyl-1H-pyrazole-3-carboxamide (51); N,N-Dibutyl-4-chloro-1-(4-(indolin-5-ylsulfonylcarbamoyl)-2-(1,2,3,4-tetrahydroisoquinoline-2-carbonyl) phenyl)-5-methyl-1H-pyrazole-3-carboxamide (52); N,N-dibutyl-4-chloro-1-(4-(1-ethylindolin-5-ylsulfonylcarbamoyl)-2-(1,2,3,4-tetrahydroisoquinoline-2-carbonyl)phenyl)-5-methyl-1H-pyrazole-3-carboxamide (53); 1-(4-(1H-indol-5-ylsulfonylcarbamoyl)-2-(1,2,3,4-tetrahydroisoquinoline-2-carbonyl)phenyl)-N,N-dibutyl-4-chloro-5-methyl-1H-pyrazole-3-carboxamide (54); N,N-dibutyl-4-chloro-1-(4-(1-(cyclohexanecarbonyl)indolin-5-ylsulfonylcarbamoyl)-2-(1,2,3,4-tetrahydroisoquinoline-2-carbonyl)phenyl)-5-methyl-1H-pyrazole-3-carboxamide (55); N,N-dibutyl-4-chloro-1-(4-(1-ethyl-1H-indol-5-ylsulfonylcarbamoyl)-2-(1,2,3,4-tetrahydroisoquinoline-2-carbonyl)phenyl)-5-methyl-1H-pyrazole-3-carboxamide (56); N,N-dibutyl-4-chloro-1-(4-(1-(cyclohexylmethyl)indolin-5-ylsulfonylcarbamoyl)-2-(1,2,3,4-tetrahydroisoquinoline-2-carbonyl) phenyl)-5-methyl-1H-pyrazole-3-carboxamide (57); N,N-dibutyl-4-chloro-1-(4-(1-(3,4-dichlorobenzoyl)indolin-5-ylsulfonylcarbamoyl)-2-(1,2,3,4-tetrahydroisoquinoline-2-carbonyl) phenyl)-5-methyl-1H-pyrazole-3-carboxamide (58); N,N-dibutyl-4-chloro-1-(4-(1-(3,4-dichlorobenzyl)indolin-5-ylsulfonylcarbamoyl)-2-(1,2,3,4-tetrahydroisoquinoline-2-carbonyl) phenyl)-5-methyl-1H-pyrazole-3-carboxamide (59); 1-(4-(1-acetylindolin-6-ylsulfonylcarbamoyl)-2-(1,2,3,4-tetrahydroisoquinoline-2-carbonyl)phenyl)-N,N-dibutyl-4-chloro-5-methyl-1H-pyrazole-3-carboxamide (60); 1-(4-(1-benzylindolin-5-ylsulfonylcarbamoyl)-2-(1,2,3,4-tetrahydroisoquinoline-2-carbonyl)phenyl)-N,N-dibutyl-4-chloro-5-methyl-1H-pyrazole-3-carboxamide (61); N,N-dibutyl-4-chloro-1-(4-(1-(3,4-difluorobenzyl) indolin-5-ylsulfonylcarbamoyl)-2-(1,2,3,4-tetrahydroisoquinoline-2-carbonyl)phenyl)-5-methyl-1H-pyrazole-3-carboxamide (62); N,N-dibutyl-4-chloro-1-(4-(1-ethylindolin-6-ylsulfonylcarbamoyl)-2-(1,2,3,4-tetrahydroisoquinoline-2-carbonyl) phenyl)-5-methyl-1H-pyrazole-3-carboxamide (63); N,N-dibutyl-4-chloro-1-(4-(1-(2-(3,4-dichlorophenyl)acetyl)indolin-5-ylsulfonylcarbamoyl)-2-(1,2,3,4-tetrahydroisoquinoline-2-carbonyl)phenyl)-5-methyl-1H-pyrazole-3-carboxamide (64); N,N-dibutyl-4-chloro-1-(4-(1-(3,4-dichlorophenethyl)indolin-5-ylsulfonylcarbamoyl)-2-(1,2,3,4-tetrahydroisoquinoline-2-carbonyl) phenyl)-5-methyl-1H-pyrazole-3-carboxamide (65); N,N-dibutyl-4-chloro-5-methyl-1-(4-(1-(2-(phenylthio)acetyl)indolin-5-ylsulfonylcarbamoyl)-2-(1,2,3,4-tetrahydroisoquinoline-2-carbonyl) phenyl)-1H-pyrazole-3-carboxamide (66); N,N-dibutyl-4-chloro-5-methyl-1-(4-(1-(2-(phenylthio) ethyl)indolin-5-ylsulfonylcarbamoyl)-2-(1,2,3,4-tetrahydroisoquinoline-2-carbonyl)phenyl)-1H-pyrazole-3-carboxamide (67); N,N-dibutyl-4-chloro-1-(4-(1-(3,4-dichlorobenzyl)-1H-indol-5-ylsulfonylcarbamoyl)-2-(1,2,3,4-tetrahydroisoquinoline-2-carbonyl)phenyl)-5-methyl-1H-pyrazole-3-carboxamide (68); N,N-dibutyl-4-chloro-1-(4-(1-((6-chloropyridin-2-yl)methyl)indolin-5-ylsulfonylcarbamoyl)-2-(1,2,3,4-tetrahydroisoquinoline-2-carbonyl)phenyl)-5-methyl-1H-pyrazole-3-carboxamide (69); N,N-dibutyl-4-chloro-5-methyl-1-(4-(1-((1-methyl-1H-indol-6-yl)methyl) indolin-5-ylsulfonylcarbamoyl)-2-(1, 2,3,4-tetrahydroisoquinoline-2-carbonyl)phenyl)-1H-pyrazole-3-carboxamide (70); 1-(4-(5-bromo-1-ethylindolin-6-ylsulfonylcarbamoyl)-2-(1,2,3,4-tetrahydroisoquinoline-2-carbonyl)phenyl)-N,N-dibutyl-4-chloro-5-methyl-1H-pyrazole-3-carboxamide (71); 1-(4-(5-bromo-1-(3,4-dichlorobenzyl)indolin-6-ylsulfonylcarbamoyl)-2-(1,2,3,4-tetrahydroisoquinoline-2-carbonyl)phenyl)-N,N-dibutyl-4-chloro-5-methyl-1H-pyrazole-3-carboxamide (72); methyl 5-(N-(4-(4-chloro-3-(dibutylcarbamoyl)-5-methyl-1H-pyrazol-1-yl)-3-(1,2,3,4-tetrahydroisoquinoline-2-carbonyl)benzoyl)sulfamoyl)-1-(3,4-dichlorobenzyl)indoline-2-carboxylate (73); N,N-dibutyl-4-chloro-5-methyl-1-(4-(1-(morpholine-4-carbonyl)indolin-5-ylsulfonylcarbamoyl)-2-(1,2,3,4-tetrahydroisoquinoline-2-carbonyl)phenyl)-1H-pyrazole-3-carboxamide (74); N,N-dibutyl-4-chloro-5-methyl-1-(4-(1-(2-morpholinoacetyl)indolin-5-ylsulfonylcarbamoyl)-2-(1,2,3,4-tetrahydroisoquinoline-2-carbonyl)phenyl)-1H-pyrazole-3-carboxamide (75); 1-(4-(7-bromo-1-ethylindolin-5-ylsulfonylcarbamoyl)-2-(1,2,3,4-tetrahydroisoquinoline-2-carbonyl)phenyl)-N,N-dibutyl-4-chloro-5-methyl-1H-pyrazole-3-carboxamide (76); N,N-dibutyl-4-chloro-5-methyl-1-(4-(1-(2-morpholinoethyl)indolin-5-ylsulfonylcarbamoyl)-2-(1,2,3,4-tetrahydroisoquinoline-2-carbonyl)phenyl)-1H-pyrazole-3-carboxamide (77); N,N-dibutyl-4-chloro-5-methyl-1-(4-(1-((2-(2-morpholinoethoxy)pyridin-3-yl)methyl)indolin-5-ylsulfonylcarbamoyl)-2-(1,2,3,4-tetrahydroisoquinoline-2-carbonyl)phenyl)-1H-pyrazole-3-carboxamide (78); 1-(4-(3-bromo-1H-indol-5-ylsulfonylcarbamoyl)-2-(1,2,3,4-tetrahydroisoquinoline-2-carbonyl)phenyl)-N,N-dibutyl-4-chloro-5-methyl-1H-pyrazole-3-carboxamide (79); 1-(4-(3-bromo-1-ethyl-1H-indol-5-ylsulfonylcarbamoyl)-2-(1,2,3,4-tetrahydroisoquinoline-2-carbonyl)phenyl)-N,N-dibutyl-4-chloro-5-methyl-1H-pyrazole-3-carboxamide (80); N,N-dibutyl-4-chloro-5-methyl-1-(4-(1-(3-morpholinopropanoyl)indolin-5-ylsulfonylcarbamoyl)-2-(1,2,3,4-tetrahydroisoquinoline-2-carbonyl)phenyl)-1H-pyrazole-3-carboxamide (81); N,N-dibutyl-4-chloro-5-methyl-1-(4-(1-(3-morpholinopropyl)-1H-indol-5-ylsulfonylcarbamoyl)-2-(1,2,3,4-tetrahydroisoquinoline-2-carbonyl)phenyl)-1H-pyrazole-3-carboxamide (82); N,N-dibutyl-4-chloro-1-(4-(3-chloro-1-ethyl-1H-indol-5-ylsulfonylcarbamoyl)-2-(1,2,3,4-tetrahydroisoquinoline-2-carbonyl)phenyl)-5-methyl-1H-pyrazole-3-carboxamide (83); N,N-dibutyl-4-chloro-1-(4-(1-ethyl-3-iodo-1H-indol-5-ylsulfonylcarbamoyl)-2-(1,2,3,4-tetrahydroisoquinoline-2-carbonyl)phenyl)-5-methyl-1H-pyrazole-3-carboxamide (84); N,N-dibutyl-4-chloro-1-(4-(3,7-dibromo-1-ethyl-1H-indol-5-ylsulfonylcarbamoyl)-2-(1,2,3,4-tetrahydroisoquinoline-2-carbonyl)phenyl)-5-methyl-1H-pyrazole-3-carboxamide (85); N,N-Dibutyl-4-chloro-1-(4-(indolin-6-ylsulfonylcarbamoyl)-2-(1,2,3,4-tetrahydroisoquinoline-2-carbonyl) phenyl)-5-methyl-1H-pyrazole-3-carboxamide (86); (E)-1-(4-(5-(But-1-enyl)-1-ethylindolin-6-ylsulfonylcarbamoyl)-2-(1,2,3,4-tetrahydroisoquinoline-2-carbonyl)phenyl)-N,N-dibutyl-4-chloro-5-methyl-1H-pyrazole-3-carboxamide (87); N,N-Dibutyl-4-chloro-1-(4-(1-ethyl-5-morpholinoindolin-6-ylsulfonylcarbamoyl)-2-(1,2,3,4-tetrahydroisoquinoline-2-carbonyl)phenyl)-5-methyl-1H-pyrazole-3-carboxamide (88); (E)-N,N-Dibutyl-4-chloro-1-(4-(1-ethyl-5-(prop-1-enyl)indolin-6-ylsulfonylcarbamoyl)-2-(1,2,3,4-tetrahydroisoquinoline-2-carbonyl)phenyl)-5-methyl-1H-pyrazole-3-carboxamide (89); N,N-Dibutyl-4-chloro-1-(4-(1-(3,4-dichlorobenzyl)indolin-6-ylsulfonylcarbamoyl)-2-(1,2,3,4-tetrahydroisoquinoline-2-carbonyl)phenyl)-5-methyl-1H-pyrazole-3-carboxamide (90); N,N-Dibutyl-4-chloro-1-(2-((S)-3-(hydroxymethyl)-1, 2,3,4-tetrahydroisoquinoline-2-carbonyl)-4-(naphthalen-2-ylsulfonylcarbamoyl)phenyl)-5-methyl-1H-pyrazole-3-carboxamide (91); 1-(2-((S)-3-(Aminomethyl)-1,2,3,4-tetrahydroisoquinoline-2-carbonyl)-4-(naphthalen-2-ylsulfonylcarbamoyl)phenyl)-N,N-dibutyl-4-chloro-5-methyl-1H-pyrazole-3-carboxamide (92); (3R)-2-(2-(4-Chloro-3-(dibutylcarbamoyl)-5-methyl-1H-pyrazol-1-yl)-5-(naphthalen-2-ylsulfonylcarbamoyl)benzoyl)-1,2,3,4-tetrahydroisoquinoline-3-carboxylic acid (93); (3S)-2-(2-(4-Chloro-3-(dibutylcarbamoyl)-5-methyl-1H-pyrazol-1-yl)-5-(naphthalen-2-ylsulfonylcarbamoyl)benzoyl)-1,2,3,4-tetrahydroisoquinoline-3-carboxylic acid (94); N,N-Dibutyl-4-chloro-1-(2-((R)-3-(hydroxymethyl)-1,2,3,4-tetrahydroisoquinoline-2-carbonyl)-4-(naphthalen-2-ylsulfonylcarbamoyl)phenyl)-5-methyl-1H-pyrazole-3-carboxamide (95); N,N-Dibutyl-4-chloro-1-(2-(3,4-dihydro-2H-benzo[e][1,3]oxazine-3-carbonyl)-4-(naphthalen-2-ylsulfonylcarbamoyl) phenyl)-5-methyl-1H-pyrazole-3-carboxamide (96); N,N-Dibutyl-4-chloro-5-methyl-1-(2-(1-methyl-1,2,3,4-tetrahydroisoquinoline-2-carbonyl)-4-(naphthalen-2-ylsulfonylcarbamoyl)phenyl)-1H-pyrazole-3-carboxamide (97); N,N-Dibutyl-4-chloro-1-(2-(4,4-dimethyl-1,2,3,4-tetrahydroisoquinoline-2-carbonyl)-4-(naphthalen-2-ylsulfonylcarbamoyl)phenyl)-5-methyl-1H-pyrazole-3-carboxamide (98); 1-(2-(7-Bromo-1,2,3,4-tetrahydroisoquinoline-2-carbonyl)-4-(naphthalen-2-ylsulfonylcarbamoyl)phenyl)-N,N-dibutyl-4-chloro-5-methyl-1H-pyrazole-3-carboxamide (99); 2-(2-(4-Chloro-3-(dibutylcarbamoyl)-5-methyl-1H-pyrazol-1-yl)-5-(naphthalen-2-ylsulfonylcarbamoyl)benzoyl)-1,2,3,4-tetrahydroisoquinoline-7-carboxylic acid (100); N,N-Dibutyl-4-chloro-5-methyl-1-(4-(naphthalen-2-ylsulfonylcarbamoyl)-2-(7-(trifluoromethyl)-1,2,3,4-tetrahydroisoquinoline-2-carbonyl)phenyl)-1H-pyrazole-3-carboxamide (101); 1-(2-(3-Bromo-5,6,7,8-tetrahydro-1,6-naphthyridine-6-carbonyl)-4-(naphthalen-2-ylsulfonylcarbamoyl)phenyl)-N,N-dibutyl-4-chloro-5-methyl-1H-pyrazole-3-carboxamide (102); N,N-Dibutyl-4-chloro-5-methyl-1-(4-(naphthalen-2-ylsulfonylcarbamoyl)-2-(1,2,3,4-tetrahydroquinazoline-3-carbonyl)phenyl)-1H-pyrazole-3-carboxamide (103); N,N-Dibutyl-4-chloro-1-(2-(1,1-dioxido-3,4-dihydro-2H-benzo[e][1,3]thiazine-3-carbonyl)-4-(naphthalen-2-ylsulfonylcarbamoyl)phenyl)-5-methyl-1H-pyrazole-3-carboxamide (104); N,N-Dibutyl-4-chloro-1-(2-((S)-3-((3-methoxypropoxy)methyl)-1,2,3,4-tetrahydroisoquinoline-2-carbonyl)-4-(naphthalen-2-ylsulfonylcarbamoyl)phenyl)-5-methyl-1H-pyrazole-3-carboxamide (105); N,N-Dibutyl-4-chloro-5-methyl-1-(2-((S)-3-((1-methylpiperidin-4-ylamino)methyl)-1,2,3,4-tetrahydroisoquinoline-2-carbonyl)-4-(naphthalen-2-ylsulfonylcarbamoyl)phenyl)-1H-pyrazole-3-carboxamide (106); N,N-Dibutyl-4-chloro-5-methyl-1-(4-(naphthalen-2-ylsulfonylcarbamoyl)-2-((S)-3-((piperidin-4-ylamino)methyl)-1,2,3,4-tetrahydroisoquinoline-2-carbonyl)phenyl)-1H-pyrazole-3-carboxamide (107); N,N-dibutyl-4-chloro-1-(2-((S)-3-((dimethylamino)methyl)-1,2,3,4-tetrahydroisoquinoline-2-carbonyl)-4-(naphthalen-2-ylsulfonylcarbamoyl)phenyl)-5-methyl-1H-pyrazole-3-carboxamide (108); N,N-dibutyl-4-chloro-5-methyl-1-(2-((S)-3-(morpholinomethyl)-1,2,3,4-tetrahydroisoquinoline-2-carbonyl)-4-(naphthalen-2-ylsulfonylcarbamoyl)phenyl)-1H-pyrazole-3-carboxamide (109); N,N-dibutyl-4-chloro-1-(2-((S)-3-((4-hydroxypiperidin-1-yl)methyl)-1,2,3,4-tetrahydroisoquinoline-2-carbonyl)-4-(naphthalen-2-ylsulfonylcarbamoyl)phenyl)-5-methyl-1H-pyrazole-3-carboxamide (110); N,N-dibutyl-4-chloro-5-methyl-1-(4-(naphthalen-2-ylsulfonylcarbamoyl)-2-((S)-3-(pyrrolidin-1- ylmethyl)-1,2,3,4-tetrahydroisoquinoline-2-carbonyl)phenyl)-1H-pyrazole-3-carboxamide (111); N,N-dibutyl-4-chloro-5-methyl-1-(2-((S)-3-((4-methylpiperazin-1-yl)methyl)-1,2,3,4-tetrahydroisoquinoline-2-carbonyl)-4-(naphthalen-2-ylsulfonylcarbamoyl)phenyl)-1H-pyrazole-3-carboxamide (112); N,N-dibutyl-4-chloro-1-(2-((S)-3-(((2-methoxyethyl)(methyl)amino)-methyl)-1,2,3,4-tetrahydroisoquinoline-2-carbonyl)-4-(naphthalen-2-ylsulfonylcarbamoyl) phenyl)-5-methyl-1H-pyrazole-3-carboxamide (113); N,N-dibutyl-4-chloro-1-(2-((S)-3-(((2-hydroxyethyl)(methyl)amino)-methyl)-1,2,3,4-tetrahydroisoquinoline-2-carbonyl)-4-(naphthalen-2-ylsulfonylcarbamoyl) phenyl)-5-methyl-1H-pyrazole-3-carboxamide (114); N,N-dibutyl-4-chloro-1-(2-((S)-3-((4-(2-hydroxyethyl)piperazin-1-yl)methyl)-1,2,3,4-tetrahydroisoquinoline-2-carbonyl)-4-(naphthalen-2-ylsulfonylcarbamoyl)phenyl)-5-methyl-1H-pyrazole-3-carboxamide (115); N,N-dibutyl-4-chloro-1-(2-((S)-3-((2-(dimethylamino) ethoxy)methyl)-1,2,3,4-tetrahydroisoquinoline-2-carbonyl)-4-(naphthalen-2-ylsulfonylcarbamoyl)phenyl)-5-methyl-1H-pyrazole-3-carboxamide (116); 1-(2-((S)-3-((2-(benzyloxy)ethoxy)methyl)-1,2,3,4-tetrahydroisoquinoline-2-carbonyl)-4-(naphthalen-2-ylsulfonylcarbamoyl)phenyl)-N,N-dibutyl-4-chloro-5-methyl-1H-pyrazole-3-carboxamide (117); N,N-dibutyl-4-chloro-5-methyl-1-(2-(3-((4-methylpiperazin-1-yl)methyl)-1,2,3,4-tetrahydroisoquinoline-2-carbonyl)-4-(naphthalen-2-ylsulfonylcarbamoyl)phenyl)-1H-pyrazole-3-carboxamide (118); N,N-Dibutyl-4-chloro-1-(2-((S)-3-((2-hydroxyethoxy)methyl)-1,2,3,4-tetrahydroisoquinoline-2-carbonyl)-4-(naphthalen-2-ylsulfonylcarbamoyl)phenyl)-5-methyl-1H-pyrazole-3-carboxamide (119); N,N-Dibutyl-4-chloro-1-(2-(3-(dimethylamino)-2,5-dihydro-1H-benzo[e][1,3]diazepine-2-carbonyl)-4-(naphthalen-2-ylsulfonylcarbamoyl)phenyl)-5-methyl-1H-pyrazole-3-carboxamide (120); (Z)—N,N-Dibutyl-4-chloro-1-(2-(3-((2-methoxyethyl)(methyl)amino)-2,5-dihydro-1H-benzo[e][1,3]diazepine-2-carbonyl)-4-(naphthalen-2-ylsulfonylcarbamoyl)phenyl)-5-methyl-1H-pyrazole-3-carboxamide (121); 3-(4-(N-Butyl-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamido)phenyl)propanoic acid (122); N-Butyl-4-chloro-N-(4-iodophenyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (123); 1-(3-(4-(N-Butyl-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamido)phenyl) propanoyl)piperidine-4-carboxylic acid (124); 4-Chloro-N-(3,4-dichlorobenzyl)-N,5-dimethyl-1-(4-(naphthalen-2-ylsulfonylcarbamoyl)-2-(1,2,3,4-tetrahydroisoquinoline-2-carbonyl)phenyl)-1H-pyrazole-3-carboxamide (125); N-butyl-4-chloro-N-(3,4-dichlorobenzyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (126); N-butyl-4-chloro-N-(3,4-dichlorophenethyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (127); N-butyl-4-chloro-5-methyl-1-(4-(naphthalen-2-ylsulfonylcarbamoyl)-2-(1,2,3,4-tetrahydroisoquinoline-2-carbonyl)phenyl)-N-(4,4,4-trifluorobutyl)-1H-pyrazole-3-carboxamide (128); 4-chloro-5-methyl-1-(4-(naphthalen-2-ylsulfonylcarbamoyl)-2-(1,2,3,4-tetrahydroisoquinoline-2-carbonyl)phenyl)-N,N-bis(4,4,4-trifluorobutyl)-1H-pyrazole-3-carboxamide (129); 4-chloro-5-methyl-1-(4-(naphthalen-2-ylsulfonylcarbamoyl)-2-(1,2,3,4-tetrahydroisoquinoline-2-carbonyl)phenyl)-N,N-bis(3,3,3-trifluoropropyl)-1H-pyrazole-3-carboxamide (130); N-butyl-4-chloro-N-(3-isopropoxybenzyl)-5-methyl-1-(4-(naphthalen-2-ylsulfonylcarbamoyl)-2-(1,2,3,4-tetrahydroisoquinoline-2-carbonyl) phenyl)-1H-pyrazole-3-carboxamide (131); N-butyl-4-chloro-N-(3-(4-chlorophenoxy)benzyl)-5-methyl-1-(4-(naphthalen-2-ylsulfonylcarbamoyl)-2-(1,2,3,4-tetrahydroisoquinoline-2-carbonyl) phenyl)-1H-pyrazole-3-carboxamide (132); N-(4-butoxybenzyl)-N-butyl-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (133); N-butyl-4-chloro-N-(3,4-dichlorophenyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (134); N-butyl-4-chloro-N-(3-chlorobenzyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (135); N-butyl-4-chloro-N-(4-chlorobenzyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (136); N-butyl-4-chloro-N-(4-(4-fluorophenoxy)phenyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (137); N-butyl-4-chloro-N-(4-(4-chlorophenoxy)phenyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (138); N-butyl-4-chloro-5-methyl-N-(1-methyl-1H-indol-2-yl)-1-(4-(naphthalen-2-ylsulfonylcarbamoyl)-2-(1,2,3,4-tetrahydroisoquinoline-2-carbonyl)phenyl)-1H-pyrazole-3-carboxamide (139); N-butyl-4-chloro-N-(3,4-dimethoxyphenyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (140); N-butyl-4-chloro-N-(4-isopropoxyphenyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (141); N-butyl-4-chloro-N-(3-chloro-4-methylphenyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (142); N-(biphenyl-4-yl)-N-butyl-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (143); N-butyl-4-chloro-N-(4-methoxyphenyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (144); N-butyl-4-chloro-N-(3-methoxyphenyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (145); N-butyl-N-(3-tert-butylphenyl)-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (146); N-(biphenyl-3-yl)-N-butyl-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (147); N-butyl-N-(4-tert-butylphenyl)-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (148); N-butyl-4-chloro-N-(2,3-dihydrobenzo[b][1,4]dioxin-6-yl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (149); N-butyl-4-chloro-N-(3-isopropoxyphenyl)-5-methyl-1-(4-

(naphthalen-2-ylsulfonylcarbamoyl)-2-(1,2,3,4-tetrahydroisoquinoline-2-carbonyl)phenyl)-1H-pyrazole-3-carboxamide (150); N-butyl-4-chloro-5-methyl-N-(naphthalen-2-ylmethyl)-1-(4-(naphthalen-2-ylsulfonylcarbamoyl)-2-(1,2,3,4-tetrahydroisoquinoline-2-carbonyl)phenyl)-1H-pyrazole-3-carboxamide (151); N-butyl-4-chloro-N-(3'-chlorobiphenyl-3-yl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (152); N-butyl-4-chloro-N-(4'-chlorobiphenyl-3-yl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (153); methyl 4-(N-butyl-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamido)benzoate (154); 4-(N-butyl-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamido)benzyl propionate (155); N-Butyl-4-chloro-5-methyl-1-(4-(naphthalen-2-ylsulfonylcarbamoyl)-2-(1,2,3,4-tetrahydroisoquinoline-2-carbonyl)phenyl)-N-phenyl-1H-pyrazole-3-carboxamide (156); N-Benzyl-N-butyl-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (157); N-Butyl-4-chloro-5-methyl-N-(3-(2-(4-methylpiperazin-1-yl)ethylamino)-3-oxopropyl)-1-(4-(naphthalen-2-ylsulfonylcarbamoyl)-2-(1,2,3,4-tetrahydroisoquinoline-2-carbonyl) phenyl)-1H-pyrazole-3-carboxamide (158); N-Butyl-4-chloro-N-(3-(1,3-dihydroxypropan-2-ylamino)-3-oxopropyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (159); N-Butyl-4-chloro-N-(3-(1,3-dihydroxy-2-(hydroxymethyl)propan-2-ylamino)-3-oxopropyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (160); 4-(N-Butyl-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamido)benzoic acid (161); 2-(4-(N-Butyl-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamido) phenyl)acetic acid (162); 4-Bromo-N,N-dibutyl-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (163); N,N-Dibutyl-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (164); N,N-Dibutyl-4-(hydroxymethyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (165); 3-(3-(Dibutylcarbamoyl)-5-methyl-1-(4-(naphthalen-2-ylsulfonylcarbamoyl)-2-(1,2,3,4-tetrahydroisoquinoline-2-carbonyl)phenyl)-1H-pyrazol-4-yl)propanoic acid (166); N,N-Dibutyl-4-(3-(dimethylamino)propyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide (167); N,N-Dibutyl-1-(4-(naphthalen-2-ylsulfonylcarbamoyl)-2-(1,2,3,4-tetrahydroisoquinoline-2-carbonyl)phenyl)-1H-pyrazole-3-carboxamide (168); N,N-Dibutyl-4-chloro-1-(4-(naphthalen-2-ylsulfonylcarbamoyl)-2-(1,2,3,4-tetrahydroisoquinoline-2-carbonyl)phenyl)-1H-pyrazole-3-carboxamide (169); N,N-Dibutyl-4-chloro-5-(2-hydroxyethyl)-1-(4-(naphthalen-2-ylsulfonylcarbamoyl)-2-(1,2,3,4-tetrahydroisoquinoline-2-carbonyl)phenyl)-1H-pyrazole-3-carboxamide (170); 2-(4-Chloro-3-(dibutylcarbamoyl)-1-(4-(naphthalen-2-ylsulfonylcarbamoyl)-2-(1,2,3,4-tetrahydroisoquinoline-2-carbonyl)phenyl)-1H-pyrazol-5-yl)acetic acid (171); N,N-Dibutyl-4-chloro-5-(2-(cyclopropanesulfonamido)-2-oxoethyl)-1-(4-(naphthalen-2-ylsulfonylcarbamoyl)-2-(1,2,3,4-tetrahydroisoquinoline-2-carbonyl)phenyl)-1H-pyrazole-3-carboxamide (172); 2-(4-Chloro-3-(dibutylcarbamoyl)-1-(4-(naphthalen-2-ylsulfonylcarbamoyl)-2-(1,2,3,4-tetrahydroisoquinoline-2-carbonyl)phenyl)-1H-pyrazol-5-yl)ethyl carbamate (173); 2-(4-Chloro-3-(dibutylcarbamoyl)-1-(4-(naphthalen-2-ylsulfonylcarbamoyl)-2-(1,2,3,4-tetrahydroisoquinoline-2-carbonyl)phenyl)-1H-pyrazol-5-yl)ethyl 4-methylpiperazine-1-carboxylate (174); 2-(4-Chloro-3-(dibutylcarbamoyl)-1-(4-(naphthalen-2-ylsulfonylcarbamoyl)-2-(1,2,3,4-tetrahydroisoquinoline-2-carbonyl)phenyl)-1H-pyrazol-5-yl)ethyl 2-(4-methylpiperazin-1-yl) ethylcarbamate (175); tent-Butyl 3-(N-butyl-4-chloro-1-(4-(7-iodonaphthalen-2-ylsulfonylcarbamoyl)-2-(1,2,3,4-tetrahydroisoquinoline-2-carbonyl)phenyl)-5-methyl-1H-pyrazole-3-carboxamido)propanoate (176); N,N-Dibutyl-4-chloro-1-(4-(8-chloronaphthalen-2-ylsulfonylcarbamoyl)-2-((S)-3-(hydroxymethyl)-1,2,3,4-tetrahydroisoquinoline-2-carbonyl)phenyl)-5-methyl-1H-pyrazole-3-carboxamide (177); N-Butyl-4-chloro-N-(3,4-dichlorobenzyl)-1-(4-(8-(ethylsulfonyl)naphthalen-2-ylsulfonylcarbamoyl)-2-(1,2,3,4-tetrahydroisoquinoline-2-carbonyl)phenyl)-5-methyl-1H-pyrazole-3-carboxamide (178); N-Butyl-4-chloro-N-(3,4-dichlorobenzyl)-1-(4-(7-iodonaphthalen-2-ylsulfonylcarbamoyl)-2-(1,2,3,4-tetrahydroisoquinoline-2-carbonyl)phenyl)-5-methyl-1H-pyrazole-3-carboxamide (179); N-Butyl-4-chloro-N-(3,4-dichlorobenzyl)-5-methyl-1-(4-(7-(4-methylpiperazine-1-carbonyl)naphthalen-2-ylsulfonylcarbamoyl)-2-(1,2,3,4-tetrahydroisoquinoline-2-carbonyl)phenyl)-1H-pyrazole-3-carboxamide (180); N-Butyl-4-chloro-1-(4-(8-chloronaphthalen-2-ylsulfonylcarbamoyl)-2-((S)-3-(hydroxymethyl)-1,2,3,4-tetrahydroisoquinoline-2-carbonyl)phenyl)-N-(3,4-dichlorobenzyl)-5-methyl-1H-pyrazole-3-carboxamide (181); N-Butyl-4-chloro-1-(4-(8-chloronaphthalen-2-ylsulfonylcarbamoyl)-2-((S)-3-(((2-hydroxyethyl)(methyl)amino)methyl)-1,2,3,4-tetrahydroisoquinoline-2-carbonyl)phenyl)-N-(3,4-dichlorobenzyl)-5-methyl-1H-pyrazole-3-carboxamide (182); N,N-Dibutyl-4-chloro-1-(2-((S)-3-(hydroxymethyl)-1,2,3,4-tetrahydroisoquinoline-2-carbonyl)-4-(8-(2-morpholinoethoxy)naphthalen-2-ylsulfonylcarbamoyl) phenyl)-5-methyl-1H-pyrazole-3-carboxamide (183); N,N-Dibutyl-4-chloro-1-(2-((S)-3-((dimethylamino)methyl)-1,2,3,4-tetrahydroisoquinoline-2-carbonyl)-4-(8-(2-morpholinoethoxy) naphthalen-2-ylsulfonylcarbamoyl) phenyl)-5-methyl-1H-pyrazole-3-carboxamide (184); N,N-Dibutyl-4-chloro-5-methyl-1-(4-(8-(2-morpholinoethoxy) naphthalen-2-ylsulfonylcarbamoyl)-2-((S)-3-(morpholinomethyl)-1,2,3,4-tetrahydroisoquinoline-2-carbonyl)phenyl)-1H-pyrazole-3-carboxamide (185); N-Butyl-4-chloro-N-(3,4-dichlorobenzyl)-5-methyl-1-(4-(8-(2-morpholinoethoxy)naphthalen-2-ylsulfonylcarbamoyl)-2-((S)-3-(morpholinomethyl)-1,2,3,4-tetrahydroisoquinoline-2-carbonyl)phenyl)-1H-pyrazole-3-carboxamide (186); N-Butyl-4-chloro-N-(3,4-dichlorobenzyl)-1-(2-((S)-3-(hydroxymethyl)-1,2,3,4-tetrahydroisoquinoline-2-carbonyl)-4-(8-(2-morpholinoethoxy)naphthalen-2-ylsulfonylcarbamoyl)phenyl)-5-methyl-1H-pyrazole-3-carboxamide (187); 1-(2-((S)-3-(Aminomethyl)-1,2,3,4-tetrahydroisoquinolin-2-carbonyl)-4-(8-(2-morpholinoethoxy)naphthalen-2-ylsulfonylcarbamoyl)phenyl)-N-butyl-4-chloro-N-(3,4-dichlorobenzyl)-5-methyl-1H-pyrazole-3-carboxamide (188); N,N-Dibutyl-4-chloro-1-(4-(1-(3,4-dichlorobenzyl)indolin-5-ylsulfonylcarbamoyl)-2-((S)-3-(hydroxymethyl)-1,2,3,4-tetrahydroisoquinoline-2-carbonyl)phenyl)-5-methyl-1H-pyrazole-3-carboxamide (189); N,N-Dibutyl-4-chloro-1-(4-(1-ethylindolin-5-ylsulfonylcarbamoyl)-2-((S)-3-(hydroxymethyl)-1,2,3,4-tetrahydroisoquinoline-2-carbonyl)phenyl)-5-methyl-1H-pyrazole-3-carboxamide (190); 4-(4-Chloro-3-(dibutylamino)-5-methyl-1H-pyrazol-1-yl)-N-(naphthalen-2-ylsulfonyl)-3-(1,2,3,4-tetrahydroisoquinoline-2-carbonyl)benzamide (191); 4-(4-Chloro-3-(dipropylamino)-5-methyl-1H-pyrazol-1-yl)-3-((S)-3-(hydroxymethyl)-1,2,3,4-tetrahydroisoquinoline-2-carbonyl)-N-(naphthalen-2-ylsulfonyl)benzamide (192); 4-(4-Chloro-3-(dipropylamino)-5-methyl-1H-pyrazol-1-yl)-N-(8-chloronaphthalen-2-ylsulfonyl)-3-((S)-3-(hydroxymethyl)-1,2,3,4-tetrahydroisoquinoline-2-carbonyl)benzamide (193); 3-((S)-3-(Aminomethyl)-1,2,3,4-tetrahydroisoquinoline-2-carbonyl)-4-(4-chloro-3-(dipropylamino)-5-methyl-1H-pyrazol-1-yl)-N-(8-chloronaphthalen-2-ylsulfonyl)benzamide (194); 4-(4-Chloro-3-(dipropylamino)-5-(trifluoromethyl)-1H-pyrazol-1-yl)-N-(8-chloronaphthalen-2-ylsulfonyl)-3-((S)-3-(hydroxymethyl)-1,2,3,4-tetrahydroisoquinoline-2-carbonyl)benzamide (195); 4-(4-Chloro-3-(dipropylamino)-5-(trifluoromethyl)-1H-pyrazol-1-yl)-N-(8-chloronaphthalen-2-ylsulfonyl)-3-(1,2,3,4-tetrahydroisoquinoline-2-carbonyl)benzamide (196); 3-(N-butyl-4-chloro-1-(4-(1-(3,4-dichlorobenzyl)indolin-5-ylsulfonylcarbamoyl)-2-(1,2,3,4-tetrahydroisoquinoline-2-carbonyl)phenyl)-5-methyl-1H-pyrazole-3-carboxamido) propanoic acid (197); N,N-dibutyl-4-chloro-1-(4-(1-(3,4-dichlorobenzyl)-1H-indol-5-ylsulfonylcarbamoyl)-2-((S)-3-(hydroxymethyl)-1,2,3,4-tetrahydroisoquinoline-2-carbonyl)phenyl)-5-methyl-1H-pyrazole-3-carboxamide (198); 1-(4-(3-bromo-1-(3,4-dichlorobenzyl)-1H-indol-5-ylsulfonylcarbamoyl)-2-((S)-3-(hydroxymethyl)-1,2,3,4-tetrahydroisoquinoline-2-carbonyl)phenyl)-N,N-dibutyl-4-chloro-5-methyl-1H-pyrazole-3-carboxamide (199); N-butyl-4-chloro-1-(4-(1-(3,4-dichlorobenzyl)indolin-5-ylsulfonylcarbamoyl)-2-(1,2,3,4-tetrahydroisoquinoline-2-carbonyl)phenyl)-5-methyl-N-(3-(2-(4-methylpiperazin-1-yl)ethylamino)-3-oxopropyl)-1H-pyrazole-3-carboxamide (200); 1-(2-((S)-3-(aminomethyl)-1,2,3,4-tetrahydroisoquinoline-2-carbonyl)-4-(3-bromo-1-(3,4-dichlorobenzyl)-1H-indol-5-ylsulfonylcarbamoyl)phenyl)-N,N-dibutyl-4-chloro-5-methyl-1H-pyrazole-3-carboxamide (201); N,N-dibutyl-4-chloro-1-(4-(8-chloronaphthalen-2-ylsulfonylcarbamoyl)-2-((S)-3-((3-methoxypropoxy)methyl)-1,2,3,4-tetrahydroisoquinoline-2-carbonyl)phenyl)-5-methyl-1H-pyrazole-3-carboxamide (202); 1-(2-((S)-3-(aminomethyl)-1,2,3,4-tetrahydroisoquinoline-2-carbonyl)-4-(8-chloronaphthalen-2-ylsulfonylcarbamoyl)phenyl)-N,N-Dibutyl-4-chloro-5-methyl-1H-pyrazole-3-carboxamide (203); (Z)—N-(8-bromo-5-chloronaphthalen-2-ylsulfonyl)-4-(4-chloro-3-(dipropylamino)-5-methyl-1H-pyrazol-1-yl)-3-(3-(dimethylamino)-2,5-dihydro-1H-benzo[e][1,3]diazepine-2-carbonyl)benzamide (204); 1-(4-(7-bromo-1-ethylindolin-5-ylsulfonylcarbamoyl)-2-((S)-3-(hydroxymethyl)-1,2,3,4-tetrahydroisoquinoline-2-carbonyl)phenyl)-N,N-dibutyl-4-chloro-5-methyl-1H-pyrazole-3-carboxamide (205); 4-chloro-1-(4-(1-ethylindolin-5-ylsulfonylcarbamoyl)-2-((S)-3-(hydroxymethyl)-1,2,3,4-tetrahydroisoquinoline-2-carbonyl)phenyl)-5-methyl-N,N-dipropyl-1H-pyrazole-3-carboxamide (206); N-(8-bromo-5-chloronaphthalen-2-ylsulfonyl)-4-(4-chloro-3-(dipropylamino)-5-methyl-1H-pyrazol-1-yl)-3-((S)-3-(hydroxymethyl)-1,2,3,4-tetrahydroisoquinoline-2-carbonyl)benzamide (207); 1-(4-(7-bromo-1-ethyl-1H-indol-5-ylsulfonylcarbamoyl)-2-((S)-3-(hydroxymethyl)-1,2,3,4-tetrahydroisoquinoline-2-carbonyl)phenyl)-N,N-dibutyl-4-chloro-5-methyl-1H-pyrazole-3-carboxamide (208); 1-(4-(7-bromo-1-ethylindolin-5-ylsulfonylcarbamoyl)-2-((S)-3-(hydroxymethyl)-1,2,3,4-tetrahydroisoquinoline-2-carbonyl)phenyl)-4-chloro-5-methyl-N,N-dipropyl-1H-pyrazole-3-carboxamide (209); N,N-dibutyl-4-chloro-1-(4-(3,7-dibromo-1-ethyl-1H-indol-5-ylsulfonylcarbamoyl)-2-((S)-3-(hydroxymethyl)-1,2,3,4-tetrahydroisoquinoline-2-carbonyl)phenyl)-5-methyl-1H-pyrazole-3-carboxamide (210); 1-(2-(6-bromo-1,2,3,4-tetrahydroisoquinoline-2-carbonyl)-4-(1-(3,4-dichlorobenzyl)indolin-5-ylsulfonylcarbamoyl)phenyl)-N,N-dibutyl-4-chloro-5-methyl-1H-pyrazole-3-carboxamide (211); N,N-dibutyl-4-chloro-1-(4-(1-(3,4-dichlorobenzyl)indolin-5-ylsulfonylcarbamoyl)-2-(6,7-dimethoxy-1,2,3,4-tetrahydroisoquinoline-2-carbonyl)phenyl)-5-methyl-1H-pyrazole-3-carboxamide (212); 2-(4'-((N-butyl-4-chloro-1-(4-(1-(3,4-dichlorobenzyl)indolin-5-ylsulfonylcarbamoyl)-2-(1,2,3,4-tetrahydroisoquinoline-2-carbonyl)phenyl)-5-methyl-1H-pyrazole-3-carboxamido) methyl) biphenyl-4-yl)acetic acid (213); 2-(4'-((4-chloro-1-(4-(1-(3,4-dichlorobenzyl)indolin-5-ylsulfonylcarbamoyl)-2-(1,2,3,4-tetrahydroisoquinoline-2-carbonyl)phenyl)-5-methyl-1H-pyrazole-3-carboxamido)methyl)biphenyl-4-yl) acetic acid (214); 4-(3-(dibutylcarbamoyl)-1-(4-(1-(3,4-dichlorobenzyl)indolin-5-ylsulfonylcarbamoyl)-2-(1,2,3,4-tetrahydroisoquinoline-2-carbonyl) phenyl)-5-methyl-1H-pyrazol-4-yl)benzoic acid (215); 4-chloro-1-(4-(1-(3,4-dichlorobenzyl)indolin-5-ylsulfonylcarbamoyl)-2-(1,2,3,4-tetrahydroisoquinoline-2-carbonyl)phenyl)-5-methyl-N,N-dipropyl-1H-pyrazole-3-carboxamide (216); 1-(4-(8-bromo-5-chloronaphthalen-2-ylsulfonylcarbamoyl)-2-(1,2,3,4-tetrahydroisoquinoline-2-carbonyl)phenyl)-N-butyl-4-chloro-N-(4'-chlorobiphenyl-3-yl)-5-methyl-1H-pyrazole-3-carboxamide (217); 1-(4-(8-bromo-5-chloronaphthalen-2-ylsulfonylcarbamoyl)-2-(1,2,3,4-tetrahydroisoquinoline-2-carbonyl)phenyl)-N-butyl-4-chloro-N-(3'-chlorobiphenyl-3-yl)-5-methyl-1H-pyrazole-3-carboxamide (218); N-butyl-4-chloro-N-((4'-chlorobiphenyl-4-yl)methyl)-1-(4-(1-(3,4-dichlorobenzyl)indolin-5-ylsulfonylcarbamoyl)-2-(1,2,3,4-tetrahydroisoquinoline-2-carbonyl)phenyl)-5-methyl-1H-pyrazole-3-carboxamide (219); N-butyl-4-chloro-N-(4-(4-chlorophenoxy)phenyl)-1-(4-(1-(3,4-dichlorobenzyl)indolin-5-ylsulfonylcarbamoyl)-2-(1,2,3,4-tetrahydroisoquinoline-2-carbonyl)phenyl)-5-methyl-1H-pyrazole-3-carboxamide (220); N-butyl-4-chloro-N-(4'-chlorobiphenyl-3-yl)-1-(4-(5,8-dichloronaphthalen-2-ylsulfonylcarbamoyl)-2-(1,2,3,4-tetrahydroisoquinoline-2-carbonyl)phenyl)-5-methyl-1H-pyrazole-3-carboxamide (221); N-butyl-4-chloro-N-(3'-chlorobiphenyl-3-yl)-1-(4-(5,8-dichloronaphthalen-2-ylsulfonylcarbamoyl)-2-(1,2,3,4-tetrahydroisoquinoline-2-carbonyl)phenyl)-5-methyl-1H-pyrazole-3-carboxamide (222); Ethyl 5-butyl-4-(4-(naphthalen-2-ylsulfonylcarbamoyl)-2-(1,2,3,4-tetrahydroisoquinoline-2-carbonyl) phenyl)-1-phenyl-1H-pyrazole-3-carboxylate (223); Ethyl 5-methyl-4-(4-(naphthalen-2-ylsulfonylcarbamoyl)-2-(1,2,3,4-tetrahydroisoquinoline-2-carbonyl)phenyl)-1-phenyl-1H-pyrazole-3-carboxylate (224); Ethyl 5-butyl-1-(4-methoxyphenyl)-4-(4-(naphthalen-2-ylsulfonylcarbamoyl)-2-(1,2,3,4-tetrahydroisoquinoline-2-carbonyl)phenyl)-1H-pyrazole-3-carboxylate (225); Ethyl 5-butyl-1-(4-isopropylphenyl)-4-(4-(naphthalen-2-ylsulfonylcarbamoyl)-2-(1,2,3,4-tetrahydroisoquinoline-2-carbonyl)phenyl)-1H-pyrazole-3-carboxylate (226); Ethyl 5-butyl-4-(4-

(naphthalen-2-ylsulfonylcarbamoyl)-2-(1,2,3,4-tetrahydroisoquinoline-2-carbonyl)phenyl)-1-(3-phenoxyphenyl)-1H-pyrazole-3-carboxylate (227); Ethyl 5-butyl-4-(4-(naphthalen-2-ylsulfonylcarbamoyl)-2-(1,2,3,4-tetrahydroisoquinoline-2-carbonyl)phenyl)-1-(4-phenoxyphenyl)-1H-pyrazole-3-carboxylate (228); Ethyl 5-butyl-1-(4-(4-chlorophenoxy)phenyl)-4-(4-(naphthalen-2-ylsulfonylcarbamoyl)-2-(1,2,3,4-tetrahydroisoquinoline-2-carbonyl)phenyl)-1H-pyrazole-3-carboxylate (229); Ethyl 5-butyl-1-(4-(3-chlorophenoxy)phenyl)-4-(4-(naphthalen-2-ylsulfonylcarbamoyl)-2-(1,2,3,4-tetrahydroisoquinoline-2-carbonyl)phenyl)-1H-pyrazole-3-carboxylate (230); Ethyl 1-(4-butoxyphenyl)-5-butyl-4-(4-(naphthalen-2-ylsulfonylcarbamoyl)-2-(1,2,3,4-tetrahydroisoquinoline-2-carbonyl)phenyl)-1H-pyrazole-3-carboxylate (231); Ethyl 5-butyl-1-(4-(2-hydroxyethyl)phenyl)-4-(4-(naphthalen-2-ylsulfonylcarbamoyl)-2-(1,2,3,4-tetrahydroisoquinoline-2-carbonyl)phenyl)-1H-pyrazole-3-carboxylate (232); Ethyl 1-(4-(allyloxy) phenyl)-5-butyl-4-(4-(naphthalen-2-ylsulfonylcarbamoyl)-2-(1,2,3,4-tetrahydroisoquinoline-2-carbonyl)phenyl)-1H-pyrazole-3-carboxylate (233); Ethyl 1-(biphenyl-4-yl)-5-butyl-4-(4-(naphthalen-2-ylsulfonylcarbamoyl)-2-(1,2,3,4-tetrahydroisoquinoline-2-carbonyl)phenyl)-1H-pyrazole-3-carboxylate (234); Ethyl 5-butyl-1-(3-(methoxycarbonyl)phenyl)-4-(4-(naphthalen-2-ylsulfonylcarbamoyl)-2-(1,2,3,4-tetrahydroisoquinoline-2-carbonyl)phenyl)-1H-pyrazole-3-carboxylate (235); 4-(5-Butyl-3-(hydroxymethyl)-1-phenyl-1H-pyrazol-4-yl)-N-(naphthalen-2-ylsulfonyl)-3-(1,2,3,4-tetrahydroisoquinoline-2-carbonyl)benzamide (236); 5-Butyl-4-(4-(naphthalen-2-ylsulfonylcarbamoyl)-2-(1,2,3,4-tetrahydroisoquinoline-2-carbonyl)phenyl)-1-phenyl-1H-pyrazole-3-carboxylic acid (237); 4-(5-Butyl-3-(hydroxymethyl)-1-(3-(hydroxymethyl)phenyl)-1H-pyrazol-4-yl)-N-(naphthalen-2-ylsulfonyl)-3-(1,2,3,4-tetrahydroisoquinoline-2-carbonyl)benzamide (238); Ethyl 5-butyl-1-phenyl-4-(2-(1,2,3,4-tetrahydroisoquinoline-2-carbonyl)-4-(2-(trimethylsilyl)ethylsulfonylcarbamoyl)phenyl)-1H-pyrazole-3-carboxylate (239); 4-(5-Butyl-3-(hydroxymethyl)-1-phenyl-1H-pyrazol-4-yl)-3-(1,2,3,4-tetrahydroisoquinoline-2-carbonyl)-N-(2-(trimethylsilyl)ethylsulfonyl)benzamide (240); 4-(5-butyl-3-(hydroxymethyl)-1-(4-phenoxyphenyl)-1H-pyrazol-4-yl)-N-(naphthalen-2-ylsulfonyl)-3-(1,2,3,4-tetrahydroisoquinoline-2-carbonyl)benzamide (241); 4-(5-butyl-1-(4-(4-chlorophenoxy)phenyl)-3-(hydroxymethyl)-1H-pyrazol-4-yl)-N-(naphthalen-2-ylsulfonyl)-3-(1,2,3,4-tetrahydroisoquinoline-2-carbonyl)benzamide (242); 4-(5-butyl-1-(4-(3-chlorophenoxy)phenyl)-3-(hydroxymethyl)-1H-pyrazol-4-yl)-N-(naphthalen-2-ylsulfonyl)-3-(1,2,3,4-tetrahydroisoquinoline-2-carbonyl)benzamide (243); 4-(5-butyl-1-(4-butoxyphenyl)-3-(hydroxymethyl)-1H-pyrazol-4-yl)-N-(naphthalen-2-ylsulfonyl)-3-(1,2,3,4-tetrahydroisoquinoline-2-carbonyl)benzamide (244); 4-(5-butyl-1-(4-(2-hydroxyethyl)phenyl)-3-(hydroxymethyl)-1H-pyrazol-4-yl)-N-(naphthalen-2-ylsulfonyl)-3-(1,2,3,4-tetrahydroisoquinoline-2-carbonyl)benzamide (245); 4-(1-(4-(allyloxy)phenyl)-5-butyl-3-(hydroxymethyl)-1H-pyrazol-4-yl)-N-(naphthalen-2-ylsulfonyl)-3-(1,2,3,4-tetrahydroisoquinoline-2-carbonyl)benzamide (246); 4-(1-(biphenyl-4-yl)-5-butyl-3-(hydroxymethyl)-1H-pyrazol-4-yl)-N-(naphthalen-2-ylsulfonyl)-3-(1,2,3,4-tetrahydroisoquinoline-2-carbonyl)benzamide (247); ethyl 5-butyl-4-(4-(8-chloronaphthalen-2-ylsulfonylcarbamoyl)-2-(1,2,3,4-tetrahydroisoquinoline-2-carbonyl)phenyl)-1-(4-(3-chlorophenoxy)phenyl)-1H-pyrazole-3-carboxylate (248); ethyl 5-butyl-1-(4-(3-chlorophenoxy)phenyl)-4-(4-(ethylsulfonylcarbamoyl)-2-(1,2,3,4-tetrahydroisoquinoline-2-carbonyl)phenyl)-1H-pyrazole-3-carboxylate (249); ethyl 5-butyl-1-(4-(3-chlorophenoxy)phenyl)-4-(4-(pentylsulfonylcarbamoyl)-2-(1,2,3,4-tetrahydroisoquinoline-2-carbonyl)phenyl)-1H-pyrazole-3-carboxylate (250); ethyl 4-(4-(8-bromo-5-chloronaphthalen-2-ylsulfonylcarbamoyl)-2-(1,2,3,4-tetrahydroisoquinoline-2-carbonyl)phenyl)-5-butyl-1-(4-(3-chlorophenoxy)phenyl)-1H-pyrazole-3-carboxylate (251); 4-(5-butyl-1-(4-(3-chlorophenoxy)phenyl)-3-(hydroxymethyl)-1H-pyrazol-4-yl)-N-(8-chloronaphthalen-2-ylsulfonyl)-3-(1,2,3,4-tetrahydroisoquinoline-2-carbonyl)benzamide (252); 4-(5-butyl-1-(4-(3-chlorophenoxy)phenyl)-3-(hydroxymethyl)-1H-pyrazol-4-yl)-N-(ethylsulfonyl)-3-(1,2,3,4-tetrahydroisoquinoline-2-carbonyl)benzamide (253); 4-(5-butyl-1-(4-(3-chlorophenoxy)phenyl)-3-(hydroxymethyl)-1H-pyrazol-4-yl)-N-(pentylsulfonyl)-3-(1,2,3,4-tetrahydroisoquinoline-2-carbonyl)benzamide (254); N-(8-bromo-5-chloronaphthalen-2-ylsulfonyl)-4-(5-butyl-1-(4-(3-chlorophenoxy)phenyl)-3-(hydroxymethyl)-1H-pyrazol-4-yl)-3-(1,2,3,4-tetrahydroisoquinoline-2-carbonyl)benzamide (255); 4-(5-Butyl-3-(hydroxymethyl)-1-(4-hydroxyphenyl)-1H-pyrazol-4-yl)-N-(naphthalen-2-ylsulfonyl)-3-(1,2,3,4-tetrahydroisoquinoline-2-carbonyl)benzamide (256); 4-(5-Butyl-3-(hydroxymethyl)-1-(4-(3-hydroxypropoxy)phenyl)-1H-pyrazol-4-yl)-N-(naphthalen-2-ylsulfonyl)-3-(1,2,3,4-tetrahydroisoquinoline-2-carbonyl)benzamide (257); (±)-4-(5-Butyl-1-(4-(2,3-dihydroxypropoxy)phenyl)-3-(hydroxymethyl)-1H-pyrazol-4-yl)-N-(naphthalen-2-ylsulfonyl)-3-(1,2,3,4-tetrahydroisoquinoline-2-carbonyl)benzamide (258); Ethyl 5-butyl-4-(2-((S)-3-(hydroxymethyl)-1,2,3,4-tetrahydroisoquinoline-2-carbonyl)-4-(naphthalen-2-ylsulfonylcarbamoyl)phenyl)-1-phenyl-1H-pyrazole-3-carboxylate (259); 4-(5-Butyl-3-(hydroxymethyl)-1-phenyl-1H-pyrazol-4-yl)-3-((S)-3-(hydroxymethyl)-1,2,3,4-tetrahydroisoquinoline-2-carbonyl)-N-(naphthalen-2-ylsulfonyl)benzamide (260); Ethyl 4-(2-((S)-3-(azidomethyl)-1,2,3,4-tetrahydroisoquinoline-2-carbonyl)-4-(naphthalen-2-ylsulfonylcarbamoyl)phenyl)-5-butyl-1-phenyl-1H-pyrazole-3-carboxylate (261); Ethyl 4-(2-((S)-3-(aminomethyl)-1,2,3,4-tetrahydroisoquinoline-2-carbonyl)-4-(naphthalen-2-ylsulfonylcarbamoyl)phenyl)-5-butyl-1-phenyl-1H-pyrazole-3-carboxylate (262); 3-((S)-3-(Aminomethyl)-1,2,3,4-tetrahydroisoquinoline-2-carbonyl)-4-(5-butyl-3-(hydroxymethyl)-1-phenyl-1H-pyrazol-4-yl)-N-(naphthalen-2-ylsulfonyl)benzamide (263); N,N-Dibutyl-1-methyl-2-(4-(naphthalen-2-ylsulfonylcarbamoyl)-2-(1,2,3,4-tetrahydroisoquinoline-2-carbonyl)phenyl)-1H-imidazole-4-carboxamide (264); N,N-Dibutyl-1-(2-(methylamino)-2-oxoethyl)-2-(4-(naphthalen-2-ylsulfonylcarbamoyl)-2-(1,2,3,4-tetrahydroisoquinoline-2-carbonyl)phenyl)-1H-imidazole-4-carboxamide (265); N,N-Dibutyl-1-(3-hydroxypropyl)-2-(4-(naphthalen-2-ylsulfonylcarbamoyl)-2-(1,2,3,4-tetrahydroisoquinoline-2-carbonyl)phenyl)-1H-imidazole-4-carboxamide (266); N,N-Dibutyl-1-(3-(dimethylamino)propyl)-2-(4-(naphthalen-2-ylsulfonylcarbamoyl)-2-(1,2,3,4-tetrahydroisoquinoline-2-carbonyl)phenyl)-1H-imidazole-4-carboxamide (267); N,N-Dibutyl-2-(4-(naphthalen-2-ylsulfonylcarbamoyl)-2-(1,2,3,4-tetrahydroisoquinoline-2-carbonyl)phenyl)-1-((2-(trimethylsilyl)ethoxy)methyl)-1H-imidazole-4-carboxamide (268); 2-(4-(Dibutylcarbamoyl)-2-(4-(naphthalen-1-ylsulfonylcarbamoyl)-2-(1,2,3,4-tetrahydroisoquinoline-2-carbonyl)phenyl)-1H-imidazol-1-yl)acetic acid (269); N,N-Dibutyl-2-(4-(8-iodonaphthalen-2-ylsulfonylcarbamoyl)-2-(1,2,3,4-tetrahydroisoquinoline-2-carbonyl)phenyl)-1-methyl-1H-imidazole-4-carboxamide (270); N,N-Dibutyl-2-(4-(8-chloronaphthalen-2-ylsulfonylcarbamoyl)-2-((S)-3-(hydroxymethyl)-1,2,3,4-tetrahydroisoquinoline-2-carbonyl)phenyl)-1-phenethyl-1H-imidazole-4-carboxamide (271); N,N-Dibutyl-2-(4-(8-chloronaphthalen-2-ylsulfonylcarbamoyl)-2-((S)-3-(hydroxymethyl)-1,2,3,4-tetrahydroisoquinoline-2-carbonyl)phenyl)-1-(3-phenylpropyl)-1H-imidazole-4-carboxamide (272); 1-Benzyl-N,N-dibutyl-2-(4-(8-chloronaphthalen-2-ylsulfonylcarbamoyl)-2-((S)-3-(hydroxymethyl)-1,2,3,4-tetrahydroisoquinoline-2-carbonyl)phenyl)-1H-imidazole-4-carboxamide (273); N,N-Dibutyl-1-(2-hydroxyethyl)-2-(2-((S)-3-(hydroxymethyl)-1,2,3,4-tetrahydroisoquinoline-2-carbonyl)-4-(naphthalen-2-ylsulfonylcarbamoyl)phenyl)-1H-imidazole-4-carboxamide (274); N,N-Dibutyl-2-(2-((S)-3-(hydroxymethyl)-1,2,3,4-tetrahydroisoquinoline-2-carbonyl)-4-(naphthalen-2-ylsulfonylcarbamoyl) phenyl)-1-(2-methoxyethyl)-1H-imidazole-4-carboxamide (275); N,N-Dibutyl-1-(2-(2-hydroxyethoxy)ethyl)-2-(2-((S)-3-(hydroxymethyl)-1,2,3,4-tetrahydroisoquinoline-2-carbonyl)-4-(naphthalen-2-ylsulfonylcarbamoyl)phenyl)-1H-imidazole-4-carboxamide (276); N,N-Dibutyl-2-(2-((S)-3-(hydroxymethyl)-1,2,3,4-tetrahydroisoquinoline-2-carbonyl)-4-(naphthalen-2-ylsulfonylcarbamoyl)phenyl)-1-(2-morpholinoethyl)-1H-imidazole-4-carboxamide (277); N,N-Dibutyl-2-(2-((S)-3-(hydroxymethyl)-1,2,3,4-tetrahydroisoquinoline-2-carbonyl)-4-(naphthalen-2-ylsulfonylcarbamoyl)phenyl)-1-(3-morpholinopropyl)-1H-imidazole-4-carboxamide (278); N,N-Dibutyl-2-(2-((S)-3-(hydroxymethyl)-1,2,3,4-tetrahydroisoquinoline-2-carbonyl)-4-(naphthalen-2-ylsulfonylcarbamoyl)phenyl)-1-(3-(4-methylpiperazin-1-yl)propyl)-1H-imidazole-4-carboxamide (279); N,N-Dibutyl-2-(2-((S)-3-(hydroxymethyl)-1,2,3,4-tetrahydroisoquinoline-2-carbonyl)-4-(naphthalen-2-ylsulfonylcarbamoyl)phenyl)-1-(2-(4-methylpiperazin-1-yl)ethyl)-1H-imidazole-4-carboxamide (280); 2-(2-((S)-3-(Aminomethyl)-1,2,3,4-tetrahydroisoquinoline-2-carbonyl)-4-(naphthalen-2-ylsulfonylcarbamoyl)phenyl)-N,N-dibutyl-1-methyl-1H-imidazole-4-carboxamide (281); 2-(2-((S)-3-(Aminomethyl)-1,2,3,4-tetrahydroisoquinoline-2-carbonyl)-4-(8-iodonaphthalen-2-ylsulfonylcarbamoyl)phenyl)-N,N-dibutyl-1-methyl-1H-imidazole-4-carboxamide (282); N,N-Dibutyl-2-(4-(8-chloronaphthalen-2-ylsulfonylcarbamoyl)-2-((S)-3-(hydroxymethyl)-1,2,3,4-tetrahydroisoquinoline-2-carbonyl)phenyl)-1-methyl-1H-imidazole-4-carboxamide (283); N,N-Dibutyl-5-(4-(8-iodonaphthalen-2-ylsulfonylcarbamoyl)-2-(1,2,3,4-tetrahydroisoquinoline-2-carbonyl) phenyl)-1-methyl-1H-imidazole-4-carboxamide (284); N,N-Dibutyl-5-(4-(8-chloronaphthalen-2-ylsulfonylcarbamoyl)-2-(1,2,3,4-tetrahydroisoquinoline-2-carbonyl)phenyl)-1-methyl-1H-imidazole-4-carboxamide (285); N,N-Dibutyl-6-(4-(naphthalen-2-ylsulfonylcarbamoyl)-2-(1,2,3,4-tetrahydroisoquinoline-2-carbonyl)phenyl)picolinamide (286); 4-(6-(Dibutylamino) pyridin-2-yl)-N-(naphthalen-2-ylsulfonyl)-3-(1,2,3,4-tetrahydroisoquinoline-2-carbonyl) benzamide (287); 4-(3-Bromo-6-(dibutylamino)pyridin-2-yl)-N-(7-chloronaphthalen-2-ylsulfonyl)-3-(1,2,3,4-tetrahydroisoquinoline-2-carbonyl)benzamide (288); 4-(3-Bromo-6-(dibutylamino)pyridin-2-yl)-N-(8-chloronaphthalen-2-ylsulfonyl)-3-(1,2,3,4-tetrahydroisoquinoline-2-carbonyl)benzamide (289); 4-(3-Bromo-6-(dibutylamino)pyridin-2-yl)-N-(1-(3,4-dichlorobenzyl)indolin-5-ylsulfonyl)-3-(1,2,3,4-tetrahydroisoquinoline-2-carbonyl)benzamide (290); 4-(2-(Dibutylamino)pyrimidin-4-yl)-N-(naphthalen-2-ylsulfonyl)-3-(1,2,3,4-tetrahydroisoquinoline-2-carbonyl) benzamide (291); N-(8-chloronaphthalen-2-ylsulfonyl)-4-(2-(dibutylamino)pyrimidin-4-yl)-3-(1,2,3,4-tetrahydroisoquinoline-2-carbonyl)benzamide (292); 4-(2-(dibutylamino)pyrimidin-4-yl)-N-(7-iodonaphthalen-2-ylsulfonyl)-3-(1,2,3,4-tetrahydroisoquinoline-2-carbonyl) benzamide (293); 4-(2-(dibutylamino)pyrimidin-4-yl)-N-(1-ethyl-1H-indol-5-ylsulfonyl)-3-(1,2,3,4-tetrahydroisoquinoline-2-carbonyl)benzamide (294); 4-(2-(dibutylamino)pyrimidin-4-yl)-N-(1-(3,4-dichlorobenzyl)-1H-indol-5-ylsulfonyl)-3-(1,2,3,4-tetrahydroisoquinoline-2-carbonyl)benzamide (295); 4-(2-(dipentylamino)pyrimidin-4-yl)-N-(naphthalen-2-ylsulfonyl)-3-(1,2,3,4-tetrahydroisoquinoline-2-carbonyl)benzamide (296); N-(naphthalen-2-ylsulfonyl)-4-(2-(3-propylpyrrolidin-1-yl)pyrimidin-4-yl)-3-(1,2,3,4-tetrahydroisoquinoline-2-carbonyl)benzamide (297); 4-(2-(butyl(3,4-dichlorobenzyl)amino)pyrimidin-4-yl)-N-(naphthalen-2-ylsulfonyl)-3-(1,2,3,4-tetrahydroisoquinoline-2-carbonyl)benzamide (298); 4-(2-(dipropylamino)pyrimidin-4-yl)-N-(naphthalen-2-ylsulfonyl)-3-(1,2,3,4-tetrahydroisoquinoline-2-carbonyl)benzamide (299); 4-(2-((cyclopropylmethyl)(propyl)amino)pyrimidin-4-yl)-N-(naphthalen-2-ylsulfonyl)-3-(1,2,3,4-tetrahydroisoquinoline-2-carbonyl)benzamide (300); 4-(2-(diethylamino)pyrimidin-4-yl)-N-(naphthalen-2-ylsulfonyl)-3-(1,2,3,4-tetrahydroisoquinoline-2-carbonyl)benzamide (301); N-(naphthalen-2-ylsulfonyl)-4-(2-(3-phenethylpyrrolidin-1-yl)pyrimidin-4-yl)-3-(1,2,3,4-tetrahydroisoquinoline-2-carbonyl)benzamide (302); (S)-4-(2-(Dibutylamino)pyrimidin-4-yl)-3-(3-(hydroxymethyl)-1,2,3,4-tetrahydroisoquinoline-2-carbonyl)-N-(naphthalen-2-ylsulfonyl)benzamide (303); (S)-3-(3-(Aminomethyl)-1,2,3,4-tetrahydroisoquinoline-2-carbonyl)-4-(2-(dibutylamino)pyrimidin-4-yl)-N-(naphthalen-2-ylsulfonyl)benzamide (304); 4-(2-(dibutylamino)pyrimidin-4-yl)-3-(isoindoline-2-carbonyl)-N-(naphthalen-2-ylsulfonyl)benzamide (305); 4-(2-(dibutylamino)pyrimidin-4-yl)-N-(naphthalen-2-ylsulfonyl)-3-(7-(trifluoromethyl)-1,2,3,4-tetrahydroisoquinoline-2-carbonyl)benzamide (306); 4-(2-(dibutylamino)pyrimidin-4-yl)-N3,N3-dimethyl-N1-(naphthalen-2-ylsulfonyl)isophthalamide (307); (S)—N-(8-Chloronaphthalen-2-ylsulfonyl)-4-(2-(dibutylamino)pyrimidin-4-yl)-3-(3-(hydroxymethyl)-1,2,3,4-tetrahydroisoquinoline-2-carbonyl)benzamide (308); (S)-4-(2-(Dibutylamino)pyrimidin-4-yl)-3-(3-(hydroxymethyl)-1,2,3,4-tetrahydroisoquinoline-2-carbonyl)-N-(7-iodonaphthalen-2-ylsulfonyl)benzamide (309); (S)-4-(2-(Dibutylamino)pyrimidin-4-yl)-N-(1-ethylindolin-5-ylsulfonyl)-3-(3-(hydroxymethyl)-1,2,3,4-tetrahydroisoquinoline-2-carbonyl)benzamide (310); 4-(5-Chloro-2-(dibutylamino)pyrimidin-4-yl)-N-(naphthalen-2-ylsulfonyl)-3-(1,2,3,4-tetrahydroisoquinoline-2-carbonyl) benzamide (311); 4-(2-(Dibutylamino)-5-methylpyrimidin-4-yl)-N-(naphthalen-2-ylsulfonyl)-3-(1,2,3,4-tetrahydroisoquinoline-2-carbonyl)benzamide (312); 4-(5-Chloro-2-(dibutylamino)pyrimidin-4-yl)-N-(8-chloronaphthalen-2-ylsulfonyl)-3-(1,2,3,4-tetrahydroisoquinoline-2-carbonyl)benzamide (313); N-(8-Chloronaphthalen-2-ylsulfonyl)-4-(2-(dibutylamino)-5-methylpyrimidin-4-yl)-3-(1,2,3,4-tetrahydroisoquinoline-2-carbonyl)benzamide (314); 4-(5-Chloro-2-(dibutylamino)pyrimidin-4-yl)-3-((S)-3-(hydroxymethyl)-1,2,3,4-tetrahydroisoquinoline-2-carbonyl)-N-(naphthalen-2-ylsulfonyl)benzamide (315); 4-(5-Bromo-2-(dibutylamino)pyrimidin-4-yl)-3-((S)-3-(hydroxymethyl)-1,2,3,4-tetrahydroisoquinoline-2-carbonyl)-N-(naphthalen-2-ylsulfonyl)benzamide (316); 4-(5-Bromo-2-(dibutylamino) pyrimidin-4-yl)-N-(8-chloronaphthalen-2-ylsulfonyl)-3-(1,2,3,4-tetrahydroisoquinoline-2-carbonyl)benzamide (317); 4-(5-Chloro-2-(dibutylamino)pyrimidin-4-yl)-N-(7-chloronaphthalen-2-ylsulfonyl)-3-(1,2,3,4-tetrahydroisoquinoline-2-carbonyl)benzamide (318); Ethyl 4-(4-(7-chloronaphthalen-2-ylsulfonylcarbamoyl)-2-(1,2,3,4-tetrahydroisoquinoline-2-carbonyl)phenyl)-2-(dibutylamino) pyrimidine-5-carboxylate (319); 4-(4-(7-Chloronaphthalen-2-ylsulfonylcarbamoyl)-2-(1,2,3,4-tetrahydroisoquinoline-2-carbonyl)phenyl)-2-(dibutylamino)pyrimidine-5-carboxylic acid (320); 4-(5-Chloro-2-(dibutylamino)pyrimidin-4-yl)-N-(1-(3,4-dichlorobenzyl)indolin-5-ylsulfonyl)-3-(1,2,3,4-tetrahydroisoquinoline-2-carbonyl)benzamide (321); 4-(2-(Butyl(3,4-dichlorobenzyl)amino)-5-chloropyrimidin-4-yl)-N-(8-chloronaphthalen-2-ylsulfonyl)-3-(1,2,3,4-tetrahydroisoquinoline-2-carbonyl)benzamide (322); 4-(5-Chloro-2-(dipropylamino)pyrimidin-4-yl)-N-(naphthalen-2-ylsulfonyl)-3-(1,2,3,4-tetrahydroisoquinoline-2-carbonyl) benzamide (323); 4-(5-Chloro-2-(dipropylamino)pyrimidin-4-yl)-3-(S)-3-(hydroxymethyl)-1,2,3,4-tetrahydroisoquinoline-2-carbonyl)-N-(naphthalen-2-ylsulfonyl)benzamide (324); 4-(5-Bromo-2-(dipropylamino) pyrimidin-4-yl)-3-((S)-3-(hydroxymethyl)-1,2,3,4-tetrahydroisoquinoline-2-carbonyl)-N-(naphthalen-2-ylsulfonyl)benzamide (325); 4-(5-Chloro-2-((cyclopropylmethyl)(propyl)amino)pyrimidin-4-yl)-3-((S)-3-(hydroxymethyl)-1,2,3,4-tetrahydroisoquinoline-2-carbonyl)-N-(naphthalen-2-ylsulfonyl)benzamide (326); 3-((S)-3-(Aminomethyl)-1,2,3,4-tetrahydroisoquinoline-2-carbonyl)-4-(5-chloro-2-(dipropylamino)pyrimidin-4-yl)-N-(naphthalen-2-ylsulfonyl)benzamide (327); 4-(5-Chloro-2-(dipropylamino)pyrimidin-4-yl)-N-(8-chloronaphthalen-2-ylsulfonyl)-3-((S)-3-(hydroxymethyl)-1,2,3,4-tetrahydroisoquinoline-2-carbonyl)benzamide (328); 3-((S)-3-(Aminomethyl)-1,2,3,4-tetrahydroisoquinoline-2-carbonyl)-4-(5-chloro-2-(dipropylamino)pyrimidin-4-yl)-N-(8-chloronaphthalen-2-ylsulfonyl)benzamide (329); 1-(4-(((1-((2-Aminoethyl)thio)isoquinolin-6-yl)sulfonyl)carbamoyl)-2-(1,2,3,4-tetrahydroisoquinoline-2-carbonyl)phenyl)-N,N-dibutyl-4-chloro-5-methyl-1H-pyrazole-3-carboxamide (330); and 2-((6-(N-(4-(4-Chloro-3-(dibutylcarbamoyl)-5-methyl-1H-pyrazol-1-yl)-3-(1,2,3,4-tetrahydroisoquinoline-2-carbonyl)benzoyl)sulfamoyl)isoquinolin-1-yl)thio)acetic acid (331).

* * * * *